US012612424B2

(12) United States Patent
Zhong et al.

(10) Patent No.: US 12,612,424 B2
(45) Date of Patent: Apr. 28, 2026

(54) HPK1 INHIBITORS AND USES THEREOF

(71) Applicant: Regor Pharmaceuticals, Inc., Cambridge, MA (US)

(72) Inventors: Wenge Zhong, Thousand Oaks, CA (US); Xiaotian Zhu, Newton, MA (US); Song Feng, Shanghai (CN); Lei Wu, Shanghai (CN); Wei Huang, Shanghai (CN); Hao Liu, San Diego, CA (US); Rongqiang Liu, Kendall Park, NJ (US); Kate Xin Wen, Shanghai (CN); Hua Zhou, Shanghai (CN)

(73) Assignee: Regor Pharmaceuticals, Inc., Cambridge, MA (US)

( * ) Notice: Subject to any disclaimer, the term of this patent is extended or adjusted under 35 U.S.C. 154(b) by 1152 days.

(21) Appl. No.: 17/624,514

(22) PCT Filed: Jul. 3, 2020

(86) PCT No.: PCT/CN2020/100134
§ 371 (c)(1),
(2) Date: Jan. 3, 2022

(87) PCT Pub. No.: WO2021/000935
PCT Pub. Date: Jan. 7, 2021

(65) Prior Publication Data

US 2022/0389037 A1 Dec. 8, 2022

(30) Foreign Application Priority Data

Jul. 4, 2019 (WO) ................ PCT/CN2019/094634

(51) Int. Cl.

| | |
|---|---|
| ***A61K 45/06*** | (2006.01) |
| ***A61P 35/00*** | (2006.01) |
| ***C07D 401/14*** | (2006.01) |
| ***C07D 405/14*** | (2006.01) |
| ***C07D 471/04*** | (2006.01) |
| ***C07D 473/32*** | (2006.01) |
| ***C07D 487/04*** | (2006.01) |
| ***C07D 491/107*** | (2006.01) |

(Continued)

(52) U.S. Cl.
CPC ............ *C07F 9/6561* (2013.01); *A61K 45/06* (2013.01); *A61P 35/00* (2018.01); *C07D 401/14* (2013.01); *C07D 405/14* (2013.01); *C07D 471/04* (2013.01); *C07D 473/32* (2013.01); *C07D 487/04* (2013.01); *C07D 491/107* (2013.01); *C07D 498/04* (2013.01); *C07D 519/00* (2013.01); *C07F 9/65583* (2013.01)

(58) Field of Classification Search
CPC .. C07F 9/6561; C07F 9/65583; C07D 519/00; C07D 498/04; C07D 491/107; C07D 487/04; C07D 473/32; C07D 471/04; C07D 405/14; C07D 401/14; A61P 35/00; A61K 45/06
See application file for complete search history.

(56) References Cited

U.S. PATENT DOCUMENTS 8,258,129 B2 * 9/2012 Engelhardt .......... C07D 487/04 544/323
2019/0256500 A1 8/2019 Vechorkin et al.
(Continued)

FOREIGN PATENT DOCUMENTS

CN 101243084 A 8/2008
CN 102459624 A 5/2012
(Continued)

OTHER PUBLICATIONS

Registry No. 1001002-41-0, File Registry on STN, entered STN Jan. 29, 2008.*
(Continued)

*Primary Examiner* — Rebecca L Anderson
(74) *Attorney, Agent, or Firm* — McCarter & English, LLP; Wei Song

(57) ABSTRACT

Provided herein is a compound represented by structural formula (I-0) or formula (II): or a pharmaceutically acceptable salt or a stereoisomer thereof useful for treating diseases (such as cancer) that are treatable by inhibiting HPK1 activity.

(I-0)

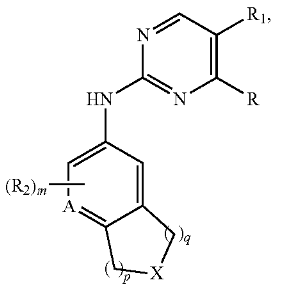

(II)

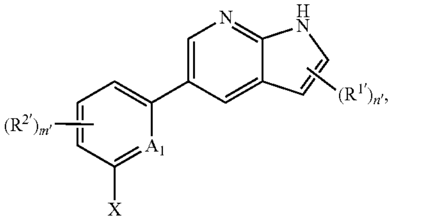

19 Claims, No Drawings

(51) Int. Cl.

| | |
|---|---|
| ***C07D 498/04*** | (2006.01) |
| ***C07D 519/00*** | (2006.01) |
| ***C07F 9/6558*** | (2006.01) |
| ***C07F 9/6561*** | (2006.01) |

(56) References Cited

U.S. PATENT DOCUMENTS

| | | | |
|---|---|---|---|
| 2020/0048241 | A1 | 2/2020 | Hummel et al. |
| 2023/0339896 | A1 | 10/2023 | Zhong et al. |

FOREIGN PATENT DOCUMENTS

| | | | |
|---|---|---|---|
| CN | 104876914 | A | 9/2015 |
| CN | 106188029 | A | 12/2016 |
| CN | 109641893 | A | 4/2019 |
| CN | 109689645 | A | 4/2019 |
| CN | 109721620 | A | 5/2019 |
| CN | 109923114 | A | 6/2019 |
| EA | 017632 | B1 | 8/2008 |
| JP | 2010-514693 | A | 5/2010 |
| WO | 2003/028724 | A1 | 4/2003 |
| WO | 2007/038314 | A2 | 4/2007 |
| WO | 2007/135398 | A1 | 11/2007 |
| WO | 2008/003766 | A2 | 1/2008 |
| WO | 2008/079988 | A2 | 7/2008 |
| WO | 2008/110508 | A1 | 9/2008 |
| WO | 2009/084695 | A1 | 7/2009 |
| WO | 2009/153313 | A1 | 12/2009 |
| WO | 2012/135631 | A1 | 10/2012 |
| WO | 2015/112441 | A1 | 7/2015 |
| WO | 2015/143692 | A1 | 10/2015 |
| WO | 2018/049214 | A1 | 3/2018 |
| WO | 2018/102366 | A1 | 6/2018 |
| WO | 2018/152220 | A1 | 8/2018 |
| WO | 2018/155916 | A2 | 8/2018 |
| WO | 2018/167147 | A1 | 9/2018 |
| WO | 2018/191587 | A1 | 10/2018 |
| WO | 2018/215668 | A1 | 11/2018 |
| WO | 2019/074979 | A1 | 4/2019 |
| WO | 2019/090198 | A1 | 5/2019 |
| WO | 2020/235902 | A1 | 11/2020 |
| WO | 2021/000935 | A1 | 1/2021 |

OTHER PUBLICATIONS

U.S. Appl. No. 18/013,402, filed Dec. 18, 2022, 2023-0339896, Published.

International Search Report and Written Opinion for Application No. PCT/CN2021/104206, dated Aug. 18, 2021, 10 pages.

STN Registry No. 507462-77-3, Butanamide, N-[5-[3-(aminosulfonyl)phenyl]-1H-pyrrolo[2,3-b]pyridin-3-yl]. 1 page, Apr. 30, 2003.

International Search Report and Written Opinion for Application No. PCT/CN2019/094634, dated Apr. 3, 2020, 20 pages.

International Search Report and Written Opinion for Application No. PCT/CN2020/100134, dated Oct. 13, 2020, 13 pages.

* cited by examiner

HPK1 INHIBITORS AND USES THEREOF

CROSS-REFERENCE TO RELATED APPLICATIONS

This application is a 35 U.S.C. § 371 national stage filing of International Application No. PCT/CN2020/100134, filed on Jul. 3, 2020, which in turn claims the benefit of priority to International Patent Application Number PCT/CN2019/094634, filed on Jul. 4, 2019. The entire contents of each of the aforementioned applications are incorporated herein by reference.

BACKGROUND OF THE INVENTION

Hematopoietic Progenitor Kinase 1 (HPK1), also known as Mitogen-Activated Protein Kinase Kinase Kinase Kinase 1 (MAP4K1), is a protein kinase that acts upstream of the classic 3-tiered MAPK pathway that includes MAP3K (MAP Kinase Kinase Kinase), which activates MAP2K (MAP Kinase Kinase), which in turn activates the dual Thr and Tyr MAPK family member JNK (c-Jun N-terminal kinase). Originally cloned in hematopoietic progenitor cells, HPK1/MAP4K1 is predominantly expressed in lymphoid organs/tissues, including the bone marrow, fetal liver, lymph node, placenta, spleen, and thymus (Hu et al., *Gene & Dev.* 10(18): 2251-2264, 1996; Kiefer et al., *The EMBO J.* 15(24): 7013-7025, 1996). At the cellular level, HPK1 is expressed in all cell types in the hematopoietic compartment, including hematopoietic progenitor cells, T cells, B cells, macrophages, dendritic cells, neutrophils, and mast cells (Hu, supra; Kiefer, supra).

HPK1/MAP4K1 is one of the six MAP4Ks that include HPK1 (MAP4K1), GCK (MAP4K2), GLK (MAP4K3), HGK/NIK (MAP4K4), KHS/GCKR (MAP4K5), and MINK (MAP4K6). Together, these MAP4Ks are members of about 26 mammalian Ste20-like serine/threonine kinases identified so far, which are homologs of the yeast sterile20 protein (Ste20p), a putative MAP4K that activates a MAP3K in the yeast pheromone signaling pathway. These mammalian Ste20-like kinases are divided into two subfamilies based on the domain structures: the p21-activated kinases (PAKs) and the germinal center kinases (GCKs). Among the GCK subfamily, several of them can activate the MAP3K kinase cascade, leading to JNK activation.

The MAP4Ks are highly similar structurally, with an N-terminal kinase domain (KD), followed by 2-4 proline-rich motifs, and a C-terminal citron-homology domain (CNH).

The ATP-binding site of the kinase domain of HPK1 includes Lys-46. Mutation of this residue to Met (HPK1-M46) abolishes catalytic activation of HPK1 (Hu, supra).

There are multiple conserved Ser/Thr phosphorylation sites within the kinase domain of HPK1, and a conserved Tyr phosphorylation site between its first two proline-rich motifs. Phosphorylation of Tyr379 (in mouse, or Tyr381 in human) by LCK/ZAP70 appears to be required for HPK1 activation, since the deficiency of LCK or ZAP70 abolishes Tyr-379 phosphorylation and kinase activity of HPK1 in Jurkat T cells upon anti-CD3 stimulation (Ling et al., *JBC* 276(22):18908-18914, 2001; Liou et al., *Immunity* 12(4): 399-408, 2000; Sauer et al., *JBC* 276(48):45207, 45216, 2001). On the other hand, Thr-355 autophosphorylation regulates ubiquitination and degradation of HPK1. Thr-355 is a PP4-targeted dephosphorylation site; this dephosphorylation prevents CUL7/Fbxw8-mediated ubiquitination and proteasomal degradation of activated HPK1 (Wang et al., *Cancer Res.* 69(3):1063-1070, 2009), thus HPK1 is also stabilized and activated by protein phosphatase 4 (PP4) (Zhou et al., *JBC* 279(47):49551-49561, 2004).

The Tyr phosphorylation site is also adjacent to a caspase cleavage site (DDVD). It has been shown that the full-length HPK1 can be cleaved by caspase-3 at this site in apoptotic cells, resulting in an enhanced catalytic activity of the N-terminal HPK1 fragment (Chen et al., *Oncogene* 18:7370-7377, 1999).

The four Pro-rich motifs of HPK1 mediate the interaction of HPK1 with many SH3 domain-containing proteins (Boomer & Tan, *JCB* 95(1): 34-44, 2005).

The CNH domain of HPK1 may be involved in HPK1-mediated lymphocyte adhesion because the citron homology domain in another Ste20-like kinase TNIK binds to Rap2 and regulates actin cytoskeleton (Taira et al., *JBC* 279(47): 49488-49496, 2004).

The MAP4Ks play important roles in the immune system, particularly in lymphocytes, through regulating cellular signaling, immune cell activation, cell transformation, and cell migration. HPK1 knock-out (KO) mice show enhanced T-cell activation, increased cytokine production, and increased antibody production after KLH immunization. HPK1 KO mice are also more susceptible to EAE induction. HPK1 KO T cells and B cells show enhanced cell activation and antigen receptor signaling. HPK1 KO dendritic cells show higher levels of co-stimulating molecules and proinflammatory cytokines (Alzabin et al., *J. Immunol.* 182(10): 6187-6194, 2009; Shui et al., *Nat. Immunol.* 8(1):84-91, 2007).

Overexpression in cell lines (e.g., HEK293 and COS-1 cells, and hematopoietic Jurkat T cells and leukemia HL-60 cells) demonstrated that HPK1 can activate the MAPK JNK (but not p38 or ERK MAP kinases) through multiple MAP3Ks (including TAK1, MEKK1, and MLK3), which all activate MAP2Ks MKK4 and MKK7, which in turn activate JNK.

Interestingly, the regulatory functions of MAP4Ks in immune cells appear to be largely mediated by JNK-independent mechanisms. It has been demonstrated that HPK1 kinase activation is required for IKK-NF-κB activation, and it is believed that HPK1 does so via regulating CARMA1. CARMA1 is an adaptor protein in the so-called CBM (CARMA1/BCL10/MALT1) complex that facilitates IKKβ activation in Jurkat T cells upon anti-CD3 stimulation. Activated IKK cleaves IκB and releases the associated NF-κB nuclear transcriptional factor. In particular, HPK1 is inducibly associated with CARMA1, and directly phosphorylates CARMA1 at Ser-551 that is required for NF-κB activation (Brenner et al., *PNAS USA,* 196(34):14508-14513, 2009).

In T cells, upon TCR stimulation, lymphocyte protein tyrosine kinase (Lck) phosphorylates the immunoreceptor tyrosine-based activation motifs (ITAMs) on the cytosolic side of the TCR/CD3 complex. Zap-70 is then recruited to the TCR/CD3 complex, where it becomes phosphorylated and activated. Activated ZAP-70 phosphorylates an adaptor protein called SLP-76, which translocates to the plasma membrane, and promotes the formation of a multi-protein signalosome complex by binding to a number of proteins including HPK1. These proteins collectively transmit TCR signaling to different effector molecules, leading to activation, survival, and proliferation of T-Lymphocytes.

During this process, HPK1 directly binds to the SH2 domain of SLP-76, and primarily serves as a negative regulator of TCR signaling. For example, TCR signaling is enhanced in HPK1 KO primary T cells, in that they show hyperproliferation and IL-2 production upon TCR ligation in vitro (Shui, supra). It is believed that HPK1 can down-regulate TCR signaling through a negative feedback mechanism, by phosphorylating the SLP-76 adaptor protein at Ser-376. Upon Ser-376 phosphorylation by HPK1, SLP-76 binds to 14-3-3 through the phosphorylated Ser-376 residue, leading to ubiquitination at Lys-30 (K30) residue of SLP-76 which is subsequently targeted for proteasome degradation. HPK1 also down-regulates TCR signaling by a similar mechanism in other adaptor proteins, including GADS (e.g., by phosphorylating Thr-254 of GADS and promote 14-3-3 interaction).

Thus it appears that HPK1 plays dual and opposite roles in JNK activation and TCR signaling. While HPK1 has been demonstrated to directly activate the JNK pathway in different overexpression systems through the MAP3K-MAP2K-MAPK pathway, HPK1-mediated inhibition of SLP-76 activation would also lead to the inhibition of JNK activity in TCR signaling. This is consistent with the observation that HPK1 knockout primary T cells show unaffected JNK activity (Shui, supra). Similarly, HPK1 seems to regulate IKK activation in two different and contrasting mechanisms—on the one hand, HPK1 activates IKK by directly phosphorylating CARMA1; on the other hand, HPK1 also negatively regulates IKK activation by inhibiting SLP-76 activation. This seemingly contrasting dual roles played by HPK1 is best understood that HPK1 facilitates JNK and IKK activation in the initial phase of TCR signaling but plays a critical role in dampening TCR signaling in the late phase.

HPK1 also plays a similar negative regulatory role in BCR-induced cell activation and proliferation in B cells. B cells use SLP-76-like adaptor protein called BLNK to transduce BCR signaling, including JNK and IKK activation. In B cells, Tyr kinases Syk and Lyn promote Tyr phosphorylation and activation of HPK1, and the resulting pY379 of HPK1 mediates HPK1-BLNK binding. The negative feedback by HPK1 of BLNK is through Thr-152 of BLNK. pT152 binding by 14-3-3 leads to BLNK ubiquitination at multiple Lys residues, and subsequent proteasome degradation of BLNK (thus dampening BCR signaling).

Interestingly, HPK1 appears to be a positive regulator of suppressive functions of regulatory T cells ($T_{reg}$) (Sawasdikosol et al., *J Immunol.* 188(supp. 1):163, 2012). HPK1 deficient mouse Foxp3$^+$ Tregs were defective in suppressing TCR-induced effector T cell proliferation, and paradoxically gained the ability to produce IL-2 following TCR engagement (Sawasdikosol, supra). Thus, HPK1 is an important regulator of Treg functions and peripheral self-tolerance.

HPK1 is also involved in PGE2-mediated inhibition of CD4$^+$ T cell activation (Ikegami et al., *J Immunol.* 166(7): 4689-4696, 2001). US2007/0087988 shows that HPK1 kinase activity was increased by exposure to physiological concentrations of PGE2 in CD4$^+$ T cells through PGE2-induced PKA activation. The proliferation of HPK1 deficient T cells was resistant to the suppressive effects of PGE2 (US 2007/0087988). Therefore, PGE2-mediated activation of HPK1 may represent a novel regulatory pathway of modulating immune response.

Other than TCR and BCR, HPK1 also transduces signals downstream of the TGF-R (transforming growth factor receptor) (Wang et al., *JBC* 272(36):22771-22775, 1997), or Gs-coupled PGE2 receptors (EP2 and EP4) (Ikegami et al., *J Immunol.* 166(7):4689-4696, 2001).

HPK1 negatively regulates immune cell adhesion. In T cells, TCR activation also induces integrin activation, resulting in T-cell adhesion and immunological synapse formation. This is achieved by SLP-76 binding of the degranulation-promoting adaptor protein (ADAP), which is required for TCR-induced integrin activation (Wang et al., J. Exp. Med. 200(8):1063-1074, 2004), though its constitutively associated SKAP55 protein that targets the activated small GTPase Rap1 to the plasma membrane, leading to integrin activation (Kliche et al., *MCB* 26(19):7130-7144, 2006). In other words, the SLP-76/ADAP/SKAP55 ternary complex relays the TCR signaling to adhesion molecules of the integrin family, thereby promoting T-cell adhesion. HPK1 negatively regulates this pathway, not only through down-regulating SLP-76 (supra) but also through competing with ADAP for the same SH2 binding site on SLP-76, which in turn dampens the activity of ADAP downstream effector Rap1 (Patzak et al., *Eur. J. Immunol.* 40(11):3220-3225, 2010).

HPK1 similarly negatively regulates integrin activation and cell adhesion in B cells. There, HPK1 is associated with a SKAP55 homologue called SKAP-HOM (Konigsberger et al., *PloS One* 5(9). pii: e12468, 2010), which is required for B-cell adhesion (Togni et al., *MCB* 25(18):8052-8063, 2005). HPK1 is believed to induce a negative phosphorylation site on SKAP-HOM, which in turn suppresses Rap1 activation.

In neutrophils, however, HPK1 positively regulates their adhesion. Neutrophil trafficking, including slow rolling, tight binding, cell spreading, and diapedesis, is controlled by the outside-in signaling of 02-Integrin activation, which induces the interaction between actin and HIP-55 (HPK1-interacting protein of 55 kDa). This reinforces the high-affinity conformation of (32-integrin, contributing to neutrophil adhesion (Hepper et al., *J. Immunol.* 188(9):4590-4601, 2012; Schymeinsky et al., *Blood* 114(19):4209-4220, 2009). HPK1 co-localizes with HIP-55 and actin at the lamellipodium of neutrophils upon (32-integrin-mediated adhesion (Jakob et al., *Blood* 121(20):4184-4194, 2013). CXCL1-mediated neutrophil adhesion is abolished by either HPK1 deficiency or HIP-55 deficiency in vitro and in vivo (Jakob, supra; Schymeinsky, supra).

Consistent with its role in down-regulating TCR and BCR function, HPK1 negatively regulates adaptive immune responses, and loss of HPK1-mediated regulation of T-cell activation and immune responses may be a crucial mechanism for autoimmune pathogenesis. In HPK1 KO mice, although the development of T and B cells appeared unaffected (Shui, supra), T cells from these animals showed dramatically increased activation of TCR proximal signaling and downstream ERK, leading to hyperproliferation of these cells in vitro upon anti-CD3 stimulation (Shui, supra). T cells from immunized HPK1-deficient mice are hyper-responsive upon antigenic specific stimulation, and produce significantly higher levels of inflammatory cytokines such as IL-2, IFN-γ, and IL-4. Such mice also produce much higher levels of IgM and IgG isoforms, suggesting enhanced functioning of HPK1 knockout B cells (Shui, supra).

HPK1 also negatively controls autoimmunity in mice, since HPK1 KO mice are more sensitive to the induction of experimental autoimmune encephalomyelitis (EAE) (Shui, supra). HPK1 attenuation also contributes to the abnormal T- and B-cell activation and to autoimmunity in human patients. HPK1 is down-regulated in peripheral blood mononuclear cells of psoriatic arthritis patients, or T cells of systemic lupus erythematosus (SLE) patients.

The physiological function of HPK1 is not limited to lymphocytes, for HPK1 also negatively regulates dendritic cell (DC) maturation and activation through an unknown mechanism (Alzabin, supra). In the HPK1 KO mice, the bone marrow-derived dendritic cells (BMDCs) display enhanced levels of co-stimulatory molecules CD80/CD86, and increased production of proinflammatory cytokines (Alzabin, supra). Consequently, antigen presentation activity of dendritic cells is more efficient in HPK1 KO mice (Alzabin, supra). More importantly, tumor eradication by HPK1 KO BMDC-mediated CTL response is more effective than that by wild-type BMDCs (Alzabin, supra). Furthermore, HPK1 can also control antitumor immunity via T- and B-lymphocyte-dependent mechanisms. It has been shown that adoptive transfer of HPK1 deficient T cells was more effective in controlling tumor growth and metastasis than wild-type T cells (Alzabin et al., *Cancer Immunol Immunother* 59(3):419-429, 2010). Similarly, BMDCs from HPK1 knockout mice were more efficient to mount a T cell response to eradicate Lewis lung carcinoma as compared to wild-type BMDCs (Alzabin et al., *J Immunol.* 182(10): 6187-6194, 2009).

Thus, there is a need for HPK1 inhibitory compounds for treating diseases or disorders through modulating HPK1 activity.

SUMMARY OF THE INVENTION

Described herein are compounds of Formulae (I-0), (I-1), (I-2), (I), (II), (II-1), (II-2), or (II-2'), and the compounds of the examples (collectively referred to herein as "the compounds of the invention"), that inhibit the activity of HPK1, and pharmaceutically acceptable salts thereof.

In one aspect, the invention provides a compound represented by structural formula (I-0):

(I-0)

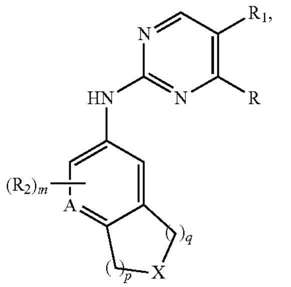

or a pharmaceutically acceptable salt or a stereoisomer thereof, wherein

X is $CR_2R_3$ or $NR_3$;

A is $CR_2$ or N;

R is 8-10 membered bicyclic nitrogen containing heteroaryl or 8-10 membered bicyclic nitrogen containing heterocyclyl optionally substituted with oxo, wherein the nitrogen containing heteroaryl or nitrogen containing heterocyclyl represented by R has 1 to 3 heteroatoms selected from N, O, and S, and is optionally substituted with one to four $R_a$, and wherein R is either connected with the pyrimidine ring via a nitrogen ring atom or R is represented by the structure below:

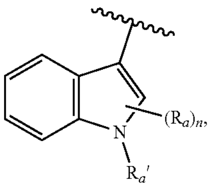

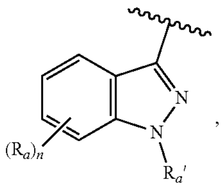

,

-continued

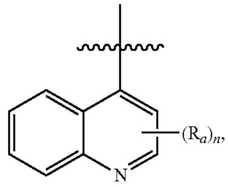

or

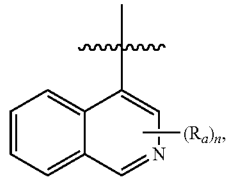

$R_1$ is H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, phenyl, 5-6 membered heteroaryl, $C_{3-6}$ cycloalkyl, or 3-7 membered heterocyclyl, wherein the alkyl, alkenyl, alkynyl, alkoxy, phenyl, heteroaryl, cycloalkyl, or heterocyclyl represented by $R_1$ or in the group represented by $R_1$ is optionally substituted with one to three substituents independently selected from the group consisting of halogen, OH, CN, $C_{1-4}$ alkyl, $C_{1-4}$ alkoxy, $C_{1-4}$ haloalkyl, $C_{1-4}$ haloalkoxy, and $NR_{11}R_{12}$; or R and $R_1$, together with the carbon atoms to which they are attached, form a ring represented below:

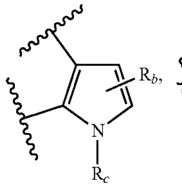

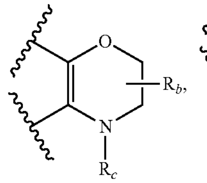

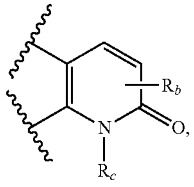

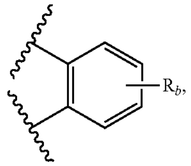

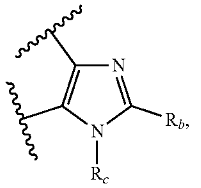

or

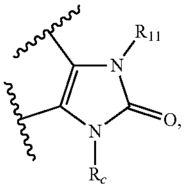

wherein the  bonds connect with the pyrimidine ring;

each instance of $R_2$ is independently H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, $P(=O)R_{11}R_{12}$, $S(=O)_2R_{11}$, or $S(=O)_2NR_{11}R_{12}$, wherein the alkyl, alkenyl, alkynyl, or alkoxy represented by $R_2$ or in the group represented by $R_2$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12}$;

$R_3$ is H, $C_{1-6}$ alkyl, $C(O)C_{1-6}$ alkyl, $C_{3-6}$ cycloalkyl, or 3-7 membered heterocyclyl, wherein the alkyl, cycloalkyl, or heterocyclyl represented by $R_3$ or in the group represented by $R_3$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, 3-7 membered heterocyclyl, and $NR_{11}R_{12}$;

each instance of $R_{11}$ and $R_{12}$ is independently H or $C_{1-6}$ alkyl, wherein the alkyl represented by $R_{11}$ or $R_{12}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, and 3-7 membered heterocyclyl, or $R_{11}$ and $R_{12}$, together with the nitrogen atom or the phosphorus atom to which they are attached, form 3-7 membered heterocyclyl optionally substituted with one to three substituents independently selected from the group consisting of halogen, OH, CN, $C_{1-4}$ alkyl, $C_{1-4}$ haloalkyl, $C_{1-4}$ alkoxy, and $C_{1-4}$ haloalkoxy;

each instance of $R_a$ is independently H, deuterium, halogen, OH, CN, $NH_2$, $NO_2$, COOH, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)NR_{11}OR_{12}$, $C(O)NR_{11}S(=O)_2R_{12}$, $C(O)C_{1-6}$ alkyl, $C(O)OR_{11}$, $NR_{11}C(O)R_{13}$, $S(=O)_3R_{11}$, $S(=O)_3NR_{11}R_{13}$, $NR_{11}S(=O)_2R_{12}$, $P(=O)R_{11}R_{12}$, $C_{3-6}$ cycloalkyl, 3-7 membered heterocyclyl, or 5-6 membered heteroaryl, wherein the alkyl, alkenyl, alkynyl, alkoxy, cycloalkyl, heterocyclyl, or heteroaryl represented by $R_a$ or in the group represented by $R_a$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, $C(O)NR_{11}OR_{12}$, $C(O)NR_{11}S(=O)_2R_{13}$, $C(O)OR_{11}$, $NR_{11}S(=O)_2R_{12}$, $P(=O)R_{11}R_{12}$, $S(=O)_2R_{11}$, $S(=O)_2NR_{11}R_{12}$, and 5-6 membered heteroaryl;

or two $R_a$, together with the carbon atom(s) to which they are attached, form $C_{3-6}$ cycloalkyl or 3-7 membered heterocyclyl, wherein the cycloalkyl, or heterocyclyl is optionally substituted with one to three substituents independently selected from the group consisting of halogen, OH, CN, $C_{1-4}$ alkyl, $C_{1-4}$ haloalkyl, $C_{1-4}$ alkoxy, and $C_{1-4}$ haloalkoxy;

each instance of $R_b$ is independently H, deuterium, halogen, OH, CN, $NH_2$, $NO_2$, COOH, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{13}$, $C(O)NR_{11}OR_{12}$, $C(O)NR_{11}S(=O)_2R_{12}$, $C(O)C_{1-6}$ alkyl, $C(O)OR_{11}$, $NR_{11}C(O)R_{12}$, $S(=O)_3R_{11}$, $S(=O)_2NR_{11}R_{12}$, $NR_{11}S(=O)_2R_{13}$, $P(=O)R_{11}R_{12}$, $C_{3-6}$ cycloalkyl, 3-7 membered heterocyclyl, or 5-6 membered heteroaryl, wherein the alkyl, alkenyl, alkynyl, alkoxy, cycloalkyl, heterocyclyl, or heteroaryl represented by $R_1$, or in the group represented by $R_b$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, $C(O)NR_{11}OR_{13}$, $C(O)NR_{11}S(=O)_2R_{12}$, $C(O)OR_{11}$, $NR_{11}S(=O)_2R_{12}$, $P(=O)R_{11}R_{12}$, $S(=O)_2R_{11}$, $S(=O)_2NR_{11}R_{12}$, and 5-6 membered heteroaryl;

each instance of $R_c$ is independently phenyl, 5-6 membered monocyclic heterocyclyl having 1 to 3 heteroatoms selected from N and 0; 5-6 membered monocyclic heteroaryl having 1 to 3 heteroatoms selected from N and O; wherein the phenyl, heterocyclyl, or heteroaryl represented by $R_c$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, and $P(O)di-C_{1-6}$ alkyl;

$R_a'$ is $C_{1-6}$ alkyl optionally substituted with OH, CN, 5-6 membered heteroaryl, $C(O)NR_{11}R_{12}$, $C(O)NR_{11}OR_{12}$, $C(O)NR_{11}S(=O)_2R_{12}$, $C(O)OR_{11}$, $NR_{11}S(=O)_2R_{12}$, $P(=O)R_{11}R_{12}$, $S(=O)_2R_{11}$, $S(=O)_2NR_{11}R_{12}$;

m is 0, 1, 2, or 3;

n is 0, 1, 2, 3, or 4;

p is 1, 2, or 3;

q is 1, 2, or 3; and $p+q\leq4$.

In another aspect, the invention provides a compound represented by structural formula (II):

(II)

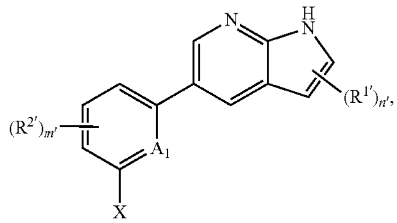

or a pharmaceutically acceptable salt or a stereoisomer thereof, wherein $A_1$ is CR' or N;

X is $-P(=O)R_{3'}R_{4'}$;

R' is H, deuterium, halogen, CN, $NO_2$, $C_{1-6}$ alkyl, $C_{2-6}$ alkenyl, $C_{2-6}$ alkynyl, $C_{1-6}$ alkoxy, $NR_{11'}R_{12'}$, $C(O)NR_{11'}R_{12'}$, $C(O)C_{1-6}$ alkyl, $C(O)OC_{1-6}$ alkyl, $NR_{11}C(O)C_{1-6}$ alkyl, wherein the alkyl, alkenyl, alkynyl, or alkoxy represented by R' or in the group represented by R' is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each instance of $R_{1'}$ is independently H, deuterium, halogen, OH, CN, $NO_2$, $C_{1-6}$ alkyl, $C_{2-6}$ alkenyl, $C_{2-6}$ alkynyl, $C_{1-6}$ alkoxy, $NR_{11'}R_{12'}$, $C(O)NR_{11'}R_{12'}$, $C(O)C_{1-6}$ alkyl, $C(O)OC_{1-6}$ alkyl, $NR_{11'}C(O)C_{1-6}$ alkyl, $C_{3-7}$ cycloalkyl, or 3-7 membered heterocyclyl, wherein the alkyl, alkenyl, alkynyl, alkoxy, cycloalkyl, or heterocyclyl represented by $R_1$, or in the group represented by $R_1$, is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each instance of $R_{2'}$ is independently H, deuterium, halogen, OH, CN, $NO_2$, $C_{1-6}$ alkyl, $C_{2-6}$ alkenyl, $C_{2-6}$ alkynyl, $C_{1-6}$ alkoxy, $NR_{11'}R_{12'}$, $C(O)NR_{11'}R_{12'}$, $C(O)C_{1-6}$ alkyl, $C(O)OC_{1-6}$ alkyl, $NR_{11'}C(O)C_{1-6}$ alkyl, phenyl, 5-6 membered heteroaryl, $C_{3-7}$ cycloalkyl, or 3-7 membered heterocyclyl, wherein the alkyl, alkenyl, alkynyl, alkoxy, phenyl, heteroaryl, cycloalkyl, or heterocyclyl represented by $R_{2'}$ or in the group represented by $R_{2'}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each $R_{3'}$ and $R_{4'}$ is independently H, $C_{1-6}$ alkyl, $C_{2-6}$ alkenyl, $C_{2-6}$ alkynyl, wherein the alkyl, alkenyl, or alkynyl represented by $R_{3'}$ or $R_{4'}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12'}$;

each instance of $R_{11'}$ and $R_{12'}$ is independently H or $C_{1-6}$ alkyl, wherein the alkyl represented by $R_{11'}$ or $R_{12'}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, and 3-7 membered heterocyclyl, or $R_{11'}$ and $R_{12'}$, together with the nitrogen atom to which they are attached, form 3-7 membered heterocyclyl optionally substituted with one to three substituents independently selected from the group consisting of halogen, OH, CN, $C_{1-4}$ alkyl, $C_{1-4}$ haloalkyl, $C_{1-4}$ alkoxy, or $C_{1-4}$ haloalkoxy;

m' is 0, 1, or 2; and n' is 0, 1, or 2.

Provided herein are pharmaceutical compositions comprising an effective amount of the compounds of the invention or a pharmaceutically acceptable salt thereof, and a pharmaceutically acceptable carrier.

Also provided is a combination comprising a therapeutically effective amount of the compounds of the invention, or a pharmaceutically acceptable salt thereof, and one or more therapeutically active co-agents.

The present invention further provides a method of inhibiting HPK1 activity in a subject in need thereof, the method comprising administering to the subject a therapeutically effective amount of the compounds of the invention, or a pharmaceutically acceptable salt thereof.

The present invention further provides a method of treating a subject with a disease or condition as described herein, such as cancer (such as breast cancer, colorectal cancer, lung cancer, ovarian cancer, and pancreatic cancer), the method comprising administering to the subject a therapeutically effective amount of the compounds of the invention, or a pharmaceutically acceptable salt thereof.

Certain embodiments disclose a compound of the present invention, or a pharmaceutically acceptable salt thereof, for use as a medicament, such as a medicament acting as a HPK1 inhibitor.

The present disclosure also provides a use of the compound of the invention or a pharmaceutically acceptable salt thereof or a pharmaceutical composition comprising the same in any of the methods of the invention described above. In one embodiment, provided is the compound of the invention or a pharmaceutically acceptable salt thereof or a pharmaceutical composition comprising the same for use in any of the method of the invention described herein. In another embodiment, provided is use of the compound of the invention or a pharmaceutically acceptable salt thereof or a pharmaceutical composition comprising the same for the manufacture of a medicament for any of the method of the invention described.

DETAILED DESCRIPTION OF THE INVENTION

1. Overview

The invention described herein provides HPK1/MAP4K1 inhibitors, pharmaceutically acceptable salts thereof, pharmaceutical compositions thereof, and methods of modulating (e.g., inhibiting) HPK1/MAP4K1 activity using the same, said method comprising administering to a patient/subject in need thereof an HPK1/MAP4K1 inhibitor compound of the invention, or a pharmaceutically acceptable salt thereof. In certain embodiments, the compounds of the invention, or pharmaceutically acceptable salts thereof, are useful for therapeutic administration to enhance, stimulate and/or increase immunity in treating cancer.

For example, a method of treating a disease or disorder associated with inhibition of HPK1 interaction can include administering to a patient in need thereof a therapeutically effective amount of a compound provided herein, or a pharmaceutically acceptable salt thereof. The compounds of the present disclosure can be used alone, in combination with other agents or therapies or as an adjuvant or neoadjuvant for the treatment of diseases or disorders, including cancers.

2. Definitions

As used herein, the term "a," "an," "the" and similar terms used in the context of the present invention (especially in the context of the claims) are to be construed to cover both the singular and plural unless otherwise indicated herein or clearly contradicted by the context.

"Halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1~4 or 1-6 carbon atoms, i.e. $(C_1\text{-}C_4)$ alkyl or $(C_1\text{-}C_6)$alkyl. Here, a "$(C_1\text{-}C_4)$alkyl" group means a radical having from 1 to 4 carbon atoms in a linear or branched arrangement. Examples include methyl, ethyl, n-propyl, iso-propyl, n-butyl, sec-butyl, isobutyl, tert-butyl, n-pentyl, isopentyl, neopentyl, n-hexyl, etc.

The term "$C_{1-6}$ alkylene" refers to divalent fully saturated branched or straight-chain monovalent hydrocarbon radical having 1 to 6 carbon atoms. Similarly, the terms "$C_{1-4}$ alkylene," "$C_{1-3}$ alkylene," and "$C_{1-2}$ alkylene" are to be construed accordingly. Representative examples of $C_{1-6}$ alkylene include, but are not limited to, methylene, ethylene, n-propylene, isopropylene, n-butylene, sec-butylene, isobutylene, tert-butylene, n-pentylene, isopentylene, neopentylene, and n-hexylene.

The term "$C_1\text{-}C_6$ alkyl optionally substituted by hydroxyl" refers to $C_1\text{-}C_6$ alkyl as defined above which may be substituted by one or more hydroxy. Examples include, but are not limited to, hydroxymethyl, hydroxyethyl, 1,2-dihydroxyethyl, 2,3-dihydroxy-propyl, etc.

As used herein, the term "di $C_{1-6}$ alkylamino" refers to a moiety of the formula $-N(R_a)-R_a$ where each $R_a$ is a $C_{1-6}$ alkyl, which may be the same or different, as defined above, in analogy thereto the term "mono $C_{1-6}$ alkylamino" which refers to a moiety of the formula $-N(H)-R_a$ where $R_a$ is a $C_{1-6}$ alkyl, as defined above.

The term "alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e. $(C_2\text{-}C_6)$alkenyl. For example, "$(C_2\text{-}C_6)$alkenyl" means a radical having from 2-6 carbon atoms in a linear or branched arrangement.

The term "alkynyl" means branched or straight-chain monovalent hydrocarbon radical containing at least one triple bond. Unless otherwise specified, an alkynyl group typically has 2-6 carbon atoms, i.e., $(C_2\text{-}C_6)$alkynyl. For example, "$(C_2\text{-}C_6)$alkynyl" means a radical having from 2-6 carbon atoms in a linear or branched arrangement.

The term "alkoxy" means an alkyl radical attached through an oxygen linking atom, represented by —O-alkyl.

For example, "$C_1$-$C_6$ alkoxy" refers to —O—$C_1$-$C_6$ alkyl, wherein alkyl is defined herein above, and "($C_1$-$C_4$)alkoxy" includes methoxy, ethoxy, propoxy, and butoxy, etc. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1 to 6 carbon atoms, 1 to 4 carbon atoms, or 1 to 2 carbon atoms.

The terms "haloalkyl" and "haloalkoxy" means alkyl or alkoxy, as the case may be, substituted with one or more halogen atoms. Examples of haloalkyl, include, but are not limited to, trifluoromethyl, trichloromethyl, pentafluoroethyl and the like.

Thus the term "$C_{1-6}$ alkyl optionally substituted by halogen" refers to $C_1$-$C_6$ alkyl as defined above which may be substituted by one or more halogens. Examples include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl, and 1-bromomethyl-2-bromoethyl.

The term "cycloalkyl" as employed herein includes saturated cyclic, bicyclic, tricyclic, or polycyclic hydrocarbon groups having 3 to 14 carbons containing the indicated number of rings and carbon atoms (for example a $C_3$-$C_{14}$ monocyclic, $C_4$-$C_{14}$ bicyclic, $C_5$-$C_{14}$tricyclic, or $C_6$-$C_{14}$ polycyclic cycloalkyl). In some embodiments "cycloalkyl" is a monocyclic cycloalkyl. Examples of monocyclic cycloalkyl groups include cyclopentyl ($C_5$), cyclohexyl ($C_6$), cyclopropyl ($C_3$) cyclobutyl ($C_4$), cycloheptyl ($C_7$) and cyclooctyl ($C_8$). In some embodiments "cycloalkyl" is a bicyclic cycloalkyl. Examples of bicyclic cycloalkyls include bicyclo[1.1.0]butane ($C_4$), bicyclo[1.1.1]pentane ($C_5$), spiro[2.2] pentane ($C_5$), bicyclo[2.1.0]pentane ($C_5$), bicyclo[2.1.1]hexane ($C_6$), bicyclo[3.3.3]undecane ($C_{11}$), decahydronaphthalene ($C_{10}$), bicyclo[4.3.2]undecane ($C_{11}$), spiro[5.5]undecane ($C_{11}$) and bicyclo[4.3.3]dodecane ($C_{12}$). In some embodiments "cycloalkyl" is a tricyclic cycloalkyl. Examples of tricyclic cycloalkyls include adamantine ($C_u$). Unless otherwise described, a "cycloalkyl" has from three to six carbon atoms and is monocyclic.

The term "aryl group" used alone or as part of a larger moiety as in "aralkyl," "aralkoxy," or "aryloxyalkyl," means a carbocyclic aromatic ring. The term "aryl" may be used interchangeably with the terms "aryl ring," "carbocyclic aromatic ring," "aryl group," and "carbocyclic aromatic group." Typically, aryl is monocyclic, bicyclic or tricyclic aryl having 6-20 carbon atoms, typically 6-14 ring carbon atoms. Furthermore, the term "aryl" as used herein, refers to an aromatic substituent which can be a single aromatic ring, or multiple aromatic rings that are fused together. Examples includes phenyl, naphthyl, anthracenyl, 1,2-dihydronaphthyl, 1,2,3,4-tetrahydronaphthyl, fluorenyl, indanyl, indenyl and the like.

A "substituted aryl group" is substituted at any one or more substitutable ring atom, which is a ring carbon atom bonded to a hydrogen. A substituted aryl is typically substituted by 1-5 (such as one, or two, or three) substituents independently selected from the group consisting of: hydroxyl, thiol, cyano, nitro, $C_1$-$C_4$ alkyl, $C_1$-$C_4$ alkenyl, $C_1$-$C_4$ alkynyl, $C_1$-$C_4$ alkoxy, $C_1$-$C_4$ thioalkyl, $C_1$-$C_4$ alkenyloxy, $C_1$-$C_4$ alkynyloxy, halogen, $C_1$-$C_4$ alkylcarbonyl, carboxy, $C_1$-$C_4$ alkoxycarbonyl, amino, $C_1$-$C_4$ alkylamino, di-$C_1$-$C_4$ alkylamino, $C_1$-$C_4$ alkylaminocarbonyl, di-$C_1$-$C_4$ alkylaminocarbonyl, $C_1$-$C_4$ alkylcarbonylamino, $C_1$-$C_4$ alkylcarbony, $C_1$-$C_4$ alkyl amino, sulfonyl, sulfamoyl, alkylsulfamoyl, and $C_1$-$C_4$ alkylaminosulfonyl, where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$ alkoxy groups.

The term "heterocyclyl group" or "heterocyclic group" means a monocyclic, non-aromatic (including partially saturated) ring with preferably 3 to 10-members containing preferably 1-4 ring heteroatoms, or a polycyclic ring with ring with preferably 7 to 20 members and from preferably 1 to 4 ring heteroatoms, wherein the polycyclic ring having one or more monocyclic non-aromatic heterocyclic ring fused with one or more aromatic or heteroaromatic ring. The heterocyclyl group typically has 3 to 7, 3 to 24, 4 to 16, 5 to 10, or 5 or 6 ring atoms; wherein optionally one to four, especially one or two ring atoms are a heteroatom (the remaining ring atoms therefore being carbon). Each heteroatom is independently selected from nitrogen, quaternary nitrogen, oxidized nitrogen (e.g., NO); oxygen; and sulfur, including sulfoxide and sulfone. The heterocyclic group can be attached at a heteroatom or a carbon atom. Examples of heterocycles include tetrahydropyran (THF), dihydrofuran, 1,4-dioxane, morpholine, 1,4-dithiane, piperazine, piperidine, 1,3-dioxolane, imidazoisdine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The heterocyclyl group can include fused or bridged rings as well as spirocyclic rings. In one embodiment, the heterocyclyl group is a bicyclic ring having a monocyclic non-aromatic heterocyclic ring fused with a phenyl group. Exemplary polycyclic heterocyclic group includes tetrahydroisoquinolinyl (such as 1,2,3,4-tetrahydroisoquinolin-7-yl, 2-methyl-1,2,3,4-tetrahydroisoquinolin-7-yl, 1,2,3,4-tetrahydroisoquinolin-6-yl and 2-methyl-1,2,3,4-tetrahydroisoquinolin-6-yl), isoindolinyl (such as 2-ethylisoindolin-5-yl, 2-methylisoindolin-5-yl), indolinyl, tetrahydrobenzo[f]oxazepinyl (e.g., 2,3,4,5-tetrahydrobenzo[f][1,4]oxazepin-7-yl).

The term "heterocycle," "heterocyclyl," or "heterocyclic" whether saturated or partially unsaturated, also refers to rings that are optionally substituted. A substituted heterocyclyl may be a heterocyclyl group independently substituted by 1-4, such as one, or two, or three, or four substituents.

In some embodiments, a heterocyclyl group is a 3-14 membered non-aromatic ring system having ring carbon atoms and 1-4 ring heteroatoms, wherein each heteroatom is independently selected from nitrogen, oxygen, and sulfur ("3-14 membered heterocyclyl").

The term "heteroaryl," "heteroaromatic," "heteroaryl ring," "heteroaryl group," "heteroaromatic ring," and "heteroaromatic group," used alone or as part of a larger moiety as in "heteroaralkyl" or "heteroarylalkoxy," refers to aromatic ring groups having 5 to 14 ring atoms selected from carbon and at least one (typically 1 to 4, more typically 1 or 2) heteroatoms (e.g., oxygen, nitrogen or sulfur). "Heteroaryl" includes monocyclic rings and polycyclic (e.g., bi- or thi-cyclic) rings in which a monocyclic heteroaromatic ring is fused to one or more other carbocyclic aromatic or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl.

Typically, the heteroaryl is a 5-10 membered ring system (e.g., 5-6 membered monocycle or an 8-10 membered bicycle) or a 5-6 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

Thus the term "heteroaryl" also refers to a group in which a heteroaromatic ring is fused to one or more aryl, cycloaliphatic, or heterocyclyl rings, where the radical or point of attachment is on the heteroaromatic ring. Non-limiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]-thiazolyl, 3-, 5-, or 8-pyrazino[2,3-d]pyridazinyl, 2-, 3-, 5-, or 6-imidazo[2,1-b]-thiazolyl, 1-, 3-, 6-, 7-, 8-, or 9-furo[3,4-c]cinnolinyl, 1-, 2-, 3-, 4-, 5-, 6-, 8-, 9-, 10-, or 11-4H-pyrido[2,3-c]carbazolyl, 2-, 3-, 8-, or 7-imidazo[1,2-b][1,2,4]triaziny1, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl.

Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

As used herein, the term a pyridin or a pyridyl optionally substituted by hydroxy e.g. 2-pyridyl, 3-pyridyl, or 4-pyridyl refers to a respective hydroxy-pyridin or hydroxy-pyridyl and may include its tautomeric form such as a respective pyridone or pyridonyl.

As used herein the term pyridin or pyridyl optionally substituted by oxo e.g. 2-pyridyl, 3-pyridyl, or 4-pyridyl, refers to a respective pyridone or pyridonyl and may include its tautomeric form such as a respective hydroxy-pyridin or hydroxy-pyridyl, provided said tautomeric form may be obtainable. Pyridin or pyridyl optionally substituted by oxo may further refer to a respective pyridine-N-oxide or pyridyl-N-oxide.

A "substituted heteroaryl group" is substituted at any one or more substitutable ring atom, which is a ring carbon or ring nitrogen atom bonded to a hydrogen.

The term "bridged bicyclic group" refers to a ring system which includes two rings that share at least three adjacent ring atoms.

As used herein, many moieties (e.g., alkyl, alkylene, cycloalkyl, aryl, heteroaryl, or heterocyclyl) are referred to as being either "substituted" or "optionally substituted." When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant invention. The optional substituents can be any substituents that are suitable to attach to the moiety.

Where suitable substituents are not specifically enumerated, exemplary substituents include, but are not limited to: $(C_1\text{-}C_5)$alkyl, $(C_1\text{-}C_5)$hydroxyalkyl, $(C_1\text{-}C_5)$haloalkyl, $(C_1\text{-}C_5)$ alkoxy, $(C_1\text{-}C_5)$ haloalkoxy, halogen, hydroxyl, cyano, amino, —CN, —$NO_2$, —$OR^{c1}$, $NR^{a1}R^{b1}$, —$S(O)_iR^{a1}$, —$NR^{a1}S(O)_iR^{b1}$, —$S(O)_iNR^{a1}R^{b1}$, —$C(=O)OR^{a1}$, —$OC(=O)OR^{a1}$, —$C(=S)OR^{a1}$, —$O(C=S)R^{a1}$, $=C(=O)NR^{a1}R^{b1}$, —$NR^{a1}C(=O)R^{b1}$, —$C(=S)NR^{a1}R^{b1}$, —$C(=O)R^{a1}$, —$C(=S)R^{a1}$, $NR^{a1}C(=S)R^{b1}$, —$O(C=O)NR^{a1}R^{b1}$, —$NR^{a1}(C=S)OR^{b1}$, —$O(C=S)NR^{a1}R^{b1}$, —$NR^{a1}(C=C)NR^{a1}R^{b1}$, —$NR^{a1}(C=S)NR^{a1}R^{b1}$, phenyl, or 5-6 membered heteroaryl. Each $R^{a1}$ and each $R^{b1}$ are independently selected from —H and $(C_1\text{-}C_5)$alkyl, optionally substituted with hydroxyl or $(C_1\text{-}C_3)$alkoxy; $R^{c1}$ is —H, $(C_1\text{-}C_5)$haloalkyl or $(C_1\text{-}C_5)$alkyl, wherein the $(C_1\text{-}C_5)$alkyl is optionally substituted with hydroxyl or $(C_1\text{-}C_3)$alkoxy.

The compounds described herein may exist in various tautomeric forms. The term "tautomers" or "tautomeric" refers to two or more interconvertible compounds/substituents resulting from at least one formal migration of a hydrogen atom and at least one change in valency (e.g., a single bond to a double bond, a triple bond to a single bond, or vice versa). Exemplary tautomerizations include keto-to-enol, amide-to-imide, lactam-to-lactim, enamine-to-imine, and enamine-to-(a different enamine) tautomerizations. The present teachings encompass compounds in the form of tautomers, which includes forms not depicted structurally. All such isomeric forms of such compounds are expressly included. If a tautomer of a compound is aromatic, this compound is aromatic.

The compounds of any one of the formulae described above may exhibit one or more kinds of isomerism (e.g. optical, geometric or tautomeric isomerism). The compounds of any one of the formulae described above may also be isotopically labelled. Such variation is implicit to the compounds of any one of the formulae described above defined as they are by reference to their structural features and therefore within the scope of the present disclosure.

Compounds of any one of the formulae described above containing one or more asymmetric carbon atoms can exist as two or more stereoisomers. Where a compound of any one of the formulae described above contains an alkenyl or alkenylene group, geometric cis/trans (or Z/E) isomers are possible. Where structural isomers are interconvertible via a low energy barrier, tautomeric isomerism ("tautomerism") can occur. This can take the form of proton tautomerism in compounds of any one of the formulae described above containing, for example, an imino, keto, or oxime group, or so-called valence tautomerism in compounds which contain an aromatic moiety. It follows that a single compound may exhibit more than one type of isomerism.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

The pharmaceutically acceptable salts of compounds of any one of the formulae described above may also contain a counterion which is optically active (e.g. d-lactate or 1-lysine) or racemic (e.g. dl-tartrate or dl-arginine).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of any one of the formulae described above contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of any one of the formulae described above (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present disclosure are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). Columns can be obtained from Chiral Technologies, Inc, West Chester, Pa., USA, a subsidiary of Daicel® Chemical Industries, Ltd., Tokyo, Japan.

It must be emphasized that the compounds of any one of the formulae described above have been drawn herein in a single tautomeric form, all possible tautomeric forms are included within the scope of the present disclosure.

The present disclosure also includes all pharmaceutically acceptable isotopically-labeled compounds of any one of the formulae described above wherein one or more atoms are replaced by atoms having the same atomic number, but an atomic mass or mass number different from the atomic mass or mass number which predominates in nature.

Examples of isotopes suitable for inclusion in the compounds of the present disclosure include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of any one of the formulae described above, for example those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of any one of the formulae described above can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the present disclosure include those wherein the solvent of crystallization may be isotopically substituted, e.g., $D_2O$, $d_6$-acetone, $d_6$-DMSO.

It is to be understood that when a compound herein is represented by a structural formula or designated by a chemical name herein, all other tautomeric forms which may exist for the compound are encompassed by the structural formula.

Any formula given herein is also intended to represent unlabeled forms as well as isotopically labeled forms of the compounds, such as 2H. Further, substitution with deuterium (i.e., 2H or D) may afford certain therapeutic advantages resulting from greater metabolic stability, for example increased in vivo half-life or reduced dosage requirements or an improvement in therapeutic index, if is understood that deuterium in this context is regarded as a substituent of a compound of the formula (I-0), (I-1) or (I-2). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The compounds of this invention can exist in free form for treatment, or where appropriate, as a pharmaceutically acceptable salt form.

As used herein, the terms "salt" or "salts" refers to an acid addition or base addition salt of a compound of the invention. "Salts" include in particular "pharmaceutically acceptable salts." The term "pharmaceutically acceptable salts" refers to salts that retain the biological effectiveness and properties of the compounds of this invention and, which typically are not biologically or otherwise undesirable, in many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophylionate, citrate, ethandisulfonate, fumarate, gluceptate, gluconate, glucuronate, hippurate, hydroiodide/iodide, isothionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases. inorganic bases from which salts can be derived include, for example, ammonium salts and metals from columns I to XII of the periodic table, in certain embodiments, the salts are derived from sodium, potassium, ammonium, calcium, magnesium, iron, silver, zinc, and copper. In certain embodiments, suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, PA, (1985); and in "Handbook of Pharmaceutical Salts: Properties, Selection, and Use" by Stahl and Wermuth (Wiley-VCH, Weinheim, Germany, 2002).

The terms "composition" and "formulation" are used interchangeably.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein, a subject is "in need of" a treatment if such subject would benefit biologically, medically or in quality of life from such treatment.

The term "administer," "administering," or "administration" refers to methods introducing a compound of the invention, or a composition thereof, in or on a subject. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, Pharmaceutical Sciences (current edition), Mack Publishing Co., Easton, Pennsylvania.

As used herein, the term "inhibit," "inhibition" or "inhibiting" refers to the reduction or suppression of a given condition, symptom, or disorder, or disease, or a significant decrease in the baseline activity of a biological activity or process.

The terms "treatment," "treat," and "treating" refer to reversing, alleviating, or inhibiting the progress of a disease described herein. In some embodiments, treatment may be administered after one or more signs or symptoms of the disease have developed or have been observed (i.e., therapeutic treatment). In other embodiments, treatment may be administered in the absence of signs or symptoms of the disease. For example, treatment may be administered to a susceptible subject prior to the onset of symptoms (i.e., prophylactic treatment) (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably. Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term "an effective amount" means an amount when administered to the subject which results in beneficial or desired results, including clinical results, e.g., inhibits, suppresses or reduces the symptoms of the condition being treated in the subject as compared to a control. For example, an effective amount can be given in unit dosage form (e.g., from 1 mg to about 50 g per day, e.g., from 1 mg to about 5 grams per day).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by HPK1, or (ii) associated with HPK1 activity, or (iii) characterized by activity (normal or abnormal) of HPK1; or (2) reducing or inhibiting the activity of HPK1; or (3) reducing or inhibiting the expression of HPK1; or (4) modifying the protein levels of HPK1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of HPK1; or reducing or inhibiting the expression of HPK1 partially or completely.

All methods described herein can be performed in any suitable order unless otherwise indicated herein or otherwise clearly contradicted by context. The use of any and another examples, or exemplary language (e.g. "such as") provided herein is intended merely to better illuminate the invention and does not pose a limitation on the scope of the invention otherwise claimed.

The general chemical terms used in the formulae above have their usual meanings.

As used herein, "h" or "hr" refers to hour or hours, "min" refers to minutes or minutes, "MCL" refers to mantle cell lymphoma, "AML" refers to acute myeloid leukemia, "CML" refers to chronic myeloid leukemia, "Boc" refers to N-tert-butoxycarbonyl, "EA" refers to ethyl acetate, "DCM" refers to dichloromethane, "DMSO" refers to dimethylsulfoxide, "DMA" refers to dimethylacetamide, "THF" refers to tetrahydrofuran, "MtBE" refers to methyl tert-butyl ether, "TEA" refers to triethylamine, "FBS" refers to fetal bovine serum, "PBS" refers to phosphate buffered saline, "BSA" refers to bovine serum albumin, "RT" refers to room temperature, "mpk" means milligrams per kilogram, "po" refers to per os (oral), "qd" means once daily dosing, "HPLC" means high pressure liquid chromatography, "q2d" means a single dose every 2 days, "q2dx10" means a single dose every 2 days times 10, "VSMC" refers to vascular smooth muscle cell and "XRD" refers to X-ray diffraction.

As used herein, the term "pharmaceutically acceptable carrier" includes any and ail solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs. in another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

3. Compounds

Disclosed herein are embodiments of a compound having the general structure of Formula (I-0) or (II):

(I-0)

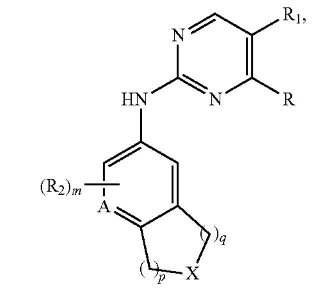

or (II)

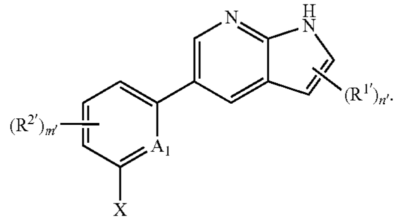

In a first embodiment of the invention, provided is a compound represented by Formula (I-0) or a pharmaceutically acceptable salt or a stereoisomer thereof, wherein X is $CR_2R_3$ or $NR_3$;

A is $CR_2$ or N;

R is 8-10 membered bicyclic nitrogen containing heteroaryl or 8-10 membered bicyclic nitrogen containing heterocyclyl optionally substituted with oxo, wherein the nitrogen containing heteroaryl or nitrogen containing heterocyclyl represented by R has 1 to 3 heteroatoms selected from N, O, and S, and is optionally substituted with one to four $R_a$, and wherein R is either connected with the pyrimidine ring via a nitrogen ring atom or R is represented by the structure below:

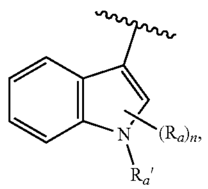

,

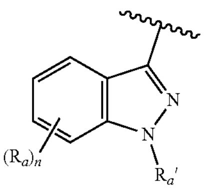

,

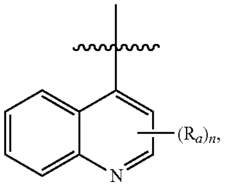

or

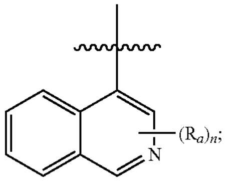

;

$R_1$ is H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, phenyl, 5-6 membered heteroaryl, $C_{3-6}$ cycloalkyl, or 3-7 membered heterocyclyl, wherein the alkyl, alkenyl, alkynyl, alkoxy, phenyl, heteroaryl, cycloalkyl, or heterocyclyl represented by $R_1$ or in the group represented by $R_1$ is optionally substituted with one to three substituents independently selected from the group consisting of halogen, OH, CN, $C_{1-4}$ alkyl, $C_{1-4}$ alkoxy, $C_{1-4}$ haloalkyl, $C_{1-4}$ haloalkoxy, and $NR_{11}R_{12}$; or R and $R_1$, together with the carbon atoms to which they are attached, form a ring represented below:

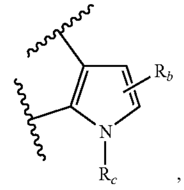

,

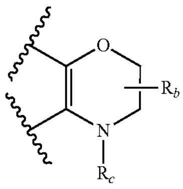

,

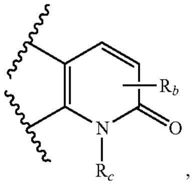

,

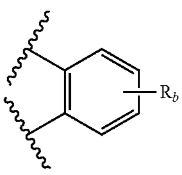

,

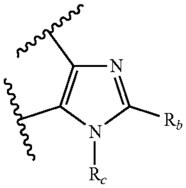

, or

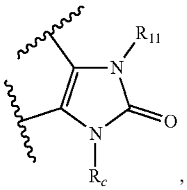

, wherein the  bonds connect with the pyrimidine ring;

each instance of $R_2$ is independently H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, $P(=O)R_{11}R_{12}$, $S(=O)_2R_{11}$, or $S(=O)_2NR_{11}R_{12}$, wherein the alkyl, alkenyl, alkynyl, or alkoxy represented by $R_2$ or in the group represented by $R_2$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12}$;

$R_3$ is H, $C_{1-6}$ alkyl, $C(O)C_{1-6}$ alkyl, $C_{3-6}$ cycloalkyl, or 3-7 membered heterocyclyl, wherein the alkyl, cycloalkyl, or heterocyclyl represented by $R_3$ or in the group represented by $R_3$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, 3-7 membered heterocyclyl, and $NR_{11}R_{12}$;

each instance of $R_{11}$ and $R_{12}$ is independently H or $C_{1-6}$ alkyl, wherein the alkyl represented by $R_{11}$ or $R_{12}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, and 3-7 membered heterocyclyl, or $R_{11}$ and $R_{12}$, together with the nitrogen atom or the phosphorus atom to which they are attached, form 3-7 membered heterocyclyl optionally substituted with one to three substituents independently selected from the group consisting of halogen, OH, CN, $C_{1-4}$ alkyl, $C_{1-4}$ haloalkyl, $C_{1-4}$ alkoxy, and $C_{1-4}$ haloalkoxy;

each instance of $R_a$ is independently H, deuterium, halogen, OH, CN, $NH_2$, $NO_2$, COOH, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)NR_{11}OR_{12}$, $C(O)NR_{11}S({=}O)_2R_{12}$, $C(O)C_{1-6}$ alkyl, $C(O)OR_{11}$, $NR_{11}C(O)R_{12}$, $S({=}O)_2R_{11}$, $S({=}O)_2NR_{11}R_{12}$, $NR_{11}S({=}O)_2R_{12}$, $P({=}O)R_{11}R_{12}$, $C_{3-6}$ cycloalkyl, 3-7 membered heterocyclyl, or 5-6 membered heteroaryl, wherein the alkyl, alkenyl, alkynyl, alkoxy, cycloalkyl, heterocyclyl, or heteroaryl represented by $R_a$ or in the group represented by $R_a$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, $C(O)NR_{11}OR_{12}$, $C(O)NR_{11}S({=}O)_2R_{12}$, $C(O)OR_{11}$, $NR_{11}S({=}O)_2R_{12}$, $P({=}O)R_{11}R_{12}$, $S({=}O)_2R_{11}$, $S({=}O)_2NR_{11}R_{12}$, and 5-6 membered heteroaryl; or two $R_a$, together with the carbon atom(s) to which they are attached, form $C_{3-6}$ cycloalkyl or 3-7 membered heterocyclyl, wherein the cycloalkyl, or heterocyclyl is optionally substituted with one to three substituents independently selected from the group consisting of halogen, OH, CN, $C_{1-4}$ alkyl, $C_{1-4}$ haloalkyl, $C_{1-4}$ alkoxy, and $C_{1-4}$ haloalkoxy;

each instance of $R_b$ is independently H, deuterium, halogen, OH, CN, $NH_2$, $NO_2$, COOH, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)NR_{11}OR_{12}$, $C(O)NR_{11}S({=}O)_2R_{12}$, $C(O)C_{1-6}$ alkyl, $C(O)OR_{11}$, $S({=}O)_2R_{11}$, $S({=}O)_2NR_{11}R_{12}$, $NR_{11}S({=}O)_2R_{12}$, $P({=}O)R_{11}R_{12}$, $C_{3-6}$ cycloalkyl, 3-7 membered heterocyclyl, or 5-6 membered heteroaryl, wherein the alkyl, alkenyl, alkynyl, alkoxy, cycloalkyl, heterocyclyl, or heteroaryl represented by $R_b$ or in the group represented by $R_b$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, $C(O)NR_{11}OR_{12}$, $C(O)NR_{11}S({=}O)_2R_{12}$, $C(O)OR_{11}$, $NR_{11}S({=}O)_2R_{12}$, $P({=}O)R_{11}R_{12}$, $S({=}O)_2R_{11}$, $S({=}O)_2NR_{11}R_{12}$, and 5-6 membered heteroaryl;

each instance of $R_c$ is independently phenyl, 5-6 membered monocyclic heterocyclyl having 1 to 3 heteroatoms selected from N and 0; 5-6 membered monocyclic heteroaryl having 1 to 3 heteroatoms selected from N and O; wherein the phenyl, heterocyclyl, or heteroaryl represented by $R_c$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$haloalkoxy, $NR_{11}R_{12}$, $C(O)NR_{11}R_{12}$, and P(O)di-$C_{1-6}$ alkyl;

$R_a'$ is $C_{1-6}$ alkyl optionally substituted with OH, CN, 5-6 membered heteroaryl, $C(O)NR_{11}R_{12}$, $C(O)NR_{11}OR_{12}$, $C(O)NR_{11}S({=}O)_2R_{12}$, $C(O)OR_{11}$, $NR_{11}S({=}O)_2R_{12}$, $P({=}O)R_{11}R_{12}$, $S({=}O)_2R_{11}$, $S({=}O)_2NR_{11}R_{12}$;

m is 0, 1, 2, or 3;

n is 0, 1, 2, 3, or 4;

p is 1, 2, or 3;

q is 1, 2, or 3; and p+q≤4.

In a second embodiment of the invention, the compound is represented by structural formula (I-1):

(I-1)

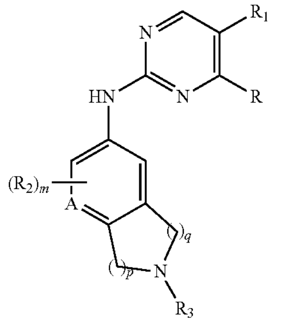

or a pharmaceutically acceptable salt or a stereoisomer thereof, and the remaining variables are as defined in the first embodiment.

In a third embodiment of the invention, the compound is represented by structural formula (I-2):

(I-2)

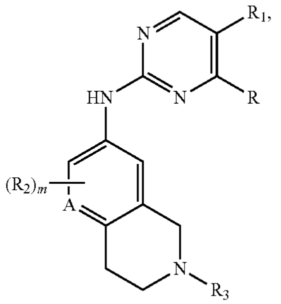

or a pharmaceutically acceptable salt or a stereoisomer thereof, and the remaining variables are as defined in the first and/or second embodiments.

In a fourth embodiment of the invention, provided is a compound of formula (I-0), (I-1), or (I-2) or a pharmaceutically acceptable salt or a stereoisomer thereof, wherein R is

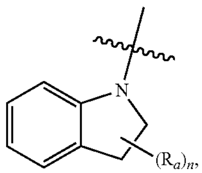

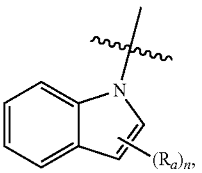

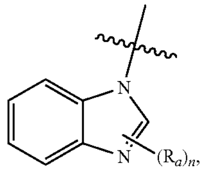

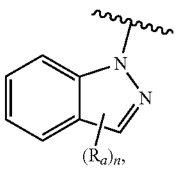

,

-continued

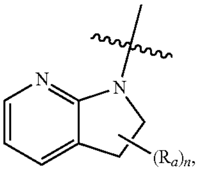
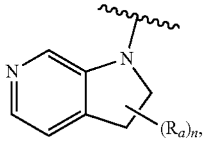
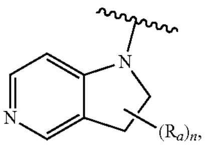
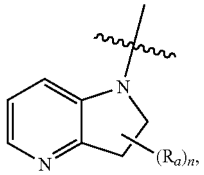
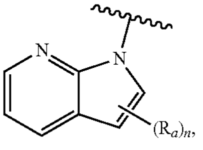
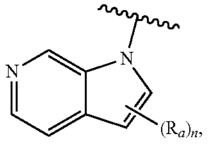
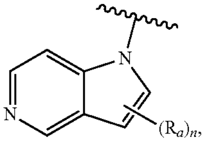
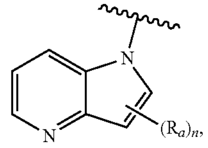
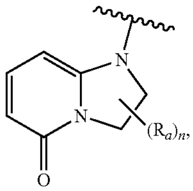
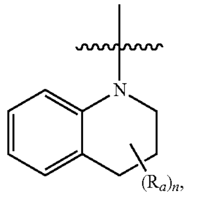
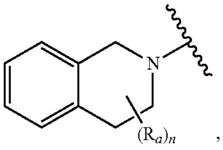
,
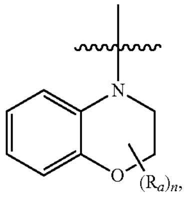
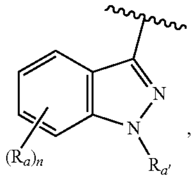
,
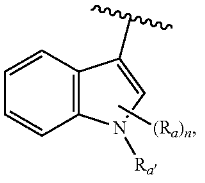
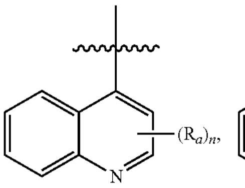
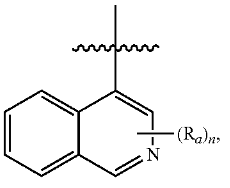
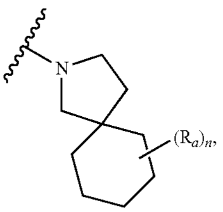
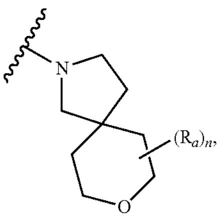

-continued

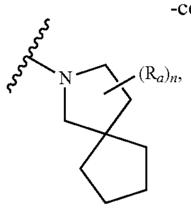
or
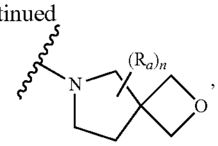
, wherein the bond connects with the pyrimidine ring, and the remaining variables are as defined in the first, second and/or third embodiments.

In a fifth embodiment, provided is a compound of formula (I-0), (I-1), or (I-2) or a pharmaceutically acceptable salt or a stereoisomer thereof, wherein each instance of $R_a$ is independently H, halogen, OH, CN, $C_{1-4}$ alkyl, $C_{1-4}$ alkoxy, $NR_{11}R_{12}$, $C(O)NR_{11}R_{12}$, $C(O)NR_{11}OR_{12}$, $C(O)NR_{11}S(=O)_2R_{12}$, $C(O)C_{1-4}$ alkyl, $C(O)OR_{11}$, $NR_{11}C(O)C_{1-4}$ alkyl, $NR_{11}S(=O)_2R_{12}$, $S(=O)_2R_{11}$, $S(=O)_2NR_{11}R_{12}$, $P(=O)R_{11}R_{12}$, $C_{3-6}$ cycloalkyl, 3-7 membered heterocyclyl, or 5-6 membered heteroaryl, wherein the alkyl, alkoxy, cycloalkyl, heterocyclyl, or heteroaryl represented by $R_a$ or in the group represented by $R_a$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, $C(O)NR_{11}OR_{12}$, $C(O)NR_{it}S(=O)_2R_{12}$, $C(O)OR_{11}$, $NR_{11}S(=O)_2R_{12}$, $P(=O)R_{11}R_{12}$, $S(=O)_2R_{11}$, $S(=O)_2NR_{11}R_{12}$, and 5-6 membered heteroaryl, and the remaining variables are as defined in the first, second, third and/or fourth embodiments.

In a sixth embodiment, provided is a compound of formula (I-0), (I-1), or (I-2) or a pharmaceutically acceptable salt or a stereoisomer thereof, wherein $R_1$ is H, halogen, CN, $C_{1-6}$ alkyl, $C_{2-6}$ alkenyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, wherein the alkyl, alkenyl, or alkoxy represented by $R_1$ or in the group represented by $R_1$ is optionally substituted with one to three substituents independently selected from the group consisting of halogen, OH, CN, $C_{1-4}$ alkyl, $C_{1-4}$ alkoxy, $C_{1-4}$ haloalkyl, $C_{1-4}$ haloalkoxy, and $NR_{11}R_{12}$, and the remaining variables are as defined in the first, second, third, fourth and/or fifth embodiments.

In a seventh embodiment, provided is a compound of formula (I-0), (I-1), or (I-2) or a pharmaceutically acceptable salt or a stereoisomer thereof, wherein each instance of $R_2$ is independently H, halogen, OH, CN, $NH_2$, $NO_2$, $C_{1-4}$ alkyl, $C_{1-4}$ alkoxy, $NR_{11}R_{12}$, $C(O)NR_{11}R_{12}$, $C(O)C_{1-4}$ alkyl, $C(O)OC_{1-4}$ alkyl, $NR_{11}C(O)C_{1-4}$ alkyl, $P(=O)R_{11}R_{12}$, $S(=O)_2R_{11}$, or $S(=O)_2NR_{11}R_{12}$, wherein the alkyl or alkoxy represented by $R_2$ or in the group represented by $R_2$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12}$, and the remaining variables are as defined in the first, second, third, fourth, fifth and/or sixth embodiments.

In an eighth embodiment, provided is a compound of formula (I-0), (I-1), or (I-2) or a pharmaceutically acceptable salt or a stereoisomer thereof, wherein $R_3$ is H, $C_{1-6}$ alkyl, or $C(O)C_{1-6}$ alkyl, wherein the alkyl represented by $R_3$ or in the group represented by $R_3$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12}$, and the remaining variables are as defined in the first, second, third, fourth, fifth, sixth, and/or seventh embodiments.

In a ninth embodiment, provided is a compound of formula (I-0), (I-1), or (I-2) or a pharmaceutically acceptable salt or a stereoisomer thereof, wherein each instance of $R_a$ is independently H, halogen, OH, CN, $C_{1-4}$ alkyl, $C_{3-6}$ cycloalkyl, $C(O)NR_{11}R_{12}$, $C(O)NR_{11}OR_{12}$, $C(O)NR_{11}S({=}O)_2R_{12}$, $C(O)OR_{11}$, $N(R_{11})S({=}O)_2R_{12}$, $S({=}O)_2R_{11}$, $S({=}O)_2NR_{11}R_{12}$, $P(O)R_{11}R_{12}$, or 5-6 membered heteroaryl, wherein the alkyl or cycloalkyl represented by $R_a$ or in the group represented by $R_a$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, $C(O)NR_{11}OR_{12}$, $C(O)NR_{11}S({=}O)_2R_{12}$, $C(O)OR_{11}$, $NR_{11}S({=}O)_2R_{12}$, $P({=}O)R_{11}R_{12}$, $S({=}O)_2R_{11}$, $S({=}O)_2NR_{11}R_{12}$, and 5-6 membered heteroaryl; each instance of $R_{11}$ and $R_{12}$ is independently H or $C_{1-6}$ alkyl, and the remaining variables are as defined in the first, second, third, fourth, fifth, sixth, seventh, and/or eighth embodiments.

In a tenth embodiment, provided is a compound of formula (I-0), (I-1), or (I-2) or a pharmaceutically acceptable salt or a stereoisomer thereof, wherein $R_1$ is H, halogen, CN, $C_{1-4}$ alkyl, $C_{1-4}$ haloalkyl, $C_{2-4}$ alkenyl, $C_{1-4}$ alkoxy, or $C_{1-4}$ haloalkoxy, and the remaining variables are as defined in the first, second, third, fourth, fifth, sixth, seventh, eighth, and/or ninth embodiments.

In an eleventh embodiment, provided is a compound of formula (I-0), (I-1), or (I-2) or a pharmaceutically acceptable salt or a stereoisomer thereof, wherein R is

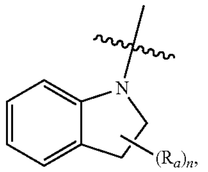 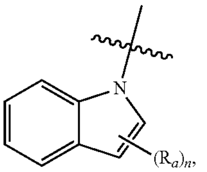

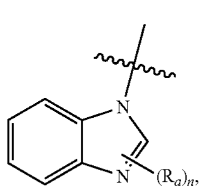 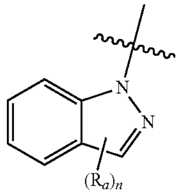 ,

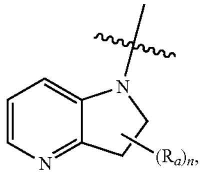 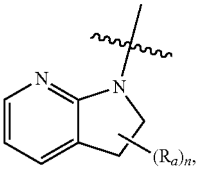

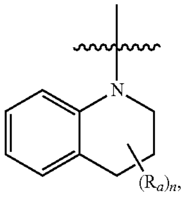 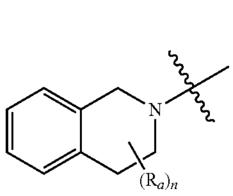 ,

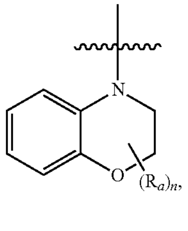 or 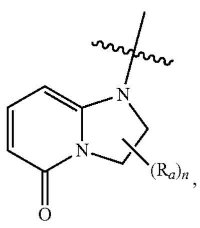

wherein the bond connects with the pyrimidine ring, and n is 0 to 4, and the remaining variables are as defined in the first, second, third, fourth, fifth, sixth, seventh, eighth, ninth, and/or tenth embodiments.

In a twelfth embodiment, provided is a compound of formula (I-0), (I-1), or (I-2) or a pharmaceutically acceptable salt or a stereoisomer thereof, wherein R is

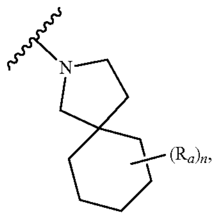 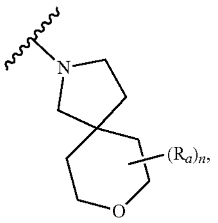

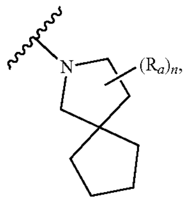 or 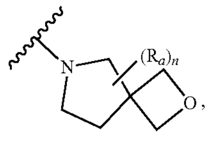

wherein the bond connects with the pyrimidine ring, and n is 0 to 2, and the remaining variables are as defined in the first, second, third, fourth, fifth, sixth, seventh, eighth, ninth, and/or tenth embodiments.

In a thirteenth embodiment, provided is a compound of formula (I-0), (I-1), or (I-2) or a pharmaceutically acceptable salt or a stereoisomer thereof, wherein R is

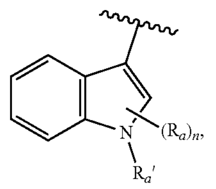 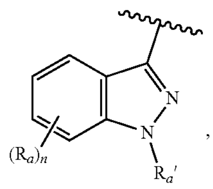 ,

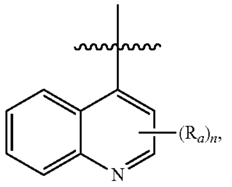 or 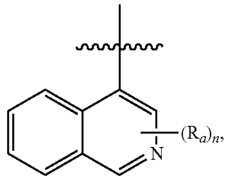

wherein the bond connects with the pyrimidine ring, and n is 0 to 2, and the remaining variables are as defined in the first, second, third, fourth, fifth, sixth, seventh, eighth, ninth, and/or tenth embodiments.

In a fourteenth embodiment, provided is a compound of formula (I-0), (I-1), or (I-2) or a pharmaceutically acceptable salt or a stereoisomer thereof, wherein each instance of $R_a$ is independently H, halogen, $C_{1-4}$ alkyl, $-(CHR_{aa})_kOH$, $-(CHR_{aa})_kCN$, $-(CHR_{aa})_kC(O)OR_{11}$, $-(CH_{aa})_kC(O)NR_{11}R_{12}$, $-(CHR_{aa})_kC(O)NR_{11}OR_{12}$, $-(CHR_{aa})_kS({=}O)_2R_{11}$, $-(CHR_{aa})_kC(O)NR_{11}S({=}O)_2R_{12}$, $-(CHR_{aa})_kS({=}O)_2NR_{11}R_{12}$, $-(CHR_{aa})_kNR_{11}S({=}O)_2R_{12}$, $-(CHR_{aa})_k$-5-6 membered heteroaryl, or $-(CHR_{aa})_kP({=}O)R_{11}R_{12}$;

$R_{aa}$ is independently H or $C_{1-3}$ alkyl optionally substituted with halogen;

$R_{11}$ and $R_{12}$ are independently H or $C_{1-4}$ alkyl; and k is 0 or 1, and the remaining variables are as defined in the first, second, third, fourth, fifth, sixth, seventh, eighth, ninth, tenth, eleventh, twelfth, and/or thirteenth embodiments.

In a fifteenth embodiment, provided is a compound of formula (I-0), (I-1), or (I-2) or a pharmaceutically acceptable salt or a stereoisomer thereof, wherein $R_1$ is H, F, Cl, CN, or $CF_3$, and the remaining variables are as defined in the first, second, third, fourth, fifth, sixth, seventh, eighth, ninth, tenth, eleventh, twelfth, thirteenth and/or fourteenth embodiments.

In a sixteenth embodiment, provided is a compound of formula (I-0), (I-1), or (I-2) or a pharmaceutically acceptable salt or a stereoisomer thereof, wherein R is

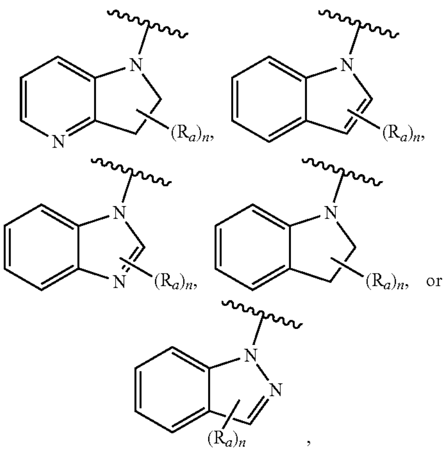

or , wherein the bond connects with the pyrimidine ring, and n is 0 to 4, and the remaining variables are as defined in the first, second, third, fourth, fifth, sixth, seventh, eighth, ninth, tenth, eleventh, twelfth, thirteenth, fourteenth, and/or fifteenth embodiments.

In a seventeenth embodiment, provided is a compound of formula (I-0), (I-1), or (I-2) or a pharmaceutically acceptable salt or a stereoisomer thereof, wherein R is

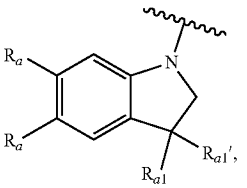

, wherein the bond connects with the pyrimidine ring, $R_{a1}$ is independently H, $C_{1-4}$ alkyl, or $C_{1-4}$hydroxyalkyl;

$R_{a1}$ is independently —$(CHR_{aa})_k$OH, —$(CHR_{aa})_k$CN, —$(CHR_{aa})_k$C(O)$OR_{11}$, —$(CHR_{aa})_k$S(=O)$_2R_{11}$, —$(CHR_{aa})_k$C(O)$NR_{11}R_{12}$, —$(CHR_{aa})_k$C(O)$NR_{11}OR_{12}$, —$(CHR_{aa})_k$C(O)$NR_{11}$S(=O)$_2R_{12}$, —$(CHR_{aa})_k$S(=O)$_2NR_{11}R_{12}$, —$(CHR_{aa})_kNR_{11}$S(=O)$_2R_{12}$, —$(CHR_{aa})_k$-5-6 membered heteroaryl, or —$(CHR_{aa})_k$P(=O)$R_{11}R_{12}$;

$R_{aa}$ is independently H or $C_{1-3}$ alkyl optionally substituted with halogen;

$R_a$ is independently H, F, or Cl;

$R_{11}$ and $R_{12}$ are independently H or $C_{1-4}$ alkyl;

k is 0 or 1, and the remaining variables are as defined in the first, second, third, fourth, fifth, sixth, seventh, eighth, ninth, and/or tenth embodiments.

In an eighteenth embodiment, provided is a compound of formula (I-0), (I-1), or (I-2) or a pharmaceutically acceptable salt or a stereoisomer thereof, wherein $R_{a1}$ is independently H, $CH_3$, or $CH_2OH$;

$R_{a1}'$ is independently —$(CHR_{aa})_k$OH, —$(CHR_{aa})_k$CN, —$(CHR_{aa})_k$C(O)$OR_{11}$, —$(CHR_{aa})_k$S(=O)$_2R_{11}$, —$(CHR_{aa})_k$C(O)$NR_{11}R_{12}$, —$(CHR_{aa})_k$C(O)$NR_{11}OR_{12}$, —$(CHR_{aa})_k$C(O)$NR_{11}$S(=O)$_2R_{12}$, —$(CHR_{aa})_k$S(=O)$_2NR_{11}R_{12}$, —$(CHR_{aa})_kNR_{11}$S(=O)$_2R_{12}$, —$(CHR_{aa})_k$-tetrazole, or —$(CHR_{aa})_k$P(=O)$R_{11}R_{12}$;

$R_{aa}$ is independently H, $CH_3$, or $CF_3$;

$R_{11}$ and $R_{12}$ are independently H or $C_{1-2}$ alkyl; and k is 0 or 1, and the remaining variables are as defined in the seventeenth embodiments.

In a nineteenth embodiment of the invention, provided is a compound of formula (I-0), (I-1), or (I-2) or a pharmaceutically acceptable salt or a stereoisomer thereof, wherein each instance of $R_a$ is independently H or F, and the remaining variables are as defined in the eighteenth embodiment.

In a twentieth embodiment of the invention, provided is a compound of formula (I-0), (I-1), or (I-2) or a pharmaceutically acceptable salt or a stereoisomer thereof, wherein $R_1$ is Cl, and the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, and/or nineteenth embodiments.

In a twenty-first embodiment, provided is a compound of formula (I-0), (I-1), or (I-2) or a pharmaceutically acceptable salt or a stereoisomer thereof, wherein R and R', together with the carbon atoms to which they are attached, form a ring represented below:

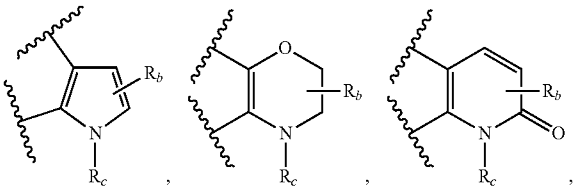

, , ,

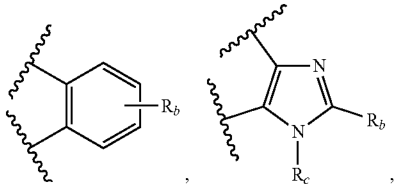

, , or

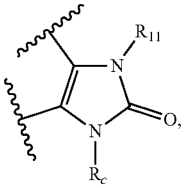

wherein the bonds connect with the pyrimidine ring, and the remaining variables are as defined in the first, second, and/or third embodiments.

In a twenty-second embodiment, provided is a compound of formula (I-0), (I-1), or (I-2) or a pharmaceutically acceptable salt or a stereoisomer thereof, wherein each instance of $R_b$ is independently H, halogen, OH, CN, $NH_2$, COOH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $NR_{11}R_{12}$, $C(O)NR_{11}R_{12}$, $C(O)C_{1-4}$ alkyl, $C(O)OC_{1-4}$ alkyl, $C(O)NR_{11}OR_{12}$, $S(=O)_2R_{11}$, $S(=O)_2NR_{11}R_{12}$, $NR_{11}(S=O)_2R_{12}$, $C(O)NR_{11}S(=O)_2R_{12}$, $P(=O)R_{11}R_{12}$, 5-6 membered heteroaryl, or $NR_{11}C(O)C_{1-4}$ alkyl; and each instance of $R_c$ is phenyl or pyridinyl, each of which is optionally substituted with one or two substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, and $P(=O)di\text{-}C_{1-6}$ alkyl, and the remaining variables are as defined in the first, second, third, and/or twenty-first embodiments.

In a twenty-third embodiment, provided is a compound of formula (I-0), (I-1), or (I-2) or a pharmaceutically acceptable salt or a stereoisomer thereof, wherein R and R', together with the carbon atoms to which they are attached, form a ring represented below:

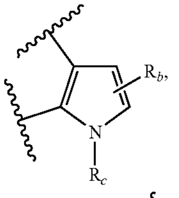

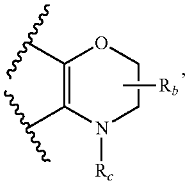

, or

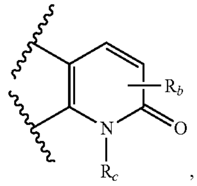

, wherein the  bonds connect with the pyrimidine ring, and the remaining variables are as defined in the first, second, third, twenty-first and/or twenty-second embodiments.

In a twenty-fourth embodiment, provided is a compound of formula (I-0), (I-1), or (I-2) or a pharmaceutically acceptable salt or a stereoisomer thereof, wherein each instance of $R_b$ is independently H, halogen, CN, COOH, $C_{1-2}$ alkyl, or $C_{1-2}$ haloalkyl;

each instance of $R_c$ is phenyl or pyridinyl, each of which is optionally substituted with one or two substituents independently selected from the group consisting of halogen, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, and $P(=O)di\text{-}C_{1-6}$ alkyl, and each instance of $R_{11}$ and $R_{12}$ is independently H or $C_{1-6}$ alkyl, and the remaining variables are as defined in the first, second, third, twenty-first, twenty-second, and/or twenty-third embodiments.

In a twenty-fifth embodiment, provided is a compound of formula (I-0), (I-1), or (I-2) or a pharmaceutically acceptable salt or a stereoisomer thereof, wherein each instance of $R_b$ is independently H, CN, or COOH; and each instance of $R_c$ is phenyl or pyridinyl, each of which is optionally substituted with one or two substituents independently selected from the group consisting of $C_{1-4}$ alkyl, $C(O)N(CH_3)_2$, and $P(=O)(CH_3)_2$, and the remaining variables are as defined in the first, second, third, twenty-first, twenty-second, twenty-third, and/or twenty-fourth embodiments.

In a twenty-sixth embodiment, provided is a compound of formula (I-0), (I-1), or (I-2) or a pharmaceutically acceptable salt or a stereoisomer thereof, wherein m is 0 or 1, and the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, and/or twenty-fifth embodiments.

In a twenty-seventh embodiment, provided is a compound of formula (I-0), (I-1), or (I-2) or a pharmaceutically acceptable salt or a stereoisomer thereof, wherein

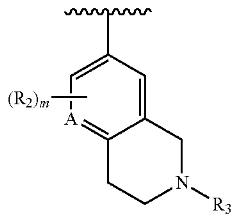

is

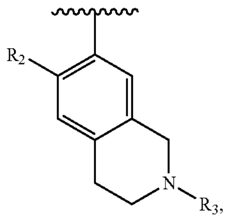

and the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, and/or twenty-sixth embodiments.

In a twenty-eighth embodiment, provided is a compound of formula (I-0), (I-1), or (I-2) or a pharmaceutically acceptable salt or a stereoisomer thereof, wherein each instance of $R_2$ is H, halogen, $C_{1-4}$ alkyl, $C_{1-4}$ haloalkyl, $C_{1-4}$ alkoxy, $C_{1-4}$ haloalkoxy; and $R_3$ is H, $C_{1-6}$ alkyl, $C_{1-6}$ hydroxyalkyl, or $COCH_2NR_{11}R_{12}$, and the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, and/or twenty-seventh embodiments.

In a twenty-ninth embodiment, provided is a compound of formula (I-0), (I-1), or (I-2) or a pharmaceutically acceptable salt or a stereoisomer thereof, wherein each instance of $R_2$ is H, F, Cl, or $OCH_3$; and $R_3$ is H or $C_{1-4}$ alkyl, and the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, and/or twenty-eighth embodiments.

In a thirtieth embodiment of the invention, provided is a compound represented by Formula (II) or a pharmaceutically acceptable salt or a stereoisomer thereof, (II)

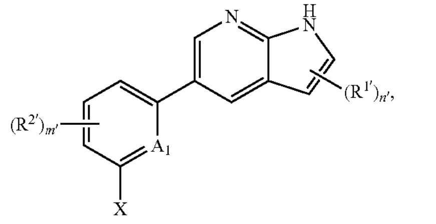

wherein $A_1$ is CR' or N;

X is —P(═O)$R_3R_4$;

R' is H, deuterium, halogen, CN, $NO_2$, $C_{1-6}$ alkyl, $C_{2-6}$ alkenyl, $C_{2-6}$ alkynyl, $C_{1-6}$ alkoxy, $NR_{11'}$, $R_{12'}$, C(O)$NR_{11'}$, $R_{12'}$, C(O)$C_{1-6}$ alkyl, C(O)O$C_{1-6}$ alkyl, $NR_{11'}$C(O)$C_{1-6}$ alkyl, wherein the alkyl, alkenyl, alkynyl, or alkoxy represented by R' or in the group represented by R' is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each instance of $R_1$ is independently H, deuterium, halogen, OH, CN, $NO_2$, $C_{1-6}$ alkyl, $C_{2-6}$ alkenyl, $C_{2-6}$ alkynyl, $C_{1-6}$ alkoxy, $NR_{11'}$, $R_{12'}$, C(O)$NR_{11'}R_{12'}$, C(O)$C_{1-6}$ alkyl, C(O)O$C_{1-6}$ alkyl, $NR_{11'}$C(O)$C_{1-6}$ alkyl, $C_{3-7}$ cycloalkyl, or 3-7 membered heterocyclyl, wherein the alkyl, alkenyl, alkynyl, alkoxy, cycloalkyl, or heterocyclyl represented by $R_1$ or in the group represented by $R_1$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each instance of $R_{2'}$ is independently H, deuterium, halogen, OH, CN, $NO_2$, $C_{1-6}$ alkyl, $C_{2-6}$ alkenyl, $C_{2-6}$ alkynyl, $C_{1-6}$ alkoxy, $NR_{11'}$, $R_{12'}$, C(O)$NR_{11'}R_{12'}$, C(O)$C_{1-6}$ alkyl, C(O)O$C_{1-6}$ alkyl, $NR_{11'}$C(O)$C_{1-6}$ alkyl, phenyl, 5-6 membered heteroaryl, $C_{3-7}$ cycloalkyl, or 3-7 membered heterocyclyl, wherein the alkyl, alkenyl, alkynyl, alkoxy, phenyl, heteroaryl, cycloalkyl, or heterocyclyl represented by $R_{2'}$ or in the group represented by $R_{2'}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each $R_{3'}$ and $R_{4'}$ is independently H, $C_{1-6}$ alkyl, $C_{2-6}$ alkenyl, $C_{2-6}$ alkynyl, wherein the alkyl, alkenyl, or alkynyl represented by $R_{3'}$ or $R_{4'}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each instance of $R_{11'}$ and $R_{12'}$ is independently H or $C_{1-6}$ alkyl, wherein the alkyl represented by $R_{11'}$ or $R_{12'}$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$haloalkoxy, $C_{3-6}$ cycloalkyl, and 3-7 membered heterocyclyl, or $R_{11'}$ and $R_{12'}$, together with the nitrogen atom to which they are attached, form 3-7 membered heterocyclyl optionally substituted with one to three substituents independently selected from the group consisting of halogen, OH, CN, $C_{1-4}$ alkyl, $C_{1-4}$ haloalkyl, $C_{1-4}$ alkoxy, or $C_{1-4}$ haloalkoxy;

m' is 0, 1, or 2; and n' is 0, 1, or 2.

In a thirty-first embodiment of the invention, the compound of Formula (II) is represented by structural formula (II-1):

(II-1)

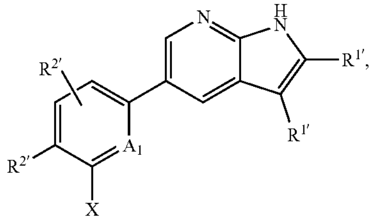

or a pharmaceutically acceptable salt or a stereoisomer thereof, wherein R' is H, halogen, $NR_{11'}$, $R_{12'}$, or $C_{1-6}$ alkyl optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}$, $R_{12'}$, and the remaining variables are as defined in the thirtieth embodiment.

In a thirty-second embodiment, the compound of formula (II) or (II-1), or a pharmaceutically acceptable salt or a stereoisomer thereof, wherein $R_{3'}$ and $R_{4'}$ are independently H or $C_{1-6}$ alkyl optionally substituted with one to three substituents independently selected from the group consisting of halogen, OH, CN, $C_{1-4}$ alkyl, $C_{1-4}$ haloalkyl, alkoxy, $C_{1-4}$ haloalkoxy, and $NR_{11'}$, $R_{12'}$, and the remaining variables are as defined in the thirtieth and/or thirty-first embodiment.

In a thirty-third embodiment, the compound of formula (II) or (II-1), or a pharmaceutically acceptable salt or a stereoisomer thereof, wherein each instance of $R_1$ is independently H, halogen, $C_{1-6}$ alkyl, $C_{2-6}$ alkenyl, $C_{2-6}$ alkynyl, $C_{3-7}$ cycloalkyl, or 3-7 membered heterocyclyl, wherein the alkyl, alkenyl, alkynyl, cycloalkyl, or heterocyclyl represented by $R_1$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each instance of $R_2$ is independently H, halogen, OH, $NO_2$, $C_{1-6}$ alkyl, $C_{1-6}$ alkoxy, $NR_{11'}R_{12'}$, C(O)$NR_{11'}R_{12'}$, C(O)$C_{1-6}$ alkyl, C(O)O$C_{1-6}$ alkyl, $NR_{11}$C(O)$C_{1-6}$ alkyl, 5-6 membered heteroaryl, or 3-7 membered heterocyclyl, wherein the alkyl, alkoxy, heteroaryl, or heterocyclyl represented by $R_2$ or in the group represented by $R_2$ is optionally substituted with one to three substituents independently selected from the group consisting of halogen, OH, CN, $C_{1-4}$ alkyl, $C_{1-4}$ haloalkyl, alkoxy, $C_{1-4}$ haloalkoxy, and $NR_{11'}R_{12'}$, and the remaining variables are as defined in the thirtieth, thirty-first, and/or thirty-second embodiments.

In a thirty-fourth embodiment, the compound of formula (II) or (II-1) is represented by structural formula (II-2) or (II-2'):

(II-2)

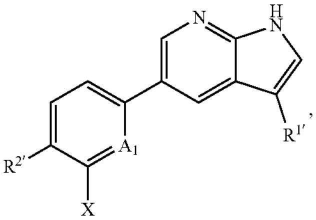

, or (II-2')

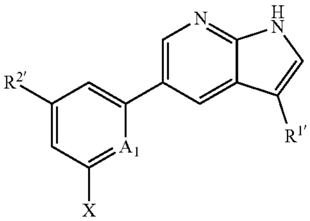

or a pharmaceutically acceptable salt or a stereoisomer thereof, wherein R' is H, halogen, or $NH_2$, and the remaining variables are as defined in the thirtieth, thirty-first, thirty-second, and/or thirty-third embodiments.

In a thirty-fifth embodiment, the compound of formula (II), (II-1), (II-2) or (II-2'), or a pharmaceutically acceptable salt or a stereoisomer thereof, wherein each instance of $R_{2'}$ is independently H, halogen, OH, $C_{1-4}$ alkyl optionally substituted with halogen or OH or $NR_{11'}R_{12'}$, $C_{1-4}$ alkoxy, $C(O)OC_{1-6}$ alkyl, $C(O)NR_{11'}R_{IT'}$, $NR_{11'}R_{12'}$, $NR_{11}C(O)C_{1-6}$ alkyl, 5-6 membered heterocyclyl, or 5-6 membered heteroaryl; and each instance of $R_1$ is independently H or $C_{1-4}$ alkyl, and the remaining variables are as defined in the thirtieth, thirty-first, thirty-second, thirty-third, and/or thirty-fourth embodiments.

In a thirty-sixth embodiment, the compound of formula (II), (II-1), (II-2) or (II-2'), or a pharmaceutically acceptable salt or a stereoisomer thereof, wherein $R_{3'}$ and $R_{4'}$ are independently $C_{1-6}$ alkyl; and each instance of $R_{2'}$ is independently H, halogen, OH, $C_{1-4}$ alkyl optionally substituted with halogen or OH or $NR_{11'}R_{12'}$, $C_{1-4}$ alkoxy, $C(O)OC_{1-4}$ alkyl, $C(O)NR_{11'}R_{IT'}$, $NR_{11'}R_{12'}$, $NHC(O)C_{1-6}$ alkyl, pyrrolidinyl, pyrrolidin-2-one, oxazole, wherein each instance of $R_{11'}$ and $R_{12'}$ is independently H or $C_{1-4}$ alkyl, and the remaining variables are as defined in the thirtieth, thirty-first, thirty-second, thirty-third, thirty-fourth, and/or thirty-fifth embodiments.

In a thirty-seventh embodiment, the compound of formula (II), (II-1), (II-2) or (II-2'), or a pharmaceutically acceptable salt or a stereoisomer thereof, wherein X is $—P(O)(CH_3)_2$ and each instance of $R_{2'}$ is independently H, F, Cl, OH, $CH_3$, $NH_2$, or $NHCOCH_3$, and the remaining variables are as defined in the thirtieth, thirty-first, thirty-second, thirty-third, thirty-fourth, thirty-fifth, and/or thirty-sixth embodiments.

1. A compound represented by structural formula (I):

(I)

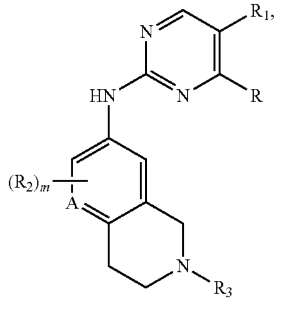

or a pharmaceutically acceptable salt thereof, wherein

A is $CR_2$ or N;

R is 8-10 membered bicyclic nitrogen containing heteroaryl or 8-10 membered bicyclic nitrogen containing heterocyclyl optionally substituted with oxo, wherein the nitrogen containing heteroaryl or nitrogen containing heterocyclyl represented by R has 1 to 3 heteroatoms selected from N, O, and S, and is optionally substituted with one to four $R_a$;

$R_1$ is H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, phenyl, 5-6 membered heteroaryl, $C_{3-6}$ cycloalkyl, or 3-7 membered heterocyclyl, wherein the alkyl, alkenyl, alkynyl, alkoxy, phenyl, heteroaryl, cycloalkyl, or heterocyclyl represented by $R_1$ or in the group represented by $R_1$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11}R_{12}$; or R and $R_1$, together with the carbon atoms to which they are attached, form a ring represented below:

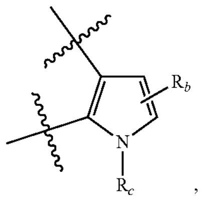

,

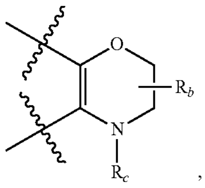

,

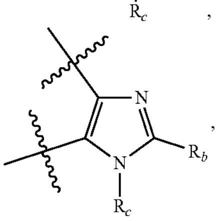

, or

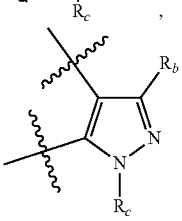

wherein the  bonds connect with the pyrimidine ring;

$R_2$ is H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, $—P(=O)R_{11}R_{12}$, $—S(=O)_2R_{11}$, or $—S(=O)_2NR_{11}R_{12}$, wherein the alkyl, alkenyl, alkynyl, or alkoxy represented by $R_2$ or in the group represented by $R_2$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11}R_{12}$;

$R_3$ is H, $C_{1-6}$ alkyl, $C(O)C_{1-6}$ alkyl, $C_{3-6}$ cycloalkyl, or 3-7 membered heterocyclyl, wherein the alkyl, cycloalkyl, or heterocyclyl represented by $R_3$ or in the group represented by $R_3$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, 3-7 membered heterocyclyl, and $NR_{11}R_{12}$;

each instance of $R_{11}$ and $R_{12}$ is independently H or $C_{1-6}$ alkyl, wherein the alkyl represented by $R_{11}$ or $R_{12}$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, and 3-7 membered heterocyclyl, or $R_{11}$ and $R_{12}$, together with the nitrogen atom or the phosphorus atom to which they are attached, form 3-7 membered heterocyclyl optionally substituted with one to three substituents independently selected from the group consisting of halogen, —OH, CN, $C_{1-4}$ alkyl, $C_{1-4}$ haloalkyl, $C_{1-4}$ alkoxy, or $C_{1-4}$ haloalkoxy;

each instance of $R_a$ is independently H, deuterium, halogen, OH, CN, $NH_2$, $NO_2$, COOH, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, $—P(=O)R_{11}R_{12}$, $—S(=O)_2R_{11}$, or $—S(=O)_2NR_{11}R_{12}$, $C_{3-6}$ cycloalkyl, or 3-7 membered heterocyclyl, wherein the alkyl, alkenyl, alkynyl, or alkoxy, cycloalkyl, or heterocyclyl represented by $R_a$ or in the group represented by $R_a$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11}R_{12}$; or two $R_a$, together with the carbon atom to which they are attached, form $C_{3-6}$ cycloalkyl or 3-7 membered heterocyclyl, wherein the cycloalkyl, or heterocyclyl is optionally substituted with one to three substituents independently selected from the group consisting of halogen, —OH, CN, $C_{1-4}$ alkyl, $C_{1-4}$ haloalkyl, $C_{1-4}$ alkoxy, and $C_{1-4}$ haloalkoxy;

each instance of $R_b$ is independently H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, or $NR_{11}C(O)C_{1-6}$ alkyl, wherein the alkyl, alkenyl, alkynyl, or alkoxy represented by $R_b$ or in the group represented by $R_b$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11}R_{12}$;

$R_c$ is phenyl, 5-6 membered monocyclic heterocyclyl having 1 to 3 heteroatoms selected from N and O; 5-6 membered monocyclic heteroaryl having 1 to 3 heteroatoms selected from N and O; wherein the phenyl, heterocyclyl, or heteroaryl represented by $R_c$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, $NR_{11}R_{12}$, $—C(O)NR_{11}R_{12}$, and $—P(O)di-C_{1-6}$ alkyl; and m is 0, 1, 2 or 3.

2. The compound of paragraph 1, or a pharmaceutically acceptable salt thereof, wherein R is

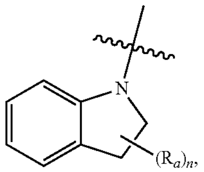
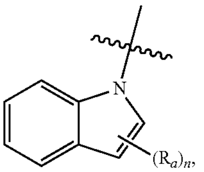
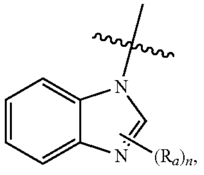
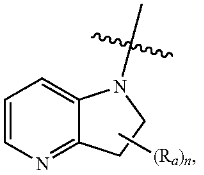
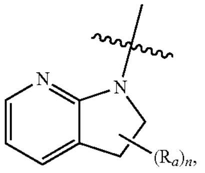
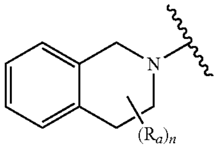
,
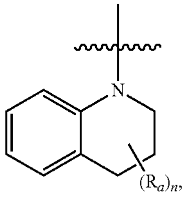
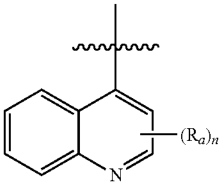
,
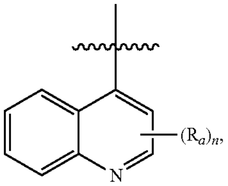
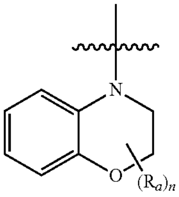
,
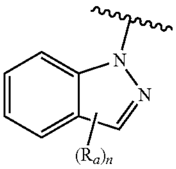
,
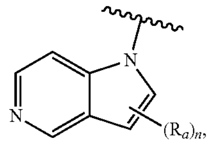
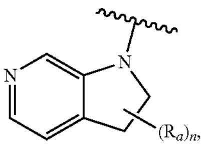
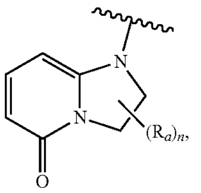
or -continued

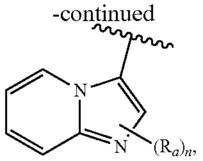

wherein the bond connects with the pyrimidine ring, and n is 0 to 4.

3. The compound of paragraph 1 or 2, or a pharmaceutically acceptable salt thereof, wherein each instance of $R_a$ is independently H, halogen, OH, $NH_2$, CN, COOH, $C_{1-4}$ alkyl, $C_{1-4}$haloalkyl, $C_{1-4}$ hydroxyalkyl, $C_{1-4}$ alkoxy, $C_{1-4}$ haloalkoxy, $C_{1-4}$ hydroxyalkoxy, $NR_{11}R_{12}$, $C(O)NR_{11}R_{12}$, $C(O)C_{1-4}$ alkyl, $C(O)OC_{1-4}$ alkyl, $NR_{11}C(O)C_{1-4}$ alkyl, —$P(=O)R_{11}R_{12}$, —$S(=O)_2R_{11}$, —$S(=O)_2NR_{11}R_{12}$, $C_{3-6}$ cycloalkyl, or 3-7 membered heterocyclyl, or two $R_a$, together with the carbon atom to which they are attached, form $C_{3-6}$ cycloalkyl or 3-7 membered heterocyclyl, wherein the cycloalkyl or heterocyclyl is optionally substituted with one to three substituents independently selected from the group consisting of halogen, —OH, CN, $C_{1-4}$ alkyl, $C_{1-4}$ haloalkyl, $C_{1-4}$ alkoxy, and $C_{1-4}$ haloalkoxy.

4. The compound of any one of paragraphs 1-3, or a pharmaceutically acceptable salt thereof, wherein $R_1$ is H, halogen, $C_{1-6}$ alkyl, $C_{1-6}$ alkoxy, $C_{2-6}$ alkenyl, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, wherein the alkyl, alkenyl, or alkoxy represented by $R_1$ or in the group represented by $R_1$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11}R_{12}$.

5. The compound of any one of paragraphs 1-4, or a pharmaceutically acceptable salt thereof, wherein each instance of $R_a$ is independently H, halo, OH, $C_{1-4}$ alkyl, COOH, $C(O)NR_{11}R_{12}$, or —$P(O)R_{11}R_{12}$, wherein each instance of $R_{11}$ and $R_{12}$ is independently H or $C_{1-6}$ alkyl.

6. The compound of any one of paragraphs 1-5, or a pharmaceutically acceptable salt thereof, wherein $R_1$ is H, halogen, $C_{1-4}$ alkyl, $C_{1-4}$ haloalkyl, $C_{2-4}$ alkenyl, $C_{1-4}$ alkoxy, or $C_{1-4}$ haloalkoxy.

7. The compound of any one of paragraphs 1-6, or a pharmaceutically acceptable salt thereof, wherein R is

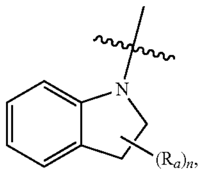
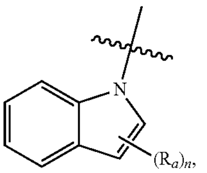
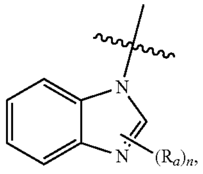
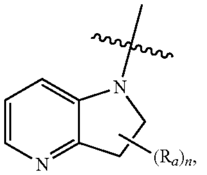

-continued

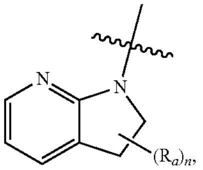
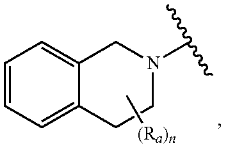
,
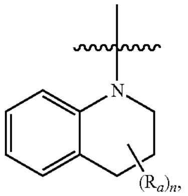
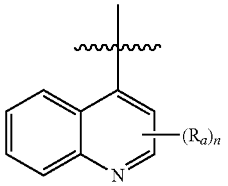
,
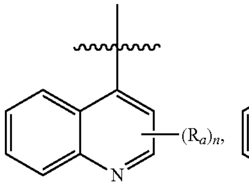
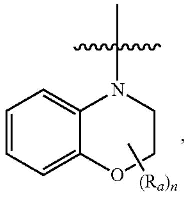
,
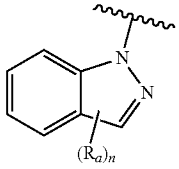
,
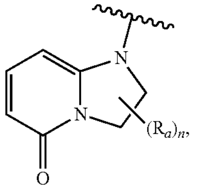
or
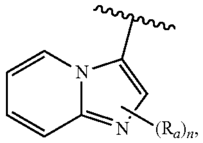

wherein the bond connects with the pyrimidine ring, and n is 0 to 2.

8. The compound of any one of paragraphs 1-7, or a pharmaceutically acceptable salt thereof, wherein R is

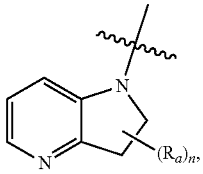
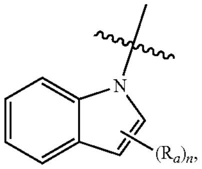
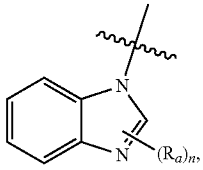
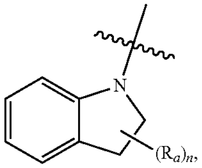
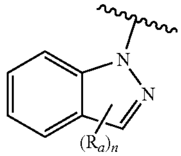
, or
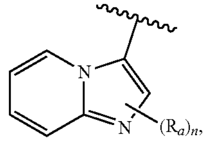

wherein the bond connects with the pyrimidine ring, and n is 0 to 2.

9. The compound of any one of paragraphs 1-8, or a pharmaceutically acceptable salt thereof, wherein each instance of $R_a$ is independently H, F, Cl, $C_{1-4}$ alkyl, COOH, $CONH_2$, $C(O)N(CH_3)_2$, or —$P(O)(CH_3)_2$.

10. The compound of any one of paragraphs 1-9, or a pharmaceutically acceptable salt thereof, wherein $R_1$ is H, Cl, or $CF_3$.

11. The compound of paragraph 1, or a pharmaceutically acceptable salt thereof, wherein R and $R^1$, together with the carbon atoms to which they are attached, form a ring represented below:

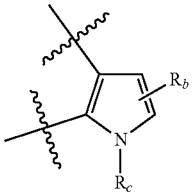
,
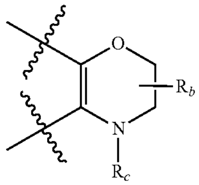
,
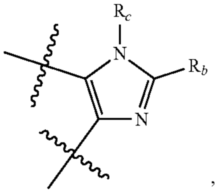
, or
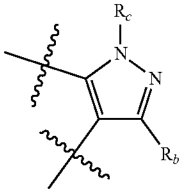

wherein the bonds connect with the pyrimidine ring.

12. The compound of paragraph 1 or 11, or a pharmaceutically acceptable salt thereof, wherein
each instance of $R_b$ is independently H, halogen, OH, $NH_2$, $C_{1-4}$ alkyl, $C_{1-4}$ haloalkyl, $C_{1-4}$ hydroxyalkyl, $C_{1-4}$ alkoxy, $C_{1-4}$haloalkoxy, $C_{1-4}$hydroxyalkoxy, $NR_{11}R_{12}$, $C(O)NR_{11}R_{12}$, $C(O)C_{1-4}$ alkyl, $C(O)OC_{1-4}$ alkyl, or $NR_{11}C(O)C_{1-4}$ alkyl; and
each instance of $R_c$ is phenyl or pyridinyl, each of which is optionally substituted with one or two substituents independently selected from the group consisting of halogen, —OH, CN, $C_{1-4}$ alkyl, $C_{1-4}$ haloalkyl, $C_{1-4}$ alkoxy, $C_{1-4}$haloalkoxy, $NR_{11}R_{12}$, —$C(O)NR_{11}R_{12}$, and —P(O)di-$C_{1-6}$ alkyl.

13. The compound of any one of paragraphs 1, 11, and 12, or a pharmaceutically acceptable salt thereof, wherein
each instance of $R_b$ is independently H, halogen, $C_{1-2}$ alkyl, $C_{1-2}$ haloalkyl; and
each instance of $R_c$ is phenyl or pyridinyl, each of which is optionally substituted with one or two substituents independently selected from the group consisting of halogen, $C_{1-4}$ alkyl, $C_{1-4}$ haloalkyl, $C_{1-4}$ alkoxy, $C_{1-4}$haloalkoxy, $NR_{11}R_{12}$, —$C(O)NR_{11}R_{12}$, and —P(O)di-$C_{1-6}$ alkyl, and
each instance of $R_{11}$ and $R_{12}$ is independently H or $C_{1-6}$ alkyl.

14. The compound of any one of paragraphs 1 and 11-13, or a pharmaceutically acceptable salt thereof, wherein
each instance of $R_b$ is independently H; and
each instance of $R_c$ is phenyl or pyridinyl, each of which is optionally substituted with one or two substituents independently selected from the group consisting of $C_{1-4}$ alkyl, —$C(O)N(CH_3)_2$, and —$P(O)(CH_3)_2$.

15. The compound of any one of paragraphs 1-14, or a pharmaceutically acceptable salt thereof, wherein $R_2$ is H, halogen, OH, CN, $NH_2$, $NO_2$, $C_{1-4}$ alkyl, $C_{1-4}$alkoxy, $NR_{11}R_{12}$, —$C(O)NR_{11}R_{12}$, $C(O)C_{1-4}$ alkyl, $C(O)OC_{1-4}$ alkyl, $NR_{11}C(O)C_{1-4}$ alkyl, —$P(=O)R_{11}R_{12}$, —$S(=O)_2R_{11}$, or —$S(=O)_2NR_{11}R_{12}$, wherein the alkyl or alkoxy represented by $R_2$ or in the group represented by $R_2$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$haloalkoxy, and $NR_{11}R_{12}$; and m is 0 or 1.

16. The compound of any one of paragraphs 1-15, or a pharmaceutically acceptable salt thereof, wherein

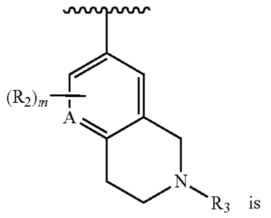
is
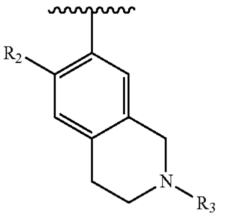
or
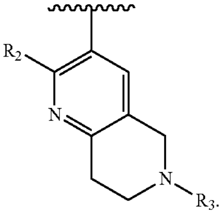

17. The compound of any one of paragraphs 1-16, or a pharmaceutically acceptable salt thereof, wherein each instance of $R_2$ is H, halogen, $C_{1-4}$ alkyl, $C_{1-4}$ haloalkyl, $C_{1-4}$ alkoxy, $C_{1-4}$haloalkoxy; and $R_3$ is H, $C_{1-6}$ alkyl, $C_{1-6}$hydroxyalkyl, or $COCH_2NR_{11}R_{12}$, wherein each instance of $R_{11}$ and $R_{12}$ is independently H or $C_{1-6}$ alkyl.

18. The compound of any one of paragraphs 1-17, or a pharmaceutically acceptable salt thereof, wherein each instance of $R_2$ is H, Cl, or $OCH_3$; and $R_3$ is H, $C_{1-4}$ alkyl, $C_{1-4}$hydroxyalkyl, or $COCH_2N(CH_3)_2$.

19. A compound represented by structural formula (II):

(II)

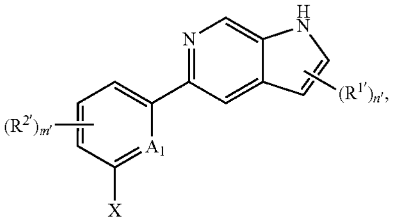

or a pharmaceutically acceptable salt thereof, wherein
$A_1$ is CR' or N;
X is —$P(=O)R_{3'}R_{4'}$ or —$S(O)_2NR_{5'}R_{6'}$;
R' is H, deuterium, halogen, CN, $NO_2$, $C_{1-6}$ alkyl, $C_{2-6}$ alkenyl, $C_{2-6}$ alkynyl, $C_{1-6}$ alkoxy, $C(O)NR_{11'}$, $R_{12'}$, $C(O)C_{1-6}$ alkyl, $C(O)OC_{1-6}$ alkyl, $NR_{11}C(O)C_{1-6}$ alkyl, wherein the alkyl, alkenyl, alkynyl, or alkoxy represented by R' or in the group represented by R' is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11'}R_{12'}$;
each instance of $R_{1'}$ is independently H, deuterium, halogen, OH, CN, $NO_2$, $C_{1-6}$ alkyl, $C_{2-6}$ alkenyl, $C_{2-6}$ alkynyl, $C_{1-6}$ alkoxy, $NR_{11'}R_{12'}$, $C(O)NR_{11'}$, $R_{12'}$, $C(O)C_{1-6}$ alkyl, $C(O)OC_{1-6}$ alkyl, $NR_{11'}C(O)C_{1-6}$ alkyl, $C_{3-7}$ cycloalkyl, or 3-7 membered heterocyclyl, wherein the alkyl, alkenyl, alkynyl, alkoxy, cycloalkyl, or heterocyclyl represented by $R_1$, or in the group represented by $R_1$, is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each instance of $R_2$ is independently H, deuterium, halogen, OH, CN, $NO_2$, $C_{1-6}$ alkyl, $C_{2-6}$ alkenyl, $C_{2-6}$ alkynyl, $C_{1-6}$ alkoxy, $NR_{11'}R_{12'}$, $C(O)NR_{11'}R_{12'}$, $C(O)C_{1-6}$ alkyl, $C(O)OC_{1-6}$ alkyl, $NR_{11'}C(O)C_{1-6}$ alkyl, phenyl, 5-6 membered heteroaryl, $C_{3-7}$ cycloalkyl, or 3-7 membered heterocyclyl, wherein the alkyl, alkenyl, alkynyl, alkoxy, phenyl, heteroaryl, cycloalkyl, or heterocyclyl represented by $R_2$ or in the group represented by $R_2$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each $R_{3'}$ and $R_{4'}$ is independently H, $C_{1-6}$ alkyl, $C_{2-6}$ alkenyl, $C_{2-6}$ alkynyl, wherein the alkyl, alkenyl, or alkynyl represented by $R_{3'}$ or $R_{4'}$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11'}R_{12'}$;

each $R_{5'}$ and $R_{6'}$ is independently H, $C_{1-6}$ alkyl, $C_{2-6}$ alkenyl, $C_{2-6}$ alkynyl, wherein the alkyl, alkenyl, or alkynyl represented by $R_{5'}$ or $R_{6'}$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11}R_{12}$; or $R_{5'}$ and $R_{6'}$, together with the nitrogen atom to which they are attached, form 3-7 membered heterocyclyl optionally substituted with one to three substituents independently selected from the group consisting of halogen, —OH, CN, $C_{1-4}$ alkyl, $C_{1-4}$ haloalkyl, $C_{1-4}$ alkoxy, or $C_{1-4}$ haloalkoxy;

each instance of $R_{11}$ and $R_{12}$ is independently H or $C_{1-6}$ alkyl, wherein the alkyl represented by $R_{11'}$ or $R_{12'}$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, $C_{3-6}$ cycloalkyl, and 3-7 membered heterocyclyl, or $R_{11'}$ and $R_{12'}$, together with the nitrogen atom to which they are attached, form 3-7 membered heterocyclyl optionally substituted with one to three substituents independently selected from the group consisting of halogen, —OH, CN, $C_{1-4}$ alkyl, $C_{1-4}$ haloalkyl, $C_{1-4}$ alkoxy, or $C_{1-4}$ haloalkoxy;

m' is 0, 1, or 2; and n' is 0, 1, or 2.

20. The compound of paragraph 19, wherein the compound is represented by structural formula (II-1):

(II-1)

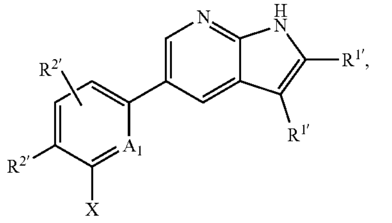

or a pharmaceutically acceptable salt thereof, wherein $A_1$ is CR' or N; and

R' is H, halogen, $NR_{11'}R_{12'}$, or $C_{1-6}$ alkyl optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11'}R_{12'}$.

21. The compound of paragraph 19 or 20, or a pharmaceutically acceptable salt thereof, wherein X is —P(=O)$R_3R_4$ or —$S(O)_2NR_5R_6$;

each $R_{3'}$ and $R_{4'}$ are independently H or $C_{1-6}$ alkyl optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11}R_{12}$; and each $R_{5'}$ and $R_{6'}$ are independently H or $C_{1-6}$alkyl, or $R_{5'}$ and $R_{6'}$, together with the nitrogen atom to which they are attached, form 3-7 membered heterocyclyl optionally substituted with one to three substituents independently selected from the group consisting of halogen, —OH, CN, $C_{1-4}$ alkyl, $C_{1-4}$ haloalkyl, $C_{1-4}$ alkoxy, or $C_{1-4}$ haloalkoxy.

22. The compound of any one of paragraphs 19-21, or a pharmaceutically acceptable salt thereof, wherein each instance of $R_1$ is independently H, halogen, $C_{1-6}$ alkyl, $C_{2-6}$ alkenyl, $C_{2-6}$ alkynyl, $C_{3-7}$ cycloalkyl, or 3-7 membered heterocyclyl, wherein the alkyl, alkenyl, alkynyl, cycloalkyl, or heterocyclyl represented by $R_1$ is optionally substituted with one to three substituents independently selected from the group consisting of halogen, —OH, CN, $C_{1-4}$ alkyl, $C_{1-4}$ haloalkyl, $C_{1-4}$ alkoxy, $C_{1-4}$ haloalkoxy, and $NR_{11'}R_{12'}$.

23. The compound of any one of paragraphs 19-22, or a pharmaceutically acceptable salt thereof, wherein each instance of $R_{2'}$ is independently H, halogen, OH, $NH_2$, $C_{1-6}$ alkyl, $C_{1-6}$ alkoxy, $NR_{11'}R_{12'}$, $C(O)NR_{11'}R_{12'}$, $C(O)C_{1-6}$ alkyl, $C(O)OC_{1-6}$ alkyl, $NR_{11}C(O)C_{1-6}$ alkyl, 5-6 membered heteroaryl, or 3-7 membered heterocyclyl, wherein the alkyl, alkoxy, heteroaryl, or heterocyclyl represented by $R_{2'}$ or in the group represented by $R_{2'}$ is optionally substituted with one to three substituents independently selected from the group consisting of halogen, —OH, CN, $C_{1-4}$ alkyl, $C_{1-4}$ haloalkyl, $C_{1-4}$alkoxy, $C_{1-4}$haloalkoxy, and $NR_{11'}R_{12'}$.

24. The compound of any one of paragraphs 19-23, wherein the compound is represented by structural formula (II-2) or (II-2'):

(II-2)

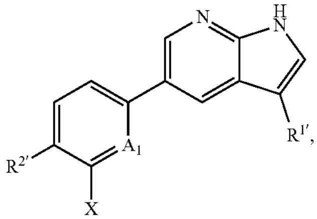

or (II-2')

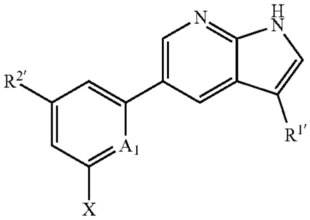

or a pharmaceutically acceptable salt thereof, wherein $A_t$ is CR' or N; and R' is H, halogen, or $NH_2$.

25. The compound of any one of paragraphs 19-24, or a pharmaceutically acceptable salt thereof, wherein each instance of $R_{2'}$ is independently H, halogen, OH, $C_{1-4}$ alkyl optionally substituted with halogen or OH or $NR_{11'}R_{12'}$, $C_{1-4}$ alkoxy, $C(O)OC_{1-6}$ alkyl, $C(O)NR_{11'}R_{12'}$, $NR_{11'}R_{12'}$, $NR_{11'}C(O)C_{1-6}$ alkyl, 5-6 membered heterocyclyl (pyrrolidinyl or pyrrolidin-2-one), or heteroaryl (oxazole).
26. The compound of any one of paragraphs 19-25, or a pharmaceutically acceptable salt thereof, wherein
X is $—P(=O)R_{3'}R_{4'}$ or $—S(O)_2NR_{5'}R_{6'}$;
$R_{3'}$ and $R_{4'}$ are independently $C_{1-6}$ alkyl; and
$R_{5'}$ and $R_{6'}$ are independently H or $C_{1-6}$ alkyl.
27. The compound of any one of paragraphs 19-26, or a pharmaceutically acceptable salt thereof, wherein each instance of $R_1$, is independently H or $C_{1-4}$ alkyl.
28. The compound of any one of paragraphs 19-27, or a pharmaceutically acceptable salt thereof, wherein each instance of $R_{2'}$ is independently H, halogen, OH, $C_{1-4}$ alkyl optionally substituted with halogen or OH or $NR_{11'}R_{12'}$, $C_{1-4}$ alkoxy, $C(O)OC_{1-4}$ alkyl, $C(O)NR_{11'}R_{12'}$, $NR_{11'}R_{12'}$, $NHC(O)C_{1-6}$ alkyl, pyrrolidinyl, pyrrolidin-2-one, oxazole, wherein each instance of $R_{11'}$ and $R_{12'}$ is independently H or $C_{1-4}$ alkyl.
29. The compound of any one of paragraphs 19-28, or a pharmaceutically acceptable salt thereof, wherein X is $—P(O)(CH_3)_2$ or $—S(O)_2NHMe$.
30. The compound of any one of paragraphs 19-29, or a pharmaceutically acceptable salt thereof, wherein each instance of $R_{2'}$ is independently H, F, Cl, OH, $CH_3$, $NH_2$, or $—NHCOCH_3$.
31. The compound of any one of paragraphs 19-30, or a pharmaceutically acceptable salt thereof, wherein X is $—P(=O)(CH_3)_2$.

In one embodiment, the compound or a pharmaceutically acceptable salt or a stereoisomer thereof is selected from the compounds of formula (I-0), (I-1), (I-2), (I), (II), (II-1), (II-2) or (II-2'), or in the Examples.

In certain embodiments, the HPK1 inhibitors (the compounds of the invention) are selective against one or more kinases selected from: Lck, ZAP70, JAK3, PKC theta, TBK1, and MAP4K3. In certain embodiments, the HPK1 inhibitors of the invention is selective against one or more kinases selected from: Lck, ZAP70, and JAK3. In certain embodiments, the HPK1 inhibitors of the invention is selective against JAK3.

For example, the subject HPK1 inhibitors are selective against Lck such that the IC50 against Lck is at least 2-, 3-, 5-, 10-, 20-, 40-, 50-, 75-, 100-, 150-, 200-, 300-, 400-, 500-, 600-, 750-, or 1000-fold higher than the IC50 against HPK1.

In certain embodiments, the HPK1 inhibitor are selective against ZAP70 such that the IC50 against ZAP70 is at least 2-, 3-, 5-, 10-, 20-, 40-, 50-, 75-, 100-, 150-, 200-, 300-, 400-, 500-, 600-, 750-, or 1000-fold higher than the IC50 against HPK1.

In certain embodiments, the HPK1 inhibitor are selective against JAK3 such that the IC50 against JAK3 is at least 2-, 3-, 5-, 10-, 20-, 40-, 50-, 75-, 100-, 150-, 200-, 300-, 400-, 500-, 600-, 750-, or 1000-fold higher than the IC50 against HPK1.

In certain embodiments, the HPK1 inhibitor are selective against PKC theta such that the IC50 against PKC theta is at least 2-, 3-, 5-, 10-, 20-, 40-, 50-, 75-, 100-, 150-, 200-, 300-, 400-, 500-, 600-, 750-, or 1000-fold higher than the IC50 against HPK1.

In certain embodiments, the HPK1 inhibitor are selective against TBK1 such that the IC50 against TBK1 is at least 2-, 3-, 5-, 10-, 20-, 40-, 50-, 75-, 100-, 150-, 200-, 300-, 400-, 500-, 600-, 750-, or 1000-fold higher than the IC50 against HPK1.

In certain embodiments, the HPK1 inhibitor are selective against MAP4K3 such that the IC50 against MAP4K3 is at least 2-, 3-, 5-, 10-, 20-, 40-, 50-, 75-, 100-, 150-, 200-, 300-, 400-, 500-, 600-, 750-, or 1000-fold higher than the IC50 against HPK1.

Activity against HPK1, Lck, ZAP70, PKC theta, JAK3, TBK1, and MAP4K3 can be measured (e.g., as measured by IC50 values) using any art recognized methods, such as exemplary protocols described in the biology examples, such as Biology Examples 1-7 (all incorporated herein by reference).

4. Treatable Diseases

The HPK1 inhibitors, pharmaceutically acceptable salts thereof, pharmaceutical compositions thereof, may be used in methods of modulating (i.e., inhibiting) HPK1 activity, said method comprising administering to a patient/subject in need thereof an HPK1 inhibitor compound of the invention, or a pharmaceutically acceptable salt thereof, as described herein.

In particular, the present invention provides the use of the compounds of the invention, or stereoisomers, tautomers, N-oxides, hydrates, solvates, and salts thereof, particularly pharmaceutically acceptable salts thereof, or mixtures of same, for use in the treatment or prophylaxis of diseases, in particular cancer (particularly hematopoietic and solid tumors) or conditions with dysregulated immune responses or other disorders associated with aberrant MAP4K1 signaling. The pharmaceutical activity of the compounds according to the invention can at least be partially explained by their activity as MAP4K1 inhibitors.

In certain embodiments, the compounds of the invention, or pharmaceutically acceptable salts thereof, are useful for therapeutic administration to a subject in need thereof to treat a disease or indication including, but not limited to, benign hyperplasia, atherosclerotic disorder, sepsis, autoimmune disorder, vascular disorder, viral infection, neurodegenerative disorder, in inflammatory disorder, and male fertility control disorder.

In certain embodiments, the compounds of the invention, or pharmaceutically acceptable salts thereof, are useful for therapeutic administration to enhance, stimulate and/or increase immunity in treating cancer.

The HPK1 inhibitor compounds of the invention can be used alone, or in combination with other agents or therapies, or as an adjuvant or neoadjuvant for the treatment of diseases or disorders, including cancers.

In certain embodiments, the methods of the invention can be used to treat cancers that include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of the above cancers.

In some embodiments, cancers treatable with compounds of the invention include melanoma (e.g., metastatic malignant melanoma), renal cancer (e.g., clear cell carcinoma), prostate cancer (e.g., hormone refractory prostate adenocarcinoma), breast cancer, triple-negative breast cancer, colon cancer and lung cancer (e.g., non-small cell lung cancer and small cell lung cancer). Additionally, refractory or recurrent malignancies whose growth may be inhibited using the compounds of the invention are also treatable.

In some embodiments, cancers that are treatable using the compounds of the invention include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, respiratory tract, brain cancer, eye cancer, thyroid and parathyroid cancer, skin cancer, cancers of the head and neck, cancer of the reproductive organs, cancer of the digestive tract, cancer of the urinary tract, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma), sarcoma, and distant metastasis thereof.

In some embodiments, diseases and indications that are treatable using the compounds of the invention include, but are not limited to, hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias, such as acute lymphoblastic leukemia (ALL), acute myelogenous leukemia (AML), acute promyelocyte leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma, and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the invention include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, and thyroid and parathyroid cancers.

In some embodiments, the subject HPK1 inhibitors may be used to treat tumors producing PGE2 (e.g., Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocyte leukemia) as well as in patient's blast cells. CD73 is up-regulated in various human carcinomas, including those of colon, lung, pancreas and ovary. Higher expression levels of CD73 have been associated with tumor neovascularization, invasiveness, and metastasis, and with shorter patient survival time in breast cancer.

Examples of treatable breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of treatable brain cancers include, but are not limited to, brain stem and hypophtalmic glioma, cerebellar and cerebral astrocytoma, glioblastoma, medulloblastoma, ependymoma, as well as neuroectodermal and pineal tumor.

Treatable tumors of the male reproductive organs include, but are not limited to, prostate and testicular cancer.

Treatable tumors of the female reproductive organs include, but are not limited to, endometrial, cervical, ovarian, vaginal, and vulvar cancer, as well as sarcoma of the uterus.

Treatable ovarian cancer include, but are not limited to serous tumor, endometrioid tumor, mucinous cystadenocarcinoma, granulosa cell tumor, Sertoli-Leydig cell tumor and arrhenoblastoma.

Treatable cervical cancer include, but are not limited to squamous cell carcinoma, adenocarcinoma, adenosquamous carcinoma, small cell carcinoma, neuroendocrine tumor, glassy cell carcinoma and villoglandular adenocarcinoma.

Treatable tumors of the digestive tract include, but are not limited to, anal, colon, colorectal, esophageal, gallbladder, gastric, pancreatic, rectal, small-intestine, and salivary gland cancers.

Treatable esophageal cancer include, but are not limited to esophageal cell carcinomas and adenocarcinomas, as well as squamous cell carcinomas, leiomyosarcoma, malignant melanoma, rhabdomyosarcoma and lymphoma.

Treatable gastric cancer include, but are not limited to intestinal type and diffuse type gastric adenocarcinoma.

Treatable pancreatic cancer include, but are not limited to ductal adenocarcinoma, adenosquamous carcinomas and pancreatic endocrine tumors.

Treatable tumors of the urinary tract include, but are not limited to, bladder, penile, kidney, renal pelvis, ureter, urethral and human papillary renal cancers.

Treatable kidney cancer include, but are not limited to renal cell carcinoma, urothelial cell carcinoma, juxtaglomerular cell tumor (reninoma), angiomyolipoma, renal oncocytoma, Bellini duct carcinoma, clear-cell sarcoma of the kidney, mesoblastic nephroma and Wilms' tumor.

Treatable bladder cancer include, but are not limited to transitional cell carcinoma, squamous cell carcinoma, adenocarcinoma, sarcoma and small cell carcinoma.

Treatable eye cancers include, but are not limited to, intraocular melanoma and retinoblastoma.

Treatable liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Treatable skin cancers include, but are not limited to, squamous cell carcinoma, Kaposi's sarcoma, malignant melanoma, Merkel cell skin cancer, and non-melanoma skin cancer.

Treatable head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Treatable lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Treatable sarcomas include, but are not limited to, sarcoma of the soft tissue, osteosarcoma, malignant fibrous histiocytoma, lymphosarcoma, and rhabdomyosarcoma.

Treatable leukemias include, but are not limited to, acute myeloid leukemia, acute lymphoblastic leukemia, chronic lymphocytic leukemia, chronic myelogenous leukemia, and hairy cell leukemia.

In certain embodiments, the compounds of the invention can be used to treat a variety of other disorders in which MAP4K1 is involved, such as cardiovascular and lung diseases.

In certain embodiments, the compounds of the invention can be used in medicaments for the treatment and/or prophylaxis of cardiovascular, inflammatory and fibrotic disorders, renal disorders, in particular of acute and chronic renal insufficiency, and also of acute and chronic renal failure.

Here, the term "renal insufficiency" comprises both acute and chronic manifestations of renal insufficiency, and also underlying or related renal disorders such as diabetic and non-diabetic nephropathies, hypertensive nephropathies, ischaemic renal disorders, renal hypoperfusion, intradialytic hypotension, obstructive uropathy, renal stenoses, glomerulopathies, glomerulonephritis (such as, for example, primary glomerulonephritides; minimal change glomerulonephritis (lipoidnephrosis); membranous glomerulonephritis; focal segmental glomerulosclerosis (FSGS); membrane-proliferative glomerulonephritis; crescentic glomerulonephritis;

mesangioproliferative glomerulonephritis (IgA nephritis, Berger's disease); post-infectious glomerulonephritis; secondary glomerulonephritides), diabetes mellitus, lupus erythematosus, amyloidosis, Goodpasture syndrome, Wegener granulomatosis, Henoch-Schonlein purpura, microscopic polyangiitis, acute glomerulonephritis, pyelonephritis (for example as a result of: urolithiasis, benign prostate hyperplasia, diabetes, malformations, abuse of analgesics, Crohn's disease), glomerulosclerosis, arteriolonecrose of the kidney, tubulointerstitial diseases, nephropathic disorders such as primary and congenital or acquired renal disorder, Alport syndrome, nephritis, immunological kidney disorders such as kidney transplant rejection and immunocomplex-induced renal disorders, nephropathy induced by toxic substances, nephropathy induced by contrast agents, diabetic and non-diabetic nephropathy, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or the need for dialysis.

In certain embodiments, the compounds of the invention can be used for the treatment and/or prophylaxis of sequelae of renal insufficiency, for example pulmonary oedema, heart failure, uremia, anemia, electrolyte disturbances (for example hypercalemia, hyponatremia) and disturbances in bone and carbohydrate metabolism.

In certain embodiments, the compounds of the invention can be used for the treatment and/or prevention of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

In certain embodiments, the compounds of the invention are further suitable for the treatment and/or prevention of polycystic kidney disease (PCKD) and of the syndrome of inappropriate ADH secretion (SIADH).

In certain embodiments, the compounds of the invention are also suitable for the treatment and/or prophylaxis of metabolic syndrome, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees 1-111 (AB block 1-111), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In certain embodiments, the compounds of the invention are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

In certain embodiments, the compounds of the invention are also effective for the control of central nervous system disorders characterized by disturbances of the NO/cGMP system. They are suitable in particular for improving perception, concentration, learning or memory after cognitive impairments like those occurring in particular in association with situations/diseases/syndromes, such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoffs psychosis.

In certain embodiments, the compounds of the invention are also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

In certain embodiments, the compounds of the invention are furthermore also suitable for controlling cerebral blood flow and thus represent effective agents for controlling migraines.

In certain embodiments, the compounds of the invention are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

In certain embodiments, the compounds of the invention have anti-inflammatory action and can therefore be used as anti-inflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

In certain embodiments, the compounds of the invention can also be used for treatment and/or prophylaxis of autoimmune diseases.

In certain embodiments, the compounds of the invention are also suitable for treatment and/or prophylaxis of fibrotic disorders of the internal organs, for example the lung, the heart, the kidney, the bone marrow and in particular the liver, and also dermatological fibroses and fibrotic eye disorders.

As used herein, the term "fibrotic disorders" includes in particular the following: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

In certain embodiments, the compounds of the invention are also suitable for controlling postoperative scarring, for example as a result of glaucoma operations.

In certain embodiments, the compounds of the invention can also be used cosmetically for ageing and keratinized skin.

In certain embodiments, the compounds of the invention are suitable for treatment and/or prophylaxis of hepatitis, neoplasms, osteoporosis, glaucoma and gastroparesis.

In certain embodiments, the compounds of the invention are suitable for treatment and/or prophylaxis of viral infections (e.g., HIV and Kaposi's sarcoma); inflammatory and autoimmune diseases (e.g., colitis, arthritis, Alzheimer's disease, glomerulonephritis and wound healing); bacterial, fungal and/or parasitic infections; skin diseases (e.g., psoriasis); diseases based on hyperplasia which are characterised by an increase in the number of cells (e.g., fibroblasts, hepatocytes, bones and bone marrow cells, cartilage or smooth muscle cells or epithelial cells (e.g., endometrial hyperplasia)); bone diseases and cardiovascular diseases (e.g., restenosis and hypertrophy).

In another embodiment, the inventive compounds can also be used to treat or to prevent uterine fibroids (uterine leiomyoma or uterine myoma) in women. Uterine fibroids are benign tumors of the myometrium, the smooth muscle layer of the uterus. Uterine fibroids grow slowly during a women's life, and their growth is dependent on the female sexual hormones estradiol and progesterone. Therefore, the highest prevalence of uterine fibroids with approx. 70% and >80% in white and afro-american women, respectively, is found from 35 years of age onwards to menopause, when they shrink due to reduced hormone levels. Approx. 30% and 45% of white and afro-american women, respectively, do show clinically relevant symptoms due to their fibroids, which are heavy menstrual bleeding and pain, which is related to the menstrual cycle (David et al., *Eur J Obstet Gynecol Reprod Biol.* 199:137-140, 2016). Heavy menstrual bleeding in this respect is defined by a blood loss of more than 80 mL in a menstrual bleeding period. Submucosal position of the uterine fibroids, e.g., those located directly below the endometrium, seems to have an even more severe effect on uterine bleeding, which may result in anemia in affected women. Furthermore, uterine fibroids, due to their symptoms, do severely affect the quality of life of affected women.

In certain embodiments, the compounds of the invention are useful for the treatment and/or prophylaxis of chronic renal disorders, acute and chronic renal insufficiency, diabetic, inflammatory or hypertensive nephropathies, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

The present invention provides a method for the treatment and/or prophylaxis of chronic renal disorders, acute and chronic renal insufficiency, diabetic, inflammatory or hypertensive nephropathies, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

The present invention further provides the use of the compounds according to the invention for treatment and/or prophylaxis of disorders, especially the disorders mentioned above.

The present invention further provides a method for treatment and/or prophylaxis of disorders, in particular the disorders mentioned above, using an effective amount of at least one of the compounds according to the invention.

Thus, compounds of the present invention can be utilized to inhibit, block, reduce or decrease MAP4K1 activation by exogenous and/or endogenous ligands for the reduction of tumor growth and the modulation of dysregulated immune responses, e.g., to block immunosuppression and increase immune cell activation and infiltration in the context of cancer and cancer immunotherapy. This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

The present invention also provides methods of treating a variety of other disorders wherein MAP4K1 is involved such as, but not limited to, disorders with dysregulated immune responses, inflammation, vaccination for infection & cancer, viral infections, obesity and diet-induced obesity, adiposity, metabolic disorders, hepatic steatosis and uterine fibroids. These disorders have been well characterized in humans, but also exist with a similar etiology in other mammals, and can be treated by administering pharmaceutical compositions of the present invention.

5. Combination Therapy

The compounds of the invention may be used in combination therapy with one or more additional/secondary therapeutic agents suitable for treating a disease or indication treatable by the subject compounds.

Thus in certain embodiments, for example, methods of the invention using compounds of the invention may comprise administering to the subject in need thereof a further therapeutic agent. The further therapeutic agent may be: (i) an immunomodulatory agent which blocks or inhibits an immune system checkpoint, which checkpoint may or may not be a component of the NF-κB pathway; and/or (ii) an agent which directly stimulates an immune effector response, such as a cytokine, or a tumor specific adoptively transferred T cell population, or an antibody specific for a protein expressed by a tumor cell; and/or (iii) a composition comprising a tumor antigen or immunogenic fragment thereof; and/or (iv) a chemotherapeutic agent.

In certain embodiments, the second therapeutic agent comprises an inhibitor of the PI3K-AKT-mTOR pathway, an inhibitor of the Raf-MAPK pathway, an inhibitors of the JAK-STAT pathway, an inhibitor of the beta catenin pathway, an inhibitor of notch pathway, an inhibitor of the hedgehog pathway, an inhibitor of the Pim kinases, and/or an inhibitor of protein chaperones and cell cycle progression. In certain embodiments, combination therapy of the invention reduces the likelihood of drug-resistance arising in a cell population, and/or reduces the toxicity of treatment.

In certain embodiments, the HPK1 inhibitor compounds of the invention can be combined with one or more inhibitors of the following kinases for the treatment of cancer: Akt1, Akt2, Akt3, TGF-βPv, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK, and B-Raf.

In certain embodiments, the HPK1 inhibitor compounds of the invention can be combined with one or more of the following inhibitors for the treatment of cancer, including an FGFR inhibitor (FGFR1, FGFR2, FGFR3 or FGFR4, e.g., AZD4547, BAY 1187982, ARQ087, BGJ398, BIBF1120, TKI258, lucitanib, dovitinib, TAS-120, J J-42756493, Debiol347, INCB54828, INCB62079, and INCB63904), a JAK inhibitor (JAK1 and/or JAK2, e.g., ruxolitinib, baricitinib, or itacitinib (INCB39110)), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Ax1, and Mer), an aryl hydrocarbon receptor (AhR) modulator (such as laquinimod, aminoflavone, CB7993113, CH223191, 6, 2',4'-trimethoxyflavone (TMF), GNF351 (N-(2-(1H-indol-3-yl)ethyl)-9-isopropyl-2-(5-methylpyridin-3-yl)-9H-purin-6-amine), aminoflavone, NKI150460, indole-3-carbinol, β-naphthoflavone and dimer thereof, diindolylmethane (DIM), 4-Hydroxytamoxifen, leflunomide, raloxifene, tranilast, flutamide, mexiletine, nimodiphine, omeprazole, sulindac, tranilast, and TCDD (2,3,7,8-tetrachlorodibenzo-p-dioxin)), an angiogenesis inhibitor, an interleukin receptor inhibitor, bromo and extra terminal family members inhibitors (for example, bromodomain inhibitors or BET inhibitors such as OTX015, CPI-0610, INCB54329, and INCB57643), and an adenosine receptor antagonist or combinations thereof.

In certain embodiments, the HPK1 inhibitor compounds of the invention can be combined with inhibitors of HDAC, such as panobinostat and vorinostat.

In certain embodiments, the HPK1 inhibitor compounds of the invention can be combined with inhibitors of c-Met, such as onartumzumab, tivantnib, and capmatinib (INC-280).

In certain embodiments, the HPK1 inhibitor compounds of the invention can be combined with inhibitors of BTK, such as ibrutinib.

In certain embodiments, the HPK1 inhibitor compounds of the invention can be combined with inhibitors of mTOR, e.g., rapamycin, sirolimus, temsirolimus, and everolimus.

In certain embodiments, the HPK1 inhibitor compounds of the invention can be combined with inhibitors of MEK, such as trametinib, selumetinib and GDC-0973.

In certain embodiments, the HPK1 inhibitor compounds of the invention can be combined with inhibitors of Hsp90 (e.g., tanespimycin), cyclin dependent kinases (e.g., palbociclib), PARP (e.g., olaparib) and Pim kinases (LGH447, INCB053914, and SGI-1776).

In certain embodiments, the HPK1 inhibitor compounds of the invention can be combined with an agonist of DNA sensor (c-GAS) and/or its downstream adaptor protein STING.

The cGAS (cyclic GMP-AMP Synthase)-STING (Stimulator of Interferon Genes) pathway is a component of the innate immune system that functions to detect the presence of cytosolic DNA and, in response, trigger expression of inflammatory genes that can lead to senescence or to the activation of defense mechanisms. Localization of DNA from the usual nuclear localization to the cytosol is associated with tumorigenesis or viral infection. cGAS is found in the cytosol and, upon direct binding to cytosolic DNA, cGAS forms dimers to catalyze production of 2'3'-cGAMP from ATP and GTP. The resulting cGAMP then acts a second messenger to bind STING and to trigger activation of the transcription factor IRF3. Activated IRF3 leads to transcription of type-1 IFN-(3, and a number of downstream target genes to initiate a diverse array of biological responses, such as viral response, tumor surveillance, autoimmunity, and cellular senescence. In many tumor cells, constitutively active DNA damage response leads to the accumulation of cytoplasmic DNA and activation of the cGAS/STING pathway. It has been shown in lymphoma cells that the NKG2D ligand, Rae 1, was upregulated in a STING/IRF3 dependent manner, so as to aid in NK-mediated tumor clearance. The activation of c-GAS-STING pathway in antigen-presenting cells, such as dendritic cells, has been shown to enhance their function and boost anti-tumor immunity.

In certain embodiments, the HPK1 inhibitor compounds of the invention can be combined with one or more immune checkpoint inhibitors.

Effector T cell activation is normally triggered by the TCR recognizing antigenic peptide presented by the MHC complex. The type and level of activation achieved is then determined by the balance between signals which stimulate and signals which inhibit the effector T cell response. "Immune system checkpoint" is used herein to refer to any molecular interaction which alters the balance in favor of inhibition of the effector T cell response. That is, a molecular interaction which, when it occurs, negatively regulates the activation of an effector T cell. Such an interaction might be direct, such as the interaction between a ligand and a cell surface receptor which transmits an inhibitory signal into an effector T cell. Or it might be indirect, such as the blocking or inhibition of an interaction between a ligand and a cell surface receptor which would otherwise transmit an activatory signal into the effector T cell, or an interaction which promotes the upregulation of an inhibitory molecule or cell, or the depletion by an enzyme of a metabolite required by the effector T cell, or any combination thereof.

Examples of immune system checkpoints include: a) The interaction between indoleamine 2,3-dioxygenase (IDOL) and its substrate; b) The interaction between PD1 and PD-L1 and/or PD1 and PD-L2; c) The interaction between CTLA-4 and CD86 and/or CTLA-4 and CD80; d) The interaction between B7-H3 and/or B7-H4 and their respective ligands; e) The interaction between HVEM and BTLA; f) The interaction between GALS and TIM3; g) The interaction between MHC class I or II and LAG 3; and h) The interaction between MHC class I or II and KIR; i) The interaction between OX40 (CD134) and OX40L (CD252); j) The interaction between CD40 and CD40L (CD154); k) The interaction between 4-1 BB (CD137) and ligands including 4-1 BBL; 1) The interaction between GITR and ligands including GITRL.

Thus exemplary immune checkpoint inhibitors include inhibitors against immune checkpoint molecules such as CD20, CD27, CD28, CD39, CD40, CD 122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1, and PD-L2.

A representative checkpoint for the purposes of the present invention is checkpoint (b), namely the interaction between PD1 and either of its ligands PD-L1 and PD-L2. PD1 is expressed on effector T cells. Engagement with either ligand results in a signal which downregulates activation. The ligands are expressed by some tumors. PD-L1 in particular is expressed by many solid tumors, including melanoma. These tumors may therefore down regulate immune mediated anti-tumor effects through activation of the inhibitory PD-1 receptors on T cells. By blocking the interaction between PD1 and one or both of its ligands, a checkpoint of the immune response may be removed, leading to augmented anti-tumor T cell responses. Therefore, PD1 and its ligands are examples of components of an immune system checkpoint which may be targeted in the method of the invention.

Another checkpoint for the purposes of the present invention is checkpoint (c), namely the interaction between the T cell receptor CTLA-4 and its ligands, the B7 proteins (B7-1 and B7-2). CTLA-4 is ordinarily upregulated on the T cell surface following initial activation, and ligand binding results in a signal which inhibits further/continued activation. CTLA-4 competes for binding to the B7 proteins with the receptor CD28, which is also expressed on the T cell surface but which upregulates activation. Thus, by blocking the CTLA-4 interaction with the B7 proteins, but not the CD28 interaction with the B7 proteins, one of the normal check points of the immune response may be removed, leading to augmented anti-tumor T cell responses. Therefore, CTLA-4 and its ligands are examples of components of an immune system checkpoint which may be targeted in the method of the invention.

In some embodiments, the immune checkpoint molecule is a stimulatory checkpoint molecule selected from CD27, CD28, CD40, ICOS, OX40, GITR, and CD137.

In some embodiments, the immune checkpoint molecule is an inhibitory checkpoint molecule selected from A2AR, B7-H3, B7-H4, BTLA, CTLA-4, IDO, KIR, LAG3, PD-1, HM3, and VISTA.

In some embodiments, the compounds provided herein can be used in combination with one or more agents selected from KIR inhibitors, TIGIT inhibitors, LAIR1 inhibitors, CD 160 inhibitors, 2B4 inhibitors and TGFR beta inhibitors.

In some embodiments, the compounds provided herein can be used in combination with immune checkpoint inhibitors that are small molecule inhibitors (SMI), which are typically small organic molecules. For example, in certain embodiments, inhibitors of IDOL include Epacadostat (INCB24360), Indoximod, GDC-0919 (NLG919) and F001287. Other inhibitors of IDO1 include 1-methyltryptophan (1 MT).

In some embodiments, the inhibitor of an immune checkpoint molecule is also known as an "immunomodulatory agent," which includes any agent which, when administered to a subject, blocks or inhibits the action of an immune system checkpoint, resulting in the upregulation of an immune effector response in the subject, typically a T cell effector response, which may comprise an anti-tumor T cell effector response.

The immunomodulatory agent used in the method of the present invention may block or inhibit any of the immune system checkpoints described above. The agent may be an antibody or any other suitable agent which results in said blocking or inhibition. The agent may thus be referred to generally as an inhibitor of a said checkpoint.

An "antibody" as used herein includes whole antibodies and any antigen binding fragment (i.e., "antigen-binding portion") or single chains thereof. An antibody may be a polyclonal antibody or a monoclonal antibody, and may be produced by any suitable method. Examples of binding fragments encompassed within the term "antigen-binding portion" of an antibody include a Fab fragment, a $F(ab')_2$ fragment, a Fab' fragment, a $F_d$ fragment, a Fv fragment, a dAb fragment, and an isolated complementarity determining region (CDR). Single chain antibodies such as scFv and heavy chain antibodies such as Will and camel antibodies are also intended to be encompassed within the term "antigen-binding portion" of an antibody.

In certain embodiments, the immunomodulatory agent used with the HPK1 inhibitor of the invention is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab (MDX-1106), pembrolizumab (Merck 3475 or Lambrolizumab), pidilizumab (CT-011), Tislelizumab (BGB-A317), Camrelizumab (SHR-1210), spartalizumab (PDR001), or AMP-514 (MEDI0680). In some embodiments, the anti-PD-1 monoclonal antibody is nivolumab or pembrolizumab. In some embodiments, the anti-PD1 antibody is pembrolizumab. In some embodiments, the anti PD-1 antibody is Camrelizumab (SHR-1210). In certain embodiments, the inhibitor of PD-1 is AMP-224 (PD-L2 $F_c$ fusion protein that binds PD-1) or AUNP-12 (anti-PD-1 peptide).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, BMS-936559 (MDX-1105), MEDI-4736 (durvalumab), MPDL3280A (also known as RG7446), YW243.55.S70 (HPAB-0381-WJ), or MSB0010718C. In some embodiments, the anti-PD-L1 monoclonal antibody is MPDL3280A or MEDI-4736. In certain embodiments, anti-PD-L1 antibodies include atezolizumab, avelumab, durvalumab or MEDI-4736, and MPDL3280A.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, or any of the antibodies disclosed in WO2014/207063 (incorporated herein by reference). Other molecules include polypeptides, or soluble mutant CD86 polypeptides. In certain embodiments, the antibody is Ipilumumab.

In certain embodiments, the inhibitor of an immune checkpoint molecule is a combination of two or more of the modulators described herein, such as a combination that targets two or more different targets (e.g., PD-1, PD-L1 and PD-L2). Exemplary combinations include: α-PD-1 and α-PD-L1; α-CTLA-4, α-PD-L1, and α-CD20; etc.

In some embodiments, the inhibitor of an immune checkpoint molecule is an antibody which blocks or inhibits the interaction between 4-1 BB and its ligand, including utomilumab.

In some embodiments, the inhibitor of an immune checkpoint molecule is an inhibitor of CSFIR, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321 or GSK2831781.

In some embodiments, the inhibitor of an immune checkpoint molecule is an inhibitor of GITR, e.g., an anti-GITR antibody. In some embodiments, the anti-GITR antibody is TRX518, MK-4166, MK1248, BMS-986156, MEDI1873, or GWN323.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MEDI6469, MOXR0916, PF-04518600, or GSK3174998. In some embodiments, the OX40L fusion protein is MEDI6383.

In some embodiments, the inhibitor of an immune checkpoint molecule is an inhibitor of TIM3, e.g., an anti-TIM3 antibody. In some embodiments, the anti-TIM3 antibody is MBG-453.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the compounds of the invention can be used in combination with one or more metabolic enzyme inhibitors. In some embodiments, the metabolic enzyme inhibitor is an inhibitor of IDO 1, TDO, or arginase. Examples of IDO1 inhibitors include epacadostat and NGL919. An example of an arginase inhibitor is CB-1158.

In some embodiments, the compounds of the invention can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the invention can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, oncolytic virotherapy and immunomodulating small molecules, including thalidomide or JAK1/2 inhibitor and the like.

The compounds of the invention can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, anastrozole, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, prednisone, procarbazine, quinacrine, rasburicase, regorafenib, reloxafine, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vinorelbine, vorinostat, and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus, and parasite infections include, but are not limited to, nivolumab, pembrolizumab, MPDL3280A, MEDI-4736, and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk, and SGK.

Other anti-cancer agents also include those that block immune cell migration such as antagonists to chemokine receptors, including CCR2 and CCR4. The compounds of the present disclosure can further be used in combination with one or more anti-inflammatory agents, steroids, immunosuppressants, or therapeutic antibodies.

In some embodiments, the compounds of the invention can be used in combination with a further therapeutic agent which directly stimulates an immune effector response, such as a cytokine, or a tumor specific adoptively transferred T cell population, or an antibody specific for a protein expressed by a tumor cell.

As used herein, "an agent which directly stimulates an immune effector response" means any suitable agent, but typically refers to a cytokine or chemokine (or an agent which stimulates production of either), a tumor specific adoptively transferred T cell population, or an antibody specific for a protein expressed by a tumor cell.

The cytokine may be an interferon selected from IFNα, IPNβ, IFNγ and IFNA, or an interleukin, such as IL-2. The chemokine may be an inflammatory mediator, for example selected from CXCL9, 10, and 11, which attract T cells expressing CXCR3. The agent which stimulates production of a cytokine or chemokine may be an adjuvant suitable for administration to humans. One example is Bacille Calmette-Guerin (BCG), which is typically administered intravesical (i.e. urethral catheter) for treatment of bladder cancer. A typical dosage regime of BCG for bladder cancer is once per week for six weeks, but given its long safety history it is also administered indefinitely as maintenance. BCG has been shown to stimulate immune responses to bladder cancer. BCG has also been used as an adjuvant in combination with compositions which comprise tumor antigens (i.e. with cancer vaccines), particularly for colon cancer when it is administered typically intradermally. Such uses of BCG are also envisaged in the present invention. The tumor specific adoptively transferred T cell population directly increases the size of the tumor specific T cell population in an individual, and may be generated by any suitable means. However, typically the process involves isolating tumor specific T cells from a tumor sample taken from a patient, and selectively culturing those cells before returning the expanded population of tumor-specific T cells to the patient. Alternatively a tumor specific T cell population may be produced by genetic engineering of the T cell receptor locus, followed by expansion of the altered cell.

Antibodies specific for proteins expressed by a tumor cell typically stimulate immune activity by binding to the tumor cell and promoting destruction of the cell via antibody-dependent cell-mediated cytotoxicity (ADCC). Examples of antibodies of this type include anti-CD20 antibodies such as ofatumumab or rituximab, and anti-CD52 antibodies such as alemtuzumab.

Thus in certain exemplary embodiments, the compounds of the invention may be used in combination with a calcineurin inhibitor, e.g., cyclosporin A or FK 506; a mTOR inhibitor, e.g., rapamycin, 40-0-(2-hydroxyethyl)-rapamycin, biolimus-7 or biolimus-9; an ascomycin having immunosuppressive properties, e.g., ABT-281, ASM981; a corticosteroid; cyclophosphamide; azathioprene; methotrexate; leflunomide; mizoribine; mycophenolic acid or salt; mycophenolate mofetil; IL-1β inhibitor.

In another embodiment, compounds of the invention are combined with a co-agent which are PI3 Kinase inhibitors.

In another embodiment, compounds of the invention are combined with co-agent that influence BTK (Bruton's tyrosine kinase).

For the treatment of oncological diseases, compounds of the invention may be used in combination with B-cell modulating agents, e.g., Rituximab, BTK or Syk inhibitors, inhibitors of PKC, PI3 kinases, PDK, PIM, JAK and mTOR and BH3 mimetics.

In some embodiments, the compounds of the invention, including salts thereof, can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

In some embodiments, the compounds of the invention or salts thereof can also be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of the invention or salts thereof can be combined with dendritic cells immunization to activate potent anti-tumor responses.

In some embodiments, the compounds of the invention can be used in combination with bispecific macrocyclic peptides that target Fe α or Fe γ receptor-expressing effectors cells to tumor cells. The compounds of the invention can also be combined with macrocyclic peptides that activate host immune responsiveness.

In some embodiments, the compounds of the invention can be used in combination with bone marrow transplant for the treatment of a variety of tumors of hematopoietic origin.

Suitable antiviral agents contemplated for use in combination with the compounds of the invention can comprise nucleoside and nucleotide reverse transcriptase inhibitors (NRTIs), non-nucleoside reverse transcriptase inhibitors (NNRTIs), protease inhibitors and other antiviral drugs. Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

It will be appreciated that many of the further therapeutic agents used in the methods of the invention may be biologicals requiring intravenous, intraperitoneal or depot administration. In a further embodiment, the compound of the invention is orally administered and the further therapeutic agent is administered parenterally, for example intravenously, intraperitoneally or as a depot.

In any of the combination therapies described herein, when more than one pharmaceutical agent is administered to a patient, they can be administered simultaneously, separately, sequentially, or in combination (e.g., for more than two agents).

In one embodiment, the invention provides a product comprising a compound of the invention, such as a subject compound or any subgroup thereof, and at least one other therapeutic agent as a combined preparation for simultaneous, separate or sequential use in therapy. Products provided as a combined preparation include a composition comprising the compound of the invention or any subgroup thereof and the other therapeutic agent(s) together in the same pharmaceutical composition, or the subject compound or any subgroup thereof and the other therapeutic agent(s) in separate form, e.g., in the form of a kit.

In one embodiment, the invention provides a kit comprising two or more separate pharmaceutical compositions, at least one of which contains a subject compound, and another contains a second therapeutic agent discussed herein. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

6. Compound Screening/Assay Methods

The compounds of the invention inhibits the kinase activity of HPK1, which kinase activity can be assayed directly using numerous biochemical assays, such as the assay described in Example 1. IC50 values of any compounds can be determined accordingly over a range of inhibitor concentrations. In addition, the inhibitory effect of the compounds can also be assess using a biological assay, to determine the effect of the compounds on cytokine secretion by T cells following TCR and CD28 stimulation.

For example, Example 5 describes such a functional assay for determining the effect of an HPK1 inhibitor on IL-2 & IFN-γ release upon stimulation of Pan T cells. The secreted IL-2 & IFN-γ can be measured/quantified by standard ELISA assay. Briefly, pan T cells can be isolated from peripheral blood (PB) mononuclear cells (MNCs), or PBMC, using commercially available kits, such as MACS (Miltenyl Biotec) Pan T isolation kit (Cat. No. 130-096-535). Primary human pan-T cells include CD4 and CD8 T cells as well as some gamma/delta T cell subsets. The pan-T cells can be isolated using the negative immunomagnetic separation technique without the use of columns.

Isolated pan-T cells can be dispensed into 96-well plates at 100,000 cells/well, and stimulated with immobilized anti-CD3 antibody and soluable anti-CD28 antibody, or PMA/Ionomycin as the positive control (or culture media as the negative control). Different concentrations of test compounds can be added to the cells to assess the compound effect on cytokine secretion following TCR-stimulation/CD28 co-stimulation. Stimulated cells are incubated for 2 more days, before the supernatant (containing secreted cytokines by pan-T cells) is collected from each well for ELISA assay and quantitation of IL-2 and IFN-γ.

Additional assays may also be used to assess the ability of any HPK1 inhibitor to inhibit HPK1, or to screen for compounds possessing HPK1 inhibitory activity.

For example, in one assay, inhibition of the HPK1 kinase activity can be assayed using a Treg assay (the Regulatory T-cell proliferation assay) described as following. Specifically, primary $CD4^+/CD25^-$ T-cells and $CD4^+/CD25^+$ regulatory T-cells are isolated from human donated Peripheral Blood Mononuclear Cells (PBMCs), using a suitable kit, such as one from Thermo Fisher Scientific (Cat. No. 11363D). $CD4^+/CD25^-$ T-cells are labeled with CFSE (Thermo Fisher Scientific, C34554) following the protocol provided by the vendor. CFSE labeled T-cells and $CD4^+$/CD25 regulatory T-cells are re-suspended at the concentration of $1\times10^6$ cells/mL in RPMI-1640 medium. 100 uL of CFSE-labeled T-cells are mixed with or without 50 μL of $CD4^+$/CD25 regulatory T-cells, treated with 5 μL of anti-CD3/CD28 beads (Thermo Fisher Scientific, 11132D) and various concentrations of compounds diluted in 50 μL of RPMI-1640 medium. Mixed populations of cells are cultured for 5 days (37° C., 5% $CO_2$), and proliferation of CFSE-labeled T-cells is analyzed by BD LSRFortessa X-20 using FITC channel on the $5^{th}$ day. Inhibition of HPK1 by the subject compounds is expected to enhance Treg function and inhibit proliferation of CFSE labeled primary $CD4^+$/$CD25^-$ T-cells.

In another example, inhibition of the HPK1 kinase activity can be assayed using the p-SLP-76 S376 HTRF assay (Cisbio) described as follows. This HTRF cell-based assay enables rapid, quantitative detection of SLP-76 phosphorylated on Serine 376 by HPK1. Phospho-SLP-76 creates a scaffold on which key signaling complexes are built, and is a marker of T-lymphocyte activation. According to the manufacture, the Phospho-SLP-76 (Ser376) assay uses two labeled antibodies: one with a donor fluorophore, the other one with an acceptor. The first antibody is specific for binding to the phosphorylated S376 motif on SLP-76, and the second for its ability to recognize SLP-76 independent of its phosphorylation state. Protein phosphorylation enables an immune-complex formation involving both labeled antibodies and which brings the donor fluorophore into close proximity to the acceptor, thereby generating a FRET signal. Its intensity is directly proportional to the concentration of phosphorylated protein present in the sample, and provides a means of assessing the protein's phosphorylation state under a no-wash assay format.

Briefly, Jurkat cells (cultured in RPMI1640 media with 10% FBS) are collected and centrifuged, followed by resuspension in appropriate media at $3\times10^6$ cells/mL. The Jurkat cells (35 μL) are then dispensed into each well of a 384-well plate. Test compounds are diluted with cell culture media for 40-fold dilution (adding 39 μL cell culture media into 1 μL of compound). The Jurkat cells in the well plate are treated with the test compounds at various concentrations (adding 5 diluted compound into 35 μL Jurkat cells, and starting from 3 μM with 1:3 dilution) for 1 hour at 37° C., 5% $CO_2$), followed by treatment with anti-CD3 (5 μg/ml, OKT3 clone) for 30 min to activate TCR and HPK1. A 1:25 dilution of 100× blocking reagent (from p-SLP76 ser376HTRF kit) with 4× Lysis Buffer (LB) is prepared, and 15 μL of the 4×LB buffer with blocking reagent is added into each well and incubated at room temperature for 45 mins with gentle shaking. The cell lysate (16 μL) is added into a Greiner white plate, treated with p-SLP76 Ser376 HTRF reagents (2 uL donor, 2 uL acceptor) and incubated at 4° C. overnight. The homogeneous time resolved fluorescence (HTRF) is measured on a PHERAstar plate reader the next day. IC50 determination is performed by fitting the curve of percent inhibition versus the log of the inhibitor concentration using the GraphPad Prism 5.0 software.

Any of the assays described above can be scaled up for large scale or high throughput screening (HTS). Using any of the assays described above, IC50 values of the subject compounds can be determined.

7. Pharmaceutical Compositions

The invention provides pharmaceutical compositions which comprise any one of the compounds described herein, or a pharmaceutically acceptable salt thereof, and one or more pharmaceutically acceptable carriers or excipients.

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical carriers and excipients are suitable for use with disclosed compounds.

These compositions optionally further comprise one or more additional therapeutic agents. Alternatively, a compound of the invention may be administered to a patient in need thereof in combination with the administration of one or more other therapeutic regimens (e.g. Gleevec or other kinase inhibitors, interferon, bone marrow transplant, farnesyl transferase inhibitors, bisphosphonates, thalidomide, cancer vaccines, hormonal therapy, antibodies, radiation, etc.). For example, additional therapeutic agents for conjoint administration or inclusion in a pharmaceutical composition with a compound of this invention may be another one or more anticancer agents.

As described herein, the compositions of the present invention comprise a compound of the invention together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

8. Formulations

This invention also encompasses a class of compositions comprising the active compounds of this invention in association with one or more pharmaceutically-acceptable carriers and/or diluents and/or adjuvants (collectively referred to herein as "carrier" materials) and, if desired, other active ingredients.

In certain embodiments, the invention provides a pharmaceutical formulation for treating cancer, in particular the cancers described herein, comprising a compound of the present invention or a pharmaceutically acceptable salt thereof together with a pharmaceutically acceptable carrier.

In certain embodiments, the invention provides a pharmaceutical formulation for treating a cancer selected from the group consisting of breast cancer, colorectal cancer, lung cancer, ovarian cancer, and pancreatic cancer, comprising a compound of the present invention or a pharmaceutically acceptable salt thereof together with a pharmaceutically acceptable carrier.

The compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, transdermally, intraorbitally, intrathecally, intraventricularly, intratumorally, intranasally, intrasternally, by implantation, by inhalation, and by infusion techniques, in dosage unit formulations containing conventional pharmaceutically acceptable carriers, adjuvants, and vehicles.

Typically, the pharmaceutical compositions are tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutically active compounds of this invention can be processed in accordance with conventional methods of pharmacy to produce medicinal agents for administration to patients, including humans and other mammals.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. As mentioned previously, the daily dose can be given in one administration or may be divided between 2, 3, 4 or more administrations.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

The compounds of this invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner.

While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anti-cancer agent, an anti-viral agent, anti-inflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, anti-inflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. Pharmaceutically acceptable carriers, adjuvants and vehicles that may be used in the pharmaceutical compositions of this invention include, but are not limited to, ion exchangers, alumina, aluminum stearate, lecithin, self emulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of compounds of the formulae described herein.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening, flavoring and/or coloring agents may be added. The pharmaceutical compositions may comprise formulations utilizing liposome or microencapsulation techniques, various examples of which are known in the art.

The pharmaceutical compositions may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

9. Treatment Kits

One aspect of the present invention relates to a kit for conveniently and effectively carrying out the methods or uses in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

The following representative examples contain important additional information, exemplification and guidance which can be adapted to the practice of this invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein.

The contents of the cited references are incorporated herein by reference to help illustrate the state of the art.

In addition, for purposes of this invention, the chemical elements are identified in accordance with the Periodic Table of the Elements, CAS version, Handbook of Chemistry and Physics, $75^{th}$ Ed., inside cover. Additionally, general principles of organic chemistry, as well as specific functional moieties and reactivity, are described in "Organic Chemistry," Thomas Sorrell, University Science Books, Sausalito: 1999, and "Organic Chemistry," Morrison & Boyd (3d Ed), the entire contents of both of which are incorporated herein by reference.

10. Synthesis Schemes

The compounds of the invention can be prepared by one of ordinary skill in the art following art recognized techniques and procedures. More specifically, the compounds of the invention can be prepared as set forth in the schemes, methods, and examples set forth below. It will be recognized by one of skill in the art that the individual steps in the following schemes may be varied to provide the compounds of the invention. The reagents and starting materials are readily available to one of ordinary skill in the art. All substituents, unless otherwise specified, are as previously defined.

EXAMPLES

The followings are the abbreviations used and meaning thereof in the specification:

EtOAc: Ethyl acetate
DCM: Dichloromethane
ACN: Acetonitrile
THF: Tetrahydrofuran
DMSO: Dimethyl sulfoxide
MeOH: Methanol
EtOH: Ethanol
DMF: N,N-Dimethylformamide
DMA: N,N-Dimethylacetamide
DMF DMA: N,N-Dimethylformamide dimethylacetal
NCS: N-Chlorosuccinimide
NBS: N-Bromosuccinimide
NIS: N-Iodosuccinimide
Pd—C: Palladium on Carbon
LDA: Lithium diisopropylamide
TFA: Trifluoroacetic acid
PTSA: p-Toluene sulfonic acid
DIBAL-H: Diisobutylaluminum hydride
LAH: Lithium aluminum hydride
Py: Pyridine
DPPA: Diphenylphosphoryl azide
CDI: 1,1-Carbonyl diimidazole
TEA: Triethylamine
DIPEA: N,N-Diisopropylethylamine
DMAP: 4-(Dimethylamino)pyridine
EDCI: N-(3-Dimethylaminopropyl)-N-ethyl carbodiimide hydrochloride
HATU: (1-[Bis(dimethylamino)methylene]-1H-1,2,3-triazolo[4,5-b]pyridinium 3-oxid hexafluorophosphate
HOBT: 1-Hydroxybenzo triazole
TfOH: Trifluoromethane sulfonic acid
dppf: 1,1 Ferrocenediyl-bis(diphenylphosphine)
DAST: (Diethylamino)sulfur trifluoride
Pd2(dba)3: Tris(dibenzylideneacetone) dipalladium(O)
Boc: tert-Butoxycarbonyl
Ac: Acetyl TMSI: Trimethyl silyliodide
TBAI: Tetrabutylammonium iodide
$PPh_3$: Triphenyl phosphine
dba: Dibenzylideneacetone
BINAP: 2,2'-Bis(diphenyl phosphino)-1,1'-bi naphthyl
MsCl: Methane sulfonyl chloride
TsCl: Toluene sulfonyl chloride
DMAP: 4-Dimethyl aminopyridine
LiHMDS: Lithium bis(trimethyl silyl)amide
NaHMDS: Sodium bis(trimethyl silyl)amide
DMS: dimethyl sulfide
DME: dimethoxyethane
DCE: Dichloroethane
NMR: Nuclear Magnetic Resonance
LC-MS: Liquid Chromatography Mass Spectrometry
ESI-MS: Electro Spray Ionization Mass Spectrometry:
GCMS: Gas Chromatography Mass Spectrometry
TLC: Thin Layer Chromatography
TCR: T cell receptor
BCR: B cell receptor
CARD: Caspase activation and recruitment domain
mM: millimolar
μM: micromolar
mL: microliter
ng: nanogram
nM: nanomolar
nm: nanometer
$IC_{50}$: Half maximal inhibitory concentration
OD: Optical density

A. Biological Examples

Biology Example 1 HPK1 Biochemical Assay

This example used the ADP-GLO™ Kinase Assay to measure the effect of potential HPK1 inhibitor compounds on HPK1 kinase activity.

The ADP-GLO™ Kinase Assay (Promega Corp., Madison, WI) measures ADP formed from a kinase reaction. According to the manufacture, the ADP formed in a kinase assay is first converted into ATP, which is then used to generate light in a luciferase reaction. The luminescence generated correlates with kinase activity. An exemplary experimental setting is described below, though minor adjustments can be made in individual assays.

Materials and Equipment

1. Reagents:

| Reagents | Vendor | Ven dor Catalog |
|---|---|---|
| HPK-1 | Signal Chem | M23-11G-10 |
| MBP | Signal Chem | M42-51N |
| ATP | From ADP-Glo kinase Kit | — |
| ADP-GLO ™ kinase Kit | Promega | V9102 |
| 10% BSA stock solution | Miltenyi | 130-091-376 |
| DTT | Sigma | D0632 |
| $MgCl_2$ | Sigma | 208337 |
| Trizma base | Sigma | T1503 |

2. Equipments & Supplies:

| Equipments | Source | Cat# |
|---|---|---|
| 96-V bottom well plate | Greiner | 651201 |
| 384-well plate | Greiner | 6007290 |
| LDV plate | Labcyte | LP0200 |

-continued

| Equipments | Source | Cat# |
|---|---|---|
| Bravo | Agilent | — |
| Envision | PerkinElmer | — |
| Water system | Millipore Milli-Q Reference system | — |
| Bravo 10 μL tips | Axygen | VT-384-10uL-R |
| Bravo 30 μL tips | Axygen | VT-384-31uL-R |
| Manual single channel pipette | RAININ | — |
| Multichannel electronic pipette | Thermo/RAININ | — |

3. Plate Setup

Serial 3-fold dilution of compounds from 10 μM (top concentration) to 0.508 nM (lowest concentration). Positive control is 10 μM Reference+enzyme+substrate. Negative control is 1% DMSO+enzyme+substrate.

4. Procedures

1. Buffer Preparation 40 mM Tris pH7.5; 20 mM $MgCl_2$, 0.1 mg/ml BSA, 50 μM DTT Buffer Stock

| |
|---|
| IM Tris, PH7.5, 121.14 g/mol |
| Add 6.057 g to 50 mL $H_2O$, adjust PH to 7.5 |
| IM $MgCl_2$, 95.21 g/mol |
| Add 4.7605 g to 50 mL $H_2O$ |

Add 20 mL 1M Tris and 10 mL 1M $MgCl_2$ to 470 mL dd$H_2O$ to get buffer stock, and stock at RT.

2. Preparing Fresh 1* Assay Buffer

| Reagent | [Stock] | [Final] | Fold | Add (mL) |
|---|---|---|---|---|
| DTT (mM) | 10 | 0.05 | 200 | 0.015 |
| BSA (mg/mL) | 100 | 0.1 | 1000 | 0.003 |
| buffer stock | | | | 3 |

3. Compounds Preparation

1) The compounds were diluted to 1 mM, by mixing 10 μL of 10 mM respective compound stocks with 90 μL of DMSO.

2) The compounds were then diluted 3-fold for 10 doses (5 μL to 10 μL dilution) by BRAVO. The top compound conc. was 1 mM (100×), DMSO Conc. was 100%.

3) Transfer 100 nL of each diluted compound sample to 384-well plate (Corning-4512) by ECHO.

4) Centrifuge the plate at 1,500 rpm for 1 minute.

4. Preparation of 2×ATP-MBP Mixture:

20 μM ATP, 0.2 μg/μL MBP in Kinase Buffer (final concentration: 10 μM ATP, 0.1 MBP)

| Reagent | [Stock] | [Working] | [Final] | Fold | Add (μL) | Assay Buffer (μL) | Total (μL) |
|---|---|---|---|---|---|---|---|
| ATP (μM) | 10,000 | 20 | 10 | 500 | 0.2 | 79.8 | 100 |
| MBP (μg/μL) | 1 | 0.2 | 0.1 | 5 | 20.00 | | |

5. Preparation of 2×HPK1 working solution with assay buffer.

HPK1 final concentration was 0.6 ng/μL. For compounds with high potency, lower concentration of HPK1 were used (0.26 ng/4-0.065 ng/6.

6. Add 5 μL/well of 2×HPK1 working solution, Centrifuge at 1,500 rpm for 1 minute.
7. Add 5 μL/well of 2×ATP-Substrate, Centrifuge at 1,500 rpm for 1 minute.
8. Incubate at 25° C. for 1 hour (or 6 hours for compounds with high potency).
9. Add 5 μL/well ADP-GLO™ Reagent to stop the kinase reaction and deplete the unconsumed ATP. Centrifuge at 1,500 rpm for 1 minute. Incubate at 25° C. for 40 min.
10. Add 10 μL of Kinase Detection Reagent to convert ADP to ATP. Centrifuge at 1,500 rpm for 1 minute. Incubate at 25° C. for 40 min.
11. Record luminescence signal on an Envision plate reader (384-CTG).

5. Data Analysis

The percent (%) inhibition at each concentration of compound is calculated based on and relative to the signal in the High and Low control wells contained within each assay plate. The High control wells served as 0% inhibition, and the low control wells that did not contain any compounds but rather DMSO (final concentration=0.5%) served as 100% inhibition. The concentrations and % inhibition values for tested compounds were plotted and the concentration of compound required for 50% inhibition (IC50) was determined with a Three-parameter logistic dose response equation. The endpoint value (IC50) for the reference peptide/compound was evaluated in each experiment as a quality control measure. If the endpoint value was within 3-fold of the expected value, then the experiment was deemed acceptable.

Biology Example 2 PKC-Theta Biochemical Assay

This example used the ADP-GLO™ Kinase Assay to measure the effect of potential HPK1 inhibitor compounds on PKC-theta kinase activity. An exemplary experimental setting is described below, though minor adjustments can be made in individual assays.

Materials and Equipment

1. Reagents:

| Description | Vendor | Catalog |
|---|---|---|
| PKC theta | Signal Chem | P74-10G-10 |
| PKCtide | Signal Chem | P15-58-1MG |
| ATP | From ADP-Glo kinase Kit | — |
| PKC lipid activator (10×, 500 μL) | Signal Chem | L51-39-500 |
| ADP-GLO ™ kinase Kit | Promega | V9102 |
| 10% BSA stock solution | Miltenyi | 130-091-376 |
| DTT | Sigma | D0632 |
| $MgCl_2$ | Sigma | 208337 |
| Trizma base | Sigma | T1503 |

2. Equipments & Supplies:

| Equipments | Source | Cat# |
|---|---|---|
| 96-V bottom well plate | Greiner | 651201 |
| 384-well plate | Corning | 4512 |
| LDV plate | Labcyte | LP0200 |
| Bravo | Agilent | — |
| Envision | PerkinElmer | — |
| Water system | Millipore Milli-Q Reference system | — |
| Bravo 10 μL tips | Axygen | VT-384-10uL-R |
| Bravo 30 μL tips | Axygen | VT-384-31uL-R |
| Manual single channel pipette | RAININ | — |
| Multichannel electronic pipette | Thermo/RAININ | — |

3. Plate Setup

Serial 3-fold dilution of compounds from 10 μM (top concentration) to 0.508 nM (lowest concentration). Positive control is 10 μM Reference+enzyme+substrate. Negative control is 1% DMSO+enzyme+substrate.

4. Procedures

1. Buffer Preparation 40 mM Tris pH7.5; 20 mM $MgCl_2$, 0.1 mg/ml BSA, 50 μM DTT Buffer Stock

| |
|---|
| IM Tris, PH7.5, 121.14 g/mol |
| Add 6.057 g to 50 mL $H_2O$, adjust PH to 7.5 |
| 1M $MgCl_2$, 95.21 g/mol |
| Add 4.7605 g to 50 mL $H_2O$ |

Add 20 mL 1M Tris and 10 mL 1M $MgCl_2$ to 470 mL $ddH_2O$ to get buffer stock, and stock at RT.

2. Preparing Fresh 1* Assay Buffer

| Reagent | [Stock] | [Final] | Fold | Add(mL) |
|---|---|---|---|---|
| DTT (mM) | 10 | 0.05 | 200 | 0.015 |
| BSA (mg/ml) | 100 | 0.1 | 1000 | 0.003 |
| PKC lipid activator | 10 | 1 | 10 | 0.3 |
| buffer stock | | | | 3 |

3. Compounds Preparation

1) The compounds were diluted to 1 mM, by mixing 104 of 10 mM respective compound stocks with 904 of DMSO.
2) The compounds were then diluted 3-fold for 10 doses (54 to 104 dilution) by BRAVO. The top compound conc. was 1 mM (100×), DMSO Conc. was 100%.
3) Transfer 50 nL of each diluted compound sample to 384-well plate (Corning-4512) by ECHO.
4) Centrifuge the plate at 1,500 rpm for 1 minute.

4. Preparation of 2× Enzyme Working Solution in Kinase Buffer:

| Enzyme | [Stock] | [Working] | [Final] | Fold | Add (μL) | Assay Buffer (μL) | Total (μL) |
|---|---|---|---|---|---|---|---|
| PKC theta (ng/μL) | 100 | 0.25 | 0.125 | 400.0 | 1.0 | 399.0 | 400 |

5. Preparation of 2×ATP-sub Mixture:

| Enzyme | [Stock] | [Working] | [Final] | Fold | Add (μL) | Assay Buffer (μL) | Total (μL) |
|---|---|---|---|---|---|---|---|
| ATP (μM) | 10,000 | 60 | 30 | 167 | 2.40 | 237.6 | 400 |
| PKC tide (μg/μL) | 1 | 0.4 | 0.2 | 2.50 | 160.00 | | |

6. Add 2.5 μL/well of 2× Enzyme working solution, Centrifuge at 1,500 rpm for 1 minute.
7. Add 2.5 μL/well of 2×ATP-Substrate, Centrifuge at 1,500 rpm for 1 minute.
8. Incubate at 25° C. for 60 min.
9. Add 5 μL/well ADP-GLO™ Reagent to stop the kinase reaction and deplete the unconsumed ATP after 1 hour. Centrifuge at 1,500 rpm for 1 minute. Incubate at 25° C. for 40 min.
10. Add 10 μL of Kinase Detection Reagent to convert ADP to ATP. Centrifuge at 1,500 rpm for 1 minute. Incubate at 25° C. for 40 min.
11. Record luminescence signal on an Envision plate reader (384-USL).

5. Data Analysis

The percent (%) inhibition at each concentration of compound is calculated based on and relative to the signal in the High and Low control wells contained within each assay plate. The High control wells served as 0% inhibition, and the low control wells that did not contain any compounds but rather DMSO (final concentration=0.5%) served as 100% inhibition. The concentrations and % inhibition values for tested compounds were plotted and the concentration of compound required for 50% inhibition (IC50) was determined with a Three-parameter logistic dose response equation. The endpoint value (IC50) for the reference peptide/compound was evaluated in each experiment as a quality control measure. If the endpoint value was within 3-fold of the expected value, then the experiment was deemed acceptable.

Biology Example 3 TBK1 Biochemical Assay

This example used the ADP-GLO™ Kinase Assay to measure the effect of potential HPK1 inhibitor compounds on TBK1 kinase activity. An exemplary experimental setting is described below, though minor adjustments can be made in individual assays.

Materials and Equipment

1. Reagents:

| Description | Vendor | Catalog |
|---|---|---|
| TBK1 | Signal Chem | T02-10G-10 |
| MBP | Signal Chem | M42-51N |
| ATP | From ADP-Glo kinase Kit | — |
| ADP-GLO ™ kinase Kit | Promega | V9102 |
| 10% BSA stock solution | Miltenyi | 130-091-376 |
| DTT | Sigma | DO632 |
| $MgCl_2$ | Sigma | 208337 |
| Trizmabase | Sigma | T1503 |

2. Equipments & Supplies:

| Equipments | Source | Cat# |
|---|---|---|
| 96-V bottom well plate | Greiner | 651201 |
| 384-well plate | Corning | 4512 |
| LDV plate | labcyte | LP0200 |
| Bravo | Agilent | — |
| Envision | PerkinElmer | — |
| Water system | Millipore Milli-Q Reference system | — |
| Bravo 10 pLtips | Axygen | VT-384-10uL-R |
| Bravo 30 pL tips | Axygen | VT-384-31uL-R |
| Manual single channel pipette | RAININ | — |
| Multichannel electronic pipette | Thermo/RAININ | — |

3. Plate setup

See above.

4. Procedures

1. Buffer Preparation 40 mM Tris pH7.5; 20 mM $MgCl_2$, 0.1 mg/ml BSA, 50 μM DTT Buffer Stock

| |
|---|
| 1M Tris, PH7.5, 121.14 g/mol |
| Add 6.057 g to 50 mL $H_2O$, adjust PH to 7.5 |
| 1M $MgCl_2$, 95.21 g/mol |
| Add 4.7605 g to 50 mL $H_2O$ |

Add 20 mL 1M Tris and 10 mL 1M $MgCl_2$ to 470 mL $ddH_2O$ to get buffer stock, and stock at RT (room temperature).

2. Preparing Fresh 1* Assay Buffer

| Reagent | [Stock] | [Final] | Fold | Add(mL) |
|---|---|---|---|---|
| DTT (mM) | 10 | 0.05 | 200 | 0.015 |
| BSA (mg/ml) | 100 | 0.1 | 1000 | 0.003 |
| buffer stock | | | | 3 |

3. Compounds Preparation

1) The compounds were diluted to 1 mM, by mixing 10 μL of 10 mM respective compound stocks with 90 μL of DMSO.

2) The compounds were then diluted 3-fold for 10 doses (5 μL to 10 μL dilution) by BRAVO. The top compound conc. was 1 mM (100×), DMSO Conc. was 100%.

3) Transfer 50 nL of each diluted compound sample to 384-well plate (Corning-4512) by ECHO.

4) Centrifuge the plate at 1,500 rpm for 1 minute.

4. Preparation of 2× Enzyme Working Solution in Kinase Buffer:

| Enzyme | [Stock] | [Working] | [Final] | Fold | Add (μL) | Assay Buffer (μL) | Total (μL) |
|---|---|---|---|---|---|---|---|
| TBK1 (ng/μL) | 100 | 1.6 | 0.8 | 62.5 | 6.4000 | 393.6 | 400 |

5. Preparation of 2×ATP-sub Mixture:

| Reagent | [Stock] | [Working] | [Final] | Fold | Add (μL) | Assay Buffer (μL) | Total (μL) |
|---|---|---|---|---|---|---|---|
| ATP (μM) | 10,000 | 50 | 25 | 200 | 2.00 | 318.0 | 400 |
| MBP (μg/μL) | 1 | 0.2 | 0.1 | 5 | 80.00 | | |

6. Add 2.5 μL/well of 2× enzyme working solution, Centrifuge at 1,500 rpm for 1 minute.
7. Add 2.5 μL/well of 2×ATP-Substrate, Centrifuge at 1,500 rpm for 1 minute.
8. Incubate at 25° C. for 60 min.
9. Add 5 μL/well ADP-GLO™ Reagent to stop the kinase reaction and deplete the unconsumed ATP after 1 hour. Centrifuge at 1,500 rpm for 1 minute. Incubate at 25° C. for 40 min.
10. Add 10 μL of Kinase Detection Reagent to convert ADP to ATP. Centrifuge at 1,500 rpm for 1 minute. Incubate at 25° C. for 40 min.
11. Record luminescence signal on an Envision plate reader (384-USL).

5. Data Analysis

The percent (%) inhibition at each concentration of compound is calculated based on and relative to the signal in the High and Low control wells contained within each assay plate. The High control wells served as 0% inhibition, and the low control wells that did not contain any compounds but rather DMSO (final concentration=0.5%) served as 100% inhibition. The concentrations and % inhibition values for tested compounds were plotted and the concentration of compound required for 50% inhibition (IC50) was determined with a Three-parameter logistic dose response equation. The endpoint value (IC50) for the reference peptide/compound was evaluated in each experiment as a quality control measure. If the endpoint value was within 3-fold of the expected value, then the experiment was deemed acceptable.

Biology Example 4 JAK3 Biochemical Assay

This example used the ADP-GLO™ Kinase Assay to measure the effect of potential HPK1 inhibitor compounds on JAK3 kinase activity. An exemplary experimental setting is described below, though minor adjustments can be made in individual assays.

Materials and Equipment

1. Reagents:

| Description | Vendor | Catalog |
|---|---|---|
| JAK3 | Thermo fisher | PV3855 |
| Poly(E4Y1) | Signal Chem | P61-58 |
| Ultra-pure ATP | Promega | From ADP-GLO ™ kinase Kit |
| ADP-GLO ™ kinase Kit | Promega | V9102 |
| 10% BSA stock solution | Miltenyi | 130-091-376 |
| DTT | Sigma | 3483-12-3 |
| $MgCl_2$ | Sigma | M1028 |
| Tris-base | Sigma | T1503 |

2. Equipments & Supplies:

| Equipments | Source | Cat# |
|---|---|---|
| Echo Qualified 384-Well Low Dead Volume Microplate | Perkinelmer | LP0200 |
| Assay plate, Corning ® 384 well microplate, low volume | Corning | C4512 |
| MICROPLATE, 96 WELL, PP, V-BOTTOM | Greiner | 651201 |
| Bravo 10 μL tips | Axygen | 301-78-401 |
| Bravo 30 μL tips | Axygen | 301-78-301 |
| ECHO | Perkinelmer | — |
| Envision | PerkinElmer | — |
| BRAVO | — | — |
| Water system | Millipore Milli-Q Reference system | — |
| Incubator | Cimo | SPX-60BSH-II |
| E1-clipTip multi-channel electric pipette (1-30 μL) | Thermo Fisher | 4671030BT |

3. Procedures

1. Prepare JAK3 kinase buffer

Freshly adding DTT and BSA into Buffer (Final Conc.: 40 mM Tris pH7.5; 20 mM $MgCl_2$, 0.1 mg/ml BSA, 50 μM DTT).

| Reagent | [Stock]) | [Final] | Fold | Add (μL) |
|---|---|---|---|---|
| DTT (mM) | 10 | 0.05 | 200 | 15 |
| BSA (mg/ml) | 100 | 0.1 | 1,000 | 3 |
| 1 × Kinase Buffer | 1× | 1× | 1 | 2,982 |
| Total | | | | 3,000 |

2. Compounds Preparation

For tested compounds: compounds were diluted to 1 mM, by mixing 5 μL of 10 mM compound stocks to 45 μL DMSO. The compounds solutions were then serially diluted 3-fold for 10 doses. The top compound concentration was 1 mM (100×), DMSO concentration was 100%.

50 nL of each of 10 doses of diluted compound were added to 384-well assay plate (Corning #4512) by ECHO.

For positive control, 50 nL of 1 mM reference compound were added to 384-well assay plate (Corning #4512) by ECHO.

For negative control: 50 nL of DMSO was transferred into 384-well assay plate as a negative control.

The assay plate was centrifuged at 1,500 rpm for 1 minute.

3. Compounds were Transferred by ECHO Following the Layout Below:

Reference and test compounds 1-15: serial 3-fold dilution from 10 μM to 0.508 nM (10 doses); negative control is 0.78 ng JAK3, 4 μM ATP & 0.2 μg/μL poly, 1% DMSO; positive control is the top dose of the reference compound, 0.78 ng JAK3, 0.2 μg/μL Poly (E4Y1), 4 μMATP, 1% DMSO.

4. Add 2.5 μL/well of 2×JAK3 working solution using pipette (Thermo, 30 μL multi-channel), Centrifuge at 1,500 rpm for 1 minute.
5. Add 2.5 μL/well of 2×ATP-Poly(E4Y1) working mixture using pipette (Thermo, 30 μL multi-channel), Centrifuge at 1,500 rpm for 1 minute.
6. Incubate the assay plate at 25° C. for 60 min.
7. Add 5 μL/well ADP-GLO™ Reagent by BRAVO to stop the kinase reaction and deplete the unconsumed ATP after 1 hour. Centrifuge at 1,500 rpm for 1 minute. Incubate at 25° C. for 40 min.
8. Add 10 uL of Kinase Detection Reagent by BRAVO to convert ADP to ATP. Centrifuge at 1,500 rpm for 1 minute. Incubate at 25° C. for 40 min.
9. Record luminescence signal on an Envision plate reader (384-USL).
10. Process data using XL-fit. Inhibition %=[1-(test well−Negative control)/(positive control−Negative control)]*100%.

5. Data Analysis

The percent (%) inhibition at each concentration of compound is calculated based on and relative to the signal in the Negative and Positive control wells contained within each assay plate. The Negative control wells served as 0% inhibition, and the Positive control wells served as 100% inhibition. The concentrations and % inhibition values for tested compounds are plotted and the concentration of compound required for 50% inhibition (IC50) is determined with a Three-parameter logistic dose response equation. The endpoint value (IC50) for the reference peptide/compound is evaluated in each experiment as a quality control measure. If the endpoint value was within 3-fold of the expected value then the experiment was deemed acceptable.

Biology Example 5 ZAP70 Biochemical Assay Protocol

This example used the ADP-GLO™ Kinase Assay to measure the effect of potential HPK1 inhibitor compounds on ZAP70 kinase activity. An exemplary experimental setting is described below, though minor adjustments can be made in individual assays.

Materials and Equipments

1. Reagents:

| Description | Vendor | Catalog |
|---|---|---|
| ZAP70 | Sigma Chem | Z02-10G |
| Poly(E4Y1) | Sigma Chem | P61-58 |
| Ultra-pure ATP | Promega | From ADP-Glo kinase Kit |
| ADP-GLO ™ kinase Kit | Promega | V9102 |
| 10% BSA stock solution | Miltenyi | 130-091-376 |
| DTT | Sigma | 3483-12-3 |
| DMSO | Sigma | D5879 |
| $MnCl_2$ | Sigma | M5505 |
| $MgCl_2$ | Sigma | M1028 |
| Tris base | Sigma | T1503 |

2. Equipments & Supplies:

| Equipments | Source | Cat# |
|---|---|---|
| Echo Qualified 384-Well Low Dead Volume Microplate | Perkinelmer | LP0200 |
| Assay plate, Corning ® 384 well microplate, low volume | Corning | C4512 |
| MICROPLATE, 96 WELL, PP, V-BOTTOM | Greiner | 651201 |
| Bravo 10 μL tips | Axygen | 301-78-401 |
| Bravo 30 μL tips | Axygen | 301-78-301 |
| ECHO | Perkinelmer | — |
| Envision | PerkinElmer | — |
| BRAVO | — | — |
| Water system | Millipore Milli-Q Reference system | — |
| Incubator | Cimo | SPX-60BSH-II |
| E1-clipTip multi-channel pipette (1-30 μL) | Thermo Fisher | 4671030BT |

3. Procedures

1. ZAP70 Kinase Buffer Preparation:

Freshly adding DTT and BSA to Buffer (Final Conc.: 40 mM Tris pH7.5; 20 mM $MgCl_2$, 0.1 mg/ml BSA, 50 μM DTT, 2 mM $MnCl_2$).

| Reagent | [Stock] | [Final] (mM) | Fold | Add (μL) |
|---|---|---|---|---|
| DTT (mM) | 10 | 0.05 | 200 | 15 |
| BSA (mg/ml) | 100 | 0.1 | 1000 | 3 |
| $MnCl_2$ | 500 mM | 2 | 250 | 12 |
| 1 × Kinase Buffer | 1× | 1× | 1 | 2970 |
| Total | | | | 3000 |

2. Compound Preparation:

For tested compounds, the compounds were first diluted to 1 mM by mixing 5 μL 10 mM compound stock to 454 of DMSO. These compounds were then diluted 3-fold for 10 doses. The top compound concentration was 1 mM (100×), DMSO concentration was 100%.

50 nL of compound solutions were transferred to 384-well assay plate (Corning #4512) by ECHO.

For positive control: 50 nL of 1 mM staurosporine was transferred into 384-well assay plate as positive control.

For negative control: 50 nL of DMSO was transferred into 384-well assay plate as negative control. Centrifuge the assay plate at 1,500 rpm for 1 minute.

3. Compounds were Transferred by ECHO Following the Layout Below:
   Staurosporine and test compounds 1-15: serial 3-fold dilution from 10 μM to 0.508 nM (10 doses); negative control is 6.25 ng ZAP70, 10 μM ATP & 0.4 μg/μL poly, 1% DMSO; positive control is 10 μM staurosporine, 6.25 ng ZAP70, 10 μM ATP & 0.4 μg/4 poly, 1% DMSO.
4. Prepare 2×ATP-Poly(E4Y1) mixture: 20 μM ATP, 0.8 μg/μL poly(E4Y1) in Kinase Buffer (final concentration: 10 μM ATP, 0.4 μg/4 poly(E4Y1).
5. Prepare 2×ZAP70 working solution: (2.5 ng/4) in Kinase Buffer (final Conc. was 1.25 ng/4).
6. Add 2.5 μL/well of 2×ZAP70 working solution using pipette (Thermo, 30 μL multi-channel), Centrifuge at 1,500 rpm for 1 minute.
7. Add 2.5 μL/well of 2×ATP-Poly(E4Y1) working mixture using pipette (Thermo, 30 μL multi-channel), Centrifuge at 1,500 rpm for 1 minute.
8. Incubate the assay plate at 25° C. for 60 min.
9. Add 5 μL/well ADP-GLO™ Reagent by BRAVO to stop the kinase reaction and deplete the unconsumed ATP after 1 hour. Centrifuge at 1,500 rpm for 1 minute. Incubate at 25° C. for 40 min.
10. Add 10 μL of Kinase Detection Reagent by BRAVO to convert ADP to ATP. Centrifuge at 1,500 rpm for 1 minute. Incubate at 25° C. for 40 min.
11. Record luminescence signal on an Envision plate reader (384-USL).
12. Process data using XL-fit. Inhibition %=[1−(test well−Negative control)/(positive control−Negative control)]*100%.

5. Data Analysis

The percent (%) inhibition at each concentration of compound is calculated based on and relative to the signal in the Negative and Positive control wells contained within each assay plate. The Negative control wells served as 0% inhibition, and the Positive control wells served as 100% inhibition. The concentrations and % inhibition values for tested compounds are plotted and the concentration of compound required for 50% inhibition (IC50) is determined with a Three-parameter logistic dose response equation. The endpoint value (IC50) for the reference peptide/compound is evaluated in each experiment as a quality control measure. If the endpoint value was within 3-fold of the expected value then the experiment was deemed acceptable.

Biology Example 6 LCK Biochemical Assay Protocol

This example used the ADP-GLO™ Kinase Assay to measure the effect of potential HPK1 inhibitor compounds on Lck kinase activity. An exemplary experimental setting is described below, though minor adjustments can be made in individual assays.

Materials and Equipments

1. Reagents:

| Description | Vendor | Catalog |
|---|---|---|
| LCK | Sigma Chem | Z03-10G |
| Poly(E4Y1) | Sigma Chem | P61-58 |
| Ultra-pure ATP | Promega | From ADP-Glo kinase Kit |
| ADP-GLO ™ kinase Kit | Promega | V9102 |
| 10% BSA stock solution | Miltynyl Biotec | 130-091-376 |
| DTT | Sigma | 3483-12-3 |
| DMSO | Sigma | D5879 |
| $MnCl_2$ | Sigma | M5505 |
| $MgCl_2$ | Sigma | M1028 |
| Tris base | Sigma | T1503 |

2. Equipments & Supplies:

| Equipments | Source | Cat# |
|---|---|---|
| Echo Qualified 384-Well Low Dead Volume Microplate | Perkinelmer | LP0200 |
| Assay plate, Corning ® 384 well microplate, low volume | Corning | C4512 |
| MICROPLATE, 96 WELL, PP, V-BOTTOM | Greiner | 651201 |
| Bravo 10 μL tips | Axygen | 301-78-401 |
| Bravo 30 μL tips | Axygen | 301-78-301 |
| ECHO | Perkinelmer | — |
| Envision | PerkinElmer | — |
| BRAVO | — | — |
| Water system | Millipore Milli-Q Reference system | — |
| Incubator | Cimo | SPX-60BSH-II |
| E1-clipTip multi-channel electric pipette (1-30 μL) | Thermo Fisher | 4671030BT |

3. Procedures
   1. LCK Kinase Buffer Preparation:
      Freshly adding DTT and BSA to Buffer (Final Conc.: 40 mM Tris pH7.5; 20 mM $MgCl_2$, 0.1 mg/ml BSA, 50 μM DTT, 2 mM $MnCl_2$).

| Reagent | [Stock] | [Final] (mM) | Fold | Add (μL) |
|---|---|---|---|---|
| DTT (mM) | 10 | 0.05 | 200 | 15 |
| BSA (mg/ml) | 100 | 0.1 | 1000 | 3 |
| $MnCl_2$ | 500 mM | 2 | 250 | 12 |
| 1 × Kinase Buffer | 1× | 1× | 1 | 2970 |
| Total | | | | 3000 |

2. Compound Preparation:
      For tested compounds, the compounds were first diluted to 1 mM by mixing 5 μL 10 mM compound stock to 45 μL of DMSO. The compounds solutions were then serially diluted 3-fold for 10 doses. The top compound concentration was 1 mM (100×), DMSO concentration was 100%.

For positive control: staurosporine was diluted to 300 μM by mixing 3 μL of 10 mM stock to 97 μL DMSO.

50 nL of compound solutions and 300 μM staurosporine were transferred to 384-well assay plate (Corning #4512) by BRAVO.

For negative control: 50 nL of DMSO was transferred into 384-well assay plate as negative control. Centrifuge the assay plate at 1,500 rpm for 1 minute.

3. Compounds were Transferred by ECHO Following the Layout Below: Staurosporine and test compounds 1-15: serial 3-fold dilution from 10 μM to 0.508 nM (10 doses); negative control is 7 ng LCK, 20 μM ATP & 0.4 μg/μL poly, 1% DMSO; positive control is 3 μM staurosporine, 7 ng LCK, 20 μM ATP&0.4 μg/μL poly, 1% DMSO.
4. Prepare 2×ATP-Poly(E4Y1) mixture: 40 μM ATP, 0.8 μg/μL poly(E4Y1) in Kinase Buffer (final concentration: 20 μM ATP, 0.4 μg/μL poly(E4Y1).
5. Prepare 2×LCK working solution: (2.8 ng/μL) in Kinase Buffer (final Conc. was 1.4 ng/4).
6. Add 2.5 μL/well of 2×LCK working solution using pipette (Thermo, 30 μL multi-channel), Centrifuge at 1,000 rpm for 1 minute.
7. Add 2.5 μL/well of 2×ATP-Poly(E4Y1) working mixture using pipette (Thermo, 30 μL multi-channel), Centrifuge at 1,000 rpm for 1 minute.
8. Incubate the assay plate at 25° C. for 60 min.
9. Add 5 μL/well ADP-GLO™ Reagent by BRAVO to stop the kinase reaction and deplete the unconsumed ATP after 1 hour. Centrifuge at 1,000 rpm for 1 minute. Incubate at 25° C. for 40 min.
10. Add 10 μL of Kinase Detection Reagent by BRAVO to convert ADP to ATP. Centrifuge at 1,000 rpm for 1 minute. Incubate at 25° C. for 30 min.
11. Record luminescence signal on an Envision plate reader (384-USL).
12. Process data using XL-fit. Inhibition %=(Negative control-test well)/(Negative control-positive control)×100%.

4. Data Analysis

The percent (%) inhibition at each concentration of compound is calculated based on and relative to the signal in the Negative and Positive control wells contained within each assay plate. The Negative control wells served as 0% inhibition, and the Positive control wells served as 100% inhibition. The concentrations and % inhibition values for tested compounds are plotted and the concentration of compound required for 50% inhibition (IC50) is determined with a Three-parameter logistic dose response equation. The endpoint value (IC50) for the reference peptide/compound is evaluated in each experiment as a quality control measure. If the endpoint value was within 3-fold of the expected value then the experiment was deemed acceptable.

Biology Example 7 MAP4K3 Protein Kinase Assay

This example provides an assay protocol for measuring the phosphorylation of a peptide substrate by the protein kinase MAP4K3.

Briefly, MAP4K3, its substrate, and cofactors (ATP and $Mg^{2+}$) are combined in a well of a microtiter plate and incubated for 5 hours at 25° C. At the end of the incubation, the reaction is quenched by the addition of an EDTA-containing buffer. Substrate and product are separated and quantified electrophoretically using the microfluidic-based LabChip 3000 Drug Discovery System from Caliper Life Sciences.

For this assay, the MAP4K3 substrate is FAM-GAGRLGRDKYKTLRQIRQ-NH2 (FAM is carboxyfluorescein). The peptide substrate is preferably >98% pure by Capillary Electrophoresis.

A typical assay setup and condition is provided below.

1. To a well of a 384-well plate, add 5 μL of 2× enzyme buffer (or control).
2. Add 100 nL of 100× compound. Enzyme and compound may be pre-incubated at this time if desired.
3. Add 5 μL of 2× substrate buffer.
4. Incubate plate at 25° C. for 5 hours.
5. Terminate reaction by adding 40 μL of 1.25× stop buffer.
6. Create job on a Caliper LabChip® 3000 Drug Discovery System using the values in the table below.

Separation Conditions for a 12 Sipper Chip

| | |
|---|---|
| Initial Delay Sip Time | 50 sec |
| Post Sample Buffer Sip Time | 40 sec |
| Post Dye Buffer Sip Time | 40 sec |
| Sample Sip Time | 0.2 sec |
| Final Delay Sip Time | 120 sec |
| Dye Sip Time | 0.2 sec |
| Pressure | −2 psi |
| Downstream Voltage | −3000 volts |
| Upstream Voltage | −800 volts |

7. Load the plate and start electrophoresis using blue laser (480 nm) for excitation and green CCD (520 nm) for detection (CCD2).

The above assay is run at the following reaction condition: 5 total hours; at 25° C., in the presence of 20 mM of 100% inhibitor EDTA.

Final assay reaction mixture is: 100 mM HEPES, pH 7.5; 0.1% BSA; 0.01% Triton X-100; 1 mM DTT; 5 mM $MgCl_2$, 10 uM Sodium Orthovanadate, 10 uM Beta-Glycerophosphate 20 uM ATP; 1% DMSO (from compound); 0.5 uM FAM-GAGRLGRDKYKTLRQIRQ-NH2; 0.5 nM MAP4K3 Enzyme.

It should be noted that specific activity of MAP4K3 vary from lot-to-lot, and enzyme concentration may need to be adjusted to yield ~10-20% conversion of substrate to product.

Substrate and product peptides present in each sample are separated electrophoretically using the LabChip 3000 capillary electrophoresis instrument. As substrate and product peptides are separated, two peaks of fluorescence are observed. Change in the relative fluorescence intensity of the substrate and product peaks is the parameter measured, reflecting enzyme activity. Capillary electrophoregramms (RDA acquisition files) are analyzed using HTS Well Analyzer software (Caliper Life Sciences). The kinase activity in each sample is determined as the product to sum ratio (PSR): P/(S+P), where P is the peak height of the product peptide, and S is the peak height of the substrate peptide.

For each compound, enzyme activity is measured at various concentrations (12 concentrations of compound spaced by 3× dilution intervals). Negative control samples (0%-inhibition in the absence of inhibitor) and positive control samples (100%-inhibition, in the presence of 20 mM EDTA) are assembled in replicates of four and are used to calculate %-inhibition values for each compound at each concentration.

Percent inhibition ($P_{inh}$) is determined using following equation:

$$P_{inh}=(PSR_{0\%}-PSR_{inh})/(PSR_{0\%}-PSR_{100}\%)*100,$$

where $PSR_{inh}$ is the product sum ratio in the presence of inhibitor, $PSR_0\%$ is the average product sum ration in the absence of inhibitor, and $PSR_{100\%}$ is the average product sum ratio in 100%-inhibition control samples.

The IC50 values of inhibitors are determined by fitting the inhibition curves (Pinhversus inhibitor concentration) by 4 parameter sigmoidal dose-response model using XLfit 4 software (IBDS).

Certain materials & buffers used in the assay are listed below for reference value.

| ITEM | VENDOR | PART NUMBER |
|---|---|---|
| Enzyme | | |
| MAP4K3 | Invitrogen | Invitrogen-PV6349-1763523 |
| Substrate | | |
| FAM-GAGRLGRDKYKTLRQIRQ-NH2 | Nanosyn | Custom synthesis |
| Control Inhibitor | | |
| «Staurosporine» | «LKT» | «S7600» |
| Buffer Components | | |
| HEPES, free acid | Calbiochem | 391338 |
| HEPES, sodium salt | Calbiochem | 391333 |

-continued

| ITEM | VENDOR | PART NUMBER |
|---|---|---|
| Triton X-100 | Sigma | T8787 |
| BSA | Sigma | A3059 |
| Magnesium Chloride | Fluka | 63020 |
| ATP disodium salt | Sigma | A7699 |
| DTT (Cleland's Reagent) | Calbiochem | 233153 |
| Sodium Orthovanadate | Sigma | S6508 |
| Beta-Glycerophosphate | Calbiochem | 35675 |
| EDTA, disodium salt, dihydrate | VWR | VW1474-01 |
| DMSO | VWR | BJ081-4 |
| Coating Reagent 3 | Caliper Life Sci. | 760050 |
| Sodium Hydroxide, 50% | VWR | VW3246-1 |
| Hydrochloric Acid, concentrated | JT Baker | 9530-33 |
| Sodium Carbonate | Mallinckrodt | 7521 |
| Sodium Bicarbonate | Sigma | S-6297 |

Biology Example 8 Compound Efficacy Study on IL2 & IFN-γ Released by Human Pan T Cell This example is an assay method that can be used to determine compound effects on IL2 & IFN-γ release using pan T cells and ELISA assay format.

Materials and Equipments

1. Reagents:

| Name | Source | Cat# |
|---|---|---|
| RPMI 1640 | ATCC | 30-2001 |
| FBS | Gibco | 10099141 |
| DMSO | Sigma | D8418 |
| Pen/Strep (100×) | Gibco | 15140122 |
| No essential amino assay solution | Gibco | 11140050 |
| Human IL-2 ELISA Set A (containing Anti-Human IL-2 monoclonal antibody (mAb), Biotinylated Anti-Human IL-2 mAb, Streptavidin-horseradish peroxidase conjugate (Sav-HRP), Recombinant human IL-2) | BD | |
| ELISA Set B (containing Coating Buffer, Assay Diluent, Substrate Reagents A and B, Stop Solution and 20 × Wash Buffer) | BD | 550534 |
| Human IFN-γ ELISA Set A (containing Anti-Human IFN-γ mAb, Biotinylated Anti-Human IFN-γ mAb, Streptavidin-horseradish peroxidase conjugate (Sav-HRP), Recombinant human IFN-γ) | BD | 555142 |
| Beta-Mercaptoethanol | Gibco | 21985023 |
| PMA | Sigma | P8139-1mg |
| lonomycin | Sigma | 407951-1MG |
| Anti-human CD3 | BioXcell | BE0001-2 |
| Anti-human CD28 | BioXcell | BE0291 |
| Pan T isolate kit | MACS | 130-096-535 |
| LS Separation columns | MACS | 130-042-401 |
| auto MACS ® Rinsing Solution | MACS | 130-091-222 |
| BSA | Sigma | B2064 |
| 0.5M EDTA | ThermoFisher | 15575020 |
| PBS | GE Healthcare Life Sciences | SH30256.01 |
| PE anti-CD3 | BD | 555333 |
| FITC anti-CD4 | BD | 555346 |
| BV421 anti-CD8 | BD | 562428 |
| Human PBMC | Allcells | PB007-3 PB006-C |

2. Equipments & Supplies:

| Name | Source | Cat# |
|---|---|---|
| MICROPLATE, 96 WELL, PP, V-BOTTOM | Greiner | 651201 |
| 96-well cell plates | Greiner | 655180 |
| Flat bottom 96-well plate (High binding plate) | Greiner | 655061 |
| 96-well supernatant dilution plate | Corning | 3599 |
| CTG assay 384 microplate | PerkinElmer | 6007290 |
| Envision plate reader | PerkinElmer | — |
| Cell Incubator | Thermo Fisher | — |
| Automated cell counter | Count star-IC-1000 | — |
| Ex-50 plate washer | BioTek | ELx50/8 |
| Centrifuge | Thermo Centrifuge ST 40R | — |
| Water system | Millipore Milli-Q Reference system | — |

3. Procedures

Procedures for Pan T isolation and Reagent preparation (Day 0):

1. Cell Growth Medium:
   RPMI1640: ATCC, Cat #30-2001
   10% FBS: Gibco, Cat #10099141
   1% Pen-Strep: Gibco, Cat #15140122
   1% Non-essential amino: Gibco, Cat #11140050
   Beta-Mercaptoethanol: Gibco, Cat #21985023
2. Pan T Isolation Buffer Preparation:
   Prepare a solution containing phosphate-buffered saline (PBS), pH 7.2, 0.5% bovine serum albumin (BSA), and 2 mM EDTA by diluting MACS® BSA Stock Solution (#130-091-376) 20 times with autoMACS® Rinsing Solution. Keep buffer at 4° C. Degas buffer before use, as air bubbles could block the column.

| Contents | [Stock] | [Final Conc.] | Fold | Vol. (mL) |
|---|---|---|---|---|
| BSA | 10% | 0.5% | 20 | 5 mL |
| EDTA | 0.5M | 2 mM | 250 | 0.4 mL |
| PBS, pH 7.2 | 1× | 1× | 1 | 94.6 mL |
| Total | | | | 100 mL |

3. Thawing of Frozen PBMC
   1) Pre-heat medium at 37° C. water bath.
   2) Rapidly thaw cells in 37° C. water bath.
   3) Add the pre-warmed medium into 15 mL tube. Transfer cells to the tube.
   4) 300×g centrifuge for 8 min. (centrifuge increase 0, decrease 0).
   5) Wash the PBMC using Rinsing buffer.
   6) Centrifuge PBMC at 300×g for 8 min, wash it twice (centrifuge increase 9, decrease 1).
   7) Resuspend the cells with Pan T cells isolation buffer and count cells number.
4. Pan T Cells Isolation:

Cell Staining with Microbead Cocktail
   1) Prepare cells and determine cell number. Filter cells by 70 μm cell strainer.
   2) Resuspend cell pellet in 40 μL of buffer per $10^7$ total cells.
   3) Add 10 μL of Pan T Cell Biotin-Antibody Cocktail per $10^7$ total cells.
   4) Mix well and incubate for 10 minutes in the refrigerator (ice).
   5) Add 30 μL of buffer per $10^7$ total cells.
   6) Add 20 μL of Pan T Cell MicroBead Cocktail per $10^7$ total cells.
   7) Mix well and incubate for 15 minutes in the refrigerator (ice).
   8) Proceed to subsequent magnetic cell separation.

Note: a. Work fast, keep cells cold, and use pre-cooled solutions (2-8° C.). b. Volumes for magnetic labeling given are for up to 10' total cells. When working with fewer cells, use the same volumes as indicated. c. When working with higher cell numbers, scale up all reagent volumes and total volumes accordingly. d. For optimal performance it is important to obtain a single-cell suspension before magnetic labeling.

Subsequent Manual Cell Separation:
   1) Place LS Column in the magnetic field of a suitable MACS Separator. For details refer to the respective MACS Column data sheet.
   2) Prepare column by rinsing with 3 mL of buffer.
   3) Apply cell suspension onto the column. Collect flow-through, which represents the enriched T cells.
   4) Wash column with 5 mL of buffer. Collect unlabeled cells that pass through, representing the enriched T cells.
      Reminder: Always wait until the column reservoir is empty before proceeding to the next step.
5. Pan T Cell FACS:
   1) Take out 50 μL of PBMC and Pan T cells to FACS tubes respectively.
   2) Incubate cells with anti-human CD3/CD4/CD8 antibodies (1 μL/1 μL/1 μL/tube) for 20 min at 4° C. For unstained control, incubate cells with FACS staining buffer.
   3) Wash 2 times with cold staining buffer (PBS with 0.2% BSA and 1 mM EDTA).
   4) Run FACS. Gate $CD3^+$, $CD3^+CD4^+$, and $CD3^+CD8^+$ population for % analysis.
   5) If the purity of Pan T cells is higher than 90%, dilute cell suspension to 1 million cells/mL with the appropriate volume of Cell Culture Media.
   6) Dispense the cell suspension into a sterile, disposable reservoir for future use.

Procedures for Preparation of Compounds and Anti-Human CD3/CD28 (Day 0):

1. Compound Preparation

Compound Serial Dilution (Source Plate 1000×)
   Compounds are solubilized in 100% DMSO to a concentration of 10 mM. Then they were 3-fold serially diluted to 8-point doses.

4× Compound Dose Preparation (Inter Plate: Corning-3599):
   Prepare 4× compound solution in culture medium. Pipet up and down. For the ZPE control, prepare 0.4% DMSO (4×) in culture medium. For the HPE control, prepare 0.4 uM of RGT003-026 (4×) in culture medium.

2. Anti-Human CD3 (Stock Conc. 6.76 mg/ml): Stored at 4° C.
   1) Dilute anti-human CD3 with PBS to final conc. of 0.5 μg/mL.
   2) Add 50 μL/well of CD3 to each well, except for the positive and negative control wells. The positive and negative control wells do not have CD3/CD28 stimulation.
   3) Incubate at 37° C. in a 5% $CO_2$ incubator for 2 hours.
   4) Remove the 50 μL antibody solution from cell culture plate. Rinse each well twice with 200 μL of sterile PBS each time.

3. Anti-Human CD28 (4×) Preparation
The antibody was diluted with culture medium from stock concentration of 11.07 mg/mL to 2 μg/mL (4×).
4. PMA/Inomycin Preparation (4×)
1) Dilute PMA to 400 ng/mL (8×) in medium.
2) Dilute Inomycin to 8 μM (8×) in medium.
3) Mix equal volume of PMA with lonomycin to get 4× mixture.

Procedures for Stimulating Cell (Day 0)
1. Transfer 1×10[5] cells/well (100 μL/well) of the cell suspension into 96-well plate (cell plate: greiner-655180).
2. Add 50 μL/well of anti-human CD28 for the tested cpds and ZPE/HPE controls. For the positive or negative control, add 50 μL/well of 4×PMA/Inomycin solution or culture medium, respectively.
3. Add 50 μL/well of compounds into cell plate according to the plate map shown below. For ZPE/HPE controls, add 50 μL/well of 0.4% DMSO solution or 0.4 μM of RGT003-026 (4×), respectively. For the positive or negative control, add 50 μL/well of culture medium.
4. Incubate the plate for 48 hours.

Procedures for IL-2 & IFN-γ ELISA:
Day 1: Coating Plates:
1) Coat micro-wells with 100 μL per well of IL-2 & IFN-γ Capture Antibody diluted in Coating Buffer. For recommended antibody coating dilution, see lot-specific Instruction/Analysis Certificate. Seal plate and incubate overnight at 4° C.

Day 2: Samples Collection:
1) After incubation in a 37° C., 5% $CO_2$ incubator for 48 hours, centrifuge the cell plates at 1,000 rpm for 10 min. Collect 100 μL/well supernatant and then perform IL-2 and IFN-γ ELISA assay. The supernatant can be stored at −80° C. and IL-2 and IFN-γ ELISA assay can be performed the following day. Supernatant may need to be diluted 30 to 40 folds to ensure the assay does not exceed the linear range of IL-2 and IFN-γ standard curve.
2) Add new medium (contain anti-CD28, P/I and compounds) to the plate, 100 μL/well.
3) Plate Map:

Day 3-4: IL-2 & IFN-γ ELISA:
1) Aspirate wells and wash 3 times with ≥300 μL/well Wash Buffer. After the last wash, invert plate and blot on absorbent paper to remove any residual buffer.
2) Block plates with ≥200 μL/well Assay Diluent. Incubate at RT for 1 hour.
3) Aspirate/wash as in step 2.
4) Prepare standards in Assay Diluent.

IL-2 Standard Stock Preparation:
add 1 mL deionized water to vial (235 ng/vial), the stock Conc. is 235 ng/mL. Aliquot standard stock at 10 μL/vial, freeze at −80° C.

IFN-γ Standard Stock Preparation:
add 1 mL deionized water to vial (145 ng/vial), the stock Conc. is 145 ng/mL. Aliquot standard stock at 10 μL/vial, freeze at −80 C.

Preparation of Standard Curve for IL-2/IFNγ:
Dilute the standard sample to top concentration of 500 pg/mL. Then run 2-fold serial dilution to 10-point doses (including the blank control). Transfer different concentrations of standards to ELISA plate, 100 μL/well.
1) Pipette 100 μL of each standard, sample, and control into appropriate wells. Seal plate and incubate for 2 hours at RT.
2) Aspirate/wash as in step 2, but with 5 total washes.
3) Add 100 μL of Working Detector (Detection Antibody+SAv-HRP reagent) to each well. Seal plate and incubate for 1 hour at RT.
4) Aspirate/wash as in step 2, but with 7 total washes. NOTE: In this final wash step, soak wells in wash buffer for 30 seconds to 1 minute for each wash.
5) Add 100 μL of Substrate Solution to each well. Incubate plate (without plate sealer) for 30 minutes at room temperature in the dark.
6) Add 50 μL of Stop Solution to each well.
7) Read absorbance at 450 nm within 30 minutes of stopping reaction. OD450 nm was normalized to the OD value at 570 nm.

4. Data Analysis:
For the biochemical assays, the percent (%) inhibition at each concentration of compound is calculated based on and relative to the signal in the HPE and ZPE wells contained within each assay plate. The HPE wells were deemed 100% effective, and the ZPE wells that didn't contain any compound but rather DMSO (final concentration=0.1%) were deemed 0% effective.

For the cellular assay, the response of IL-2 or IFN-γ (data not shown) over DMSO control at each concentration of compound is calculated. See Table 2. EC2× presents the concertation of compound that give 200% response (2 folds), and EC50 is calculated by using GraphPad Prism.

The biochemical and cellular data obtained from exemplary compounds are listed in the Tables 1 and 2 below.

TABLE 1

| Example | | HPK1 IC50 (nM) Relative | | JAK3 IC50 (nM) Relative | | JAKs/HPK1 IC50 Ratio | |
|---|---|---|---|---|---|---|---|
| Number | Compound Structure | B* | N* | B* | N* | B* | N* |
| 1 | (1-(5-Chloro-2-((6-methoxy-2-methyl-1,2,3,4-tetrahydroisoquinolin-7-yl)amino)pyrimidin-4-yl)-1H-indol-3-yl)dimethylphosphine oxide | ++++ | ++++ | + | + | 285 | >558 |
| 2 | N-(5-chloro-4-(1H-indol-1-yl)pyrimidin-2-yl)-6-methoxy-2-methyl-1,2,3,4-tetrahydroisoquinolin-7-amine | ++++ | ++++ | | + | | 642 |
| 3 | N-(4-(1H-indol-1-yl)-5-(trifluoromethyl)pyrimidin-2-yl)-6-methoxy-2-methyl-1,2,3,4-tetrahydroisoquinolin-7-amine | ++++ | | + | | 408 | |
| 4 | N-(5-Chloro-4-(indolin-1-yl)pyrimidin-2-yl)-6-methoxy-2-methyl-1,2,3,4-tetrahydroisoquinolin-7-amine | ++++ | ++++ | + | +++ | 337 | 601 |
| 5 | N-(5-chloro-4-(3,4-dihydroisoquinolin-2(1H)-yl)pyrimidin-2-yl)-6-methoxy-2-methyl-1,2,3,4-tetrahydroisoquinolin-7-amine | +++ | | | | | |

TABLE 1-continued

| Example Number | Compound Structure | HPK1 IC50 (nM) Relative B* | N* | JAK3 IC50 (nM) Relative B* | N* | JAKs/HPK1 IC50 Ratio B* | N* |
|---|---|---|---|---|---|---|---|
| 6 | N-(5-chloro-4-(3,4-dihydroquinolin-1(2H)-yl)pyrimidin-2-yl)-6-methoxy-2-methyl-1,2,3,4-tetrahydroisoquinolin-7-amine | ++++ | | + | | | |
| 7 | N-(5-chloro-4-(2,3-dihydro-4H-benzo[b][1,4]oxazin-4-yl)pyrimidin-2-yl)-6-methoxy-2-methyl-1,2,3,4-tetrahydroisoquinolin-7-amine | ++++ | | + | | >118 | |
| 8 | 1-(5-Chloro-2-((6-methoxy-2-methyl-1,2,3,4-tetrahydroisoquinolin-7-yl)amino)pyrimidin-4-yl)-N,N-dimethyl-1H-indole-3-carboxamide | ++++ | ++++ | | + | | >2457 |
| 9 | N-(4-(1H-benzo[d]imidazol-1-yl)-5-chloropyrimidin-2-yl)-6-methoxy-2-methyl-1,2,3,4-tetrahydroisoquinolin-7-amine | ++++ | ++++ | | + | | 571 |
| 10 | N-(4-(1H-indol-1-yl)-5-(trifluoromethyl)pyrimidin-2-yl)-6-methoxy-2-methyl-1,2,3,4-tetrahydroisoquinolin-7-amine | ++++ | | + | | >298 | |
| 11 | N-(5-Chloro-4-(3-fluoro-1H-indol-1-yl)pyrimidin-2-yl)-6-methoxy-2-methyl-1,2,3,4-tetrahydroisoquinolin-7-amine | ++++ | | | | | |
| 12 | N-(5-chloro-4-(4-chloroindolin-1-yl)pyrimidin-2-yl)-6-methoxy-2-methyl-1,2,3,4-tetrahydroisoquinolin-7-amine | +++ | | | | | |
| 13 | N-(5-chloro-4-(5-chloroindolin-1-yl)pyrimidin-2-yl)-6-methoxy-2-methyl-1,2,3,4-tetrahydroisoquinolin-7-amine | ++++ | | ++ | | 62 | |
| 14 | N-(5-Chloro-4-(indolin-1-yl)pyrimidin-2-yl)-2-methyl-1,2,3,4-tetrahydroisoquinolin-7-amine | ++++ | ++++ | ++++ | ++++ | 6 | 11 |
| 15 | 6-Chloro-N-(5-chloro-4-(indolin-1-yl)pyrimidin-2-yl)-2-methyl-1,2,3,4-tetrahydroisoquinolin-7-amine | ++++ | | + | | 174 | |
| 16 | N-(5-chloro-4-(2,3-dihydro-1H-pyrrolo[3,2-b]pyridin-1-yl)pyrimidin-2-yl)-6-methoxy-2-methyl-1,2,3,4-tetrahydroisoquinolin-7-amine | ++++ | | + | | | |
| 17 | N-(5-chloro-4-(2,3-dihydro-1H-pyrrolo[2,3-b]pyridin-1-yl)pyrimidin-2-yl)-6-methoxy-2-methyl-1,2,3,4-tetrahydroisoquinolin-7-amine | +++ | | | | | |
| 18 | N-(5-chloro-4-(6-chloroindolin-1-yl)pyrimidin-2-yl)-6-methoxy-2-methyl-1,2,3,4-tetrahydroisoquinolin-7-amine | ++++ | | + | | >446 | |
| 19 | N-(5-chloro-4-(indolin-1-yl)pyrimidin-2-yl)-2-methoxy-6-methyl-5,6,7,8-tetrahydro-1,6-naphthyridin-3-amine | ++++ | ++++ | ++ | +++ | | |
| 20 | N-(5-chloro-4-(5-fluoroindolin-1-yl)pyrimidin-2-yl)-6-methoxy-2-methyl-1,2,3,4-tetrahydroisoquinolin-7-amine | ++++ | | +++ | | 88 | |
| 21 | N-(5-chloro-4-(6-fluoroindolin-1-yl)pyrimidin-2-yl)-6-methoxy-2-methyl-1,2,3,4-tetrahydroisoquinolin-7-amine | ++++ | | + | | 280 | |
| 22 | N-(5-chloro-4-(indolin-1-yl)pyrimidin-2-yl)-2-isopropyl-6-methoxy-1,2,3,4-tetrahydroisoquinolin-7-amine | ++++ | | + | | 223 | |
| 23 | N-(5-chloro-4-(indolin-1-yl)pyrimidin-2-yl)-6-methoxy-1,2,3,4-tetrahydroisoquinolin-7-amine | ++++ | | +++ | | 59 | |
| 24 | N-(5-Chloro-4-(1H-indazol-1-yl)pyrimidin-2-yl)-6-methoxy-2-methyl-1,2,3,4-tetrahydroisoquinolin-7-amine | ++++ | | + | | 79 | |
| 25 | N-(5-Chloro-4-(3,3-dimethylindolin-1-yl)pyrimidin-2-yl)-6-methoxy-2-methyl-1,2,3,4-tetrahydroisoquinolin-7-amine | ++++ | | +++ | | 218 | |
| 26 | 1-(7-((5-Chloro-4-(indolin-1-yl)pyrimidin-2-yl)amino)-6-methoxy-3,4-dihydroisoquinolin-2(1H)-yl)-2-(dimethylamino)ethan-1-one | ++++ | | | | | |
| 27 | 2-(7-((5-Chloro-4-(indolin-1-yl)pyrimidin-2-yl)amino)-6-methoxy-3,4-dihydroisoquinolin-2(1H)-yl)ethan-1-ol | ++++ | | | | | |
| 28 | 1-(5-Chloro-2-((6-methoxy-2-methyl-1,2,3,4-tetrahydroisoquinolin-7-yl)amino)pyrimidin-4-yl)-N,N-dimethyl-1H-indole-2-carboxamide | + | | | | | |
| 29 | N-(5-Chloro-4-(2,3-dihydro-1H-pyrrolo[3,2-b]pyridin-1-yl)pyrimidin-2-yl)-2-methoxy-6-methyl-5,6,7,8-tetrahydro-1,6-naphthyridin-3-amine | ++++ | ++++ | ++ | +++ | 223 | 286 |
| 31 | 1-(5-Chloro-2-((6-methoxy-2-methyl-1,2,3,4-tetrahydroisoquinolin-7-yl)amino)pyrimidin-4-yl)-2,3-dihydroimidazo[1,2-a]pyridin-5(1H)-one | +++ | | + | | 31 | |
| 32 | 1-(5-Chloro-2-((6-methoxy-2-methyl-1,2,3,4-tetrahydroisoquinolin-7-yl)amino)pyrimidin-4-yl)indoline-3-carboxylic acid | ++++ | | ++++ | | 90 | |
| 33 | 1-(5-Chloro-2-((6-methoxy-2-methyl-1,2,3,4-tetrahydroisoquinolin-7-yl)amino)pyrimidin-4-yl)indoline-3-carboxamide | ++++ | | ++++ | | 140 | |
| 34 | 1-(5-Chloro-2-((6-methoxy-2-methyl-1,2,3,4-tetrahydroisoquinolin-7-yl)amino)pyrimidin-4-yl)-1H-indole-3-carboxamide | ++++ | | ++ | | 101 | |
| 35 | 1-(5-Chloro-2-((6-methoxy-2-methyl-1,2,3,4-tetrahydroisoquinolin-7-yl)amino)pyrimidin-4-yl)-1H-indole-3-carboxylic acid | ++++ | | +++ | | 78 | |
| 36 | 6-Methoxy-2-methyl-N-(7-phenyl-7H-pyrrolo[2,3-d]pyrimidin-2-yl)-1,2,3,4-tetrahydroisoquinohn-7-amine | ++++ | ++++ | | + | | 287 |

TABLE 1-continued

| Example Number | Compound Structure | HPK1 IC50 (nM) Relative B* | HPK1 IC50 (nM) Relative N* | JAK3 IC50 (nM) Relative B* | JAK3 IC50 (nM) Relative N* | JAKs/HPK1 IC50 Ratio B* | JAKs/HPK1 IC50 Ratio N* |
|---|---|---|---|---|---|---|---|
| 37 | 6-Methoxy-2-methyl-N-(7-(pyridin-2-yl)-7H-pyrrolo[2,3-d]pyrimidin-2-yl)-1,2,3,4-tetrahydroisoquinolin-7-amine | ++++ | ++++ | | + | | 608 |
| 38 | 2-(2-((6-Methoxy-2-methyl-1,2,3,4-tetrahydroisoquinolin-7-yl)amino)-7H-pyrrolo[2,3-d]pyrimidin-7-yl)-N,N-dimethylbenzamide | +++ | ++++ | | + | | >163 |
| 39 | (2-(2-((6-Methoxy-2-methyl-1,2,3,4-tetrahydroisoquinolin-7-yl)amino)-7H-pyrrolo[2,3-d]pyrimidin-7-yl)phenyl)dimethylphosphine oxide | ++ | | + | | >18 | |
| 40 | 6-Methoxy-2-methyl-N-(7-(pyridin-3-yl)-7H-pyrrolo[2,3-d]pyrimidin-2-yl)-1,2,3,4-tetrahydroisoquinolin-7-amine | ++++ | | | | | |
| 41 | 6-Methoxy-2-methyl-N-(7-(2-methylpyridin-3-yl)-7H-pyrrolo[2,3-d]pyrimidin-2-yl)-1,2,3,4-tetrahydroisoquinolin-7-amine | ++++ | | +++ | | 30 | |
| 43 | 6-Methoxy-2-methyl-N-(9-phenyl-9H-purin-2-yl)-1,2,3,4-tetrahydroisoquinolin-7-amine | + | + | | + | | >10 |
| 44 | 2-(2-((6-Methoxy-2-methyl-1,2,3,4-tetrahydroisoquinolin-7-yl)amino)-9H-purin-9-yl)-N,N-dimethylbenzamide | + | + | | + | | >10 |
| 45 | (2-(2-((6-Methoxy-2-methyl-1,2,3,4-tetrahydroisoquinolin-7-yl)amino)-9H-purin-9-yl)phenyl)dimethylphosphine oxide | + | | | | | |
| 46 | N-(6-methoxy-2-methyl-1,2,3,4-tetrahydroisoquinolin-7-yl)-8-phenyl-7,8-dihydro-6H-pyrimido[5,4-b][1,4]oxazin-2-amine | +++ | | | | | |
| 47 | (2-(2-((6-Methoxy-2-methyl-1,2,3,4-tetrahydroisoquinolin-7-yl)amino)-6H-pyrimido[5,4-b][1,4]oxazin-8(7H)-yl)phenyl)dimethylphosphine oxide | +++ | | + | | >22 | |
| 48 | N-(5-chloro-4-(isoquinolin-4-yl)pyrimidin-2-yl)-6-methoxy-2-methyl-1,2,3,4-tetrahydroisoquinolin-7-amine | ++++ | | + | | >179 | |
| 49 | N-(5-chloro-4-(quinolin-4-yl)pyrimidin-2-yl)-6-methoxy-2-methyl-1,2,3,4-tetrahydroisoquinolin-7-amine | +++ | | | | | |
| 50 | (5-(3-Ethyl-1H-pyrrolo[2,3-b]pyridin-5-yl)-2-methylphenyl)dimethylphosphine | ++++ | ++++ | + | + | 163 | 101 |
| 51 | (5-(3-Ethyl-1H-pyrrolo[2,3-b]pyridin-5-yl)-2-fluorophenyl)dimethylphosphine oxide | ++++ | | + | | 51 | |
| 52 | (2-Chloro-5-(3-ethyl-1H-pyrrolo[2,3-b]pyridin-5-yl)phenyl)dimethylphosphine oxide | ++++ | | | | | |
| 53 | (3-(3-Ethyl-1H-pyrrolo[2,3-b]pyridin-5-yl)phenyl)dimethylphosphine oxide | +++ | | | | | |
| 54 | (5-(3-Ethyl-1H-pyrrolo[2,3-b]pyridin-5-yl)-2-methoxyphenyl)dimethylphosphine oxide | +++ | | | | | |
| 55 | (5-(3-Ethyl-1H-pyrrolo[2,3-b]pyridin-5-yl)-2-hydroxyphenyl)dimethylphosphine oxide | ++++ | | +++ | | 20 | |
| 56 | (3-(3-Ethyl-1H-pyrrolo[2,3-b]pyridin-5-yl)-5-methylphenyl)dimethylphosphine oxide | ++ | | | | | |
| 57 | (3-Amino-5-(3-ethyl-1H-pyrrolo[2,3-b]pyridin-5-yl)phenyl)dimethylphosphine oxide | ++++ | | ++ | | 22 | |
| 58 | N-(2-(dimethylphosphoryl)-4-(3-ethyl-1H-pyrrolo[2,3-b]pyridin-5-yl)phenyl)acetamide | ++++ | | +++ | | 4 | |
| 59 | N-(2-bromo-4-(3-ethyl-1H-pyrrolo[2,3-b]pyridin-5-yl)phenyl)acetamide | +++ | | | | | |
| 60 | (2-Amino-3-(3-ethyl-1H-pyrrolo[2,3-b]pyridin-5-yl)-6-fluorophenyl)dimethylphosphine oxide | ++++ | | + | | 25 | |
| 61 | (2-(Difluoromethyl)-5-(3-ethyl-1H-pyrrolo[2,3-b]pyridin-5-yl)phenyl)dimethylphosphine oxide | +++ | | + | | 15 | |
| 62 | (3-(3-Ethyl-1H-pyrrolo[2,3-b]pyridin-5-yl)-2-fluoro-6-methylphenyl)dimethylphosphine oxide | ++++ | | + | | 54 | |
| 63 | (5-(3-Ethyl-1H-pyrrolo[2,3-b]pyridin-5-yl)-2-(oxazol-2-yl)phenyl)dimethylphosphine oxide | +++ | | + | | 19 | |
| 64 | (6-(3-Ethyl-1H-pyrrolo[2,3-b]pyridin-5-yl)-3-methylpyridin-2-yl)dimethylphosphine oxide | ++++ | | + | | 44 | |
| 65 | (2-((Dimethylamino)methyl)-5-(3-ethyl-1H-pyrrolo[2,3-b]pyridin-5-yl)phenyl)dimethylphosphine oxide | ++ | | + | | >10 | |
| 66 | 1-(2-(Dimethylphosphoryl)-4-(3-ethyl-1H-pyrrolo[2,3-b]pyridin-5-yl)phenyl)pyrrolidin-2-one | +++ | | + | | 3 | |
| 67 | 2-(Dimethylphosphoryl)-4-(3-ethyl-1H-pyrrolo[2,3-b]pyridin-5-yl)benzamide | +++ | | + | | 10 | |
| 68 | N-(3-(dimethylphosphoryl)-5-(3-ethyl-1H-pyrrolo[2,3-b]pyridin-5-yl)phenyl)acetamide | ++ | | + | | 2 | |
| 69 | (2-Amino-5-(2-chloro-3-ethyl-1H-pyrrolo[2,3-b]pyridin-5-yl)phenyl)dimethylphosphine oxide | ++++ | ++++ | | ++ | | 52 |
| 70 | (2-Amino-5-(3-ethyl-1H-pyrrolo[2,3-b]pyridin-5-yl)phenyl)dimethylphosphine oxide | ++++ | ++++ | ++ | ++ | 70 | 50 |
| 71 | (5-(3-Ethyl-1H-pyrrolo[2,3-b]pyridin-5-yl)-2-(methylamino)phenyl)dimethylphosphine oxide | +++ | | | | | |

TABLE 1-continued

| Example Number | Compound Structure | HPK1 IC50 (nM) Relative B* | HPK1 IC50 (nM) Relative N* | JAK3 IC50 (nM) Relative B* | JAK3 IC50 (nM) Relative N* | JAKs/HPK1 IC50 Ratio B* | JAKs/HPK1 IC50 Ratio N* |
|---|---|---|---|---|---|---|---|
| 72 | Methyl 2-(dimethylphosphoryl)-4-(3-ethyl-1H-pyrrolo[2,3-b]pyridin-5-yl)benzoate | +++ | | + | | 11 | |
| 73 | (5-(3-Ethyl-1H-pyrrolo[2,3-b]pyridin-5-yl)-2-(hydroxymethyl)phenyl)dimethylphosphine oxide | +++ | | ++ | | 5 | |
| 74 | (5-(3-Ethyl-1H-pyrrolo[2,3-b]pyridin-5-yl)-2-(fluoromethyl)phenyl)dimethylphosphine oxide | +++ | | + | | 19 | |
| 75 | (3-Amino-6-(3-ethyl-1H-pyrrolo[2,3-b]pyridin-5-yl)pyridin-2-yl)dimethylphosphine oxide | ++++ | | + | | 59 | |
| 76 | (5-(3-Ethyl-1H-pyrrolo[2,3-b]pyridin-5-yl)-2-(oxetan-3-ylamino)phenyl)dimethylphosphine oxide | ++ | | + | | 4 | |
| 77 | (2-Amino-5-(3-isopropyl-1H-pyrrolo[2,3-b]pyridin-5-yl)phenyl)dimethylphosphine oxide | ++++ | | + | | 76 | |
| 78 | (5-(3-Ethyl-1H-pyrrolo[2,3-b]pyridin-5-yl)-2-(trifluoromethyl)phenyl)dimethylphosphine oxide | ++ | | + | | >15 | |
| 80 | N-(5-chloro-4-(3-(methylsulfonyl)-1H-indol-1-yl)pyrimidin-2-yl)-6-methoxy-2-methyl-1,2,3,4-tetrahydroisoquinolin-7-amine | ++++ | | + | | >1172 | |
| 81 | N-(5-chloro-4-(3-(methylsulfonyl)indolin-1-yl)pyrimidin-2-yl)-6-methoxy-2-methyl-1,2,3,4-tetrahydroisoquinolin-7-amine | ++++ | | ++ | | 444 | |
| 82 | N-(5-chloro-4-(3-((methylsulfonyl)methyl)-1H-indol-1-yl)pyrimidin-2-yl)-6-methoxy-2-methyl-1,2,3,4-tetrahydroisoquinolin-7-amine | ++++ | | + | | 800 | |
| 83 | 1-(5-Chloro-2-((6-methoxy-2-methyl-1,2,3,4-tetrahydroisoquinolin-7-yl)amino)pyrimidin-4-yl)-1H-indole-3-sulfonamide | ++++ | | + | | 232 | |
| 84 | N-(5-chloro-4-(spiro[cyclopropane-1,3'-indolin]-1'-yl)pyrimidin-2-yl)-6-methoxy-2-methyl-1,2,3,4-tetrahydroisoquinolin-7-amine | ++++ | | +++ | | 250 | |
| 85 | N-(4-(5-bromoindolin-1-yl)-5-chloropyrimidin-2-yl)-6-methoxy-2-methyl-1,2,3,4-tetrahydroisoquinolin-7-amine | ++++ | | + | | 178 | |
| 86 | (1-(5-Chloro-2-((6-methoxy-2-methyl-1,2,3,4-tetrahydroisoquinolin-7-yl)amino)pyrimidin-4-yl)indolin-5-yl)dimethylphosphine oxide | ++++ | | + | | 67 | |
| 87 | (1-(5-Chloro-2-((6-methoxy-2-methyl-1,2,3,4-tetrahydroisoquinolin-7-yl)amino)pyrimidin-4-yl)indolin-3-yl)methanol | ++++ | | +++ | | 275 | |
| 88 | (1-(5-Chloro-2-((6-methoxy-2-methyl-1,2,3,4-tetrahydroisoquinolin-7-yl)amino)pyrimidin-4-yl)indolin-3-yl)dimethylphosphine oxide | ++++ | | + | | >1292 | |
| 89 | N-(5-chloro-4-(4-methoxyindolin-1-yl)pyrimidin-2-yl)-6-methoxy-2-methyl-1,2,3,4-tetrahydroisoquinolin-7-amine | ++++ | | + | | 944 | |
| 90 | N-(5-chloro-4-(5-(difluoromethyl)indolin-1-yl)pyrimidin-2-yl)-6-methoxy-2-methyl-1,2,3,4-tetrahydroisoquinolin-7-amine | ++++ | | + | | 413 | |
| 91 | N-(5-chloro-4-(6-(difluoromethyl)indolin-1-yl)pyrimidin-2-yl)-6-methoxy-2-methyl-1,2,3,4-tetrahydroisoquinolin-7-amine | ++++ | | + | | >1500 | |
| 92 | N-(5-chloro-4-(4-(difluoromethyl)indolin-1-yl)pyrimidin-2-yl)-6-methoxy-2-methyl-1,2,3,4-tetrahydroisoquinolin-7-amine | ++++ | | + | | 393 | |
| 93 | 3-(1-(5-Chloro-2-((6-methoxy-2-methyl-1,2,3,4-tetrahydroisoquinolin-7-yl)amino)pyrimidin-4-yl)-1H-indol-3-yl)oxetan-3-ol | +++ | | + | | N.D. | |
| 94 | N-(1-(5-chloro-2-((6-methoxy-2-methyl-1,2,3,4-tetrahydroisoquinolin-7-yl)amino)pyrimidin-4-yl)-1H-indol-3-yl)methanesulfonamide | ++++ | | + | | 449 | |
| 95 | (S)-1-(5-chloro-2-((6-methoxy-2-methyl-1,2,3,4-tetrahydroisoquinolin-7-yl)amino)pyrimidin-4-yl)indoline-3-carboxylic acid | ++++ | | + | | 150 | |
| 96 | (R)-1-(5-chloro-2-((6-methoxy-2-methyl-1,2,3,4-tetrahydroisoquinolin-7-yl)amino)pyrimidin-4-yl)indoline-3-carboxylic acid | ++++ | | ++++ | | 80 | |
| 97 | 1-(5-Chloro-2-((6-methoxy-2-methyl-1,2,3,4-tetrahydroisoquinolin-7-yl)amino)pyrimidin-4-yl)-N-methylindoline-3-carboxamide | ++++ | | + | | 800 | |
| 98 | 1-(5-Chloro-2-((6-methoxy-2-methyl-1,2,3,4-tetrahydroisoquinolin-7-yl)amino)pyrimidin-4-yl)-N-(methylsulfonyl)indoline-3-carboxamide | ++++ | | + | | 508 | |
| 99 | 1-(5-Chloro-2-((6-methoxy-2-methyl-1,2,3,4-tetrahydroisoquinolin-7-yl)amino)pyrimidin-4-yl)indoline-3-carbonitrile | ++++ | | ++++ | | 100 | |

TABLE 1-continued

| Example Number | Compound Structure | HPK1 IC50 (nM) Relative B* | HPK1 IC50 (nM) Relative N* | JAK3 IC50 (nM) Relative B* | JAK3 IC50 (nM) Relative N* | JAKs/HPK1 IC50 Ratio B* | JAKs/HPK1 IC50 Ratio N* |
|---|---|---|---|---|---|---|---|
| 100 | N-(4-(3-(2H-tetrazol-5-yl)indolin-1-yl)-5-chloropyrimidin-2-yl)-6-methoxy-2-methyl-1,2,3,4-tetrahydroisoquinolin-7-amine | ++++ | | +++ | | 200 | |
| 101 | 1-(5-Chloro-2-((6-methoxy-2-methyl-1,2,3,4-tetrahydroisoquinolin-7-yl)amino)pyrimidin-4-yl)-N-hydroxyindoline-3-carboxamide | ++++ | | + | | 373 | |
| 102 | 1-(5-Chloro-2-((6-methoxy-2-methyl-1,2,3,4-tetrahydroisoquinolin-7-yl)amino)pyrimidin-4-yl)-N-hydroxy-N-methylindoline-3-carboxamide | ++++ | | + | | >2603 | |
| 103 | 1-(5-Chloro-2-((6-methoxy-2-methyl-1,2,3,4-tetrahydroisoquinolin-7-yl)amino)pyrimidin-4-yl)-N-methoxyindoline-3-carboxamide | ++++ | | ++ | | 540 | |
| 104 | 1-(5-Chloro-2-((6-methoxy-2-methyl-1,2,3,4-tetrahydroisoquinolin-7-yl)amino)pyrimidin-4-yl)-5-fluoroindoline-3-carboxylic acid | ++++ | | ++++ | | 45 | |
| 105 | 1-(5-Chloro-2-((6-methoxy-2-methyl-1,2,3,4-tetrahydroisoquinolin-7-yl)amino)pyrimidin-4-yl)-6-fluoroindoline-3-carboxylic acid | ++++ | | +++ | | 140 | |
| 106 | 1-(5-Chloro-2-((6-methoxy-2-methyl-1,2,3,4-tetrahydroisoquinolin-7-yl)amino)pyrimidin-4-yl)-5-methoxyindoline-3-carboxylic acid | ++++ | | ++++ | | 11 | |
| 107 | 1-(5-Chloro-2-((6-methoxy-2-methyl-1,2,3,4-tetrahydroisoquinolin-7-yl)amino)pyrimidin-4-yl)-6-methoxyindoline-3-carboxylic acid | ++++ | | + | | 2200 | |
| 108 | 1-(5-Chloro-2-((6-methoxy-2-methyl-1,2,3,4-tetrahydroisoquinolin-7-yl)amino)pyrimidin-4-yl)-4-methoxyindoline-3-carboxylic acid | ++++ | | + | | 886 | |
| 109 | 1-(5-Fluoro-2-((6-methoxy-2-methyl-1,2,3,4-tetrahydroisoquinolin-7-yl)amino)pyrimidin-4-yl)indoline-3-carboxylic acid | ++++ | | ++ | | 269 | |
| 110 | 1-(5-Cyano-2-((6-methoxy-2-methyl-1,2,3,4-tetrahydroisoquinolin-7-yl)amino)pyrimidin-4-yl)indoline-3-carboxylic acid | ++++ | | + | | 477 | |
| 111 | 1-(5-Chloro-2-((6-isopropoxy-2-methyl-1,2,3,4-tetrahydroisoquinolin-7-yl)amino)pyrimidin-4-yl)indoline-3-carboxylic acid | ++++ | | + | | >236 | |
| 112 | Methyl 1-(5-(difluoromethyl)-2-((6-methoxy-2-methyl-1,2,3,4-tetrahydroisoquinolin-7-yl)amino)pyrimidin-4-yl)indoline-3-carboxylate | ++++ | | + | | >3309 | |
| 113 | 1-(5-Chloro-2-((6-methoxy-2-methyl-1,2,3,4-tetrahydroisoquinolin-7-yl)amino)pyrimidin-4-yl)-1H-indazole-3-carboxylic acid | ++++ | | + | | 293 | |
| 114 | Methyl 1-(5-chloro-2-((6-methoxy-2-methyl-1,2,3,4-tetrahydroisoquinolin-7-yl)amino)pyrimidin-4-yl)-1H-indole-3-carboxylate | ++++ | | + | | >118 | |
| 115 | Methyl 1-(5-chloro-2-((6-methoxy-2-methyl-1,2,3,4-tetrahydroisoquinolin-7-yl)amino)pyrimidin-4-yl)indoline-3-carboxylate | ++++ | | + | | 1275 | |
| 116 | Methyl 1-(5-chloro-2-((6-methoxy-2-methyl-1,2,3,4-tetrahydroisoquinolin-7-yl)amino)pyrimidin-4-yl)-3-methylindoline-3-carboxylate | ++++ | | + | | 890 | |
| 117 | 1-(5-Chloro-2-((6-methoxy-2-methyl-1,2,3,4-tetrahydroisoquinolin-7-yl)amino)pyrimidin-4-yl)-3-methylindoline-3-carboxylic acid | ++++ | | ++++ | | 5 | |
| 118 | (R)-1-(5-chloro-2-((6-methoxy-2-methyl-1,2,3,4-tetrahydroisoquinolin-7-yl)amino)pyrimidin-4-yl)-3-methylindoline-3-carboxylic acid | ++++ | | + | | 80 | |
| 119 | (S)-1-(5-chloro-2-((6-methoxy-2-methyl-1,2,3,4-tetrahydroisoquinolin-7-yl)amino)pyrimidin-4-yl)-3-methylindoline-3-carboxylic acid | ++++ | | ++++ | | 10 | |
| 120 | 1-(5-Chloro-2-((6-methoxy-2-methyl-1,2,3,4-tetrahydroisoquinolin-7-yl)amino)pyrimidin-4-yl)-3-methylindoline-3-carboxamide | ++++ | | ++++ | | 120 | |
| 121 | 1-(5-Chloro-2-((6-methoxy-2-methyl-1,2,3,4-tetrahydroisoquinolin-7-yl)amino)pyrimidin-4-yl)-3-methylindoline-3-carbonitrile | ++++ | | ++++ | | 50 | |
| 122 | 1-(5-Chloro-2-((6-methoxy-2-methyl-1,2,3,4-tetrahydroisoquinolin-7-yl)amino)pyrimidin-4-yl)-N,3-dimethylindoline-3-carboxamide | ++++ | | ++++ | | 100 | |
| 123 | (1-(5-Chloro-2-((6-methoxy-2-methyl-1,2,3,4-tetrahydroisoquinolin-7-yl)amino)pyrimidin-4-yl)-3-methylindolin-3-yl)methanol | ++++ | | ++++ | | 60 | |

TABLE 1-continued

| Example Number | Compound Structure | HPK1 IC50 (nM) Relative B* | HPK1 IC50 (nM) Relative N* | JAK3 IC50 (nM) Relative B* | JAK3 IC50 (nM) Relative N* | JAKs/HPK1 IC50 Ratio B* | JAKs/HPK1 IC50 Ratio N* |
|---|---|---|---|---|---|---|---|
| 124 | 1-(5-Chloro-2-((6-methoxy-2-methyl-1,2,3,4-tetrahydroisoquinolin-7-yl)amino)pyrimidin-4-yl)-3-(hydroxymethyl)indoline-3-carboxylic acid | ++++ | | ++++ | | 20 | |
| 125 | 1-(5-Chloro-2-((6-methoxy-2-methyl-1,2,3,4-tetrahydroisoquinolin-7-yl)amino)pyrimidin-4-yl)-5-fluoro-3-methylindoline-3-carboxylic acid | ++++ | | ++++ | | 6 | |
| 126 | 1-(5-Chloro-2-((6-methoxy-2-methyl-1,2,3,4-tetrahydroisoquinolin-7-yl)amino)pyrimidin-4-yl)-6-fluoro-3-methylindoline-3-carboxylic acid | ++++ | | ++++ | | 9 | |
| 127 | 1-(5-Chloro-2-((6-methoxy-1,2,3,4-tetrahydroisoquinolin-7-yl)amino)pyrimidin-4-yl)-3-methylindoline-3-carboxylic acid | ++++ | | ++++ | | 4 | |
| 128 | 2-(1-(5-Chloro-2-((6-methoxy-2-methyl-1,2,3,4-tetrahydroisoquinolin-7-yl)amino)pyrimidin-4-yl)indolin-3-yl)acetic acid | ++++ | | +++ | | 280 | |
| 129 | 2-(1-(5-Chloro-2-((6-methoxy-2-methyl-1,2,3,4-tetrahydroisoquinolin-7-yl)amino)pyrimidin-4-yl)-1H-indol-3-yl)acetic acid | ++++ | | ++ | | 640 | |
| 130 | Isopropyl 2-(1-(5-chloro-2-((6-methoxy-2-methyl-1,2,3,4-tetrahydroisoquinolin-7-yl)amino)pyrimidin-4-yl)-1H-indol-3-yl)acetate | ++++ | | + | | >243 | |
| 131 | 2-Ethylbutyl 2-(1-(5-chloro-2-((6-methoxy-2-methyl-1,2,3,4-tetrahydroisoquinolin-7-yl)amino)pyrimidin-4-yl)-1H-indol-3-yl)acetate | +++ | | + | | >82 | |
| 132 | Ethyl 2-(1-(5-chloro-2-((6-methoxy-2-methyl-1,2,3,4-tetrahydroisoquinolin-7-yl)amino)pyrimidin-4-yl)-1H-indol-3-yl)acetate | ++++ | | + | | >426 | |
| 133 | 2-(1-(5-Chloro-2-((6-methoxy-2-methyl-1,2,3,4-tetrahydroisoquinolin-7-yl)amino)pyrimidin-4-yl)-1H-indol-3-yl)acetamide | ++++ | | + | | 870 | |
| 134 | 2-(1-(5-Chloro-2-((6-methoxy-2-methyl-1,2,3,4-tetrahydroisoquinolin-7-yl)amino)pyrimidin-4-yl)-1H-indol-3-yl)acetonitrile | ++++ | | ++ | | 243 | |
| 135 | N-(4-(3-((2H-tetrazol-5-yl)methyl)-1H-indol-1-yl)-5-chloropyrimidin-2-yl)-6-methoxy-2-methyl-1,2,3,4-tetrahydroisoquinolin-7-amine | ++++ | | ++ | | 269 | |
| 136 | 2-(1-(5-Chloro-2-((6-methoxy-2-methyl-1,2,3,4-tetrahydroisoquinolin-7-yl)amino)pyrimidin-4-yl)-1H-indol-3-yl)-N-methylacetamide | ++++ | | ++ | | 438 | |
| 137 | 2-(1-(5-Chloro-2-((6-methoxy-2-methyl-1,2,3,4-tetrahydroisoquinolin-7-yl)amino)pyrimidin-4-yl)-1H-indol-3-yl)-N-(cyanomethyl)acetamide | ++++ | | + | | 1304 | |
| 138 | 2-(1-(5-Chloro-2-((6-methoxy-2-methyl-1,2,3,4-tetrahydroisoquinolin-7-yl)amino)pyrimidin-4-yl)-5-fluoro-1H-indol-3-yl)acetic acid | ++++ | | +++ | | 382 | |
| 139 | 2-(1-(5-Chloro-2-((6-methoxy-2-methyl-1,2,3,4-tetrahydroisoquinolin-7-yl)amino)pyrimidin-4-yl)-6-fluoro-1H-indol-3-yl)acetic acid | ++++ | | +++ | | 520 | |
| 140 | 2-(1-(5-Chloro-2-((6-methoxy-2-methyl-1,2,3,4-tetrahydroisoquinolin-7-yl)amino)pyrimidin-4-yl)-5,6-difluoro-1H-indol-3-yl)acetic acid | ++++ | | ++ | | 783 | |
| 141 | 2-(1-(5-Chloro-2-((6-methoxy-2-methyl-1,2,3,4-tetrahydroisoquinolin-7-yl)amino)pyrimidin-4-yl)-1H-indazol-3-yl)acetic acid | ++++ | | + | | 541 | |
| 142 | 2-(1-(5-Chloro-2-((6-methoxy-2-methyl-1,2,3,4-tetrahydroisoquinolin-7-yl)amino)pyrimidin-4-yl)-1H-indol-3-yl)propanoic acid | ++++ | | ++ | | 117 | |
| 143 | 1-(1-(5-Chloro-2-((6-methoxy-2-methyl-1,2,3,4-tetrahydroisoquinolin-7-yl)amino)pyrimidin-4-yl)-1H-indol-3-yl)cyclopropane-1-carboxylic acid | ++++ | | + | | 433 | |
| 144 | 2-(1-(5-Chloro-2-((6-methoxy-2-methyl-1,2,3,4-tetrahydroisoquinolin-7-yl)amino)pyrimidin-4-yl)-1H-indol-3-yl)-3,3,3-trifluoropropanoic acid | ++++ | | + | | 250 | |
| 145 | Methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate | ++++ | | + | | 476 | |
| 146 | 2-(1-(5-Chloro-2-((6-methoxy-2-methyl-1,2,3,4-tetrahydroisoquinolin-7-yl)amino)pyrimidin-4-yl)-3-methylindolin-3-yl)acetic acid | ++++ | | ++++ | | 90 | |
| 147 | (R)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid | ++++ | | + | | 132 | |

TABLE 1-continued

| Example | | HPK1 IC50 (nM) Relative | | JAK3 IC50 (nM) Relative | | JAKs/HPK1 IC50 Ratio | |
|---|---|---|---|---|---|---|---|
| Number | Compound Structure | B* | N* | B* | N* | B* | N* |
| 148 | (S)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid | ++++ | | ++++ | | 209 | |
| 149 | Ethyl 2-(1-(5-chloro-2-((6-methoxy-2-methyl-1,2,3,4-tetrahydroisoquinolin-7-yl)amino)pyrimidin-4-yl)-3-methylindolin-3-yl)acetate | ++++ | | + | | >944 | |
| 150 | 2-(1-(5-Chloro-2-((6-methoxy-2-methyl-1,2,3,4-tetrahydroisoquinolin-7-yl)amino)pyrimidin-4-yl)-5-fluoro-3-methylindolin-3-yl)acetic acid | ++++ | | +++ | | 171 | |
| 151 | 2-(1-(5-Chloro-2-((6-methoxy-2-methyl-1,2,3,4-tetrahydroisoquinolin-7-yl)amino)pyrimidin-4-yl)-6-fluoro-3-methylindolin-3-yl)acetic acid | ++++ | | ++++ | | 187 | |
| 152 | (S)-2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid | ++++ | | +++ | | 253 | |
| 153 | (R)-2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid | ++++ | | + | | 358 | |
| 154 | 2-(1-(5-Chloro-2-((6-methoxy-2-methyl-1,2,3,4-tetrahydroisoquinolin-7-yl)amino)pyrimidin-4-yl)-5,6-difluoro-3-methylindolin-3-yl)acetic acid | ++++ | | +++ | | 430 | |
| 155 | 2-(1-(5-Chloro-2-((2-methoxy-6-methyl-5,6,7,8-tetrahydro-1,6-naphthyridin-3-yl)amino)pyrimidin-4-yl)-3-methylindolin-3-yl)acetic acid | ++++ | | + | | >111 | |
| 156 | 2-(1-(5-Chloro-2-((6-fluoro-2-methyl-1,2,3,4-tetrahydroisoquinolin-7-yl)amino)pyrimidin-4-yl)-3-methylindolin-3-yl)acetic acid | ++++ | | ++++ | | 29 | |
| 157 | 2-(1-(5-Chloro-2-((2-ethyl-6-methoxy-1,2,3,4-tetrahydroisoquinolin-7-yl)amino)pyrimidin-4-yl)-3-methylindolin-3-yl)acetic acid | ++++ | | +++ | | 176 | |
| 158 | 2-(1-(5-Chloro-2-((2-isopropyl-6-methoxy-1,2,3,4-tetrahydroisoquinolin-7-yl)amino)pyrimidin-4-yl)-3-methylindolin-3-yl)acetic acid | ++++ | | +++ | | 192 | |
| 159 | 2-(1-(5-Chloro-2-((6-methoxy-2-methylisoindolin-5-yl)amino)pyrimidin-4-yl)-3-methylindolin-3-yl)acetic acid | ++++ | | ++++ | | 71 | |
| 160 | 2-(1-(5-Chloro-2-((6-methoxy-1,2,3,4-tetrahydroisoquinolin-7-yl)amino)pyrimidin-4-yl)-3-methylindolin-3-yl)acetic acid methanesulfonic acid | ++++ | | ++++ | | 97 | |
| 161 | 2-(3-(5-Chloro-2-((6-methoxy-2-methyl-1,2,3,4-tetrahydroisoquinolin-7-yl)amino)pyrimidin-4-yl)-1H-indol-1-yl)acetic acid | ++++ | | ++ | | 510 | |
| 162 | 2-(3-(5-Chloro-2-((6-methoxy-2-methyl-1,2,3,4-tetrahydroisoquinolin-7-yl)amino)pyrimidin-4-yl)-1H-indazol-1-yl)acetic acid | ++++ | | + | | 415 | |
| 163 | 1-(2-((6-Methoxy-2-methyl-1,2,3,4-tetrahydroisoquinolin-7-yl)amino)pyrimidin-4-yl)indoline-3-carboxylic acid | ++++ | | + | | 456 | |
| 164 | 2-((6-Methoxy-2-methyl-1,2,3,4-tetrahydroisoquinolin-7-yl)amino)-7-phenyl-7H-pyrrolo[2,3-d]pyrimidine-6-carbonitrile | ++++ | | ++ | | 306 | |
| 165 | 2-((6-Methoxy-2-methyl-1,2,3,4-tetrahydroisoquinolin-7-yl)amino)-7-phenyl-7H-pyrrolo[2,3-d]pyrimidine-6-carboxylic acid | ++++ | | + | | 421 | |
| 166 | 2-((6-Methoxy-2-methyl-1,2,3,4-tetrahydroisoquinolin-7-yl)amino)-7-methyl-9-phenyl-7,9-dihydro-8H-purin-8-one | +++ | | + | | N.D. | |
| 167 | 2-(5-Chloro-2-((6-methoxy-2-methyl-1,2,3,4-tetrahydroisoquinolin-7-yl)amino)pyrimidin-4-yl)-2-azaspiro[4.5]decane-4-carboxylic acid | ++++ | | + | | 995 | |
| 168 | 2-(5-Chloro-2-((6-methoxy-2-methyl-1,2,3,4-tetrahydroisoquinolin-7-yl)amino)pyrimidin-4-yl)-8-oxa-2-azaspiro[4.5]decane-4-carboxylic acid | ++++ | | + | | 737 | |
| 169 | 2-(5-Chloro-2-((6-methoxy-2-methyl-1,2,3,4-tetrahydroisoquinolin-7-yl)amino)pyrimidin-4-yl)-2-azaspiro[4.4]nonane-4-carboxylic acid | ++++ | | + | | 1482 | |
| 170 | N-(5-chloro-4-(2-oxa-6-azaspiro[3.4]octan-6-yl)pyrimidin-2-yl)-6-methoxy-2-methyl-1,2,3,4-tetrahydroisoquinolin-7-amine | +++ | | + | | 77 | |
| 171 | 2-((6-Methoxy-2-methyl-1,2,3,4-tetrahydroisoquinolin-7-yl)amino)-8-phenylpyrido[2,3-d]pyrimidin-7(8H)-one | ++++ | | + | | 121 | |
| 172 | (2-((6-Methoxy-2-methyl-1,2,3,4-tetrahydroisoquinolin-7-yl)amino)quinazolin-7-yl)dimethylphosphine oxide | +++ | | | | | |

N.D.: Not Determined.

B*: Testing performed in a first testing facility.

N*: Testing performed in a second testing facility.

TABLE 2

| Example | Compound Structure | IL-2 Max Fold Response | EC2x (nM) | EC50 (nM) |
|---|---|---|---|---|
| 1 | (1-(5-Chloro-2-((6-methoxy-2-methyl-1,2,3,4-tetrahydroisoquinolin-7-yl)amino)pyrimidin-4-yl)-1H-indol-3-yl)dimethylphosphine oxide | <2 | N.A. | N.A. |
| 2 | N-(5-chloro-4-(1H-indol-1-yl)pyrimidin-2-yl)-6-methoxy-2-methyl-1,2,3,4-tetrahydroisoquinolin-7-amine | <2 | N.A. | N.A. |
| 3 | N-(4-(1H-indol-1-yl)-5-(trifluoromethyl)pyrimidin-2-yl)-6-methoxy-2-methyl-1,2,3,4-tetrahydroisoquinolin-7-amine | >2 | ++ | +++ |
| 4 | N-(5-Chloro-4-(indolin-1-yl)pyrimidin-2-yl)-6-methoxy-2-methyl-1,2,3,4-tetrahydroisoquinolin-7-amine | >2 | +++ | +++ |
| 8 | 1-(5-Chloro-2-((6-methoxy-2-methyl-1,2,3,4-tetrahydroisoquinolin-7-yl)amino)pyrimidin-4-yl)-N,N-dimethyl-1H-indole-3-carboxamide | <2 | N.A. | N.A. |
| 9 | N-(4-(1H-benzo[d]imidazol-1-yl)-5-chloropyrimidin-2-yl)-6-methoxy-2-methyl-1,2,3,4-tetrahydroisoquinolin-7-amine | >2 | ++ | +++ |
| 10 | N-(4-(1H-indol-1-yl)-5-(trifluoromethyl)pyrimidin-2-yl)-6-methoxy-2-methyl-1,2,3,4-tetrahydroisoquinolin-7-amine | <2 | N.A. | N.A. |
| 11 | N-(5-Chloro-4-(3-fluoro-1H-indol-1-yl)pyrimidin-2-yl)-6-methoxy-2-methyl-1,2,3,4-tetrahydroisoquinolin-7-amine | <2 | N.A. | N.A. |
| 13 | N-(5-chloro-4-(5-chloroindolin-1-yl)pyrimidin-2-yl)-6-methoxy-2-methyl-1,2,3,4-tetrahydroisoquinolin-7-amine | <2 | N.A. | + |
| 14 | N-(5-Chloro-4-(indolin-1-yl)pyrimidin-2-yl)-2-methyl-1,2,3,4-tetrahydroisoquinolin-7-amine | <2 | N.A. | N.A. |
| 15 | 6-Chloro-N-(5-chloro-4-(indolin-1-yl)pyrimidin-2-yl)-2-methyl-1,2,3,4-tetrahydroisoquinolin-7-amine | >2 | + | + |
| 16 | N-(5-chloro-4-(2,3-dihydro-1H-pyrrolo[3,2-b]pyridin-1-yl)pyrimidin-2-yl)-6-methoxy-2-methyl-1,2,3,4-tetrahydroisoquinolin-7-amine | <2 | N.A. | +++ |
| 18 | N-(5-chloro-4-(6-chloroindolin-1-yl)pyrimidin-2-yl)-6-methoxy-2-methyl-1,2,3,4-tetrahydroisoquinolin-7-amine | <2 | N.A. | +++ |
| 19 | N-(5-chloro-4-(indolin-1-yl)pyrimidin-2-yl)-2-methoxy-6-methyl-5,6,7,8-tetrahydro-1,6-naphthyridin-3-amine | >2 | +++ | +++ |
| 20 | N-(5-chloro-4-(5-fluoroindolin-1-yl)pyrimidin-2-yl)-6-methoxy-2-methyl-1,2,3,4-tetrahydroisoquinolin-7-amine | >2 | +++ | +++ |
| 21 | N-(5-chloro-4-(6-fluoroindolin-1-yl)pyrimidin-2-yl)-6-methoxy-2-methyl-1,2,3,4-tetrahydroisoquinolin-7-amine | >2 | +++ | +++ |
| 22 | N-(5-chloro-4-(indolin-1-yl)pyrimidin-2-yl)-2-isopropyl-6-methoxy-1,2,3,4-tetrahydroisoquinolin-7-amine | >2 | +++ | ++ |
| 23 | N-(5-chloro-4-(indolin-1-yl)pyrimidin-2-yl)-6-methoxy-1,2,3,4-tetrahydroisoquinolin-7-amine | <2 | N.A. | +++ |
| 24 | N-(5-Chloro-4-(1H-indazol-1-yl)pyrimidin-2-yl)-6-methoxy-2-methyl-1,2,3,4-tetrahydroisoquinolin-7-amine | <2 | N.A. | ++ |
| 25 | N-(5-Chloro-4-(3,3-dimethylindolin-1-yl)pyrimidin-2-yl)-6-methoxy-2-methyl-1,2,3,4-tetrahydroisoquinolin-7-amine | >2 | +++ | ++ |
| 27 | 2-(7-((5-Chloro-4-(indolin-1-yl)pyrimidin-2-yl)amino)-6-methoxy-3,4-dihydroisoquinolin-2(1H)-yl)ethan-1-ol | >2 | + | + |
| 29 | N-(5-Chloro-4-(2,3-dihydro-1H-pyrrolo[3,2-b]pyridin-1-yl)pyrimidin-2-yl)-2-methoxy-6-methyl-5,6,7,8-tetrahydro-1,6-naphthyridin-3-amine | <2 | N.A. | ++ |
| 32 | 1-(5-Chloro-2-((6-methoxy-2-methyl-1,2,3,4-tetrahydroisoquinolin-7-yl)amino)pyrimidin-4-yl)indoline-3-carboxylic acid | >2 | +++ | +++ |
| 33 | 1-(5-Chloro-2-((6-methoxy-2-methyl-1,2,3,4-tetrahydroisoquinolin-7-yl)amino)pyrimidin-4-yl)indoline-3-carboxamide | <2 | N.A. | N.A. |
| 34 | 1-(5-Chloro-2-((6-methoxy-2-methyl-1,2,3,4-tetrahydroisoquinolin-7-yl)amino)pyrimidin-4-yl)-1H-indole-3-carboxamide | <2 | N.A. | N.A. |
| 35 | 1-(5-Chloro-2-((6-methoxy-2-methyl-1,2,3,4-tetrahydroisoquinolin-7-yl)amino)pyrimidin-4-yl)-1H-indole-3-carboxylic acid | >2 | + | ++ |
| 36 | 6-Methoxy-2-methyl-N-(7-phenyl-7H-pyrrolo[2,3-d]pyrimidin-2-yl)-1,2,3,4-tetrahydroisoquinolin-7-amine | <2 | N.A. | N.A. |
| 37 | 6-Methoxy-2-methyl-N-(7-(pyridin-2-yl)-7H-pyrrolo[2,3-d]pyrimidin-2-yl)-1,2,3,4-tetrahydroisoquinolin-7-amine | <2 | N.A. | +++ |
| 81 | N-(5-chloro-4-(3-(methylsulfonyl)indolin-1-yl)pyrimidin-2-yl)-6-methoxy-2-methyl-1,2,3,4-tetrahydroisoquinolin-7-amine | >2 | +++ | ++ |
| 83 | 1-(5-Chloro-2-((6-methoxy-2-methyl-1,2,3,4-tetrahydroisoquinolin-7-yl)amino)pyrimidin-4-yl)-1H-indole-3-sulfonamide | <2 | N.A. | +++ |
| 84 | N-(5-chloro-4-(spiro[cyclopropane-1,3'-indolin]-1'-yl)pyrimidin-2-yl)-6-methoxy-2-methyl-1,2,3,4-tetrahydroisoquinolin-7-amine | <2 | N.A. | ++ |
| 86 | (1-(5-Chloro-2-((6-methoxy-2-methyl-1,2,3,4-tetrahydroisoquinolin-7-yl)amino)pyrimidin-4-yl)indolin-5-yl)dimethylphosphine oxide | >2 | + | +++ |
| 87 | (1-(5-Chloro-2-((6-methoxy-2-methyl-1,2,3,4-tetrahydroisoquinolin-7-yl)amino)pyrimidin-4-yl)indolin-3-yl)methanol | <2 | N.A. | +++ |
| 88 | (1-(5-Chloro-2-((6-methoxy-2-methyl-1,2,3,4-tetrahydroisoquinolin-7-yl)amino)pyrimidin-4-yl)indolin-3-yl)dimethylphosphine oxide | <2 | N.A. | ++ |
| 90 | N-(5-chloro-4-(5-(difluoromethyl)indolin-1-yl)pyrimidin-2-yl)-6-methoxy-2-methyl-1,2,3,4-tetrahydroisoquinolin-7-amine | <2 | N.A. | + |
| 91 | N-(5-chloro-4-(6-(difluoromethyl)indolin-1-yl)pyrimidin-2-yl)-6-methoxy-2-methyl-1,2,3,4-tetrahydroisoquinolin-7-amine | <2 | N.A. | N.A. |
| 92 | N-(5-chloro-4-(4-(difluoromethyl)indolin-1-yl)pyrimidin-2-yl)-6-methoxy-2-methyl-1,2,3,4-tetrahydroisoquinolin-7-amine | <2 | N.A. | N.A. |
| 93 | 3-(1-(5-Chloro-2-((6-methoxy-2-methyl-1,2,3,4-tetrahydroisoquinolin-7-yl)amino)pyrimidin-4-yl)-1H-indol-3-yl)oxetan-3-ol | <2 | N.A. | N.A. |
| 96 | (R)-1-(5-chloro-2-((6-methoxy-2-methyl-1,2,3,4-tetrahydroisoquinolin-7-yl)amino)pyrimidin-4-yl)indoline-3-carboxylic acid | >2 | +++ | +++ |

TABLE 2-continued

| Example | Compound Structure | IL-2 Max Fold Response | EC2x (nM) | EC50 (nM) |
|---|---|---|---|---|
| 97 | 1-(5-Chloro-2-((6-methoxy-2-methyl-1,2,3,4-tetrahydroisoquinolin-7-yl)amino)pyrimidin-4-yl)-N-methylindoline-3-carboxamide | >2 | ++ | +++ |
| 98 | 1-(5-Chloro-2-((6-methoxy-2-methyl-1,2,3,4-tetrahydroisoquinolin-7-yl)amino)pyrimidin-4-yl)-N-(methylsulfonyl)indoline-3-carboxamide | <2 | N.A. | N.A. |
| 99 | 1-(5-Chloro-2-((6-methoxy-2-methyl-1,2,3,4-tetrahydroisoquinolin-7-yl)amino)pyrimidin-4-yl)indoline-3-carbonitrile | <2 | N.A. | N.A. |
| 100 | N-(4-(3-(2H-tetrazol-5-yl)indolin-l-yl)-5-chloropyrimidin-2-yl)-6-methoxy-2-methyl-1,2,3,4-tetrahydroisoquinolin-7-amine | >2 | + | + |
| 101 | 1-(5-Chloro-2-((6-methoxy-2-methyl-1,2,3,4-tetrahydroisoquinolin-7-yl)amino)pyrimidin-4-yl)-N-hydroxyindoline-3-carboxamide | <2 | N.A. | N.A. |
| 102 | 1-(5-Chloro-2-((6-methoxy-2-methyl-1,2,3,4-tetrahydroisoquinolin-7-yl)amino)pyrimidin-4-yl)-N-hydroxy-N-methylindoline-3-carboxamide | <2 | N.A. | N.A. |
| 103 | 1-(5-Chloro-2-((6-methoxy-2-methyl-1,2,3,4-tetrahydroisoquinolin-7-yl)amino)pyrimidin-4-yl)-N-methoxyindoline-3-carboxamide | <2 | N.A. | N.A. |
| 104 | 1-(5-Chloro-2-((6-methoxy-2-methyl-1,2,3,4-tetrahydroisoquinolin-7-yl)amino)pyrimidin-4-yl)-5-fluoroindoline-3-carboxylic acid | >2 | +++ | +++ |
| 105 | 1-(5-Chloro-2-((6-methoxy-2-methyl-1,2,3,4-tetrahydroisoquinolin-7-yl)amino)pyrimidin-4-yl)-6-fluoroindoline-3-carboxylic acid | >2 | +++ | ++++ |
| 107 | 1-(5-Chloro-2-((6-methoxy-2-methyl-1,2,3,4-tetrahydroisoquinolin-7-yl)amino)pyrimidin-4-yl)-6-methoxyindoline-3-carboxylic acid | <2 | N.A. | N.A. |
| 108 | 1-(5-Chloro-2-((6-methoxy-2-methyl-1,2,3,4-tetrahydroisoquinolin-7-yl)amino)pyrimidin-4-yl)-4-methoxyindoline-3-carboxylic acid | <2 | N.A. | + |
| 109 | 1-(5-Fluoro-2-((6-methoxy-2-methyl-1,2,3,4-tetrahydroisoquinolin-7-yl)amino)pyrimidin-4-yl)indoline-3-carboxylic acid | >2 | ++ | +++ |
| 110 | 1-(5-Cyano-2-((6-methoxy-2-methyl-1,2,3,4-tetrahydroisoquinolin-7-yl)amino)pyrimidin-4-yl)indoline-3-carboxylic acid | <2 | N.A. | N.A. |
| 112 | Methyl 1-(5-(difluoromethyl)-2-((6-methoxy-2-methyl-1,2,3,4-tetrahydroisoquinolin-7-yl)amino)pyrimidin-4-yl)indoline-3-carboxylate | <2 | N.A. | N.A. |
| 113 | 1-(5-Chloro-2-((6-methoxy-2-methyl-1,2,3,4-tetrahydroisoquinolin-7-yl)amino)pyrimidin-4-yl)-1H-indazole-3-carboxylic acid | <2 | N.A. | + |
| 115 | Methyl 1-(5-chloro-2-((6-methoxy-2-methyl-1,2,3,4-tetrahydroisoquinolin-7-yl)amino)pyrimidin-4-yl)indoline-3-carboxylate | >2 | +++ | +++ |
| 116 | Methyl 1-(5-chloro-2-((6-methoxy-2-methyl-1,2,3,4-tetrahydroisoquinolin-7-yl)amino)pyrimidin-4-yl)-3-methylindoline-3-carboxylate | >2 | ++ | ++ |
| 118 | (R)-1-(5-chloro-2-((6-methoxy-2-methyl-1,2,3,4-tetrahydroisoquinolin-7-yl)amino)pyrimidin-4-yl)-3-methylindoline-3-carboxylic acid | <2 | N.A. | + |
| 119 | (S)-1-(5-chloro-2-((6-methoxy-2-methyl-1,2,3,4-tetrahydroisoquinolin-7-yl)amino)pyrimidin-4-yl)-3-methylindoline-3-carboxylic acid | >2 | ++++ | ++++ |
| 120 | 1-(5-Chloro-2-((6-methoxy-2-methyl-1,2,3,4-tetrahydroisoquinolin-7-yl)amino)pyrimidin-4-yl)-3-methylindoline-3-carboxamide | <2 | N.A. | N.A. |
| 121 | l-(5-Chloro-2-((6-methoxy-2-methyl-1,2,3,4-tetrahydroisoquinolin-7-yl)amino)pyrimidin-4-yl)-3-methylindoline-3-carbonitrile | <2 | N.A. | N.A. |
| 122 | 1-(5-Chloro-2-((6-methoxy-2-methyl-1,2,3,4-tetrahydroisoquinolin-7-yl)amino)pyrimidin-4-yl)-N,3-dimethylindoline-3-carboxamide | <2 | N.A. | N.A. |
| 123 | (1-(5-Chloro-2-((6-methoxy-2-methyl-1,2,3,4-tetrahydroisoquinolin-7-yl)amino)pyrimidin-4-yl)-3-methylindolin-3-yl)methanol | <2 | N.A. | +++ |
| 125 | 1-(5-Chloro-2-((6-methoxy-2-methyl-1,2,3,4-tetrahydroisoquinolin-7-yl)amino)pyrimidin-4-yl)-5-fluoro-3-methylindoline-3-carboxylic acid | >2 | ++++ | ++++ |
| 126 | 1-(5-Chloro-2-((6-methoxy-2-methyl-1,2,3,4-tetrahydroisoquinolin-7-yl)amino)pyrimidin-4-yl)-6-fluoro-3-methylindoline-3-carboxylic acid | >2 | ++++ | ++++ |
| 128 | 2-(1-(5-Chloro-2-((6-methoxy-2-methyl-1,2,3,4-tetrahydroisoquinolin-7-yl)amino)pyrimidin-4-yl)indolin-3-yl)acetic acid | >2 | +++ | +++ |
| 129 | 2-(1-(5-Chloro-2-((6-methoxy-2-methyl-1,2,3,4-tetrahydroisoquinolin-7-yl)amino)pyrimidin-4-yl)-1H-indol-3-yl)acetic acid | >2 | +++ | +++ |
| 130 | Isopropyl 2-(1-(5-chloro-2-((6-methoxy-2-methyl-1,2,3,4-tetrahydroisoquinolin-7-yl)amino)pyrimidin-4-yl)-1H-indol-3-yl)acetate | <2 | N.A. | N.A. |
| 133 | 2-(1-(5-Chloro-2-((6-methoxy-2-methyl-1,2,3,4-tetrahydroisoquinolin-7-yl)amino)pyrimidin-4-yl)-1H-indol-3-yl)acetamide | <2 | N.A. | + |
| 134 | 2-(1-(5-Chloro-2-((6-methoxy-2-methyl-1,2,3,4-tetrahydroisoquinolin-7-yl)amino)pyrimidin-4-yl)-1H-indol-3-yl)acetonitrile | <2 | N.A. | + |
| 135 | H-(4-(3-((2H-tetrazol-5-yl)methyl)-1H-indol-1-yl)-5-chloropyrimidin-2-yl)-6-methoxy-2-methyl-1,2,3,4-tetrahydroisoquinolin-7-amine | <2 | N.A. | + |
| 136 | 2-(1-(5-Chloro-2-((6-methoxy-2-methyl-1,2,3,4-tetrahydroisoquinolin-7-yl)amino)pyrimidin-4-yl)-1H-indol-3-yl)-N-methylacetamide | <2 | N.A. | ++ |
| 137 | 2-(1-(5-Chloro-2-((6-methoxy-2-methyl-1,2,3,4-tetrahydroisoquinolin-7-yl)amino)pyrimidin-4-yl)-1H-indol-3-yl)-N-(cyanomethyl)acetamide | <2 | N.A. | ++ |
| 138 | 2-(1-(5-Chloro-2-((6-methoxy-2-methyl-1,2,3,4-tetrahydroisoquinolin-7-yl)amino)pyrimidin-4-yl)-5-fluoro-1H-indol-3-yl)acetic acid | >2 | +++ | +++ |
| 139 | 2-(1-(5-Chloro-2-((6-methoxy-2-methyl-1,2,3,4-tetrahydroisoquinolin-7-yl)amino)pyrimidin-4-yl)-6-fluoro-1H-indol-3-yl)acetic acid | >2 | ++++ | ++++ |
| 140 | 2-(1-(5-Chloro-2-((6-methoxy-2-methyl-1,2,3,4-tetrahydroisoquinolin-7-yl)amino)pyrimidin-4-yl)-5,6-difluoro-1H-indol-3-yl)acetic acid | >2 | +++ | +++ |
| 141 | 2-(1-(5-Chloro-2-((6-methoxy-2-methyl-1,2,3,4-tetrahydroisoquinolin-7-yl)amino)pyrimidin-4-yl)-1H-indazol-3-yl)acetic acid | >2 | ++ | + |
| 142 | 2-(1-(5-Chloro-2-((6-methoxy-2-methyl-1,2,3,4-tetrahydroisoquinolin-7-yl)amino)pyrimidin-4-yl)-1H-indol-3-yl)propanoic acid | <2 | N.A. | +++ |

TABLE 2-continued

| Example | Compound Structure | IL-2 Max Fold Response | EC2x (nM) | EC50 (nM) |
|---|---|---|---|---|
| 145 | Methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate | <2 | N.A. | N.A. |
| 146 | 2-(1-(5-Chloro-2-((6-methoxy-2-methyl-1,2,3,4-tetrahydroisoquinolin-7-yl)amino)pyrimidin-4-yl)-3-methylindolin-3-yl)acetic acid | >2 | ++++ | ++++ |
| 147 | (R)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid | <2 | N.A. | ++ |
| 148 | (S)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid | >2 | ++++ | ++++ |
| 149 | Ethyl 2-(1-(5-chloro-2-((6-methoxy-2-methyl-1,2,3,4-tetrahydroisoquinolin-7-yl)amino)pyrimidin-4-yl)-3-methylindolin-3-yl)acetate | <2 | N.A. | N.A. |
| 150 | 2-(1-(5-Chloro-2-((6-methoxy-2-methyl-1,2,3,4-tetrahydroisoquinolin-7-yl)amino)pyrimidin-4-yl)-5-fluoro-3-methylindolin-3-yl)acetic acid | >2 | ++++ | ++++ |
| 151 | 2-(1-(5-Chloro-2-((6-methoxy-2-methyl-1,2,3,4-tetrahydroisoquinolin-7-yl)amino)pyrimidin-4-yl)-6-fluoro-3-methylindolin-3-yl)acetic acid | >2 | ++++ | ++++ |
| 152 | (S)-2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid | >2 | ++++ | ++++ |
| 153 | (R)-2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid | >2 | +++ | +++ |
| 154 | 2-(1-(5-Chloro-2-((6-methoxy-2-methyl-1,2,3,4-tetrahydroisoquinolin-7-yl)amino)pyrimidin-4-yl)-5,6-difluoro-3-methylindolin-3-yl)acetic acid | >2 | ++++ | ++++ |
| 156 | 2-(1-(5-Chloro-2-((6-fluoro-2-methyl-1,2,3,4-tetrahydroisoquinolin-7-yl)amino)pyrimidin-4-yl)-3-methylindolin-3-yl)acetic acid | >2 | ++++ | ++++ |
| 157 | 2-(1-(5-Chloro-2-((2-ethyl-6-methoxy-1,2,3,4-tetrahydroisoquinolin-7-yl)amino)pyrimidin-4-yl)-3-methylindolin-3-yl)acetic acid | >2 | ++++ | ++++ |
| 158 | 2-(1-(5-Chloro-2-((2-isopropyl-6-methoxy-1,2,3,4-tetrahydroisoquinolin-7-yl)amino)pyrimidin-4-yl)-3-methylindolin-3-yl)acetic acid | >2 | ++++ | ++++ |
| 159 | 2-(1-(5-Chloro-2-((6-methoxy-2-methylisoindolin-5-yl)amino)pyrimidin-4-yl)-3-methylindolin-3-yl)acetic acid | >2 | ++++ | ++++ |
| 160 | 2-(1-(5-Chloro-2-((6-methoxy-1,2,3,4-tetrahydroisoquinolin-7-yl)amino)pyrimidin-4-yl)-3-methylindolin-3-yl)acetic acid methanesulfonic acid | >2 | ++++ | ++++ |
| 161 | 2-(3-(5-Chloro-2-((6-methoxy-2-methyl-1,2,3,4-tetrahydroisoquinolin-7-yl)amino)pyrimidin-4-yl)-1H-indol-1-yl)acetic acid | >2 | + | + |
| 162 | 2-(3-(5-Chloro-2-((6-methoxy-2-methyl-1,2,3,4-tetrahydroisoquinolin-7-yl)amino)pyrimidin-4-yl)-1H-indazol-1-yl)acetic acid | <2 | N.A. | N.A. |
| 163 | 1-(2-((6-Methoxy-2-methyl-1,2,3,4-tetrahydroisoquinolin-7-yl)amino)pyrimidin-4-yl)indoline-3-carboxylic acid | >2 | + | + |
| 164 | 2-((6-Methoxy-2-methyl-1,2,3,4-tetrahydroisoquinolin-7-yl)amino)-7-phenyl-7H-pyrrolo[2,3-d]pyrimidine-6-carbonitrile | <2 | N.A. | ++++ |
| 167 | 2-(5-Chloro-2-((6-methoxy-2-methyl-1,2,3,4-tetrahydroisoquinolin-7-yl)amino)pyrimidin-4-yl)-2-azaspiro[4.5]decane-4-carboxylic acid | >2 | +++ | ++ |
| 169 | 2-(5-Chloro-2-((6-methoxy-2-methyl-1,2,3,4-tetrahydroisoquinolin-7-yl)amino)pyrimidin-4-yl)-2-azaspiro[4.4]nonane-4-carboxylic acid | >2 | ++ | + |

N.A.: Not Available.

In Tables 1 and 2, the IC50, EC2x and EC50 values are indicated as "++++", for values less than or equal to 100 nM; "+++", for higher values than "++++" but less than or equal to 500 nM; "++", for higher values than "+++" but less than or equal to 1 μM; and "+", for greater than 1 μM, respectively.

B. Synthetic Examples

Equipment Description

NMR spectra were measured with a Varian Mercury spectrometer operating at 400 MHz ($^1$H), 376 MHz ($^{19}$F) or 75 MHz ($^{13}$C). Solvents used for samples are specified in the experimental procedures for each compound. Chemical shifts are expressed in parts per million (ppm, 8 units). Coupling constants are in units of hertz (Hz). Splitting patterns describe apparent multiplicities and are designated as s (singlet), d (doublet), t (triplet), q (quartet), quint (quintet), m (multiplet), br (broad).

The following system was used for LCMS: Agilent 6120 (Binary Gradient Module pump), XBridge analytical column $C_{18}$, 5 μm, 4.6×50 mm, 25° C., 5 μL injection volume, 2 mL/min, with a gradient of acetonitrile in aqueous 0.1% Ammonium acetate according to the following timings:

| Time (min) | Acetonitrile (%) | 0.1% aqueous Ammonium acetate (%) |
|---|---|---|
| 0.50 | 5 | 95 |
| 4.50 | 95 | 5 |
| 6.00 | 95 | 5 |

Experimental procedures: All reactions were conducted under an atmosphere of dry nitrogen unless specified otherwise. TLC plates were visualised with u.v. light. Flash chromatography refers to column chromatography over silica gel (40-60 μm) using glass columns. Alternatively, automated chromatography was performed using Biotage SP1 or Biotage Isolera systems with u.v. detection at 220 or 254 nm and employing Biotage normal phase or reverse phase silica cartridges. Further details can be found under the relevant experimental procedure.

General Methods and Preparations

The compounds, including those of general formula (I-0), (I-1), (I-2), (I), (II), (II-1), (II-2), or (II-2'), intermediates and specific examples are prepared through the synthetic methods described herein. In the experimental procedures, the modifications to reaction conditions, such as, temperature, concentration of solutions, volume of solvents, application of microwave conditions, duration of the reaction or combinations thereof, are envisioned as part of the present invention, and besides specifically mentioned acids, bases, reagents, coupling reagents, solvents, etc., alternative suitable acids, bases, reagents, coupling reagents, solvents etc. may be used and are included within the scope of the present invention. All possible geometrical isomers, stereoisomers, salt forms are envisioned within the scope of this invention.

General scheme and synthetic procedures of pyrimidine compounds:

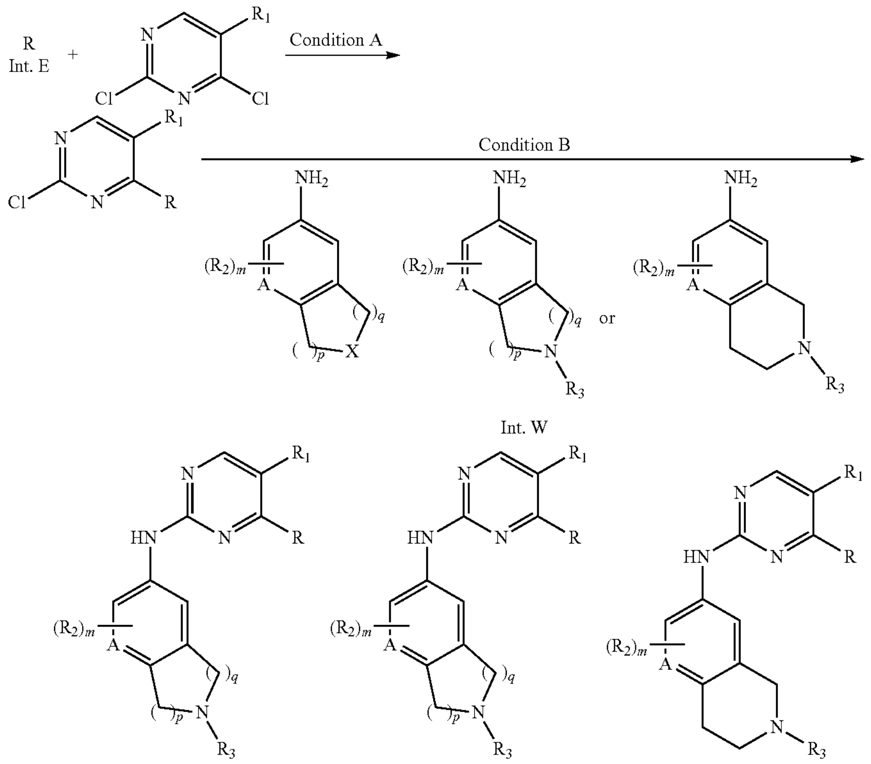

(I-0) (I-1) (I-2)

Condition A1: To a solution of Int. E (or commercially available reagent) (1.0 eq.) in DMF was added sodium hydride (60% dispersion in mineral oil, 1.2 eq.) at 0° C. and the mixture was stirred at 0° C. for 30 minutes. To the above reaction mixture was added 5-$R_1$ substituted 2,4-dichloropyrimidine (1.0-1.3 eq.) at 0° C., and the resulting mixture was then stirred at room temperature for 1 hour, cooled to 0° C., and quenched with ice-$H_2O$. The crude product was purified to provide 4-R and 5-$R_1$ substituted 2-Cl-pyrimidine.

Condition A2: To a solution of 5-$R_1$ substituted 2,4-dichloropyrimidine (1.0-1.5 eq.) in DMF were added potassium carbonate (2.0 eq.) and Int. E (or commercially available reagent) (1.0 eq.). The mixture was stirred at 80° C. overnight, cooled to room temperature, diluted with $H_2O$, and extracted with EA. The crude product was purified to provide 4-R and 5-$R_1$ substituted 2-Cl-pyrimidine.

Condition A3: To a solution of Int. E (or commercially available reagent) (1.0 eq.) in n-butanol were added 5-$R_1$ substituted 2,4-dichloropyrimidine (1.0-1.5 eq.) and DIPEA (1.0-2.0 eq.) subsequently. The reaction mixture was stirred at 100° C. for 18 hours, diluted with water, and extracted with EA. The crude product was purified to provide 4-R and 5-$R_1$ substituted 2-Cl-pyrimidine.

Condition B1: To a solution of Int. W (1.0-1.4 eq.) in 2-methoxyethanol were added 4-R and 5-$R_1$ substituted 2-Cl-pyrimidine (1.0 eq.) and HCl in EtOH solution (3.0 eq.). The resulting mixture was stirred at 120° C. for 20 hours and concentrated in vacuo. The residue was purified with flash column chromatography on silica gel, and/or prep-HPLC.

Condition B2: To a solution of 4-R and 5-$R_1$ substituted 2-Cl-pyrimidine (1.0 eq.) and Int. W (1-1.3 eq.) in isopropanol was added trifluoroacetic acid (1.0-3.0 eq.). The mixture was stirred under $N_2$ at 100° C. for 20 hours, cooled to room temperature, basified with saturated $NaHCO_3$ aqueous solution to pH~8, extracted with DCM. The organic phases were washed with brine, dried over anhydrous $Na_2SO_4$, and filtered. The filtrate was concentrated in vacuo, and the residue was purified by flash column chromatography on silica gel, and/or prep-HPLC.

Condition B3: To a solution of 4-R and 5-$R_1$ substituted 2-Cl-pyrimidine (1.0 eq.) and Int. W (1-1.3 eq.) in isopropanol was added $TsOH \cdot H_2O$ (1.0-1.2 eq.). The mixture was stirred at 100° C. overnight, cooled to room temperature, basified with saturated $NaHCO_3$ aqueous solution to pH~8, extracted with DCM. The organic phases were washed with brine, dried over anhydrous $Na_2SO_4$, and filtered. The filtrate was concentrated in vacuo, and the residue was purified by flash column chromatography on silica gel, and/or prep-HPLC.

Condition B4: To a solution of 4-R and 5-$R_1$ substituted 2-Cl-pyrimidine (1.0 eq.) in dioxane were added Int. W (1.0-1.2 eq.), $Pd_2(dba)_3$ (0.2 eq.), Xantphos (0.2 eq.), and potassium carbonate (2.0 eq.). The mixture was stirred at 100° C. under $N_2$ for 12 hours, cooled to room temperature, and filtered. The residue was purified with flash column chromatography on silica gel, and/or prep-HPLC.

There were additional conversions of 4-R and 5-$R_1$ substituted 2-Cl-pyrimidine between Condition A and B, and further conversions after Condition B, depending on specific examples.

Intermediates

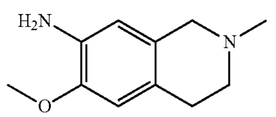

Int. W1

6-Methoxy-2-methyl-1,2,3,4-tetrahydroisoquinolin-7-amine

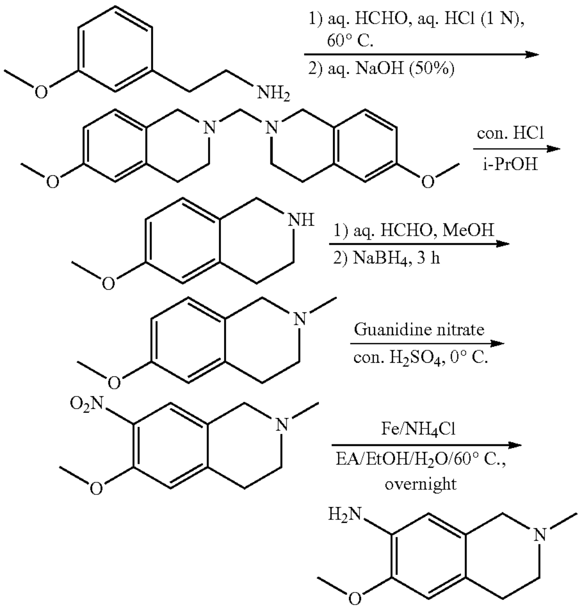

Step 1: To a mixture of 2-(3-methoxyphenyl)ethanamine (20.0 g, 132.27 mmol, 19.23 mL) in aqueous HCl solution (1 N, 192 mL, 192 mmol) was added an aqueous solution of formaldehyde (37% w.t., 41.64 g, 529.08 mmol). The mixture was stirred at 60° C. for 1 hour, cooled down to 0° C., and basified by dropwise addition of 50% aqueous NaOH solution (17.44 g, 218 mmol) at 0° C. The resulting mixture was stirred at room temperature overnight and filtered. The filtrate was concentrated to provide bis(6-methoxy-3,4-dihydroisoquinolin-2(1H)-yl)methane as white solid (23 g, 100% yield).

Step 2: To a suspension of bis(6-methoxy-3,4-dihydroisoquinolin-2(1H)-yl)methane (28 g, 82.73 mmol) in i-PrOH (200 mL) was added dropwise concentrated HCl (15.20 g, 182.01 mmol, 15.3 mL) at 0° C., and the mixture was stirred at room temperature for 18 hours. MTBE (70 mL) was added to above mixture and the suspension was stirred at room temperature for additional 4 hours. After filtration, the cake was washed with a mixture of MTBE/i-PrOH (100 mL, 1/1 v/v) and dried to provide 6-methoxy-1,2,3,4-tetrahydroisoquinoline hydrochloride as white solid, which was suspended in DCM (300 mL). To the mixture was added saturated aqueous $NaHCO_3$ solution (500 mL), and the mixture was stirred at room temperature for 2 hours. After separation, the aqueous layer was extracted with DCM (50 mL×4). The combined organic layers were dried over anhydrous $Na_2SO_4$, filtered, and concentrated to provide 6-methoxy-1,2,3,4-tetrahydroisoquinoline as yellow oil (10 g, 75% yield). LC-MS (ESI) m/z: 164 $[M+H]^+$.

Step 3: To a solution of 6-methoxy-1,2,3,4-tetrahydroisoquinoline (1.63 g, 9.99 mmol) in MeOH (30 mL) was added aqueous formaldehyde (37% w/w, 4.8 g, 59.92 mmol, 1.67 mL) at room temperature. The mixture was stirred at room temperature for 15 minutes, and cooled down to 0° C., to which was added $NaBH_4$ (1.13 g, 29.96 mmol) in portions. The mixture was stirred at room temperature for 3 hours, quenched with ice-water (10 mL) and extracted with DCM (20 mL×5). The organic layer was dried over anhydrous sodium sulfate, filtered, and concentrated. The residue was purified with flash column chromatography on silica gel (DCM/MeOH=10/1 v/v) to provide 6-methoxy-2-methyl-1,2,3,4-tetrahydroisoquinoline as yellow oil (1.7 g, 96% yield). LC-MS (ESI) m/z: 178 $[M+H]^+$.

Step 4: To a pre-cooled solution (0° C.) of concentrated sulfuric acid (4 mL) were subsequently added 6-methoxy-2-methyl-1,2,3,4-tetrahydroisoquinoline (2 g, 11.28 mmol), and guanidine nitrate (1.17 g, 9.59 mmol) at 0° C. The resulting mixture was stirred at 0° C. for 30 minutes, quenched with ice-water (20 mL), basified to pH 10-11 with aqueous NaOH solution (4 N), and extracted with DCM (50 mL×4). The combined organic layers were dried over anhydrous $Na_2SO_4$, filtered, and concentrated. The residue was purified with flash column chromatography on silica gel (PE 100% v/v, PE/EA=1/1 v/v, EA 100% v/v, and then DCM/MeOH=20/1, v/v) to provide 6-methoxy-2-methyl-7-nitro-1,2,3,4-tetrahydroisoquinoline as yellow solid (0.9 g, 36% yield). LC-MS (ESI) m/z: 223 $[M+H]^+$.

Step 5: To a solution of 6-methoxy-2-methyl-7-nitro-1,2,3,4-tetrohydroisoquinoline (4.2 g, 14.40 mmol) in EA (32 mL), $H_2O$ (16 mL), and EtOH (144 mL) were added Fe powder (5.5 g, 93.99 mmol) and ammonia chloride (793.96 mg, 13.08 mmol). The mixture was stirred at 60° C. for 48 hours, cooled down to room temperature, and filtered. The cake was washed with methanol (30 mL×3), and the filtrate was concentrated. The residue was purified with flash column chromatography on silica gel (DCM/MeOH=20/1 to 10/1 v/v) to provide 6-methoxy-2-methyl-1,2,3,4-tetrahydroisoquinolin-7-amine hydrochloride as yellow solid (4.5 g, 100% yield). LC-MS (ESI) m/z: 193 $[M+H]^+$.

Alternative Synthetic Method:

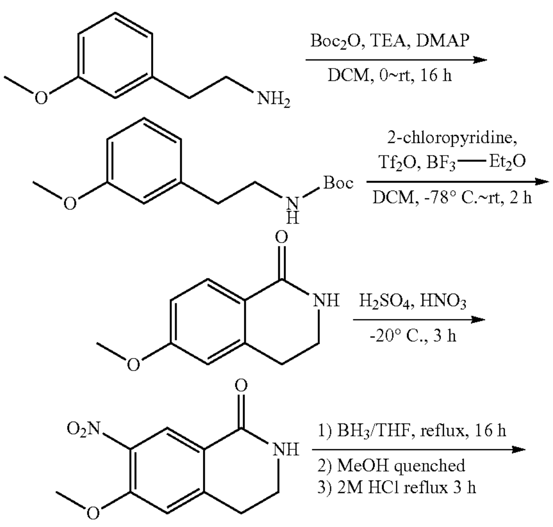

-continued

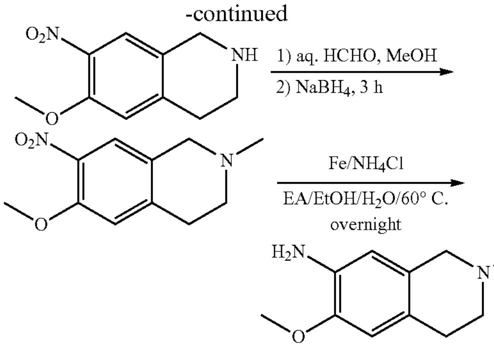

Step 1: To a solution of triethylamine (13.38 g, 132.27 mmol, 18.44 mL), 2-(3-methoxyphenyl)ethanamine (10 g, 66.13 mmol) and DMAP (807.96 mg, 6.61 mmol) in DCM (100 mL) was added $Boc_2O$ (15.88 g, 72.75 mmol, 16.70 mL) slowly at 0° C. the mixture was then stirred at room temperature for 16 hours, diluted with ice water (200 mL) and extracted with EtOAc (3×200 mL). The combined organic phase was washed with brine (100 mL), dried over anhydrous $Na_2SO_4$, filtered and concentrated in vacuo. The residue was purified with flash chromatography ($SiO_2$, petroleum ether/ethyl acetate=10/1) to provide tert-butyl (3-methoxyphenethyl)carbamate (14.6 g, 79.06% yield, 90% purity) as colorless liquid. LC-MS (ESI) m/z: 196 $[M+H-56]^+$.

Step 2: To a solution of tert-butyl (3-methoxyphenethyl) carbamate (7 g, 27.85 mmol) and 2-chloropyridine (4.74 g, 41.78 mmol, 3.92 mL) in $CH_2Cl_2$ (50 mL) was added a solution of $Tf_2O$ (8.64 g, 30.64 mmol, 5.15 mL) in $CH_2Cl_2$ (5 mL) at −78° C. 20 minutes later, $BH_3$'$Et_2O$ (19.77 g, 139.26 mmol) was added dropwise to the above solution. The reaction mixture was then warmed to room temperature, stirred for 2 hours, and quenched with the saturated $NaHCO_3$ solution carefully. The resulting mixture was extracted with $CH_2Cl_2$ (3×100 mL). The combined organic layer was washed with brine (50 mL), dried over anhydrous $Na_2SO_4$, filtered and concentrated in vacuo. The residue was purified with flash chromatography ($SiO_2$, petroleum ether/ethyl acetate/methanol=5/I/O to 10/10/1) to provide 6-methoxy-3,4-dihydroisoquinolin-1(2H)-one (3.4 g, 68.89% yield) as off-white solid. LC-MS (ESI) m/z: 178 $[M+H]^+$.

Step 3: To a solution of 6-methoxy-3,4-dihydroisoquinolin-1(2H)-one (3.8 g, 21.44 mmol, 9.62 mL) in concentrated $H_2SO_4$ (50 mL) was added $HNO_3$ (2.16 g, 22.29 mmol, 65% purity) dropwise at −20° C. The mixture was stirred at −20° C.∼−25° C. for 3 hours and poured into ice water (300 mL). The aqueous layer was extracted with dichloromethane (3×200 mL). The combined organic layers were concentrated in vacuo, and the residue was purified with flash column chromatography ($SiO_2$, Petroleum ether/ethyl acetate/methanol=10/1/0∼10/10/1) to provide 6-methoxy-7-nitro-3,4-dihydroisoquinolin-1(2H)-one (2.02 g, 40.78% yield). LC-MS (ESI) m/z: 223 $[M+H]^+$.

Step 4: To a solution of 6-methoxy-7-nitro-3,4-dihydroisoquinolin-1(2H)-one (2.02 g, 9.09 mmol) in THF (200 mL) was added 1M $BH_3$/THF (45.46 mmol, 45.5 mL). The mixture was stirred under reflux for 20 hours and quenched with methanol (30 mL) carefully. The resulting solution was concentrated in vacuo. The residue was heated in 2N HCl (50 mL) at 80° C. for 3 hours, cooled, basified with aqueous ammonium hydroxide, and extracted with dichloromethane (3×100 mL). The combined organic layer was dried over anhydrous sodium sulfate, filtered, and concentrated to provide 6-methoxy-7-nitro-1,2,3,4-tetrahydroisoquinoline (1.89 g, 100.00% yield). LC-MS (ESI) m/z: 209 $[M+H]^+$.

Step 5: To a solution of 6-methoxy-7-nitro-1,2,3,4-tetrahydroisoquinoline (1.89 g, 9.08 mmol, 9.62 mL) in methanol (30 mL) was added formaldehyde (1.64 g, 54.46 mmol, 1.51 mL) at room temperature. The mixture was stirred at room temperature for 15 minutes and cooled down to 0° C. Then $NaBH_4$ (1.03 g, 27.23 mmol) was added to the above mixture in portions. The resulting mixture was stirred at room temperature for 3 hours, quenched with ice-water (10 mL) and extracted with DCM (20 mL×5). The combined organic layer was dried over anhydrous sodium sulfate, filtered, and concentrated. The residue was purified with flash column chromatography on silica gel (DCM/MeOH=10/1, v/v) to provide 6-methoxy-2-methyl-7-nitro-1,2,3,4-tetrahydroisoquinoline (1.4 g, 69.40% yield) as yellow oil. LC-MS (ESI) m/z: 223 $[M+H]^+$.

Step 6: To a solution of 6-methoxy-2-methyl-7-nitro-1,2,3,4-tetrahydroisoquinoline (1.3 g, 5.85 mmol) in EtOAc (2 mL), $H_2O$ (1 mL), and EtOH (10 mL) were added Fe (2.19 g, 39.19 mmol) and ammonia chloride (284.74 mg, 5.32 mmol). The mixture was stirred at 60° C. for 16 hours, cooled down to room temperature, and filtered. The cake was washed with methanol (30 mL×3), and the filtrate was concentrated. The residue was purified with flash column chromatography on silica gel (DCM/MeOH=20/1 to 10/1 v/v) to provide 6-methoxy-2-methyl-1,2,3,4-tetrahydroisoquinolin-7-amine hydrochloride as yellow solid (0.85 g, 75.6% yield). LC-MS (ESI) m/z: 193 $[M+H]^+$.

Int. W2

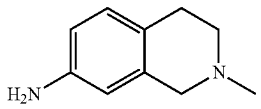

2-Methyl-1,2,3,4-tetrahydroisoquinolin-7-amine

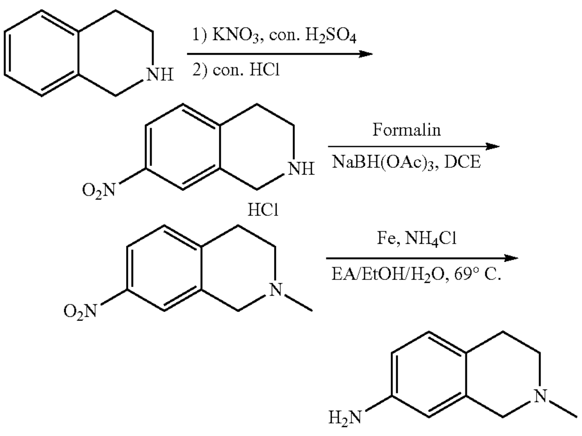

Step 1: To an ice-cold solution of 1,2,3,4-tetrahydroisoquinoline (4.8 g, 36.04 mmol) in concentrated sulfuric acid (20 mL) was added potassium nitrate (4.01 g, 47.21 mmol) in small portions, keeping the temperature below 5° C. The reaction mixture was stirred at room temperature overnight, poured into ice (100 g), adjusted to pH∼9 with $NH_3H_2O$, and extracted with $CH_2Cl_2$ (50 mL×3). The combined organic layers were dried over anhydrous sodium sulfate, filtered, and concentrated. The residue was crystallized in methanol to provide 7-nitro-1,2,3,4-tetrahydroisoquinoline hydrochloride as yellow solid (4.2 g, 54% yield). LC-MS (ESI) m/: 179 $[M+H]^+$.

Step 2: To a stirred mixture of 7-nitro-1,2,3,4-tetrahydroisoquinoline hydrochloride (5.0 g, 23.29 mmol) in dry 1,2-dichloroethane (200 mL) was added formalin (37% aqueous formaldehyde, 2.0 mL, 25.86 mmol), followed by triacetoxyborohydride (19.81 g, 104.82 mmol). The reaction mixture was vigorously stirred at room temperature for 4 hours, and concentrated. The residue was diluted with EtOAc (400 mL), slowly quenched with saturated aqueous $NaHCO_3$ solution (400 mL), and stirred for 30 minutes. The mixture was extracted with EA (100 mL×4). The organic layer was dried over anhydrous sodium sulfate, filtered and concentrate to provide 2-methyl-7-nitro-1,2,3,4-tetrahydroisoquinoline as brown solid (3.8 g, 85% yield). LC-MS (ESI) m/: 193 $[M+H]^+$.

Step 3: A suspension of 2-methyl-7-nitro-1,2,3,4-tetrahydroisoquinoline (3.8 g, 19.77 mmol), Fe (5.52 g, 98.85 mmol), $NH_4Cl$ (15.86 g, 296.54 mmol) in EA (10 mL), EtOH (100 mL), and $H_2O$ (20 mL) was stirred vigorously at 70° C. for 24 hours. After filtration, the cake was washed with a mixed solvent of EA/EtOH (100 mL, 10/1, v/v) and the filtrate was concentrated. The residue was purified with flash column chromatography on silica gel (MeOH in DCM, from 0% to 25% v/v) to provide 2-methyl-1,2,3,4-tetrahydroisoquinolin-7-amine as yellow solid (1.84 g, 57% yield). LC-MS (ESI) m/z: 163 $[M+H]^+$.

Int. W3

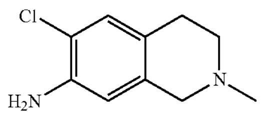

6-Chloro-2-methyl-1,2,3,4-tetrahydroisoquinolin-7-amine

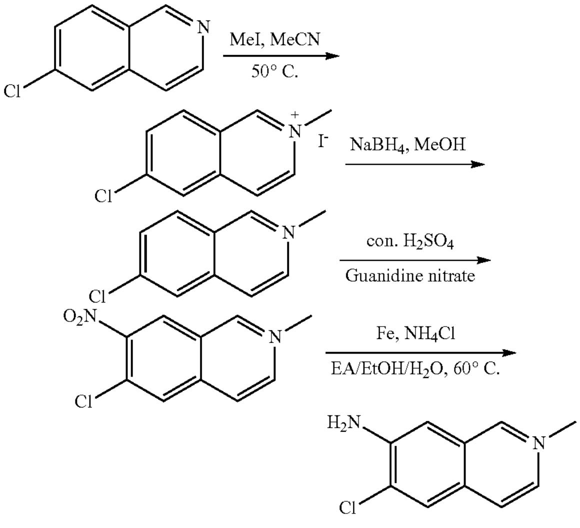

Step 1: To a solution of 6-chloroisoquinoline (2.0 g, 12.22 mmol) in MeCN (15 mL) was added MeI (5.21 g, 36.67 mmol) at room temperature. The mixture was stirred at 50° C. in a sealed tube for 2 days. After cooled down to room temperature, the solid was collected by filtration dried to provide 6-chloro-2-methylisoquinolin-2-ium iodide as yellow solid (3.2 g, 86% yield). LC-MS (ESI) m/z: 178 $[M+H]^+$.

Step 2: To a solution of 6-chloro-2-methylisoquinolin-2-ium iodide (200 mg, 0.65 mmol) in MeOH (8 mL) was added $NaBH_4$ (127.06 mg, 3.36 mmol) in portions at 0° C. The mixture was stirred at room temperature for 3 hours, adjusted to pH~9 with saturated aqueous $NaHCO_3$ solution, and extracted with DCM (30 mL×3). The organic layer was dried over anhydrous sodium sulfate, filtered and concentrated. The residue was purified with prep-TLC (DCM/MeOH=20/1, v/v) to provide 6-chloro-2-methyl-1,2,3,4-tetrahydroisoquinoline as yellow solid (90 mg, 44% yield). LC-MS (ESI) m/z: 182 $[M+H]^+$.

Step 3&4: The same procedures as Step 4&5 of Int. W1, using 6-chloro-2-methyl-1,2,3,4-tetrahydroisoquinoline in place of 6-methoxy-2-methyl-1,2,3,4-tetrahydroisoquinoline. LC-MS (ESI) m/z: 197 $[M+H]^+$.

Int. W4

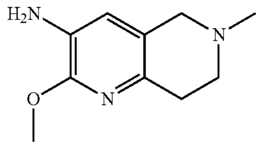

2-Methoxy-6-methyl-5,6,7,8-tetrahydro-1,6-naphthyridin-3-amine

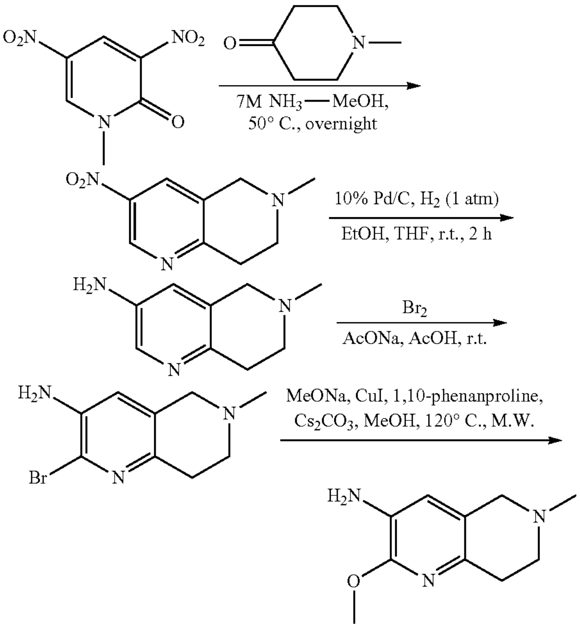

Step 1: A solution of 1-methyl-3,5-dinitro-pyridin-2-one (4.5 g, 22.60 mmol) and 1-methylpiperidin-4-one (2.81 g, 24.86 mmol) in $NH_3$/MeOH (7 N, 50 mL) was stirred in a sealed tube at 50° C. overnight. After cooled down to room temperature, the mixture was concentrated, and the residue was partitioned between DCM (100 mL) and saturated aqueous $NaHCO_3$ solution (50 mL). The layers were separated, and the aqueous layer was extracted with DCM (50 mL×2). The combined organic layers were dried over anhydrous $Na_2SO_4$, filtered, and concentrated to provide 6-methyl-3-nitro-5,6,7,8-tetrahydro-1,6-naphthyridine as red solid (2.84 g, 65% yield). LC-MS (ESI) m/z: 194 $[M+H]^+$.

Step 2: To a solution of 6-methyl-3-nitro-7,8-dihydro-5H-1,6-naphthyridine (1.3 g, 6.73 mmol) in ethanol (35 mL) and THF (35 mL) was added 10% Pd/C (817.20 mg), and the mixture was stirred under $H_2$ (1 atm) for 2 hours. After filtration, the cake was washed with EtOH (5 mL×2) and the filtrate was concentrated to provide 6-methyl-5,6,7,8-tetrahydro-1,6-naphthyridin-3-amine as yellow solid (1.1 g, 100% yield). LC-MS (ESI) m/z: 164 $[M+H]^+$.

Step 3: To a solution of 6-methyl-5,6,7,8-tetrahydro-1,6-naphthyridin-3-amine (1.2 g, 7.35 mmol) and AcONa (1.21 g, 14.70 mmol) in acetic acid (25 mL) was added bromine (1.17 g, 7.35 mmol) at room temperature and the mixture was stirred at room temperature for 1 hour. The mixture was diluted in DCM (100 mL) and water (30 mL), and slowly adjusted to pH~9 with $NaHCO_3$. The organic layer was dried over anhydrous $Na_2SO_4$, filtered, and concentrated. The residue was purified with flash column chromatography on silica gel (DCM/MeOH=20/1, v/v) to provide 2-bromo-6-methyl-5,6,7,8-tetrahydro-1,6-naphthyridin-3-amine as yellow solid (570 mg, 32%). LC-MS (ESI) m/z: 242 [M+H].

Step 4: To a mixture of 2-bromo-6-methyl-5,6,7,8-tetrahydro-1,6-naphthyridin-3-amine (250 mg, 1.03 mmol), cesium carbonate (672.86 mg, 2.07 mmol) and MeONa (83.67 mg, 1.55 mmol) in MeOH (2 mL) were added CuI (19.67 mg, 103.26 umol) and 1,10-phenanthroline monohydrate (40.94 mg, 206.51 umol). The mixture was stirred under microwave conditions protected by $N_2$ at 120° C. for 2 hours. After cooled down to room temperature, the residue was purified with prep-TLC (DCM/MeOH=15/1, v/v) to provide 2-methoxy-6-methyl-5,6,7,8-tetrahydro-1,6-naphthyridin-3-amine as yellow solid (74 mg, 37% yield). LC-MS (ESI) m/z: 194 $[M+H]^+$.

Int. W5

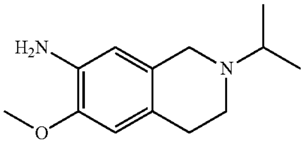

2-Isopropyl-6-methoxy-1,2,3,4-tetrahydroisoquinolin-7-amine

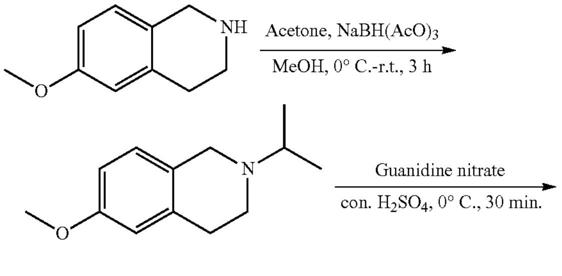

-continued

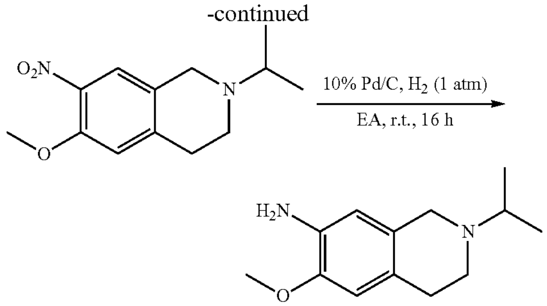

Step 1: To a mixture of 6-methoxy-1,2,3,4-tetrahydroisoquinoline (340 mg, 2.08 mmol) in MeOH (10 mL) was added dropwise acetone (725.93 mg, 12.50 mmol, 917.74 uL) at room temperature, and the mixture was stirred at room temperature for 30 minutes. Then $NaBH(AcO)_3$ (6.25 mmol) was added in portions to the above mixture at 0° C., and the resulting mixture was stirred at room temperature for 3 hours, quenched with saturated aqueous $NaHCO_3$ solution (10 mL) at 0° C., and concentrated. The residue was extracted with DCM (50 mL×2), and the combined organic layers were washed with brine (20 mL×2), dried over anhydrous $Na_2SO_4$, filtered and concentrated. The residue was purified with flash column chromatography on silica gel (DCM/MeOH=20/1, v/v) to provide 2-isopropyl-6-methoxy-1,2,3,4-tetrahydroisoquinoline as white solid (150 mg, 35% yield). LC-MS (ESI) m/z: 206 $[M+H]^+$.

Step 2: The same procedures as Step 4 of Int. W1, using 2-isopropyl-6-methoxy-1,2,3,4-tetrahydroisoquinoline in place of 6-methoxy-2-methyl-1,2,3,4-tetrahydroisoquinoline. LC-MS (ESI) m/z: 251 $[M+H]^+$.

Step 3: A mixture of 2-isopropyl-6-methoxy-7-nitro-1,2,3,4-tetrahydroisoquinoline (200 mg, 799.06 umol), and 10% palladium on carbon (30 mg, 799.06 umol) in EA (6 mL) was stirred under $H_2$ (1 atm) at room temperature for 16 hours, and filtered. The filtrate was concentrated, and the residue was purified with prep-TLC (DCM/MeOH=10/1, v/v) to provide 2-isopropyl-6-methoxy-1,2,3,4-tetrahydroisoquinolin-7-amine as white solid (50 mg, 28% yield). LC-MS (ESI) m/z: 221 $[M+H]^+$.

Int. W6

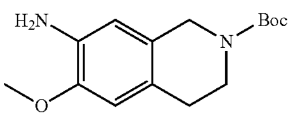

tert-Butyl 7-amino-6-methoxy-3,4-dihydroisoquinoline-2(1H)-carboxylate

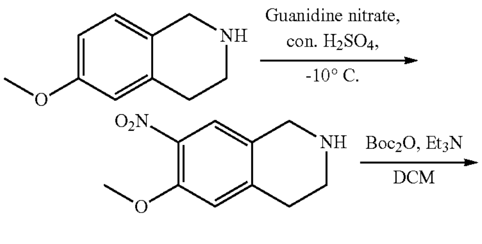

-continued

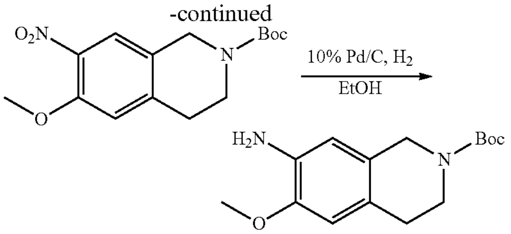

Step 1: To a cold solution of concentrated $H_2SO_4$ (5 mL) was added 6-methoxy-1,2,3,4-tetrahydroisoquinoline (1.0 g, 1.84 mmol) under −10° C. Guanidine nitrate (758 mg, 6.13 mmol) was added to the above mixture in portions at −10° C. The mixture was stirred at −10° C. for 30 minutes, poured into cold-water (20 mL), adjusted to pH~8 with aqueous NaOH solution (4 N), and extracted with EA (40 mL×4). The combined organic layers were dried over anhydrous sodium sulfate, filtered and concentrated. The residue was purified with flash column chromatography on silica gel (DCM 100% v/v, and then DCM/MeOH=10/1, v/v) to provide 6-methoxy-7-nitro-1,2,3,4-tetrahydroisoquinoline as yellow solid (200 mg, 16% yield). LC-MS (ESI) m/z: 209 $[M+H]^+$.

Step 2: A mixture of 6-methoxy-7-nitro-1,2,3,4-tetrahydroisoquinoline (100 mg, 0.48 mmol), $Boc_2O$ (157 mg, 0.72 mmol), and $Et_3N$ (97 mg, 0.96 mmol) in DCM (5 mL) was stirred at room temperature for 4 hours, and concentrated. The residue was purified with flash column chromatography on silica gel (DCM 100% v/v, and then DCM/MeOH=10/1, v/v) to provide tert-butyl 6-methoxy-7-nitro-3,4-dihydroisoquinoline-2(1H)-carboxylate as yellow oil (150 mg, 100% yield). LC-MS (ESI) m/z: 209 $[M-100+1]^+$.

Step 3: A mixture of tert-butyl 6-methoxy-7-nitro-3,4-dihydroisoquinoline-2(1H)-carboxylate (150 mg, 0.48 mmol) and 10% Pd/C (50 mg) in EtOH (5 mL) was stirred under $H_2$ (1 atm) at room temperature for 16 hours, and filtered. The filtrate was concentrated to provide tert-butyl 7-amino-6-methoxy-3,4-dihydroisoquinoline-2(1H)-carboxylate as yellow solid (110 mg, 81% yield). LC-MS (ESI) m/z: 223 $[M-55]^+$.

Int. W7

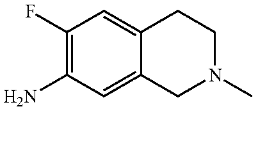

6-Fluoro-2-methyl-1,2,3,4-tetrahydroisoquinolin-7-amine

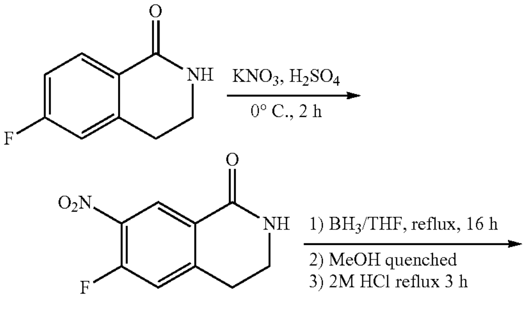

-continued

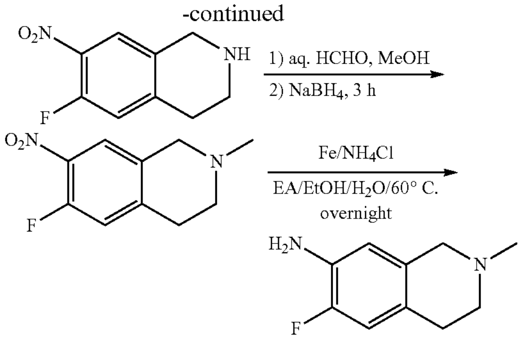

Step 1: To a solution of 6-fluoro-3,4-dihydro-2H-isoquinolin-1-one (900 mg, 5.45 mmol) in $H_2SO_4$ (9 mL) was added potassium nitrate (578.47 mg, 5.72 mmol) in portions at 0° C. The resulting mixture was stirred at 0° C. for 2 hours and poured into ice-water. The white solid was precipitated, collected by filtration, and dried in vacuo to provide 6-fluoro-7-nitro-3,4-dihydro-2H-isoquinolin-1-one (1.04 g, 86% yield). LC-MS (ESI) m/z: 211 $[M+H]^+$.

Step 2&3&4: The same procedures as Step 4&5&6 of alternative synthetic method of Int. W1, using 6-fluoro-7-nitro-3,4-dihydro-2H-isoquinolin-1-one in place of 6-methoxy-7-nitro-3,4-dihydro-2H-isoquinolin-1-one. LC-MS (ESI) m/z: 181 $[M+H]^+$.

Int. W8

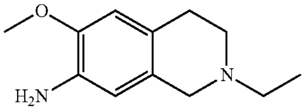

2-Ethyl-6-methoxy-1,2,3,4-tetrahydroisoquinolin-7-amine

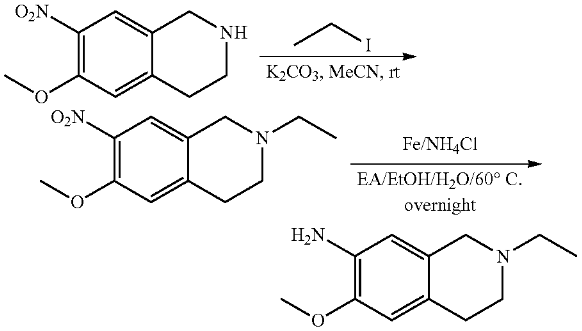

Step 1: To a solution of 6-methoxy-7-nitro-1,2,3,4-tetrahydroisoquinoline (300 mg, 1.44 mmol) in $CH_3CN$ (10 mL) were added iodoethane (224.72 mg, 1.44 mmol, 115.83 uL) and $K_2CO_3$ (796.52 mg, 5.76 mmol). The reaction mixture was stirred at 20° C. for 16 hours and partitioned between ethyl acetate (100 mL) and water (100 mL). The organic layer was separated, dried over anhydrous magnesium sulfate, and filtered. The filtrate was concentrated in vacuo, and the residue was purified by flash column chromatography on silica gel (0-20% methanol in dichloromethane with aqueous ammonium hydroxide) to provide 2-ethyl-6-methoxy-7-nitro-1,2,3,4-tetrahydroisoquinoline (136 mg, 40% yield). LC-MS (ESI) m/z: 237 $[M+H]^+$.

Step 2: The same procedures as Step 6 of alternative synthetic method of Int. W1, using 2-ethyl-6-methoxy-7-nitro-1,2,3,4-tetrahydroisoquinoline in place of 2-methyl-6-methoxy-7-nitro-1,2,3,4-tetrahydroisoquinoline. LC-MS (ESI) m/z: 207 $[M+H]^+$.

Int. W9

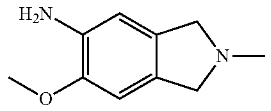

6-Methoxy-2-methylisoindolin-5-amine

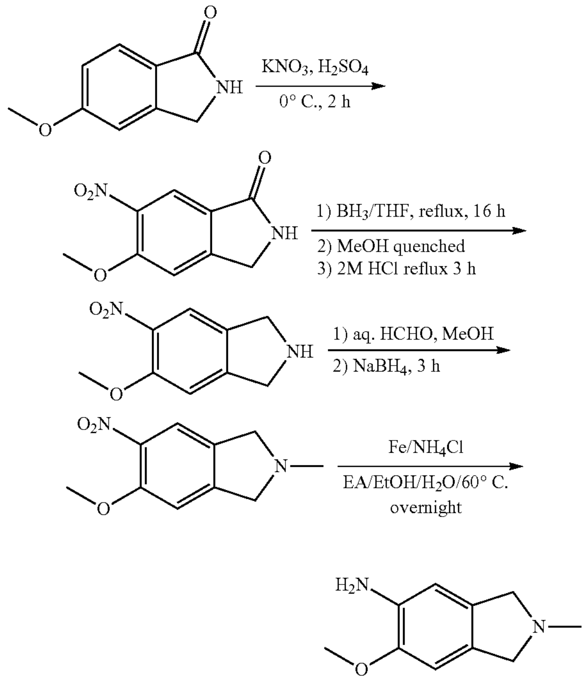

Step 1: The same procedures as Step 1 of Int. W7, using 5-methoxyisoindolin-1-one in place of 6-fluoro-3,4-dihydroisoquinolin-1(2H)-one. LC-MS (ESI) m/z: 209 $[M+H]^+$.

Step 2&3&4: The same procedures as Step 4&5&6 of alternative synthetic method of Int. W1, using 5-methoxy-6-nitroisoindolin-1-one in place of 6-methoxy-7-nitro-3,4-dihydro-2H-isoquinolin-1-one. LC-MS (ESI) m/z: 179 $[M+H]^+$.

Int. W10

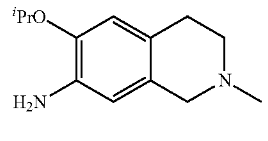

6-Isopropoxy-2-methyl-1,2,3,4-tetrahydroisoquinolin-7-amine

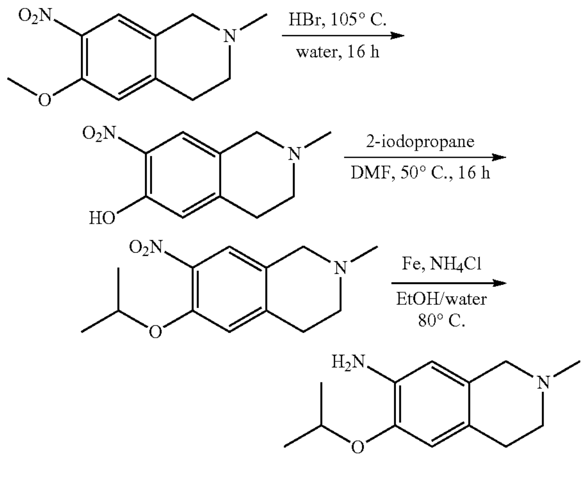

Step 1: To a solution of 6-methoxy-2-methyl-7-nitro-1,2,3,4-tetrahydroisoquinoline (50 mg, 224.98 umol) in water (5 mL) was added 1M hydrogen bromide (1 mL). The mixture was stirred under reflux for 16 hours, basified to pH 8 with saturated sodium bicarbonate aqueous solution and extracted with dichloromethane/methanol (v/v, 10/1, 20 mL×3). The organic phases were dried over anhydrous sodium sulfate and filtered. The filtrate was concentrated in vacuo to provide crude 2-methyl-7-nitro-1,2,3,4-tetrahydroisoquinolin-6-ol (46.84 mg, 90% yield). LC-MS (ESI) m/z: 209 $[M+H]^+$.

Step 2: To a solution of 2-methyl-7-nitro-1,2,3,4-tetrahydroisoquinolin-6-ol (230 mg, 1.10 mmol) and 2-iodopropane (187.78 mg, 1.10 mmol, 110.46 uL) in DMF (2 mL) was added potassium carbonate (229.00 mg, 1.66 mmol). The mixture was stirred at room temperature for 16 hours and diluted with brine (10 mL). The aqueous phase was separated and extracted with ethyl acetate (20 mL×3). The organic phases were dried over anhydrous sodium sulfate and filtered. The filtrate was concentrated in vacuo, and the residue was purified by flash column chromatography on silica gel (EA/PE: 1050%) to provide 6-isopropoxy-2-methyl-7-nitro-1,2,3,4-tetrahydroisoquinoline (240 mg, 87% yield). LC-MS (ESI) m/z: 251 $[M+H]^+$.

Step 3: The same procedures as Step 6 of alternative synthetic method of Int. W1, using 6-isopropoxy-2-methyl-7-nitro-1,2,3,4-tetrahydroisoquinoline in place of 6-methoxy-2-methyl-7-nitro-1,2,3,4-tetrahydroisoquinoline 5-methoxy-6-nitroisoindolin-1-one. LC-MS (ESI) m/z: 221 $[M+H]^+$.

Int. W11

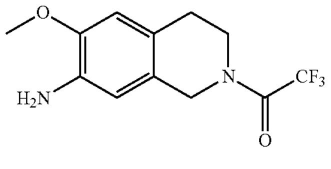

1-(7-Amino-6-methoxy-3,4-dihydroisoquinolin-2(1H)-yl)-2,2,2-trifluoroethan-1-one

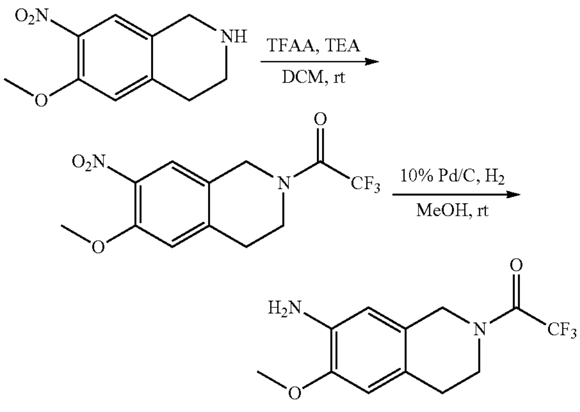

Step 1: To a solution of 6-methoxy-7-nitro-1,2,3,4-tetrahydroisoquinoline (908 mg, 4.14 mmol) in dichloromethane (15 mL) was added triethylamine (838.43 mg, 8.29 mmol, 1.15 mL) at 0° C., followed by the addition of trifluoroacetic anhydride (1.04 g, 4.97 mmol, 700.78 uL). The reaction mixture was stirred at room temperature for 3 hours, basified to pH 8 with saturated $NaHCO_3$ aqueous solution, and exacted with dichloromethane (10 mL×3). The combined organic phase was dried over anhydrous sodium sulfate and filtered. The filtrate was concentrated in vacuo to provide crude 2,2,2-trifluoro-1-(6-methoxy-7-nitro-3,4-dihydroisoquinolin-2 (1H)-yl)ethan-1-one as yellow solid (1.26 g, 95% yield). LC-MS (ESI) m/z: 305 $[M+H]^+$.

Step 2: A mixture of 2,2,2-trifluoro-1-(6-methoxy-7-nitro-3,4-dihydroisoquinolin-2(1H)-yl)ethan-1-one (1.33 g, 4.14 mmol) and 10% palladium on carbon (400 mg, 3.76 mmol) in methanol (30 mL) was stirred at 25° C. for 16 hours under $H_2$ atmosphere and filtered through celite. The cake was washed with methanol (30 mL×3), and the filtrate was concentrated in vacuo to provide 1-(7-amino-6-methoxy-3,4-dihydroisoquinolin-2(1H)-yl)-2,2,2-trifluoroethan-1-one as light-yellow solid (1.14 g, 95% yield). LC-MS (ESI) m/z: 275 $[M+H]^+$.

Int. E1

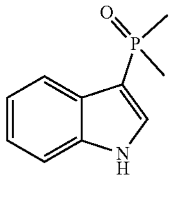

(1H-indol-3-yl)dimethylphosphine oxide

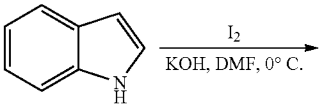

-continued

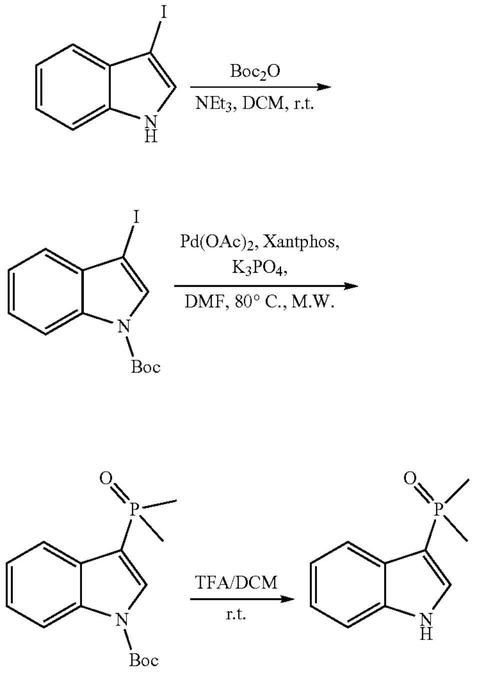

Step 1: To a mixture of 1H-indole (2.34 g, 19.97 mmol) and KOH (1.34 g, 23.97 mmol) in DMF (40 mL) was added dropwise a solution of $I_2$ (5.08 g, 19.97 mmol) in DMF (10 mL) at 0° C. The resulting mixture was stirred at 0° C. for 30 minutes, diluted with cold water (200 mL), and stirred for another 30 minutes. The solid was collected by filtration, washed with $H_2O$ (30 mL×3) and dried in vacuo to provide 3-iodo-1H-indole as yellow solid (2.58 g, 53% yield).

Step 2: To a solution of 3-iodo-1H-indole (2.4 g, 9.87 mmol) in DCM (15 mL) were added triethylamine (3.00 g, 4.13 mL, 29.62 mmol), $Boc_2O$ (4.31 g, 19.75 mmol), and DMAP (120.64 mg, 0.99 mmol). The mixture was stirred at room temperature for 1 hour and concentrated in vacuo. The residue was purified with flash column chromatography on silica gel (EA/PE=20/1, v/v) to provide tert-butyl 3-iodo-1H-indole-1-carboxylate as brown oil (4.6 g, 100% yield).

Step 3: A mixture of tert-butyl 3-iodoindole-1-carboxylate (1.0 g, 2.91 mmol), dimethylphosphine oxide (250.19 mg, 3.21 mmol), $Pd(OAc)_2$ (65.42 mg, 0.29 mmol), Xantphos (168.61 mg, 0.29 mmol), and $K_3PO_4$ (680.40 mg, 3.21 mmol) in DMF (8 mL) was stirred at 80° C. under microwave condition protected by $N_2$ for 5 hours. After cooling down to room temperature, the mixture was concentrated and the residue was purified with flash column chromatography on silica gel (DCM 100% v/v, and then DCM/MeOH=20/1 v/v) to provide tert-butyl 3-(dimethylphosphoryl)-1H-indole-1-carboxylate as brown oil (1 g, 100% yield). LC-MS (ESI) m/z: 294 $[M+H]^+$.

Step 4: To a solution of tert-butyl 3-(dimethylphosphoryl)-1H-indole-1-carboxylate (1.0 g, 3.41 mmol) in DCM (6 mL) was added TFA (3 mL) at 0° C. The mixture was stirred at room temperature overnight, and concentrated in vacuo. The residue was purified with flash column chromatography on silica gel (DCM/MeOH=20/1, v/v) to provide (1H-indol-3-yl)dimethylphosphine oxide as white solid (460 mg, 70% yield). LC-MS (ESI) m/z: 194 $[M+H]^+$.

Int. E2

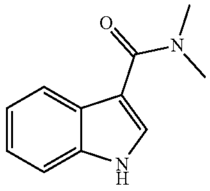

N,N-dimethyl-1H-indole-3-carboxamide

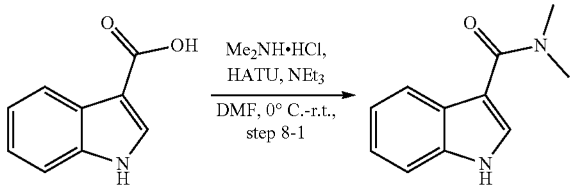

To a solution of 1H-indole-3-carboxylic acid (1.0 g, 6.21 mmol), HATU (4.72 g, 12.41 mmol), and dimethylamine hydrochloride (1.01 g, 12.41 mmol) in DMF (15 mL) was added dropwise triethylamine (2.51 g, 3.46 mL, 24.82 mmol) at 0° C. The mixture was stirred at room temperature for 14 hours, diluted with $H_2O$ (100 mL), and extracted with ethyl acetate (100 mL×3). The combined organic layers were washed with brine (100 mL×5), dried over anhydrous sodium sulfate and filtered. The filtrate was concentrated in vacuo to provide N,N-dimethyl-1H-indole-3-carboxamide as white solid (650 mg, 56% yield). LC-SM (ESI) m/z: 189 $[M+H]^+$.

Int. E3

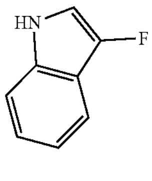

3-Fluoro-1H-indole

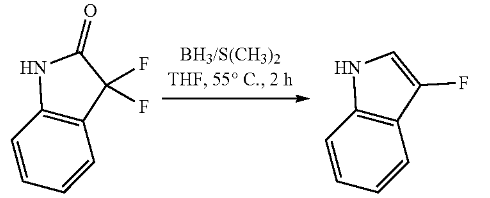 [SMILES: O=C1Nc2ccccc2C1(F)F ; Fc1c[nH]c2ccccc12]

Step 1: To a solution of 3,3-difluoroindolin-2-one (300 mg, 1.77 mmol) in THF (5 mL) was added $BH_3/S(CH_3)_2$ (2 M) (6.21 mmol, 3 mL) dropwise at 0° C. The mixture was stirred at room temperature for 2 hours, quenched with 10% citric acid aqueous solution at 0° C., and diluted with water. The resulting mixture was extracted with ethyl acetate (50 mL×3), and the organic phases were washed with brine (100 mL), dried over anhydrous sodium sulfate and filtered. The filtrate was concentrated in vacuo to provide 3-fluoro-1H-indole (220 mg, 91.78% yield) as yellow solid. LC-MS (ESI) m/z: 136.1 $[M+H]^+$.

Int. E4

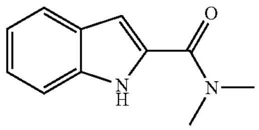

N,N-dimethyl-1H-indole-2-carboxamide

The same procedures as Int. E2, using 1H-indole-2-carboxylic acid in place of 1H-indole-3-carboxylic acid. LC-MS (ESI) m/z: 189 $[M+H]^+$.

Int. E5

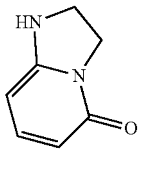

2,3-Dihydroimidazo[1,2-a]pyridin-5(1H)-one

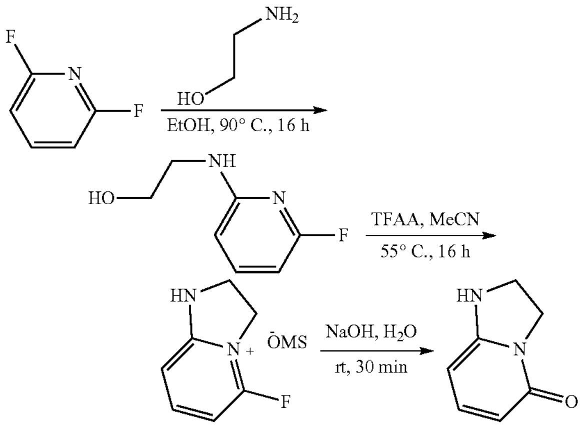

Step 1: A mixture of 2,6-difluoropyridine (2.3 g, 19.99 mmol, 1.81 mL) and 2-aminoethanol (12.21 g, 199.86 mmol, 12.09 mL) in ethanol (40 mL) was stirred for 16 hours at 90° C., quenched with water (50 mL) and extracted with EtOAc (3×100 mL). The combined organic phase was washed with brine (50 mL), dried over anhydrous $Na_2SO_4$, filtered and concentrated in vacuo. The residue was purified with flash chromatography ($SiO_2$, ethyl acetate 100%) to provide afford 2-((6-fluoropyridin-2-yl)amino)ethan-1-ol (3 g, 93.24% yield, 97% purity) as colorless liquid. LC-MS (ESI) m/z: 157.2 $[M+H]^+$.

Step 2: A mixture of 2-((6-fluoropyridin-2-yl)amino) ethan-1-ol (500 mg, 3.20 mmol) and (2,2,2-trifluoroacetyl) 2,2,2-trifluoroacetate (1.68 g, 8.00 mmol, 1.13 mL) in MeCN (1 mL) was stirred for 16 hours at 55° C. in a sealed tube, and concentrated in vacuo. The residue was used in next step without purification.

Step 3: A portion of crude 5-fluoro-2,3-dihydro-1H-imidazo[1,2-a]pyridin-4-ium (500 mg, 3.59 mmol) was dissolved in water (25 mL) with NaOH (503.05 mg, 12.58 mmol) in 236.18 uL of water. The mixture was stirred at room temperature for 30 hours, neutralized with concentrated HCl, and concentrated in vacuo. The resulting solid was suspended in DCM, filtered through a pad of celite and washed with EtOAc. The combined organic phase was concentrated in vacuo, and the residue was purified with silica gel chromatography (DCM/MeOH=20/1) to provide 2,3-dihydroimidazo[1,2-a]pyridin-5(1H)-one (100 mg, 10.22% yield, 50% purity). LC-MS (ESI) m/z: 137.1 [M+H]$^+$.

Int. E6

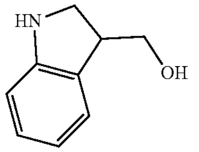

Indolin-3-ylmethanol

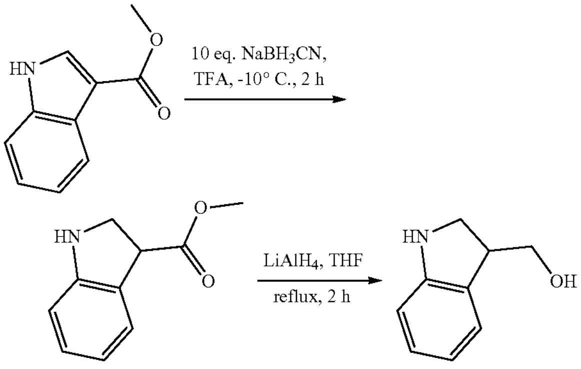

Step 1: To a solution of methyl 1H-indole-3-carboxylate (1.75 g, 9.99 mmol) in TFA (30 mL) was added $NaBH_3CN$ (6.28 g, 99.90 mmol) in portions at −10° C. Then the mixture was stirred at the same temperature for another hour and quenched with aqueous NaOH (10%, 100 mL). The resulting mixture was extracted with dichloromethane (3×100 mL). The combined organic layer was dried over anhydrous $Na_2SO_4$ and filtered. The filtrate was concentrated in vacuo to afford methyl indoline-3-carboxylate (0.54 g, 1.52 mmol, 50% purity). LC-MS (ESI) m/z: 178 [M+H]$^+$.

Step 2: A solution of methyl indoline-3-carboxylate (0.2 g, 1.13 mmol) in THF (10 mL) was treated with 1.0 M $LiAlH_4$ (94.24 mg, 2.48 mmol) in THF and stirred under reflux for 2 hours. The mixture was quenched via careful addition of methanol (10 mL). The resulting solution was concentrated in vacuo. The resulting residue was purified by flash column chromatography on silica gel (MeOH/DCM=0-10%) to afford indolin-3-ylmethanol as colorless oil (90 mg, 53% yield). LC-MS (ESI) m/z: 150 [M+H]$^+$.

Int. E7

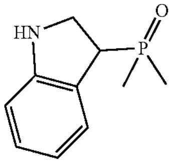

Indolin-3-yldimethylphosphine oxide

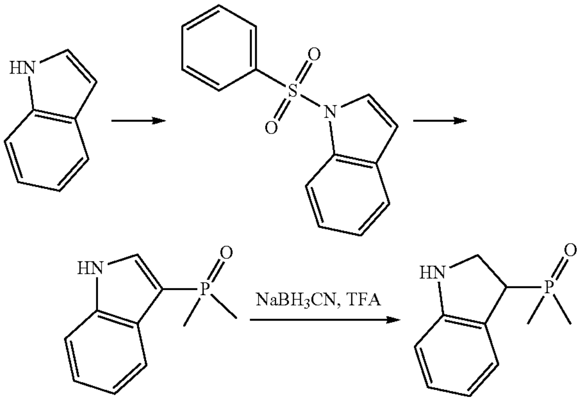

Step 1: To a solution of indole (2 g, 17.07 mmol) in THF (20 mL) was added NaH (819.40 mg, 20.49 mmol, 60% in mineral oil) at 0° C. The mixture was stirred at 0° C. for 30 minutes, and benzenesulfonyl chloride (3.62 g, 20.49 mmol) was added to the above mixture. The resulting mixture was stirred at room temperature for an hour, cooled to 0° C., and quenched with ice-water (100 mL). The mixture was extracted with ethyl acetate (3×50 mL), and the combined organic phases were dried over anhydrous sodium sulfate and filtered. The filtrate was concentrated in vacuo, and the residue was purified by flash column chromatography on silica gel (EA/PE=9/1) to provide 1-(phenylsulfonyl)-1H-indole as colorless oil (3.8 g, 87% yield). LC-MS (ESI) m/z: 258 [M+H]$^+$.

Step 2: The mixture of 1-(phenylsulfonyl)-1H-indole (500 mg, 1.94 mmol) and $AgNO_3$ (330.34 mg, 1.94 mmol) in $CH_3CN$ (30 mL) was stirred under $N_2$ atmosphere at room temperature for 2 hours, followed by the addition of dimethylphosphine oxide (455.00 mg, 5.83 mmol). The mixture was stirred for 16 hours at 100° C. and filtered through silica gel. The filtrate was concentrated in vacuo, and the residue was purified by flash column chromatography on silica gel (DCM/MeOH=10/1) to provide (1H-indol-3-yl)dimethylphosphine oxide as yellow oil (150 mg, 13% yield). LC-MS (ESI) m/z: 194 [M+H]$^+$.

Step 3: To a solution of (1H-indol-3-yl)dimethylphosphine oxide (175 mg, 905.88 umol) in TFA (5 mL) was added $NaBH_3CN$ (570.71 mg, 9.06 mmol) in batches at −5° C. The reaction mixture was stirred at room temperature overnight, adjusted to pH 9-10 with 2 N NaOH solution, and diluted with dichloromethane/methanol (10/1). The aqueous phase was extracted with dichloromethane/methanol (10/1, 20 mL×3). The organic phases were dried over anhydrous sodium sulfate and filtered. The filtrate was concentrated in vacuo to provide indolin-3-yldimethylphosphine oxide as colorless oil (40 mg, 14% yield). LC-MS (ESI) m/z: 196 [M+H]$^+$.

Int. E8

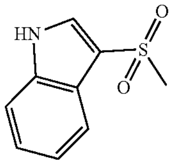

3-(Methylsulfonyl)-1H-indole

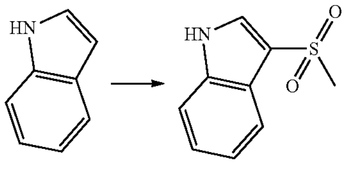

To a solution of indole (1 g, 8.54 mmol) in THF (20 mL) was added potassium 2-methylpropan-2-olate (1.05 g, 9.39 mmol). The reaction mixture was stirred at 25° C. for 30 minutes, followed by the addition of triethylborane (920.15 mg, 9.39 mmol) and me thanesulfonyl chloride (1.08 g, 9.39 mmol, 726.77 uL) sequentially. The reaction mixture was stirred at −15° C. for 16 hours, quenched with saturated ammonium chloride solution (50 mL), and extracted with ethyl acetate (30 mL×3). The organic phase was dried over anhydrous sodium sulfate and filtered. The filtrate was concentrated in vacuo, and the residue was purified by flash column chromatography on silica gel (PE/EA=5/1) to provide 3-methylsulfonyl-1H-indole as light-yellow solid (810 mg, 46% yield). LC-MS (ESI) m/z: 196 $[M+H]^+$.

Int. E9

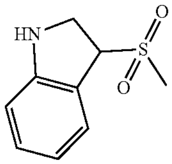

3-(Methylsulfonyl)indoline

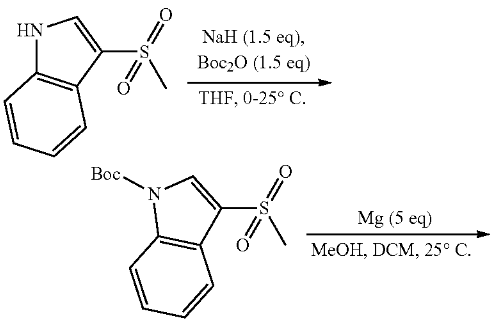

-continued

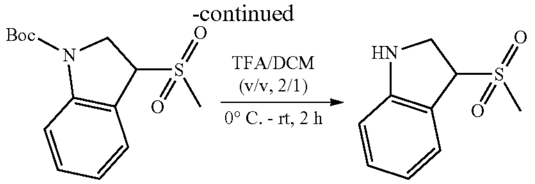

Step 1: To a solution of 3-methylsulfonyl-1H-indole (546 mg, 2.8 mmol) in THF (5 mL) was added NaH (172 mg, 4.3 mmol, 60% in mineral oil) slowly at 0° C. The reaction mixture was stirred at 0° C. for 30 minutes, followed by the addition of $Boc_2O$ (934 mg, 4.3 mmol). The reaction mixture was stirred at 25° C. for 16 hours, quenched with saturated ammonium chloride solution (10 mL), and extracted with ethyl acetate (10 mL×3). The organic phase was dried over anhydrous sodium sulfate and filtered. The filtrate was concentrated in vacuo, and residue was purified through chromatography column on silica gel (PE/EA=5/1) to provide tert-butyl 3-(methylsulfonyl)-1H-indole-1-carboxylate as yellow solid (530 mg, 64% yield). LC-MS (ESI) m/z: 296 $[M+H]^+$.

Step 2: To a stirring solution of tert-butyl 3-(methylsulfonyl)-1H-indole-1-carboxylate (530 mg, 1.70 mmol) in dichloromethane (14 mL) and methanol (52 mL) was added magnesium (207. mg, 8.52 mmol) slowly. The reaction mixture was stirred at 25° C. for 16 hours, diluted with saturated ammonium chloride solution (60 mL), and extracted with dichloromethane (60 mL×3). The organic phase was dried over anhydrous sodium sulfate and filtered. The filtrate was concentrated in vacuo, and the residue was purified through flash column chromatography on silica gel (eluted with 10% to 20% ethyl acetate in petroleum ether) to provide tert-butyl 3-(methylsulfonyl)indoline-1-carboxylate (260 mg, 49% yield) as light-yellow solid. LC-MS (ESI) m/z: 298 $[M+H]^+$.

Step 3: To a solution of tert-butyl 3-(methylsulfonyl) indoline-1-carboxylate (260 mg, 0.831 mmol) in dichloromethane (4 mL) was added 2,2,2-trifluoroacetic acid (2 mL) at 0° C. The resulting solution was stirred at 25° C. for 2 hours and concentrated in vacuo to provide crude 3-methylsulfonyl)indoline, which was used without further purification. LC-MS (ESI) m/z: 198 $[M+H]^+$.

Int. E10

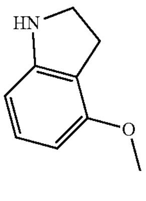

4-Methoxyindoline

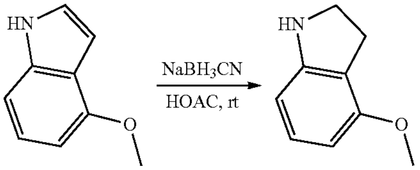

To a solution of 4-methoxy-1H-indole (500 mg, 3.40 mmol) in AcOH (5 mL) was added sodium cyanoborohydride (895.00 mg, 13.59 mmol) in portions over 10 minutes. The mixture was stirred at room temperature for 30 minutes, diluted with water (40 mL) and concentrated in vacuo. The residue was extracted with ethyl acetate (25 mL×3). The combined organic phase was washed with saturated $NaHCO_3$ aqueous solution (50 mL) and brine (50 mL), dried over anhydrous $Na_2SO_4$ and filtered. The filtrate was concentrated in vacuo to provide crude 4-methoxyindoline (500 mg, 79% yield), which was used immediately without further purification. LC-MS (ESI) m/z: 150 $[M+H]^+$.

Int. E11

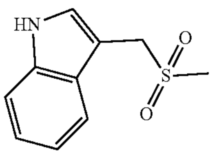

3-((Methylsulfonyl)methyl)-1H-indole

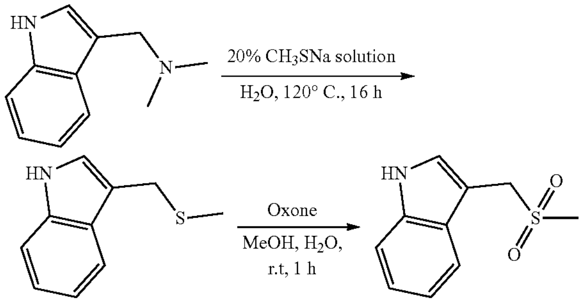

Step 1: To a suspension of 1-(1H-indol-3-yl)-N,N-dimethylmethanamine (1 g, 5.74 mmol) in water (15 mL) was added 20% sodium methanethiolate in water (402.25 mg, 5.74 mmol, 5 mL). The reaction mixture was stirred at 105° C. for 16 hours, cooled to room temperature and extracted with chloromethane (50 mL×3). The organic phase was washed with 0.5 M HCl aqueous solution (40 mL), saturated sodium bicarbonate aqueous solution (50 mL), and brine (50 mL), dried over anhydrous sodium sulfate and filtered. The filtrate was concentrated in vacuo, and the residue was purified by flash column chromatography on silica gel (PE/EA=10/1) to provide 3-((methylthio)methyl)-1H-indole as white solid (594 mg, 55% yield). LC-MS (ESI) m/z: 178 $[M+H]^+$.

Step 2: 3-((Methylsulfonyl)methyl)-1H-indole. To a solution of 3-((methylthio)methyl)-1H-indole (250 mg, 1.34 mmol) in methanol (0.5 mL) was added oxone (904.90 mg, 1.47 mmol). The reaction mixture was stirred at 25° C. for 16 hours, basified to pH 8 with saturated sodium bicarbonate aqueous solution, and extracted with ethyl acetate (10 mL×3). The organic phase was dried over anhydrous sodium sulfate and filtered. The filtrate was concentrated in vacuo, and the residue was purified by flash column chromatography on silica gel (PE/EA=10/1) to provide 3-(methylsulfonylmethyl)-1H-indole as white solid (139 mg, 47% yield). LC-MS (ESI) m/z: 210 $[M+H]^+$.

Int. E12

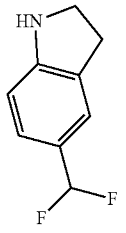

5-(Difluoromethyl)indoline

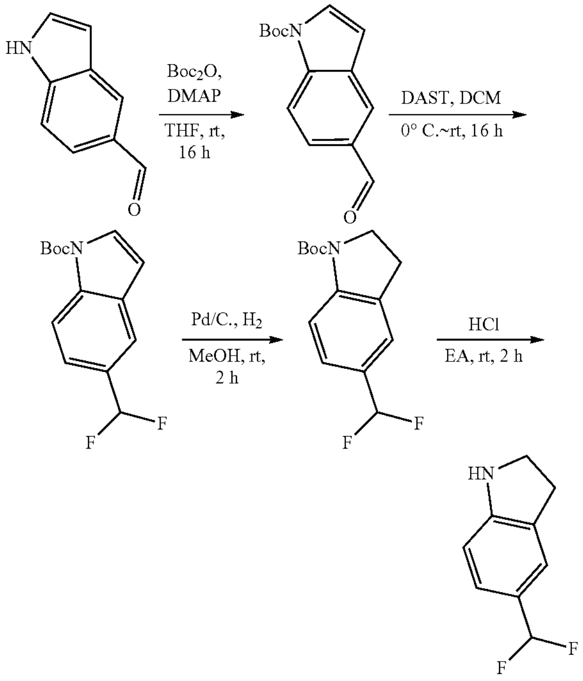

Step 1: The mixture of DMAP (896.50 mg, 7.34 mmol), 1H-indole-5-carbaldehyde (986.30 mg, 6.79 mmol) and di-tert-butyl dicarbonate (1.63 g, 7.47 mmol) in THF (15 mL) was stirred for 16 hours at room temperature, quenched by the addition of 10 mL of water, and extracted with ethyl acetate (3×50 mL). The organic layers were dried over anhydrous sodium sulfate and filtered. The filtrate was concentrated in vacuo to provide tert-butyl 5-formyl-1H-indole-1-carboxylate (1.4 g, 84% yield). LC-MS (ESI) m/z: 246 $[M+H]^+$.

Step 2: To a solution of tert-butyl 5-formyl-1H-indole-1-carboxylate (500 mg, 2.04 mmol) in DCM (20 mL) was added N-ethyl-N-(trifluoro-sulfanyl)ethanamine (1.64 g, 10.19 mmol, 1.35 mL) at 0° C. Then the mixture was stirred at room temperature for 16 hours, basified to pH 8 with saturated $NaHCO_3$ aqueous solution, and extracted with dichloromethane (50 mL×3). The organic phases were dried over anhydrous sodium sulfate and filtered. The filtrate was concentrated in vacuo, and the residue was purified by flash column chromatography on silica gel (EA/PE, 1/9) to provide tert-butyl 5-(difluoromethyl)-1H-indole-1-carboxylate as white solid (336 mg, 62% yield).

Step 3: A mixture of tert-butyl 5-(difluoromethyl)-1H-indole-1-carboxylate (200 mg, 748.30 umol) and palladium (79.63 mg, 748.30 umol) in MeOH (5 mL) was stirred at 25° C. for an hour under $N_2$ atmosphere, and filtered. The filtrate was concentrated in vacuo to provide crude tert-butyl 5-(difluoromethyl)indoline-1-carboxylate as yellow oil (200 mg, 99% yield).

Step 4: A solution of tert-butyl 5-(difluoromethyl)indoline-1-carboxylate (200 mg, 742.70 umol) in HCl-EA (568.67 mg, 15.60 mmol, 710.84 uL) was stirred at 0° C. for 2 hours, and concentrated in vacuo to provide 5-(difluoromethyl)indoline as white solid (126.59 mg, 81% yield). LC-MS (ESI) m/z: 170 $[M+H]^+$.

Int. E13

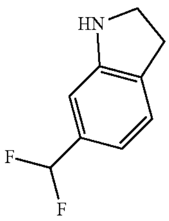

6-(Difluoromethyl)indoline

The same procedures as Int. E12, using 1H-indole-6-carbaldehyde in place of 1H-indole-5-carbaldehyde. LC-MS (ESI) m/z: 170 $[M+H]^+$.

Int. E14

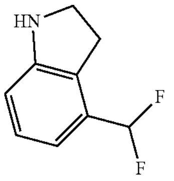

4-(Difluoromethyl)indoline hydrochloride

The same procedures as Int. E12, using 1H-indole-4-carbaldehyde in place of 1H-indole-5-carbaldehyde. LC-MS (ESI) m/z: 170 $[M+H]^+$.

Int. E15

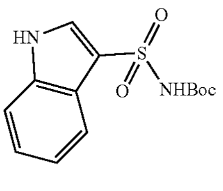

tert-Butyl ((1H-indol-3-yl)sulfonyl)carbamate

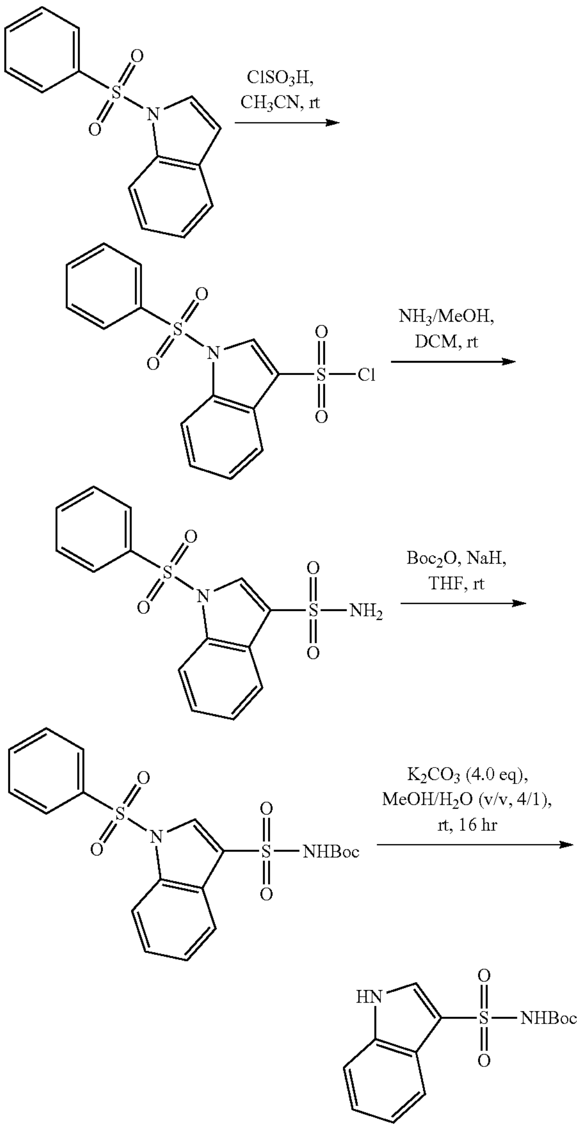

Step 1: To a solution of 1-(phenylsulfonyl)-1H-indole (1 g, 3.89 mmol) in anhydrous $CH_3CN$ (10 mL) was carefully added chlorosulfonic acid (1.36 g, 11.66 mmol, 776.33 uL) at 0° C. Then the reaction mixture was warmed to room temperature over 4 hours, stirred overnight, poured into ice water (50 mL) and extracted with dichloromethane (30 mL×2). The combined organic layer was washed with saturated sodium bicarbonate aqueous solution (50 mL×2) and brine (50 mL), dried over anhydrous sodium sulfate and filtered. The filtrate was concentrated in vacuo to provide 1-(phenylsulfonyl)-1H-indole-3-sulfonyl chloride as white solid (868 mg, 63% yield).

Step 2: To a solution of 1-(phenylsulfonyl)-1H-indole-3-sulfonyl chloride (800 mg, 2.25 mmol) in $CH_2Cl_2$ (16 mL) was added $NH_3$/MeOH (960.00 mg, 56.47 mmol, 8 mL) slowly at 0° C. Then the mixture was stirred at room temperature overnight, diluted with water (20 mL) and extracted with $CH_2Cl_2$ (20 mL×3). The combined organic layer was sequentially washed with 1M HCl (20 mL), water (20 mL) and brine (20 mL), dried over anhydrous sodium sulfate and filtered. The filtrate was concentrated in vacuo to provide 1-(phenylsulfonyl)-1H-indole-3-sulfonamide as white solid (639 mg, 84% yield). LC-MS (ESI) m/z: 359 $[M+Na]^+$.

Step 3: To a solution of 1-(phenylsulfonyl)-1H-indole-3-sulfonamide (1.03 g, 3.06 mmol) in THF (10 mL) was added NaH (612 mg, 15.31 mmol, 60% suspended in mineral oil) at 0° C. The mixture was stirred at 0° C. for 30 minutes, followed by the addition of $Boc_2O$ (2.67 g, 12.25 mmol). The resulting mixture was stirred at room temperature for 16 hours and poured into ice water. The two phases were separated, and the aqueous phases was extracted with dichloromethane/methanol (v/v, 10/1, 20 mL×3). The combined organic phases were dried over anhydrous sodium sulfate and filtered. The filtrate was concentrated in vacuo, and the residue was purified by flash column chromatography on silica gel (DCM/MeOH=9/1) to afford tert-butyl ((1-(phenyl sulfonyl)-1H-indol-3-yl)sulfonyl)carbamate (438 mg, 31% yield) as off-white solid. LC-MS (ESI) m/z: 381 $[M+H-56]^+$.

Step 4: A mixture of tert-butyl ((1-(phenylsulfonyl)-1H-indol-3-yl)sulfonyl)carbamate (438 mg, 1.00 mmol) and $K_2CO_3$ (553.90 mg, 4.01 mmol) in methanol (8 mL) and $H_2O$ (2 mL) was stirred at room temperature overnight, acidified to pH 5 with acetic acid and separated. The organic phase was dried over anhydrous sodium sulfate and filtered. The filtrate was concentrated in vacuo, and the residue was purified by reverse phase chromatography ($H_2O$/methanol) to provide tert-butyl ((1H-indol-3-yl)sulfonyl)carbamate as white solid (200 mg, 67% yield). LC-MS (ESI) m/z: 319 [M+Na]

Int. E16

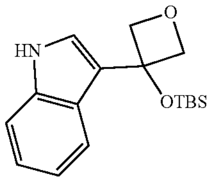

3-(3-((tert-Butyldimethylsilyl)oxy)oxetan-3-yl)-1H-indole

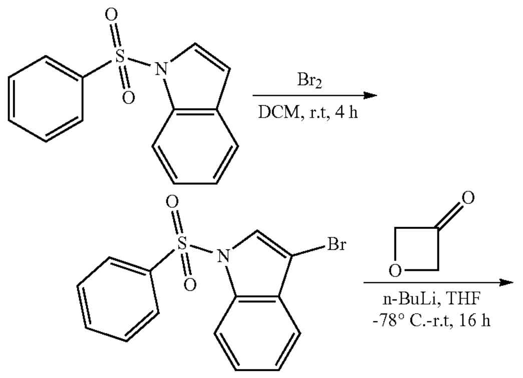

-continued

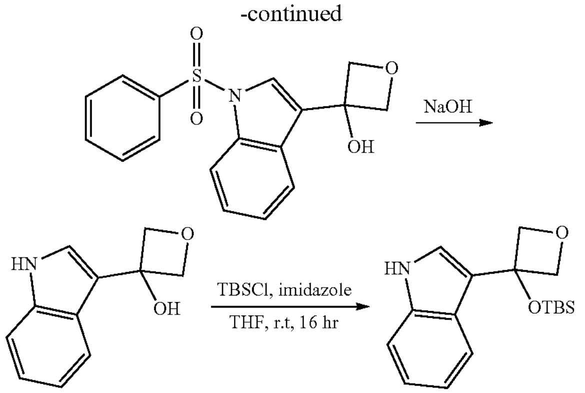

Step 1: To a solution of 1-(phenylsulfonyl)-1H-indole (2 g, 7.38 mmol) in DCM (60 mL) was added bromine (1.18 g, 7.38 mmol, 378.23 uL) dropwise. The red reaction mixture was then stirred at 25° C. for 4.5 hours, poured into saturated sodium bicarbonate aqueous solution (50 mL) and separated. The organic layer was washed with saturated sodium thiosulfate aqueous solution (50 mL), water (50 mL), and brine (50 mL), dried over anhydrous $MgSO_4$ and filtered. The filtrate was concentrated in vacuo, and the residue was purified by flash column chromatography on silica gel (20% EA/PE) to provide 3-bromo-1-(phenylsulfonyl)-1H-indole as white solid (1.5 g, 57% yield). LC-MS (ESI) m/z: 336 $[M+H]^+$.

Step 2: To a solution of 3-bromo-1-(phenylsulfonyl)-1H-indole (200 mg, 0.595 mmol) in THF (5 mL) was added 2.5M butyllithium (0.36 mL, 0.892 mmol) at −78° C. The reaction mixture was stirred at −78° C. for 30 minutes, followed by the addition of oxetan-3-one (85.74 mg, 1.19 mmol, 76.55 uL) at −78° C. 30 minutes later at −78° C., the reaction mixture was stirred at 25° C. for 16 hours, poured into saturated ammonium chloride aqueous solution (30 mL), and separated. The organic layer was washed with brine (50 mL), dried over anhydrous sodium sulfate and filtered. The filtrate was concentrated in vacuo, and the residue was purified by flash column chromatography on silica gel (10% EA/PE) to provide 3-(1-(phenyl sulfonyl)-1H-indol-3-yl)oxetan-3-ol as light-yellow solid (110 mg, 53% yield). LC-MS (ESI) m/z: 276 $[M+H]^+$.

Step 3: A solution of 3-(1-(phenylsulfonyl)-1H-indol-3-yl)oxetan-3-ol (383 mg, 1.16 mmol) in the mixed solvent of 2M NaOH solution (5 mL) and methanol (5 mL) was stirred at 85° C. for 16 hours, diluted with water (20 mL) and separated. The organic layer was washed with brine (20 mL), dried over anhydrous sodium sulfate and filtered. The filtrate was concentrated in vacuo, and the residue was purified by flash column chromatography on silica gel (10%-100% EA/PE) to provide 3-(1H-indol-3-yl)oxetan-3-ol as light-yellow solid (182 mg, 79% yield). LC-MS (ESI) m/z: 190 $[M+H]^+$.

Step 4: To a solution of 3-(1H-indol-3-yl)oxetan-3-ol (600 mg, 3.01 mmol) in DMF (6 mL) were added tert-butylchlorodimethylsilane (1.14 g, 7.53 mmol, 1.40 mL) and imidazole (615.25 mg, 9.04 mmol) at 0° C. The reaction mixture was stirred at 25° C. for 16 hours, diluted with water (20 mL), basified to pH 8 with saturated sodium bicarbonate aqueous solution, and extracted with ethyl acetate (10 mL×3). The organic layer was washed with brine (20 mL×3), dried over anhydrous sodium sulfate and filtered. The filtrate was concentrated in vacuo, and the residue was purified through flash column chromatography on silica gel (10%-100% EA/PE) to provide 3-(3-((tert-butyldimethylsilyl)oxy)oxetan-3-yl)-1H-indole as light yellow solid (890 mg, 92% yield). LC-MS (ESI) m/z: 304 $[M+H]^+$.

Int. E17

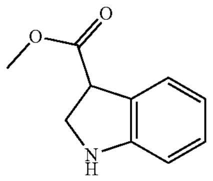

Methyl indoline-3-carboxylate

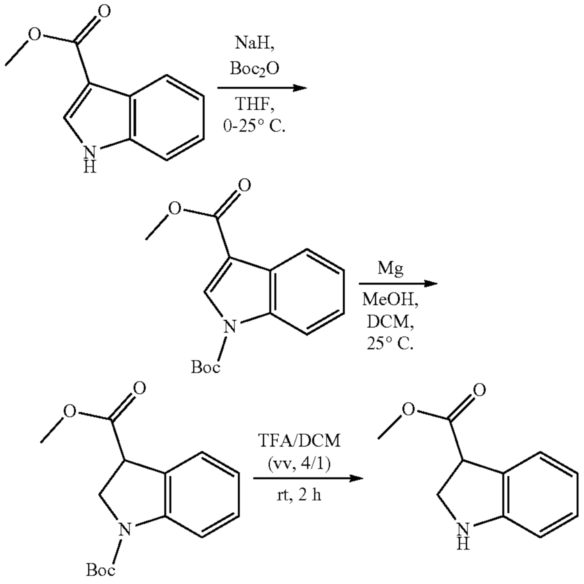

Step 1: To a solution of methyl 1H-indole-3-carboxylate (5 g, 28.54 mmol) in THF (50 mL) was added NaH (1.71 g, 42.81 mmol, 60% in mineral oil) slowly at 0° C. The reaction mixture was stirred at 0° C. for 30 minutes, followed by the addition of $Boc_2O$ (9.34 g, 42.81 mmol). The reaction mixture was stirred at 25° C. for 16 hours, quenched with saturated ammonium chloride solution (100 mL), and extracted with ethyl acetate (100 mL×3). The organic phase was dried over anhydrous sodium sulfate and filtered. The filtrate was concentrated in vacuo, and residue was purified by flash column chromatography on silica gel (PE/EA=5/1) to provide 1-(tert-butyl) 3-methyl 1H-indole-1,3-dicarboxylate as yellow solid (5.3 g, 64% yield). LC-MS (ESI) m/z: 276 $[M+H]^+$.

Step 2: To a stirring solution of 1-(tert-butyl) 3-methyl 1H-indole-1,3-dicarboxylate (2 g, 6.90 mmol) in dichloromethane (60 mL) and methanol (211 mL) was added magnesium (838.72 mg, 34.51 mmol) slowly. The reaction mixture was stirred at 25° C. for 16 hours, diluted with saturated ammonium chloride solution (100 mL), and extracted with dichloromethane (100 mL×3). The organic phase was dried over anhydrous sodium sulfate and filtered. The filtrate was concentrated in vacuo, and the residue was purified by flash column chromatography on silica gel (EA/PE: 10-20%) to provide 1-(tert-butyl) 3-methyl indoline-1,3-dicarboxylate as light-yellow oil (1.1 g, 55% yield). LC-MS (ESI) m/z: 222 $[M+H-56]^+$.

Step 3: To a solution of 1-(tert-butyl) 3-methyl indoline-1,3-dicarboxylate (500 mg, 1.71 mmol) in DCM (5 mL) was added trifluoroacetic acid (1.25 mL). The resulting mixture was stirred at room temperature for 2 hours and concentrated in vacuo. The residue was dissolved in DCM (100 mL) and washed with saturated with $NaHCO_3$ aqueous solution (30 mL×3). The organic phase was dried over anhydrous $Na_2SO_4$ and filtered. The filtrate was concentrated in vacuo to provide methyl indoline-3-carboxylate (308 mg, 94% yield), which was used without further purifications. LC-MS (ESI) m/z: 178 $[M+H]^+$.

Int. E18

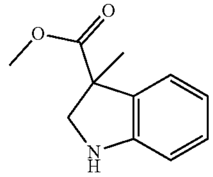

Methyl 3-methylindoline-3-carboxylate

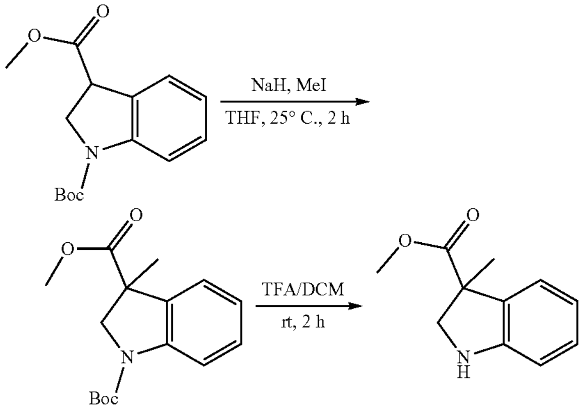

Step 1: To a solution of 1-(tert-butyl) 3-methyl indoline-1,3-dicarboxylate (320 mg, 1.15 mmol) and iodomethane (491.36 mg, 3.46 mmol) in DMF (8 mL) was added sodium hydride (50.77 mg, 1.27 mmol, 60% in mineral oil) at 25° C. The mixture was stirred at 25° C. for 2 hours diluted with EA (200 mL), and then washed with water (20 mL×3) and brine (30 mL). The organic layers were dried over anhydrous $Na_2SO_4$ and filtered. The filtrate was concentrated in vacuo, and the residue was purified by flash column chromatography on silica gel (EA/PE: 15%) to provide 1-(tert-butyl) 3-methyl 3-methylindoline-1,3-dicarboxylate as light-yellow oil (244 mg, 70% yield). LC-MS (ESI) m/z: 236 $[M+H-56]^+$.

Step 2: To a solution of 1-(tert-butyl) 3-methyl 3-methylindoline-1,3-dicarboxylate (240 mg, 0.824 mmol) in dichloromethane (4 mL) was added trifluoroacetic acid (1 mL) at 25° C. The mixture was stirred at room temperature for 2 hours and concentrated in vacuo to provide crude methyl 3-methylindoline-3-carboxylate without further purifications. LC-MS (ESI) m/z: 192 $[M+H]^+$.

Int. E19

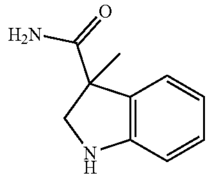

3-Methylindoline-3-carboxamide

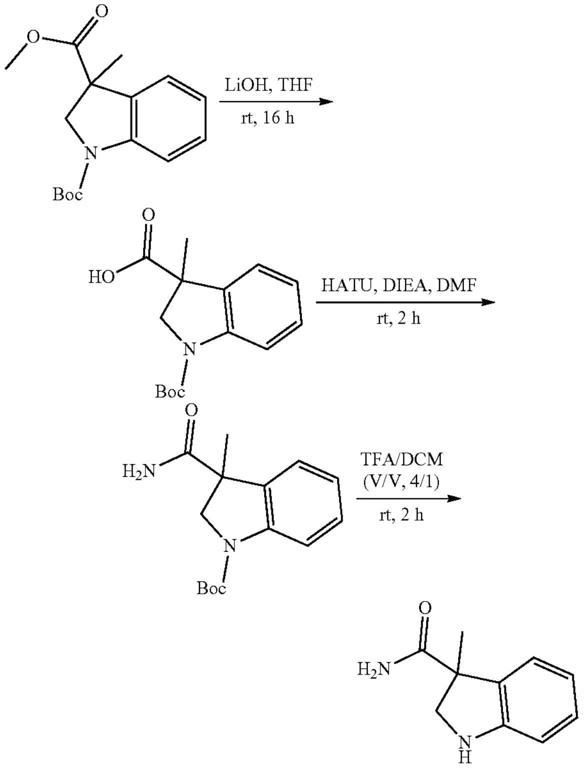

Step 1: To a solution of 1-(tert-butyl) 3-methyl 3-methylindoline-1,3-dicarboxylate (500 mg, 1.63 mmol) in THF (10 mL) was added LiOH aqueous solution (2N, 5 mL) dropwise. The reaction mixture was stirred at 25° C. for 16 hours, adjusted to pH~4 with 1 M HCl solution (10 mL) at 0° C., and concentrated in vacuo. The residue was extracted with EA (10 mL×3). The organic phases were washed with brine (20 mL), dried over anhydrous sodium sulfate and filtered. The filtrate was concentrated in vacuo to provide 1-tert-butoxycarbonyl-3-methyl-indoline-3-carboxylic acid (452 mg) as light-yellow solid. LC-MS (ESI) m/z: 278 $[M+H]^+$.

Step 2: To a solution 1-tert-butoxycarbonyl-3-methyl-indoline-3-carboxylic acid (452 mg, 1.55 mmol) in DMF (5 mL) were added ammonium chloride (414.1 mg, 7.74 mmol), DIEA (600.4 mg, 4.65 mmol) and HATU (765.4 mg, 2.01 mmol) sequentially. The reaction mixture was stirred at 25° C. for 16 hours, diluted with saturated ammonium chloride solution (15 mL) and extracted with EA (10 mL×3). The organic phases were washed with brine (15 mL×3), dried over anhydrous sodium sulfate and filtered. The filtrate was concentrated in vacuo, and the residue was purified by flash column chromatography on silica gel (PE/EA=10/1) to provide tert-butyl 3-carbamoyl-3-methyl-indoline-1-carboxylate as white solid (420 mg, 93% yield). LC-MS (ESI) m/z: 277 $[M+H]^+$.

Step 3: The same procedure as Step 3 of Int. 18, using tert-butyl 3-carbamoyl-3-methyl-indoline-1-carboxylate in place of 1-(tert-butyl) 3-methyl 3-methylindoline-1,3-dicarboxylate. LC-MS (ESI) m/z: 177 $[M+H]^+$.

Int. E20

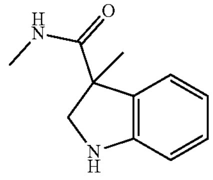

N,3-dimethylindoline-3-carboxamide

The same procedures as of Step 2&3 of Int. E19, methylamine hydrochloride in place of ammonium chloride. LC-MS (ESI) m/z: 191 $[M+H]^+$.

Int. E21

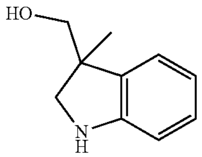

(3Methylindolin-3-yl)methanol

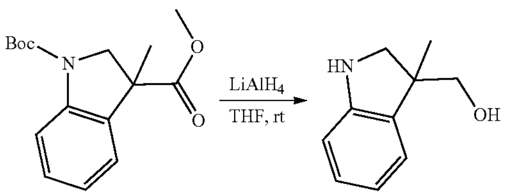

To a solution of 1-(tert-butyl) 3-methyl 3-methylindoline-1,3-dicarboxylate (150 mg, 0.515 mmol) in THF (10 mL) was added 1.0M $LiAlH_4$ (1 mL, 1.13 mmol) in THF at room temperature. The reaction mixture was stirred under reflux for 2 hours and quenched by careful addition of methanol (10 mL) at room temperature. The resulting mixture was concentrated in vacuo, and the residue was purified by flash column chromatography on silica gel (MeOH/DCM=0-10%) to provide (3-methylindolin-3-yl)methanol (60 mg, 71% yield). LC-MS (ESI) m/z: 164 $[M+H]^+$.

Int. E22

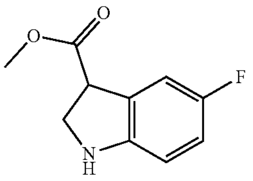

Methyl 5-fluoroindoline-3-carboxylate

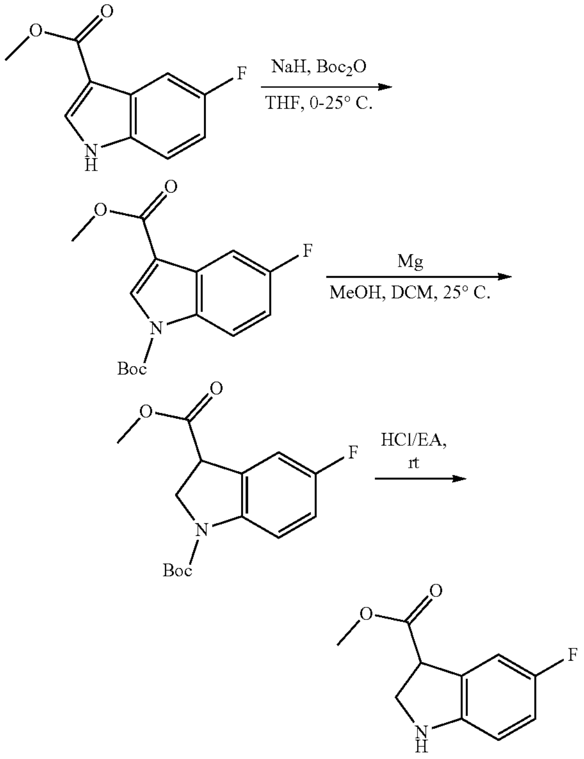

Step 1 & 2: The same procedures as of Step 1 & 2 of Int. E17, using 5-fluoro-1H-indole-3-carboxylate in place of 1H-indole-3-carboxylate. LC-MS (ESI) m/z: 318 $[M+Na]^+$.

Step 3: A solution of 1-(tert-butyl) 3-methyl 5-fluoroindoline-1,3-dicarboxylate (176 mg, 0.596 mmol) in HCl/EA (4M, 3 mL) was stirred at room temperature for an hour and concentrated in vacuo to obtain methyl 5-fluoroindoline-3-carboxylate (110 mg, 94.6% yield) as white solid. LC-MS (ESI) m/z: 196 $[M+H]^+$.

Int. E23

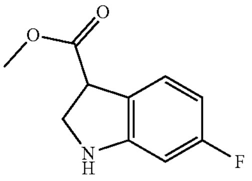

Methyl 6-fluoroindoline-3-carboxylate

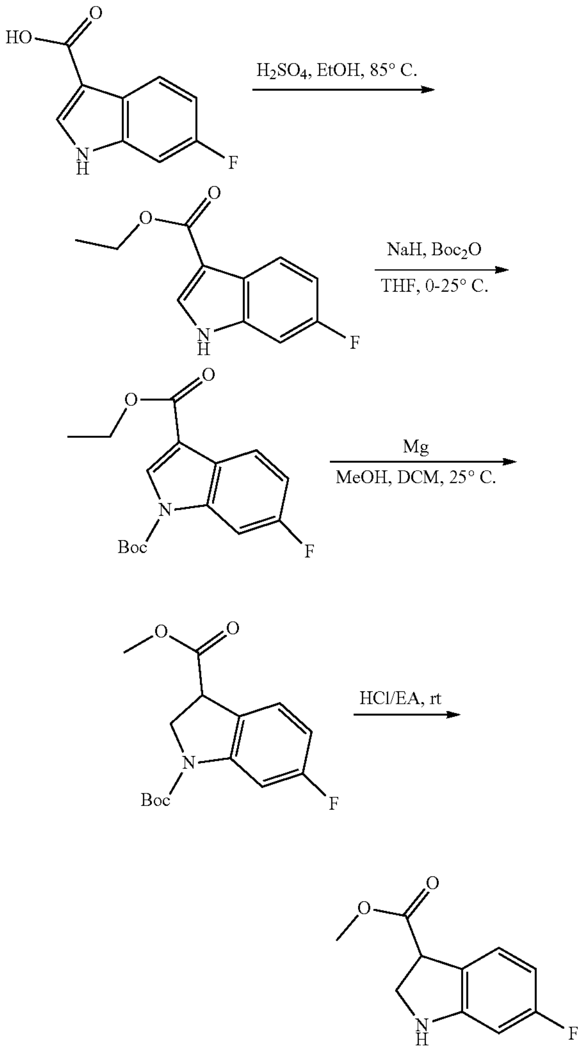

Step 1: To a solution of 6-fluoro-1H-indole-3-carboxylic acid (600 mg, 3.35 mmol) in ethanol (50 mL) was added concentrated sulfuric acid (0.1 mL). The reaction mixture was stirred at 85° C. for 16 hours, cooled to room temperature and neutralized with saturated sodium bicarbonate aqueous solution, and extracted with EA (10 mL×3). The organic phases were dried over anhydrous sodium sulfate and filtered. The filtrate was concentrated in vacuo, and the residue was purified by flash column chromatography on silica gel (PE/EA=10/1) to give ethyl 6-fluoro-1H-indole-3-carboxylate (646 mg, 94.9% yield) as light yellow solid. LC-MS (ESI) m/z: 208 $[M+H]^+$.

Step 2&3: The same procedures as of Step 1 & 2 of Int. E17, using ethyl 6-fluoro-1H-indole-3-carboxylate in place of 1H-indole-3-carboxylate (transesterification with MeOH). LC-MS (ESI) m/z: 296 $[M+H]^+$.

Step 4: The same procedures as of Step 3 of Int. E22, using 1-(tert-butyl) 3-ethyl 6-fluoroindoline-1,3-dicarboxylate in place of 1-(tert-butyl) 3-methyl 5-fluoroindoline-1,3-dicarboxylate. LC-MS (ESI) m/z: 196 $[M+H]^+$.

Int. E24

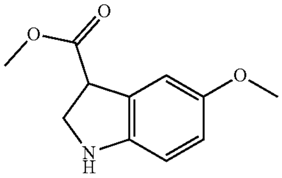

Methyl 5-methoxyindoline-3-carboxylate

The same procedures as Int. E17, using 5-methoxy-1H-indole-3-carboxylate in place of 1H-indole-3-carboxylate. LC-MS (ESI) m/z: 208 [M+H]+.

Int. E25

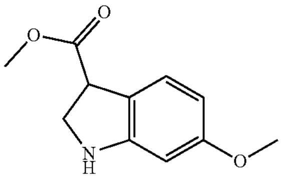

Methyl 6-methoxyindoline-3-carboxylate

The same procedures as Int. E23, using 6-methoxy-1H-indole-3-carboxylic acid in place of 6-fluoro-1H-indole-3-carboxylic acid. LC-MS (ESI) m/z: 208 [M+H]+.

Int. E26

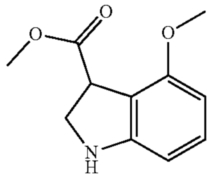

Methyl 4-methoxyindoline-3-carboxylate

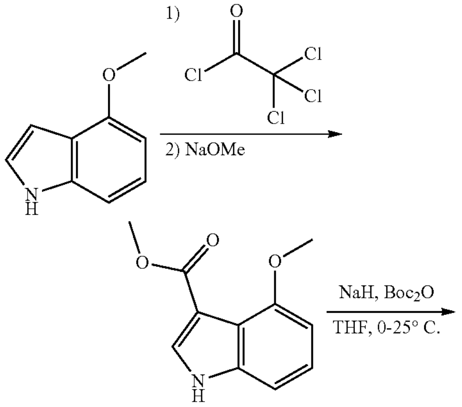

-continued

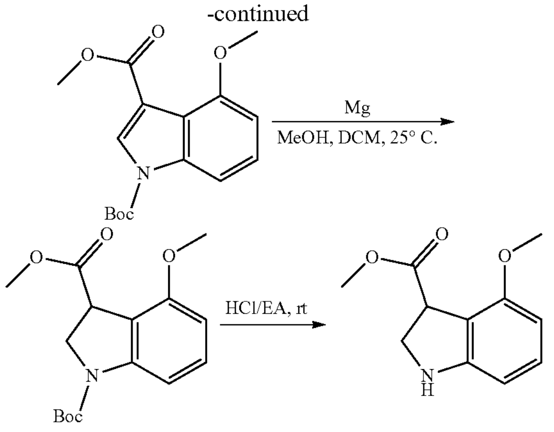

Step 1: To a solution of 4-methoxy-1H-indole (1.4 g, 9.51 mmol) and pyridine (3.76 g, 47.56 mmol, 3.85 mL) in DCM (10 mL) was added 2,2,2-trichloroacetyl chloride (8.65 g, 47.56 mmol) dropwise in DCM (10 mL) at 0° C. After stirring at 0° C. for 1.5 hours, the mixture was concentrated in vacuo. The residue was dissolved in methanol (20 ml), which was added to a stirring suspension of sodium methoxide (1.54 g, 28.54 mmol, 1.59 mL) in methanol (50 mL) over 20 minutes. The mixture was stirred at room temperature for an hour, cooled to 0° C., diluted with water (50 mL), and extracted with DCM (30 mL×3). The organic phases were dried over anhydrous $Na_2SO_4$ and filtered. The filtrate was concentrated in vacuo, and the residue was purified by flash column chromatography on silica gel (MeOH/DCM=1%-10%) to provide methyl 4-methoxy-1H-indole-3-carboxylate (800 mg, 38% yield). LC-MS (ESI) m/z: 206 [M+H]+.

Step 2&3&4: The same procedures as Int. E22, using methyl 4-methoxy-1H-indole-3-carboxylate in place of 5-fluoro-1H-indole-3-carboxylate. LC-MS (ESI) m/z: 208 [M+H]+.

Int. E27

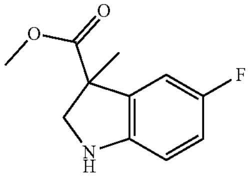

Methyl 5-fluoro-3-methylindoline-3-carboxylate

The same procedures as Int. E18, in Step 1 using 1-(tert-butyl) 3-methyl 5-fluoroindoline-1,3-dicarboxylate in place of 1-(tert-butyl) 3-methyl indoline-1,3-dicarboxylate; in Step 2, under HCl/EA deprotection condition as Step 3 of Int. 22. LC-MS (ESI) m/z: 210 [M+H]+.

Int. E28

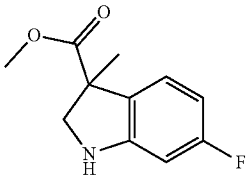

Methyl 6-fluoro-3-methylindoline-3-carboxylate

The same procedures as Int. E18, in Step 1 using 1-(tert-butyl) 3-methyl 5-fluoroindoline-1,3-dicarboxylate in place of 1-(tert-butyl) 3-methyl indoline-1,3-dicarboxylate; in Step 2, under HCl/EA deprotection condition as Step 3 of Int. 22. LC-MS (ESI) m/z: 210 $[M+H]^+$.

Int. E29

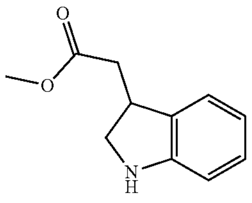

Methyl 2-(indolin-3-yl)acetate

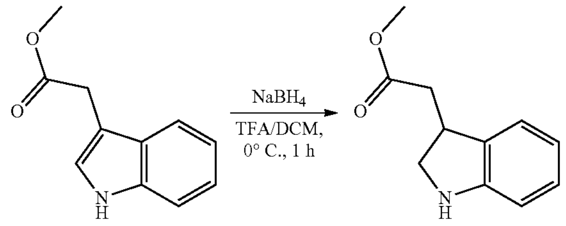

To a solution of methyl 2-(1H-indol-3-yl)acetate (500 mg, 2.64 mmol) in dichloromethane (16 mL) and TFA (3 mL) was added sodium borohydride (199.95 mg, 5.29 mmol) at 0° C. The mixture was stirred at 0° C. for 2 hours, diluted with DCM (200 mL) and quenched with saturated $NaHCO_3$ aqueous solution (10 mL). The organic phase was separated, dried over anhydrous sodium sulfate, and filtered. The filtrate was concentrated in vacuo to provide methyl 2-indolin-3-ylacetate as brown oil (477 mg, 85% yield). LC-MS (ESI) m/z: 196 $[M+H]^+$.

Int. E30

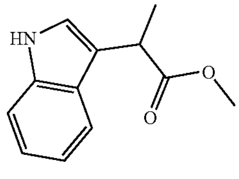

Methyl 2-(1H-indol-3-yl)propanoate

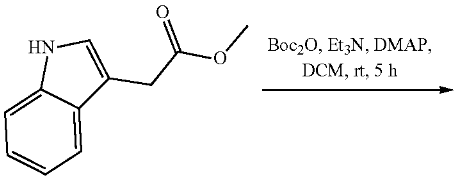

-continued

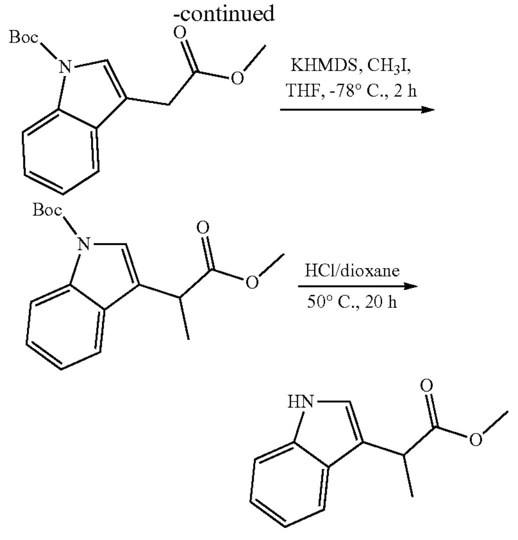

Step 1: To a solution of methyl 2-(1H-indol-3-yl) acetate (1 g, 5.29 mmol) in DCM (10 mL) were added triethylamine (2.14 g, 21.14 mmol), DMAP (129.13 mg, 1.06 mmol) and di-tert-butyl carbonate (1.73 g, 7.93 mmol) under argon atmosphere at room temperature. After stirring for 5 hours, the reaction mixture was diluted with aqueous saturated $NH_4Cl$ aqueous solution (20 mL) and extracted with DCM (20 mL×2). The organic phases were washed with brine (20 mL), dried over anhydrous $Na_2SO_4$ and filtered. The filtrate was concentrated in vacuo, and the residue was purified by flash column chromatography on silica gel (0-20% EA/PE) to provide tert-butyl 3-(2-methoxy-2-oxoethyl)-1H-indole-1-carboxylate as light-yellow oil (1.46 g, 95% yield). LC-MS (ESI) m/z: 307 [M+18]'.

Step 2: To a solution of tert-butyl 3-(2-methoxy-2-oxo-ethyl)-1H-indole-1-carboxylate (300 mg, 1.04 mmol) in anhydrous THF (10 mL) was added KHMDS (227.53 mg, 1.14 mmol) dropwise at −20° C. over 30 minutes under $N_2$. Then the solution was stirred at −78° C. for another 40 minutes, followed by the dropwise addition of iodomethane (147.18 mg, 1.04 mmol) at −78° C. After stirring at the same temperature for 1.5 hours, the reaction mixture was quenched with saturated $NH_4Cl$ aqueous solution (20 mL) and separated. The aqueous layer was extracted with EtOAc (20 mL×3), and the combined organic phases were washed with brine (20 mL), dried over anhydrous $Na_2SO_4$, and filtered. The filtrate was concentrated in vacuo, and the residue was purified by flash column chromatography on silica gel (0-20% EA/PE) to provide tert-butyl 3-(1-methoxy-1-oxopropan-2-yl)-1H-indole-1-carboxylate as colorless oil (105 mg, 30% yield). LC-MS (ESI) m/z: 326 $[M+Na]^+$.

Step 3: A solution of tert-butyl 3-(2-methoxy-1-methyl-2-oxo-ethyl)indole-1-carboxylate (550 mg, 1.81 mmol) in hydrochloric acid/dioxane (4N, 15 mL) was stirred at 25° C. for 48 hours and concentrated in vacuo. The residue was purified by reverse phase chromatography (0.01% TFA/methanol) to afford methyl 2-(1H-indol-3-yl)propanoate (110 mg, 51% purity) as colourless oil. LC-MS (ESI) m/z: 204 $[M+H]^+$.

Int. E31

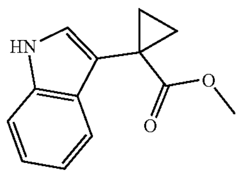

Methyl 1-(1H-indol-3-yl)cyclopropane-1-carboxylate

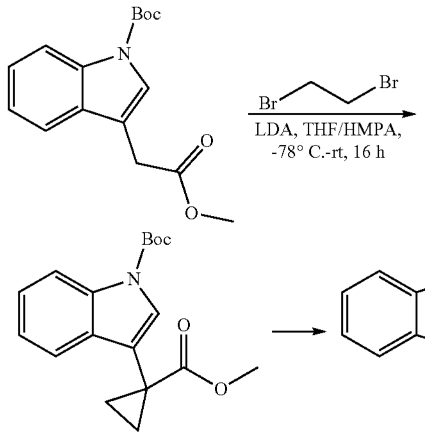

Step 1: To a solution of tert-butyl 3-(2-methoxy-2-oxo-ethyl)indole-1-carboxylate (100 mg, 0.346 mmol) in THF/HMPA (v/v, 10/1) (5.5 mL) was added LDA (81.5 mg, 0.760 mmol) at −78° C., followed by the addition of 1,2-dibromoethane (97.4 mg, 0.518 mmol) 30 minutes later. Then the reaction mixture was stirred at room temperature overnight, quenched by the addition of ice-water and separated. The aqueous phase was extracted with dichloromethane/methanol (v/v, 10/1, 20 mL×3). The organic phases were dried over anhydrous sodium sulfate and filtered. The filtrate was concentrated in vacuo, and the residue was purified by flash column chromatography on silica gel (EA/PE=1/9) to provide tert-butyl 3-(1-methoxycarbonyl)cyclopropyl-1H-indole-1-carboxylate as yellow oil (120 mg, 78% yield). LC-MS (ESI) m/z: 338 $[M+Na]^+$.

Step 2: The same procedure as Step 3 of Int. E30, using tert-butyl 3-(1-methoxycarbonyl)cyclopropyl-1H-indole-1-carboxylate in place of tert-butyl 3-(2-methoxy-1-methyl-2-oxo-ethyl)indole-1-carboxylate. LC-MS (ESI) m/z: 238 [M+Na]

Int. E32

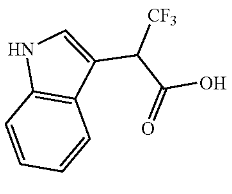

3,3,3-Trifluoro-2-(1H-indol-3-yl)propanoic acid

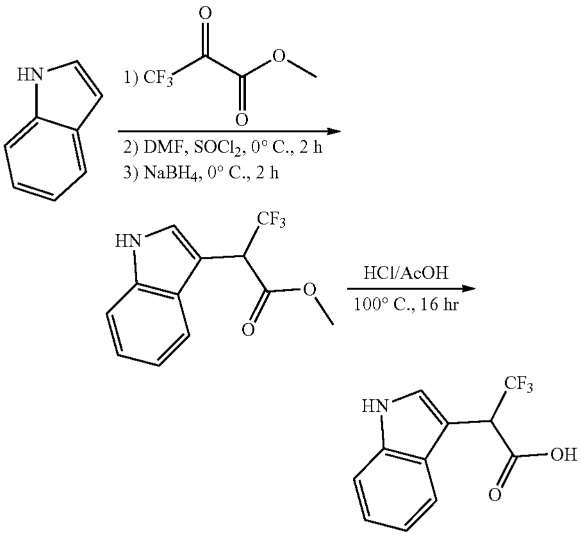

Step 1: To methyl 3,3,3-trifluoro-2-oxo-propanoate (4.68 g, 29.96 mmol) was added indole (117 mg, 0.999 mmol) with vigorous stirring. The mixture was solidified in about 1 minute, dissolved in DMF (40 mL) and cooled to 0° C., followed by the dropwise addition of $SOCl_2$ (8.91 g, 74.91 mmol). The resulting mixture was stirred at the same temperature until the conversion was over monitor by LCMS. Thereto was added $NaBH_4$ (3.40 g, 89.89 mmol) slowly in portions. The mixture was then stirred for 3 hours at 0° C., and poured to 100 mL of saturated $NH_4Cl$ aqueous solution with stirring. The resulting solid was filtered off and the filtrate was extracted with ethyl acetate (50 mL×3). The organic phases were dried over anhydrous sodium sulfate and filtered. The filtrate was concentrated in vacuo, and the residue was purified by flash column chromatography on silica gel (PE/EA=0-20%) to provide methyl 3,3,3-trifluoro-2-(1H-indol-3-yl)propanoate as yellow solid (6.5 g, 84% yield). LC-MS (ESI) m/z: 258 $[M+H]^+$.

Step 2: The solution of methyl 3,3,3-trifluoro-2-(1H-indol-3-yl)propanoate (2.0 g, 7.78 mmol) in a mixed solvent of concentrated HCl (12 mL) and AcOH (60 mL) was stirred under vigorous reflux for 16 hours, cool to room temperature, and concentrated in vacuo. The residue which was purified by reverse phase chromatography ($H_2O$/MeOH=100/050/50) to provide 3,3,3-trifluoro-2-(1H-indol-3-yl)propanoic acid as off-white powder (1 g, 50% yield). LC-MS (ESI) m/z: 244 $[M+H]^+$.

Int. E33

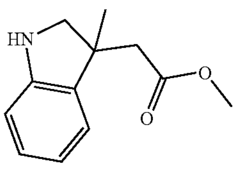

Methyl 2-(3-methylindolin-3-yl)acetate

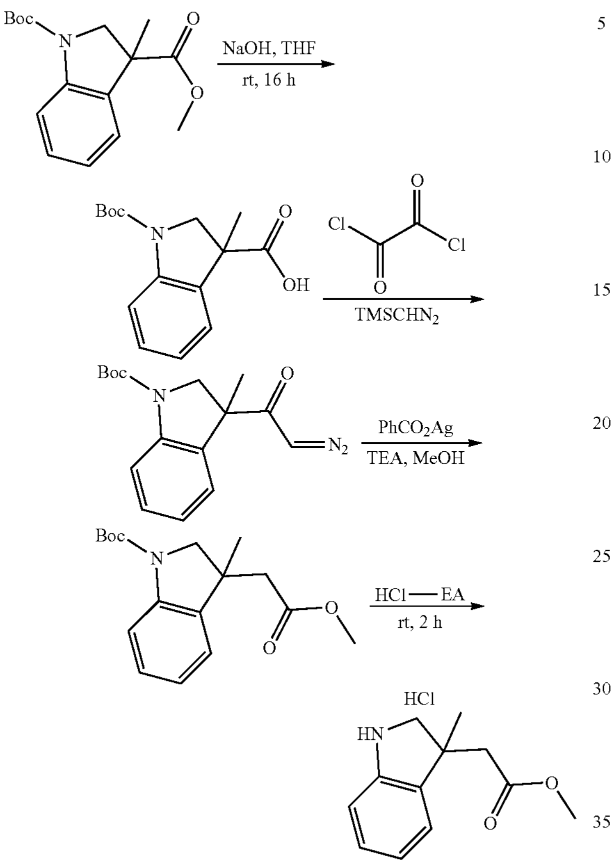

Step 1: To a solution of 1-(tert-butyl) 3-methyl 3-methylindoline-1,3-dicarboxylate (730 mg, 2.51 mmol) in THF (20 mL) was added aqueous solution of sodium hydroxide (3.01 g, 75.17 mmol) in water (1.41 mL). The mixture was stirred for 16 hours at room temperature, acidified with aqueous 1 M HCl solution, and extracted with EtOAc (100 mL×3). The organic phases were washed with brine (50 mL), dried over anhydrous $Na_2SO_4$, and filtered. The filtrate was concentrated in vacuo to provide crude 1-tert-butoxycarbonyl-3-methylindoline-3-carboxylic acid as yellow oil (620 mg, 85% yield). LC-MS (ESI) m/z: 222 $[M+H-56]^+$.

Step 2: To a mixture of 1-tert-butoxycarbonyl-3-methylindoline-3-carboxylic acid (630 mg, 2.27 mmol) in DCM (15 mL) were added slowly oxalyl dichloride (865.1 mg, 6.82 mmol) at 0° C. and N,N-dimethylformamide (8.3 mg, 0.114 mmol). The mixture was stirred for 16 hours at room temperature and concentrated in vacuo. The residue (670 mg, 1.13 mmol) was dissolved in THF (10 mL) and MeCN (5.00 mL), and diazomethyl(trimethyl)silane (258.75 mg, 2.27 mmol) (2 M solution in diethyl ether) was added slowly to the above solution. The reaction mixture was stirred for 2 hours under $N_2$, quenched with 10% citric acid (10 mL), and partitioned between DCM (50 mL) and water (50 mL). The organic phases were dried over anhydrous sodium sulfate and filtered. The filtrate was concentrated in vacuo, and the residue was purified by flash column chromatography on silica gel (EA/PE=0-10%) to provide tert-butyl 3-(2-diazoacetyl)-3-methylindoline-1-carboxylate as yellow oil (200 mg, 56% yield).

Step 3: To a solution of tert-butyl 3-(2-diazoacetyl)-3-methylindoline-1-carboxylate (200 mg, 0.664 mmol) in methanol (5 mL) was added silver benzoate (76.0 mg, 0.332 mmol). The reaction mixture was stirred for 1.5 hours at room temperature under $N_2$ and diluted with DCM (50 mL) and water (50 mL). The organic layer was separated, dried over anhydrous sodium sulfate, and filtered. The filtrate was concentrated in vacuo, and the residue was purified by flash column chromatography on silica gel (EA/PE=0-15%) to provide tert-butyl 3-(2-methoxy-2-oxoethyl)-3-methylindoline-1-carboxylate as colorless oil (100 mg, 42% yield). LC-MS (ESI) m/z: 250 $[M+H-56]^+$.

Step 4: A mixture of tert-butyl 3-(2-methoxy-2-oxoethyl)-3-methylindoline-1-carboxylate (100 mg, 0.278 mmol) and HCl/EA (4M, 1.5 mL) in DCM (3 mL) was stirred for 2 hours at room temperature and concentrated in vacuo to provide crude methyl 2-(3-methylindolin-3-yl)acetate without further purifications. LC-MS (ESI) m/z: 206 $[M+H]^+$.

Alternative Synthetic Method:

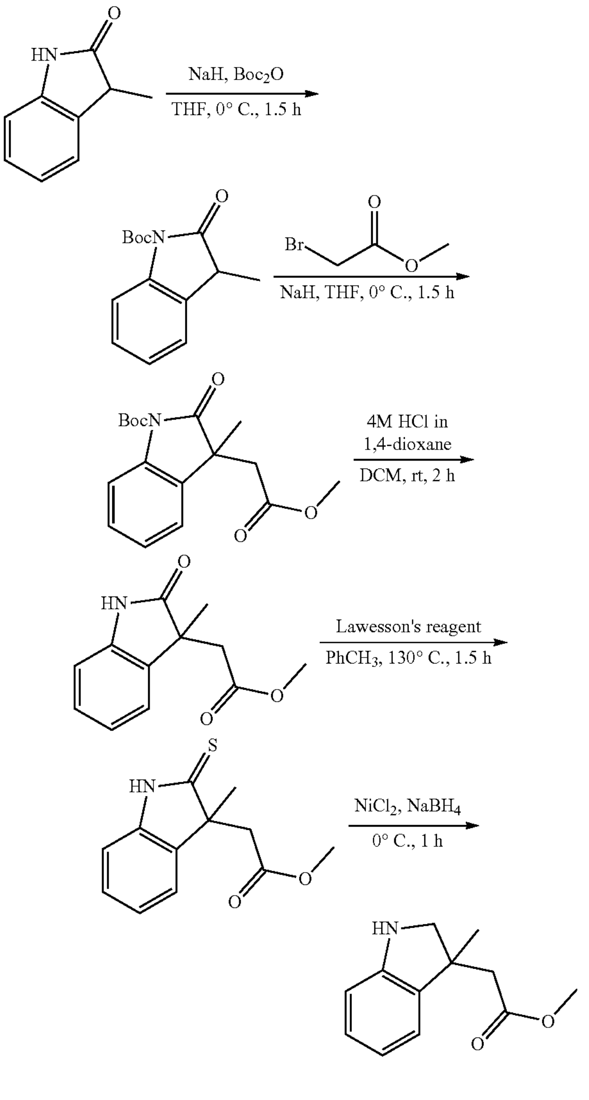

Step 1: To a solution of 3-methylindolin-2-one (20 g, 135.89 mmol) in THF (200 mL) was added NaH (6.52 g, 163.09 mmol, 60% suspended in mineral oil) at 0° C. over 30 minutes. The reaction mixture was stirred at 0° C. for 30 minutes, followed by the dropwise addition of the solution of di-tert-butyl carbonate (29.07 g, 133.18 mmol) in THF (50 mL), the reaction mixture was stirred for an hour, diluted with saturated $NH_4Cl$ aqueous solution (50 mL), and extracted with $CH_2Cl_2$ (100 mL×2). The combined organic phase was dried over anhydrous $Na_2SO_4$ and filtered. The filtrate was concentrated in vacuo, and the residue was purified by flash column chromatography on silica gel (PE/EA=9/1) to provide tert-butyl 3-methyl-2-oxoindoline-1-carboxylate (30 g, 74% yield) as yellow oil. LC-MS (ESI) m/z: 192 $[M+H]^+$.

Step 2: To a solution of tert-butyl 3-methyl-2-oxoindoline-1-carboxylate (30 g, 103.12 mmol) in THF (300 mL) was added NaH (4.95 g, 123.74 mmol, 60% in mineral oil) at 0° C. over 30 minutes. The reaction mixture was stirred at 0° C. for 30 minutes, followed by the dropwise addition of methyl 2-bromoacetate (18.93 g, 123.74 mmol). The reaction mixture was stirred for an hour, quenched with saturated $NH_4Cl$ aqueous solution (100 mL), and extracted with $CH_2Cl_2$ (200 mL×2). The combined organic phase was dried over anhydrous $Na_2SO_4$ and filtered. The filtrate was concentrated in vacuo, and the residue was purified by flash column chromatography on silica gel (PE/EA=8/2) to provide tert-butyl 3-(2-methoxy-2-oxoethyl)-3-methyl-2-oxoindoline-1-carboxylate (28 g, 83% yield) as white solid. LC-MS (ESI) m/z: 264 $[M+H-56]^+$.

Step 3: A mixture of 4 M HCl in 1,4-dioxane (35 mL) and tert-butyl 3-(2-methoxy-2-oxoethyl)-3-methyl-2-oxoindoline-1-carboxylate (28 g, 87.68 mmol) in $CH_2Cl_2$ (200 mL) was stirred at room temperature for 2 hours and concentrated in vacuo. The residue was partitioned between $CH_2Cl_2$ (200 mL) and saturated $NaHCO_3$ aqueous solution (50 mL). The separated aqueous layer was extracted with $CH_2Cl_2$ (50 mL×3), and the combined organic layer was dried over anhydrous $Na_2SO_4$ and filtered. The filtrate was concentrated in vacuo to provide methyl 2-(3-methyl-2-oxoindolin-3-yl)acetate (17.6 g, 82% yield). LC-MS (ESI) m/z: 220 $[M+H]^+$.

Step 4: A mixture of methyl 2-(3-methyl-2-oxoindolin-3-yl)acetate (15.6 g, 71.16 mmol) and Lawesson's reagent (14.71 g, 36.38 mmol) in toluene (220 mL) was stirred at 130° C. for 1.5 hours and concentrated in vacuo. The residue was purified by flash column chromatography on silica gel (PE/EA=80:20) to provide methyl 2-(3-methyl-2-thioxoindolin-3-yl)acetate (15.5 g, 74% yield) as white solid. LC-MS (ESI) m/z: 236 $[M+H]^+$.

Step 5: To a mixture methyl 2-(3-methyl-2-thioxoindolin-3-yl)acetate (9.5 g, 40.37 mmol) and nickel chloride (10.46 g, 80.75 mmol) in mixed THF (70 mL) and methanol (70 mL) was added $NaBH_4$ (9.16 g, 242.24 mmol) in portions at 0° C. over an hour. The resulting mixture was stirred for 10 minutes and filtered through a pad of Celite. The solid cake was washed with MeOH (100 mL), and the filtrate was concentrated in vacuo. The residue was dissolved in EA (200 mL) and washed with water (60 mL×3). The organic phase was dried over anhydrous sodium sulfate and filtered. The filtrate was concentrated in vacuo, and the residue was purified by flash column chromatography on silica gel ($CH_2Cl_2$: methanol=95:5) to provide methyl 2-(3-methylindolin-3-yl)acetate (6.5 g, 75% yield) as yellow oil. LC-MS (ESI) m/z: 206 $[M+H]^+$.

Int. E34

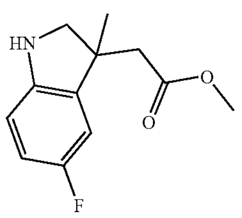

Methyl 2-(5-fluoro-3-methylindolin-3-yl)acetate

The same procedures as Int. E33, using 1-(tert-butyl) 3-methyl 5-fluoro-3-methylindoline-1,3-dicarboxylate in place of 1-(tert-butyl) 3-methyl 3-methylindoline-1,3-dicarboxylate. LC-MS (ESI) m/z: 224 $[M+H]^+$.

Int. E35

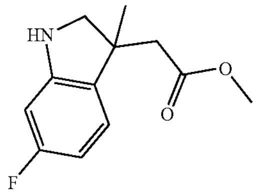

Methyl 2-(6-fluoro-3-methylindolin-3-yl)acetate

The same procedures as Int. E33, using 1-(tert-butyl) 3-methyl 6-fluoro-3-methylindoline-1,3-dicarboxylate in place of 1-(tert-butyl) 3-methyl 3-methylindoline-1,3-dicarboxylate. LC-MS (ESI) m/z: 224 $[M+H]^+$.

Int. E36

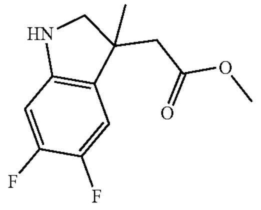

Methyl 2-(5,6-difluoro-3-methylindolin-3-yl)acetate

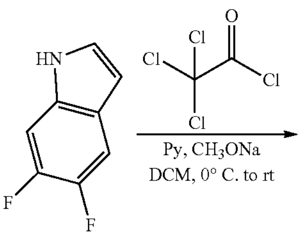

-continued

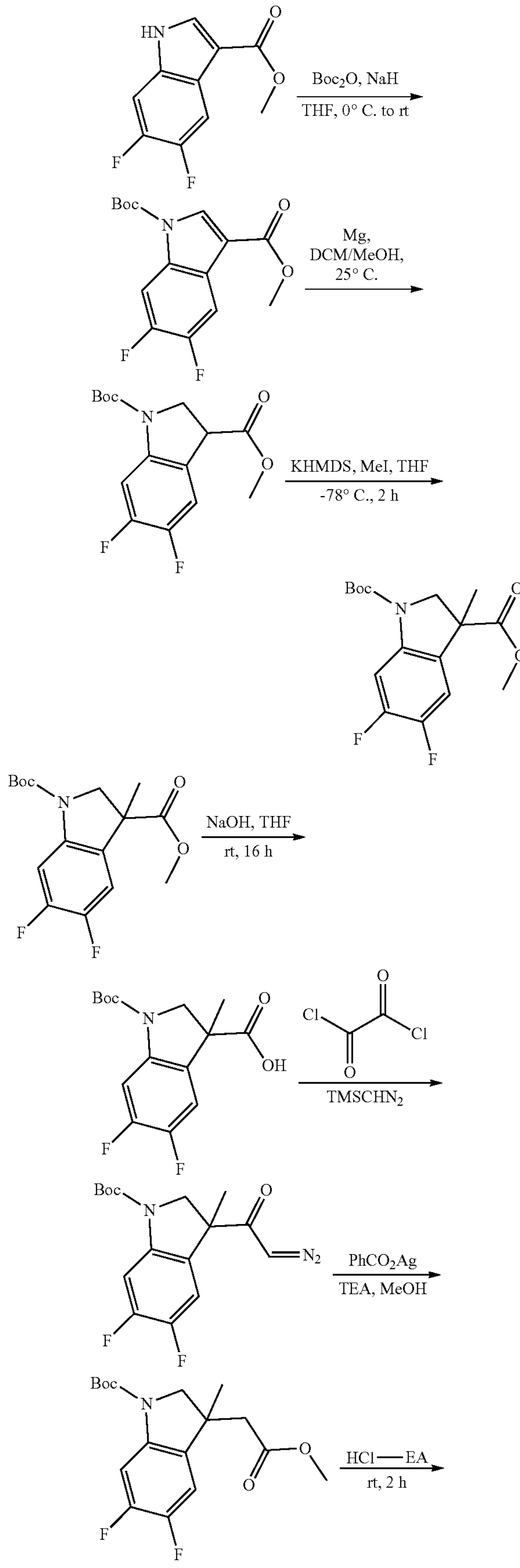

-continued

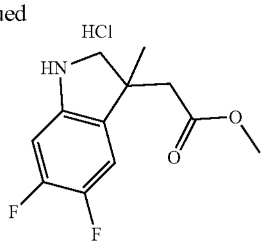

Step 1 & 2&3: The same procedure as Step 1 & 2&3 of Int. E26, using 5,6-difluoro-1H-indole in place of 4-methoxy-1H-indole. LC-MS (ESI) m/z: 258 $[M+H-56]^+$.

Step 4: To a solution of 1-(tert-butyl) 3-methyl 5,6-difluoroindoline-1,3-dicarboxylate (910 mg, 2.90 mmol) in anhydrous THF (60 mL) were added iodomethane (494.7 mg, 3.49 mmol) at −78° C. over 20 minutes and 1M KHMDS (3.2 mL) at −78° C. over 45 minutes under the protection of $N_2$. The reaction mixture was stirred at −78° C. for 2 hours, quenched with saturated $NH_4Cl$ aqueous solution (50 mL) and separated. The aqueous layer was extracted with EA (50 mL×3), and the combined organic phase was washed with brine (40 mL), dried over anhydrous $Na_2SO_4$ and filtered. The filtrate was concentrated in vacuo, and the residue was purified by flash column chromatography on silica gel (1020% EA/PE) to provide 1-(tert-butyl) 3-methyl 5,6-difluoro-3-methylindoline-1,3-dicarboxylate as colorless oil (810 mg, 82% yield). LC-MS (ESI) m/z: 272 $[M+H-56]^+$.

Step 5&6&7&8: The same procedures as Int. E33, using 1-(tert-butyl) 3-methyl 5-fluoro-3-methylindoline-1,3-dicarboxylate in place of 1-(tert-butyl) 3-methyl 3-methylindoline-1,3-dicarboxylate. LC-MS (ESI) m/z: 242 $[M+H]^+$.

Int. E37

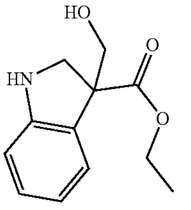

Ethyl 3-(hydroxymethyl)indoline-3-carboxylate

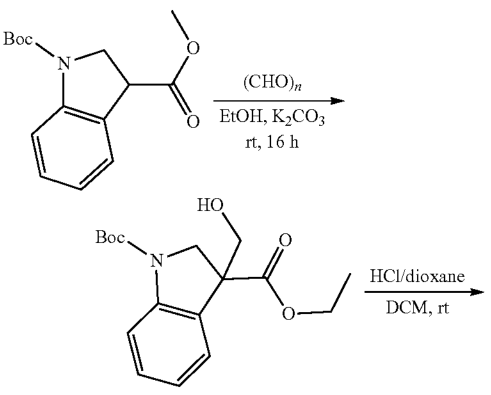

-continued

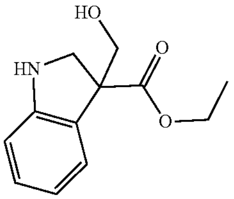

Step 1: To a solution of 1-(tert-butyl) 3-methyl indoline-1,3-dicarboxylate (300 mg, 1.08 mmol) in ethanol (5 mL) were added paraformaldehyde (48.72 mg, 1.62 mmol) and $K_2CO_3$ (448.53 mg, 3.25 mmol). The reaction mixture was stirred at room temperature for 16 hours and filtered. The filtrate was concentrated in vacuo to provide crude 1-(tert-butyl) 3-ethyl 3-(hydroxymethyl)indoline-1,3-dicarboxylate (330 mg, 99% yield). LC-MS (ESI) m/z: 222 $[M+H-100]^+$.

Step 2: To a solution of 1-(tert-butyl) 3-ethyl indoline-1,3-dicarboxylate (300 mg, 1.08 mmol) in DCM (5 mL) was added 4M HCl in dioxane (3 mL) at 0° C. The reaction mixture was stirred at room temperature for 16 hours, neutralized to pH~8 with saturated $NaHCO_3$ aqueous solution (5 mL) and extracted with DCM/MeOH (v/v, 10/1, 20 mL×3). The organic phases were dried over anhydrous sodium sulfate and filtered. The filtrate was concentrated in vacuo to afford crude ethyl 3-(hydroxymethyl)indoline-3-carboxylate (239 mg, 89.9% yield). LC-MS (ESI) m/z: 222 $[M+H]^+$.

Int. E38

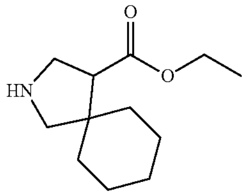

Ethyl 2-azaspiro[4.5]decane-4-carboxylate

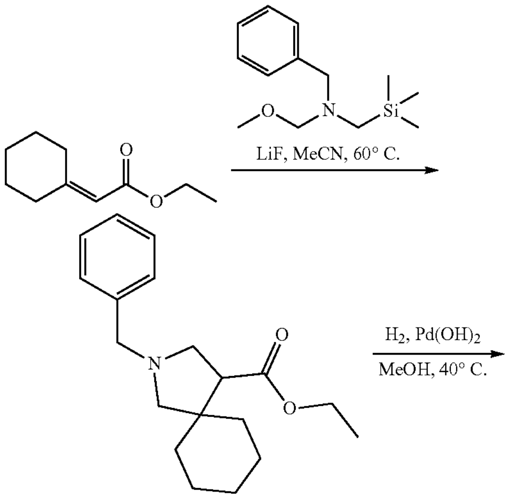

-continued

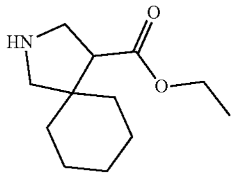

Step 1: A mixture of ethyl 2-cyclohexylideneacetate (5 g, 29.72 mmol), N-(methoxymethyl)-1-phenyl-N-(trimethylsilylmethyl)methanamine (14.11 g, 59.44 mmol) and lithium fluoride (2.31 g, 89.16 mmol) in MeCN (50 mL) was stirred at 60° C. for 48 hours and concentrated in vacuo. The residue was dissolved in EA (100 mL), which was washed with a prechilled $K_2CO_3$ aqueous solution (10%, 100 mL×2), saturated $CuSO_4$ aqueous solution (100 mL×3) and brine (100 mL). The organic phase was dried over anhydrous $Na_2SO_4$ and filtered. The filtrate was concentrated in vacuo, and the residue was purified by reverse phase chromatography (0.03% $NH_4HCO_3$/MeOH) to afford ethyl 2-benzyl-2-azaspiro[4.5]decane-4-carboxylate (5.55 g, 52.7% yield, 85% purity) as light-yellow oil. LC-MS (ESI) m/z: 302 $[M+H]^+$.

Step 2: To a solution of ethyl 2-benzyl-2-azaspiro[4.5]decane-4-carboxylate (2.65 g, 8.79 mmol) in methanol (30 mL) was added dihydroxypalladium (679.1 mg, 4.84 mmol). The mixture was stirred at 40° C. under hydrogen atmosphere (14 psi) for 24 hours and filtered. The filtrate was concentrated in vacuo to provide crude ethyl 2-azaspiro[4.5]decane-4-carboxylate. LC-MS (ESI) m/z: 212 $[M+H]^+$.

Int. E39

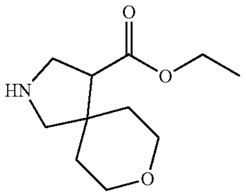

Ethyl 8-oxa-2-azaspiro[4.5]decane-4-carboxylate

The same procedures as Int. E38, using ethyl 2-tetrahydropyran-4-ylideneacetate in place of ethyl 2-cyclohexylideneacetate. LC-MS (ESI) m/z: 214 $[M+H]^+$.

Int. E40

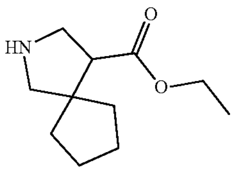

Ethyl 2-azaspiro[4.4]nonane-4-carboxylate

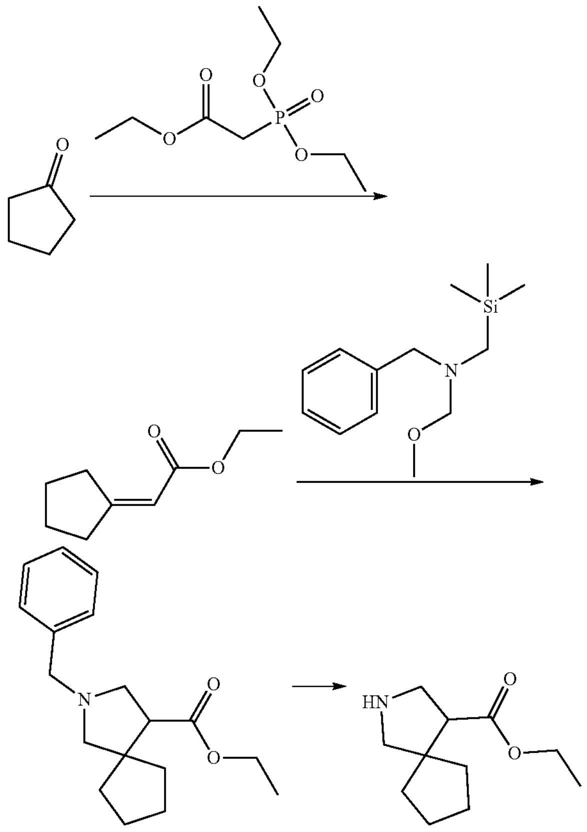

Step 1: To a stirring suspension of sodium hydride (2.08 g, 52.04 mmol, 60% dispersion in mineral oil) in diethyl ether (120 mL) was added ethyl 2-diethoxyphosphorylacetate (11.64 g, 51.94 mmol) at 0° C. The resulting mixture was stirred for 5 minutes, followed by the addition of the solution of cyclopentanone (4.25 g, 50.53 mmol) in diethyl ether (10 mL). The reaction mixture was stirred at 25° C. for 4 hours, quenched with saturated ammonium chloride aqueous solution (30 mL) in at 0° C., diluted with water (100 mL), and extracted with diethyl ether (50 mL×3). The combined organic phase was dried over anhydrous sodium sulfate and filtered. The filtrate was concentrated in vacuo, and the residue was purified by flash column chromatography on silica gel (petroleum ether/diethyl ether=10/1) to provide ethyl 2-cyclopentylideneacetate as light-yellow oil (6.0 g, 73% yield). LC-MS (ESI) m/z: 155 $[M+H]^+$.

Step 2&3: The same procedures as Int. E38, using ethyl 2-cyclopentylideneacetate in place of ethyl 2-cyclohexylideneacetate. LC-MS (ESI) m/z: 198 $[M+H]^+$.

Intermediate 12

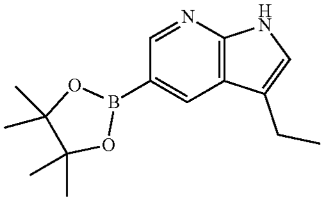

3-Ethyl-5-(4,4,5,5-tetramethyl-1,3,2-dioxaborolan-2-yl)-1H-pyrrolo[2,3-b]pyridine

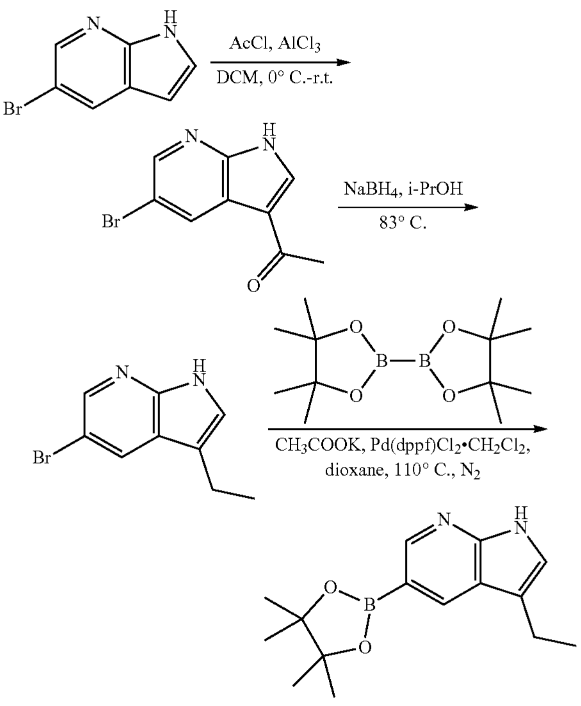

Step 1: To a suspension of anhydrous $AlCl_3$ (3.40 g, 25.50 mmol) in anhydrous DCM (50 mL) under $N_2$ was added 5-bromo-1H-pyrrolo[2,3-b]pyridine (1.01 g, 5.10 mmol). The mixture was stirred for 1 hour at room temperature and AcCl (2.00 g, 25.50 mmol, 1.8 mL) was added dropwise thereto. The resulting mixture was stirred for 30 minutes, cooled to 0° C., and quenched carefully by addition of MeOH until the solution became clear. The mixture was concentrated, and the residue was diluted with $H_2O$ (30 mL), adjusted to pH~4 with aqueous NaOH solution (1 N), and extracted with ethyl acetate (30 mL×3). The combined organic layers were washed with brine (30 mL×2), dried over anhydrous $Na_2SO_4$, filtered and concentrated. The residue was sonicated in EA and filtered to provide 1-(5-bromo-1H-pyrrolo[2,3-b]pyridin-3-yl)ethan-1-one as light yellow solid (0.87 g, 71% yield). LC-MS (ESI) m/z: 239 $[M+H]^+$.

Step 2: To a stirred solution of 1-(5-bromo-1H-pyrrolo[2,3-b]pyridin-3-yl)ethan-1-one (200 mg, 0.84 mmol) in isopropyl alcohol (7 mL) was added $NaBH_4$ (158.24 mg, 4.18 mmol) in portions at 0° C. The reaction mixture was refluxed at 83° C. for 24 hours, cooled down to 0° C., and diluted with water (15 mL). The resulting mixture was extracted with ethyl acetate (30 mL×3). The organic layer was washed with brine (20 mL×2), dried over anhydrous $Na_2SO_4$, filtered, and concentrated. The residue was purified with prep-TLC (PE/EA=3/2 v/v) to provide 5-bromo-3-ethyl-1H-pyrrolo[2,3-b]pyridine as off-white solid (70 mg, 33% yield). LC-MS (ESI) m/z: 225 $[M+H]^+$.

Step 3: To a solution of 5-bromo-3-ethyl-1H-pyrrolo[2,3-b]pyridine (200 mg, 888.55 umol) and 4,4,4',4',5,5,5',5'-octamethyl-2,2'-bi(1,3,2-dioxaborolane) (270.77 mg, 1.07 mmol) in 1,4-dioxane (6 mL) were added $CH_3COOK$ (174.41 mg, 1.78 mmol) and $Pd(dppf)Cl_2CH_2Cl_2$ (72.56 mg, 88.86 umol).

The mixture was stirred at 110° C. under nitrogen atmosphere overnight, cooled down to room temperature, and filtered. The filtrate was concentrated, and the residue was purified with flash column chromatography on silica gel (PE/EA=2/1 v/v), and further sonication in PE (10 mL) to provide 3-ethyl-5-(4,4,5,5-tetramethyl-1,3,2-dioxaborolan-2-yl)-1H-pyrrolo[2,3-b]pyridine as white solid (40 mg, 9% yield). LC-MS (ESI) m/z: 273 $[M+H]^+$.

Intermediate 13

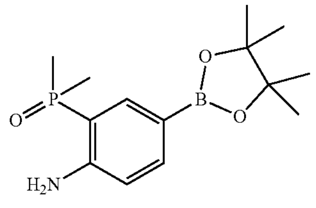

(2-Amino-5-(4,4,5,5-tetramethyl-1,3,2-dioxaborolan-2-yl)phenyl)dimethylphosphine oxide

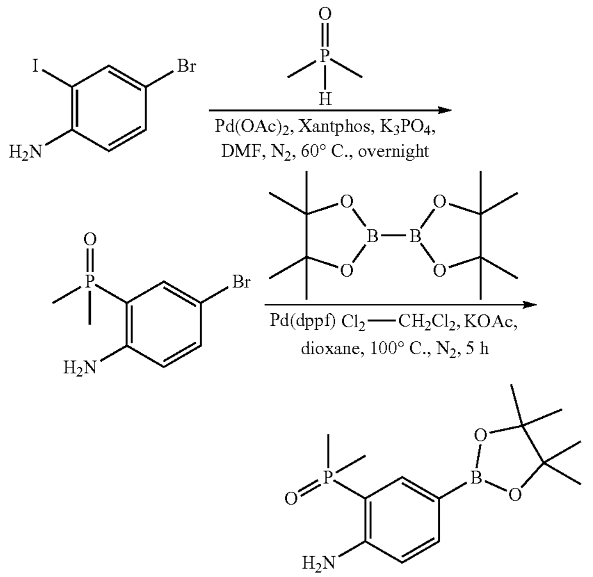

Step 1: A mixture of 4-bromo-2-iodo-aniline (2.0 g, 6.71 mmol), dimethylphosphine oxide (628.76 mg, 8.06 mmol), $Pd(OAc)_2$ (150.71 mg, 671.33 umol), Xantphos (776.86 mg, 1.34 mmol), and $K_3PO_4$ (2.85 g, 13.41 mmol) in DMF (20 mL) was stirred under $N_2$ at 60° C. overnight. After cooled down to room temperature, the mixture was filtered and washed with EA (40 mL). The filtrate was diluted with $H_2O$ (40 mL) and extracted with EA (50 mL×30). The organic layer was washed with brine (40 mL×3), dried over anhydrous sodium sulfate, filtered, and concentrated. The residue was purified with flash column chromatography on silica gel (DCM/MeOH=60/1 v/v) to provide (2-amino-5-bromophenyl)dimethylphosphine oxide as yellow solid (1.6 g, 96% yield). LC-MS (ESI) m/z: 248 $[M+H]^+$.

Step 2: A mixture of (2-amino-5-bromophenyl)dimethylphosphine oxide (1.53 g, 6.17 mmol), 4,4,5,5-tetramethyl-2-(4,4,5,5-tetramethyl-1,3,2-dioxaborolan-2-yl)-1,3,2-dioxaborolane (1.88 g, 7.41 mmol), $Pd(dppf)Cl_2{}^-CH_2Cl_2$ (503.70 mg, 616.80 umol), and KOAc (1.21 g, 12.34 mmol) in dioxane (20 mL) was stirred under $N_2$ at 100° C. for 5 hours. After cooled down to room temperature, the mixture was filtered and washed with EA (150 mL). The organic layer was concentrated and purified with flash column chromatography on silica gel (DCM/MeOH=20/1 v/v) to provide (2-amino-5-(4,4,5,5-tetramethyl-1,3,2-dioxaborolan-2-yl)phenyl)dimethylphosphine oxide as black oil (1.16 g, 64% yield). LC-MS (ESI) m/z: 296 $[M+H]^+$.

Intermediate 14

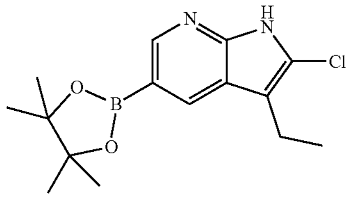

2-Chloro-3-ethyl-5-(4,4,5,5-tetramethyl-1,3,2-dioxaborolan-2-yl)-1H-pyrrolo[2,3-b]pyridine

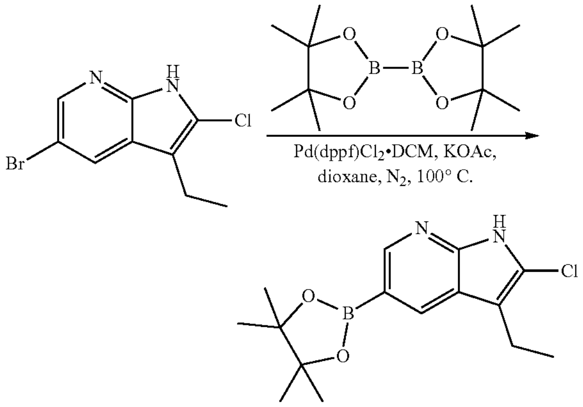

A mixture of 5-bromo-2-chloro-3-ethyl-2,3-dihydro-1H-pyrrolo[2,3-b]pyridine (50 mg, 0.19 mmol), 4,4,6,6-tetramethyl-2-(4,4,5,5-tetramethyl-1,3,2-dioxaborolan-2-yl)-1,3,2-dioxaborinane (73 mg, 0.27 mmol), anhydrous AcOK (56 mg, 0.58 mmol), and $Pd(dppf)Cl_2DCM$ (15 mg, 0.02 mmol) in anhydrous dioxane (1.5 mL) was stirred under microwave conditions protected by nitrogen at 100° C. for 3 hours. After cooled down to room temperature, the mixture was filtrated and the filtrate was concentrated to provide crude 2-chloro-3-ethyl-5-(4,4,5,5-tetramethyl-1,3,2-dioxaborolan-2-yl)-1H-pyrrolo[2,3-b]pyridine (50 mg), which was used in next step without further purification. LC-MS (ESI) m/z: 307 $[M+H]^+$.

Intermediate 15

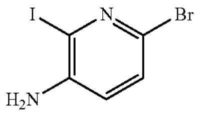

6-Bromo-2-iodopyridin-3-amine

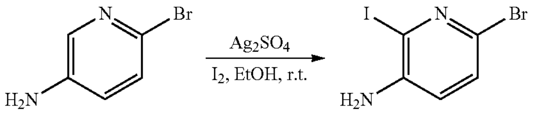

To a suspension of 6-bromopyridin-3-amine (1 g, 5.68 mmol) and silver sulfate (1.77 g, 5.68 mmol) in ethanol (20 mL) was added iodine (1.44 g, 5.68 mmol), and the reaction mixture was stirred at room temperature overnight, diluted with PE (20 mL) and filtered. The filtrate was concentrated, and the residue was sonicated in EA (30 mL). The solid was collected by filtration and dried to provide 6-bromo-2-iodo-pyridin-3-amine as brown solid (380 mg, 22% yield). LC-MS (ESI) m/z: 299 $[M+H]^+$.

Intermediate 16

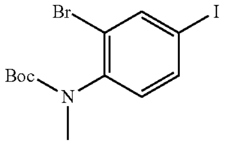

tert-Butyl (2-bromo-4-iodophenyl)(methyl)carbamate

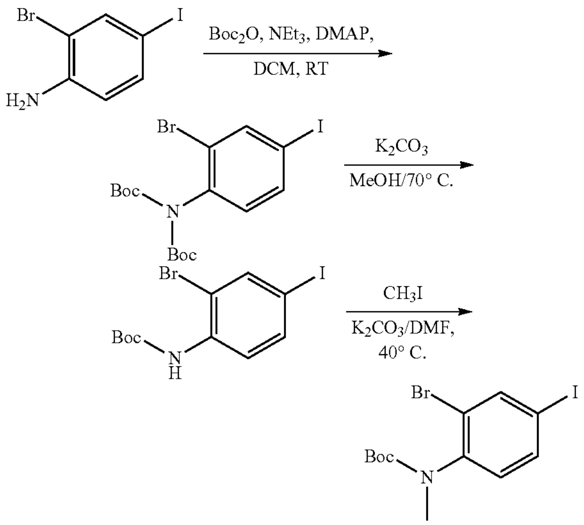

Step 1: To a solution of 2-bromo-4-iodo-aniline (1 g, 3.36 mmol) in DCM (10 mL) were added TEA (339.66 mg, 467.85 uL), DMAP (410.08 mg, 3.36 mmol), and $Boc_2O$ (732.58 mg, 3.36 mmol). The mixture was stirred at room temperature for 5 hours, and concentrated. The residue was purified with flash column chromatography on silica gel (PE/EA=10/1 v/v) to provide tert-butyl N-(2-bromo-4-iodo-phenyl)-N-tert-butoxycarbonyl-carbamate as white solid (732.58 mg, 43% yield).

Step 2: To a solution of tert-butyl N-(2-bromo-4-iodo-phenyl)-N-tert-butoxycarbonyl-carbamate (800 mg, 1.61 mmol) in methanol (20 mL) was added potassium carbonate (665.87 mg, 4.82 mmol). The mixture was stirred at 70° C. for 2 hours, and concentrated. The residue was purified with flash column chromatography on silica gel (PE/EA=10/1 v/v) to provide tert-butyl N-(2-bromo-4-iodo-phenyl)carbamate as white solid (462 mg, 72% yield).

Step 3: To a solution of tert-butyl N-(2-bromo-4-iodo-phenyl)carbamate (400 mg, 1.00 mmol) in DMF (10 mL) were added potassium carbonate (277.79 mg, 2.01 mmol) and iodomethane (213.96 mg, 1.51 mmol). The mixture was stirred at 40° C. overnight. After cooled down to room temperature, the mixture was diluted with $H_2O$ (30 mL) and extracted with EA (30 mL×3). The organic layer was washed with brine (20 mL×3), dried over anhydrous $Na_2SO_4$, filtered, and concentrated. The residue was purified with flash column chromatography on silica gel (PE/EA=10/1 v/v) to provide tert-butyl N-(2-bromo-4-iodo-phenyl)-N-methyl-carbamate as yellow solid (400 mg, 96% yield). LC-MS (ESI) m/z: 356 [M+H-55]

Intermediate 17

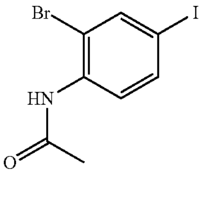

N-(2-bromo-4-iodophenyl)acetamide

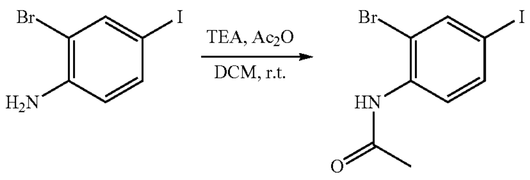

To a stirred solution of 2-bromo-4-iodo-aniline (1.0 g, 3.36 mmol) in DCM (10 mL) was added triethylamine (680.00 mg, 6.72 mmol, 0.94 mL), followed by acetic anhydride (411.63 mg, 4.03 mmol, 381.14 uL). The mixture was stirred at room temperature overnight, and heated at 40° C. for 4 hours. After cooled down to room temperature, the mixture was concentrated to provide N-(2-bromo-4-iodo-phenyl)acetamide as grey solid (1.1 g, 96% yield). LC-MS (ESI) m/z: 340 $[M+H]^+$.

Intermediate 18

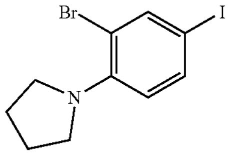

1-(2-Bromo-4-iodophenyl)pyrrolidine

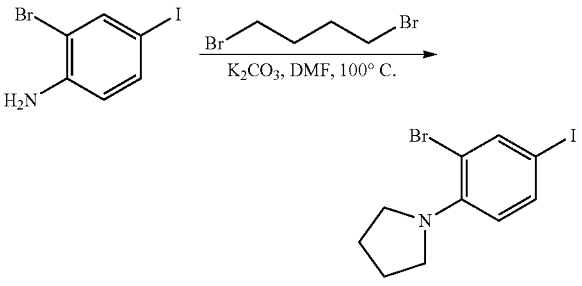

A mixture of 2-bromo-4-iodo-aniline (1.0 g, 3.36 mmol), 1,4-dibromobutane (869.69 mg, 4.03 mmol), and potassium carbonate (927.84 mg, 6.71 mmol) in DMF (20 mL) was stirred at 100° C. overnight. After cooled down to room temperature, the mixture was poured into water (40 mL) and extracted with EA (50 mL×3). The organic layer was washed with brine (30 mL×3), dried and over anhydrous sodium sulfate, filtered and concentrated. The residue was purified with flash column chromatography on silica gel (PE, 100% v/v) to provide 1-(2-bromo-4-iodo-phenyl)pyrrolidine as yellow oil (200 mg, 17% yield). LC-MS (ESI) m/z: 352 $[M+H]^+$.

Intermediate 19

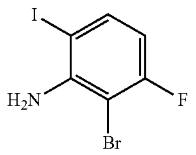

2-Bromo-3-fluoro-6-iodoaniline

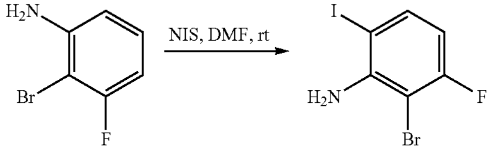 [SMILES: Nc1cccc(F)c1Br ; Nc1c(I)ccc(F)c1Br]

To a solution of 2-bromo-3-fluoro-aniline (200 mg, 1.05 mmol) in DMF (2 mL) was added dropwise a solution of NIS (236.81 mg, 1.05 mmol) in DMF (2 mL) at room temperature. The reaction mixture was stirred at room temperature for 3 hours, diluted with EA (30 mL), and washed with brine (20 mL×2). The organic layer was dried over anhydrous $Na_2SO_4$, filtered and concentrated. The residue was purified with flash column chromatography on silica gel (PE/EA=20/1 v/v) to provide 2-bromo-3-fluoro-6-iodo-aniline as brown solid (330 mg, 99% yield). LC-MS (ESI) m/z: 316 $[M+H]^+$.

Intermediate 20

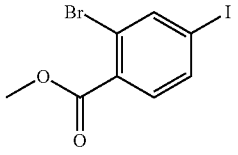

Methyl 2-bromo-4-iodobenzoate

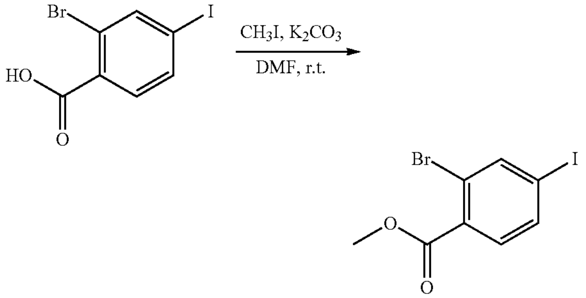

To a solution of 2-bromo-4-iodo-benzoic acid (1 g, 3.06 mmol), potassium carbonate (845.55 mg, 6.12 mmol) in DMF (15 mL) was added iodomethane (651.27 mg, 4.59 mmol). The reaction mixture was stirred at room temperature overnight, quenched with $H_2O$ (50 mL) and extracted with EA (25 mL×2). The combined organic layers were washed with brine (30 mL×3), dried over anhydrous sodium sulfate, filtered, and concentrated to provide methyl 2-bromo-4-iodo-benzoate as brown oil (1 g, 95% yield). LC-MS (ESI) m/z: 341 $[M+H]^+$.

Intermediate 21

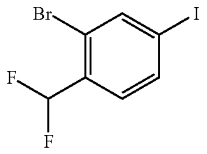

2-Bromo-1-(difluoromethyl)-4-iodobenzene

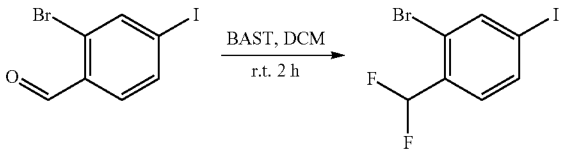 [SMILES: O=Cc1ccc(I)cc1Br ; FC(F)c1ccc(I)cc1Br]

To a solution of 2-bromo-4-iodobenzaldehyde (200 mg, 0.64 mmol) in DCM (6 mL) was added BAST (284 mg, 1.29 mmol) at 0° C. The mixture was stirred at room temperature for 2 hours, and concentrated. The residue was purified with flash column chromatography on silica gel (EA/PE=20/1 v/v) to provide 2-bromo-1-(difluoromethyl)-4-iodobenzene as white solid. (180 mg, 84% yield).

Intermediate 22

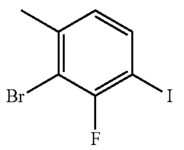

2-Bromo-3-fluoro-4-iodo-1-methylbenzene

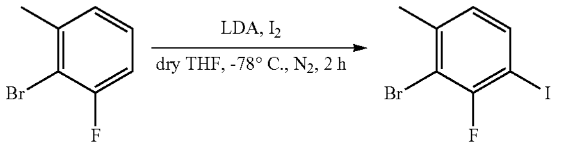

To a solution of 2-bromo-1-fluoro-3-methyl-benzene (500 mg, 2.65 mmol) in anhydrous THF (5 mL) was dropwise added LDA (2 N in THF, 2 mL, 4.0 mmol) under $N_2$ at −70° C. over 10 minutes and the mixture was stirred at −70° C. for 30 minutes. A solution of $I_2$ (2.01 g, 7.94 mmol) in anhydrous THF (2 mL) was added dropwise to the above mixture at −70° C. and the resulting mixture was stirred at −70° C. for 3 hours. After warmed to room temperature, the mixture was poured into saturated aqueous $NH_4Cl$ solution (20 mL) and extracted with EA (20 mL×2). The combined organic layers were washed with brine (30 mL×2), dried over anhydrous $Na_2SO_4$, filtered and concentrated. The residue was purified with prep-TLC (PE, 100% v/v) to provide 3-bromo-2-fluoro-1-iodo-4-methyl-benzene as colorless oil (110 mg, 13% yield).

Intermediate 24

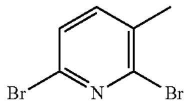

2,6-Dibromo-3-methylpyridine

To a solution of 6-bromo-5-methyl-pyridin-2-amine (100 mg, 0.535 mmol) in 48% aqueous Hydrobromic acid solution (3 mL) was added dropwise bromine (69.2 mg, 0.855 mmol) at −5° C. A solution of sodium nitrite (99.6 mg, 1.44 mmol) in water (2 mL) was added dropwise to the above mixture at −5° C. The resulting mixture was stirred at room temperature for 3 hours, cooled to −5° C., quenched with a solution of KOH (100 mg) in water (5 mL) and extracted with EA (20 mL×2). The combined organic layers were washed with brine (20 mL), dried over anhydrous $Na_2SO_4$, and filtered. The filtrate was concentrated in vacuo, and the residues was purified by prep-TLC (PE/EA=10/1 v/v) to provide 2,6-dibromo-3-methyl-pyridine as white solid (20 mg, 15% yield). LC-MS (ESI) m/z: 250 $[M+H]^+$.

Intermediate 25

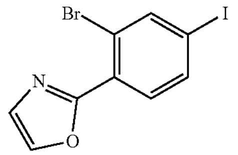

2-(2-Bromo-4-iodophenyl)oxazole

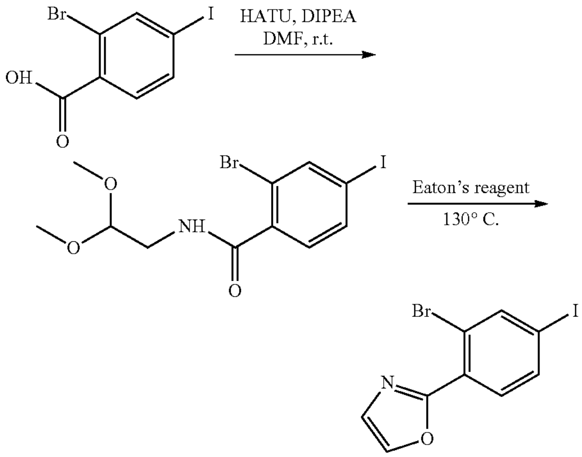

Step 1: To a stirred solution of 2-bromo-4-iodo-benzoic acid (1 g, 3.06 mmol) in DMF (10 mL) were added HATU (1.74 g, 4.59 mmol) and DIPEA (1.19 g, 9.18 mmol, 1.60 mL). After stirring for 10 minutes, 2,2-dimethoxy-ethanamine (418.08 mg, 3.98 mmol, 433.25 uL) was added to the above mixture. The mixture was stirred overnight, diluted with EA (20 mL), and washed with aqueous $NaHCO_3$ solution (30 mL×2). The organic layer was dried over anhydrous sodium sulfate, filtered, and concentrated in vacuo. The residue was purified with flash column chromatography on silica gel (PE/EA=10/1 v/v) to provide 2-bromo-N-(2,2-dimethoxyethyl)-4-iodo-benzamide as yellow solid (1 g, 2.42 mmol). LC-MS (ESI) m/z: 382 $[M-MeO]^+$.

Step 2: A solution of 2-bromo-N-(2,2-dimethoxyethyl)-4-iodo-benzamide (1 g, 2.42 mmol) in Eaton's reagent (10 mL) was stirred at 130° C. overnight. After cooled down to room temperature, the solution was poured into ice-water (60 mL). The resulting suspension was filtered and dried to provide 2-(2-bromo-4-iodo-phenyl)oxazole as grey solid (840 mg, 2.40 mmol, 99% yield). LC-MS (ESI) m/z: 350 $[M+H]^+$.

Intermediate 26

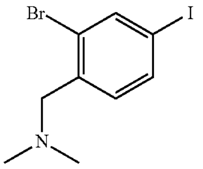

1-(2-Bromo-4-iodophenyl)-N,N-dimethylmethanamine

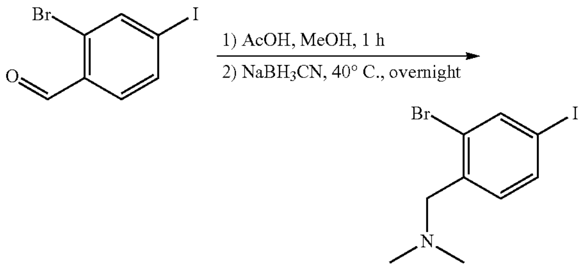

A mixture of 2-bromo-4-iodobenzaldehyde (300 mg, 0.94 mmol), dimethylamine (2 M in THF, 0.58 mL, 1.16 mmol), and AcOH (5 drops) in MeOH (8 mL) was stirred under $N_2$ at room temperature for 1 hour. Then $NaBH_3CN$ (90 mg, 1.45 mmol) was added to the above mixture and the resulting mixture was stirred at 40° C. for 16 hours. After cooled down to room temperature, the mixture was concentrated and the residue was purified with flash column chromatography on silica gel (PE 100% v/v, and then PE/EA=5/1, v/v) to provide 1-(2-bromo-4-iodophenyl)-N,N-dimethylmethanamine as yellow oil (10 mg, 29% yield). LC-MS (ESI) m/z: 340 $[M+H]^+$.

Intermediate 27

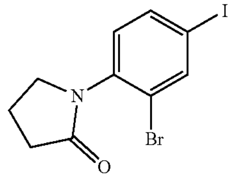

1-(2-Bromo-4-iodophenyl)pyrrolidin-2-one

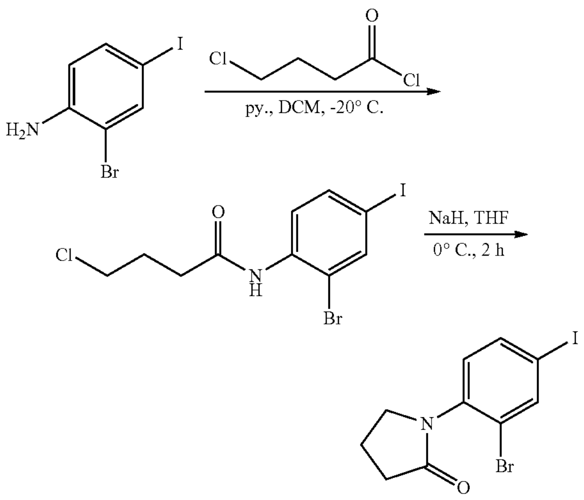

Step 1: To a mixture of 2-bromo-4-iodoaniline (600 mg, 2.0 mmol) in DCM (10 mL) were added pyridine (175 mg, 2.2 mmol) and 4-chlorobutanoyl chloride (312 mg, 2.2 mmol) dropwise at under −20° C. The reaction mixture was stirred at −20° C. for 3 hours, diluted with water (20 mL), washed with aqueous HCl solution (2 N), and extracted with EA (30 mL×3). The organic layer was dried over anhydrous $Na_2SO_4$, filtered, and concentrated to provide N-(2-bromo-4-iodophenyl)-4-chlorobutanamide as black solid (700 mg, 86% yield). LC-MS (ESI) m/z: 402 $[M+H]^+$.

Step 2: To a solution of N-(2-bromo-4-iodophenyl)-4-chlorobutanamide (700 mg, 1.74 mmol) in dry THF (10 mL) was added NaH (60% suspend in oil, 138 mg, 3.48 mmol) at 0° C. The mixture was stirred under $N_2$ at room temperature for 2 hours, diluted with cold-water (20 mL) and extracted with EA (30 mL×3). The organic layer was washed with brine (20 mL), dried over anhydrous sodium sulfate, filtered and concentrated. The residue was purified with flash column chromatography on silica gel (PE 100% v/v, and then PE/EA=5/1, v/v) to provide 1-(2-bromo-4-iodophenyl) pyrrolidin-2-one as white solid (500 mg, 78% yield). LC-MS (ESI) m/z: 366 $[M+H]^+$.

Intermediate 28

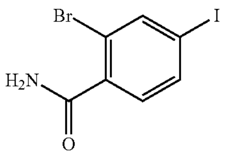

2-Bromo-4-iodobenzamide

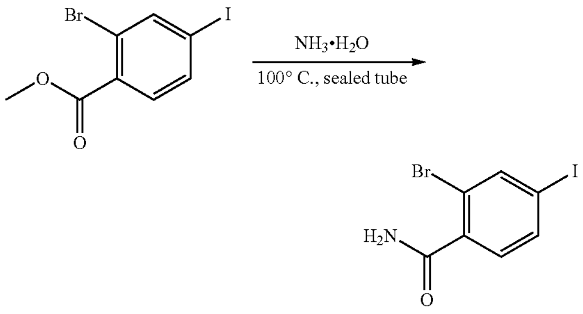

A mixture of methyl 2-bromo-4-iodo-benzoate (500 mg, 1.47 mmol) in 28% ammonium hydroxide (5 mL) was stirred at 100° C. in sealed tube for 5 hours, cooled down to room temperature, and filtered. The filtrate was concentrated to provide 2-bromo-4-iodo-benzamide as white solid (400 mg, 84% yield). LC-MS (ESI) m/z: 326 $[M+H]^+$.

Intermediate 29

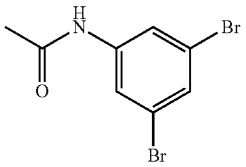

N-(3,5-dibromophenyl)acetamide

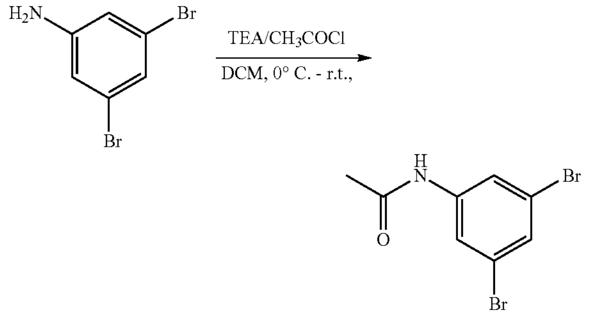

To a solution of 3,5-dibromoaniline (200 mg, 797.07 umol) in DCM (5 mL) were added TEA (241.97 mg, 2.39 mmol, 333.29 uL) and acetyl chloride (93.85 mg, 1.20 mmol, 72.75 uL) at 0° C. The mixture was stirred at room temperature for 2 hours, diluted with $H_2O$ (20 mL) and extracted with DCM (30 mL×3). The combined extracts were dried over anhydrous $Na_2SO_4$ filtered, and concentrated. The residue was purified with flash column chromatography on silica gel (PE/EA=10/1 v/v) to provide N-(3,5-dibromophenyl)acetamide as yellow solid (185 mg, 79% yield). LC-MS (ESI) m/z: 292 $[M+H]^+$.

Intermediate 30

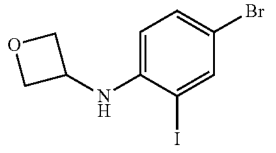

N-(4-bromo-2-iodophenyl)oxetan-3-amine

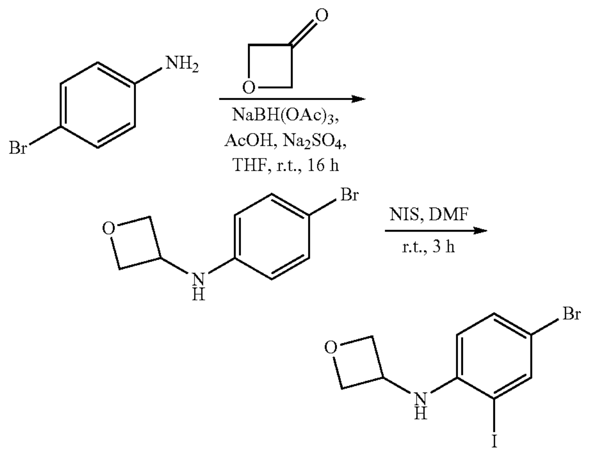

Step 1: A mixture of 4-bromoaniline (4 g, 23.25 mmol), oxetan-3-one (2.18 g, 30.23 mmol, 1.94 mL), anhydrous $Na_2SO_4$ (3.30 g, 23.25 mmol) in THF (20 mL) was stirred at room temperature for 1 hour. Then $NaBH(OAc)_3$ (7.39 g, 34.88 mmol) was added to the above mixture at room temperature. The mixture was stirred at room temperature for 16 hours, diluted with water (50 mL) and extracted with EA (100 mL×2). The combined organic layers were washed with saturated aqueous $NaHCO_3$ solution (30 mL×3) and brine (20 mL×2), dried over anhydrous $Na_2SO_4$, filtered and concentrated. The residue was purified with flash column chromatography on silica gel (EA/PE=2/1 v/v) to provide N-(4-bromophenyl)oxetan-3-amine as white solid (3.4 g, 64% yield). LC-MS (ESI) m/z: 228 $[M+H]^+$.

Step 2: To a solution of N-(4-bromophenyl)oxetan-3-amine (1.5 g, 6.58 mmol) in DMF (8 mL) was added dropwise a solution of NIS (1.48 g, 6.58 mmol) in DMF (3 mL) at room temperature. The mixture was stirred at room temperature for 3 hours, quenched with saturated aqueous $NaHSO_3$ solution (10 mL) and extracted with EA (60 mL×2). The combined organic layers were washed with brine (20 mL), dried over anhydrous $Na_2SO_4$, filtered and concentrated. The residue was purified with flash column chromatography on silica gel (EA/PE=4/1 v/v) to provide crude N-(4-bromo-2-iodo-phenyl)oxetan-3-amine as yellow solid (630 mg, 30% yield, 50% purity). LC-MS (ESI) m/z: 354 $[M+H]^+$.

Exemplified Compounds

Example 1

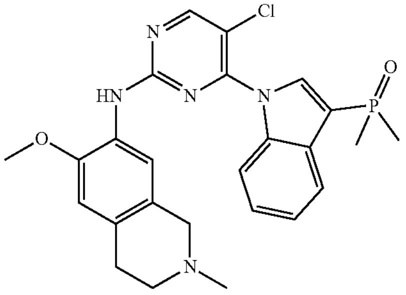

(1-(5-Chloro-2-((6-methoxy-2-methyl-1,2,3,4-tetrahydroisoquinolin-7-yl)amino)pyrimidin-4-yl)-1H-indol-3-yl)dimethylphosphine oxide Step 1: To a solution of Int. E1 (200 mg, 1.04 mmol) in DMF (5 mL) was added sodium hydride (60% dispersion in mineral oil, 50 mg, 1.24 mmol) at 0° C. and the mixture was stirred at 0° C. for 30 minutes. To the above reaction mixture was added 2,4,5-trichloropyrimidine (227.9 mg, 1.24 mmol) at 0° C., and the resulting mixture was then stirred at room temperature for 1 hour, cooled to 0° C., and quenched with ice-$H_2O$ (20 mL), and extracted with EA (30 mL×3). The organic phases were dried over anhydrous sodium sulfate and filtered. The filtrate was concentrated in vacuo, and the residue was purified by prep-HPLC (MeCN/0.1% HCOOH) to provide (1-(2,5-dichloropyrimidin-4-yl)-1H-indol-3-yl)dimethylphosphine oxide as white solid (110 mg, 31% yield). LC-MS (ESI) m/z: 340 $[M+H]^+$.

Step 2: To a solution of Int. W1 (25.4 mg, 0.13 mmol) in 2-methoxyethanol (3 mL) were added (1-(2,5-dichloropyrimidin-4-yl)-1H-indol-3-yl)dimethylphosphine oxide (30 mg, 0.09 mmol) and HCl in EtOH solution (2 N, 0.2 mL). The resulting mixture was stirred at 120° C. for 20 hours and concentrated in vacuo. The residue was purified by flash column chromatography on silica gel (DCM/MeOH=15/1 v/v), and prep-HPLC (MeCN/0.1% HCOOH) to provide (1-(5-chloro-2-((6-methoxy-2-methyl-1,2,3,4-tetrahydroisoquinolin-7-yl)amino)pyrimidin-4-yl)-1H-indol-3-yl) dimethylphosphine oxide as yellow solid (8.3 mg, 19% yield). LC-MS (ESI) m/z: 496 $[M+H]^+$. $^1H$ NMR (400 MHz, $CD_3OD$): δ 1.92 (s, 3H), 1.95 (s, 3H), 2.54 (s, 3H), 2.90-2.97 (m, 4H), 3.59 (s, 2H), 3.91 (s, 3H), 6.83 (s, 1H), 7.35-7.40 (m, 2H), 7.86-7.88 (m, 1H), 7.91-7.94 (m, 1H), 7.97 (s, 1H), 8.22 (d, J=4.8 Hz, 1H), 8.65 (s, 1H).

Example 2

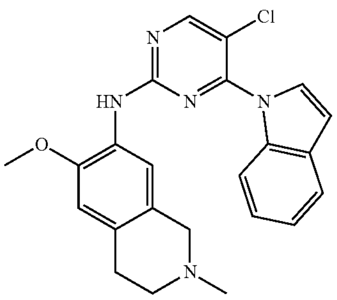 [SMILES: COc1cc2c(cc1Nc1ncc(Cl)c(-n3ccc4ccccc43)n1)CN(C)CC2]

N-(5-chloro-4-(1H-indol-1-yl)pyrimidin-2-yl)-6-methoxy-2-methyl-1,2,3,4-tetrahydroisoquinolin-7-amine The same procedures as Example 1, using indole in place of Int. E1 in Step 1. LC-MS (ESI) m/z: 420 $[M+H]^+$. $^1H$ NMR (400 MHz, $CD_3OD$): δ 2.79 (s, 3H), 3.07-3.10 (m, 2H), 3.26-3.27 (m, 2H), 3.94 (s, 5H), 6.75 (d, J=3.6 Hz, 1H), 6.89 (s, 1H), 7.21-7.30 (m, 2H), 7.65 (d, J=8.4 Hz, 1H), 7.83 (d, J=3.6 Hz, 1H), 7.81 (d, J=8.4 Hz, 1H), 8.13 (s, 1H), 8.60 (s, 1H).

Example 3

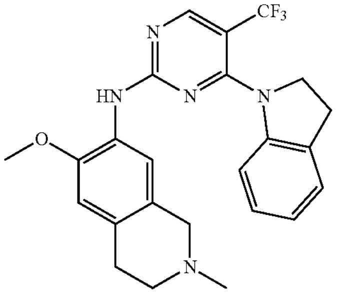 [SMILES: COc1cc2c(cc1Nc1ncc(C(F)(F)F)c(N3CCc4ccccc43)n1)CN(C)CC2]

N-(4-(1H-indol-1-yl)-5-(trifluoromethyl)pyrimidin-2-yl)-6-methoxy-2-methyl-1,2,3,4-tetrahydroisoquinolin-7-amine The same procedures as Example 1, using indoline and 2,4-dichloro-5-(trifluoromethyl)pyrimidine in place of Int. E1 and 2,4,5-trichloropyrimidine in Step 1. LC-MS (ESI) m/z: 420 $[M+H]^+$. $^1H$ NMR (400 MHz, $CD_3OD$): δ 2.55 (s, 3H), 2.92-2.96 (m, 4H), 3.19 (t, J=8.0 Hz, 2H), 3.45 (s, 2H), 3.88 (s, 3H), 4.16 (t, J=8.0 Hz, 2H), 6.78 (s, 1H), 7.02-7.07 (m, 1H), 7.17 (d, J=7.2 Hz, 1H), 7.31 (d, J=7.2 Hz, 1H), 7.55 (d, J=8.0 Hz, 1H), 7.90 (s, 1H), 8.49 (s, 1H).

Example 4

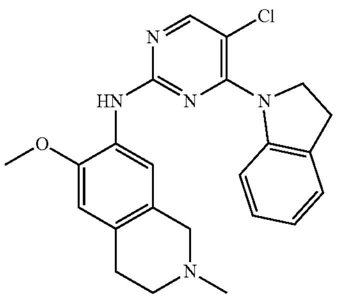 [SMILES: COc1cc2c(cc1Nc1ncc(Cl)c(N3CCc4ccccc43)n1)CN(C)CC2]

N-(5-Chloro-4-(indolin-1-yl)pyrimidin-2-yl)-6-methoxy-2-methyl-1,2,3,4-tetrahydroisoquinolin-7-amine Step 1: To a solution of 2,4,5-trichloropyrimidine (1 g, 5.45 mmol) in DMF (20 mL) were added potassium carbonate (1.51 g, 10.90 mmol) and indoline (649.7 mg, 5.45 mmol). The mixture was stirred at 80° C. overnight, cooled to room temperature, diluted with $H_2O$ (50 mL), and extracted with EA (50 mL×2). The organic phases were dried over anhydrous sodium sulfate and filtered. The filtrate was concentrated in vacuo, and the residue was purified by flash column chromatography on silica gel (EA/PE=1/30, v/v) to provide 1-(2,5-dichloropyrimidin-4-yl)indoline as white solid (900 mg, 61% yield). LC-MS (ESI) m/z: 266 $[M+H]^+$.

Step 2: Int. W1 (30 mg, 0.16 mmol) and 1-(2,5-dichloropyrimidin-4-yl)indoline (41.5 mg, 0.16 mmol) were used under Condition B1 (as exemplified in Step 2 of Example 1) to provide N-(5-chloro-4-(indolin-1-yl)pyrimidin-2-yl)-6-methoxy-2-methyl-1,2,3,4-tetrahydroisoquinolin-7-amine as yellow solid (35 mg, 53% yield), after purification by flash column chromatography on silica gel (DCM/MeOH=10/1). LC-MS (ESI) m/z: 422 $[M+H]^+$. $^1H$ NMR (400 MHz, DMSO-$d_6$): δ 2.33 (s, 3H), 2.59 (t, J=5.2 Hz, 2H), 2.78 (t, J=5.2 Hz, 2H), 3.13 (t, J=8.0 Hz, 2H), 3.31 (s, 2H), 3.78 (s, 3H), 4.27 (t, J=8.4 Hz, 2H), 6.75 (s, 1H), 6.93 (t, J=7.6 Hz, 1H), 7.08 (t, J=7.6 Hz, 1H), 7.25 (d, J=6.8 Hz, 1H), 7.35 (d, J=8.0 Hz, 1H), 7.56 (s, 1H), 7.96 (s, 1H), 8.24 (s, 2H).

Example 5

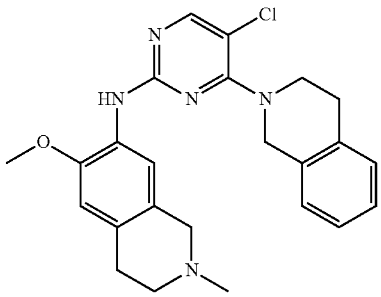 [SMILES: COc1cc2c(cc1Nc1ncc(Cl)c(N3CCc4ccccc4C3)n1)CN(C)CC2]

N-(5-chloro-4-(3,4-dihydroisoquinolin-2(1H)-yl) pyrimidin-2-yl)-6-methoxy-2-methyl-1,2,3,4-tetrahydroisoquinolin-7-amine The same procedures as Example 4, using 1,2,3,4-tetrahydroisoquinoline in place of indoline in Step 1. LC-MS (ESI) m/z: 436 $[M+H]^+$. $^1$H NMR (400 MHz, $CD_3OD$): δ 2.66 (s, 3H), 2.99-3.05 (m, 6H), 3.84 (s, 2H), 3.89 (s, 3H), 4.00 (t, J=6.0 Hz, 2H), 4.87 (s, 2H), 6.79 (s, 1H), 7.19 (s, 4H), 7.99 (s, 1H), 8.10 (s, 1H).

Example 6

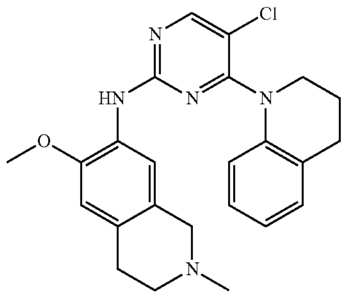 [SMILES: COc1cc2c(cc1Nc1ncc(Cl)c(N3CCCc4ccccc43)n1)CN(C)CC2]

N-(5-chloro-4-(3,4-dihydroquinolin-1(2H)-yl)pyrimidin-2-yl)-6-methoxy-2-methyl-1,2,3,4-tetrahydroisoquinolin-7-amine The same procedures as Example 4, using 1,2,3,4-tetrahydroquinoline in place of indoline in Step 1. LC-MS (ESI) m/z: 436 $[M+H]^+$. $^1$H NMR (400 MHz, $CD_3OD$): δ 1.99-2.06 (m, 2H), 2.51 (s, 3H), 2.80-2.86 (m, 4H), 2.91 (t, J=6.0 Hz, 2H), 3.44 (s, 2H), 3.87-3.90 (m, 5H), 6.73 (s, 1H), 6.85 (d, J=8.0 Hz, 1H), 6.99-7.03 (m, 1H), 7.06-7.10 (m, 1H), 7.19 (d, J=8.0 Hz, 1H), 7.87 (s, 1H), 8.14 (s, 1H).

Example 7

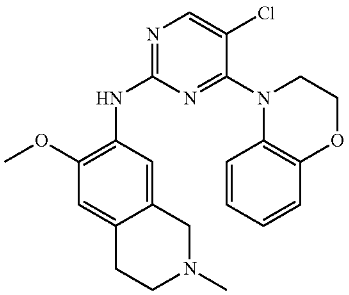 [SMILES: COc1cc2c(cc1Nc1ncc(Cl)c(N3CCOc4ccccc43)n1)CN(C)CC2]

N-(5-chloro-4-(2,3-dihydro-4H-benzo[b][1,4]oxazin-4-yl)pyrimidin-2-yl)-6-methoxy-2-methyl-1,2,3,4-tetrahydroisoquinolin-7-amine The same procedures as Example 4, using 3,4-dihydro-2H-benzo[b][1,4]oxazine in place of indoline in Step 1. LC-MS (ESI) m/z: 438 $[M+H]^+$. $^1$H NMR (400 MHz, $CD_3OD$): δ (ppm) 2.48 (s, 3H), 2.77 (t, J=6.0 Hz, 2H), 2.88 (t, J=6.0 Hz, 2H), 3.31 (s, 2H), 3.87 (s, 3H), 3.96 (t, J=4.4 Hz, 2H), 4.28 (t, J=4.4 Hz, 2H), 6.71 (s, 1H), 6.83-6.87 (m, 1H), 6.92-7.03 (m, 3H), 7.79 (s, 1H), 8.24 (s, 1H).

Example 8

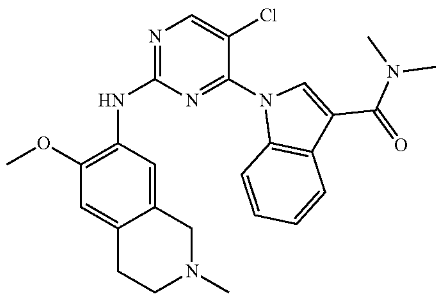

1-(5-Chloro-24(6-methoxy-2-methyl-1,2,3,4-tetrahydroisoquinolin-7-yl)amino)pyrimidin-4-yl)-N,N-dimethyl-1H-indole-3-carboxamide Step 1: Int. E2 (200 mg, 1.06 mmol) and 2,4,5-trichloropyrimidine (194.90 mg, 1.06 mmol) were used under Condition A2 (as exemplified in Step 1 of Example 4) to provide 1-(2,5-dichloropyrimidin-4-yl)-N,N-dimethyl-1H-indole-3-carboxamide as white solid (165 mg, 46% yield), after purification by flash column chromatography on silica gel (EA/PE=1/1, v/v). LC-MS (ESI) m/z: 335 $[M+H]^+$.

Step 2: To a solution of 1-(2,5-dichloropyrimidin-4-yl)-N,N-dimethyl-1H-indole-3-carboxamide (52 mg, 0.16 mmol) and Int. W1 (29.8 mg, 0.16 mmol) in isopropanol (2 mL) was added trifluoroacetic acid (53.1 mg, 0.48 mmol). The mixture was stirred under $N_2$ at 100° C. for 20 hours, cooled to room temperature, and purified by prep-HPLC (MeCN/0.1% HCOOH) to provide 1-(5-chloro-2-((6-methoxy-2-methyl-1,2,3,4-tetrahydroisoquinolin-7-yl) amino)pyrimidin-4-yl)-N,N-dimethyl-1H-indole-3-carboxamide as yellow solid (7.0 mg, 9% yield). LC-MS (ESI) m/z: 491 $[M+H]^+$. $^1$H NMR (400 MHz, $CD_3OD$): δ (ppm) 2.63 (s, 3H), 3.01-3.05 (m, 4H), 3.22 (s, 6H), 3.71 (s, 2H), 3.91 (s, 3H), 6.85 (s, 1H), 7.31-7.36 (m, 2H), 7.78-7.81 (m, 2H), 8.02 (s, 1H), 8.12 (s, 1H), 8.63 (s, 1H).

Example 9

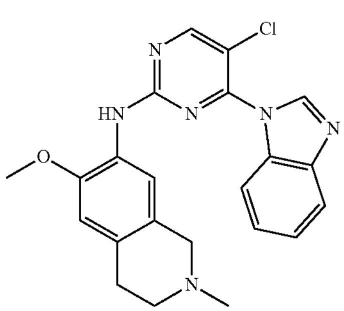 [SMILES: COc1cc2c(cc1Nc1ncc(Cl)c(-n3cnc4ccccc43)n1)CN(C)CC2]

N-(4-(1H-benzo[d]imidazol-1-yl)-5-chloropyrimidin-2-yl)-6-methoxy-2-methyl-1,2,3,4-tetrahydroisoquinolin-7-amine The same procedures as Example 8, using 1H-benzo[d] imidazole in place of Int. E2 in Step 1. LC-MS (ESI) m/z:

421 [M+H]+. $^1$H NMR (400 MHz, $CD_3OD$): δ 2.87 (s, 3H), 3.12 (t, J=6.8 Hz, 2H), 3.38 (t, J=6.8 Hz, 2H), 3.93 (s, 3H), 4.06 (s, 2H), 6.91 (s, 1H), 7.41-7.44 (m, 2H), 7.78-7.81 (m, 1H), 7.85-7.88 (m, 1H), 8.03 (s, 1H), 8.69 (s, 1H), 8.79 (s, 1H).

Example 10

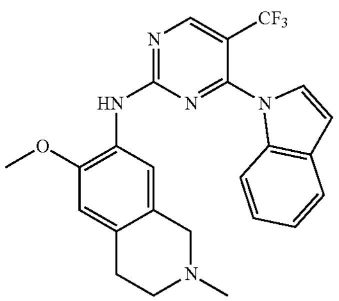

N-(4-(1H-indol-1-yl)-5-(trifluoromethyl)pyrimidin-2-yl)-6-methoxy-2-methyl-1,2,3,4-tetrahydroisoquinolin-7-amine Step 1: 1H-indole (349.9 mg, 3.0 mmol) and 2,4-dichloro-5-(trifluoromethyl)pyrimidine (650.9 mg, 3.0 mmol) were used under Condition A1 (as exemplified in Step 1 of Example 1) to provide 1-(2-chloro-5-(trifluoromethyl)pyrimidin-4-yl)-1H-indole as yellow solid (88 mg, 7% yield), after purification by prep-HPLC. LC-MS (ESI) m/z: 298 $[M+H]^+$.

Step 2: To a solution of 1-(2-chloro-5-(trifluoromethyl) pyrimidin-4-yl)-1H-indole (20 mg, 0.067 mmol) and Int. W1 (15.4 mg, 0.067 mmol) in isopropanol (3 mL) was added TsOH·$H_2O$ (11.6 mg, 0.067 mmol). The mixture was stirred at 100° C. overnight, cooled to room temperature, basified with saturated $NaHCO_3$ aqueous solution to pH~8, extracted with DCM (10 mL×3). The organic phases were dried over anhydrous $Na_2SO_4$ and filtered. The filtrate was concentrated in vacuo, and the residue was purified by flash column chromatography on silica gel (DCM/MeOH=10/1 v/v) to provide N-(4-(1H-indol-1-yl)-5-(trifluoromethyl)pyrimidin-2-yl)-6-methoxy-2-methyl-1,2,3,4-tetrahydroisoquinolin-7-amine as white solid (17 mg, 55% yield). LC-MS (ESI) m/z: 454 $[M+H]^+$. $^1$H NMR (400 MHz, $CD_3OD$): δ 2.56 (s, 3H), 2.96-2.99 (m, 4H), 3.60 (brs, 2H), 3.91 (s, 3H), 6.73 (d, J=3.6 Hz, 1H), 6.85 (s, 1H), 7.20-7.28 (m, 2H), 7.48 (d, J=2.8 Hz, 1H), 7.63 (d, J=8.4 Hz, 1H), 7.89 (d, J=8.0 Hz, 1H), 7.97 (s, 1H), 8.83 (s, 1H).

Example 11

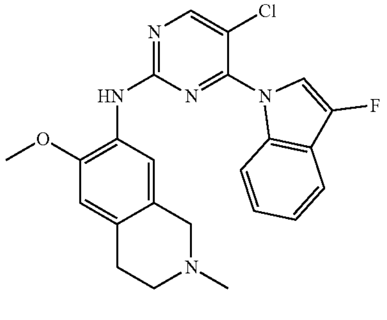 [SMILES: COc1cc2c(cc1Nc1ncc(Cl)c(-n3cc(F)c4ccccc43)n1)CN(C)CC2]

N-(5-Chloro-4-(3-fluoro-1H-indol-1-yl)pyrimidin-2-yl)-6-methoxy-2-methyl-1,2,3,4-tetrahydroisoquinolin-7-amine The same procedures as Example 10, using Int. E3 and 2,4,5-trichloropyrimidine in place of 1H-indole and 2,4-dichloro-5-(trifluoromethyl)pyrimidine in Step 1. LC-MS (ESI) m/z: 438 $[M+H]^+$. $^1$H NMR (400 MHz, DMSO-$d_6$) δ 8.79 (s, 1H), 8.63 (s, 1H), 7.91 (d, J=2.4 Hz, 1H), 7.83 (d, J=6.8 Hz, 1H), 7.64 (dd, J=6.0, 2.4 Hz, 1H), 7.37 (s, 1H), 7.33-7.17 (m, 2H), 6.73 (d, J=55.3 Hz, 1H), 3.96-3.68 (m, 3H), 3.33 (s, 2H), 2.79 (t, J=5.6 Hz, 2H), 2.55 (t, J=5.9 Hz, 2H), 2.30 (s, 3H).

Example 80

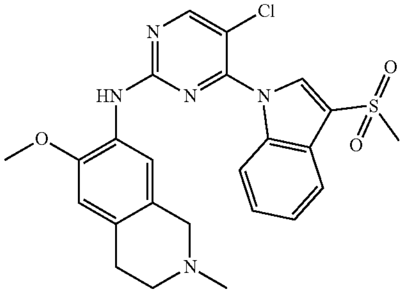

N-(5-chloro-4-(3-(methylsulfonyl)-1H-indol-1-yl) pyrimidin-2-yl)-6-methoxy-2-methyl-1,2,3,4-tetrahydroisoquinolin-7-amine The same procedures as Example 10, using Int. E8 and 2,4,5-trichloropyrimidine in place of 1H-indole and 2,4-dichloro-5-(trifluoromethyl)pyrimidine in Step 1. LC-MS (ESI) m/z: 498 $[M+H]^+$. $^1$H NMR (500 MHz, DMSO-$d_6$) δ 9.00 (s, 1H), 8.74 (s, 1H), 8.42 (s, 1H), 7.94-7.85 (m, 1H), 7.79-7.72 (m, 1H), 7.41 (dd, J=6.1, 3.1 Hz, 2H), 7.33 (s, 1H), 6.79 (s, 1H), 3.79 (s, 3H), 3.34 (s, 2H), 3.30 (s, 3H), 2.77 (d, J=5.8 Hz, 2H), 2.54 (d, J=5.7 Hz, 2H), 2.30 (s, 3H).

Example 81

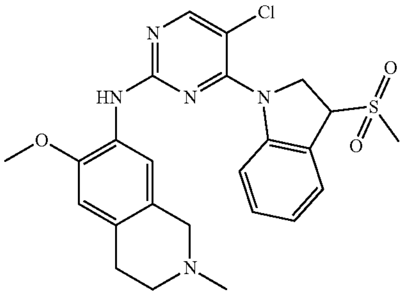

N-(5-chloro-4-(3-(methylsulfonyl)indolin-1-yl)pyrimidin-2-yl)-6-methoxy-2-methyl-1,2,3,4-tetrahydroisoquinolin-7-amine The same procedures as Example 10, using Int. E9 and 2,4,5-trichloropyrimidine in place of 1H-indole and 2,4- dichloro-5-(trifluoromethyl)pyrimidine in Step 1. LC-MS (ESI) m/z: 500 $[M+H]^+$. $^1H$ NMR (500 MHz, DMSO-$d_6$) δ 8.31 (s, 1H), 8.12 (s, 1H), 7.49 (d, J=6.9 Hz, 2H), 7.41 (d, J=8.1 Hz, 1H), 7.27 (t, J=7.7 Hz, 1H), 7.06 (t, J=7.3 Hz, 1H), 6.75 (s, 1H), 5.06 (d, J=7.5 Hz, 1H), 4.72 (dd, J=12.4, 9.5 Hz, 1H), 4.58 (dd, J=12.5, 2.6 Hz, 1H), 3.77 (s, 3H), 3.28-3.21 (m, 2H), 2.89 (s, 3H), 2.77 (d, J=5.5 Hz, 2H), 2.55 (t, J=5.7 Hz, 2H), 2.30 (s, 3H).

Example 82

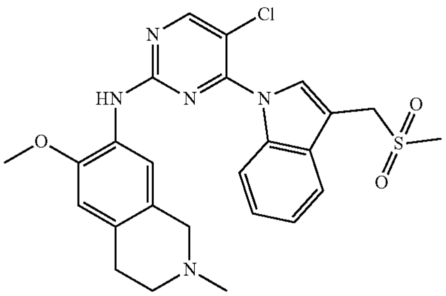

N-(5-chloro-4-(3-((methylsulfonyl)methyl)-1H-indol-1-yl)pyrimidin-2-yl)-6-methoxy-2-methyl-1,2,3,4-tetrahydroisoquinolin-7-amine The same procedures as Example 10, using Int. E11 and 2,4,5-trichloropyrimidine in place of 1H-indole and 2,4-dichloro-5-(trifluoromethyl)pyrimidine in Step 1. LC-MS (ESI) m/z: 512 $[M+H]^+$.

NMR (400 MHz, DMSO-$d_6$) δ 8.78 (s, 1H), 8.66 (s, 1H), 7.98 (s, 1H), 7.80 (s, 2H), 7.42 (s, 1H), 7.25 (dd, J=6.0, 3.1 Hz, 2H), 6.80 (s, 1H), 4.71 (s, 2H), 3.79 (s, 3H), 3.33 (s, 2H), 2.95 (s, 3H), 2.78 (s, 2H), 2.55 (d, J=5.6 Hz, 2H), 2.30 (s, 3H).

Example 83

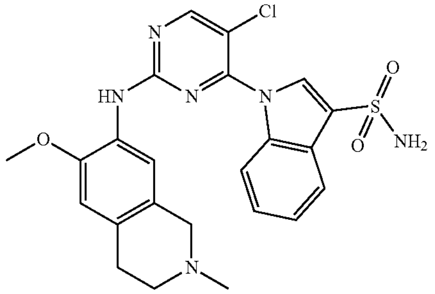 [SMILES: COc1cc2c(cc1Nc1ncc(Cl)c(-n3cc(S(N)(=O)=O)c4ccccc43)n1)CN(C)CC2]

1-(5-Chloro-2-((6-methoxy-2-methyl-1,2,3,4-tetrahydroisoquinolin-7-yl)amino)pyrimidin-4-yl)-1H-indole-3-sulfonamide The same procedures as Example 10, using Int. E15 and 2,4,5-trichloropyrimidine in place of 1H-indole and 2,4-dichloro-5-(trifluoromethyl)pyrimidine in Step 1. LC-MS (ESI) m/z: 499 $[M+H]^+$. $^1H$ NMR (400 MHz, DMSO-$d_6$) δ 8.69 (d, J=20.3 Hz, 1H), 8.47 (s, 1H), 7.96 (s, 1H), 7.71 (dd, J=5.7, 3.1 Hz, 1H), 7.53 (dd, J=6.1, 3.1 Hz, 1H), 7.16 (s, 2H), 7.12 (dd, J=6.8, 3.7 Hz, 3H), 6.56 (s, 1H), 3.55 (s, 3H), 3.24 (s, 2H), 2.54 (s, 2H), 2.31 (d, J=5.7 Hz, 2H), 2.07 (d, J=14.9 Hz, 3H).

Example 14

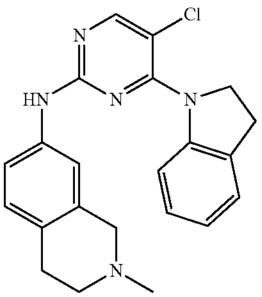 [SMILES: CN1CCc2ccc(Nc3ncc(Cl)c(N4CCc5ccccc54)n3)cc2C1]

N-(5-Chloro-4-(indolin-1-yl)pyrimidin-2-yl)-2-methyl-1,2,3,4-tetrahydroisoquinolin-7-amine Int. W2 (36.58 mg, 0.23 mmol) and 1-(2,5-dichloropyrimidin-4-yl)indoline (60 mg, 0.23 mmol) were used under Condition B3 to provide N-(5-chloro-4-(indolin-1-yl)pyrimidin-2-yl)-2-methyl-1,2,3,4-tetrahydroisoquinolin-7-amine as yellow solid (10.4 mg, 12% yield), after purification by prep-HPLC. LC-MS (ESI) m/z: 392 $[M+H]^+$. $^1H$ NMR (400 MHz, $CD_3OD$): δ 2.51 (s, 3H), 2.83-2.93 (m, 4H), 3.17 (t, J=8.0 Hz, 2H), 3.57 (s, 2H), 4.33 (t, J=8.0 Hz, 2H), 6.93-7.02 (m, 2H), 7.12 (t, J=3.6 Hz, 1H), 7.24-7.32 (m, 2H), 7.42 (d, J=8.0 Hz, 1H), 7.52 (d, J=8.0 Hz, 1H), 8.14 (s, 1H).

Example 15

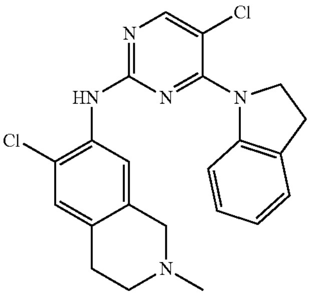 [SMILES: CN1CCc2cc(Cl)c(Nc3ncc(Cl)c(N4CCc5ccccc54)n3)cc2C1]

6-Chloro-N-(5-chloro-4-(indolin-1-yl)pyrimidin-2-yl)-2-methyl-1,2,3,4-tetrahydroisoquinolin-7-amine Int. W3 (50 mg, 0.25 mmol) and 1-(2,5-dichloropyrimidin-4-yl)indoline (67.66 mg, 0.25 mmol) were used under Condition B3 to provide 6-chloro-N-(5-chloro-4-(indolin-1-yl)pyrimidin-2-yl)-2-methyl-1,2,3,4-tetrahydroisoquinolin-7-amine as yellow solid (11.6 mg, 11% yield), after purification by prep-HPLC. LC-MS (ESI) m/z: 426 $[M+H]^+$. $^1H$ NMR (400 MHz, $CD_3OD$): δ 2.54 (s, 3H), 2.89-2.96 (m, 4H), 3.18 (t, J=8.0 Hz, 2H), 3.54 (s, 2H), 4.36 (t, J=8.0 Hz, 2H), 6.96-7.00 (m, 1H), 7.11 (t, J=8.0 Hz, 1H), 7.24-7.28 (m, 2H), 7.40 (d, J=8.0 Hz, 1H), 7.93 (s, 1H), 8.19 (s, 1H).

Example 19

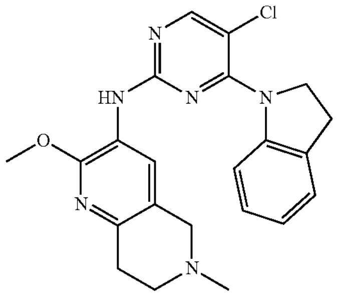 [SMILES: COc1nc2c(cc1Nc1ncc(Cl)c(N3CCc4ccccc43)n1)CN(C)CC2]

N-(5-chloro-4-(indolin-1-yl)pyrimidin-2-yl)-2-methoxy-6-methyl-5,6,7,8-tetrahydro-1,6-naphthyridin-3-amine Int. W4 (30 mg, 155.24 umol) and 1-(2,5-dichloropyrimidin-4-yl)indoline (41.31 mg, 155.24 umol) were used under Condition B3 (microwave for 2 hours) to provide N-(5-chloro-4-(indolin-1-yl)pyrimidin-2-yl)-2-methoxy-6-methyl-5,6,7,8-tetrahydro-1,6-naphthyridin-3-amine (TFA salt) as yellow solid (6.6 mg, 10% yield), after purification by flash column chromatography (DCM/MeOH=10/1, v/v) and prep-HPLC (MeCN/0.05% TFA). LC-MS (ESI) m/z: 423 $[M+H]^+$. $^1H$ NMR (400 MHz, $CD_3OD$): δ 3.03 (s, 3H), 3.08-3.22 (m, 4H), 3.44-3.56 (m, 1H), 3.73-3.83 (m, 1H), 4.02 (s, 3H), 4.16 (d, J=6.4 Hz, 2H), 4.38 (t, J=8.0 Hz, 2H), 7.06 (t, J=7.6 Hz, 1H), 7.20 (t, J=7.4 Hz, 1H), 7.31 (d, J=8.0 Hz, 1H), 7.42 (d, J=8.0 Hz, 1H), 8.25 (s, 1H), 8.34 (s, 1H).

Example 22

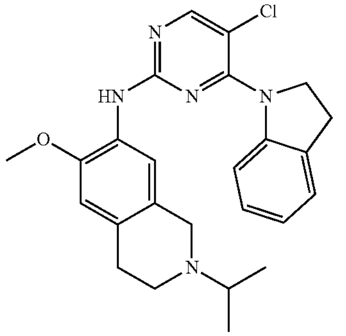 [SMILES: COc1cc2c(cc1Nc1ncc(Cl)c(N3CCc4ccccc43)n1)CN(C(C)C)CC2]

N-(5-chloro-4-(indolin-1-yl)pyrimidin-2-yl)-2-isopropyl-6-methoxy-1,2,3,4-tetrahydroisoquinolin-7-amine Int. W5 (50 mg, 0.227 mmol) and 1-(2,5-dichloropyrimidin-4-yl)indoline (60 mg, 0.227 mmol) were used under Condition B3 (microwave for 2 hours) to provide N-(5-chloro-4-(indolin-1-yl)pyrimidin-2-yl)-2-isopropyl-6-methoxy-1,2,3,4-tetrahydroisoquinolin-7-amine as yellow solid (2.5 mg, 2% yield), after purification by flash column chromatography (DCM/MeOH=10/1, v/v). LC-MS (ESI) m/z: 450 $[M+H]^+$. $^1H$ NMR (400 MHz, $CD_3OD$): δ 1.17 (d, J=6.4 Hz, 6H), 2.86-2.92 (m, 5H), 3.19 (t, J=8.4 Hz, 2H), 3.49 (s, 2H), 3.88 (s, 3H), 4.36 (t, J=8.4 Hz, 2H), 6.73 (s, 1H), 6.99 (t, J=6.8 Hz, 1H), 7.17 (t, J=7.6 Hz, 1H), 7.29 (d, J=7.2 Hz, 1H), 7.50 (d, J=8.0 Hz, 1H), 7.99 (s, 1H), 8.16 (s, 1H).

Example 23

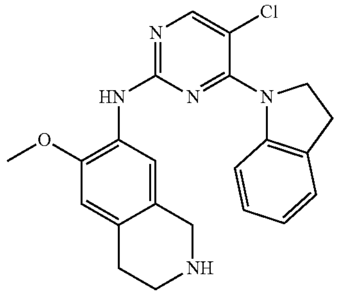 [SMILES: COc1cc2c(cc1Nc1ncc(Cl)c(N3CCc4ccccc43)n1)CNCC2]

N-(5-chloro-4-(indolin-1-yl)pyrimidin-2-yl)-6-methoxy-1,2,3,4-tetrahydroisoquinolin-7-amine Int. W6 (110 mg, 0.39 mmol) and 1-(2,5-dichloropyrimidin-4-yl)indoline (105 mg, 0.39 mmol) were used under Condition B3 (microwave for 2 hours) to provide N-(5-chloro-4-(indolin-1-yl)pyrimidin-2-yl)-6-methoxy-1,2,3,4-tetrahydroisoquinolin-7-amine (1.0 TsOH salt) as yellow solid (130 mg, 58% yield). The solid was collected by filtration. LC-MS (ESI) m/z: 408 $[M+H]^+$. $^1H$ NMR (400 MHz, DMSO-$d_6$): δ 2.29 (s, 3H), 2.98 (t, J=6.4 Hz, 2H), 3.16 (t, J=8.0 Hz, 2H), 3.28-3.40 (m, 2H), 3.82 (s, 3H), 4.04 (d, J=4.6 Hz, 2H), 4.37 (t, J=8.0 Hz, 2H), 6.95 (s, 1H), 7.02 (dd, J=7.4, 1.0 Hz, 1H), 7.07-7.20 (m, 3H), 7.30 (dd, J=7.4, 1.0 Hz, 1H), 7.46-7.48 (m, 3H), 7.65 (s, 1H), 8.34 (s, 1H), 8.72 (s, 1H), 9.26 (s, 2H).

Example 26

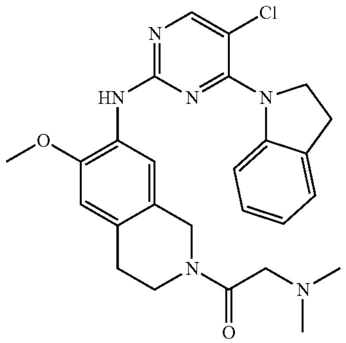

1-(74(5-Chloro-4-(indolin-1-yl)pyrimidin-2-yl)amino)-6-methoxy-3,4-dihydroisoquinolin-2(1H)-yl)-2-(dimethylamino)ethan-1-one To a solution of 2-(dimethylamino)acetic acid (5.06 mg, 49.03 umol), N-(5-chloro-4-indolin-1-yl-pyrimidin-2-yl)-6- methoxy-1,2,3,4-tetrahydroisoquinolin-7-amine tosylate (20 mg, 34.48 umol), and HATU (18.64 mg, 49.03 umol) in dry $CH_2Cl_2$ (3 mL) was added dropwise DIPEA (19.01 mg, 147.10 umol, 25.62 uL) at 0° C. The reaction mixture was stirred at room temperature for 3 hours and concentrated in vacuo. The residue was purified by prep-HPLC (MeCN/0.1% HCOOH) to provide 1-(7-((5-chloro-4-(indolin-1-yl)pyrimidin-2-yl)amino)-6-methoxy-3,4-dihydroisoquinolin-2(1H)-yl)-2-(dimethylamino)ethan-1-one as white solid (13.5 mg, 56% yield). LC-MS (ESI) m/z: 493 $[M+H]^+$. $^1H$ NMR (400 MHz, $CD_3OD$): δ 2.57 (s, 3H), 2.62 (s, 3H), 2.75 (t, J=6.4 Hz, 1H), 2.86 (t, J=6.4 Hz, 1H), 3.14 (t, J=8.4 Hz, 2H), 3.54 (s, 1H), 3.64-3.69 (m, 2H), 3.71 (s, 1H), 3.88 (d, J=6.4 Hz, 3H), 4.30 (s, 1H), 4.32-4.36 (m, 2H), 4.42 (s, 1H), 6.75 (s, 1H), 6.98-7.04 (m, 1H), 7.16 (t, J=8.0 Hz, 1H), 7.24-7.29 (m, 1H), 7.39-7.46 (m, 1H), 8.01 (d, J=17.2 Hz, 1H), 8.15 (d, J=9.6 Hz, 1H).

Example 27

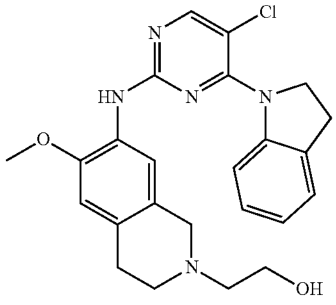 [SMILES: COc1cc2c(cc1Nc1ncc(Cl)c(N3CCc4ccccc43)n1)CN(CCO)CC2]

2-(74(5-Chloro-4-(indolin-1-yl)pyrimidin-2-yl)amino)-6-methoxy-3,4-dihydroisoquinolin-2(1H)-yl)ethan-1-ol A mixture of N-(5-chloro-4-(indolin-1-yl)pyrimidin-2-yl)-6-methoxy-1,2,3,4-tetrahydroisoquinolin-7-amine tosylate (30 mg, 0.073 mmol), 2-((tert-butyldimethylsilyl)oxy)acetaldehyde (13 mg, 0.073 mmol), and AcOH (2 drops) in MeOH (4 mL) was stirred at under $N_2$ for 1 hours. Then $NaBH(OAc)_3$ (24 mg, 011 mmol) was added to the above mixture and the mixture was stirred at room temperature for 16 hours, and concentrated in vacuo. The residue was purified by flash column chromatography on silica gel (DCM 100% v/v, and then DCM/MeOH=5/1 v/v) to provide 2-(7-((5-chloro-4-(indolin-1-yl)pyrimidin-2-yl)amino)-6-methoxy-3,4-dihydroisoquinolin-2(1H)-yl)ethan-1-ol as yellow solid (6.4 mg, 20% yield). LC-MS (ESI) m/z: 452 $[M+H]^+$. $^1H$ NMR (400 MHz, $CD_3OD$): δ 2.72 (t, J=6.4 Hz, 2H), 2.86-2.91 (m, 4H), 3.19 (t, J=8.4 Hz, 2H), 3.47 (s, 2H), 3.77 (t, J=6.4 Hz, 2H), 3.88 (s, 3H), 4.35 (t, J=8.4 Hz, 2H), 6.73 (s, 1H), 7.02 (t, J=7.6 Hz, 1H), 7.18 (t, J=8.0 Hz, 1H), 7.29 (d, J=7.6 Hz, 1H), 7.46 (d, J=8.0 Hz, 1H), 7.96 (s, 1H), 8.16 (s, 1H).

Example 28

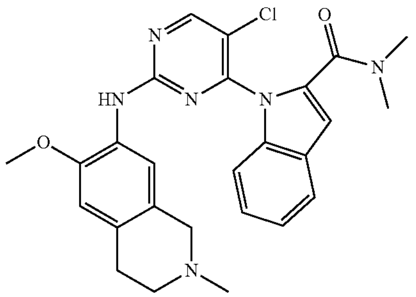

1-(5-Chloro-24(6-methoxy-2-methyl-1,2,3,4-tetrahydroisoquinolin-7-yl)amino)pyrimidin-4-yl)-N,N-dimethyl-1H-indole-2-carboxamide Step 1: Int. E4 (673 mg, 3.58 mmol) and 2,4,5-trichloropyrimidine (787 mg, 4.29 mmol) were used under Condition A1 (as exemplified in Step 1 of Example 1) to provide 1-(2,5-dichloropyrimidin-4-yl)-N,N-dimethyl-indole-2-carboxamide as white solid (160 mg, 22% yield), after purification by flash column chromatography on silica gel (EA/PE=1/3, v/v) and prep-HPLC. LC-MS (ESI) m/z: 335. $[M+H]^+$.

Step 2: To a solution of 1-(2,5-dichloropyrimidin-4-yl)-N,N-dimethyl-indole-2-carboxamide (50 mg, 0.15 mmol) in dioxane (4 mL) were added Int. W1 (28.7 mg, 0.15 mmol), $Pd_2(dba)_3$ (27.3 mg, 0.03 mmol), Xantphos (17.3 mg, 0.03 mmol), and potassium carbonate (41.2 mg, 0.3 mmol). The mixture was stirred at 100° C. under $N_2$ for 12 hours, cooled down to room temperature, and filtered. The filtrated was concentrated, and the residue was purified with prep-HPLC (MeCN/0.1% HCOOH) to provide 1-(5-chloro-2-((6-methoxy-2-methyl-1,2,3,4-tetrahydroisoquinolin-7-yl)amino)pyrimidin-4-yl)-N,N-dimethyl-1H-indole-2-carboxamide as yellow solid (2.4 mg, 3% yield)[HCOOH salt]. LC-MS (ESI) m/z: 491 $[M+H]^+$. $^1H$ NMR (400 MHz, $CD_3OD$): δ 2.71 (s, 3H), 2.99 (s, 3H), 3.02-3.05 (m, 2H), 3.14-3.17 (m, 2H), 3.30 (s, 3H), 3.88 (s, 2H), 3.91 (s, 3H), 6.85 (s, 1H), 7.10 (s, 1H), 7.26 (t, J=8.0 Hz, 1H), 7.35 (t, J=8.0 Hz, 1H), 7.49 (d, J=8.0 Hz, 1H), 7.73 (d, J=8.0 Hz, 1H), 8.02 (s, 1H), 8.50 (brs, 1H), 8.57 (s, 1H).

Example 12

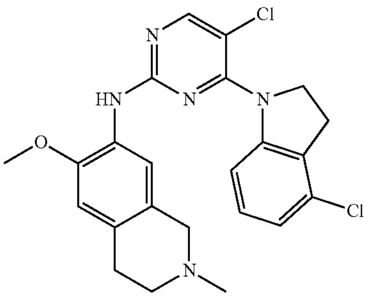 [SMILES: COc1cc2c(cc1Nc1ncc(Cl)c(N3CCc4c(Cl)cccc43)n1)CN(C)CC2]

N-(5-chloro-4-(4-chloroindolin-1-yl)pyrimidin-2-yl)-6-methoxy-2-methyl-1,2,3,4-tetrahydroisoquinolin-7-amine Step 1: 4-Chloroindoline (111 mg, 1.06 mmol) and 2,4,5-trichloropyrimidine (200 mg, 1.09 mmol) were used under Condition A2 (as exemplified in Step 1 of Example 4) to provide 4-chloro-1-(2,5-dichloropyrimidin-4-yl)indoline as white solid (160 mg, 59% yield), after purification by flash column chromatography on silica gel (EA/PE=20/1, v/v). LC-MS (ESI) m/z: 300 $[M+H]^+$.

Step 2: Int. W1 (68.5 mg, 299.43 umol) and 4-chloro-1-(2,5-dichloropyrimidin-4-yl)indoline (90 mg, 299.43 umol) were used under Condition B3 (as exemplified in Step 2 of Example 10) to provide N-(5-chloro-4-(4-chloroindolin-1-yl)pyrimidin-2-yl)-6-methoxy-2-methyl-1,2,3,4-tetrahydroisoquinolin-7-amine (TsOH salt) as yellow solid (115 mg, 84% yield). The solid was collected by filtration. LC-MS (ESI) m/z: 456 $[M+H]^+$. $^1H$ NMR (400 MHz, $CD_3OD$): δ 2.35 (s, 3H), 3.02 (s, 3H), 3.05-3.16 (m, 1H), 3.16-3.30 (m, 3H), 3.41-3.45 (m, 1H), 3.74-3.77 (m, 1H), 3.87 (s, 3H), 4.13-4.17 (m, 1H), 4.32-4.35 (m, 1H), 4.67 (t, J=8.4 Hz, 2H), 7.04 (s, 1H), 7.13-7.21 (m, 4H), 7.49 (s, 1H), 7.65-7.67 (m, 3H), 8.21 (s, 1H).

Example 13

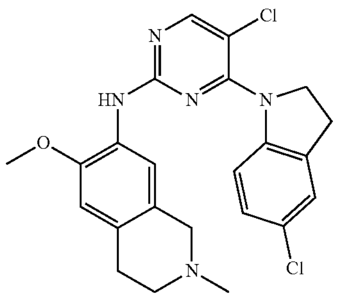 [SMILES: COc1cc2c(cc1Nc1ncc(Cl)c(N3CCc4cc(Cl)ccc43)n1)CN(C)CC2]

N-(5-chloro-4-(5-chloroindolin-1-yl)pyrimidin-2-yl)-6-methoxy-2-methyl-1,2,3,4-tetrahydroisoquinolin-7-amine The same procedures as Example 12, using 5-chloroindoline and in place of 4-chloroindoline in Step 1. LC-MS (ESI) m/z: 456 $[M+H]^+$. $^1H$ NMR (400 MHz, $CD_3OD$): δ 2.35 (s, 3H), 3.04 (s, 3H), 3.17-3.29 (m, 4H), 3.41-3.48 (m, 1H), 3.75-3.79 (m, 1H), 3.88 (s, 3H), 4.13-4.16 (m, 1H), 4.27-4.31 (m, 1H), 4.64 (t, J=8.0 Hz, 2H), 7.04 (s, 1H), 7.16-7.21 (m, 3H), 7.38 (brs, 1H), 7.53 (s, 1H), 7.65-7.72 (m, 3H), 8.20 (s, 1H).

Example 18

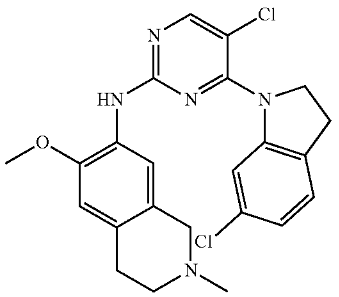 [SMILES: COc1cc2c(cc1Nc1ncc(Cl)c(N3CCc4ccc(Cl)cc43)n1)CN(C)CC2]

N-(5-chloro-4-(6-chloroindolin-1-yl)pyrimidin-2-yl)-6-methoxy-2-methyl-1,2,3,4-tetrahydroisoquinolin-7-amine The same procedures as Example 12, using 6-chloroindoline and in place of 4-chloroindoline in Step 1. LC-MS (ESI) m/z: 456 $[M+H]^+$. $^1H$ NMR (400 MHz, $CD_3OD$): δ 2.35 (s, 0.45H), 3.01 (s, 3H), 3.13-3.20 (m, 4H), 3.35-3.40 (m, 1H), 3.73-3.77 (m, 1H), 3.90 (s, 3H), 4.10-4.14 (m, 1H), 4.31-4.35 (m, 1H), 4.59 (t, J=8.4 Hz, 2H), 7.02 (s, 1H), 7.09-7.12 (m, 1H), 7.21 (d, J=8.0 Hz, 0.3H), 7.29 (d, J=8.0 Hz, 1H), 7.6-7.69 (m, 2.3H), 8.24 (s, 1H).

Example 16

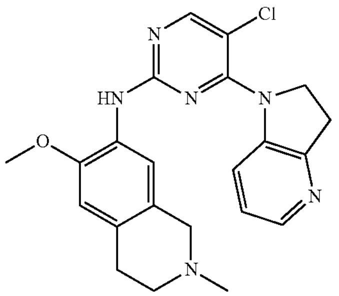 [SMILES: COc1cc2c(cc1Nc1ncc(Cl)c(N3CCc4ncccc43)n1)CN(C)CC2]

N-(5-chloro-4-(2,3-dihydro-1H-pyrrolo[3,2-b]pyridin-1-yl)pyrimidin-2-yl)-6-methoxy-2-methyl-1,2,3,4-tetrahydroisoquinolin-7-amine The same procedures as Example 12, using 2,3-dihydro-1H-pyrrolo[3,2-b]pyridine hydrochloride and in place of 4-chloroindoline in Step 1. LC-MS (ESI) m/z: 423 $[M+H]^+$. $^1H$ NMR (400 MHz, DMSO-$d_6$): δ 2.39 (s, 3H), 2.67 (brs, 2H), 2.81-2.84 (m, 2H), 3.21 (t, J=8.4 Hz, 2H), 3.41 (s, 2H), 3.76 (s, 3H), 4.36 (t, J=8.4 Hz, 2H), 6.79 (s, 1H), 6.99-7.02 (m, 1H), 7.41 (s, 1H), 7.65 (d, J=8.0 Hz, 1H), 8.03 (dd, J=5.2, 1.2 Hz, 1H), 8.17 (s, 1H), 8.25 (s, 1H).

Example 29

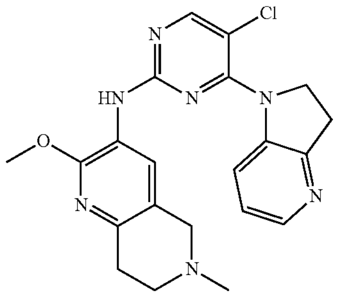 [SMILES: COc1nc2c(cc1Nc1ncc(Cl)c(N3CCc4ncccc43)n1)CN(C)CC2]

N-(5-Chloro-4-(2,3-dihydro-1H-pyrrolo[3,2-b]pyridin-1-yl)pyrimidin-2-yl)-2-methoxy-6-methyl-5,6,7,8-tetrahydro-1,6-naphthyridin-3-amine The same procedure as Step 2 of Example 28, using 1-(2,5-dichloropyrimidin-4-yl)-2,3-dihydropyrrolo[3,2-b]pyridine and Int. W4 in place of 1-(2,5-dichloropyrimidin-4-yl)-N,N-dimethyl-indole-2-carboxamide and Int. W1. LC-MS (ESI) m/z: 424 $[M+H]^+$. $^1$H NMR (400 MHz, $CD_3OD$): δ 2.51 (s, 3H), 2.89-2.92 (m, 4H), 3.27-3.34 (m, 2H), 3.47 (s, 2H), 3.97 (s, 3H), 4.45 (t, J=8.8 Hz, 2H), 7.16-7.19 (m, 1H), 7.76 (dd, J=8.0, 0.8 Hz, 1H), 8.05 (dd, J=4.8, 1.2 Hz, 1H), 8.09 (s, 1H), 8.25 (s, 1H), 8.51 (br, 1H).

Example 17

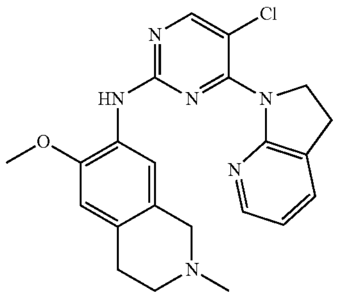 [SMILES: COc1cc2c(cc1Nc1ncc(Cl)c(N3CCc4cccnc43)n1)CN(C)CC2]

N-(5-chloro-4-(2,3-dihydro-1H-pyrrolo[2,3-b]pyridin-1-yl)pyrimidin-2-yl)-6-methoxy-2-methyl-1,2,3,4-tetrahydroisoquinolin-7-amine The same procedures as Example 12, using 2,3-dihydro-1H-pyrrolo[2,3-b]pyridine and in place of 4-chloroindoline in Step 1. LC-MS (ESI) m/z: 423 $[M+H]^+$. $^1$H NMR (400 MHz, $CD_3OD$): δ 2.44 (s, 3H), 2.71-2.74 (m, 2H), 2.87-2.91 (m, 2H), 3.21 (t, J=8.0 Hz, 2H), 3.47 (s, 2H), 3.87 (s, 3H), 4.25 (t, J=8.4 Hz, 2H), 6.73 (s, 1H), 6.89-6.92 (m, 1H), 7.61 (dd, J=7.2, 1.6 Hz, 1H), 8.00 (s, 2H), 8.30 (s, 1H).

Example 20

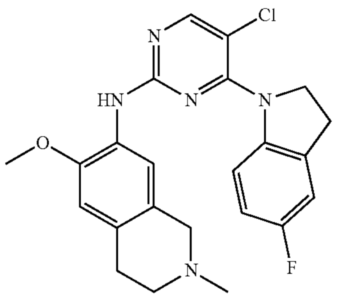 [SMILES: COc1cc2c(cc1Nc1ncc(Cl)c(N3CCc4cc(F)ccc43)n1)CN(C)CC2]

N-(5-chloro-4-(5-fluoroindolin-1-yl)pyrimidin-2-yl)-6-methoxy-2-methyl-1,2,3,4-tetrahydroisoquinolin-7-amine The same procedures as Example 12, using 5-fluoroindoline and in place of 4-chloroindoline in Step 1. LC-MS (ESI) m/z: 440 $[M+H]^+$. $^1$H NMR (400 MHz, $CD_3OD$): δ 2.35 (s, 1.5H), 2.79 (s, 3H), 3.06 (t, J=6.0 Hz, 2H), 3.19 (t, J=8.4 Hz, 2H), 3.25 (t, J=6.0 Hz, 2H), 3.84 (s, 2H), 3.90 (s, 3H), 4.38 (t, J=8.4 Hz, 2H), 6.82 (s, 1H), 6.90-6.95 (m, 1H), 7.06 (dd, J=8.4, 2.4 Hz, 1H), 7.20 (d, J=8.4 Hz, 1H), 7.38-7.41 (m, 1H), 7.67 (d, J=8.4 Hz, 1H), 7.98 (s, 1H), 8.18 (s, 1H).

Example 21

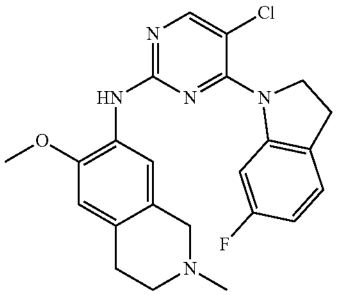 [SMILES: COc1cc2c(cc1Nc1ncc(Cl)c(N3CCc4ccc(F)cc43)n1)CN(C)CC2]

N-(5-chloro-4-(6-fluoroindolin-1-yl)pyrimidin-2-yl)-6-methoxy-2-methyl-1,2,3,4-tetrahydroisoquinolin-7-amine The same procedures as Example 12, using 6-fluoroindoline and in place of 4-chloroindoline in Step 1. LC-MS (ESI) m/z: 440 $[M+H]^+$. $^1$H NMR (400 MHz, $CD_3OD$): δ 2.35 (s, 0.24H), 3.04 (s, 3H), 3.20 (m, 3H), 3.35-3.45 (m, 2H), 3.75-3.80 (m, 1H), 3.87 (s, 3H), 4.17 (d, J=14.8 Hz, 1H), 4.42 (d, J=14.8 Hz, 1H), 4.70 (t, J=7.6 Hz, 2H), 6.87-6.92 (m, 1H), 7.06 (s, 1H), 7.21 (d, J=8.0 Hz, 0.2H), 7.28-7.32 (m, 1H), 7.42 (s, 1H), 7.42-7.46 (m, 1H), 7.67 (d, J=8.4 Hz, 0.16H), 8.22 (s, 1H).

Example 24

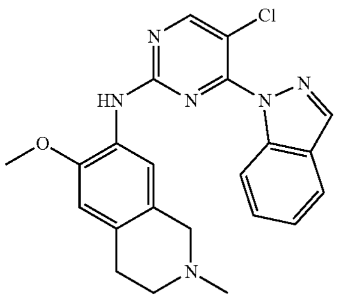 [SMILES: COc1cc2c(cc1Nc1ncc(Cl)c(-n3ncc4ccccc43)n1)CN(C)CC2]

N-(5-Chloro-4-(1H-indazol-1-yl)pyrimidin-2-yl)-6-methoxy-2-methyl-1,2,3,4-tetrahydroisoquinolin-7-amine The same procedures as Example 12, using 1H-indazole and in place of 4-chloroindoline in Step 1. LC-MS (ESI) m/z: 421 $[M+H]^+$. $^1H$ NMR (400 MHz, DMSO-$d_6$) δ 8.88 (s, 1H), 8.61 (s, 1H), 8.50 (s, 1H), 8.23 (s, 1H), 8.07 (d, J=7.9 Hz, 1H), 7.89 (d, J=7.9 Hz, 1H), 7.48-7.39 (m, 1H), 7.35 (dd, J=8.9, 5.9 Hz, 2H), 6.84 (s, 1H), 3.77 (s, 3H), 3.37-3.37 (m, 2H), 2.83 (t, J=5.8 Hz, 2H), 2.59 (t, J=5.7 Hz, 2H), 2.30 (d, J=13.4 Hz, 3H).

Example 25

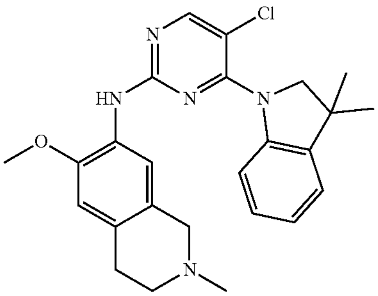

N-(5-Chloro-4-(3,3-dimethylindolin-1-yl)pyrimidin-2-yl)-6-methoxy-2-methyl-1,2,3,4-tetrahydroisoquinolin-7-amine Step 1: To a solution of 3,3-dimethylindoline (200 mg, 1.36 mmol) in n-butanol (2 mL) were added 2,4,5-trichloropyrimidine (250 mg, 1.36 mmol) and DIPEA (175.6 mg, 1.36 mmol) subsequently. The reaction mixture was stirred at 100° C. for 18 hours, diluted with water (5 mL), and extracted with EA (10 mL×3). The organic phases were dried over anhydrous sodium sulfate and filtered. The filtrate was concentrated in vacuo, and the residue was purified by flash column chromatography on silica gel (EA/PE=1/10, v/v) to provide 1-(2,5-dichloropyrimidin-4-yl)-3,3-dimethyl-indoline (385 mg, 94.41% yield) as white solid. LC-MS (ESI) m/z: 296 $[M+H]^+$.

Step 2: Int. W1 (86 mg, 0.323 mmol) and 1-(2,5-dichloropyrimidin-4-yl)-3,3-dimethyl-indoline (100 mg, 0.323 mmol) were used under Condition B3 (as exemplified in Step 2 of Example 10) to provide N-(5-chloro-4-(3,3-dimethylindolin-1-yl)pyrimidin-2-yl)-6-methoxy-2-methyl-1,2,3,4-tetrahydroisoquinolin-7-amine (85.5 mg, 58.84% yield) as white solid, after purification by prep-HPLC (MeCN/10 mM $NH_4HCO_3$, 0.025% $NH_3{\cdot}H_2O$). LC-MS (ESI) m/z: 450 $[M+H]^+$. $^1H$ NMR (400 MHz, DMSO-$d_6$) δ 8.25 (s, 1H), 7.98 (s, 1H), 7.56 (s, 1H), 7.33 (d, J=7.9 Hz, 1H), 7.24 (d, J=6.5 Hz, 1H), 7.14-7.05 (m, 1H), 6.98 (dd, J=7.8, 7.0 Hz, 1H), 6.74 (s, 1H), 4.00 (s, 2H), 3.77 (s, 3H), 3.28 (s, 2H), 2.77 (t, J=5.7 Hz, 2H), 2.55 (t, J=5.8 Hz, 2H), 2.30 (s, 3H), 1.29 (s, 6H).

Example 84

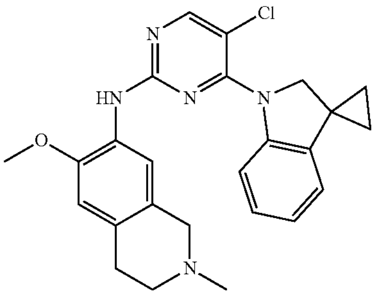 [SMILES: COc1cc2c(cc1Nc1ncc(Cl)c(N3CC4(CC4)c4ccccc43)n1)CN(C)CC2]

N-(5-chloro-4-(spiro[cyclopropane-1,3'-indolin]-1'-yl)pyrimidin-2-yl)-6-methoxy-2-methyl-1,2,3,4-tetrahydroisoquinolin-7-amine The same procedures as Example 25, using 3,3-spiro[cyclopropane-1,3'-indoline] hydrochloride in place of 3,3-dimethylindoline in Step 1. LC-MS (ESI) m/z: 440 $[M+H]^+$. $^1H$ NMR (400 MHz, DMSO-$d_6$) δ 8.24 (s, 1H), 8.01 (s, 1H), 7.51 (s, 1H), 7.41 (d, J=8.0 Hz, 1H), 7.08-6.97 (m, 1H), 6.94-6.86 (m, 1H), 6.85-6.68 (m, 2H), 4.28 (s, 2H), 3.78 (s, 3H), 3.27 (s, 2H), 2.77 (t, J=5.7 Hz, 2H), 2.55 (t, J=5.9 Hz, 2H), 2.30 (s, 3H), 1.15-1.06 (m, 2H), 1.03 (dd, J=6.6, 4.5 Hz, 2H).

Example 85

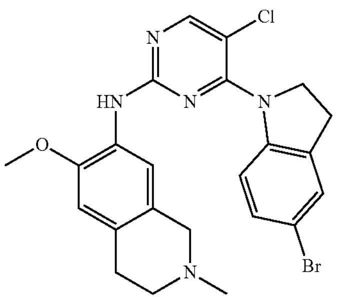 [SMILES: COc1cc2c(cc1Nc1ncc(Cl)c(N3CCc4cc(Br)ccc43)n1)CN(C)CC2]

N-(4-(5-bromoindolin-1-yl)-5-chloropyrimidin-2-yl)-6-methoxy-2-methyl-1,2,3,4-tetrahydroisoquinolin-7-amine The same procedures as Example 25, using 5-bromoindoline in place of 3,3-dimethylindoline in Step 1. LC-MS (ESI) m/z: 502 [M+H]$^+$. $^1$H NMR (500 MHz, DMSO-$d_6$) δ 8.26 (s, 1H), 8.00 (s, 1H), 7.52 (s, 1H), 7.43 (s, 1H), 7.30 (d, J=8.6 Hz, 1H), 7.21 (s, 1H), 6.76 (s, 1H), 4.28 (d, J=7.7 Hz, 2H), 3.78 (s, 3H), 3.24 (s, 2H), 3.15 (s, 2H), 2.77 (s, 2H), 2.55 (s, 2H), 2.33 (s, 3H).

Example 86

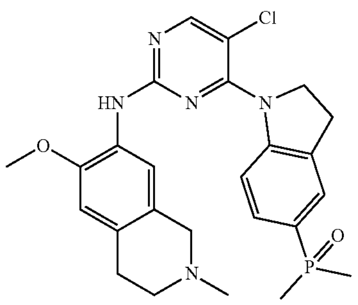

(1-(5-Chloro-24(6-methoxy-2-methyl-1,2,3,4-tetrahydroisoquinolin-7-yl)amino)pyrimidin-4-yl)indolin-5-yl)dimethylphosphine oxide A mixture of N-(4-(5-bromoindolin-1-yl)-5-chloropyrimidin-2-yl)-6-methoxy-2-methyl-1,2,3,4-tetrahydroisoquinolin-7-amine (110 mg, 208.66 umol), dimethylphosphine oxide (26.65 mg, 341.44 umol), $Pd_2(dba)_3$ (10.42 mg, 11.38 umol), Xantphos (6.59 mg, 11.38 umol), and triethylamine (69.10 mg, 682.88 umol, 95.18 uL) in dioxane (2 mL) was purged with nitrogen and stirred at 110° C. for 16 hours. The reaction mixture was purified by prep-HPLC (MeCN/10 mM $NH_4HCO_3$) to provide (1-(5-chloro-2-((6-methoxy-2-methyl-1,2,3,4-tetrahydroisoquinolin-7-yl)amino)pyrimidin-4-yl)indolin-5-yl)dimethylphosphine oxide as white solid (57.3 mg, 55% yield). LC-MS (ESI) m/z: 498 [M+H]$^+$. $^1$H NMR (400 MHz, DMSO-$d_6$) δ 8.29 (s, 1H), 8.09 (s, 1H), 7.61 (d, J=10.9 Hz, 1H), 7.53-7.36 (m, 3H), 6.77 (s, 1H), 4.31 (t, J=8.2 Hz, 2H), 3.78 (s, 3H), 3.29 (s, 2H), 3.18 (t, J=7.8 Hz, 2H), 2.77 (s, 2H), 2.55 (s, 2H), 2.31 (s, 3H), 1.62 (d, J=13.2 Hz, 6H).

Example 87

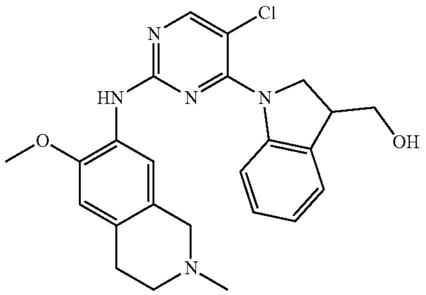 [SMILES: COc1cc2c(cc1Nc1ncc(Cl)c(N3CC(CO)c4ccccc43)n1)CN(C)CC2]

(1-(5-Chloro-24(6-methoxy-2-methyl-1,2,3,4-tetrahydroisoquinolin-7-yl)amino)pyrimidin-4-yl)indolin-3-yl)methanol The same procedures as Example 25, using Int. E6 in place of 3,3-dimethylindoline in Step 1. LC-MS (ESI) m/z: 502 [M+H]$^+$. $^1$H NMR (400 MHz, DMSO-$d_6$) δ 10.00 (s, 1H), 8.28 (s, 1H), 8.16 (s, 1H), 7.70 (d, J=4.0 Hz, 1H), 7.41 (d, J=8.0 Hz, 1H), 7.31 (d, J=7.3 Hz, 1H), 7.18 (t, J=7.7 Hz, 1H), 6.98 (t, J=7.3 Hz, 1H), 6.93 (s, 1H), 4.38-4.33 (m, 1H), 4.26 (s, 1H), 4.16 (s, 2H), 3.82 (s, 3H), 3.66 (d, J=5.6 Hz, 2H), 3.54-3.38 (m, 2H), 3.30 (s, 1H), 3.14-2.95 (m, 2H), 2.92 (d, J=3.6 Hz, 3H).

Example 88

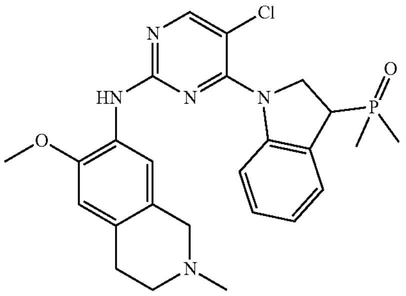

(1-(5-Chloro-24(6-methoxy-2-methyl-1,2,3,4-tetrahydroisoquinolin-7-yl)amino)pyrimidin-4-yl)indolin-3-yl)dimethylphosphine oxide The same procedures as Example 25, using Int. E7 in place of 3,3-dimethylindoline in Step 1. LC-MS (ESI) m/z: 502 [M+H]$^+$. $^1$H NMR (400 MHz, DMSO-$d_6$) δ 8.30 (s, 1H), 8.02 (s, 1H), 7.59 (s, 1H), 7.37 (d, J=7.4 Hz, 1H), 7.27 (d, J=8.0 Hz, 1H), 7.16 (t, J=7.7 Hz, 1H), 6.99 (t, J=7.5 Hz, 1H), 6.74 (s, 1H), 4.70-4.48 (m, 1H), 4.35 (ddd, J=18.3, 11.1, 3.6 Hz, 1H), 3.85 (d, J=9.9 Hz, 1H), 3.84-3.67 (m, 3H), 3.27-3.15 (m, 2H), 2.76 (t, J=5.6 Hz, 2H), 2.55 (d, J=5.7 Hz, 1H), 2.29 (s, 3H), 1.31 (dt, J=33.1, 16.5 Hz, 6H).

Example 89

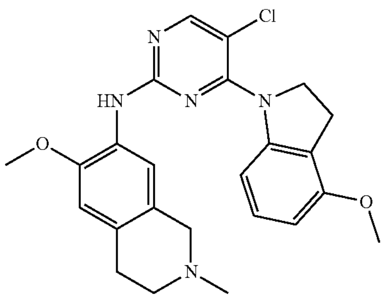

N-(5-chloro-4-(4-methoxyindolin-1-yl)pyrimidin-2-yl)-6-methoxy-2-methyl-1,2,3,4-tetrahydroisoquinolin-7-amine The same procedures as Example 25, using Int. E10 in place of 3,3-dimethylindoline in Step 1. LC-MS (ESI) m/z: 452 [M+H]$^+$. $^1$H NMR (400 MHz, DMSO-$d_6$) δ 8.23 (s, 1H), 7.93 (s, 1H), 7.56 (s, 1H), 7.02 (dd, J=19.1, 8.0 Hz, 2H), 6.74 (s, 1H), 6.61 (d, J=8.0 Hz, 1H), 4.27 (t, J=8.3 Hz, 2H), 3.80

(s, 3H), 3.78 (s, 3H), 3.27 (s, 2H), 3.01 (t, J=8.2 Hz, 2H), 2.77 (t, J=5.6 Hz, 2H), 2.55 (t, J=5.8 Hz, 2H), 2.31 (s, 3H).

Example 90

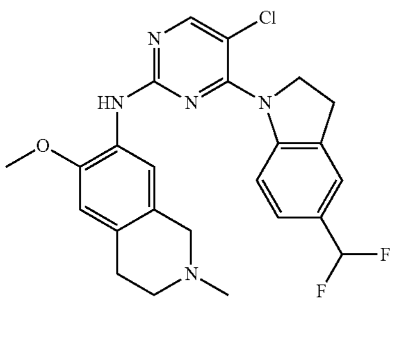 [SMILES: COc1cc2c(cc1Nc1ncc(Cl)c(N3CCc4cc(C(F)F)ccc43)n1)CN(C)CC2]

N-(5-chloro-4-(5-(difluoromethyl)indolin-1-yl)pyrimidin-2-yl)-6-methoxy-2-methyl-1,2,3,4-tetrahydroisoquinolin-7-amine The same procedures as Example 25, using Int. E12 in place of 3,3-dimethylindoline in Step 1. LC-MS (ESI) m/z: 472 $[M+H]^+$. $^1H$ NMR (500 MHz, DMSO-$d_6$) δ 8.29 (s, 1H), 8.04 (s, 1H), 7.55 (s, 1H), 7.49-7.39 (m, 2H), 7.29 (d, J=8.2 Hz, 1H), 6.95 (t, J=56.3 Hz, 1H), 6.76 (s, 1H), 4.31 (t, J=8.3 Hz, 2H), 3.79 (s, 3H), 3.27 (s, 2H), 3.19 (t, J=8.2 Hz, 2H), 2.78 (s, 2H), 2.56 (br, 2H), 2.31 (s, 3H).

Example 91

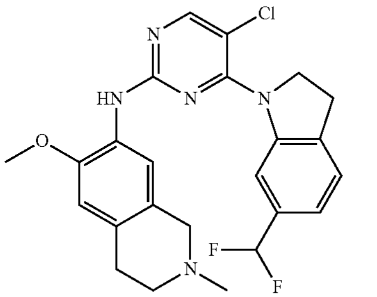 [SMILES: COc1cc2c(cc1Nc1ncc(Cl)c(N3CCc4ccc(C(F)F)cc43)n1)CN(C)CC2]

N-(5-chloro-4-(6-(difluoromethyl)indolin-1-yl)pyrimidin-2-yl)-6-methoxy-2-methyl-1,2,3,4-tetrahydroisoquinolin-7-amine The same procedures as Example 25, using Int. E13 in place of 3,3-dimethylindoline in Step 1. LC-MS (ESI) m/z: 472 $[M+H]^+$. $^1H$ NMR (500 MHz, DMSO-$d_6$) δ 8.29 (s, 1H), 8.03 (s, 1H), 7.52 (s, 1H), 7.43-7.32 (m, 2H), 7.13 (d, J=7.6 Hz, 1H), 6.91 (s, 1H), 6.80 (s, 1H), 6.75 (s, 1H), 6.69 (s, 1H), 4.30 (t, J=8.3 Hz, 2H), 3.79 (d, J=19.8 Hz, 3H), 3.25 (s, 2H), 3.18 (t, J=8.1 Hz, 2H), 2.77 (t, J=5.6 Hz, 2H), 2.54 (t, J=5.9 Hz, 2H), 2.28 (s, 3H).

Example 92

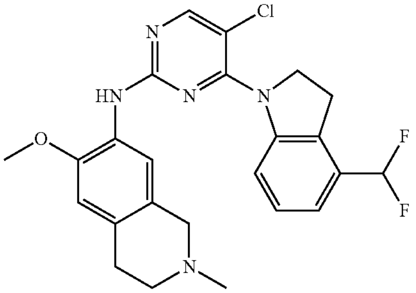 [SMILES: COc1cc2c(cc1Nc1ncc(Cl)c(N3CCc4c(C(F)F)cccc43)n1)CN(C)CC2]

N-(5-chloro-4-(4-(difluoromethyl)indolin-1-yl)pyrimidin-2-yl)-6-methoxy-2-methyl-1,2,3,4-tetrahydroisoquinolin-7-amine The same procedures as Example 25, using Int. E14 in place of 3,3-dimethylindoline in Step 1. LC-MS (ESI) m/z: 472 $[M+H]^+$. $^1H$ NMR (500 MHz, DMSO-$d_6$) δ 8.30 (s, 1H), 8.27 (s, 1H), 8.05 (s, 1H), 7.93 (s, 1H), 7.48 (s, 1H), 7.19 (dd, J=13.6, 5.6 Hz, 1H), 7.13-7.04 (m, 1H), 6.75 (d, J=5.8 Hz, 1H), 4.32 (t, J=8.3 Hz, 2H), 3.78 (d, J=9.6 Hz, 3H), 3.32-3.20 (m, 4H), 2.77 (s, 2H), 2.55 (t, J=5.8 Hz, 2H), 2.31 (s, 3H).

Example 31

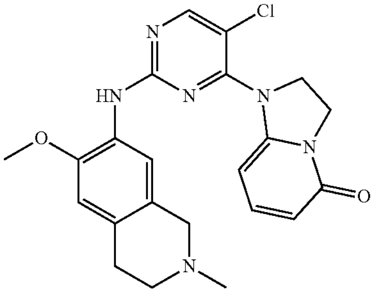 [SMILES: COc1cc2c(cc1Nc1ncc(Cl)c(N3CCn4c3cccc4=O)n1)CN(C)CC2]

1-(5-Chloro-24(6-methoxy-2-methyl-1,2,3,4-tetrahydroisoquinolin-7-yl)amino)pyrimidin-4-yl)-2,3-dihydroimidazo[1,2-a]pyridin-5(1H)-one Step 1: A mixture of Int. E5 (65 mg, 0.239 mmol), 2,4,5-trichloropyrimidine (53 mg, 0.286 mmol), $NaO^tBu$ (45.9 mg, 0.477 mmol), BINAP (3.9 mg, 0.006 mmol) and Palladium (II) acetate (1.3 mg, 0.006 mmol) in DMF/dioxane (2 mL/2 mL) was stirred for 16 hours at 70° C. under $N_2$, quenched with ice-cold water (10 mL) and extracted with EA (20 mL×3). The organic phases were washed with brine, dried over anhydrous $Na_2SO_4$, and filtered. The filtrate was concentrated in vacuo. The residue was purified by flash column chromatography on silica gel (DCM/MeOH=10/1) to provide 1-(2,5-dichloropyrimidin-4-yl)-2,3-dihydroimidazo[1,2-a]pyridin-5-one (45 mg, 26.63% yield, 40% purity). LC-MS (ESI) m/z: 283.0 $[M+H]^+$.

Step 2: 1-(2,5-Dichloropyrimidin-4-yl)-2,3-dihydroimidazo[1,2-a]pyridin-5-one (40 mg, 0.056 mmol) and Int. W1 (10.9 mg, 0.056 mmol) were used under Condition B3 (as exemplified in Step 2 of Example 10) to provide 1-(5-chloro-2-((6-methoxy-2-methyl-1,2,3,4-tetrahydroisoquinolin-7-yl)amino)pyrimidin-4-yl)-2,3-dihydroimidazo[1,2-a]pyridin-5(1H)-one as yellow solid (2.5 mg, 9.73% yield), after purification by prep-HPLC (MeCN/0.1% HCOOH). LC-MS (ESI) m/z: 439.0 $[M+H]^+$.

Example 48

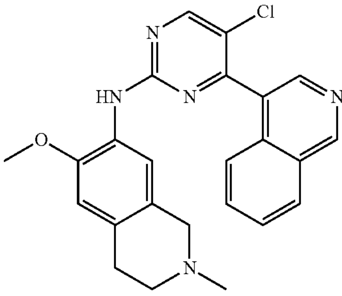

N-(5-chloro-4-(isoquinolin-4-yl)pyrimidin-2-yl)-6-methoxy-2-methyl-1,2,3,4-tetrahydroisoquinolin-7-amine Step 1: To a solution of 4-isoquinolylboronic acid (100 mg, 578.12 umol) in DME/$H_2O$ (3 mL/1 mL) were added potassium carbonate (159.8 mg, 1156 umol), 1,1'-bis(diphenylphosphino)ferrocene]dichloropalladium(II) (42.3 mg, 57.82 umol), and 2,4,5-trichloropyrimidine (106.0 mg, 578.12 umol). The mixture was stirred at 100° C. under $N_2$ atmosphere overnight, cooled down to room temperature, and diluted with EA (10 mL). After filtration, the filtrate was concentrated in vacuo. The residue was purified by flash column chromatography on silica gel (PE/EA=4/1 v/v) to provide 4-(2,5-dichloropyrimidin-4-yl)isoquinoline as yellow solid (50 mg, 63% yield). LC-MS (ESI) m/z: 276 $[M+H]^+$.

Step 2: 4-(2,5-Dichloropyrimidin-4-yl)isoquinoline (50 mg, 0.181 mmol) and Int. W1 (41.4 mg, 0.181 mmol) were used under Condition B3 (as exemplified in Step 2 of Example 10) to provide N-(5-chloro-4-(isoquinolin-4-yl)pyrimidin-2-yl)-6-methoxy-2-methyl-1,2,3,4-tetrahydroisoquinolin-7-amine as yellow solid (12 mg, 12% yield), after purification by prep-HPLC (MeCN/0.05% TFA). LC-MS (ESI) m/z: 432 $[M+H]^+$. $^1H$ NMR (400 MHz, $CD_3OD$): δ 2.98 (s, 3H), 3.06-3.25 (m, 3H), 3.65-3.73 (m, 1H), 3.93 (s, 3H), 4.12-4.16 (m, 1H), 4.34-4.30 (m, 1H), 6.91 (s, 1H), 7.85-7.89 (m, 2H), 7.93-7.97 (m, 1H), 8.12 (s, 1H), 8.35 (d, J=7.6 Hz, 1H), 8.61 (s, 1H), 8.68 (s, 1H), 9.52 (s, 1H).

Example 49

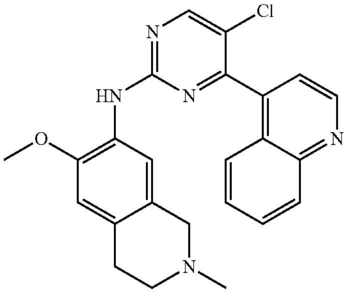 [SMILES: COc1cc2c(cc1Nc1ncc(Cl)c(-c3ccnc4ccccc34)n1)CN(C)CC2]

N-(5-chloro-4-(quinolin-4-yl)pyrimidin-2-yl)-6-methoxy-2-methyl-1,2,3,4-tetrahydroisoquinolin-7-amine The same procedures as Example 48, using 4-quinolylboronic acid in place of 4-isoquinolylboronic acid in Step 1. LC-MS (ESI) m/z: 432 $[M+H]^+$. $^1H$ NMR (400 MHz, $CD_3OD$): δ 2.36 (s, 1.8H), 2.54 (s, 3H), 2.90-2.95 (m, 4H), 3.61 (s, 2H), 3.88 (s, 3H), 6.79 (s, 1H), 7.22 (d, J=8.0 Hz, 1.2H), 7.61 (d, J=4.4 Hz, 1H), 7.62-7.66 (m, 1H), 7.69 (d, J=8.0 Hz, 1.2H), 7.78 (d, J=8.4 Hz, 1H), 7.82-7.87 (m, 1H), 7.96 (s, 1H), 8.16 (d, J=8.4 Hz, 1H), 8.63 (s, 1H), 9.00 (d, J=4.4 Hz, 1H).

Example 93

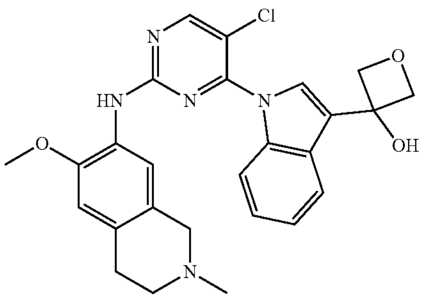 [SMILES: COc1cc2c(cc1Nc1ncc(Cl)c(-n3cc(C4(O)COC4)c4ccccc43)n1)CN(C)CC2]

3-(1-(5-Chloro-24(6-methoxy-2-methyl-1,2,3,4-tetrahydroisoquinolin-7-yl)amino)pyrimidin-4-yl)-1H-indol-3-yl)oxetan-3-ol Step 1: Int. E16 (440 mg, 1.45 mmol) and 2,4,5-trichloropyrimidine (293 mg, 1.59 mmol) were used under Condition A1 to provide 3-(3-((tert-butyldimethyl silyl)oxy)oxetan-3-yl)-1-(2,5-dichloropyrimidin-4-yl)-1H-indole (400 mg, 58% yield) as light yellow solid, after purification by flash column chromatography on silica gel (PE/EA=10/1). LC-MS (ESI) m/z: 450 $[M+H]^+$.

Step 2: 3-(3-((tert-Butyldimethylsilyl)oxy)oxetan-3-yl)-1-(2,5-dichloropyrimidin-4-yl)-1H-indole (200 mg, 0.444 mmol) and Int. W1 (142 mg, 0.533 mmol) were used under Condition B3 to provide N-(4-(3-(3-((tert-butyldimethylsilyl)oxy)oxetan-3-yl)-1H-indol-1-yl)-5-chloropyrimidin-2-yl)-6-methoxy-2-methyl-1,2,3,4-tetrahydroisoquinolin-7-amine (170 mg, 73% yield) as red solid, after purification by flash column chromatography on silica gel (PE/EA=10/1). LC-MS (ESI) m/z: 606 $[M+H]^+$.

Step 3: To a solution of N-(4-(3-(3-((tert-butyldimethylsilyl)oxy)oxetan-3-yl)-1H-indol-1-yl)-5-chloropyrimidin-2-yl)-6-methoxy-2-methyl-1,2,3,4-tetrahydroisoquinolin-7-amine (80 mg, 131.96 umol) in mixed solvent of THF (2 mL) and water (0.3 mL) was added formic acid (1 mL). The reaction mixture was stirred at 80° C. for 3 hours, and purified through prep-HPLC (10 mM $NH_4HCO_3$ & 0.025% $NH_3$. $H_2O$/acetonitrile) to provide 3-(1-(5-chloro-2-((6-methoxy-2-methyl-1,2,3,4-tetrahydroisoquinolin-7-yl)amino)pyrimidin-4-yl)-1H-indol-3-yl)oxetan-3-ol as yellow solid (2.0 mg, 3% yield). LC-MS (ESI) m/z: 492 $[M+H]^+$. $^1H$ NMR (400 MHz, DMSO-$d_6$) δ 12.46 (s, 1H), 8.19 (s, 1H), 8.08 (s, 1H), 7.93 (d, J=8.0 Hz, 1H), 7.57 (d, J=8.0 Hz, 1H), 7.26 (t, J=7.5 Hz, 1H), 7.19 (t, J=8.1 Hz, 1H), 6.60 (s, 1H), 6.43 (s, 1H), 6.04 (s, 1H), 5.33 (s, 1H), 4.39 (d, J=14.9 Hz, 1H), 4.11 (d, J=14.8 Hz, 1H), 3.83 (d, J=30.4 Hz, 2H), 3.62 (s, 3H), 3.36 (s, 2H), 2.76 (s, 2H), 2.58 (s, 2H), 2.33 (s, 3H).

Example 94

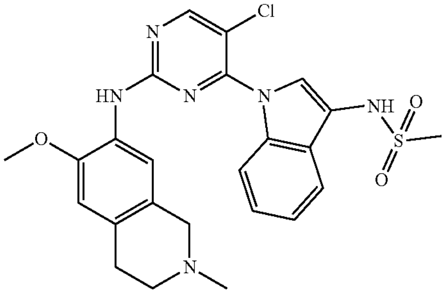

N-(1-(5-chloro-2-((6-methoxy-2-methyl-1,2,3,4-tetrahydroisoquinolin-7-yl)amino)pyrimidin-4-yl)-1H-indol-3-yl)methanesulfonamide Step 1: 3-Nitro-1H-indole (100 mg, 0.617 mmol) and 2,4,5-trichloropyrimidine (125 mg, 0.678 mmol) were used under Condition A1 to provide 1-(2,5-dichloropyrimidin-4-yl)-3-nitro-1H-indole (78 mg, 30% yield) as yellow solid, after purification by flash column chromatography on silica gel (PE/EA=10/1). LC-MS (ESI) m/z: 309 $[M+H]^+$.

Step 2: To a solution of 1-(2,5-dichloropyrimidin-4-yl)-3-nitro-1H-indole (78 mg, 252.34 umol) in mixed solvent of 1,4-dioxane (0.5 mL) and water (0.2 mL) were added zinc (5.42 mg, 82.89 umol) and $NH_4Cl$ (5.2 mg, 97.05 umol) sequentially at 0° C. The reaction mixture was stirred at room temperature for an hour and filtered through celite. The filtrate was diluted with ethyl acetate (10 mL), washed with water (5 mL) and brine (5 mL), dried over anhydrous sodium sulfate and filtered. The filtrate was concentrated in vacuo to provide 1-(2,5-dichloropyrimidin-4-yl)-1H-indol-3-amine as brown solid (60 mg, 85% yield). LC-MS (ESI) m/z: 279 $[M+H]^+$.

Step 3: To a suspension of 1-(2,5-dichloropyrimidin-4-yl)-1H-indol-3-amine (60 mg, 214.96 umol) in anhydrous DCM (2 mL) was added MsCl (138.09 mg, 214.96 umol) at 0° C. After stirring at 0° C. for 4 hours, the mixture was partitioned between 5% aqueous citric acid (20 mL) and DCM (20 mL). The combined organic phase was washed with water (10 mL), dried over anhydrous $Na_2SO_4$ and filtered. The filtrate was concentrated in vacuo, and the residue was purified by flash column chromatography on silica gel (PE/EA=1/10~1/5) to provide N-(1-(2,5-dichloropyrimidin-4-yl)-1H-indol-3-yl)methanesulfonamide as yellow solid (75 mg, 97% yield). LC-MS (ESI) m/z: 357 $[M+H]^+$.

Step 4: N-(1-(2,5-dichloropyrimidin-4-yl)-1H-indol-3-yl) methane sulfonamide (75 mg, 0.210 mmol) and Int. W1 (49 mg, 0.252 mmol) were used under Condition B3 to provide N-(1-(5-chloro-2-((6-methoxy-2-methyl-1,2,3,4-tetrahydroisoquinolin-7-yl)amino)pyrimidin-4-yl)-1H-indol-3-yl) methanesulfonamide (5.2 mg, 5% yield) as white solid, after purification by prep-HPLC (MeCN/0.1% HCOOH). LC-MS (ESI) m/z: 513 $[M+H]^+$. $^1H$ NMR (400 MHz, DMSO-$d_6$) δ 8.75 (s, 1H), 8.62 (s, 1H), 8.28 (s, 1H), 7.86-7.72 (m, 2H), 7.47 (d, J=8.0 Hz, 1H), 7.40 (s, 1H), 7.28-7.20 (m, 2H), 7.11 (d, J=7.9 Hz, 1H), 6.80 (s, 1H), 3.79 (s, 3H), 2.99 (s, 3H), 2.79 (t, J=5.8 Hz, 2H), 2.56 (t, J=5.8 Hz, 2H), 2.31 (s, 3H), 2.29 (s, 2H).

Example 32

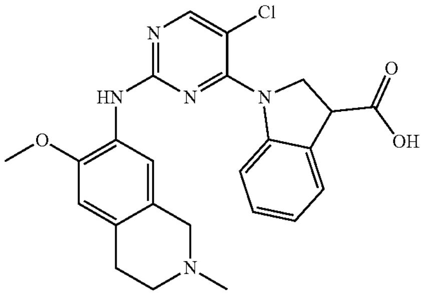

1-(5-Chloro-2-((6-methoxy-2-methyl-1,2,3,4-tetrahydroisoquinolin-7-yl)amino)pyrimidin-4-yl)indoline-3-carboxylic acid Example 115

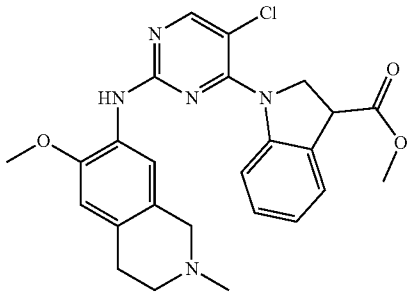 [SMILES: COC(=O)C1CN(c2nc(Nc3cc4c(cc3OC)CCN(C)C4)ncc2Cl)c2ccccc21]

Methyl 1-(5-chloro-2-((6-methoxy-2-methyl-1,2,3,4-tetrahydroisoquinolin-7-yl)amino)pyrimidin-4-yl) indoline-3-carboxylate Step 1: A mixture of 2,4,5-trichloropyrimidine (220 mg, 1.20 mmol) and indoline-3-carboxylic acid (163 mg, 0.999 mmol) in NMP (0.6 mL) was stirred for 15 minutes at 150°

C., and purified by reverse phase chromatography (0-80% Methanol in water) to give 1-(2,5-dichloropyrimidin-4-yl) indoline-3-carboxylic acid (160 mg, 48.55% yield, 94% purity) as yellow solid. LC-MS (ESI) m/z: 310.0 $[M+H]^+$.

Step 2: A mixture of 1-(2,5-dichloropyrimidin-4-yl)indoline-3-carboxylic acid (30 mg, 0.097 mmol) and Int. W1 (19 mg, 0.097 mmol) and TsOH·$H_2O$ (18.4 mg, 0.097 mmol) in i-PrOH (2.5 mL) was stirred for 5 hours at 85° C. and purified by prep-HPLC (10 mM $NH_4HCO_3$ & 0.025% $NH_3$·$H_2O$/acetonitrile) to provide 1-(5-chloro-2-((6-methoxy-2-methyl-1,2,3,4-tetrahydroisoquinolin-7-yl) amino)pyrimidin-4-yl)indoline-3-carboxylic acid (1.8 mg, 4% yield) as yellow solid. LC-MS (ESI) m/z: 466 $[M+H]^+$. $^1$H NMR (400 MHz, DMSO-$d_6$) δ 8.25 (s, 1H), 8.03 (s, 1H), 7.51 (s, 1H), 7.40 (dd, J=7.7, 3.9 Hz, 2H), 7.12 (t, J=7.6 Hz, 1H), 6.97 (t, J=7.3 Hz, 1H), 6.76 (s, 1H), 4.56 (dd, J=10.6, 6.4 Hz, 1H), 4.38 (t, J=10.1 Hz, 1H), 4.23 (s, 1H), 3.77 (s, 3H), 2.78 (d, J=5.6 Hz, 2H), 2.67 (s, 1H), 2.60-2.55 (m, 3H), 2.32 (s, 3H).

Alternative Synthetic Method:

Step 1: A mixture of Int. E17 (300 mg, 1.59 mmol), 2,4,5-trichloropyrimidine (292 mg, 1.59 mmol) and DIPEA (411.4 mg, 3.18 mmol) in n-BuOH (5 mL) was stirred for 16 hours at 100° C., quenched with ice-cold water (20 mL) and extracted with EA (30 mL×3). The organic phases were washed with brine (30 mL), dried over anhydrous $Na_2SO_4$ and filtered. The filtrate was concentrated in vacuo. The residue was purified by flash column chromatography on silica gel (MeOH/DCM: 0-15%) to provide methyl 1-(2,5-dichloropyrimidin-4-yl)indoline-3-carboxylate (556 mg, 95% yield) as yellow solid. LC-MS (ESI) m/z: 324 $[M+H]^+$.

Step 2: A mixture of methyl 1-(2,5-dichloropyrimidin-4-yl)indoline-3-carboxylate (250 mg, 0.678 mmol), Int. W1 (155 mg, 0.678 mmol) and TsOH·$H_2O$ (129.1 mg, 0.679 mmol) in i-PrOH (10 mL) was stirred for 16 hours at 100° C., quenched with saturated $NaHCO_3$ aqueous solution (10 mL) and extracted with DCM/MeOH (10/1, 30 mL×3). The organic phases were washed with brine (30 mL), dried over anhydrous $Na_2SO_4$ and filtered. The filtrate was concentrated in vacuo. The residue was purified by flash column chromatography on silica gel (MeOH/DCM: 0-15%) to provide a mixture of methyl 1-(5-chloro-2-((6-methoxy-2-methyl-1,2,3,4-tetrahydroisoquinolin-7-yl)amino)pyrimidin-4-yl)indoline-3-carboxylate and isopropyl 1-(5-chloro-2-((6-methoxy-2-methyl-1,2,3,4-tetrahydroisoquinolin-7-yl)amino)pyrimidin-4-yl)indoline-3-carboxylate (530 mg) as yellow solid. LC-MS (ESI) m/z: 480 (methyl ester), 508 (isopropyl ester) $[M+H]^+$.

A small amount of the mixture was further purified by prep-HPLC to provide methyl 1-(5-chloro-2-((6-methoxy-2-methyl-1,2,3,4-tetrahydroisoquinolin-7-yl)amino)pyrimidin-4-yl)indoline-3-carboxylate as yellow solid. LC-MS (ESI) m/z: 480 $[M+H]^+$. $^1$H NMR (400 MHz, DMSO-$d_6$) δ 8.28 (s, 1H), 8.09 (s, 1H), 7.48 (s, 1H), 7.37 (dd, J=15.3, 7.7 Hz, 2H), 7.16 (t, J=7.4 Hz, 1H), 6.99 (t, J=7.2 Hz, 1H), 6.76 (s, 1H), 4.54 (q, J=10.8 Hz, 1H), 4.50-4.38 (m, 2H), 3.79 (d, J=15.6 Hz, 3H), 3.71 (s, 3H), 3.29 (s, 2H), 2.78 (t, J=5.7 Hz, 2H), 2.56 (t, J=5.9 Hz, 2H), 2.31 (s, 3H).

Step 3: A mixture of methyl 1-(5-chloro-2-((6-methoxy-2-methyl-1,2,3,4-tetrahydroisoquinolin-7-yl)amino)pyrimidin-4-yl)indoline-3-carboxylate and isopropyl 1-(5-chloro-2-((6-methoxy-2-methyl-1,2,3,4-tetrahydroisoquinolin-7-yl)amino)pyrimidin-4-yl)indoline-3-carboxylate (530 mg) and LiOH aqueous solution (2N, 4 mL) in THF (5 mL) was stirred for 16 hours at room temperature, adjusted to pH~5 with formic acid and extracted with DCM (30 mL×3). The combined organic phases were dried over anhydrous $Na_2SO_4$ and filtered. The filtrate was concentrated in vacuo, and the residue was purified by prep-HPLC (10 mM $NH_4HCO_3$&0.025% $NH_3$·$H_2O$/acetonitrile) to afford 1-(5-chloro-2-((6-methoxy-2-methyl-1,2,3,4-tetrahydroisoquinolin-7-yl)amino)pyrimidin-4-yl)indoline-3-carboxylic acid (158 mg, 84% yield) as light-yellow solid. LC-MS (ESI) m/z: 466 $[M+H]^+$.

Examples 95 & 96

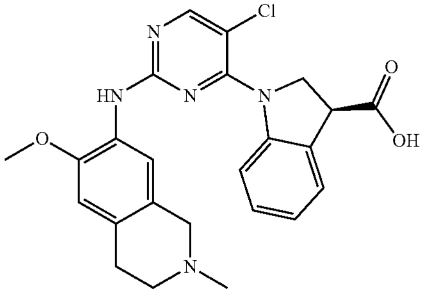

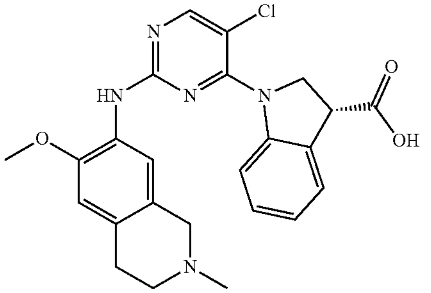

(S)-1-(5-chloro-2-((6-methoxy-2-methyl-1,2,3,4-tetrahydroisoquinolin-7-yl)amino)pyrimidin-4-yl) indoline-3-carboxylic acid & (R)-1-(5-chloro-2-((6-methoxy-2-methyl-1,2,3,4-tetrahydroisoquinolin-7-yl)amino)pyrimidin-4-yl)indoline-3-carboxylic acid Synthesized after chiral-separation of the racemic 1-(5-chloro-2-((6-methoxy-2-methyl-1,2,3,4-tetrahydroisoquinolin-7-yl)amino)pyrimidin-4-yl)indoline-3-carboxylic acid (20 mg). The stereochemistry was not confirmed, and two products (4.5 mg, 5.1 mg separately) were arbitrarily assigned.

LC-MS (ESI) m/z: 466 $[M+H]^+$. $^1$H NMR (500 MHz, DMSO-$d_6$) δ 8.27 (s, 1H), 8.05 (s, 1H), 7.51 (s, 1H), 7.40 (d, J=7.9 Hz, 2H), 7.15 (t, J=7.8 Hz, 1H), 6.98 (t, J=7.5 Hz, 1H), 6.77 (s, 1H), 4.54 (dd, J=10.6, 6.1 Hz, 1H), 4.40 (t, J=10.0 Hz, 1H), 4.31-4.27 (m, 1H), 3.77 (s, 3H), 3.26-3.24 (m, 2H), 2.80 (d, J=5.6 Hz, 2H), 2.65 (d, J=6.5 Hz, 2H), 2.37 (s, 3H). Chiral-HPLC retention time: 1.285 min; ee value: >99%.

LC-MS (ESI) m/z: 466 $[M+H]^+$. $^1$H NMR (500 MHz, DMSO-$d_6$) δ 8.26 (s, 1H), 8.03 (s, 1H), 7.51 (s, 1H), 7.39 (d, J=8.0 Hz, 2H), 7.15 (d, J=7.7 Hz, 1H), 6.99 (d, J=7.5 Hz, 1H), 6.76 (s, 1H), 4.54 (dd, J=10.5, 6.2 Hz, 1H), 4.39 (t, J=10.1 Hz, 1H), 4.28 (d, J=6.1 Hz, 1H), 3.77 (s, 3H), 3.34 (s, 2H), 2.79 (t, J=5.5 Hz, 2H), 2.61 (t, J=5.7 Hz, 2H), 2.34 (s, 3H). Chiral-HPLC retention time: 2.078 min; ee value: >99%.

SFC Separation Conditions:

Instrument: SFC-150 (Thar, Waters)

Column: IG 20*250 mm, 10 um (Daicel)

Column temperature: 35° C.

Mobile phase: $CO_2$/EtOH (0.2% Methanol/Ammonia)=50/50

Flow rate: 120 g/min

Back pressure: 100 bar

Detection wavelength: 214 nm

Cycle time: 8 min

Example 33

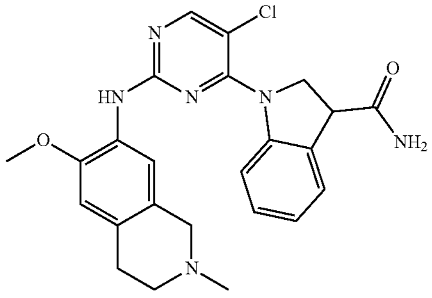 [SMILES: COc1cc2c(cc1Nc1ncc(Cl)c(N3CC(C(N)=O)c4ccccc43)n1)CN(C)CC2]

1-(5-Chloro-2-((6-methoxy-2-methyl-1,2,3,4-tetrahydroisoquinolin-7-yl)amino)pyrimidin-4-yl)indoline-3-carboxamide Step 1: A mixture of 1-(2,5-dichloropyrimidin-4-yl)indoline-3-carboxylic acid (60 mg, 193.46 umol), ammonium chloride (51.74 mg, 967.32 umol), HATU (110.34 mg, 290.20 umol) and triethylamine (58.73 mg, 580.39 umol, 80.90 uL) in DMF (1 mL) was stirred for 3 hours at room temperature, quenched with ice-cold water (15 mL) and extracted with EtOAc (20 mL×3). The combined organic phase was washed with brine (15 mL), dried over anhydrous $Na_2SO_4$, and filtered. The filtrate was concentrated in vacuo. The residue was purified by flash column chromatography on silica gel (EA/PE=0-100%) to provide 1-(2,5-dichloropyrimidin-4-yl)indoline-3-carboxamide (15 mg, 50.16% yield, 100% purity) as white solid. LC-MS (ESI) m/z: 309 $[M+H]^+$.

Step 2: 1-(2,5-Dichloropyrimidin-4-yl)indoline-3-carboxamide (45 mg, 0.146 mmol) and Int. W1 (28 mg, 0.146 mmol) were used under Condition B3 to provide 1-(5-chloro-2-((6-methoxy-2-methyl-1,2,3,4-tetrahydroisoquinolin-7-yl)amino)pyrimidin-4-yl)indoline-3-carboxamide (26.9 mg, 55% yield) as white solid, after purification by prep-HPLC (10 mM $NH_4HCO_3$&0.025% $NH_3 \cdot H_2O$/acetonitrile). LC-MS (ESI) m/z: 465 $[M+H]^+$. $^1$H NMR (500 MHz, DMSO-$d_6$) δ 8.24 (s, 1H), 8.00 (s, 1H), 7.80 (s, 1H), 7.50 (s, 1H), 7.39 (dd, J=31.8, 7.8 Hz, 2H), 7.22 (s, 1H), 7.10 (t, J=7.7 Hz, 1H), 6.97 (t, J=7.4 Hz, 1H), 6.75 (s, 1H), 4.54 (dd, J=10.3, 6.3 Hz, 1H), 4.36 (t, J=9.9 Hz, 1H), 4.15 (dd, J=9.3, 6.5 Hz, 1H), 3.77 (s, 3H), 3.28 (d, J=12.2 Hz, 2H), 2.77 (t, J=5.6 Hz, 2H), 2.55 (t, J=5.9 Hz, 2H), 2.30 (s, 3H).

Example 97

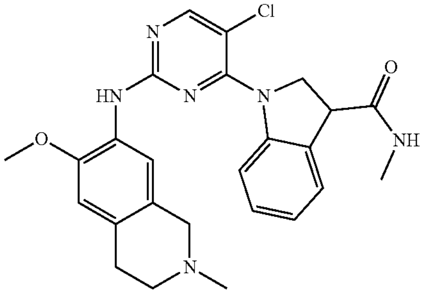 [SMILES: CNC(=O)C1CN(c2nc(Nc3cc4c(cc3OC)CCN(C)C4)ncc2Cl)c2ccccc21]

1-(5-Chloro-2-((6-methoxy-2-methyl-1,2,3,4-tetrahydroisoquinolin-7-yl)amino)pyrimidin-4-yl)-N-methylindoline-3-carboxamide The same procedures as Example 33, using methylamine hydrochloride in place of ammonium chloride in Step 1. LC-MS (ESI) m/z: 479 $[M+H]^+$. $^1$H NMR (400 MHz, DMSO-$d_6$) δ 8.31-8.26 (m, 1H), 8.24 (s, 1H), 8.02 (s, 1H), 7.49 (s, 1H), 7.42 (d, J=8.3 Hz, 1H), 7.28 (d, J=7.5 Hz, 1H), 7.10 (t, J=7.7 Hz, 1H), 6.95 (t, J=7.4 Hz, 1H), 6.75 (s, 1H), 4.54 (dd, J=10.4, 6.5 Hz, 1H), 4.37 (t, J=10.0 Hz, 1H), 4.22-4.05 (m, 1H), 3.77 (s, 3H), 3.28 (s, 2H), 2.77 (d, J=5.7 Hz, 2H), 2.66 (d, J=4.6 Hz, 3H), 2.56 (d, J=5.8 Hz, 2H), 2.30 (s, 3H).

Example 98

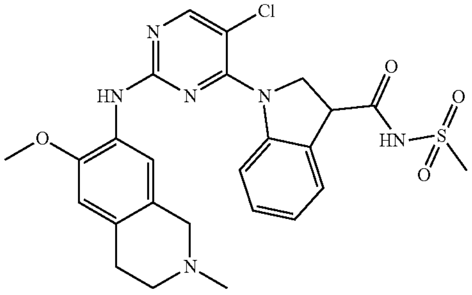

1-(5-Chloro-24(6-methoxy-2-methyl-1,2,3,4-tetrahydroisoquinolin-7-yl)amino)pyrimidin-4-yl)-N-(methylsulfonyl)indoline-3-carboxamide Step 1: A mixture of 1-(2,5-dichloropyrimidin-4-yl)indoline-3-carboxylic acid (60 mg, 0.193 mmol) and CDI (31.47 mg, 0.193 mmol) in DCM (5 mL) was stirred for an hour at room temperature, followed by the addition of methanesulfonamide (27.6 mg, 0.290 mmol). After the mixture was stirred for an additional hour, DBU (29.5 mg, 0.193 mmol) was added to the mixture. The reaction mixture was then stirred for 16 hours at room temperature, quenched with HCl aqueous solution (1N, 20 mL) and extracted with EtOAc (20 mL×3). The combined organic phases were dried over anhydrous sodium sulfate and filtered. The filtrate was concentrated in vacuo, and the residue was purified by flash column chromatography on silica gel (MeOH/DCM=0-

15%) to provide 1-(2,5-dichloropyrimidin-4-yl)-N-methylsulfonyl-indoline-3-carboxamide as yellow oil (45 mg, 37% yield, 62% purity). LC-MS (ESI) m/z: 387 $[M+H]^+$.

Step 2: 1-(2,5-Dichloropyrimidin-4-yl)-N-methylsulfonyl-indoline-3-carboxamide (45 mg, 0.072 mmol) and Int. W1 (13.9 mg, 0.072 mmol) were used under Condition B3 to provide 1-(5-chloro-2-((6-methoxy-2-methyl-1,2,3,4-tetrahydroisoquinolin-7-yl)amino)pyrimidin-4-yl)-N-(methylsulfonyl)indoline-3-carboxamide (29 mg, 74.1% yield) as light yellow solid, after purification by prep-HPLC (0.1% FA/acetonitrile). LC-MS (ESI) m/z: 543 $[M+H]^+$. $^1$H NMR (400 MHz, DMSO-$d_6$) δ 8.25 (s, 1H), 8.05 (s, 1H), 7.66 (s, 1H), 7.47 (d, J=7.0 Hz, 1H), 7.33 (d, J=8.4 Hz, 1H), 7.11 (t, J=7.9 Hz, 1H), 6.94 (t, J=7.4 Hz, 1H), 6.85 (s, 1H), 4.64-4.56 (m, 1H), 4.28 (t, J=9.8 Hz, 1H), 4.00 (d, J=7.8 Hz, 1H), 3.81 (s, 3H), 3.09 (s, 2H), 2.93 (s, 2H), 2.82 (s, 3H), 2.67 (s, 2H), 2.52 (s, 3H).

Example 99

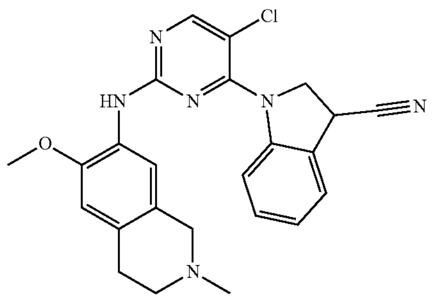 [SMILES: COc1cc2c(cc1Nc1ncc(Cl)c(N3CC(C#N)c4ccccc43)n1)CN(C)CC2]

1-(5-Chloro-2-((6-methoxy-2-methyl-1,2,3,4-tetrahydroisoquinolin-7-yl)amino)pyrimidin-4-yl)indoline-3-carbonitrile Step 1: To a solution of 1-(2,5-dichloropyrimidin-4-yl) indoline-3-carboxamide (100 mg, 0.210 mmol) and pyridine (67 mg, 0.841 mmol) in DCM (5 mL) was added slowly trifluoroacetic anhydride (88.3 mg, 0.421 mmol) in DCM (1 mL) at 0° C. The mixture was stirred at 0° C. for an hour and room temperature for 6 hours and quenched with 1 N HCl (10 mL). The resulting mixture was extracted with DCM (20 mL×3), and the organic phases were washed with brine (15 mL), dried over anhydrous $Na_2SO_4$, and filtered. The filtrate was concentrated in vacuo to provide crude 1-(2,5-dichloropyrimidin-4-yl)indoline-3-carbonitrile (60 mg, 40.2% yield, 40% purity). LC-MS (ESI) m/z: 291 $[M+H]^+$.

Step 2: 1-(2,5-Dichloropyrimidin-4-yl)indoline-3-carbonitrile (60 mg, 40% purity) and Int. W1 (10.8 mg, 0.056 mmol) were used under Condition B3 to provide 1-(5-chloro-2-((6-methoxy-2-methyl-1,2,3,4-tetrahydroisoquinolin-7-yl)amino)pyrimidin-4-yl)indoline-3-carbonitrile (19.7 mg, 77.7% yield) as white solid, after purification by prep-HPLC (10 mM $NH_4HCO_3$&0.025% $NH_3 \cdot H_2O$/acetonitrile). LC-MS (ESI) m/z: 447 $[M+H]^+$. $^1$H NMR (400 MHz, DMSO-$d_6$) δ 8.32 (s, 1H), 8.22 (s, 1H), 8.15 (s, 1H), 7.52-7.42 (m, 2H), 7.33 (d, J=7.7 Hz, 1H), 7.24 (t, J=7.5 Hz, 1H), 7.07 (t, J=7.4 Hz, 1H), 6.76 (s, 1H), 4.89-4.80 (m, 1H), 4.58 (t, J=10.0 Hz, 1H), 4.44 (dd, J=10.7, 6.8 Hz, 1H), 3.77 (s, 3H), 3.29 (s, 2H), 2.77 (d, J=5.8 Hz, 2H), 2.57-2.54 (m, 2H), 2.31 (s, 3H).

Example 100

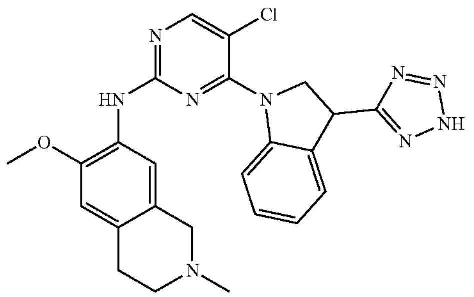 [SMILES: COc1cc2c(cc1Nc1ncc(Cl)c(N3CC(c4nn[nH]n4)c4ccccc43)n1)CN(C)CC2]

N-(4-(3-(2H-tetrazol-5-yl)indolin-1-yl)-5-chloropyrimidin-2-yl)-6-methoxy-2-methyl-1,2,3,4-tetrahydroisoquinolin-7-amine A mixture of 1-(5-chloro-2-((6-methoxy-2-methyl-1,2,3,4-tetrahydroisoquinolin-7-yl)amino)pyrimidin-4-yl)indoline-3-carbonitrile (45 mg, 0.101 mmol), sodium azide (9.8 mg, 0.151 mmol) and ammonia acetate (11.6 mg, 0.151 mmol) in DMF (1.5 mL) was stirred for 5 hours at 120° C., cooled to room temperature, diluted with HCl aqueous solution (1 N, 5 mL) and stirred for another 30 minutes. The mixture was extracted with EA (20 mL×3). The organic phases were washed with brine (15 mL) dried over anhydrous $Na_2SO_4$ and filtered. The filtrate was concentrated in vacuo, and the residue was purified by prep-HPLC (MeCN/0.1% formic acid) to provide N-(4-(3-(2H-tetrazol-5-yl) indolin-1-yl)-5-chloropyrimidin-2-yl)-6-methoxy-2-methyl-1,2,3,4-tetrahydroisoquinolin-7-amine as white solid (13.4 mg, 27% yield). LC-MS (ESI) m/z: 490 $[M+H]^+$. $^1$H NMR (500 MHz, DMSO-$d_6$) δ 8.29 (s, 1H), 8.15 (s, 1H), 8.06 (s, 1H), 7.72 (s, 1H), 7.32 (d, J=7.7 Hz, 1H), 7.21-7.08 (m, 2H), 6.93 (t, J=7.5 Hz, 1H), 6.83 (s, 1H), 4.89 (t, J=9.1 Hz, 1H), 4.72 (s, 1H), 4.56 (s, 1H), 3.81 (s, 3H), 3.77 (s, 2H), 3.01 (s, 2H), 2.90 (d, J=5.5 Hz, 2H), 2.63 (s, 3H).

Example 101

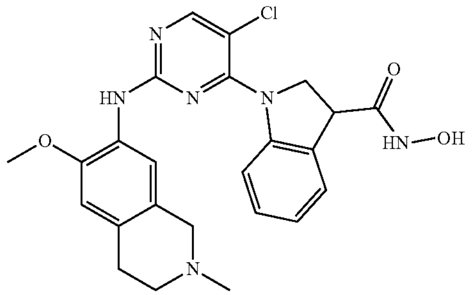 [SMILES: COc1cc2c(cc1Nc1ncc(Cl)c(N3CC(C(=O)NO)c4ccccc43)n1)CN(C)CC2]

1-(5-Chloro-2-((6-methoxy-2-methyl-1,2,3,4-tetrahydroisoquinolin-7-yl)amino)pyrimidin-4-yl)-N-hydroxyindoline-3-carboxamide Step 1: A mixture of 1-(2,5-dichloropyrimidin-4-yl)indoline-3-carboxylic acid (150 mg, 0.484 mmol), oxalyl dichloride (61.4 mg, 0.484 mmol) and N,N-dimethylformamide (1.8 mg, 0.024 mmol) in DCM (5 mL) was stirred for 2 hours at room temperature and concentrated in vacuo to provide the crude 1-(2,5-dichloropyrimidin-4-yl)indoline-3-carbonyl chloride, which was used in the next step without further purification.

Step 2: To a suspension of hydroxylamine hydrochloride (79.3 mg, 1.14 mmol) in MeOH (3 mL) was added slowly KOH (63.8 mg, 1.14 mmol) at 0° C. The reaction mixture was stirred for 10 minutes under $N_2$, and thereto was added 1-(2,5-dichloropyrimidin-4-yl)indoline-3-carbonyl chloride (75 mg, 0.228 mmol) in methanol (5 mL) at 0° C. The resulting mixture was then stirred for 16 hours, quenched with ice-cold water (10 mL) and extracted with EtOAc (20 mL×3). The organic phases were washed with brine (5 mL) dried over anhydrous $Na_2SO_4$ and filtered. The filtrate was concentrated in vacuo, and the residue was purified by flash column chromatography on silica gel (MeOH/DCM=0-10/1) to provide 1-(2,5-dichloropyrimidin-4-yl)-N-hydroxyindoline-3-carboxamide as white solid (50 mg, 43% yield, 64% purity). LC-MS (ESI) m/z: 325 $[M+H]^+$.

Step 3: 1-(2,5-Dichloropyrimidin-4-yl)-N-hydroxyindoline-3-carboxamide (50 mg, 64% purity) and Int. W1 (18.9 mg, 0.098 mmol) were used under Condition B3 to provide 1-(5-chloro-2-((6-methoxy-2-methyl-1,2,3,4-tetrahydroisoquinolin-7-yl)amino)pyrimidin-4-yl)-N-hydroxyindoline-3-carboxamide (12.6 mg, 25.4% yield) as white solid, after purification by prep-HPLC (10 mM $NH_4HCO_3$&0.025% $NH_3 \cdot H_2O$/acetonitrile). LC-MS (ESI) m/z: 481 $[M+H]^+$. $^1H$ NMR (400 MHz, DMSO-$d_6$) δ 10.94 (s, 1H), 9.04 (s, 1H), 8.25 (s, 1H), 8.03 (s, 1H), 7.50-7.34 (m, 2H), 7.25 (d, J=7.1 Hz, 1H), 7.11 (t, J=7.6 Hz, 1H), 6.97 (t, J=7.7 Hz, 1H), 6.75 (s, 1H), 4.51 (dd, J=10.3, 6.7 Hz, 1H), 4.39 (t, J=10.0 Hz, 1H), 4.08-3.99 (m, 1H), 3.77 (s, 3H), 3.27 (s, 2H), 2.77 (d, J=5.8 Hz, 2H), 2.56 (d, J=5.7 Hz, 2H), 2.30 (s, 3H).

Example 102

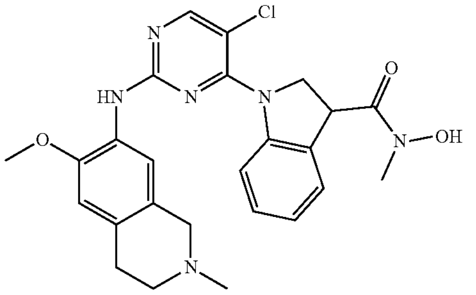 [SMILES: COc1cc2c(cc1Nc1ncc(Cl)c(N3CC(C(=O)N(C)O)c4ccccc43)n1)CN(C)CC2]

1-(5-Chloro-24(6-methoxy-2-methyl-1,2,3,4-tetrahydroisoquinolin-7-yl)amino)pyrimidin-4-yl)-N-hydroxy-N-methylindoline-3-carboxamide The same procedures as Example 101, using N-methylhydroxylamine in place of hydroxylamine hydrochloride in Step 2. LC-MS (ESI) m/z: 495 $[M+H]^+$. $^1H$ NMR (400 MHz, DMSO-$d_6$) δ 10.28 (s, 1H), 8.25 (s, 1H), 8.01 (s, 1H), 7.51 (s, 1H), 7.38 (dd, J=19.3, 7.6 Hz, 2H), 7.11 (t, J=7.5 Hz, 1H), 6.95 (t, J=7.4 Hz, 1H), 6.75 (s, 1H), 4.90-4.79 (m, 1H), 4.51 (dd, J=10.4, 6.4 Hz, 1H), 4.38 (t, J=9.9 Hz, 1H), 3.77 (s, 3H), 3.28 (s, 2H), 3.18 (s, 3H), 2.76 (d, J=5.7 Hz, 2H), 2.56 (d, J=5.7 Hz, 2H), 2.30 (s, 3H).

Example 103

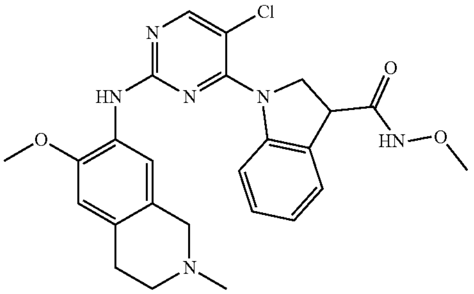

1-(5-Chloro-2-((6-methoxy-2-methyl-1,2,3,4-tetrahydroisoquinolin-7-yl)amino)pyrimidin-4-yl)-N-methoxyindoline-3-carboxamide The same procedures as Example 101, using O-methylhydroxylamine hydrochloride in place of hydroxylamine hydrochloride in Step 2. LC-MS (ESI) m/z: 495 $[M+H]^+$. $^1H$ NMR (400 MHz, DMSO-$d_6$) δ 11.60 (s, 1H), 8.25 (s, 1H), 8.05 (s, 1H), 7.50-7.39 (m, 2H), 7.26 (d, J=7.5 Hz, 1H), 7.12 (t, J=7.8 Hz, 1H), 6.97 (t, J=7.1 Hz, 1H), 6.75 (s, 1H), 4.51 (dd, J=10.4, 6.7 Hz, 1H), 4.39 (t, J=10.0 Hz, 1H), 4.04-3.96 (m, 1H), 3.77 (s, 3H), 3.64 (s, 3H), 3.28 (s, 2H), 2.78 (s, 2H), 2.56 (d, J=5.9 Hz, 2H), 2.30 (s, 3H).

Example 163

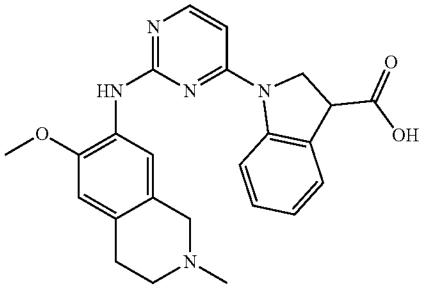 [SMILES: COc1cc2c(cc1Nc1nccc(N3CC(C(=O)O)c4ccccc43)n1)CN(C)CC2]

1-(2-((6-Methoxy-2-methyl-1,2,3,4-tetrahydroisoquinolin-7-yl)amino)pyrimidin-4-yl)indoline-3-carboxylic acid Step 1: A mixture of a mixture of methyl 1-(5-chloro-2-((6-methoxy-2-methyl-1,2,3,4-tetrahydroisoquinolin-7-yl)amino)pyrimidin-4-yl)indoline-3-carboxylate and isopropyl 1-(5-chloro-2-((6-methoxy-2-methyl-1,2,3,4-tetrahydroisoquinolin-7-yl)amino)pyrimidin-4-yl)indoline-3-carboxylate (100 mg) and Pd/C (18.2 mg, 0.171 mmol) in methanol (10 mL) was stirred for 16 hours at room temperature under $H_2$ and filtered through a pad of Celite. The solid cake was washed with EA (20 mL), and the filtrate was concentrated in vacuo to provide a crude mixture of methyl 1-(2-((6-methoxy-2-methyl-1,2,3,4-tetrahydroisoquinolin-7-yl)amino)pyrimidin-4-yl)indoline-3-carboxylate and isopropyl 1-(2-((6-methoxy-2-methyl-1,2,3,4-tetrahydroisoquinolin-7-yl)amino)pyrimidin-4-yl)indoline-3-carboxylate, which was used in next step without purifications. LC-MS (ESI) m/z: 446 (methyl ester), 474 (isopropyl ester) $[M+H]^+$.

Step 2: The same procedure as Step 3 of Alternative synthetic method of Example 32, using a mixture of methyl 1-(2-((6-methoxy-2-methyl-1,2,3,4-tetrahydroisoquinolin-7-yl)amino)pyrimidin-4-yl)indoline-3-carboxylate and isopropyl 1-(2-((6-methoxy-2-methyl-1,2,3,4-tetrahydroisoquinolin-7-yl)amino)pyrimidin-4-yl)indoline-3-carboxylate in place of a mixture of methyl 1-(5-chloro-2-((6-methoxy-2-methyl-1,2,3,4-tetrahydroisoquinolin-7-yl)amino)pyrimidin-4-yl)indoline-3-carboxylate and isopropyl 1-(5-chloro-2-((6-methoxy-2-methyl-1,2,3,4-tetrahydroisoquinolin-7-yl)amino)pyrimidin-4-yl)indoline-3-carboxylate. LC-MS (ESI) m/z: 432 $[M+H]^+$. $^1H$ NMR (400 MHz, DMSO-$d_6$) δ 8.29 (s, 1H), 8.14 (dd, J=16.9, 6.9 Hz, 2H), 7.82 (s, 1H), 7.62 (s, 1H), 7.43 (d, J=7.3 Hz, 1H), 7.08 (t, J=7.7 Hz, 1H), 6.92 (t, J=7.3 Hz, 1H), 6.80 (s, 1H), 6.27 (d, J=5.8 Hz, 1H), 4.32 (dd, J=9.8, 5.0 Hz, 1H), 4.17-4.03 (m, 2H), 3.80 (d, J=9.1 Hz, 3H), 3.28 (m, 2H), 2.84 (t, J=5.6 Hz, 2H), 2.66 (t, J=5.7 Hz, 2H), 2.36 (s, 3H).

Example 104

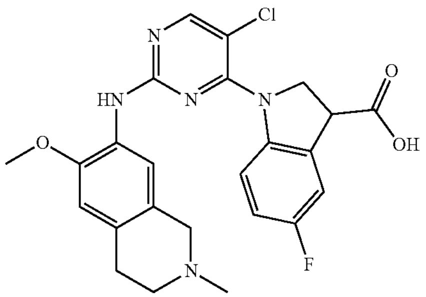 [SMILES: COc1cc2c(cc1Nc1ncc(Cl)c(N3CC(C(=O)O)c4cc(F)ccc43)n1)CN(C)CC2]

1-(5-Chloro-24(6-methoxy-2-methyl-1,2,3,4-tetrahydroisoquinolin-7-yl)amino)pyrimidin-4-yl)-5-fluoroindoline-3-carboxylic acid The same procedures as Alternative synthetic method of Example 32, using Int. E22 in place of Int. E17 in Step 1. LC-MS (ESI) m/z: 484 $[M+H]^+$. $^1H$ NMR (500 MHz, DMSO-$d_6$) δ 8.23 (s, 2H), 8.02 (s, 1H), 7.49 (s, 1H), 7.40 (dd, J=8.6, 4.7 Hz, 1H), 7.21 (d, J=6.7 Hz, 1H), 6.92 (dd, J=8.9, 6.8 Hz, 1H), 6.78 (s, 1H), 4.60 (dd, J=10.5, 6.2 Hz, 1H), 4.39 (t, J=10.1 Hz, 1H), 4.22-4.10 (m, 1H), 3.77 (s, 3H), 3.42 (s, 2H), 2.82 (d, J=5.5 Hz, 2H), 2.69 (t, J=19.4 Hz, 2H), 2.40 (s, 3H).

Example 105

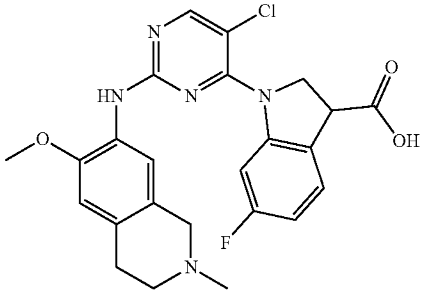

1-(5-Chloro-24(6-methoxy-2-methyl-1,2,3,4-tetrahydroisoquinolin-7-yl)amino)pyrimidin-4-yl)-6-fluoroindoline-3-carboxylic acid The same procedures as Alternative synthetic method of Example 32, using Int. E23 in place of Int. E17 in Step 1. LC-MS (ESI) m/z: 484 $[M+H]^+$. $^1H$ NMR (400 MHz, DMSO-$d_6$) δ 8.33-8.25 (m, 1H), 8.20 (d, J=6.6 Hz, 1H), 7.42 (s, 1H), 7.36 (dd, J=14.4, 6.5 Hz, 1H), 7.20 (d, J=10.7 Hz, 1H), 6.85-6.65 (m, 2H), 4.61 (dd, J=10.4, 6.1 Hz, 1H), 4.42 (t, J=10.0 Hz, 1H), 4.21-4.12 (m, 1H), 3.79 (d, J=3.1 Hz, 1H), 3.75 (d, J=10.4 Hz, 3H), 3.36-3.33 (m, 1H), 2.79 (t, J=5.5 Hz, 2H), 2.63 (t, J=5.1 Hz, 2H), 2.31 (d, J=20.7 Hz, 3H).

Example 106

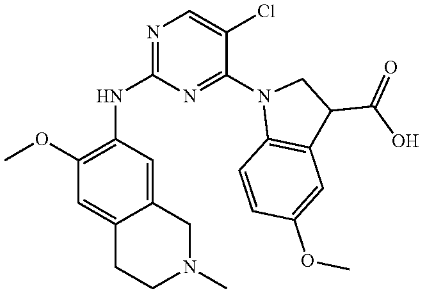 [SMILES: COc1ccc2c(c1)C(C(=O)O)CN2c1nc(Nc2cc3c(cc2OC)CCN(C)C3)ncc1Cl]

1-(5-Chloro-2-((6-methoxy-2-methyl-1,2,3,4-tetrahydroisoquinolin-7-yl)amino)pyrimidin-4-yl)-5-methoxyindoline-3-carboxylic acid The same procedures as Alternative synthetic method of Example 32, using Int. E24 in place of Int. E17 in Step 1. LC-MS (ESI) m/z: 496 $[M+H]^+$. $^1H$ NMR (400 MHz, DMSO-$d_6$) δ 8.20 (s, 1H), 7.96 (s, 1H), 7.50 (s, 1H), 7.39 (d, J=8.8 Hz, 1H), 6.96 (d, J=2.0 Hz, 1H), 6.83-6.58 (m, 1H), 4.69-4.50 (m, 1H), 4.40 (s, 1H), 4.25 (d, J=6.2 Hz, 1H), 3.76 (d, J=11.4 Hz, 6H), 3.41 (s, 1H), 2.79 (d, J=5.6 Hz, 2H), 2.64 (d, J=5.4 Hz, 2H), 2.35 (s, 3H).

Example 107

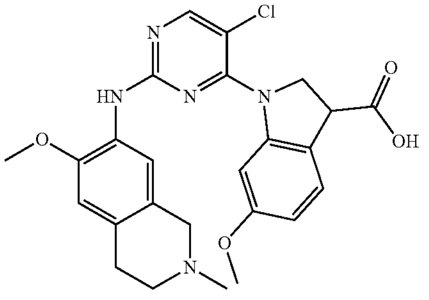

1-(5-Chloro-2-((6-methoxy-2-methyl-1,2,3,4-tetrahydroisoquinolin-7-yl)amino)pyrimidin-4-yl)-6-methoxyindoline-3-carboxylic acid The same procedures as Alternative synthetic method of Example 32, using Int. E25 in place of Int. E17 in Step 1.

LC-MS (ESI) m/z: 496 $[M+H]^+$. $^1H$ NMR (500 MHz, DMSO-$d_6$) δ 8.45 (s, 1H), 8.14 (s, 1H), 7.51 (d, J=11.9 Hz, 1H), 7.39 (dd, J=8.3, 2.3 Hz, 1H), 7.19 (d, J=9.4 Hz, 1H), 7.03 (s, 1H), 6.76 (d, J=8.4 Hz, 1H), 4.69 (d, J=2.6 Hz, 1H), 4.62 (t, J=10.0 Hz, 1H), 4.36-4.22 (m, 2H), 4.10 (d, J=11.4 Hz, 1H), 3.85 (d, J=1.7 Hz, 3H), 3.70 (d, J=3.6 Hz, 4H), 3.33 (s, 1H), 3.14 (s, 1H), 3.07 (d, J=17.0 Hz, 1H), 2.94 (s, 3H).

Example 108

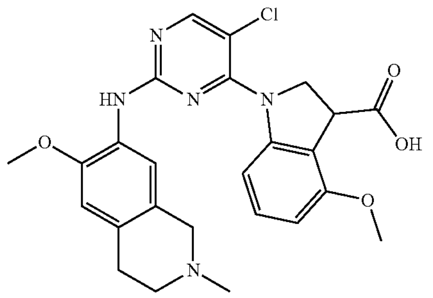 [SMILES: COc1cc2c(cc1Nc1ncc(Cl)c(N3CC(C(=O)O)c4c(OC)cccc43)n1)CN(C)CC2]

1-(5-Chloro-2-((6-methoxy-2-methyl-1,2,3,4-tetrahydroisoquinolin-7-yl)amino)pyrimidin-4-yl)-4-methoxyindoline-3-carboxylic acid The same procedures as Alternative synthetic method of Example 32, using Int. E26 in place of Int. E17 in Step 1. LC-MS (ESI) m/z: 496 $[M+H]^+$. $^1H$ NMR (400 MHz, DMSO-$d_6$) δ 8.24 (s, 1H), 8.00 (s, 1H), 7.52 (s, 1H), 7.11 (t, J=8.1 Hz, 1H), 7.03 (d, J=8.0 Hz, 1H), 6.75 (s, 1H), 6.63 (d, J=8.1 Hz, 1H), 4.51 (t, J=10.2 Hz, 1H), 4.32 (dd, J=10.6, 4.8 Hz, 1H), 4.10 (dd, J=9.7, 4.7 Hz, 1H), 3.77 (s, 7H), 2.78 (t, J=5.6 Hz, 2H), 2.58 (t, J=5.7 Hz, 2H), 2.49-2.48 (m, 1H), 2.33 (s, 3H).

Example 109

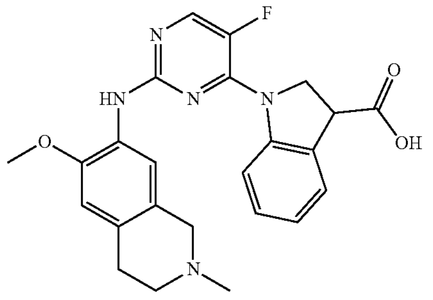 [SMILES: COc1cc2c(cc1Nc1ncc(F)c(N3CC(C(=O)O)c4ccccc43)n1)CN(C)CC2]

1-(5-Fluoro-2-((6-methoxy-2-methyl-1,2,3,4-tetrahydroisoquinolin-7-yl)amino)pyrimidin-4-yl)indoline-3-carboxylic acid The same procedures as Alternative synthetic method of Example 32, using 2,4-dichloro-5-fluoropyrimidine in place of 2,4,5-trichloropyrimidine in Step 1. LC-MS (ESI) m/z: 450 $[M+H]^+$. $^1H$ NMR (400 MHz, DMSO-$d_6$) δ 8.19 (d, J=5.8 Hz, 1H), 7.90 (d, J=19.6 Hz, 1H), 7.85 (d, J=8.2 Hz, 1H), 7.50 (s, 1H), 7.40 (d, J=7.4 Hz, 1H), 7.10 (t, J=7.6 Hz, 1H), 6.98 (t, J=7.4 Hz, 1H), 6.78 (s, 1H), 4.53 (dt, J=10.5, 5.3 Hz, 1H), 4.41-4.31 (m, 1H), 4.27 (dd, J=9.8, 5.7 Hz, 1H), 3.77 (s, 3H), 3.41 (s, 2H), 2.82 (t, J=5.5 Hz, 2H), 2.64 (t, J=5.9 Hz, 2H), 2.35 (s, 3H).

Example 110

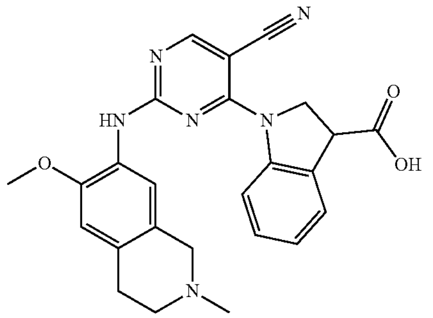 [SMILES: COc1cc2c(cc1Nc1ncc(C#N)c(N3CC(C(=O)O)c4ccccc43)n1)CN(C)CC2]

1-(5-Cyano-2-((6-methoxy-2-methyl-1,2,3,4-tetrahydroisoquinolin-7-yl)amino)pyrimidin-4-yl)indoline-3-carboxylic acid The same procedures as Alternative synthetic method of Example 32, using 2,4-dichloropyrimidine-5-carbonitrile in place of 2,4,5-trichloropyrimidine in Step 1. LC-MS (ESI) m/z: 457 $[M+H]^+$. $^1H$ NMR (500 MHz, DMSO-$d_6$) δ 9.13 (s, 1H), 8.54 (s, 1H), 7.41 (d, J=65.9 Hz, 2H), 6.98 (d, J=75.7 Hz, 3H), 4.45 (s, 1H), 4.20 (s, 2H), 3.70 (s, 3H), 3.16-3.08 (m, 2H), 2.91 (s, 2H), 2.65 (s, 2H), 2.35 (s, 3H).

Example 111

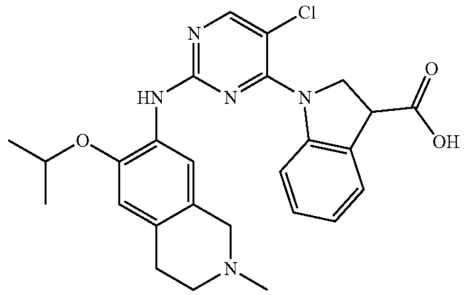 [SMILES: CC(C)Oc1cc2c(cc1Nc1ncc(Cl)c(N3CC(C(=O)O)c4ccccc43)n1)CN(C)CC2]

1-(5-Chloro-2-((6-isopropoxy-2-methyl-1,2,3,4-tetrahydroisoquinolin-7-yl)amino)pyrimidin-4-yl)indoline-3-carboxylic acid The same procedures as Alternative synthetic method of Example 32, using Int. W9 in place of Int. W1 in Step 2. LC-MS (ESI) m/z: 494 $[M+H]^+$.

Example 112

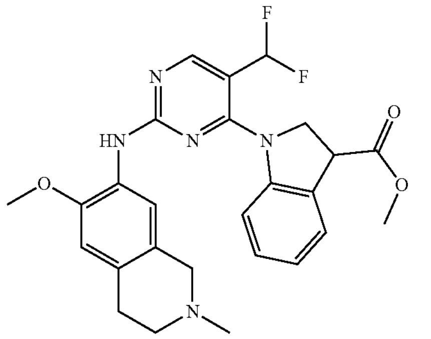 [SMILES: COC(=O)C1CN(c2nc(Nc3cc4c(cc3OC)CCN(C)C4)ncc2C(F)F)c2ccccc21]

Methyl 1-(5-(difluoromethyl)-2-(((6-methoxy-2-methyl-1,2,3,4-tetrahydroisoquinolin-7-yl)amino)pyrimidin-4-yl)indoline-3-carboxylate Step 1: To a solution of 2,4-dichloropyrimidine-5-carbaldehyde (300 mg, 1.70 mmol) in DCM (5 mL) was added N-ethyl-N-(trifluoro-sulfanyl)ethanamine (1.37 g, 8.48 mmol) dropwise at 0° C. The reaction mixture was stirred at 25° C. for 16 hours, cooled to 0° C., basified to pH~8 with saturated sodium bicarbonate aqueous solution, and extracted with dichloromethane (5 mL×3). The organic phases were dried over anhydrous sodium sulfate and filtered. The filtrate was concentrated in vacuo to provide 2,4-dichloro-5-(difluoromethyl)pyrimidine as light yellow oil (303 mg, 85% yield). LC-MS (ESI) m/z: 335 $[M+H]^+$.

Step 2: Int. E17 (115.8 mg, 0.653 mmol) and 2,4-dichloro-5-(difluoromethyl)pyrimidine (130 mg, 0.653 mmol) were used under Condition A3 to provide methyl 1-(2-chloro-5-(difluoromethyl)pyrimidin-4-yl)indoline-3-carboxylate (160 mg, 68.5% yield) as light yellow solid, after purification by flash column chromatography on silica gel (PE/EA=10/1). LC-MS (ESI) m/z: 340 $[M+H]^+$.

Step 3: Methyl 1-(2-chloro-5-(difluoromethyl)pyrimidin-4-yl)indoline-3-carboxylate (159 mg, 0.445 mmol) and Int. W1 (102.6 mg, 0.534 mmol) was used under Condition B3 to provide methyl 1-(5-(difluoromethyl)-2-((6-methoxy-2-methyl-1,2,3,4-tetrahydroisoquinolin-7-yl)amino)pyrimidin-4-yl)indoline-3-carboxylate (30 mg, 10.9% yield) as light yellow solid, after purification by flash column chromatography on silica gel (PE/EA=10/1). LC-MS (ESI) m/z: 496 $[M+H]^+$. $^1$H NMR (500 MHz, DMSO-$d_6$) δ 8.44 (s, 1H), 8.39 (s, 1H), 7.58 (s, 1H), 7.42 (s, 1H), 7.35 (d, J=7.4 Hz, 1H), 7.12 (d, J=8.6 Hz, 1H), 7.00 (t, J=7.3 Hz, 1H), 6.84 (d, J=10.3 Hz, 1H), 4.47-4.39 (m, 2H), 4.34 (t, J=9.6 Hz, 1H), 3.76 (s, 3H), 3.69 (s, 3H), 3.56 (s, 2H), 2.88 (m, 4H), 2.49-2.46 (s, 3H).

Example 113

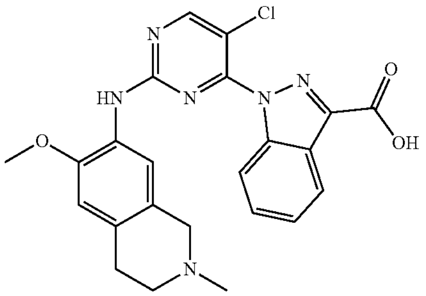 [SMILES: COc1cc2c(cc1Nc1ncc(Cl)c(-n3nc(C(=O)O)c4ccccc43)n1)CN(C)CC2]

1-(5-Chloro-24(6-methoxy-2-methyl-1,2,3,4-tetrahydroisoquinolin-7-yl)amino)pyrimidin-4-yl)-1H-indazole-3-carboxylic acid The same procedures as Alternative synthetic method of Example 32, using methyl 1H-indazole-3-carboxylate in place of Int. E17 in Step 1. LC-MS (ESI) m/z: 465 $[M+H]^+$. $^1$H NMR (400 MHz, DMSO-$d_6$) δ 8.87 (s, 1H), 8.63 (s, 1H), 8.38-8.22 (m, 2H), 7.99 (d, J=8.1 Hz, 1H), 7.55-7.28 (m, 3H), 6.83 (s, 1H), 3.77 (s, 3H), 3.39-3.38 (m, 2H), 2.82 (d, J=5.3 Hz, 2H), 2.61 (t, J=5.7 Hz, 2H), 2.33 (s, 3H).

Example 34

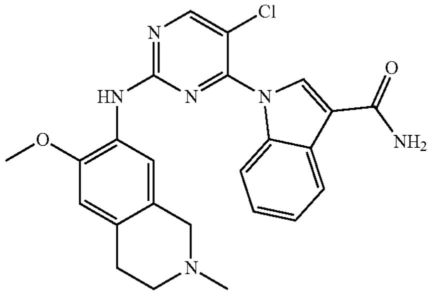 [SMILES: COc1cc2c(cc1Nc1ncc(Cl)c(-n3cc(C(N)=O)c4ccccc43)n1)CN(C)CC2]

1-(5-Chloro-24(6-methoxy-2-methyl-1,2,3,4-tetrahydroisoquinolin-7-yl)amino)pyrimidin-4-yl)-1H-indole-3-carboxamide Step 1: 1H-indole-3-carboxylic acid (500 mg, 3.10 mmol) and 2,4,5-trichloropyrimidine (625.99 mg, 3.41 mmol) were used under Condition A1 to provide 1-(2,5-dichloropyrimidin-4-yl)indole-3-carboxylic acid (200 mg, 19.88% yield, 95% purity) as yellow solid, after purification by flash column chromatography on silica gel (DCM/MeOH, 50/1). LC-MS (ESI) m/z: 308.1 $[M+H]^+$.

Step 2&3: The same procedures as conditions as Step 1 & 2 of Example 33, using 1-(2,5-dichloropyrimidin-4-yl)indole-3-carboxylic acid in place of 1-(2,5-dichloropyrimidin-4-yl)indoline-3-carboxylic acid. LC-MS (ESI) m/z: 463.1 $[M+H]^+$. $^1$H NMR (400 MHz, DMSO-$d_6$) δ 8.87 (s, 1H), 8.71 (s, 1H), 8.49 (s, 1H), 8.29-8.15 (m, 1H), 7.78-7.64 (m, 2H), 7.39 (s, 1H), 7.31-7.21 (m, 2H), 7.11 (s, 1H), 6.79 (s, 1H), 3.79 (s, 3H), 3.33 (d, J=5.8 Hz, 2H), 2.85-2.70 (m, 2H), 2.54 (t, J=5.9 Hz, 2H), 2.29 (s, 3H).

Example 114

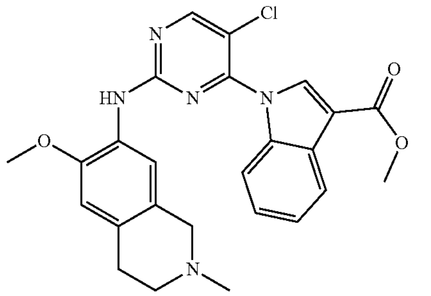 [SMILES: COC(=O)c1cn(-c2nc(Nc3cc4c(cc3OC)CCN(C)C4)ncc2Cl)c2ccccc12]

Methyl 1-(5-chloro-24(6-methoxy-2-methyl-1,2,3,4-tetrahydroisoquinolin-7-yl)amino)pyrimidin-4-yl)-1H-indole-3-carboxylate Example 35

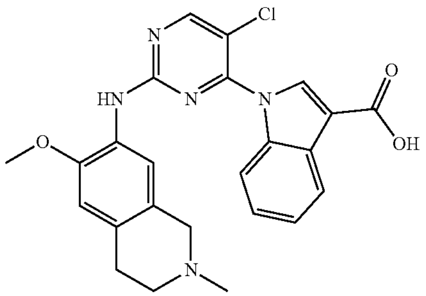 [SMILES: COc1cc2c(cc1Nc1ncc(Cl)c(-n3cc(C(=O)O)c4ccccc43)n1)CN(C)CC2]

1-(5-Chloro-24(6-methoxy-2-methyl-1,2,3,4-tetrahydroisoquinolin-7-yl)amino)pyrimidin-4-yl)-1H-indole-3-carboxylic acid Step 1: Methyl 1H-indole-3-carboxylate (1 g, 5.71 mmol) and 2,4,5-trichloropyrimidine (1.15 g, 6.28 mmol) were used under Condition A1 to provide methyl 1-(2,5-dichloropyrimidin-4-yl)-1H-indole-3-carboxylate (800 mg, 43.5% yield) as light yellow solid, after purification by flash column chromatography on silica gel (DCM/MeOH=100/1). LC-MS (ESI) m/z: 322 $[M+H]^+$.

Step 2: Methyl 1-(2,5-dichloropyrimidin-4-yl)-1H-indole-3-carboxylate (200 mg, 0.621 mmol) and Int. W1 (143.2 mg, 0.745 mmol) were used under Condition B3 to provide methyl 1-(5-chloro-2-((6-methoxy-2-methyl-1,2,3,4-tetrahydroisoquinolin-7-yl)amino)pyrimidin-4-yl)-1H-indole-3-carboxylate (138 mg, 44.2% yield) as white solid, after purification by flash column chromatography on silica gel (DCM/MeOH=100/1). LC-MS (ESI) m/z: 478 $[M+H]^+$. $^1H$ NMR (400 MHz, DMSO-$d_6$) δ 8.95 (s, 1H), 8.72 (s, 1H), 8.48 (s, 1H), 8.09 (dd, J=6.4, 2.3 Hz, 1H), 7.76 (dd, J=6.6, 2.1 Hz, 1H), 7.47-7.24 (m, 3H), 6.79 (s, 1H), 3.87 (s, 3H), 3.78 (s, 3H), 3.33 (s, 2H), 2.78 (t, J=5.7 Hz, 2H), 2.55 (d, J=5.7 Hz, 2H), 2.30 (s, 3H).

Step 3: A mixture of methyl 1-(5-chloro-2-((6-methoxy-2-methyl-1,2,3,4-tetrahydroisoquinolin-7-yl)amino)pyrimidin-4-yl)-1H-indole-3-carboxylate (454 mg, 0.950 mmol), AcOH (456 mg, 7.60 mmol) and HCl aqueous solution (6 N, 36 mL) was stirred at 50° C. for 16 hours, and purified by prep-HPLC (MeCN/0.04% formic acid) to provide 1-(5-chloro-2-((6-methoxy-2-methyl-1,2,3,4-tetrahydroisoquinolin-7-yl)amino)pyrimidin-4-yl)-1H-indole-3-carboxylic acid (33.1 mg, 7.5% yield) as white solid. LC-MS (ESI) m/z: 464.2 $[M+H]^+$. $^1H$ NMR (400 MHz, DMSO-$d_6$) δ 8.88 (s, 1H), 8.69 (s, 1H), 8.33 (d, J=20.1 Hz, 2H), 8.18 (s, 1H), 7.75 (d, J=7.8 Hz, 1H), 7.37 (s, 1H), 7.28 (s, 2H), 6.80 (s, 1H), 3.79 (s, 3H), 3.34-3.33 (m, 2H), 2.78 (s, 2H), 2.55 (s, 2H), 2.30 (s, 3H)

Example 116

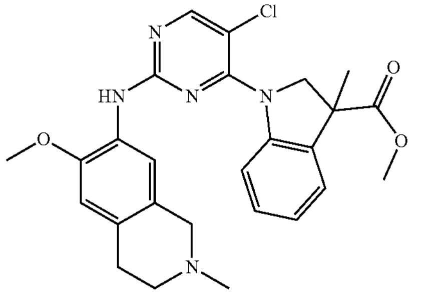 [SMILES: COC(=O)C1(C)CN(c2nc(Nc3cc4c(cc3OC)CCN(C)C4)ncc2Cl)c2ccccc21]

Methyl 1-(5-chloro-24(6-methoxy-2-methyl-1,2,3,4-tetrahydroisoquinolin-7-yl)amino)pyrimidin-4-yl)-3-methylindoline-3-carboxylate Example 117

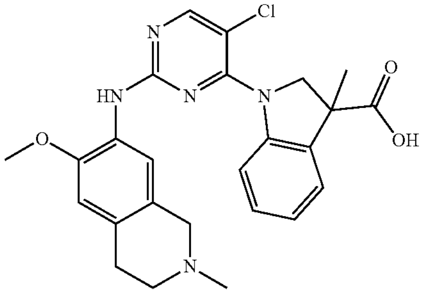 [SMILES: COc1cc2c(cc1Nc1ncc(Cl)c(N3CC(C)(C(=O)O)c4ccccc43)n1)CN(C)CC2]

1-(5-Chloro-24(6-methoxy-2-methyl-1,2,3,4-tetrahydroisoquinolin-7-yl)amino)pyrimidin-4-yl)-3-methylindoline-3-carboxylic acid Step 1: A mixture of Int. E18 (158 mg, 0.826 mmol), 2,4,5-trichloropyrimidine (197.0 mg, 1.07 mmol) and DIPEA (427.2 mg, 3.30 mmol) in n-butanol (4 mL) was stirred at 100° C. for 12 hours, cooled to room temperature and diluted with DCM/MeOH (10/1, 100 mL) and water (30 mL). The aqueous phase was separated and extracted with DCM/MeOH (10/1, 30 mL×3). The combined organic phases were washed with brine (40 mL), dried over anhydrous sodium sulfate and filtered. The filtrate was concentrated in vacuo, and the residue was purified by flash column chromatography on silica gel (EA/PE: 30%) to provide methyl 1-(2,5-dichloropyrimidin-4-yl)-3-methylindoline-3-carboxylate (257 mg, 89.2% yield) as light yellow solid, after purification by flash column chromatography on silica gel (EA/PE: 30%). LC-MS (ESI) m/z: 338 $[M+H]^+$.

Step 2: A mixture of methyl 1-(2,5-dichloropyrimidin-4-yl)-3-methylindoline-3-carboxylate (50 mg, 0.148 mmol), Int. W1 (40.6 mg, 0.177 mmol) and $TsOH \cdot H_2O$ (28.1 mg, 0.148 mmol) in isopropanol (3 mL) was stirred at 120° C. for 12 hours, cooled to room temperature, neutralized with saturated $NaHCO_3$ aqueous solution (4 mL) and extracted with DCM (20 mL×3). The organic phases were dried over anhydrous sodium sulfate and filtered. The filtrate was concentrated in vacuo, and the residue was purified by prep-HPLC (MeCN/10 mM $NH_4HCO_3$, 0.025% $NH_3H_2O$) to provide methyl 1-(5-chloro-2-((6-methoxy-2-methyl-1,2,3,4-tetrahydroisoquinolin-7-yl)amino)pyrimidin-4-yl)-3-methylindoline-3-carboxylate (20 mg, 27.4% yield) as yellow solid. LC-MS (ESI) m/z: 494 $[M+H]^+$. $^1H$ NMR (400 MHz, DMSO-$d_6$) δ 8.27 (s, 1H), 8.08 (s, 1H), 7.49 (s, 1H), 7.35 (dd, J=12.7, 7.8 Hz, 2H), 7.16 (t, J=7.8 Hz, 1H), 7.00 (t, J=7.5 Hz, 1H), 6.75 (s, 1H), 4.75 (d, J=10.8 Hz, 1H), 4.09 (d, J=10.8 Hz, 1H), 3.76 (s, 3H), 3.63 (s, 3H), 3.29 (s, 2H), 2.77 (t, J=5.5 Hz, 2H), 2.56 (d, J=5.8 Hz, 2H), 2.31 (s, 3H), 1.56 (s, 3H).

Step 3: A mixture of methyl 1-(5-chloro-2-((6-methoxy-2-methyl-1,2,3,4-tetrahydroisoquinolin-7-yl)amino)pyrimidin-4-yl)-3-methylindoline-3-carboxylate (20 mg, 0.040 mmol) and lithium hydroxide aqueous solution (2N, 0.1 mL) in THF (2.5 mL) was stirred for 3 hours at room temperature, adjusted to pH-5 with formic acid and extracted with DCM (15 mL×3). The combined organic phases were dried over anhydrous sodium sulfate and filtered. The filtrate was concentrated in vacuo, and the residue was purified by prep-HPLC (MeCN/0.1% formic acid) to provide 1-(5-chloro-2-((6-methoxy-2-methyl-1,2,3,4-tetrahydroisoquinolin-7-yl)amino)pyrimidin-4-yl)-3-methylindoline-3-carboxylic acid as white solid (10.7 mg, 55% yield). LC-MS (ESI) m/z: 480 $[M+H]^+$. $^1H$ NMR (400 MHz, DMSO-$d_6$) δ 8.26 (s, 1H), 8.04 (s, 1H), 7.52 (s, 1H), 7.36 (t, J=8.0 Hz, 2H), 7.15 (t, J=7.7 Hz, 1H), 6.99 (t, J=7.4 Hz, 1H), 6.76 (s, 1H), 4.76 (d, J=10.6 Hz, 1H), 4.04 (d, J=10.6 Hz, 1H), 3.35 (s, 2H), 2.79 (t, J=5.5 Hz, 2H), 2.61 (t, J=5.7 Hz, 2H), 2.34 (s, 3H), 1.53 (s, 3H).

Examples 118 & 119

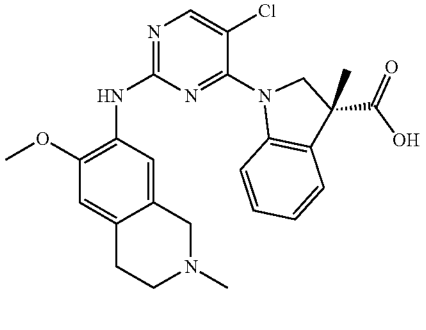

-continued

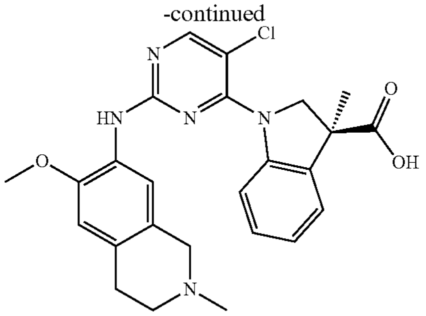

(R)-1-(5-chloro-24(6-methoxy-2-methyl-1,2,3,4-tetrahydroisoquinolin-7-yl)amino)pyrimidin-4-yl)-3-methylindoline-3-carboxylic acid & (S)-1-(5-chloro-24(6-methoxy-2-methyl-1,2,3,4-tetrahydroisoquinolin-7-yl)amino)pyrimidin-4-yl)-3-methylindoline-3-carboxylic acid Synthesized after chiral-separation of the racemic 1-(5-chloro-2-((6-methoxy-2-methyl-1,2,3,4-tetrahydroisoquinolin-7-yl)amino)pyrimidin-4-yl)-3-methylindoline-3-carboxylic acid. The stereochemistry was not confirmed, and two products were arbitrarily assigned.

LC-MS (ESI) m/z: 480 $[M+H]^+$. $^1H$ NMR (400 MHz, DMSO-$d_6$) δ 8.25 (s, 1H), 8.00 (s, 1H), 7.52 (s, 1H), 7.37 (t, J=7.3 Hz, 2H), 7.13 (t, J=7.7 Hz, 1H), 6.99 (t, J=7.4 Hz, 1H), 6.75 (s, 1H), 4.77 (d, J=10.7 Hz, 1H), 4.02 (d, J=10.7 Hz, 1H), 3.77 (s, 3H), 3.11-3.01 (m, 2H), 2.77 (d, J=5.9 Hz, 2H), 2.57 (t, J=5.7 Hz, 2H), 2.32 (s, 3H), 1.52 (s, 3H). Chiral-HPLC retention time: 1.079 min; ee value: >99%.

LC-MS (ESI) m/z: 480 $[M+H]^+$. $^1H$ NMR (400 MHz, DMSO-$d_6$) δ 8.26 (s, 1H), 8.02 (s, 1H), 7.53 (s, 1H), 7.37 (t, J=7.4 Hz, 2H), 7.14 (t, J=8.0 Hz, 1H), 7.00 (t, J=7.5 Hz, 1H), 6.76 (s, 1H), 4.77 (d, J=10.7 Hz, 1H), 4.04 (d, J=10.5 Hz, 1H), 3.77 (s, 3H), 3.07-2.97 (m, 2H), 2.79 (s, 2H), 2.59 (d, J=5.9 Hz, 2H), 2.33 (s, 3H), 1.53 (s, 3H). Chiral-HPLC retention time: 1.501 min; ee value: >99%.

SFC Separation Conditions:

Instrument: SFC-150 (Thar, Waters)
Column: IG 20*250 mm, 10 um (Daicel)
Column temperature: 35° C.
Mobile phase: $CO_2$/EtOH (0.5% methanol/ammonia)=45/55
Flow rate: 120 g/min
Back pressure: 100 bar
Detection wavelength: 214 nm
Cycle time: 3 min

Example 120

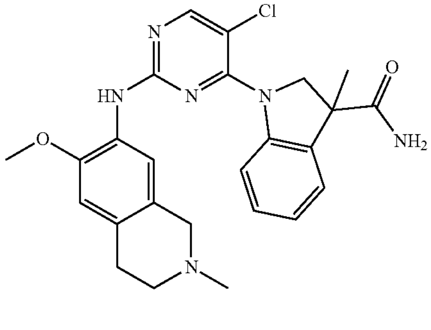 [SMILES: COc1cc2c(cc1Nc1ncc(Cl)c(N3CC(C)(C(N)=O)c4ccccc43)n1)CN(C)CC2]

1-(5-Chloro-2-((6-methoxy-2-methyl-1,2,3,4-tetrahydroisoquinolin-7-yl)amino)pyrimidin-4-yl)-3-methylindoline-3-carboxamide Step 1: Int. E19 (148 mg, 0.798 mmol) and 2,4,5-trichloropyrimidine (146.4 mg, 0.798 mmol) were used under Condition A3 to provide 1-(2,5-dichloropyrimidin-4-yl)-3-methylindoline-3-carboxamide (199 mg, 69.5% yield) as white solid, after purification by flash column chromatography on silica gel (EA/PE: 1/5). LC-MS (ESI) m/z: 323 $[M+H]^+$.

Step 2: 1-(2,5-Dichloropyrimidin-4-yl)-3-methylindoline-3-carboxamide (199 mg, 0.585 mmol) and Int. W1 (135.0 mg, 0.702 mmol) were used under Condition B3 to provide 1-(5-chloro-2-((6-methoxy-2-methyl-1,2,3,4-tetrahydroisoquinolin-7-yl)amino)pyrimidin-4-yl)-3-methylindoline-3-carboxamide (82.5 mg, 28.3% yield) as white solid, after purification by prep-HPLC (MeCN/10 mM $NH_4HCO_3$). LC-MS (ESI) m/z: 479 [M+I-1]'. $^1H$ NMR (500 MHz, DMSO-$d_6$) δ 8.25 (s, 1H), 7.99 (s, 1H), 7.52 (s, 1H), 7.46 (d, J=7.5 Hz, 1H), 7.37 (d, J=8.1 Hz, 1H), 7.28 (s, 1H), 7.18 (s, 1H), 7.13 (t, J=7.7 Hz, 1H), 7.00 (t, J=7.4 Hz, 1H), 6.75 (s, 1H), 4.81 (d, J=10.4 Hz, 1H), 3.97 (d, J=10.4 Hz, 1H), 3.77 (s, 3H), 3.29 (d, J=5.1 Hz, 2H), 2.77 (t, J=5.7 Hz, 2H), 2.55 (t, J=5.8 Hz, 2H), 2.31 (s, 3H), 1.53 (s, 3H).

Example 121

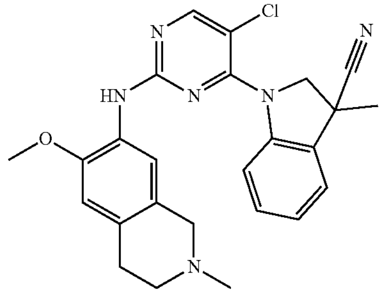

1-(5-Chloro-2-((6-methoxy-2-methyl-1,2,3,4-tetrahydroisoquinolin-7-yl)amino)pyrimidin-4-yl)-3-methylindoline-3-carbonitrile The same procedures as Example 99, using 1-(2,5-dichloropyrimidin-4-yl)-3-methylindoline-3-carboxamide in place of 1-(2,5-dichloropyrimidin-4-yl)indoline-3-carboxamide. LC-MS (ESI) m/z: 461 $[M+H]^+$. $^1H$ NMR (500 MHz, DMSO-$d_6$) δ 8.33 (s, 1H), 8.16 (s, 1H), 7.60-7.43 (m, 2H), 7.33 (d, J=8.0 Hz, 1H), 7.26 (t, J=7.7 Hz, 1H), 7.09 (t, J=7.4 Hz, 1H), 6.75 (s, 1H), 4.65 (d, J=10.9 Hz, 1H), 4.27 (d, J=10.9 Hz, 1H), 3.77 (d, J=5.8 Hz, 3H), 3.29 (s, 2H), 2.77 (t, J=5.7 Hz, 2H), 2.55 (t, J=5.8 Hz, 2H), 2.31 (s, 3H), 1.73 (s, 3H).

Example 122

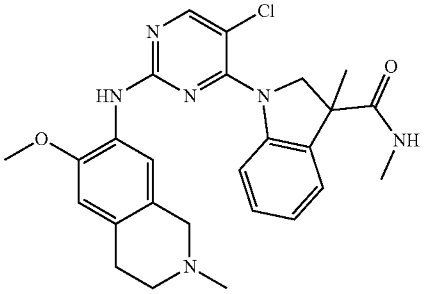 [SMILES: CNC(=O)C1(C)CN(c2nc(Nc3cc4c(cc3OC)CCN(C)C4)ncc2Cl)c2ccccc21]

1-(5-Chloro-24(6-methoxy-2-methyl-1,2,3,4-tetrahydroisoquinolin-7-yl)amino)pyrimidin-4-yl)-N,3-dimethylindoline-3-carboxamide Step 1: Int. E20 (68 mg, 0.357 mmol) and 2,4,5-trichloropyrimidine (72.1 mg, 0.393 mmol) were used under Condition A3 to provide 1-(2,5-dichloropyrimidin-4-yl)-N,3-dimethylindoline-3-carboxamide (72 mg, 59.7% yield) as colorless oil, after purification by flash column chromatography on silica gel (DCM/MeOH: 10/1). LC-MS (ESI) m/z: 337 $[M+H]^+$.

Step 2: 1-(2,5-Dichloropyrimidin-4-yl)-N,3-dimethylindoline-3-carboxamide (72 mg, 0.214 mmol) and Int. W1 (41.1 mg, 0.214 mmol) were used under Condition B3 to provide 1-(5-chloro-2-((6-methoxy-2-methyl-1,2,3,4-tetrahydroisoquinolin-7-yl)amino)pyrimidin-4-yl)-N,3-dimethylindoline-3-carboxamide (45.6 mg, 43.3% yield) as white solid, after purification by prep-HPLC (MeCN/0.1% FA). LC-MS (ESI) m/z: 493 $[M+H]^+$. $^1H$ NMR (400 MHz, DMSO-$d_6$) δ 8.29 (d, J=32.1 Hz, 1H), 8.02 (s, 1H), 7.70 (s, 1H), 7.51 (s, 1H), 7.38 (t, J=7.2 Hz, 2H), 7.14 (t, J=7.1 Hz, 1H), 7.01 (d, J=6.7 Hz, 1H), 6.75 (s, 1H), 4.81 (d, J=10.3 Hz, 1H), 3.99 (d, J=10.3 Hz, 1H), 3.77 (s, 3H), 3.31 (s, 2H), 2.78 (s, 2H), 2.58 (s, 5H), 2.32 (s, 3H), 1.61 (d, J=64.4 Hz, 3H).

Example 123

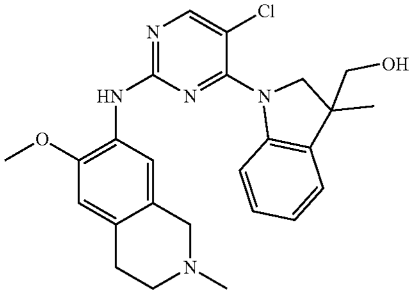 [SMILES: COc1cc2c(cc1Nc1ncc(Cl)c(N3CC(C)(CO)c4ccccc43)n1)CN(C)CC2]

(1-(5-Chloro-24(6-methoxy-2-methyl-1,2,3,4-tetrahydroisoquinolin-7-yl)amino)pyrimidin-4-yl)-3-methylindolin-3-yl)methanol Step 1: Int. E21 (60 mg, 0.382 mmol) and 2,4,5-trichloropyrimidine (70 mg, 0.382 mmol) were used under Condition A3 to provide (1-(2,5-dichloropyrimidin-4-yl)-3- methylindolin-3-yl)methanol (85 mg, 64.6% yield) as yellow oil, after purification by flash column chromatography on silica gel (DCM/MeOH: 10/1). LC-MS (ESI) m/z: 310 $[M+H]^+$.

Step 2: (1-(2,5-Dichloropyrimidin-4-yl)-3-methylindolin-3-yl)methanol (85 mg, 0.273 mmol) and Int. W1 (62.9 mg, 0.327 mmol) were used under Condition B3 to provide (1-(5-chloro-2-((6-methoxy-2-methyl-1,2,3,4-tetrahydroisoquinolin-7-yl)amino)pyrimidin-4-yl)-3-methylindolin-3-yl)methanol (22.4 mg, 17.6%) as white solid, after purification by prep-HPLC (MeCN/0.1% FA). LC-MS (ESI) m/z: 466 $[M+H]^+$. $^1H$ NMR (400 MHz, DMSO-$d_6$) δ 8.23 (s, 1H), 7.97 (s, 1H), 7.54 (s, 1H), 7.37 (d, J=8.1 Hz, 1H), 7.21 (d, J=7.0 Hz, 1H), 7.10 (s, 1H), 6.97 (d, J=7.4 Hz, 1H), 6.75 (s, 1H), 5.01 (t, J=5.3 Hz, 1H), 4.26 (d, J=10.5 Hz, 1H), 3.87 (d, J=10.5 Hz, 1H), 3.77 (s, 3H), 3.39-3.35 (m, 2H), 3.30-3.28 (m, 2H), 2.80-2.75 (m, 2H), 2.58-2.54 (m, 2H), 2.31 (s, 3H), 1.29 (s, 3H).

Example 124

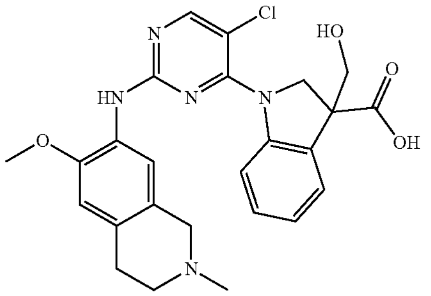 [SMILES: COc1cc2c(cc1Nc1ncc(Cl)c(N3CC(CO)(C(=O)O)c4ccccc43)n1)CN(C)CC2]

1-(5-Chloro-24(6-methoxy-2-methyl-1,2,3,4-tetrahydroisoquinolin-7-yl)amino)pyrimidin-4-yl)-3-(hydroxymethyl)indoline-3-carboxylic acid The same procedures as Example 117, using Int. E37 in place of Int. E18 in Step 1. LC-MS (ESI) m/z: 498 $[M+H]^+$. $^1H$ NMR (400 MHz, DMSO-$d_6$) δ 8.25 (s, 1H), 8.21 (s, 1H), 8.00 (d, J=9.3 Hz, 1H), 7.51 (s, 1H), 7.39 (t, J=8.0 Hz, 2H), 7.12 (t, J=7.7 Hz, 1H), 6.95 (t, J=7.4 Hz, 1H), 6.76 (s, 1H), 4.75 (d, J=10.7 Hz, 1H), 4.24 (d, J=10.7 Hz, 1H), 3.86 (d, J=10.4 Hz, 2H), 3.77 (s, 3H), 3.49 (br, 1H), 3.33 (br, 2H), 2.78 (t, J=5.5 Hz, 2H), 2.59 (t, J=5.7 Hz, 2H), 2.33 (s, 3H).

Example 125

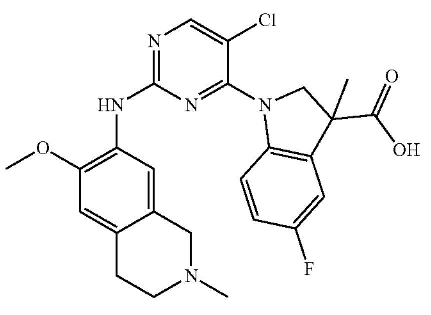

1-(5-Chloro-24(6-methoxy-2-methyl-1,2,3,4-tetrahydroisoquinolin-7-yl)amino)pyrimidin-4-yl)-5-fluoro-3-methylindoline-3-carboxylic acid The same procedures as Example 117, using Int. E27 in place of Int. E18 in Step 1. LC-MS (ESI) m/z: 498 $[M+H]^+$. $^1H$ NMR (400 MHz, DMSO-$d_6$) δ 8.24 (s, 1H), 8.05 (s, 1H), 7.47 (s, 1H), 7.39 (dd, J=8.8, 4.7 Hz, 1H), 7.18 (dd, J=8.5, 2.7 Hz, 1H), 6.95 (td, J=9.0, 2.7 Hz, 1H), 6.77 (s, 1H), 4.78 (d, J=10.7 Hz, 1H), 4.06 (d, J=10.7 Hz, 1H), 3.76 (s, 4H), 2.80 (d, J=5.7 Hz, 2H), 2.67 (t, J=5.8 Hz, 2H), 2.51 (s, 1H), 2.36 (d, J=12.7 Hz, 3H), 1.52 (s, 3H).

Example 126

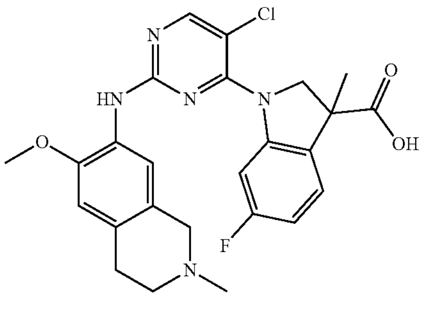

1-(5-Chloro-24(6-methoxy-2-methyl-1,2,3,4-tetrahydroisoquinolin-7-yl)amino)pyrimidin-4-yl)-6-fluoro-3-methylindoline-3-carboxylic acid The same procedures as Example 117, using Int. E28 in place of Int. E18 in Step 1. LC-MS (ESI) m/z: 498 $[M+H]^+$. $^1H$ NMR (500 MHz, DMSO-$d_6$) δ 8.27 (s, 1H), 8.20 (s, 1H), 7.41 (s, 1H), 7.37-7.27 (m, 1H), 7.18 (d, J=10.4 Hz, 1H), 6.75 (s, 2H), 4.81 (d, J=10.3 Hz, 1H), 4.08 (d, J=10.4 Hz, 1H), 3.76 (s, 3H), 3.35 (s, 2H), 2.78 (s, 2H), 2.60 (s, 2H), 2.33 (s, 3H), 1.50 (s, 3H).

Example 127

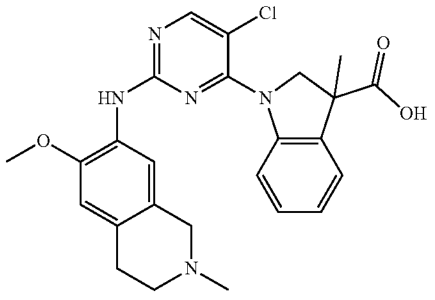 [SMILES: COc1cc2c(cc1Nc1ncc(Cl)c(N3CC(C)(C(=O)O)c4ccccc43)n1)CN(C)CC2]

1-(5-Chloro-2-((6-methoxy-1,2,3,4-tetrahydroisoquinolin-7-yl)amino)pyrimidin-4-yl)-3-methylindoline-3-carboxylic acid The same procedures as Example 117, using Int. W11 in place of Int. W1 in Step 2. LC-MS (ESI) m/z: 466 $[M+H]^+$. $^1H$ NMR (500 MHz, DMSO-$d_6$) δ 8.47 (s, 1H), 8.14 (s, 1H), 7.60 (s, 1H), 7.48 (s, 1H), 7.46 (d, J=6.8 Hz, 1H), 7.24 (t, J=7.6 Hz, 1H), 7.17 (t, J=7.2 Hz, 1H), 7.03 (s, 1H), 5.01 (d, J=11.0 Hz, 1H), 4.30 (d, J=11.0 Hz, 1H), 4.14 (d, J=6.3 Hz, 2H), 3.82 (s, 3H), 3.42 (t, J=6.3 Hz, 2H), 3.04 (t, J=6.1 Hz, 2H), 1.60 (s, 3H).

Example 128

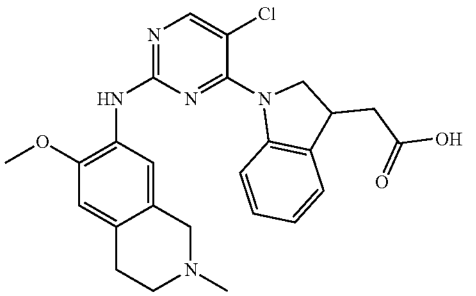 [SMILES: COc1cc2c(cc1Nc1ncc(Cl)c(N3CC(CC(=O)O)c4ccccc43)n1)CN(C)CC2]

2-(1-(5-Chloro-24(6-methoxy-2-methyl-1,2,3,4-tetrahydroisoquinolin-7-yl)amino)pyrimidin-4-yl)indolin-3-yl)acetic acid The same procedures as Example 117, using Int. E29 in place of Int. E18 in Step 1. LC-MS (ESI) m/z: 480 $[M+H]^+$. $^1$H NMR (400 MHz, DMSO-$d_6$) δ 8.26 (d, J=21.1 Hz, 1H), 7.98 (s, 1H), 7.55 (s, 1H), 7.30 (dd, J=22.6, 7.7 Hz, 2H), 7.10 (t, J=7.7 Hz, 1H), 6.94 (t, J=7.4 Hz, 1H), 6.74 (s, 1H), 4.56-4.36 (m, 1H), 3.98 (dd, J=10.6, 7.0 Hz, 1H), 3.77 (s, 3H), 3.69 (s, 2H), 3.29 (s, 2H), 2.84-2.70 (m, 3H), 2.56 (t, J=5.8 Hz, 2H), 2.31 (s, 3H).

Example 129

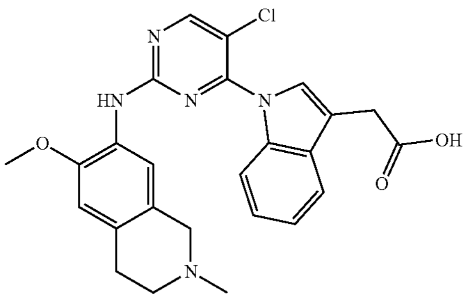

2-(1-(5-Chloro-24(6-methoxy-2-methyl-1,2,3,4-tetrahydroisoquinolin-7-yl)amino)pyrimidin-4-yl)-1H-indol-3-yl)acetic acid Example 130

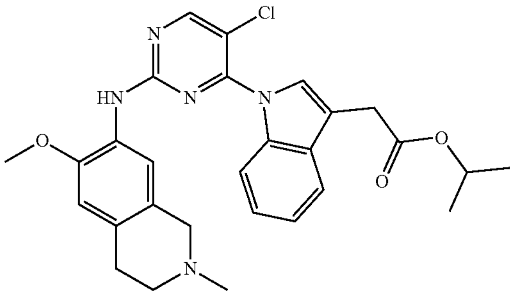 [SMILES: COc1cc2c(cc1Nc1ncc(Cl)c(-n3cc(CC(=O)OC(C)C)c4ccccc43)n1)CN(C)CC2]

Isopropyl 2-(1-(5-chloro-2-((6-methoxy-2-methyl-1,2,3,4-tetrahydroisoquinolin-7-yl)amino)pyrimidin-4-yl)-1H-indol-3-yl)acetate Example 131

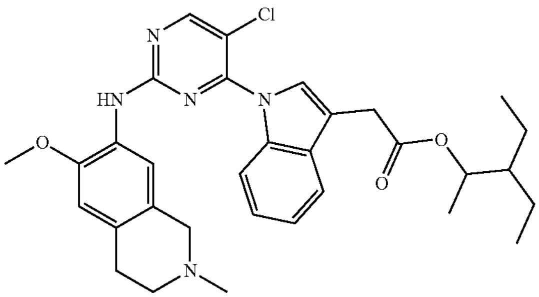 [SMILES: CCC(CC)C(C)OC(=O)Cc1cn(-c2nc(Nc3cc4c(cc3OC)CCN(C)C4)ncc2Cl)c2ccccc12]

2-Ethylbutyl 2-(1-(5-chloro-2-((6-methoxy-2-methyl-1,2,3,4-tetrahydroisoquinolin-7-yl)amino)pyrimidin-4-yl)-1H-indol-3-yl)acetate Step 1: 2-(1H-indol-3-yl)acetic acid (300 mg, 1.71 mmol) and 2,4,5-trichloropyrimidine (314.1 mg, 1.71 mmol) were used under Condition A1 to provide 2-(1-(2,5-dichloropyrimidin-4-yl)-1H-indol-3-yl)acetic acid (93 mg, 16.0% yield) as light yellow solid, after purification by reverse phase chromatography. LC-MS (ESI) m/z: 322 $[M+H]^+$.

Step 2: 2-(1-(2,5-Dichloropyrimidin-4-yl)-1H-indol-3-yl)acetic acid (93 mg, 0.274 mmol) and Int. W1 (66.6 mg, 0.329 mmol) were used under Condition B3 to provide isopropyl 2-(1-(5-chloro-2-((6-methoxy-2-methyl-1,2,3,4-tetrahydroisoquinolin-7-yl)amino)pyrimidin-4-yl)-1H-indol-3-yl)acetate (120 mg, 80.0% yield) as light yellow solid, after purification by flash column chromatography on silica gel (PE/EA=10/1). LC-MS (ESI) m/z: 520 $[M+H]^+$. $^1$H NMR (400 MHz, DMSO-$d_6$) δ 8.70 (s, 1H), 8.62 (s, 1H), 7.86-7.77 (m, 2H), 7.57 (dd, J=6.0, 2.8 Hz, 1H), 7.43 (s, 1H), 7.21 (dd, J=6.0, 3.1 Hz, 2H), 6.80 (s, 1H), 4.94 (dt, J=12.5, 6.3 Hz, 1H), 3.80 (s, 2H), 3.79 (s, 3H), 3.32 (s, 2H), 2.78 (t, J=5.5 Hz, 2H), 2.55 (t, J=5.9 Hz, 2H), 2.30 (s, 3H), 1.21 (d, J=6.3 Hz, 6H).

2-Ethylbutyl 2-(1-(5-chloro-2-((6-methoxy-2-methyl-1,2,3,4-tetrahydroisoquinolin-7-yl)amino)pyrimidin-4-yl)-1H-indol-3-yl)acetate was obtained in Step 2, using 2-ethylbutan-1-ol as the solvent. LC-MS (ESI) m/z: 562 $[M+H]^+$. $^1H$ NMR (400 MHz, DMSO-$d_6$) δ 8.69 (s, 1H), 8.63 (s, 1H), 8.36 (s, 1H), 7.85-7.74 (m, 2H), 7.60-7.52 (m, 1H), 7.45 (s, 1H), 7.28-7.14 (m, 2H), 6.78 (d, J=12.8 Hz, 1H), 3.99 (d, J=5.8 Hz, 2H), 3.85 (s, 2H), 3.79 (s, 3H), 3.31 (s, 2H), 2.78 (t, J=5.6 Hz, 2H), 2.55 (t, J=5.8 Hz, 2H), 2.30 (d, J=8.2 Hz, 3H), 1.45 (dd, J=12.4, 6.2 Hz, 1H), 1.29-1.23 (m, 4H), 0.80 (t, J=7.4 Hz, 6H).

Step 3: Isopropyl 2-(1-(5-chloro-2-((6-methoxy-2-methyl-1,2,3,4-tetrahydroisoquinolin-7-yl)amino)pyrimidin-4-yl)-1H-indol-3-yl)acetate (142 mg, 0.273 mmol) was used under the same condition as Step 3 of Example 117 to provide 2-(1-(5-chloro-2-((6-methoxy-2-methyl-1,2,3,4-tetrahydroisoquinolin-7-yl)amino)pyrimidin-4-yl)-1H-indol-3-yl)acetic acid as white solid (57.9 mg, 44.4% yield), after purification by prep-HPLC (MeCN/10 mM $NH_4HCO_3$). LC-MS (ESI) m/z: 480 $[M+H]^+$. $^1H$ NMR (400 MHz, DMSO-$d_6$) δ 8.79 (s, 1H), 8.64 (s, 1H), 7.80 (d, J=6.8 Hz, 2H), 7.55 (s, 1H), 7.26 (d, J=7.7 Hz, 1H), 7.22 (d, J=7.6 Hz, 1H), 6.91 (s, 1H), 3.92 (s, 2H), 3.83 (s, 3H), 3.75 (s, 2H), 3.17 (s, 2H), 2.98 (s, 2H), 2.69 (s, 3H).

Example 132

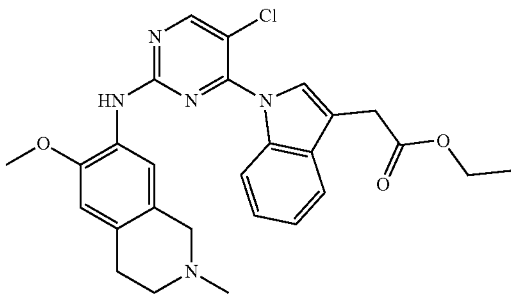 [SMILES: CCOC(=O)Cc1cn(-c2nc(Nc3cc4c(cc3OC)CCN(C)C4)ncc2Cl)c2ccccc12]

Ethyl 2-(1-(5-chloro-24(6-methoxy-2-methyl-1,2,3,4-tetrahydroisoquinolin-7-yl)amino)pyrimidin-4-yl)-1H-indol-3-yl)acetate To a solution of 2-(1-(5-chloro-2-((6-methoxy-2-methyl-1,2,3,4-tetrahydroisoquinolin-7-yl)amino)pyrimidin-4-yl)-1H-indol-3-yl)acetic acid (60 mg, 0.126 mmol) in ethanol (1 mL) was added $SOCl_2$ (29.9 mg, 0.251 mmol) dropwise. The reaction mixture was stirred at 85° C. for 3 hours, cooled to room temperature, basified to pH 8 with saturated sodium bicarbonate aqueous solution, and extracted with ethyl acetate (10 mL×3). The organic phase was dried over anhydrous sodium sulfate and filtered. The filtrate was concentrated in vacuo, and the residue was purified by prep-HPLC (10 mM $NH_4HCO_3$&0.025% $NH_3 \cdot H_2O$/acetonitrile) to provide ethyl 2-(1-(5-chloro-2-((6-methoxy-2-methyl-1,2,3,4-tetrahydroisoquinolin-7-yl)amino)pyrimidin-4-yl)-1H-indol-3-yl)acetate as light-yellow solid (7.8 mg, 12% yield). LC-MS (ESI) m/z: 506 $[M+H]^+$. $^1H$ NMR (400 MHz, DMSO-$d_6$) δ 8.70 (s, 1H), 8.62 (s, 1H), 7.83 (s, 1H), 7.82-7.76 (m, 1H), 7.64-7.53 (m, 1H), 7.43 (s, 1H), 7.28-7.16 (m, 2H), 6.80 (s, 1H), 4.11 (q, J=7.1 Hz, 2H), 3.84 (s, 2H), 3.79 (s, 3H), 3.33 (s, 2H), 2.78 (t, J=5.5 Hz, 2H), 2.55 (t, J=5.8 Hz, 2H), 2.30 (s, 3H), 1.20 (t, J=7.1 Hz, 3H).

Example 133

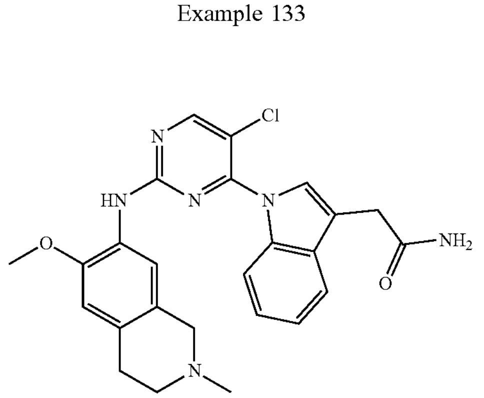

2-(1-(5-Chloro-24(6-methoxy-2-methyl-1,2,3,4-tetrahydroisoquinolin-7-yl)amino)pyrimidin-4-yl)-1H-indol-3-yl)acetamide To a mixture of 2-(1-(5-chloro-2-((6-methoxy-2-methyl-1,2,3,4-tetrahydroisoquinolin-7-yl)amino)pyrimidin-4-yl)-1H-indol-3-yl)acetic acid (30 mg, 0.060 mmol), ammonium chloride (31.9 mg, 0.596 mmol), and HATU (34.0 mg, 0.089 mmol) in DMF (1 mL) was added DIPEA (115.6 mg, 0.894 mmol). The reaction mixture was stirred at 25° C. for 16 hours and purified by prep-HPLC (MeCN/10 mM $NH_4HCO_3$, 0.025% $NH_3 \cdot H_2O$) to give 2-(1-(5-chloro-2-((6-methoxy-2-methyl-1,2,3,4-tetrahydroisoquinolin-7-yl)amino)pyrimidin-4-yl)-1H-indol-3-yl)acetamide (9.1 mg, 32.0% yield) as white solid. LC-MS (ESI) m/z: 477 $[M+H]^+$. $^1H$ NMR (400 MHz, DMSO-$d_6$) δ 8.67 (s, 1H), 8.61 (s, 1H), 7.81 (dd, J=6.3, 3.0 Hz, 1H), 7.77 (s, 1H), 7.62 (dd, J=5.5, 3.3 Hz, 1H), 7.51 (s, 1H), 7.45 (s, 1H), 7.20 (dd, J=6.0, 3.1 Hz, 2H), 6.94 (s, 1H), 6.80 (s, 1H), 3.79 (s, 3H), 3.54 (s, 2H), 3.30 (s, 1H), 2.78 (d, J=5.6 Hz, 2H), 2.56 (d, J=5.8 Hz, 2H), 2.30 (s, 3H).

Example 134

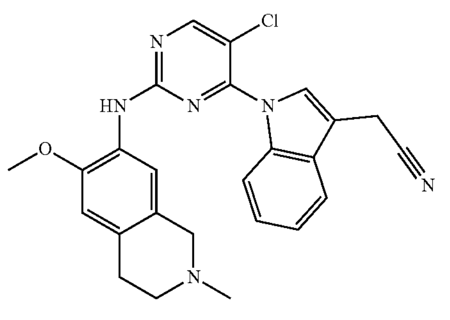 [SMILES: COc1cc2c(cc1Nc1ncc(Cl)c(-n3cc(CC#N)c4ccccc43)n1)CN(C)CC2]

2-(1-(5-Chloro-24(6-methoxy-2-methyl-1,2,3,4-tetrahydroisoquinolin-7-yl)amino)pyrimidin-4-yl)-1H-indol-3-yl)acetonitrile To a solution of 2-(1-(5-chloro-2-((6-methoxy-2-methyl-1,2,3,4-tetrahydroisoquinolin-7-yl)amino)pyrimidin-4-yl)-1H-indol-3-yl)acetamide (50 mg, 0.105 mmol) and pyridine (33.2 mg, 0.419 mmol) in DCM (2 mL) was added trifluoroacetic anhydride (44.0 mg, 0.210 mmol) at 0° C. dropwise. The mixture was stirred at 0° C. for an hour and room temperature for 6 hours, quenched with HCl aqueous solution (1N, 10 mL) and extracted with DCM (20 mL×3). The organic phases were washed with brine (15 mL), dried over anhydrous $Na_2SO_4$, and filtered. The filtrate was concentrated in vacuo, and the residue was purified by prep-HPLC (0.1% FA/MeCN) to provide 2-(1-(5-chloro-2-((6-methoxy-2-methyl-1,2,3,4-tetrahydroisoquinolin-7-yl)amino)pyrimidin-4-yl)-1H-indol-3-yl)acetonitrile (19.3 mg, 39.7% yield) as white solid. LC-MS (ESI) m/z: 459 $[M+H]^+$. $^1H$ NMR (400 MHz, DMSO-$d_6$) δ 8.76 (s, 1H), 8.65 (s, 1H), 8.35 (s, 2H), 7.89 (s, 1H), 7.81 (dd, J=6.3, 2.9 Hz, 1H), 7.69 (dd, J=6.1, 2.8 Hz, 1H), 7.42 (s, 1H), 7.28 (dd, J=6.1, 3.2 Hz, 2H), 6.80 (s, 1H), 4.18 (s, 2H), 3.79 (s, 3H), 3.33 (s, 2H), 2.78 (t, J=5.6 Hz, 2H), 2.55 (t, J=5.8 Hz, 2H), 2.30 (s, 3H).

Example 135

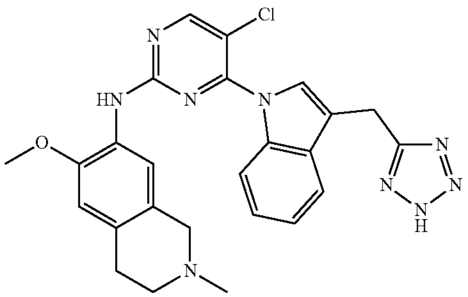 [SMILES: COc1cc2c(cc1Nc1ncc(Cl)c(-n3cc(Cc4nn[nH]n4)c4ccccc43)n1)CN(C)CC2]

N-(4-(3-((2H-tetrazol-5-yl)methyl)-1H-indol-1-yl)-5-chloropyrimidin-2-yl)-6-methoxy-2-methyl-1,2,3,4-tetrahydroisoquinolin-7-amine The same procedure as Example 100, using 2-(1-(5-chloro-2-((6-methoxy-2-methyl-1,2,3,4-tetrahydroisoquinolin-7-yl)amino)pyrimidin-4-yl)-1H-indol-3-yl)acetonitrile in place of 1-(5-chloro-2-((6-methoxy-2-methyl-1,2,3,4-tetrahydroisoquinolin-7-yl)amino)pyrimidin-4-yl)indoline-3-carbonitrile. LC-MS (ESI) m/z: 502 $[M+H]^+$. $^1H$ NMR (500 MHz, DMSO-$d_6$) δ 8.76 (s, 1H), 8.63 (s, 1H), 8.15 (s, 1H), 7.75 (d, J=4.8 Hz, 2H), 7.56 (d, J=7.6 Hz, 1H), 7.47 (s, 1H), 7.25-7.16 (m, 2H), 6.84 (s, 1H), 4.37 (s, 2H), 3.80 (s, 3H), 3.64 (s, 2H), 2.87 (s, 4H), 2.52 (s, 3H).

Example 136

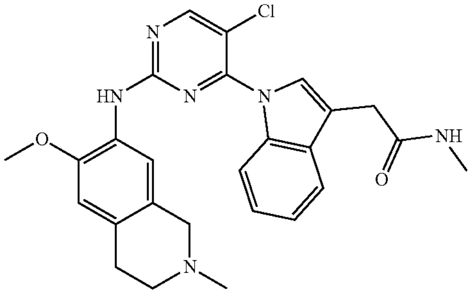

2-(1-(5-Chloro-24(6-methoxy-2-methyl-1,2,3,4-tetrahydroisoquinolin-7-yl)amino)pyrimidin-4-yl)-1H-indol-3-yl)-N-methylacetamide The same procedure as Example 133, using methylamine in place of ammonium chloride. LC-MS (ESI) m/z: 491 $[M+H]^+$. $^1H$ NMR (400 MHz, DMSO-$d_6$) δ 8.68 (s, 1H), 8.62 (s, 1H), 7.97 (s, 1H), 7.80 (dd, J=6.2, 3.0 Hz, 1H), 7.76 (s, 1H), 7.61 (dd, J=5.6, 3.1 Hz, 1H), 7.44 (s, 1H), 7.20 (dd, J=6.0, 3.1 Hz, 2H), 6.79 (s, 1H), 3.79 (s, 3H), 3.56 (s, 2H), 3.30 (s, 2H), 2.78 (d, J=5.1 Hz, 2H), 2.59 (d, J=4.6 Hz, 3H), 2.56 (d, J=5.7 Hz, 2H), 2.30 (s, 3H).

Example 137

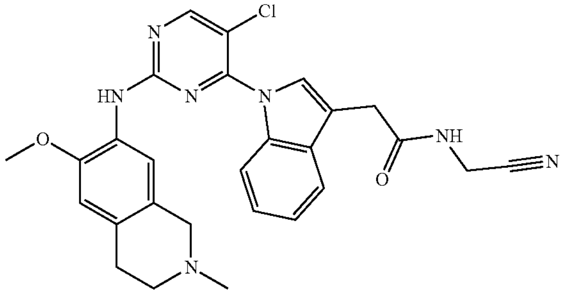 [SMILES: COc1cc2c(cc1Nc1ncc(Cl)c(-n3cc(CC(=O)NCC#N)c4ccccc43)n1)CN(C)CC2]

2-(1-(5-Chloro-24(6-methoxy-2-methyl-1,2,3,4-tetrahydroisoquinolin-7-yl)amino)pyrimidin-4-yl)-1H-indol-3-yl)-N-(cyanomethyl)acetamide The same procedure as Example 133, using 2-aminoacetonitrile sulfuric acid in place of ammonium chloride. LC-MS (ESI) m/z: 516 $[M+H]^+$. $^1H$ NMR (400 MHz, DMSO-$d_6$) δ 8.75 (s, 1H), 8.69 (s, 1H), 8.62 (s, 1H), 7.84-7.78 (m, 2H), 7.63-7.53 (m, 1H), 7.43 (s, 1H), 7.25-7.15 (m, 2H), 6.80 (s, 1H), 4.15 (d, J=5.5 Hz, 2H), 3.79 (s, 3H), 3.67 (s, 2H), 3.30 (s, 2H), 2.79 (s, 2H), 2.56 (d, J=5.5 Hz, 2H), 2.30 (s, 3H).

Example 138

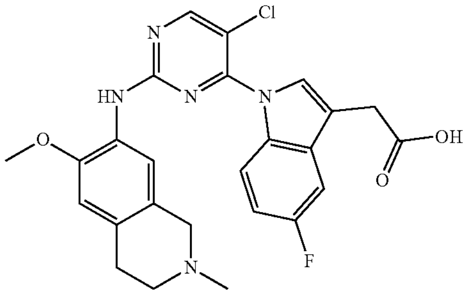 [SMILES: COc1cc2c(cc1Nc1ncc(Cl)c(-n3cc(CC(=O)O)c4cc(F)ccc43)n1)CN(C)CC2]

2-(1-(5-Chloro-24(6-methoxy-2-methyl-1,2,3,4-tetrahydroisoquinolin-7-yl)amino)pyrimidin-4-yl)-5-fluoro-1H-indol-3-yl)acetic acid The same procedures as Example 129, using 2-(5-fluoro-1H-indol-3-yl)acetic acid in place of 2-(1H-indol-3-yl)acetic acid. LC-MS (ESI) m/z: 496 $[M+H]^+$. $^1H$ NMR (400 MHz, DMSO-$d_6$) δ 8.77 (d, J=28.9 Hz, 1H), 8.61 (s, 1H), 7.90 (s, 1H), 7.81 (dd, J=9.0, 4.5 Hz, 1H), 7.46-7.24 (m, 2H), 7.04 (td, J=9.1, 2.4 Hz, 1H), 6.81 (s, 1H), 3.79 (s, 3H), 3.72 (s, 2H), 3.35 (s, 2H), 2.80 (d, J=5.4 Hz, 2H), 2.59 (t, J=5.7 Hz, 2H), 2.32 (s, 3H).

Example 139

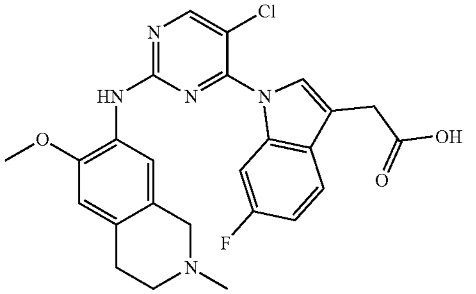 [SMILES: COc1cc2c(cc1Nc1ncc(Cl)c(-n3cc(CC(=O)O)c4ccc(F)cc43)n1)CN(C)CC2]

2-(1-(5-Chloro-24(6-methoxy-2-methyl-1,2,3,4-tetrahydroisoquinolin-7-yl)amino)pyrimidin-4-yl)-6-fluoro-1H-indol-3-yl)acetic acid The same procedures as Example 129, using 2-(6-fluoro-1H-indol-3-yl)acetic acid in place of 2-(1H-indol-3-yl)acetic acid. LC-MS (ESI) m/z: 496 $[M+H]^+$. $^1H$ NMR (400 MHz, DMSO-$d_6$) δ 8.79 (s, 1H), 8.61 (s, 1H), 8.24 (d, J=10.5 Hz, 1H), 7.82 (s, 1H), 7.67-7.52 (m, 2H), 7.38 (s, 1H), 7.08 (td, J=9.3, 2.4 Hz, 1H), 6.79 (s, 1H), 3.79 (s, 3H), 3.71 (s, 2H), 3.34 (s, 2H), 2.79 (t, J=5.6 Hz, 2H), 2.56 (t, J=5.8 Hz, 2H), 2.30 (s, 3H).

Example 140

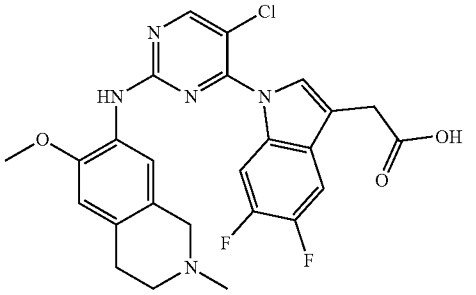 [SMILES: COc1cc2c(cc1Nc1ncc(Cl)c(-n3cc(CC(=O)O)c4cc(F)c(F)cc43)n1)CN(C)CC2]

2-(1-(5-Chloro-24(6-methoxy-2-methyl-1,2,3,4-tetrahydroisoquinolin-7-yl)amino)pyrimidin-4-yl)-5,6-difluoro-1H-indol-3-yl)acetic acid The same procedures as Example 129, using 2-(5,6-difluoro-1H-indol-3-yl)acetic acid in place of 2-(1H-indol-3-yl)acetic acid. LC-MS (ESI) m/z: 514 $[M+H]^+$. $^1H$ NMR (400 MHz, DMSO-$d_6$) δ 8.84 (s, 1H), 8.61 (s, 1H), 8.23 (s, 1H), 7.92 (s, 1H), 7.88-7.79 (m, 1H), 7.61 (dd, J=10.8, 8.0 Hz, 1H), 7.35 (s, 1H), 6.79 (d, J=17.2 Hz, 1H), 3.78 (s, 3H), 3.72 (s, 2H), 3.35 (s, 2H), 2.80 (t, J=5.3 Hz, 2H), 2.57 (s, 2H), 2.32 (d, J=13.1 Hz, 3H).

Example 141

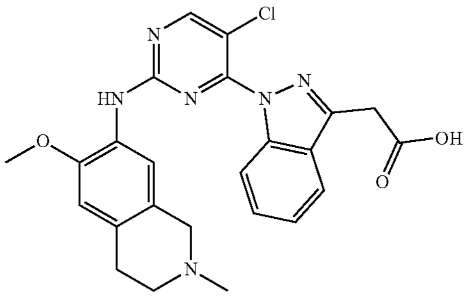 [SMILES: COc1cc2c(cc1Nc1ncc(Cl)c(-n3nc(CC(=O)O)c4ccccc43)n1)CN(C)CC2]

2-(1-(5-Chloro-24(6-methoxy-2-methyl-1,2,3,4-tetrahydroisoquinolin-7-yl)amino)pyrimidin-4-yl)-1H-indazol-3-yl)acetic acid The same procedures as Example 129, using 2-(1H-indazol-3-yl)acetic acid in place of 2-(1H-indol-3-yl)acetic acid. LC-MS (ESI) m/z: 479 $[M+H]^+$.

Example 142

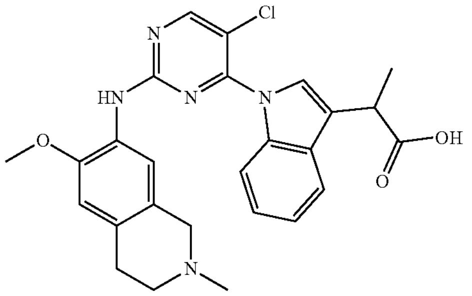 [SMILES: COc1cc2c(cc1Nc1ncc(Cl)c(-n3cc(C(C)C(=O)O)c4ccccc43)n1)CN(C)CC2]

2-(1-(5-Chloro-24(6-methoxy-2-methyl-1,2,3,4-tetrahydroisoquinolin-7-yl)amino)pyrimidin-4-yl)-1H-indol-3-yl)propanoic acid The same procedures as Example 129, using Int. E30 in place of 2-(1H-indol-3-yl)acetic acid. LC-MS (ESI) m/z: 492 $[M+H]^+$. $^1H$ NMR (400 MHz, DMSO-$d_6$) δ 8.69 (s, 1H), 8.62 (s, 1H), 8.26 (s, 1H), 7.80-7.74 (m, 1H), 7.72 (s, 1H), 7.65 (d, J=8.6 Hz, 1H), 7.44 (s, 1H), 7.24-7.15 (m, 2H), 6.79 (s, 1H), 3.93 (d, J=7.1 Hz, 1H), 3.78 (s, 3H), 3.34 (s, 2H), 2.77 (d, J=5.5 Hz, 2H), 2.56 (t, J=5.8 Hz, 2H), 2.30 (s, 3H), 1.49 (d, J=7.1 Hz, 3H).

Example 143

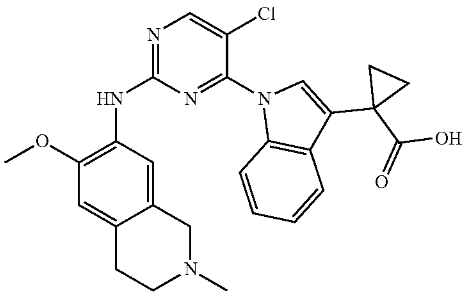 [SMILES: COc1cc2c(cc1Nc1ncc(Cl)c(-n3cc(C4(C(=O)O)CC4)c4ccccc43)n1)CN(C)CC2]

1-(1-(5-Chloro-24(6-methoxy-2-methyl-1,2,3,4-tetrahydroisoquinolin-7-yl)amino)pyrimidin-4-yl)-1H-indol-3-yl)cyclopropane-1-carboxylic acid The same procedures as Example 129, using Int. E31 in place of 2-(1H-indol-3-yl)acetic acid. LC-MS (ESI) m/z: 504 $[M+H]^+$. $^1H$ NMR (400 MHz, DMSO-$d_6$) δ 8.68 (s, 1H), 8.62 (s, 1H), 8.27 (s, 1H), 7.81-7.75 (m, 1H), 7.72 (s, 1H), 7.59-7.53 (m, 1H), 7.44 (s, 1H), 7.23-7.18 (m, 2H), 6.79 (s, 1H), 3.79 (s, 3H), 3.35 (s, 2H), 2.78 (t, J=5.5 Hz, 2H), 2.56 (t, J=5.7 Hz, 2H), 2.31 (s, 3H), 1.49 (d, J=2.7 Hz, 2H), 1.13 (d, J=2.1 Hz, 2H).

Example 144

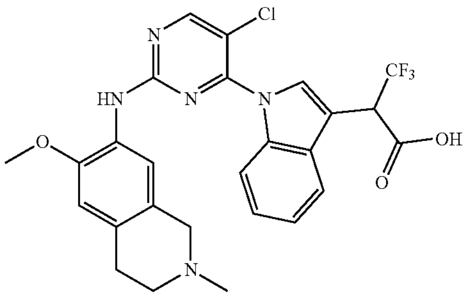 [SMILES: COc1cc2c(cc1Nc1ncc(Cl)c(-n3cc(C(C(=O)O)C(F)(F)F)c4ccccc43)n1)CN(C)CC2]

2-(1-(5-Chloro-24(6-methoxy-2-methyl-1,2,3,4-tetrahydroisoquinolin-7-yl)amino)pyrimidin-4-yl)-1H-indol-3-yl)-3,3,3-trifluoropropanoic acid Step 1: Int. E32 (200 mg, 0.822 mmol)) and 2,4,5-trichloropyrimidine (226.3 mg, 1.23 mmol) were used under Condition A1 to provide 2-(1-(2,5-dichloropyrimidin-4-yl)-1H-indol-3-yl)-3,3,3-trifluoropropanoic acid (190 mg, 47.4% yield, 80% purity), after purification by reverse phase chromatography (MeCN/0.03% TFA). LC-MS (ESI) m/z: 390 $[M+H]^+$.

Step 2: Int. W1 (112.4 mg, 0.584 mmol) and 2-(1-(2,5-dichloropyrimidin-4-yl)-1H-indol-3-yl)-3,3,3-trifluoropropanoic acid (190 mg, 0.487 mmol) were used under Condition B3 to provide 1-(1-(5-chloro-2-((6-methoxy-2-methyl-1,2,3,4-tetrahydroisoquinolin-7-yl)amino)pyrimidin-4-yl)-1H-indol-3-yl)cyclopropane-1-carboxylic acid as white solid (9.3 mg, 3.4% yield), after purification by prep-HPLC (MeCN/0.1% HCOOH). LC-MS (ESI) m/z: 546 $[M+H]^+$. $^1H$ NMR (400 MHz, DMSO-$d_6$) δ 8.82 (s, 1H), 8.65 (s, 1H), 8.17 (s, 1H), 7.82 (s, 1H), 7.73 (d, J=7.6 Hz, 1H), 7.63 (d, J=7.7 Hz, 1H), 7.45 (s, 1H), 7.25-7.19 (m, 2H), 6.82 (s, 1H), 4.63 (d, J=9.0 Hz, 1H), 3.77 (s, 3H), 3.63 (br, 2H), 2.88 (br, 5H), 2.56 (br, 2H).

Example 145

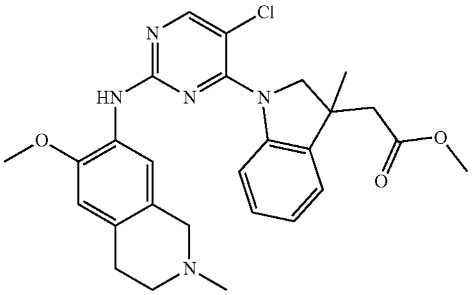

Methyl 2-(1-(5-chloro-24(6-methoxy-2-methyl-1,2,3,4-tetrahydroisoquinolin-7-yl)amino)pyrimidin-4-yl)-3-methylindolin-3-yl)acetate Example 146

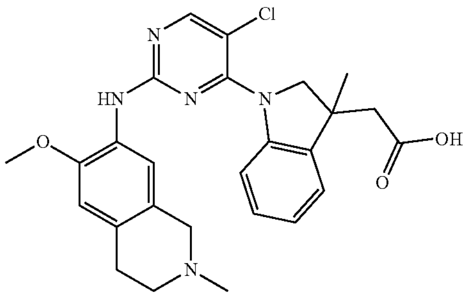 [SMILES: COc1cc2c(cc1Nc1ncc(Cl)c(N3CC(C)(CC(=O)O)c4ccccc43)n1)CN(C)CC2]

2-(1-(5-Chloro-24(6-methoxy-2-methyl-1,2,3,4-tetrahydroisoquinolin-7-yl)amino)pyrimidin-4-yl)-3-methylindolin-3-yl)acetic acid Step 1: To a mixture of Int. E33 (67 mg, 0.248 mmol) in n-BuOH (3 mL) were added slowly 2,4,5-trichloropyrimidine (45.5 mg, 0.248 mmol) and DIPEA (96.19 mg, 0.744 mmol). The mixture was stirred for 16 hours at 100° C., quenched with ice-cold water (20 mL) and extracted with EA (30 mL×3). The organic phases were washed with brine (20 mL), dried over anhydrous $Na_2SO_4$, and filtered. The filtrate was concentrated in vacuo, and the residue was purified by flash column chromatography on silica gel (DCM/PE=0-100%) to afford methyl 2-(1-(2,5-dichloropyrimidin-4-yl)-3-methylindolin-3-yl)acetate (80 mg, 83.3% yield) as yellow solid. LC-MS (ESI) m/z: 352 $[M+H]^+$.

Step 2: To a mixture of methyl 2-(1-(2,5-dichloropyrimidin-4-yl)-3-methylindolin-3-yl)acetate (80 mg, 0.227 mmol) in i-PrOH (5 mL) were added slowly Int. W1 (51.5 mg, 0.227 mmol) and $TsOH·H_2O$ (43.2 mg, 0.227 mmol). The mixture was stirred for 16 hours at 100° C., quenched with saturated $NaHCO_3$ aqueous solution (10 mL) and extracted with DCM/MeOH (v/v=10/1, 30 mL×3). The organic phases were washed with brine (30 mL), dried over anhydrous $Na_2SO_4$, and filtered. The filtrate was concentrated in vacuo, and the residue was purified by flash column chromatography on silica gel (DCM/MeOH=0-15%) to afford methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate (70 mg, 42.5% yield) as yellow solid. LC-MS (ESI) m/z: 508 $[M+H]^+$. $^1H$ NMR (500 MHz, DMSO-$d_6$) δ 8.26 (s, 1H), 7.98 (s, 1H), 7.59 (s, 1H), 7.30 (t, J=8.8 Hz, 2H), 7.12 (s, 1H), 6.98 (s, 1H), 6.74 (s, 1H), 4.38 (d, J=10.7 Hz, 1H), 4.05 (d, J=10.7 Hz, 1H), 3.78 (s, 3H), 3.50 (s, 3H), 3.27 (s, 2H), 2.78 (dd, J=10.3, 4.8 Hz, 3H), 2.68 (s, 1H), 2.55 (t, J=5.7 Hz, 2H), 2.30 (s, 3H), 1.36 (s, 3H).

Step 3: A mixture of methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate (70 mg, 0.096 mmol) and LiOH aqueous solution (2N, 1 mL) in THF (5 mL) was stirred for 16 hours at room temperature, adjusted to pH~5 with formic acid and extracted with DCM (30 mL×3). The combined organic phases were dried over anhydrous sodium sulfate and filtered. The filtrate was concentrated in vacuo, and the residue was purified by prep-HPLC (MeCN/10 mM $NH_4HCO_3$, 0.025% $NH_3H_2O$) to afford 2-(1-(5-chloro-2-((6-methoxy-2-methyl-1,2,3,4-tetrahydroisoquinolin-7-yl)amino)pyrimidin-4-yl)-3-methylindolin-3-yl)acetic acid (23.0 mg, 46.2% yield) as white solid. LC-MS (ESI) m/z: 494 $[M+H]^+$. $^1H$ NMR (500 MHz, DMSO-$d_6$) δ 8.25 (s, 1H), 7.99 (s, 1H), 7.57 (s, 1H), 7.29 (dd, J=17.2, 7.6 Hz, 2H), 7.11 (t, J=7.3 Hz, 1H), 6.98 (d, J=7.3 Hz, 1H), 6.75 (s, 1H), 4.42 (d, J=10.7 Hz, 1H), 4.02 (d, J=10.6 Hz, 1H), 3.78 (s, 3H), 3.30 (s, 2H), 2.78 (s, 2H), 2.69 (d, J=15.4 Hz, 1H), 2.58 (d, J=6.1 Hz, 3H), 2.32 (s, 3H), 1.34 (s, 3H).

Examples 147 & 148

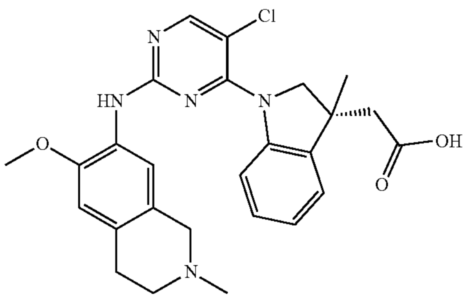

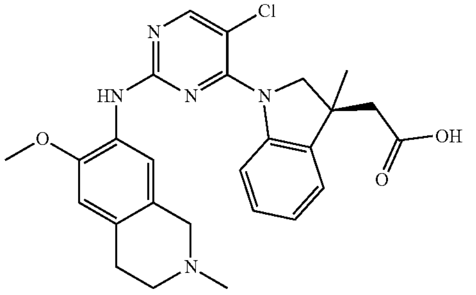

(R)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid & (S)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid Method 1:

Step 1: SFC chiral separation of methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate (157 mg) to provide (R)-methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate and (S)-methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate (67 mg, 63 mg separately). The stereochemistry was not confirmed, and two products were arbitrarily assigned.

LC-MS (ESI) m/z: 508 $[M+H]^+$. Chiral-HPLC retention time: 1.829 min; ee value: 98.3%.

LC-MS (ESI) m/z: 508 $[M+H]^+$. Chiral-HPLC retention time: 3.427 min; ee value: >99%.

SFC Separation Conditions:

Instrument: SFC-80 (Thar, Waters)

Column: AD-H 20*250 mm, 10 um (Daicel)

Column temperature: 35° C.

Mobile phase: $CO_2$/EtOH (0.2% methanol/ammonia)=50/50

Flow rate: 80 g/min

Back pressure: 100 bar

Detection wavelength: 214 nm

Cycle time: 6.9 min

Step 2: (R)-methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate and (S)-methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate were hydrolyzed under the same condition as Step 3 of Example 146 separately to provide (R)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid and (S)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid (17.6 mg, 33.8 mg separately). The stereochemistry was not confirmed, and two products were arbitrarily assigned.

LC-MS (ESI) m/z: 494 $[M+H]^+$. $^1H$ NMR (400 MHz, DMSO-$d_6$) δ 8.25 (s, 1H), 8.00 (s, 1H), 7.57 (s, 1H), 7.30 (dd, J=13.7, 7.7 Hz, 2H), 7.11 (t, J=7.6 Hz, 1H), 6.97 (t, J=7.3 Hz, 1H), 6.75 (s, 1H), 4.42 (d, J=10.7 Hz, 1H), 4.02 (d, J=10.8 Hz, 1H), 3.78 (s, 3H), 3.30 (s, 2H), 2.78 (s, 2H), 2.69 (d, J=15.4 Hz, 1H), 2.62-2.54 (m, 3H), 2.32 (s, 3H), 1.34 (s, 3H). Chiral-HPLC retention time: 1.384 min; ee value: >99%.

LC-MS (ESI) m/z: 494 $[M+H]^+$. $^1H$ NMR (400 MHz, DMSO-$d_6$) δ 8.25 (s, 1H), 8.00 (s, 1H), 7.56 (s, 1H), 7.29 (dd, J=13.6, 7.4 Hz, 2H), 7.10 (t, J=7.1 Hz, 1H), 6.97 (t, J=7.4 Hz, 1H), 6.75 (s, 1H), 4.41 (d, J=10.8 Hz, 1H), 4.02 (d, J=10.8 Hz, 1H), 3.77 (s, 3H), 3.29 (s, 2H), 2.77 (t, J=5.6 Hz, 2H), 2.69 (d, J=15.4 Hz, 1H), 2.57 (dd, J=13.1, 7.1 Hz, 3H), 2.30 (d, J=11.1 Hz, 3H), 1.34 (s, 2H). Chiral-HPLC retention time: 1.132 min; ee value: >99%.

Method 2:

Step 1: SFC chiral separation of methyl 2-(1-(2,5-dichloropyrimidin-4-yl)-3-methylindolin-3-yl)acetate to provide (R)-methyl 2-(1-(2,5-dichloropyrimidin-4-yl)-3-methylindolin-3-yl)acetate and (S)-methyl 2-(1-(2,5-dichloropyrimidin-4-yl)-3-methylindolin-3-yl)acetate. The stereochemistry was not confirmed, and two products were arbitrarily assigned.

LC-MS (ESI) m/z: 352 $[M+H]^+$. Chiral-HPLC retention time: 1.191 min; ee value: >99%.

LC-MS (ESI) m/z: 352 $[M+H]^+$. Chiral-HPLC retention time: 1.519 min; ee value: >99%.

SFC Separation Conditions:

Instrument: SFC-80 (Thar, Waters)
Column: AD-H 20*250 mm, 10 um (Daicel)
Column temperature: 35° C.
Mobile phase: $CO_2$/isopropanol (0.2% methanol/ammonia)=87/13
Flow rate: 80 g/min
Back pressure: 100 bar
Detection wavelength: 214 nm
Cycle time: 2.8 min (One Stereoisomer as Representative Example of Step 2&3)

Step 2: A mixture of Int. W1 (1.36 g, 5.96 mmol), (S)-methyl 2-(1-(2,5-dichloropyrimidin-4-yl)-3-methylindolin-3-yl)acetate (2.1 g, 5.96 mmol) and TsOH $H_2O$ (1.13 g, 5.96 mmol) in t-butanol (25 mL) was stirred for 12 hours at 100° C., cooled to room temperature, and poured into saturated $NaHCO_3$ aqueous solution (10 mL) and extracted with EA (30 mL×3). The organic phases were dried over anhydrous $Na_2SO_4$ and filtered. The filtrate was concentrated in vacuo, and the residue was purified by flash column chromatography on silica gel (DCM/MeOH=20:1) to provide (S)-methyl 2-(1-(5-chloro-2-((6-methoxy-2-methyl-1,2,3,4-tetrahydroisoquinolin-7-yl) amino)pyrimidin-4-yl)-3-methylindolin-3-yl)acetate (1.8 g, 56.3% yield) as light yellow solid. LC-MS (ESI) m/z: 508 $[M+H]^+$.

Step 3: A mixture of a solution of lithium hydroxide hydrate (264 mg, 6.3 mmol) in water (5 mL) and (S)-methyl 2-(1-(5-chloro-2-((6-methoxy-2-methyl-1,2,3,4-tetrahydroisoquinolin-7-yl)amino)pyrimidin-4-yl)-3-methylindolin-3-yl)acetate (1.6 g, 3.15 mmol) in MeOH (5 mL) was stirred for 16 hours at room temperature and acidified to pH~3 with acetic acid. The resulting mixture was purified by prep-HPLC (MeCN/10 mM $NH_4HCO_3$) to provide (S)-2-(1-(5-chloro-2-((6-methoxy-2-methyl-1,2,3,4-tetrahydroisoquinolin-7-yl)amino)pyrimidin-4-yl)-3-methylindolin-3-yl)acetic acid (839.3 mg, 53.9% yield) as pale yellow solid. LC-MS (ESI) m/z: 494 $[M+H]^+$. $^1H$ NMR (400 MHz, DMSO-$d_6$) δ 8.30 (s, 1H), 8.02 (s, 1H), 7.63 (s, 1H), 7.37 (d, J=8.0 Hz, 1H), 7.33 (d, J=8.0 Hz, 1H), 7.16 (t, J=8.0 Hz, 1H), 7.02 (t, J=8.0 Hz, 1H), 6.80 (s, 1H), 4.48 (d, J=10.8 Hz, 1H), 4.08 (d, J=10.8 Hz, 1H), 3.83 (s, 3H), 2.83 (t, J=5.6 Hz, 2H), 2.74 (d, J=15.2 Hz, 1H), 2.66-2.59 (m, 3H), 2.37 (s, 3H), 1.40 (s, 3H). Chiral-HPLC retention time: 1.132 min; ee value: >99%.

Example 149

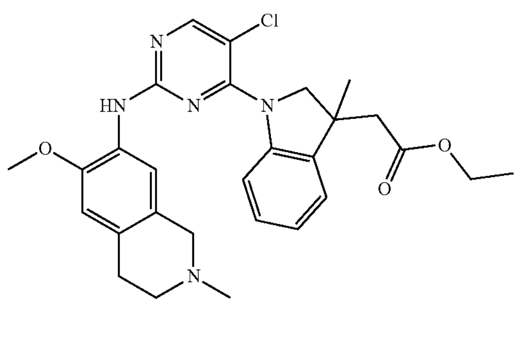 [SMILES: CCOC(=O)CC1(C)CN(c2nc(Nc3cc4c(cc3OC)CCN(C)C4)ncc2Cl)c2ccccc21]

Ethyl 2-(1-(5-chloro-24(6-methoxy-2-methyl-1,2,3,4-tetrahydroisoquinolin-7-yl)amino)pyrimidin-4-yl)-3-methylindolin-3-yl)acetate The same procedure as Example 132, using 2-(1-(5-chloro-2-((6-methoxy-2-methyl-1,2,3,4-tetrahydroisoquinolin-7-yl)amino)pyrimidin-4-yl)-3-methylindolin-3-yl)acetic acid in place of 2-(1-(5-chloro-2-((6-methoxy-2-methyl-1,2,3,4-tetrahydroisoquinolin-7-yl)amino)pyrimidin-4-yl)-1H-indol-3-yl)acetic acid. LC-MS (ESI) m/z: 522 $[M+H]^+$. $^1H$ NMR (400 MHz, DMSO-$d_6$) δ 8.25 (s, 1H), 7.97 (s, 1H), 7.57 (s, 1H), 7.36-7.24 (m, 2H), 7.12 (dd, J=11.1, 4.3 Hz, 1H), 6.98 (s, 1H), 6.74 (s, 1H), 4.41 (d, J=10.8 Hz, 1H), 4.05 (d, J=10.7 Hz, 1H), 3.96 (dd, J=7.1, 1.5 Hz, 2H), 3.77 (d, J=3.3 Hz, 3H), 3.27 (s, 2H), 2.75 (dd, J=10.1, 7.2 Hz, 3H), 2.65 (s, 1H), 2.55 (d, J=5.7 Hz, 2H), 2.30 (s, 3H), 1.35 (s, 3H), 1.06 (t, J=7.1 Hz, 3H).

Example 150

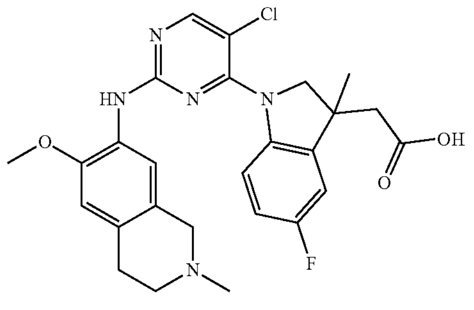 [SMILES: COc1cc2c(cc1Nc1ncc(Cl)c(N3CC(C)(CC(=O)O)c4cc(F)ccc43)n1)CN(C)CC2]

2-(1-(5-Chloro-2-((6-methoxy-2-methyl-1,2,3,4-tetrahydroisoquinolin-7-yl)amino)pyrimidin-4-yl)-5-fluoro-3-methylindolin-3-yl)acetic acid Step 1: A solution of Int. E34 (295 mg, 1.32 mmol), 2,4,5-trichloropyrimidine (266.6 mg, 1.45 mmol) and DIPEA (170.5 mg, 1.32 mmol) in n-BuOH (2 mL) was stirred at 100° C. for 2 hours, cooled to room temperature, poured into water, and extracted DCM/MeOH (v/v, 10/1, 20 mL×3). The organic phases were dried over anhydrous sodium sulfate and filtered. The filtrate was concentrated in vacuo, and the residue was purified by flash column chromatography on silica gel (EA/PE=1/4) to afford methyl 2-(1-(2,5-dichloropyrimidin-4-yl)-5-fluoro-3-methylindolin-3-yl)acetate (416 mg, 85.0% yield) as off-white solid. LC-MS (ESI) m/z: 370 $[M+H]^+$.

Step 2: A solution methyl 2-(1-(2,5-dichloropyrimidin-4-yl)-5-fluoro-3-methylindolin-3-yl)acetate (100 mg, 0.270 mmol), Int. W1 (62.3 mg, 0.324 mmol) and TsOH·$H_2O$ (51.3 mg, 0.270 mmol) in i-PrOH (2 mL) was stirred at 100° C. for 16 hours, cooled to room temperature, and neutralized to pH 8 with saturated $NaHCO_3$ aqueous solution. The mixture was extracted with DCM/MeOH (v/v, 10/1, 20 mL×3). The organic phases were dried over anhydrous sodium sulfate and filtered. The filtrate was concentrated in vacuo, and the residue was purified by flash column chromatography on silica gel (EA/PE=1/4) to afford methyl 2-(1-(5-chloro-2-((6-methoxy-2-methyl-1,2,3,4-tetrahydroisoquinolin-7-yl) amino)pyrimidin-4-yl)-5-fluoro-3-methylindolin-3-yl)acetate (186 mg, 80.7% yield, 60% purity) as light yellow solid. LC-MS (ESI) m/z: 526 $[M+H]^+$.

Step 3: A mixture of methyl 2-(1-(5-chloro-2-((6-methoxy-2-methyl-1,2,3,4-tetrahydroisoquinolin-7-yl)amino)pyrimidin-4-yl)-5-fluoro-3-methylindolin-3-yl)acetate (186 mg, 0.354 mmol) and LiOH aqueous solution (2N, 3.5 mL) in THF (8 mL) was stirred overnight at room temperature, adjusted to pH~5 with formic acid and extracted with DCM/MeOH (v/v, 10/1, 10 mL×3). The combined organic phases were dried over anhydrous sodium sulfate and filtered. The filtrate was concentrated in vacuo, and the residue was purified by prep-HPLC (MeCN/10 mM $NH_4HCO_3$, 0.025% $NH_3H_2O$) to afford 2-(1-(5-chloro-2-((6-methoxy-2-methyl-1,2,3,4-tetrahydroisoquinolin-7-yl)amino)pyrimidin-4-yl)-5-fluoro-3-methylindolin-3-yl)acetic acid (57.6 mg, 31.8% yield) as white solid. LC-MS (ESI) m/z: 512 $[M+H]^+$. $^1H$ NMR (400 MHz, DMSO-$d_6$) δ 8.23 (s, 1H), 8.02 (s, 1H), 7.51 (s, 1H), 7.34 (dd, J=8.7, 4.7 Hz, 1H), 7.20 (dd, J=8.6, 2.7 Hz, 1H), 6.89 (td, J=9.0, 2.7 Hz, 1H), 6.75 (s, 1H), 4.44 (d, J=10.9 Hz, 1H), 4.06 (d, J=10.8 Hz, 1H), 3.77 (s, 3H), 3.28 (s, 2H), 2.78 (t, J=5.7 Hz, 2H), 2.71 (d, J=15.6 Hz, 1H), 2.62 (s, 1H), 2.59-2.55 (m, 2H), 2.31 (s, 3H), 1.33 (s, 3H).

Example 151

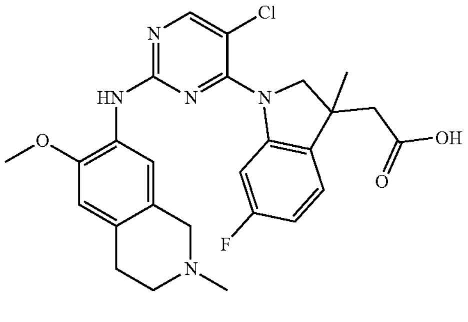

2-(1-(5-Chloro-24(6-methoxy-2-methyl-1,2,3,4-tetrahydroisoquinolin-7-yl)amino)pyrimidin-4-yl)-6-fluoro-3-methylindolin-3-yl)acetic acid Step 1: A solution of Int. E35 (78 mg, 0.349 mmol), 2,4,5-trichloropyrimidine (64.1 mg, 0.349 mmol) and DIPEA (135.2 mg, 1.05 mmol) in n-BuOH (2 mL) was stirred at 100° C. for 16 hours, cooled to room temperature, poured into water, and extracted DCM/MeOH (v/v, 10/1, 20 mL×3). The organic phases were dried over anhydrous sodium sulfate and filtered. The filtrate was concentrated in vacuo, and the residue was purified by flash column chromatography on silica gel (EA/PE=1/10) to afford methyl 2-(1-(2,5-dichloropyrimidin-4-yl)-6-fluoro-3-methylindolin-3-yl)acetate (100 mg, 73.4% yield) as light yellow oil. LC-MS (ESI) m/z: 370 $[M+H]^+$.

Step 2: A solution methyl 2-(1-(2,5-dichloropyrimidin-4-yl)-6-fluoro-3-methylindolin-3-yl)acetate (82.7 mg, 0.232 mmol), Int. W1 (63.8 mg, 0.279 mmol) and TsOH·$H_2O$ (53.0 mg, 0.279 mmol) in i-PrOH (2 mL) was stirred at 120° C. for 16 hours, cooled to room temperature, and neutralized to pH 8 with saturated $NaHCO_3$ aqueous solution. The mixture was extracted with DCM/MeOH (v/v, 10/1, 20 mL×3). The organic phases were dried over anhydrous sodium sulfate and filtered. The filtrate was concentrated in vacuo, and the residue was purified by flash column chromatography on silica gel (DCM/MeOH=10/1) to afford methyl 2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetate (81 mg, 62.9% yield) as light yellow solid. LC-MS (ESI) m/z: 526 $[M+H]^+$.

Step 3: A mixture of methyl 2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetate (81 mg, 0.154 mmol) and LiOH aqueous solution (1N, 4 mL) in dioxane (4 mL) was stirred overnight at room temperature, adjusted to pH~5 with formic acid and extracted with EA (30 mL×3). The combined organic phases were dried over anhydrous sodium sulfate and filtered. The filtrate was concentrated in vacuo, and the residue was purified by prep-HPLC (MeCN/10 mM $NH_4HCO_3$, 0.025% $NH_3H_2O$) to afford 2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid (29.8 mg, 37.8% yield) as white solid. LC-MS (ESI) m/z: 512 $[M+H]^+$. $^1H$ NMR (400 MHz, DMSO-$d_6$) δ 8.26 (s, 1H), 8.17 (s, 1H), 7.46 (s, 1H), 7.31-7.23 (m, 1H), 7.14 (d, J=10.0 Hz, 1H), 6.75 (s, 2H), 4.46 (d, J=10.7 Hz, 1H), 4.07 (d, J=10.6 Hz, 1H), 3.77 (s, 3H), 3.31 (s, 2H), 2.77 (s, 2H), 2.69 (d, J=15.6 Hz, 1H), 2.58 (d, J=14.8 Hz, 3H), 2.31 (s, 3H), 1.33 (s, 3H).

Examples 152 & 153

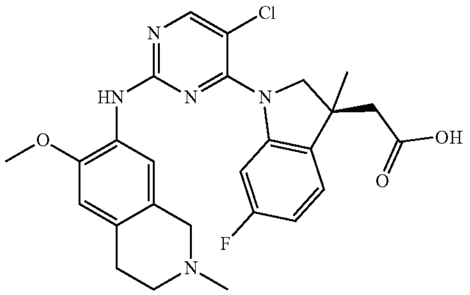

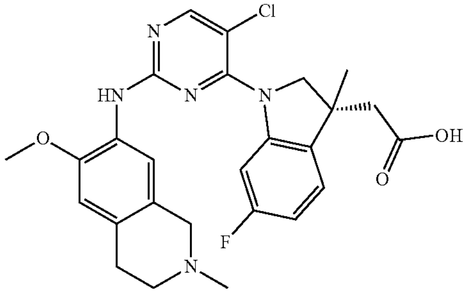 [SMILES: COc1cc2c(cc1Nc1ncc(Cl)c(N3CC(C)(CC(=O)O)c4ccc(F)cc43)n1)CN(C)CC2]

(S)-2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid & (R)-2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid Synthesized after chiral-separation of the racemic 2-(1-(5-chloro-2-((6-methoxy-2-methyl-1,2,3,4-tetrahydroisoquinolin-7-yl)amino)pyrimidin-4-yl)-6-fluoro-3-methylindolin-3-yl)acetic acid. The stereochemistry was not confirmed, and two products were arbitrarily assigned.

LC-MS (ESI) m/z: 512 $[M+H]^+$. Chiral-HPLC retention time: 11.913 min; ee value: 80.4%.

LC-MS (ESI) m/z: 512 $[M+H]^+$. Chiral-HPLC retention time: 16.631 min; ee value: 98.9%.

SFC Separation Conditions:

Instrument: Gilson-281

Column: IG 20*250 mm, 10 um

Mobile Phase: n-hexane (0.1% dimethylamine)/EtOH (0.1% diethylamine)=65:35

Flow Rate: 40 mL/min

Cycle time: 22 min

Example 154

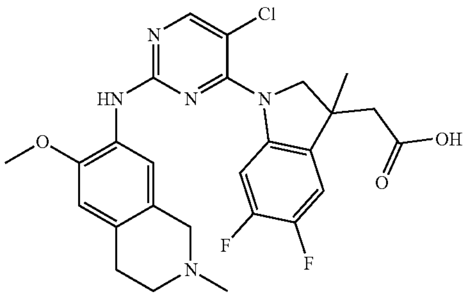 [SMILES: COc1cc2c(cc1Nc1ncc(Cl)c(N3CC(C)(CC(=O)O)c4cc(F)c(F)cc43)n1)CN(C)CC2]

2-(1-(5-Chloro-24(6-methoxy-2-methyl-1,2,3,4-tetrahydroisoquinolin-7-yl)amino)pyrimidin-4-yl)-5,6-difluoro-3-methylindolin-3-yl)acetic acid The same procedures as Example 146, using Int. E36 in place of Int. E33. LC-MS (ESI) m/z: 530 $[M+H]^+$. $^1H$ NMR (500 MHz, DMSO-$d_6$) δ 8.24 (s, 1H), 8.20 (s, 1H), 7.45-7.36 (m, 3H), 6.75 (s, 1H), 4.46 (d, J=10.8 Hz, 1H), 4.08 (d, J=10.7 Hz, 1H), 3.76 (s, 3H), 3.27 (s, 2H), 2.77 (t, J=5.5 Hz, 2H), 2.70 (d, J=15.6 Hz, 1H), 2.61 (s, 1H), 2.56 (dd, J=12.0, 6.2 Hz, 2H), 2.29 (s, 3H), 1.31 (s, 3H).

Example 155

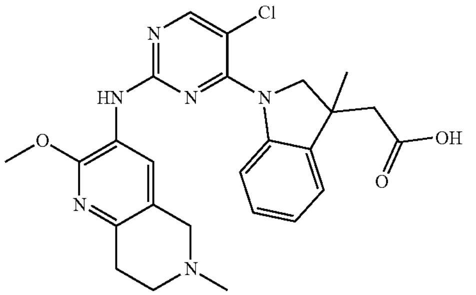 [SMILES: COc1nc2c(cc1Nc1ncc(Cl)c(N3CC(C)(CC(=O)O)c4ccccc43)n1)CN(C)CC2]

2-(1-(5-Chloro-24(2-methoxy-6-methyl-5,6,7,8-tetrahydro-1,6-naphthyridin-3-yl)amino)pyrimidin-4-yl)-3-methylindolin-3-yl)acetic acid The same procedures as Example 146, using Int. W4 in place of Int. W1 in Step 2, and omitting Step 3 because of the hydrolysis of methyl ester in Step 2. LC-MS (ESI) m/z: 495 $[M+H]^+$. $^1H$ NMR (500 MHz, DMSO-$d_6$) δ 11.87 (s, 1H), 8.37 (s, 1H), 7.99 (s, 1H), 7.87 (s, 1H), 7.35 (t, J=8.6 Hz, 2H), 7.23 (t, J=7.7 Hz, 1H), 7.03 (t, J=7.3 Hz, 1H), 4.39 (d, J=10.7 Hz, 1H), 4.07 (d, J=10.7 Hz, 1H), 3.47 (s, 3H), 3.31 (s, 1H), 3.09 (s, 2H), 2.80 (d, J=15.0 Hz, 1H), 2.71-2.63 (m, 1H), 2.56 (s, 1H), 2.54 (s, 2H), 2.31 (s, 3H), 1.37 (s, 3H).

Example 156

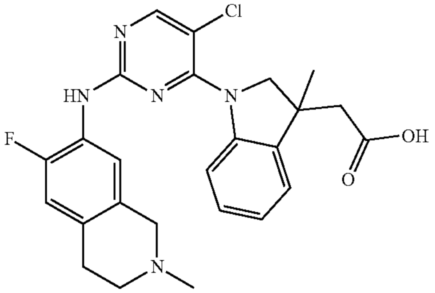 [SMILES: CN1CCc2cc(F)c(Nc3ncc(Cl)c(N4CC(C)(CC(=O)O)c5ccccc54)n3)cc2C1]

2-(1-(5-Chloro-24(6-fluoro-2-methyl-1,2,3,4-tetrahydroisoquinolin-7-yl)amino)pyrimidin-4-yl)-3-methylindolin-3-yl)acetic acid Step 1: A solution methyl 2-(1-(2,5-dichloropyrimidin-4-yl)-3-methylindolin-3-yl)acetate (195.4 mg, 0.555 mmol), Int. W7 (100 mg, 0.555 mmol) and TsOH·$H_2O$ (105.5 mg, 0.555 mmol) in i-PrOH (4 mL) was stirred at 120° C. for 16 hours, cooled to room temperature, and neutralized to pH~8 with saturated $NaHCO_3$ aqueous solution. The mixture was extracted with DCM/MeOH (v/v, 10/1, 20 mL×3). The organic phases were dried over anhydrous sodium sulfate and filtered. The filtrate was concentrated in vacuo, and the residue was purified by flash column chromatography on silica gel (DCM/MeOH=10/1) to afford a mixture of methyl 2-(1-(5-chloro-2-((6-fluoro-2-methyl-1,2,3,4-tetrahydroisoquinolin-7-yl)amino)pyrimidin-4-yl)-3-methylindolin-3-yl)acetate and isopropyl 2-(1-(5-chloro-2-((6-fluoro-2-methyl-1,2,3,4-tetrahydroisoquinolin-7-yl)amino)pyrimidin-4-yl)-3-methylindolin-3-yl)acetate (440 mg) as light yellow solid, which was used in the next step without further purifications. LC-MS (ESI) m/z: 496 (methyl ester), 524 (isopropyl ester) $[M+H]^+$.

Step 3: A mixture of a mixture of methyl 2-(1-(5-chloro-2-((6-fluoro-2-methyl-1,2,3,4-tetrahydroisoquinolin-7-yl) amino)pyrimidin-4-yl)-3-methylindolin-3-yl)acetate and isopropyl 2-(1-(5-chloro-2-((6-fluoro-2-methyl-1,2,3,4-tetrahydroisoquinolin-7-yl) amino)pyrimidin-4-yl)-3-methylindolin-3-yl)acetate (220 mg) and LiOH aqueous solution (2N, 4 mL) in THF (4 mL) was stirred at room temperature for 5 hours and 50° C. for 16 hours, adjusted to pH~5 with formic acid and extracted with DCM/MeOH (10/1, 20 mL×3). The combined organic phases were dried over anhydrous sodium sulfate and filtered. The filtrate was concentrated in vacuo, and the residue was purified by prep-HPLC (MeCN/10 mM $NH_4HCO_3$) to afford 2-(1-(5-chloro-2-((6-fluoro-2-methyl-1,2,3,4-tetrahydroisoquinolin-7-yl)amino)pyrimidin-4-yl)-3-methylindolin-3-yl)acetic acid (26.5 mg, 12.4% yield) as white solid. LC-MS (ESI) m/z: 482 $[M+H]^+$. $^1H$ NMR (400 MHz, DMSO-$d_6$) δ 8.93 (s, 1H), 8.22 (s, 1H), 7.35-7.24 (m, 3H), 7.07-6.92 (m, 3H), 4.41 (d, J=10.7 Hz, 1H), 4.03 (d, J=10.8 Hz, 1H), 3.36 (s, 2H), 2.78 (d, J=5.4 Hz, 2H), 2.68 (d, J=15.5 Hz, 1H), 2.60-2.54 (m, 3H), 2.32 (s, 3H), 1.33 (s, 3H).

Example 157

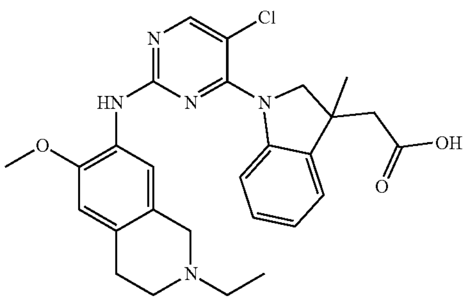 [SMILES: CCN1CCc2cc(OC)c(Nc3ncc(Cl)c(N4CC(C)(CC(=O)O)c5ccccc54)n3)cc2C1]

2-(1-(5-Chloro-2-((2-ethyl-6-methoxy-1,2,3,4-tetrahydroisoquinolin-7-yl)amino)pyrimidin-4-yl)-3-methylindolin-3-yl)acetic acid The same procedures as Example 146, using Int. W8 in place of Int. W1 in Step 2. LC-MS (ESI) m/z: 508 $[M+H]^+$. $^1$H NMR (400 MHz, DMSO-$d_6$) δ 8.25 (s, 1H), 7.97 (s, 1H), 7.61 (s, 1H), 7.31 (dd, J=21.0, 7.7 Hz, 2H), 7.12 (t, J=7.5 Hz, 1H), 6.96 (t, J=7.2 Hz, 1H), 6.74 (s, 1H), 4.42 (d, J=10.7 Hz, 1H), 4.02 (d, J=10.7 Hz, 1H), 3.78 (s, 3H), 3.34 (s, 2H), 2.76 (s, 2H), 2.66-2.55 (m, 4H), 2.50-2.45 (d, J=6.8 Hz, 2H), 1.34 (s, 3H), 1.08 (t, J=7.0 Hz, 3H).

Example 158

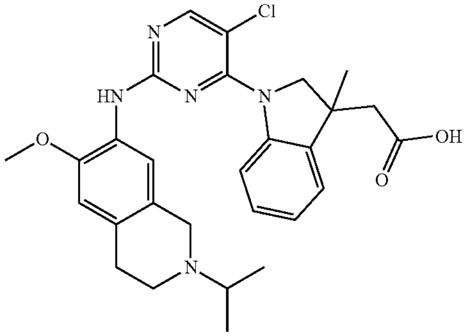 [SMILES: COc1cc2c(cc1Nc1ncc(Cl)c(N3CC(C)(CC(=O)O)c4ccccc43)n1)CN(C(C)C)CC2]

2-(1-(5-Chloro-2-((2-isopropyl-6-methoxy-1,2,3,4-tetrahydroisoquinolin-7-yl)amino)pyrimidin-4-yl)-3-methylindolin-3-yl)acetic acid The same procedures as Example 146, using Int. W5 in place of Int. W1 in Step 2. LC-MS (ESI) m/z: 522 $[M+H]^+$. $^1$H NMR (400 MHz, DMSO-$d_6$) δ 8.26 (s, 1H), 8.22 (s, 1H), 7.97 (s, 1H), 7.63 (s, 1H), 7.34 (d, J=8.0 Hz, 1H), 7.28 (d, J=6.9 Hz, 1H), 7.17-7.05 (m, 1H), 6.96 (t, J=7.4 Hz, 1H), 6.73 (s, 1H), 4.42 (d, J=10.8 Hz, 1H), 4.02 (d, J=10.8 Hz, 1H), 3.78 (s, 3H), 3.47 (s, 2H), 2.93-2.81 (m, 1H), 2.77-2.68 (m, 4H), 2.66-2.54 (m, 2H), 1.34 (s, 3H), 1.06 (d, J=6.5 Hz, 6H).

Example 159

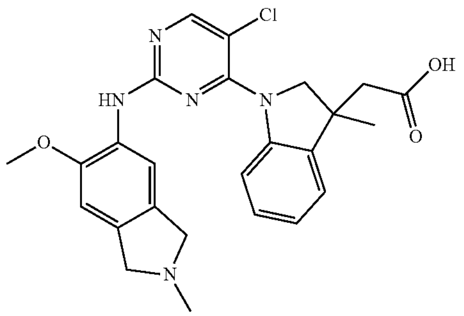 [SMILES: COc1cc2c(cc1Nc1ncc(Cl)c(N3CC(C)(CC(=O)O)c4ccccc43)n1)CN(C)C2]

2-(1-(5-Chloro-2-((6-methoxy-2-methylisoindolin-5-yl)amino)pyrimidin-4-yl)-3-methylindolin-3-yl)acetic acid The same procedures as Example 146, using Int. W9 in place of Int. W1 in Step 2. LC-MS (ESI) m/z: 480 $[M+H]^+$. $^1$H NMR (500 MHz, DMSO-$d_6$) δ 8.26 (s, 1H), 8.02 (s, 1H), 7.77 (s, 1H), 7.34 (d, J=8.0 Hz, 1H), 7.28 (d, J=7.1 Hz, 1H), 7.11 (t, J=7.3 Hz, 1H), 6.98 (t, J=7.2 Hz, 1H), 6.94 (s, 1H), 4.41 (d, J=10.8 Hz, 1H), 4.02 (d, J=10.7 Hz, 1H), 3.80 (s, 5H), 3.70 (s, 2H), 2.69 (d, J=15.5 Hz, 1H), 2.57 (d, J=15.4 Hz, 1H), 2.47 (s, 3H), 1.34 (s, 3H).

Example 160

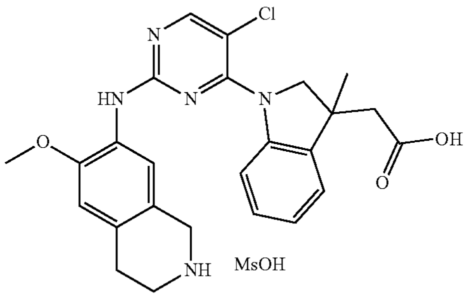 [SMILES: "MsOH" ; COc1cc2c(cc1Nc1ncc(Cl)c(N3CC(C)(CC(=O)O)c4ccccc43)n1)CNCC2]

2-(1-(5-Chloro-2-((6-methoxy-1,2,3,4-tetrahydroisoquinolin-7-yl)amino)pyrimidin-4-yl)-3-methylindolin-3-yl)acetic acid methanesulfonic acid The same procedures as Example 146, using Int. W11 in place of Int. W1 in Step 2. LC-MS (ESI) m/z: 480 $[M+H]^+$.

To a solution of 2-(1-(5-chloro-2-((6-methoxy-1,2,3,4-tetrahydroisoquinolin-7-yl)amino)pyrimidin-4-yl)-3-methylindolin-3-yl)acetic acid (40 mg, 0.083 mmol) in acetonitrile (20 mL) was added methanesulfonic acid (8.0 mg, 0.083 mmol). The reaction mixture was stirred at 25° C. for 30 minutes and concentrated in vacuo. The residue was diluted with water (15 mL), and lyophilized to methanesulfonic acid salt of 2-(1-(5-chloro-2-((6-methoxy-1,2,3,4-tetrahydroisoquinolin-7-yl)amino)pyrimidin-4-yl)-3-methylindolin-3-yl)acetic acid (39.4 mg, 81.3% yield) as white solid. LC-MS (ESI) m/z: 480 $[M+H]^+$. $^1$H NMR (400 MHz, DMSO-$d_6$) δ 7.97 (d, J=14.2 Hz, 2H), 7.56 (s, 1H), 6.74 (s, 1H), 4.00 (s, 2H), 3.88 (d, J=11.4 Hz, 1H), 3.82 (s, 3H), 3.55 (s, 1H), 3.42 (s, 2H), 2.86 (t, J=7.5 Hz, 1H), 2.77 (s, 2H), 2.58 (s, 2H), 2.32 (s, 3H), 1.76-1.24 (m, 10H).

Example 161

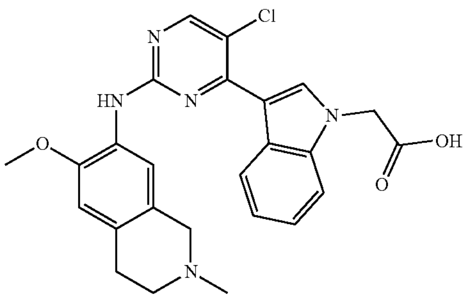 [SMILES: COc1cc2c(cc1Nc1ncc(Cl)c(-c3cn(CC(=O)O)c4ccccc34)n1)CN(C)CC2]

2-(3-(5-Chloro-2-(6-methoxy-2-methyl-1,2,3,4-tetrahydroisoquinolin-7-yl)amino)pyrimidin-4-yl)-1H-indol-1-yl)acetic acid Step 1: To a solution of indole (600.0 mg, 5.12 mmol) in anhydrous THF (10 mL) was added methylmagnesium bromide solution in THF (1M, 5 mL) at 0° C., followed by the addition of 2,4,5-trichloropyrimidine (466 mg, 2.54 mmol) 10 minutes later. The reaction mixture was stirred at 60° C. for 3 hours, cooled to room temperature and concentrated in vacuo. The residue was partitioned between water (10 mL) and DCM (20 mL×3). The organic phases were washed with brine (30 mL), dried over anhydrous sodium sulfate and filtered. The filtrate was concentrated in vacuo, and the residue was purified by flash column chromatography on silica gel (5-10% EA/PE) to provide 3-(2,5-dichloropyrimidin-4-yl)-1H-indole as yellow solid (160 mg, 12% yield). LC-MS (ESI) m/z: 264 $[M+H]^+$.

Step 2: To a solution of 3-(2,5-dichloropyrimidin-4-yl)-1H-indole (160 mg, 0.606 mmol) and ethyl 2-bromoacetate (303.5 mg, 1.82 mmol, 201.00 uL) in DMF (5 mL) was added sodium bicarbonate (254.5 mg, 3.03 mmol) at 25° C. The mixture was stirred at 80° C. for 16 hours, cooled to room temperature, diluted with water (20 mL), and extracted with EA (20 mL×3). The combined organic phases were washed with brine (30 mL), dried over anhydrous $Na_2SO_4$, and filtered. The filtrate was concentrated in vacuo, and the residue was purified by flash column chromatography on silica gel (20-30% EA/PE) to provide ethyl 2-(3-(2,5-dichloropyrimidin-4-yl)-1H-indol-1-yl)acetate as light-yellow oil (220 mg, 93% yield). LC-MS (ESI) m/z: 315 $[M+H]^+$.

Step 3: Ethyl 2-(3-(2,5-dichloropyrimidin-4-yl)-1H-indol-1-yl)acetate (100 mg, 0.286 mmol) and Int. W1 (78.4 mg, 0.343 mmol) were used under Condition B3 to provide isopropyl 2-(3-(5-chloro-2-((6-methoxy-2-methyl-1,2,3,4-tetrahydroisoquinolin-7-yl)amino)pyrimidin-4-yl)-1H-indol-1-yl)acetate (238 mg, 72.9% yield) as light yellow oil, after purification by flash column chromatography on silica gel (30-60% MeOH/DCM). LC-MS (ESI) m/z: 520 $[M+H]^+$.

Step 4: To a solution of isopropyl 2-(3-(5-chloro-2-((6-methoxy-2-methyl-1,2,3,4-tetrahydroisoquinolin-7-yl)amino)pyrimidin-4-yl)-1H-indol-1-yl)acetate (238 mg, 0.412 mmol) in THF (6 mL) and water (3 mL) was added $LiOH \cdot H_2O$ (480.1 mg, 11.44 mmol). The mixture was stirred at 25° C. for 2 hours, acidified with formic acid to pH~5, and purified by prep-HPLC (0.1% formic acid/acetonitrile) to afford 2-(3-(5-chloro-2-((6-methoxy-2-methyl-1,2,3,4-tetrahydroisoquinolin-7-yl)amino)pyrimidin-4-yl)-1H-indol-1-yl)acetic acid (124.9 mg, 63.4% yield) as a light yellow solid. LC-MS (ESI) m/z: 478 $[M+H]^+$. $^1H$ NMR (500 MHz, DMSO-$d_6$) δ 8.56 (s, 1H), 8.47-8.30 (m, 2H), 8.23 (d, J=32.9 Hz, 1H), 7.62 (s, 1H), 7.42 (d, J=8.1 Hz, 1H), 7.21 (t, J=7.5 Hz, 1H), 7.07 (t, J=7.4 Hz, 1H), 6.84 (s, 1H), 5.01 (s, 2H), 3.79 (s, 3H), 3.51 (s, 2H), 2.88 (s, 2H), 2.74 (s, 2H), 2.39 (s, 3H).

Example 162

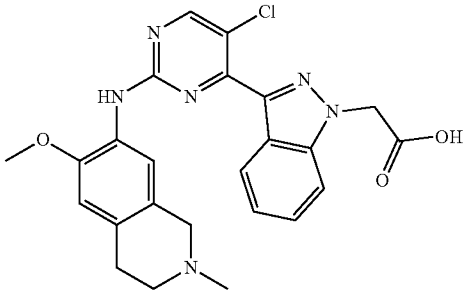 [SMILES: COc1cc2c(cc1Nc1ncc(Cl)c(-c3nn(CC(=O)O)c4ccccc34)n1)CN(C)CC2]

2-(3-(5-Chloro-2-((6-methoxy-2-methyl-1,2,3,4-tetrahydroisoquinolin-7-yl)amino)pyrimidin-4-yl)-1H-indazol-1-yl)acetic acid Step 1: To a solution of 3-iodo-1H-indazole (500 mg, 2.05 mmol) in THF (15 mL) was added potassium tert-butoxide (344.9 mg, 3.07 mmol) in small portions at 0° C., followed by the dropwise addition of ethyl 2-bromoacetate (684.3 mg, 4.10 mmol) an hour later. The mixture was stirred at 25° C. for 16 hours and concentrated in vacuo. The residue was partitioned between EA (20 mL) and water (20 mL). The organic phase was separated, and the aqueous phase was extracted with EA (20 mL×3), the combined organic phases were dried over anhydrous $Na_2SO_4$ and filtered. The filtrate was concentrated in vacuo, and the residue was purified by flash column chromatography on silica gel (15-20% EA/PE) to provide ethyl 2-(3-iodo-1H-indazol-1-yl)acetate as colorless oil (549 mg, 81% yield). LC-MS (ESI) m/z: 331 $[M+H]^+$.

Step 2: A mixture of ethyl 2-(3-iodo-1H-indazol-1-yl)acetate (520 mg, 1.58 mmol), hexamethyldistannane (1.03 g, 3.15 mmol) and $Pd(PPh_3)_4$ (182.1 mg, 0.158 mmol) in dioxane (10 mL) was purged with $N_2$, stirred at 100° C. for 16 hours, cooled to 0° C. and quenched with 1M KF solution (10 mL). The resulting mixture was stirred at room temperature for 30 minutes, diluted with water (30 mL), and extracted dichloromethane/methanol (v/v, 10/1, 20 mL×3), the combined organic phase was dried over anhydrous sodium sulfate and filtered. The filtrate was concentrated in vacuo, and the residue was purified by flash column chromatography on silica gel (EA/PE=1/4) to provide ethyl 2-(3-(trimethylstannyl)-1H-indazol-1-yl)acetate as colorless oil (145 mg, 25% yield). LC-MS (ESI) m/z: 369 $[M+H]^+$.

Step 3: A mixture of ethyl 2-(3-(trimethylstannyl)-1H-indazol-1-yl)acetate (145 mg, 0.395 mmol), 2,4,5-trichloropyrimidine (72.5 mg, 0.395 mmol) and $Pd(PPh_3)_4$ (45.7 mg, 0.040 mmol) in dioxane (5 mL) was purged with $N_2$, stirred at 100° C. for 16 hours, and concentrated in vacuo. The residue was purified by flash column chromatography on silica gel (EA/PE=1/4) to provide ethyl 2-(3-(2,5-dichloropyrimidin-4-yl)-1H-indazol-1-yl)acetate as white solid (68 mg, 49% yield). LC-MS (ESI) m/z: 351 $[M+H]^+$.

Step 4&5: The same procedures as Step 3 & 4 of Example 161, using ethyl 2-(3-(2,5-dichloropyrimidin-4-yl)-1H-indazol-1-yl)acetate in place of 2-(3-(2,5-dichloropyrimidin-4-yl)-1H-indol-1-yl)acetate. LC-MS (ESI) m/z: 479 $[M+H]^+$. $^1H$ NMR (400 MHz, DMSO-$d_6$) δ 8.57 (d, J=13.2 Hz, 2H), 8.18 (d, J=7.8 Hz, 1H), 7.67 (d, J=8.5 Hz, 1H), 7.58 (s, 1H), 7.51-7.35 (m, 1H), 7.27-7.13 (m, 1H), 6.88 (s, 1H), 5.23 (s, 2H), 3.79 (s, 3H), 3.62 (s, 2H), 2.91 (d, J=5.2 Hz, 2H), 2.85 (d, J=5.0 Hz, 2H), 2.47 (s, 3H).

Example 167

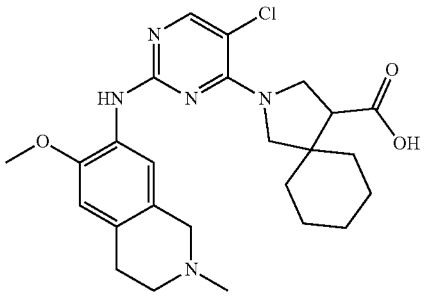 [SMILES: COc1cc2c(cc1Nc1ncc(Cl)c(N3CC(C(=O)O)C4(CCCCC4)C3)n1)CN(C)CC2]

2-(5-Chloro-2-((6-methoxy-2-methyl-1,2,3,4-tetrahydroisoquinolin-7-yl)amino)pyrimidin-4-yl)-2-azaspiro[4.5]decane-4-carboxylic acid Step 1: To a solution of Int. E38 (500 mg, 2.37 mmol) and 2,4,5-trichloropyrimidine (434.0 mg, 2.37 mmol) in DCM (5 mL) was added DIPEA (917.5 mg, 7.10 mmol) dropwise at 0° C. The mixture was stirred at 25° C. for 2 hours, quenched with ice-cold saturated $NH_4Cl$ aqueous solution (30 mL) and extracted with EA (50 mL×3). The organic phases were washed with brine (20 mL), dried over anhydrous $Na_2SO_4$ and filtered. The filtrate was concentrated in vacuo, and the residue was purified by flash column chromatography on silica gel (PE/EA=5-15%) to afford ethyl 2-(2,5-dichloropyrimidin-4-yl)-2-azaspiro[4.5]decane-4-carboxylate (798 mg, 94.1% yield) as a light yellow solid. LC-MS (ESI) m/z: 358 $[M+H]^+$.

Step 2: Ethyl 2-(2,5-dichloropyrimidin-4-yl)-2-azaspiro[4.5]decane-4-carboxylate (100 mg, 0.279 mmol) and Int. W1 (63.8 mg, 0.279 mmol) were used under Condition B3 to provide ethyl 2-(5-chloro-2-((6-methoxy-2-methyl-1,2,3,4-tetrahydroisoquinolin-7-yl)amino)pyrimidin-4-yl)-2-azaspiro[4.5]decane-4-carboxylate (116 mg, 70.3% yield, 87% purity) as light-yellow solid, after purification by flash column chromatography on silica gel (MeOH/DCM=5-10%). LC-MS (ESI) m/z: 514 $[M+H]^+$.

Step 3: The same procedure as Step 3 of Example 117, using ethyl 2-(5-chloro-2-((6-methoxy-2-methyl-1,2,3,4-tetrahydroisoquinolin-7-yl)amino)pyrimidin-4-yl)-2-azaspiro[4.5]decane-4-carboxylate in place of methyl 1-(5-chloro-2-((6-methoxy-2-methyl-1,2,3,4-tetrahydroisoquinolin-7-yl)amino)pyrimidin-4-yl)-3-methylindoline-3-carboxylate. LC-MS (ESI) m/z: 486 $[M+H]^+$. $^1H$ NMR (400 MHz, DMSO-$d_6$) δ 7.97 (d, J=14.2 Hz, 2H), 7.56 (s, 1H), 6.74 (s, 1H), 4.00 (s, 2H), 3.88 (d, J=11.4 Hz, 1H), 3.82 (s, 3H), 3.55 (s, 1H), 3.42 (s, 2H), 2.86 (t, J=7.5 Hz, 1H), 2.77 (s, 2H), 2.58 (s, 2H), 2.32 (s, 3H), 1.76-1.24 (m, 10H).

Example 168

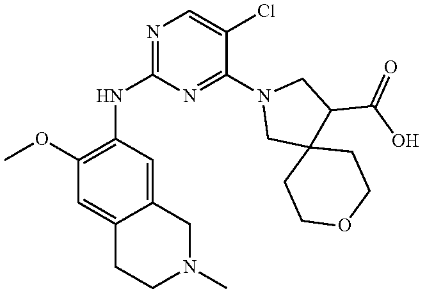 [SMILES: COc1cc2c(cc1Nc1ncc(Cl)c(N3CC(C(=O)O)C4(CCOCC4)C3)n1)CN(C)CC2]

2-(5-Chloro-24(6-methoxy-2-methyl-1,2,3,4-tetrahydroisoquinolin-7-yl)amino)pyrimidin-4-yl)-8-oxa-2-azaspiro[4.5]decane-4-carboxylic acid The same procedures as Example 167, using Int. E39 in place of Int. E38. LC-MS (ESI) m/z: 488 $[M+H]^+$. $^1H$ NMR (400 MHz, DMSO-$d_6$) δ 7.97 (d, J=7.8 Hz, 2H), 7.57 (s, 1H), 6.75 (s, 1H), 3.99 (t, J=10.3 Hz, 3H), 3.82 (s, 3H), 3.77 (d, J=11.1 Hz, 2H), 3.66 (d, J=10.6 Hz, 1H), 3.50 (s, 2H), 3.46 (s, 2H), 2.95 (t, J=7.2 Hz, 1H), 2.78 (s, 2H), 2.62 (s, 2H), 2.34 (s, 3H), 1.98 (s, 1H), 1.56-1.44 (m, 3H).

Example 169

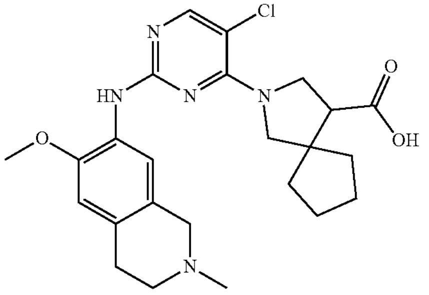 [SMILES: COc1cc2c(cc1Nc1ncc(Cl)c(N3CC(C(=O)O)C4(CCCC4)C3)n1)CN(C)CC2]

2-(5-Chloro-2-((6-methoxy-2-methyl-1,2,3,4-tetrahydroisoquinolin-7-yl)amino)pyrimidin-4-yl)-2-azaspiro[4.4]nonane-4-carboxylic acid The same procedures as Example 167, using Int. E40 in place of Int. E38. LC-MS (ESI) m/z: 472 $[M+H]^+$. $^1H$ NMR (400 MHz, DMSO-$d_6$) δ 7.96 (s, 1H), 7.94 (s, 1H), 7.54 (s, 1H), 6.73 (s, 1H), 3.95 (d, J=5.9 Hz, 2H), 3.81 (s, 3H), 3.72 (d, J=10.5 Hz, 1H), 3.57 (d, J=10.1 Hz, 1H), 3.41 (s, 2H), 2.98 (t, J=7.1 Hz, 1H), 2.75 (d, J=5.5 Hz, 2H), 2.58 (t, J=5.7 Hz, 2H), 2.32 (s, 3H), 1.89 (s, 1H), 1.69-1.54 (m, 6H), 1.49 (s, 1H).

Example 170

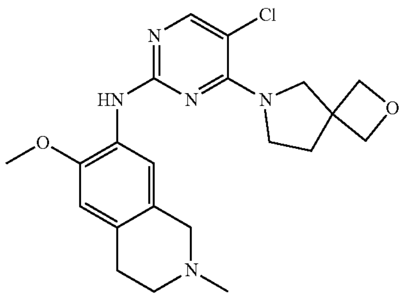 [SMILES: COc1cc2c(cc1Nc1ncc(Cl)c(N3CCC4(COC4)C3)n1)CN(C)CC2]

N-(5-chloro-4-(2-oxa-6-azaspiro[3.4]octan-6-yl)pyrimidin-2-yl)-6-methoxy-2-methyl-1,2,3,4-tetrahydroisoquinolin-7-amine Step 1: A mixture of 2,4,5-trichloropyrimidine (1 g, 5.45 mmol) and sodium hydroxide aqueous solution (1N, 1 mL) in THF (3 mL) was stirred at room temperature for 3 hours, acidified to pH~6 with 1 N HCl and extracted with $CH_2Cl_2$ (50 mL×3). The combined organic phase was dried over anhydrous $Na_2SO_4$ and filtered. The filtrate was concentrated in vacuo, and the residue was purified by recrystallization in 20% $CH_2Cl_2$/Petroleum ether to provide 2,5-dichloropyrimidin-4(3H)-one (374 mg, 29% yield). LC-MS (ESI) m/z: 165 $[M+H]^+$.

Step 2: 2,5-Dichloropyrimidin-4(3H)-one (351 mg, 1.38 mmol) and Int. W1 (347.9 mg, 1.52 mmol) were used under Condition B3 to provide 5-chloro-2-((6-methoxy-2-methyl-1,2,3,4-tetrahydroisoquinolin-7-yl)amino)pyrimidin-4(3H)-one (419 mg, 78.4% yield), after purification by flash column chromatography on silica gel (PE/EA=4/1). LC-MS (ESI) m/z: 321 $[M+H]^+$.

Step 3: A solution of 5-chloro-2-((6-methoxy-2-methyl-1,2,3,4-tetrahydroisoquinolin-7-yl)amino)pyrimidin-4(3H)-one (150 mg, 0.388 mmol) in phosphoryl trichloride (1 mL) was stirred at 95° C. for 18 hours cooled to room temperature, poured to saturated $NaHCO_3$ aqueous solution (50 mL) and extracted with dichloromethane (20 mL×3). The combined organic phase was dried over anhydrous $Na_2SO_4$ and filtered. The filtrate was concentrated in vacuo to provide crude N-(4,5-dichloropyrimidin-2-yl)-6-methoxy-2-methyl-1,2,3,4-tetrahydroisoquinolin-7-amine (160 mg, 36% yield, 30% purity). LC-MS (ESI) m/z: 339 $[M+H]^+$.

Step 4: N-(4,5-dichloropyrimidin-2-yl)-6-methoxy-2-methyl-1,2,3,4-tetrahydroisoquinolin-7-amine (140 mg, 0.124 mmol, 30% purity) and 2-oxa-7-azaspiro[3.4]octane (16.8 mg, 0.149 mmol) were used under Condition A3 to provide N-(5-chloro-4-(2-oxa-6-azaspiro[3.4]octan-6-yl)pyrimidin-2-yl)-6-methoxy-2-methyl-1,2,3,4-tetrahydroisoquinolin-7-amine (11.8 mg, 22.9% yield), after purification by prep-HPLC (MeCN/10 mM $NH_4HCO_3$, 0.025% $NH_3H_2O$). LC-MS (ESI) m/z: 415 $[M+H]^+$. $^1$H NMR (400 MHz, $CDCl_3$) δ 8.08 (s, 1H), 7.91 (s, 1H), 7.40 (s, 1H), 6.59 (s, 1H), 4.72 (d, J=6.2 Hz, 2H), 4.64 (d, J=6.2 Hz, 2H), 4.06 (s, 2H), 3.87-3.83 (m, 2H), 3.85 (s, 3H), 3.55 (s, 2H), 2.87 (t, J=5.8 Hz, 2H), 2.68 (t, J=5.9 Hz, 2H), 2.47 (s, 3H), 2.25 (t, J=7.0 Hz, 2H).

Example 36

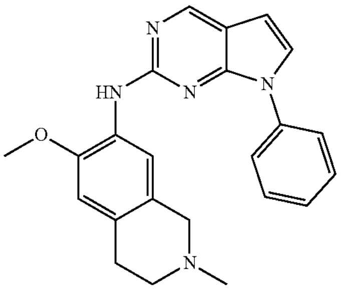 [SMILES: COc1cc2c(cc1Nc1ncc3ccn(-c4ccccc4)c3n1)CN(C)CC2]

6-Methoxy-2-methyl-N-(7-phenyl-7H-pyrrolo[2,3-d]pyrimidin-2-yl)-1,2,3,4-tetrahydroisoquinolin-7-amine Step 1: A mixture of 2-chloro-7H-pyrrolo[2,3-d]pyrimidine (153 mg, 1.0 mmol), 1-bromo-2-iodo-benzene (422.78 mg, 1.50 mmol), potassium carbonate (413.09 mg, 3.0 mmol), CuI (379.49 mg, 2.0 mmol), and (1S,2S)—$N^1$,$N^2$-dimethylcyclohexane-1,2-diamine (282.95 mg, 2.0 mmol) in DMF (8 mL) was stirred under $N_2$ at 120° C. for 18 hours. After cooled down to room temperature, the mixture was filtered and washed with ethyl acetate (100 mL). The filtrate was diluted with $H_2O$ (100 mL) and separated. The aqueous phase was extracted with ethyl acetate (100 mL×2). The combined organic layers were washed with brine (100 mL×4), dried over anhydrous sodium sulfate and filtered. The filtrate was concentrated in vacuo. The residue was purified by flash column chromatography on silica gel (EA/PE=1/15 v/v) to provide 2-chloro-7-phenyl-pyrrolo[2,3-d]pyrimidine as yellow solid (40 mg, 17% yield). LC-MS (ESI) m/z: 230 $[M+H]^+$.

Step 2: 2-Chloro-7-phenyl-pyrrolo[2,3-d]pyrimidine (60 mg, 0.26 mmol) and Int. W1 (60.3 mg, 0.31 mmol) were used under Condition B4 (as exemplified in Step 2 of Example 28) to provide 6-methoxy-2-methyl-N-(7-phenyl-7H-pyrrolo[2,3-d]pyrimidin-2-yl)-1,2,3,4-tetrahydroisoquinolin-7-amine (21.4 mg, 21% yield) as yellow solid, after purification by prep-HPLC (MeCN/0.1% FA). LC-MS (ESI) m/z: 386 $[M+H]^+$. $^1$H NMR (400 Mhz, $CD_3OD$): δ (ppm) 2.73 (s, 3H), 2.98-3.01 (m, 2H), 3.08-3.12 (m, 2H), 3.83 (s, 2H), 3.91 (s, 3H), 6.65 (d, J=4.0 Hz, 1H), 6.77 (s, 1H), 7.41-7.45 (m, 1H), 7.47 (d, J=4.0 Hz, 1H), 7.57-7.62 (m, 2H), 7.82 (d, J=8.0 Hz, 2H), 8.38 (s, 1H), 8.68 (s, 1H).

Example 37

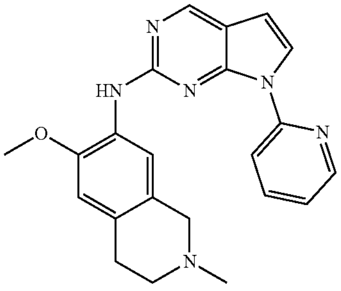

6-Methoxy-2-methyl-N-(7-(pyridin-2-yl)-7H-pyrrolo[2,3-d]pyrimidin-2-yl)-1,2,3,4-tetrahydroisoquinolin-7-amine The same procedures as Example 36, using 2-bromopyridine in place of 1-bromo-2-iodo-benzene in Step 1. LC-MS (ESI) m/z: 387 [M+H]. $^1$H NMR (400 MHz, $CD_3OD$): δ (ppm) 2.99 (s, 3H), 3.11-3.14 (m, 2H), 3.44-3.47 (m, 2H), 3.23 (s, 3H), 4.23 (s, 2H), 6.63 (d, J=4.0 Hz, 1H), 6.83 (s, 1H), 7.31-7.35 (m, 1H), 7.99-8.04 (m, 2H), 8.28 (s, 1H), 8.50-8.51 (m, 1H), 8.58 (d, J=8.0 Hz, 1H), 8.65 (s, 1H).

Example 38

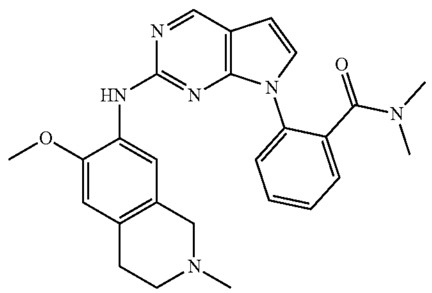

2-(24(6-Methoxy-2-methyl-1,2,3,4-tetrahydroisoquinolin-7-yl)amino)-7H-pyrrolo[2,3-d]pyrimidin-7-yl)-N,N-dimethylbenzamide The same procedures as Example 36, using bromo-N,N-dimethylbenzamide in place of 1-bromo-2-iodo-benzene in Step 1. LC-MS (ESI) m/z: 457 [M+H]. $^1$H NMR (400 MHz, $CD_3OD$): δ (ppm) 2.56 (s, 3H), 2.77 (s, 3H), 2.83 (s, 3H), 3.01 (t, J=7.6 Hz, 2H), 3.16 (t, J=7.6 Hz, 2H), 3.82 (s, 2H), 3.91 (s, 3H), 6.65 (d, J=3.6 Hz, 1H), 6.78 (s, 1H), 7.20 (d, J=3.6 Hz, 1H), 7.57-7.59 (m, 1H), 7.61-7.66 (m, 1H), 7.72-7.79 (m, 2H), 8.72 (s, 1H), 8.50 (brs, 1H), 8.72 (s, 1H).

Example 39

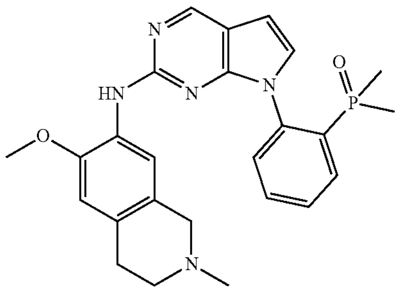

(2-(2-((6-Methoxy-2-methyl-1,2,3,4-tetrahydroisoquinolin-7-yl)amino)-7H-pyrrolo[2,3-d]pyrimidin-7-yl)phenyl)dimethylphosphine oxide Step 1: To a mixture of 2-chloro-7H-pyrrolo[2,3-d]pyrimidine (153 mg, 996.29 umol), (2-bromophenyl)boronic acid (600.25 mg, 2.99 mmol), and $Cu(OAc)_2$ (361.9 mg, 1.99 mmol) in dry DCM (12 mL) was added $NEt_3$ (403.3 mg, 3.99 mmol) at room temperature. The mixture was stirred at room temperature for 4 days and filtered. The filtrate was concentrated in vacuo and the residue was purified by flash column chromatography on silica gel (EA/PE=1/5 v/v) to provide 7-(2-bromophenyl)-2-chloro-pyrrolo[2,3-d]pyrimidine as white solid (36 mg, 12% yield). LC-MS (ESI) m/z: 308 $[M+H]^+$.

Step 2: 7-(2-Bromophenyl)-2-chloro-pyrrolo[2,3-d]pyrimidine (100 mg, 0.324 mmol), and Int. W1 (62.3 mg, 0.324 mmol) were used under Condition B3 to provide N-(7-(2-bromophenyl)-7H-pyrrolo[2,3-d]pyrimidin-2-yl)-6-methoxy-2-methyl-1,2,3,4-tetrahydroisoquinolin-7-amine as yellow solid (94 mg, 62% yield), after purification by prep-TLC (DCM/MeOH=15/1). LC-MS (ESI) m/z: 464 $[M+H]^+$.

Step 3: The same procedure as Step 3 of Int. E1, using N-(7-(2-bromophenyl)-7H-pyrrolo[2,3-d]pyrimidin-2-yl)-6-methoxy-2-methyl-1,2,3,4-tetrahydroisoquinolin-7-amine in place of tert-butyl 3-iodoindole-1-carboxylate. LC-MS (ESI) m/z: 462 $[M+H]^+$. $^1$H NMR (400 MHz, $CD_3OD$): δ (ppm) 1.43 (s, 3H), 1.46 (s, 3H), 2.78 (s, 3H), 3.00 (t, J=2.0 Hz, 2H), 3.18 (t, J=2.0 Hz, 2H), 3.67 (s, 2H), 3.89 (s, 3H), 6.73 (d, J=3.6 Hz, 1H), 6.77 (s, 1H), 7.39 (d, J=3.6 Hz, 1H), 7.48-7.51 (m, 1H), 7.64-7.70 (m, 1H), 7.80-7.89 (m, 1H), 8.04 (s, 1H), 8.13-8.20 (m, 1H), 8.76 (s, 1H).

Example 40

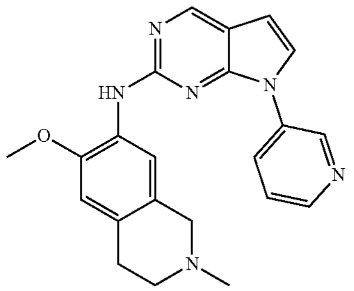 [SMILES: COc1cc2c(cc1Nc1ncc3ccn(-c4cccnc4)c3n1)CN(C)CC2]

6-Methoxy-2-methyl-N-(7-(pyridin-3-yl)-7H-pyrrolo[2,3-d]pyrimidin-2-yl)-1,2,3,4-tetrahydroisoquinolin-7-amine Step 1: The mixture of 2-chloro-7H-pyrrolo[2,3-d]pyrimidine (0.500 g, 3.26 mmol), 3-pyridylboronic acid (1.000 g, 8.14 mmol) and copper diacetate (0.887 g, 4.88 mmol) were stirred in pyridine (12.5 mL) under $O_2$ at 60° C. for 16 hours, concentrated in vacuo, diluted with water (100 mL), and extracted with EA (50 mL×2). The combined organic phase was dried over anhydrous sodium sulfate, filtered and concentrated. The residue was purified by silica gel flash column chromatography (EA/PE=1/5) to provide 2-chloro-7-(pyridin-3-yl)-7H-pyrrolo[2,3-d]pyrimidine (520 mg, 62.3% yield, 90% purity). LC-MS (ESI) m/z: 231.1 $[M+H]^+$.

Step 2: 2-Chloro-7-(3-pyridyl)pyrrolo[2,3-d]pyrimidine (100 mg, 0.434 mmol), and Int. W1 (100 mg, 0.520 mmol) were used under Condition B4 to provide methoxy-2-methyl-N-(7-(pyridin-3-yl)-7H-pyrrolo[2,3-d]pyrimidin-2-yl)-1,2,3,4-tetrahydroisoquinolin-7-amine (40.9 mg, 24.4% yield) as white solid, after purification by prep-HPLC (10 mM $NH_4HCO_3$, 0.025% $NH_3H_2O$/MeCN). LC-MS (ESI) m/z: 387 $[M+H]^+$. $^1$H NMR (400 MHz, DMSO-$d_6$) δ 9.17 (d, J=1.9 Hz, 1H), 8.81 (s, 1H), 8.61 (d, J=4.2 Hz, 1H), 8.36

(d, J=8.0 Hz, 1H), 8.03 (s, 1H), 7.90 (s, 1H), 7.77 (d, J=3.6 Hz, 1H), 7.61 (dd, J=8.1, 4.7 Hz, 1H), 6.75 (d, J=3.7 Hz, 2H), 3.83 (s, 3H), 3.43 (s, 2H), 2.77 (s, 2H), 2.57 (t, J=5.5 Hz, 2H), 2.28 (d, J=66.6 Hz, 3H).

Example 41

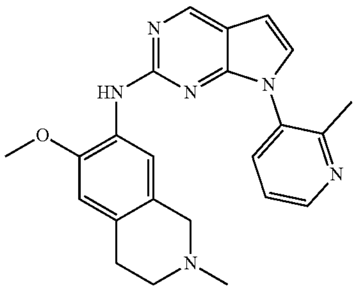

6-Methoxy-2-methyl-N-(7-(2-methylpyridin-3-yl)-7H-pyrrolo[2,3-d]pyrimidin-2-yl)-1,2,3,4-tetrahydroisoquinolin-7-amine The same procedures as Example 40, using (2-methylpyridin-3-yl)boronic acid in place of 3-pyridylboronic acid in Step 1. LC-MS (ESI) m/z: 401 $[M+H]^+$. $^1H$ NMR (400 MHz, DMSO-$d_6$) δ 8.80 (s, 1H), 8.62 (d, J=4.7 Hz, 1H), 7.89 (d, J=7.9 Hz, 2H), 7.75 (s, 1H), 7.59-7.35 (m, 2H), 6.71 (d, J=4.7 Hz, 2H), 3.80 (s, 3H), 3.20 (s, 2H), 2.72 (t, J=5.6 Hz, 2H), 2.54 (d, J=5.8 Hz, 2H), 2.32 (s, 6H).

Example 164

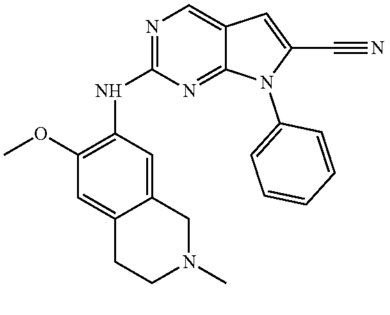 [SMILES: COc1cc2c(cc1Nc1ncc3cc(C#N)n(-c4ccccc4)c3n1)CN(C)CC2]

2-((6-Methoxy-2-methyl-1,2,3,4-tetrahydroisoquinolin-7-yl)amino)-7-phenyl-7H-pyrrolo[2,3-d]pyrimidine-6-carbonitrile Step 1: To a stirred mixture of 5-bromo-2-chloro-N-phenyl-pyrimidin-4-amine (1.5 g, 5.27 mmol) and 1,1'-bis(diphenylphosphino)ferrocene]dichloropalladium(II) (192.87 mg, 263.58 umol) in THF (30 mL) were added triethylamine (800.16 mg, 7.91 mmol, 1.10 mL) and 3,3-diethoxyprop-1-yne (1.01 g, 7.91 mmol, 1.13 mL) sequentially at room temperature. The mixture was purged with $N_2$ and stirred at room temperature for 10 minutes followed by the addition of CuI (50.20 mg, 263.58 umol). The reaction mixture was purged again with $N_2$, stirred at 60° C. for 48 hours, cooled to room temperature, diluted with EtOAc (100 mL) and filtered. The filtrate was diluted with water (50 mL) and separated. The aqueous phase was extracted with EtOAc (30 mL×3), and the combined organic phase was dried over anhydrous $Na_2SO_4$ and filtered. The filtrate was concentrated in vacuo, and the residue was purified by flash column chromatography on silica gel (5% EtOAc/petroleum ether to 20% EtOAc/petroleum ether) to provide 2-chloro-5-(3,3-diethoxyprop-1-ynyl)-N-phenyl-pyrimidin-4-amine as yellow solid (1.18 g, 67% yield). LC-MS (ESI) m/z: 332 $[M+H]^+$.

Step 2: To a stirred solution of 2-chloro-5-(3,3-diethoxyprop-1-ynyl)-N-phenyl-pyrimidin-4-amine (400 mg, 1.21 mmol) in THF (2 mL) was added 1N TBAF in THF (6.03 mmol, 6 mL) at room temperature. The reaction mixture was stirred at 60° C. for 2 hours, cooled to room temperature, and diluted with $H_2O$ (50 mL) and dichloromethane (50 mL). The phases were separated, and the aqueous layer was extracted with dichloromethane (20 mL×3). The combined organic layers were dried over anhydrous $Na_2SO_4$ and filtered. The filtrate was concentrated in vacuo, and the residue was purified by flash column chromatography on silica gel (10% EtOAc/petroleum ether to 30% EtOAc/petroleum ether) to provide 2-chloro-6-(diethoxymethyl)-7-phenyl-7H-pyrrolo[2,3-d]pyrimidine as grey solid (280 mg, 70% yield). LC-MS (ESI) m/z: 332 $[M+H]^+$.

Step 3: 2-Chloro-6-(diethoxymethyl)-7-phenyl-7H-pyrrolo[2,3-d]pyrimidine (100 mg, 0.3 mmol) and Int. W1 (57.8 mg, 0.3 mmol) were used under Condition B4 to provide N-(6-(diethoxymethyl)-7-phenyl-7H-pyrrolo[2,3-d]pyrimidin-2-yl)-6-methoxy-2-methyl-1,2,3,4-tetrahydroisoquinolin-7-amine (60 mg, 40.9% yield) as off-white solid, after purification by flash column chromatography on silica gel (MeOH/DCM: 5-10%). LC-MS (ESI) m/z: 488 $[M+H]^+$.

Step 4: To a stirred solution of N-(6-(diethoxymethyl)-7-phenyl-7H-pyrrolo[2,3-d]pyrimidin-2-yl)-6-methoxy-2-methyl-1,2,3,4-tetrahydroisoquinolin-7-amine (60 mg, 0.123 mmol) in dioxane (1 mL) was added 12 N HCl (0.2 mL) at room temperature. The reaction mixture was stirred for 30 minutes, basified to pH 8 with 2 N NaOH, and extracted with EtOAc (5 mL×3). The combined organic phase was dried over anhydrous $Na_2SO_4$ and filtered. The filtrate was concentrated in vacuo to provide 2-((6-methoxy-2-methyl-1,2,3,4-tetrahydroisoquinolin-7-yl)amino)-7-phenyl-7H-pyrrolo[2,3-d]pyrimidine-6-carbaldehyde as grey solid (50 mg, 98% yield). LC-MS (ESI) m/z: 414 $[M+H]^+$.

Step 5: To a stirred solution of 2-((6-methoxy-2-methyl-1,2,3,4-tetrahydroisoquinolin-7-yl)amino)-7-phenyl-7H-pyrrolo[2,3-d]pyrimidine-6-carbaldehyde (50 mg, 0.121 mmol) and pyrazine (19.7 mg, 0.246 mmol) in ethanol (1 mL) was added hydroxylamine hydrochloride (10.3 mg, 0.148 mmol) at room temperature. The reaction mixture was stirred at 90° C. for 2 hours and concentrated in vacuo. The residue was diluted with water (10 mL) and extracted with EtOAc (10 mL×3). The combined organic phase was washed with brine (10 mL) dried over anhydrous $Na_2SO_4$ and filtered. The filtrate was concentrated in vacuo to provide 2-((6-methoxy-2-methyl-1,2,3,4-tetrahydroisoquinolin-7-yl)amino)-7-phenyl-7H-pyrrolo[2,3-d]pyrimidine-6-carbaldehyde oxime as yellow solid (52 mg, 99% yield). LC-MS (ESI) m/z: 429 $[M+H]^+$.

Step 6: To a stirred solution of 2-((6-methoxy-2-methyl-1,2,3,4-tetrahydroisoquinolin-7-yl)amino)-7-phenyl-7H-pyrrolo[2,3-d]pyrimidine-6-carbaldehyde oxime (52 mg, 0.121 mmol) in TEA (2 mL) was added acetic anhydride (24.78 mg, 0.243 mmol). The reaction mixture was stirred at 90° C. for 2 hours, cooled to room temperature and concentrated in vacuo. The residue was purified by prep-HPLC (0.1% formic acid/MeCN) to provide 2-((6-methoxy-2- methyl-1,2,3,4-tetrahydroisoquinolin-7-yl)amino)-7-phenyl-7H-pyrrolo[2,3-d]pyrimidine-6-carbonitrile as yellow solid (3.1 mg, 6% yield). LC-MS (ESI) m/z: 411 $[M+H]^+$. $^1H$ NMR (400 MHz, DMSO-$d_6$) δ 8.98 (s, 1H), 8.37 (s, 1H), 8.24 (br, 1H), 7.87 (s, 1H), 7.78-7.63 (m, 5H), 7.61-7.59 (m, 1H)), 6.74 (s, 1H), 3.80 (s, 3H), 3.28 (s, 2H), 2.75 (s, 2H), 2.55 (s, 2H), 2.35 (s, 3H).

Example 165

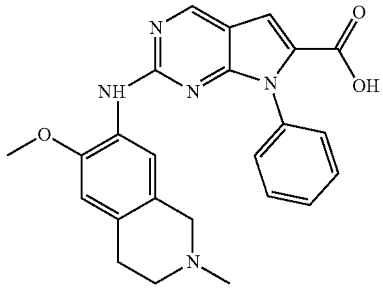 [SMILES: COc1cc2c(cc1Nc1ncc3cc(C(=O)O)n(-c4ccccc4)c3n1)CN(C)CC2]

2-((6-Methoxy-2-methyl-1,2,3,4-tetrahydroisoquinolin-7-yl)amino)-7-phenyl-7H-pyrrolo[2,3-d]pyrimidine-6-carboxylic acid To a solution of 2-((6-methoxy-2-methyl-1,2,3,4-tetrahydroisoquinolin-7-yl)amino)-7-phenyl-7H-pyrrolo[2,3-d]pyrimidine-6-carbaldehyde (30 mg, 0.073 mmol) in mixed solvent of water (3 mL) and ethanol (3 mL) were added sodium hydroxide (14.5 mg, 0.363 mmol) and silver oxide (33.6 mg, 0.145 mmol). The reaction mixture was stirred at 80° C. for 16 hours, cooled to room temperature, diluted with water (20 mL), and acidified to pH 3-4. The mixture was extracted with DCM (20 mL×3), and the organic phases were dried over anhydrous sodium sulfate and filtered. The filtrate was concentrated in vacuo, and the residue was purified by prep-HPLC to give 2-((6-methoxy-2-methyl-1,2,3,4-tetrahydroisoquinolin-7-yl)amino)-7-phenyl-7H-pyrrolo[2,3-d]pyrimidine-6-carboxylic acid (4.4 mg, 14.1% yield) as yellow solid. LC-MS (ESI) m/z: 430 $[M+H]^+$. $^1H$ NMR (400 MHz, DMSO-$d_6$) δ 8.88 (s, 1H), 7.92 (s, 1H), 7.89 (s, 1H), 7.53-7.51 (m, 2H), 7.47-7.42 (m, 3H), 7.25 (s, 1H), 6.71 (s, 1H), 3.81 (s, 3H), 3.26 (s, 2H), 2.74-2.73 (m, 2H), 2.61-2.59 (m, 2H), 2.39 (s, 3H).

Example 43

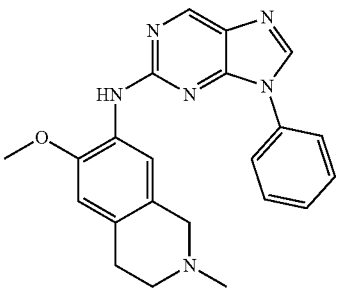

6-Methoxy-2-methyl-N-(9-phenyl-9H-purin-2-yl)-1,2,3,4-tetrahydroisoquinolin-7-amine Step 1: To a solution of 2,4-dichloro-5-nitro-pyrimidine (1 g, 5.16 mmol) in dioxane (20 mL) was slowly added aniline (0.96 mg, 10.31 mmol) at room temperature. The mixture was then stirred at room temperature for 1 hour and filtered. The filtrate was concentrated to provide 2-chloro-5-nitro-N-phenyl-pyrimidin-4-amine as yellow solid (800 mg, 62% yield). LC-SM (ESI) m/z: 251 $[M+H]^+$.

Step 2: To a mixture of 2-chloro-5-nitro-N-phenyl-pyrimidin-4-amine (500 mg, 1.99 mmol) in ethyl acetate/EtOH/$H_2O$ (6 mL/27 mL/3 mL) were added Fe (557.1 mg, 9.97 mmol) and $NH_4Cl$ (74.7 mg, 1.40 mmol) at room temperature. The mixture was stirred at 60° C. for 2 hours. After cooled down to room temperature, the mixture was filtered and washed with methanol (30 mL). The filtrate was concentrated and the residue was purified by flash column chromatography on silica gel (DCM/MeOH=20/1 v/v) to provide 2-chloro-$N^4$-phenyl-pyrimidine-4,5-diamine as pale-yellow solid (350 mg, 79% yield). LC-MS (ESI) m/z: 221 $[M+H]^+$.

Step 3: To a solution of 2-chloro-$N^4$-phenyl-pyrimidine-4,5-diamine (300 mg, 1.36 mmol) in triethyl orthoformate (10 mL) and DMF (5 mL) was added concentrated HCl (0.6 mL). The reaction mixture was stirred at room temperature for 2 hours, diluted with $H_2O$ (20 mL), and extracted with EA (20 mL×2). The combined organic layers were dried over anhydrous $Na_2SO_4$, filtered, and concentrated to dryness. The residue was purified by flash column chromatography on silica gel column (EA/PE=1/2 v/v) to provide 2-chloro-9-phenyl-purine as yellow solid (220 mg, 70% yield). LC-MS (ESI) m/z: 231 $[M+H]^+$.

Step 4: 2-Chloro-9-phenyl-purine (30 mg, 0.13 mmol), and Int. W1 (25 mg, 0.13 mmol) were used under Condition B4 to provide 6-methoxy-2-methyl-N-(9-phenyl-9H-purin-2-yl)-1,2,3,4-tetrahydroisoquinolin-7-amine (8 mg) as yellow solid, after purification by prep-HPLC (0.05% TFA/MeCN). LC-MS (ESI) m/z: 387 [M+H]. $^1H$ NMR (400 MHz, $CD_3OD$): δ 3.07 (s, 3H), 3.12-3.13 (m, 1H), 3.19-3.27 (m, 1H), 3.39-3.48 (m, 1H), 3.74-3.75 (m, 1H), 3.95 (s, 3H), 4.25-4.41 (m, 2H), 6.91 (s, 1H), 7.53-7.57 (m, 1H), 7.66-7.89 (m, 2H), 7.91 (d, J=1.2 Hz, 2H), 8.40 (s, 1H), 8.57 (s, 1H), 8.67 (s, 1H).

Example 44

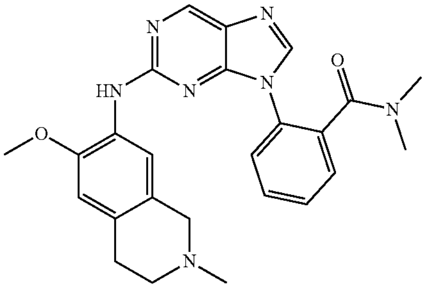

2-(2-((6-Methoxy-2-methyl-1,2,3,4-tetrahydroisoquinolin-7-yl)amino)-9H-purin-9-yl)-N,N-dimethylbenzamide The same procedures as Example 43, using 2-amino-N,N-dimethylbenzamide in place of aniline in Step 1. LC-MS (ESI) m/z: 458 [M+H]. $^1$H NMR (400 MHz, $CD_3OD$): δ 2.73 (s, 3H), 2.77 (s, 3H), 2.84 (s, 3H), 3.03 (t, J=6.0 Hz, 2H), 3.18 (t, J=6.0 Hz, 2H), 3.88 (s, 2H), 3.90 (s, 3H), 6.81 (s, 1H), 7.61-7.64 (m, 1H), 7.68-7.76 (m, 1H), 7.76-7.78 (m, 2H), 8.18 (s, 1H), 8.19 (s, 1H), 8.45 (brs, 1H), 8.83 (s, 1H).

Example 45

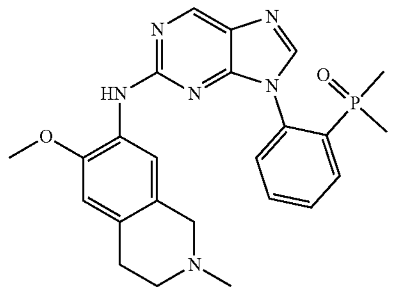

(2-(2-((6-Methoxy-2-methyl-1,2,3,4-tetrahydroisoquinolin-7-yl)amino)-9H-purin-9-yl)phenyl)dimethylphosphine oxide The same procedures as Example 43, using (2-aminophenyl)dimethylphosphine oxide in place of aniline in Step 1. LC-MS (ESI) m/z: 463 [M+H]. $^1$H NMR (400 MHz, $CD_3OD$): δ 1.62 (s, 3H), 1.65 (s, 3H), 2.87 (s, 3H), 3.07 (t, J=6.0 Hz, 2H), 3.33 (t, J=6.0 Hz, 2H), 3.89 (s, 3H), 3.94 (s, 2H), 6.82 (s, 1H), 7.60-7.63 (m, 1H), 7.81-7.91 (m, 2H), 8.01-8.07 (m, 1H), 8.12 (s, 1H), 8.35 (s, 1H), 8.45 (brs, 1H), 8.85 (s, 1H).

Example 166

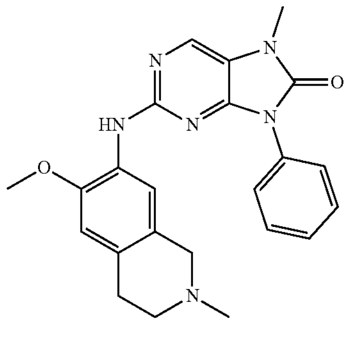 [SMILES: COc1cc2c(cc1Nc1ncc3c(n1)n(-c1ccccc1)c(=O)n3C)CN(C)CC2]

2-((6-Methoxy-2-methyl-1,2,3,4-tetrahydroisoquinolin-7-yl)amino)-7-methyl-9-phenyl-7,9-dihydro-8H-purin-8-one Step 1: To a solution of 2-chloro-$N^4$-phenyl-pyrimidine-4,5-diamine (410 mg, 1.86 mmol) in dichloromethane (30 mL) was added CDI (301.29 mg, 1.86 mmol). The mixture was stirred at 25° C. for 16 hours, diluted with saturated $NaHCO_3$ aqueous solution (20 mL) and separated. The aqueous phase was extracted with DCM/MeOH (v/v, 10/1, 20 mL×3). The combined organic phase was dried over anhydrous $Na_2SO_4$ and filtered. The filtrate was concentrated in vacuo, and the residue was purified by flash column chromatography on silica gel (80-100% EtOAc/hexanes) to provide 2-chloro-9-phenyl-7,9-dihydro-8H-purin-8-one as light-yellow solid (264 mg, 58% yield). LC-MS (ESI) m/z: 247 $[M+H]^+$.

Step 2: To a solution of 2-chloro-9-phenyl-7,9-dihydro-8H-purin-8-one (230 mg, 932.49 umol) and iodomethane (463.3 mg, 3.26 mmol) in THF (10 mL) was added sodium hydride (111.9 mg, 2.80 mmol, 60% dispersion in mineral oil) at 0° C. The mixture was stirred at 0-25° C. for 6 hours, quenched with water (10 mL) and separated. The aqueous phase was extracted with dichloromethane/methanol (v/v, 10/1, 20 mL×3). The combined organic layer was dried over anhydrous $Na_2SO_4$ and filtered. The filtrate was concentrated in vacuo, and the residue was purified through flash column chromatography on silica gel (30-40% EtOAc in petroleum ether) to provide 2-chloro-7-methyl-9-phenyl-7,9-dihydro-8H-purin-8-one as light-yellow solid (80 mg, 24% yield). LC-MS (ESI) m/z: 261 $[M+H]^+$.

Step 3: 2-Chloro-7-methyl-9-phenyl-7,9-dihydro-8H-purin-8-one (70 mg, 0.268 mmol), and Int. W1 (21.4 mg, 0.268 mmol) were used under Condition B3 to provide 2-((6-methoxy-2-methyl-1,2,3,4-tetrahydroisoquinolin-7-yl)amino)-7-methyl-9-phenyl-7,9-dihydro-8H-purin-8-one (44.2 mg, 39.5% yield) as yellow solid, after purification by prep-HPLC (0.1% FA/MeCN). LC-MS (ESI) m/z: 417 $[M+H]^+$. $^1$H NMR (400 MHz, DMSO-$d_6$) δ 8.29 (s, 1H), 8.25 (s, 1H), 7.88 (s, 1H), 7.67 (s, 2H), 7.58 (t, J=7.7 Hz, 2H), 7.47 (t, J=7.3 Hz, 1H), 6.71 (s, 1H), 3.79 (s, 3H), 3.40 (s, 3H), 3.28-3.20 (m, 2H), 2.74 (s, 2H), 2.55 (s, 2H), 2.34 (s, 3H).

Example 46

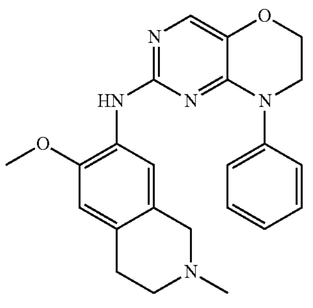 [SMILES: COc1cc2c(cc1Nc1ncc3c(n1)N(c1ccccc1)CCO3)CN(C)CC2]

N-(6-methoxy-2-methyl-1,2,3,4-tetrahydroisoquinolin-7-yl)-8-phenyl-7,8-dihydro-6H-pyrimido[5,4-b][1,4]oxazin-2-amine Step 1: To a solution of 2,4-dichloro-5-methoxy-pyrimidine (1.00 g, 5.59 mmol) in dioxane (15 mL) were added DIPEA (1.44 g, 11.17 mmol, 1.95 mL) and aniline (0.520 mg, 5.59 mmol). The mixture was stirred at 120° C. under $N_2$ atmosphere overnight, and concentrated. The residue was purified by flash column chromatography on silica gel column (PE/EA=2/1 v/v) to provide 2-chloro-5-methoxy-N-phenyl-pyrimidin-4-amine as yellow solid (950 mg, 72% yield). LC-MS (ESI) m/z: 236 $[M+H]^+$.

Step 2: To a solution of 2-chloro-5-methoxy-N-phenyl-pyrimidin-4-amine (100 mg, 0.424 mmol) in DCM (5 mL) was added boron tribromide (1.06 g, 4.24 mmol) at 0° C. The mixture was stirred under nitrogen at room temperature for 3 days, poured into MeOH (30 mL) at 0° C. and concentrated. The residue was purified by flash column chromatography on silica gel (PE/EA=1/1 v/v, and then DCM/MeOH=10/1 v/v) to provide 4-anilino-2-chloro-pyrimidin-5-ol as white solid (94 mg, 100% yield). LC-MS (ESI) m/z: 222 $[M+H]^+$.

Step 3: To a solution of 4-anilino-2-chloro-pyrimidin-5-ol (94 mg, 0.424 mmol) in DMF (5 mL) were added potassium carbonate (175.85 mg, 1.27 mmol) and 1-bromo-2-chloroethane (91.2 mg, 0.636 mmol). The mixture was stirred at room temperature for 16 hours, diluted with $H_2O$ (20 mL) and extracted with EA (20 mL×3). The organic layers were dried over anhydrous $Na_2SO_4$, filtered and concentrated. The residue was purified by flash column chromatography on silica gel (PE/EA=2/1) to provide 2-chloro-8-phenyl-6,7-dihydropyrimido[5,4-b][1,4]oxazine as white solid (60 mg, 57% yield). LC-MS (ESI) m/z: 248 $[M+H]^+$.

Step 4: 2-Chloro-8-phenyl-6,7-dihydropyrimido[5,4-b][1,4]oxazine (50 mg, 0.202 mmol), and Int. W1 (46.2 mg, 0.202 mmol) were used under Condition B3 to provide N-(6-methoxy-2-methyl-1,2,3,4-tetrahydroisoquinolin-7-yl)-8-phenyl-7,8-dihydro-6H-pyrimido[5,4-b][1,4]oxazin-2-amine (48 mg, 59% yield) as white solid, which was collected by filtration. LC-MS (ESI) m/z: 404 $[M+H]^+$. $^1H$ NMR (400 MHz, $CD_3OD$): δ 3.03 (s, 3H), 3.06-3.10 (m, 1H), 3.12-3.28 (m, 2H), 3.68-3.71 (m, 1H), 3.80-3.81 (m, 2H), 3.90 (s, 3H), 4.09 (t, J=4.0 Hz, 2H), 4.44 (t, J=4.0 Hz, 2H), 6.89 (s, 1H), 7.36 (s, 1H), 7.52-7.54 (m, 2H), 7.56-7.60 (m, 1H), 7.63-7.67 (m, 2H), 7.72 (s, 1H).

Example 47

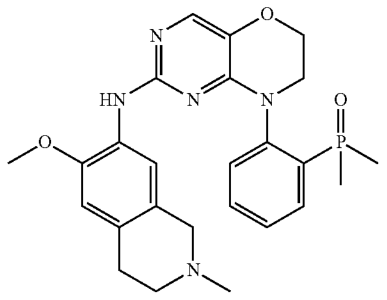

(2-(2-((6-Methoxy-2-methyl-1,2,3,4-tetrahydroisoquinolin-7-yl)amino)-6H-pyrimido[5,4-b][1,4]oxazin-8(7H)-yl)phenyl)dimethylphosphine oxide The same procedures as Example 46, using 2-dimethylphosphorylaniline in place of aniline in Step 1. LC-MS (ESI) m/z: 480 $[M+H]^+$. $^1H$ NMR (400 MHz, $CD_3OD$): δ 1.63 (d, J=13.2 Hz, 3H), 1.80 (d, J=13.6 Hz, 3H), 2.88 (s, 3H), 2.98 (t, J=6.0 Hz, 2H), 3.26 (t, J=6.4 Hz, 2H), 3.46-3.55 (m, 2H), 3.84 (s, 3H), 3.87-3.94 (m, 2H), 4.38-4.45 (m, 2H), 6.70 (s, 1H), 7.31 (s, 1H), 7.54-7.58 (m, 1H), 7.71-7.76 (m, 2H), 7.85 (t, J=8.0 Hz, 1H), 7.98-8.04 (m, 1H), 8.46 (brs, 1H).

Example 171

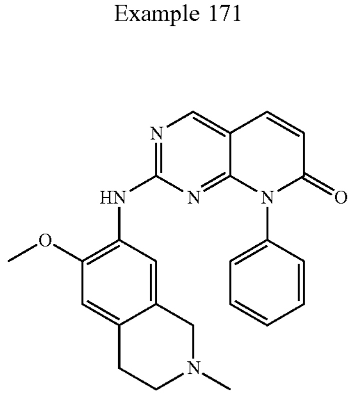

2-((6-Methoxy-2-methyl-1,2,3,4-tetrahydroisoquinolin-7-yl)amino)-8-phenylpyrido[2,3-d]pyrimidin-7(8H)-one Step 1: To a solution of 5-bromo-2,4-dichloro-pyrimidine (1.2 g, 5.27 mmol) in MeCN (20 mL) were added triethylamine (639.45 mg, 6.32 mmol, 880.78 uL) and aniline (529.64 mg, 5.69 mmol) at 0° C. The reaction mixture was stirred for 16 hours at 25° C. and concentrated in vacuo. The residue was purified by flash column chromatography on silica gel (PE/EtOAc=0-50%) to provide 5-bromo-2-chloro-N-phenylpyrimidin-4-amine as yellow solid (1.2 g, 76% yield). LC-MS (ESI) m/z: 284 $[M+H]^+$.

Step 2: To a solution of 5-bromo-2-chloro-N-phenylpyrimidin-4-amine (283 mg, 994.59 umol), acrylic acid (358.4 mg, 4.97 mmol) and DIPEA (1.29 g, 9.95 mmol) in THF (4 mL) were added bis(benzonitrile)palladium(II) chloride (19.07 mg, 49.73 umol) and tris-o-tolylphosphane (15.14 mg, 0.050 mmol). The mixture was stirred for 24 hours at 70° C. under $N_2$ atmosphere. The reaction mixture was used in the next step without any purification. LC-MS (ESI) m/z: 276 $[M+H]^+$.

Step 3: To the above reaction mixture was added acetic anhydride (540.00 mg, 5.29 mmol). The mixture was then stirred for 24 hours at 80° C. and concentrated in vacuo. The residue was diluted with DCM (50 mL) and water (50 mL) and separated. The organic phase was washed with 1N HCl (10 mL), dried over anhydrous $Na_2SO_4$ and filtered. The filtrate was concentrated in vacuo, and the residue was purified through flash column chromatography on silica gel (EA/PE=0-60%) to provide 2-chloro-8-phenylpyrido[2,3-d]pyrimidin-7(8H)-one as yellow solid (88 mg, 34% yield). LC-MS (ESI) m/z: 258 $[M+H]^+$.

Step 4: 2-Chloro-8-phenylpyrido[2,3-d]pyrimidin-7(8H)-one (40 mg, 0.155 mmol) and Int. W1 (35.5 mg, 0.155 mmol) were used under Condition B3 to provide 2-((6-methoxy-2-methyl-1,2,3,4-tetrahydroisoquinolin-7-yl)amino)-8-phenylpyrido[2,3-d]pyrimidin-7(8H)-one (17.1 mg, 26.6% yield) as white solid, after purification by prep-HPLC (10 mM $NH_4HCO_3$, 0.025% $NH_3H_2O$/MeCN). LC-MS (ESI) m/z: 414 $[M+H]^+$. $^1H$ NMR (500 MHz, DMSO-$d_6$) δ 8.81 (s, 1H), 8.11 (s, 1H), 7.94 (d, J=9.4 Hz, 1H), 7.61 (s, 2H), 7.53 (t, J=7.4 Hz, 1H), 7.34 (d, J=7.2 Hz, 2H), 7.14 (s, 1H), 6.68 (s, 1H), 6.49 (d, J=9.4 Hz, 1H), 3.79 (s, 3H), 2.91 (s, 2H), 2.68 (s, 2H), 2.47 (s, 2H), 2.35 (s, 3H).

Example 172

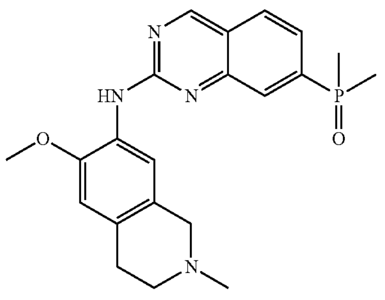

(24(6-Methoxy-2-methyl-1,2,3,4-tetrahydroisoquinolin-7-yl)amino)quinazolin-7-yl)dimethylphosphine oxide Step 1: 7-Bromo-2-chloroquinazoline (100 mg, 0.411 mmol) and Int. W1 (94.8 mg, 0.493 mmol) were used under Condition B3 to provide 7-bromo-N-(6-methoxy-2-methyl-1,2,3,4-tetrahydroisoquinolin-7-yl)quinazolin-2-amine (90 mg, 52.1% yield) as yellow solid, after purification by flash column chromatography on silica gel (PE/EA: 5/1). LC-MS (ESI) m/z: 401 $[M+H]^+$.

Step 2: A mixture of 7-bromo-N-(6-methoxy-2-methyl-1,2,3,4-tetrahydroisoquinolin-7-yl)quinazolin-2-amine (80 mg, 200.36 umol), dimethylphosphine oxide (23.5 mg, 300.54 umol), $Pd_2(dba)_3$ (9.2 mg, 10.02 umol), Xantphos (5.8 mg, 10.02 umol), and triethylamine (60.8 mg, 601.08 umol) in dioxane (1 mL) was purged with nitrogen and stirred at 110° C. for 16 hours. The reaction mixture was purified by prep-HPLC (MeCN/10 mM $NH_4HCO_3$, 0.025% $NH_3H_2O$) to provide (2-((6-methoxy-2-methyl-1,2,3,4-tetrahydroisoquinolin-7-yl)amino)quinazolin-7-yl)dimethylphosphine oxide as yellow solid (2.9 mg, 3.6% yield). LC-MS (ESI) m/z: 496 $[M+H]^+$. $^1H$ NMR (400 MHz, DMSO-$d_6$) δ 9.35 (s, 1H), 8.34 (s, 1H), 8.28 (s, 1H), 8.09 (s, 1H), 8.03 (dd, J=12.7, 7.7 Hz, 2H), 7.69 (t, J=9.0 Hz, 1H), 6.81 (s, 1H), 3.83 (s, 3H), 3.52 (s, 2H), 2.81 (d, J=5.5 Hz, 2H), 2.61 (t, J=5.7 Hz, 2H), 2.37 (s, 3H), 1.75 (d, J=13.4 Hz, 6H).

Example 50

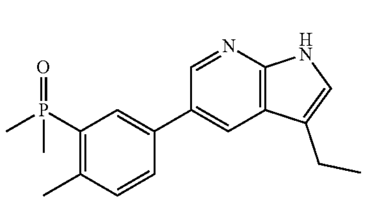 [SMILES: CCc1c[nH]c2ncc(-c3ccc(C)c(P(C)(C)=O)c3)cc12]

(5-(3-Ethyl-1H-pyrrolo[2,3-b]pyridin-5-yl)-2-methylphenyl)dimethylphosphine oxide Step 1: A mixture of Intermediate 12 (200 mg, 734.89 umol), 2-bromo-4-iodo-1-methylbenzene (181.84 mg, 612.41 umol), $Pd(dppf)Cl_2CH_2Cl_2$ (50.01 mg, 61.24 umol), and $K_2CO_3$ (253.92 mg, 1.84 mmol) in 1,4-dioxane (6 mL) and $H_2O$ (0.6 mL) was stirred at 80° C. under nitrogen atmosphere for 3 hours, cooled down to room temperature, and filtered. The filtrate was concentrated, and the residue was purified with flash column chromatography on silica gel (PE/EA=1/9 v/v) to provide 5-(3-bromo-4-methylphenyl)-3-ethyl-1H-pyrrolo[2,3-b]pyridine as light yellow powder (100 mg, 49% yield). LC-MS (ESI) m/z: 315 $[M+H]^+$).

Step 2: A mixture of 5-(3-bromo-4-methylphenyl)-3-ethyl-1H-pyrrolo[2,3-b]pyridine (49 mg, 154.48 umol), dimethylphosphine oxide (14.47 mg, 185.38 umol), $Pd(OAc)_2$ (1.73 mg, 7.72 umol), Xantphos (4.47 mg, 7.72 umol), and $K_3PO_4$ (36.07 mg, 169.93 umol) in DMF (4 mL) was stirred under microwave conditions protected by nitrogen atmosphere at 140° C. for 2 hours. After cooled down to room temperature, the mixture was diluted with $H_2O$ (20 mL) and extracted with EA (20 mL×3). The combined organic layers were washed with brine (20 mL), dried over anhydrous $Na_2SO_4$, filtered and concentrated. The residues was purified with prep-HPLC (MeCN/0.1% HCOOH) to provide (5-(3-ethyl-1H-pyrrolo[2,3-b]pyridin-5-yl)-2-methylphenyl)dimethylphosphine oxide as white solid (14.6 mg, 30% yield). LC-MS (ESI) m/z: 313 $[M+H]^+$.

Example 51

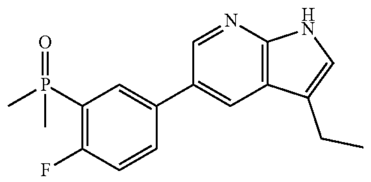 [SMILES: CCc1c[nH]c2ncc(-c3ccc(F)c(P(C)(C)=O)c3)cc12]

(5-(3-Ethyl-1H-pyrrolo[2,3-b]pyridin-5-yl)-2-fluorophenyl)dimethylphosphine oxide The same procedures as Example 50, using 2-bromo-1-fluoro-4-iodobenzene in place of 2-bromo-4-iodo-1-methylbenzene in Step 1. LC-MS (ESI) m/z: 317 $[M+H]^+$.

Example 52

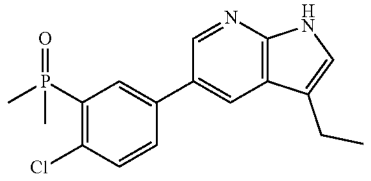 [SMILES: CCc1c[nH]c2ncc(-c3ccc(Cl)c(P(C)(C)=O)c3)cc12]

(2-Chloro-5-(3-ethyl-1H-pyrrolo[2,3-b]pyridin-5-yl)phenyl)dimethylphosphine oxide Example 53

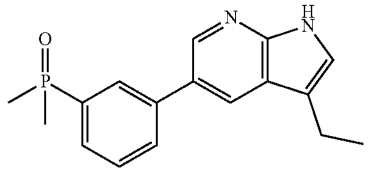 [SMILES: CCc1c[nH]c2ncc(-c3cccc(P(C)(C)=O)c3)cc12]

(3-(3-Ethyl-1H-pyrrolo[2,3-b]pyridin-5-yl)phenyl) dimethylphosphine oxide

The same procedures as Example 50, using 2-bromo-1-chloro-4-iodobenzene in place of 2-bromo-4-iodo-1-methylbenzene in Step 1. Example 53 was obtained as byproduct in Step 2.

(2-Chloro-5-(3-ethyl-1H-pyrrolo[2,3-b]pyridin-5-yl)phenyl)dimethylphosphine oxide: LC-MS (ESI) m/z: 333 $[M+H]^+$.

(3-(3-Ethyl-1H-pyrrolo[2,3-b]pyridin-5-yl)phenyl)dimethylphosphine oxide: LC-MS (ESI) m/z: 299 $[M+H]^+$.

Example 54

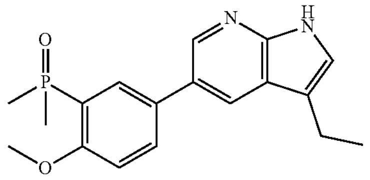 [SMILES: CCc1c[nH]c2ncc(-c3ccc(OC)c(P(C)(C)=O)c3)cc12]

(5-(3-Ethyl-1H-pyrrolo[2,3-b]pyridin-5-yl)-2-methoxyphenyl)dimethylphosphine oxide The same procedures as Example 50, using 2-bromo-4-iodo-1-methoxybenzene in place of 2-bromo-4-iodo-1-methylbenzene in Step 1. LC-MS (ESI) m/z: 329 $[M+H]^+$.

Example 55

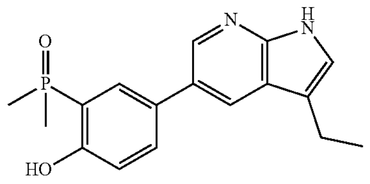

(5-(3-Ethyl-1H-pyrrolo[2,3-b]pyridin-5-yl)-2-hydroxyphenyl)dimethylphosphine oxide To a stirred solution of Example 54 (28 mg, 85.28 umol) in anhydrous DCM (5 mL) was dropwise added boron tribromide (68.67 mg, 274.10 umol, 0.2 mL) at room temperature. The reaction mixture was stirred for 2 hours at room temperature and quenched carefully by addition of MeOH. The resulting mixture was concentrated, and the residue was purified with prep-HPLC (MeCN/0.1% HCOOH) to provide (5-(3-Ethyl-1H-pyrrolo[2,3-b]pyridin-5-yl)-2-hydroxyphenyl)dimethylphosphine oxide as white solid (21 mg, 78% yield). LC-MS (ESI) m/z: 315 $[M+H]^+$.

Example 56

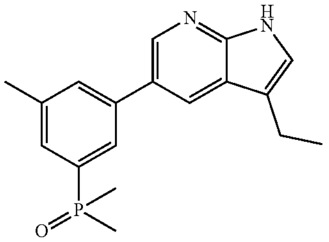 [SMILES: CCc1c[nH]c2ncc(-c3cc(C)cc(P(C)(C)=O)c3)cc12]

(3-(3-Ethyl-1H-pyrrolo[2,3-b]pyridin-5-yl)-5-methylphenyl)dimethylphosphine oxide The same procedures as Example 50, using 1,3-dibromo-5-methyl-benzene in place of 2-bromo-4-iodo-1-methylbenzene in Step 1. LC-MS (ESI) m/z: 313 $[M+H]^+$.

Example 57

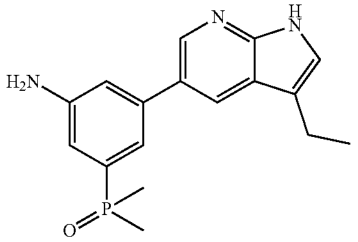 [SMILES: CCc1c[nH]c2ncc(-c3cc(N)cc(P(C)(C)=O)c3)cc12]

(3-Amino-5-(3-ethyl-1H-pyrrolo[2,3-b]pyridin-5-yl) phenyl)dimethylphosphine oxide The same procedures as Example 50, using 3,5-dibromoaniline in place of 2-bromo-4-iodo-1-methylbenzene in Step 1. LC-MS (ESI) m/z: 314 $[M+H]^+$.

Example 58

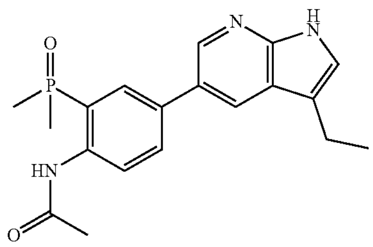 [SMILES: CCc1c[nH]c2ncc(-c3ccc(NC(C)=O)c(P(C)(C)=O)c3)cc12]

N-(2-(dimethylphosphoryl)-4-(3-ethyl-1H-pyrrolo[2,3-b]pyridin-5-yl)phenyl)acetamide The same procedures as Example 50, using Intermediate 17 in place of 2-bromo-4-iodo-1-methylbenzene in Step 1. LC-MS (ESI) m/z: 356 $[M+H]^+$.

Example 59

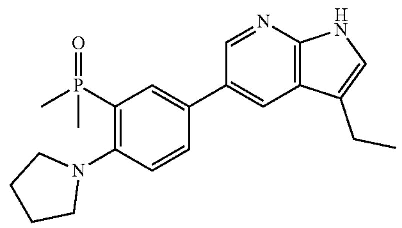 [SMILES: CCc1c[nH]c2ncc(-c3ccc(N4CCCC4)c(P(C)(C)=O)c3)cc12]

N-(2-bromo-4-(3-ethyl-1H-pyrrolo[2,3-b]pyridin-5-yl)phenyl)acetamide

The same procedures as Example 50, using Intermediate 18 in place of 2-bromo-4-iodo-1-methylbenzene in Step 1. LC-MS (ESI) m/z: 368 $[M+H]^+$.

Example 60

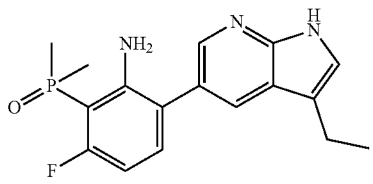 [SMILES: CCc1c[nH]c2ncc(-c3ccc(F)c(P(C)(C)=O)c3N)cc12]

(2-Amino-3-(3-ethyl-1H-pyrrolo[2,3-b]pyridin-5-yl)-6-fluorophenyl)dimethylphosphine oxide The same procedures as Example 50, using Intermediate 19 in place of 2-bromo-4-iodo-1-methylbenzene in Step 1. LC-MS (ESI) m/z: 332 $[M+H]^+$.

Example 61

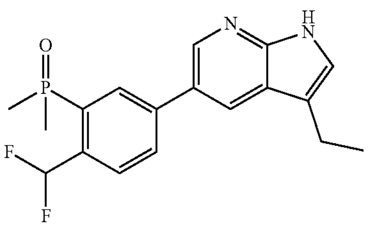 [SMILES: CCc1c[nH]c2ncc(-c3ccc(C(F)F)c(P(C)(C)=O)c3)cc12]

(2-(Difluoromethyl)-5-(3-ethyl-1H-pyrrolo[2,3-b]pyridin-5-yl)phenyl)dimethylphosphine oxide The same procedures as Example 50, using Intermediate 21 in place of 2-bromo-4-iodo-1-methylbenzene in Step 1. LC-MS (ESI) m/z: 349 $[M+H]^+$.

Example 62

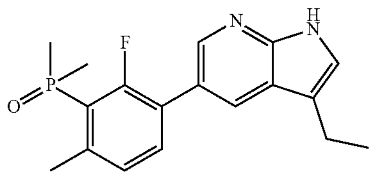 [SMILES: CCc1c[nH]c2ncc(-c3ccc(C)c(P(C)(C)=O)c3F)cc12]

(3-(3-Ethyl-1H-pyrrolo[2,3-b]pyridin-5-yl)-2-fluoro-6-methylphenyl)dimethylphosphine oxide The same procedures as Example 50, using Intermediate 22 in place of 2-bromo-4-iodo-1-methylbenzene in Step 1. LC-MS (ESI) m/z: 331 $[M+H]^+$.

Example 63

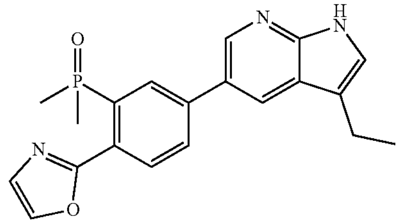 [SMILES: CCc1c[nH]c2ncc(-c3ccc(-c4ncco4)c(P(C)(C)=O)c3)cc12]

(5-(3-Ethyl-1H-pyrrolo[2,3-b]pyridin-5-yl)-2-(oxazol-2-yl)phenyl)dimethylphosphine oxide The same procedures as Example 50, using Intermediate 25 in place of 2-bromo-4-iodo-1-methylbenzene in Step 1. LC-MS (ESI) m/z: 366 $[M+H]^+$.

Example 64

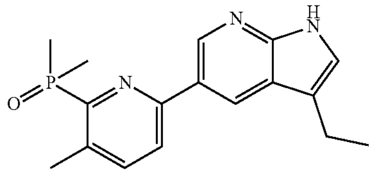 [SMILES: CCc1c[nH]c2ncc(-c3ccc(C)c(P(C)(C)=O)n3)cc12]

(6-(3-Ethyl-1H-pyrrolo[2,3-b]pyridin-5-yl)-3-methylpyridin-2-yl)dimethylphosphine oxide The same procedures as Example 50, using Intermediate 24 in place of 2-bromo-4-iodo-1-methylbenzene in Step 1. LC-MS (ESI) m/z: 314 $[M+H]^+$.

Example 65

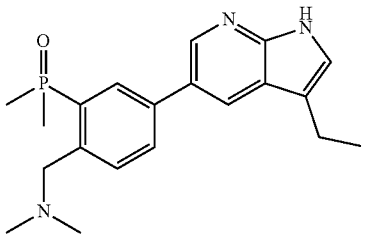 [SMILES: CCc1c[nH]c2ncc(-c3ccc(CN(C)C)c(P(C)(C)=O)c3)cc12]

(2-((Dimethylamino)methyl)-5-(3-ethyl-1H-pyrrolo[2,3-b]pyridin-5-yl)phenyl)dimethylphosphine oxide The same procedures as Example 50, using Intermediate 26 in place of 2-bromo-4-iodo-1-methylbenzene in Step 1. LC-MS (ESI) m/z: 356 $[M+H]^+$.

Example 66

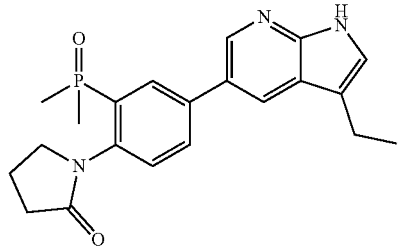 [SMILES: CCc1c[nH]c2ncc(-c3ccc(N4CCCC4=O)c(P(C)(C)=O)c3)cc12]

1-(2-(Dimethylphosphoryl)-4-(3-ethyl-1H-pyrrolo[2,3-b]pyridin-5-yl)phenyl)pyrrolidin-2-one The same procedures as Example 50, using Intermediate 27 in place of 2-bromo-4-iodo-1-methylbenzene in Step 1. LC-MS (ESI) m/z: 382 $[M+H]^+$.

Example 67

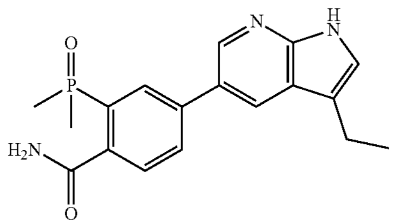 [SMILES: CCc1c[nH]c2ncc(-c3ccc(C(N)=O)c(P(C)(C)=O)c3)cc12]

2-(Dimethylphosphoryl)-4-(3-ethyl-1H-pyrrolo[2,3-b]pyridin-5-yl)benzamide

The same procedures as Example 50, using Intermediate 28 in place of 2-bromo-4-iodo-1-methylbenzene in Step 1. LC-MS (ESI) m/z: 342 $[M+H]^+$.

Example 68

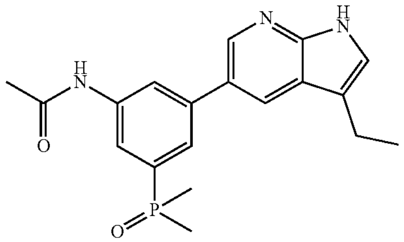 [SMILES: CCc1c[nH]c2ncc(-c3cc(NC(C)=O)cc(P(C)(C)=O)c3)cc12]

N-(3-(dimethylphosphoryl)-5-(3-ethyl-1H-pyrrolo[2,3-b]pyridin-5-yl)phenyl)acetamide The same procedures as Example 50, using Intermediate 29 in place of 2-bromo-4-iodo-1-methylbenzene in Step 1. LC-MS (ESI) m/z: 356 $[M+H]^+$.

Example 69

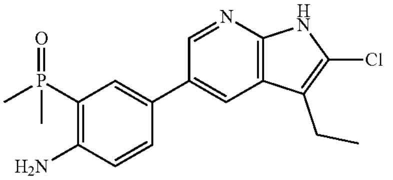 [SMILES: CCc1c(Cl)[nH]c2ncc(-c3ccc(N)c(P(C)(C)=O)c3)cc12]

(2-Amino-5-(2-chloro-3-ethyl-1H-pyrrolo[2,3-b]pyridin-5-yl)phenyl)dimethylphosphine oxide Example 70

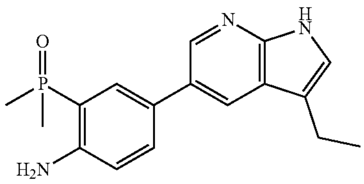 [SMILES: CCc1c[nH]c2ncc(-c3ccc(N)c(P(C)(C)=O)c3)cc12]

(2-Amino-5-(3-ethyl-1H-pyrrolo[2,3-b]pyridin-5-yl)phenyl)dimethylphosphine oxide The same procedures as Example 50, using 2-bromo-4-iodoaniline and Intermediate 14 in place of 2-bromo-4-iodo-1-methylbenzene and Intermediate 12 in Step 1.

(2-Amino-5-(2-chloro-3-ethyl-1H-pyrrolo[2,3-b]pyridin-5-yl)phenyl)dimethylphosphine oxide: [HCOOH salt] LC-MS (ESI) m/z: 348 [M+H].

(2-Amino-5-(3-ethyl-1H-pyrrolo[2,3-b]pyridin-5-yl)phenyl)dimethylphosphine oxide: [HCOOH salt] was obtained as byproduct in Step 2. LC-MS (ESI) m/z: 314 $[M+H]^+$.

Example 71

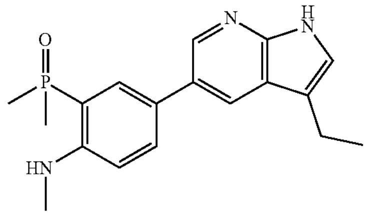 [SMILES: CCc1c[nH]c2ncc(-c3ccc(NC)c(P(C)(C)=O)c3)cc12]

(5-(3-Ethyl-1H-pyrrolo[2,3-b]pyridin-5-yl)-2-(methylamino)phenyl)dimethylphosphine oxide Step 1 & 2: The same procedures as Example 50, using Intermediate 16 in place of 2-bromo-4-iodo-1-methylbenzene in Step 1. LC-MS (ESI) m/z: 428 $[M+H]^+$.

Step 3: To a solution of tert-butyl (2-(dimethylphosphoryl)-4-(3-ethyl-1H-pyrrolo[2,3-b]pyridin-5-yl)phenyl)(methyl)carbamate (25 mg, 58.48 umol) in DCM (5 mL) was added TFA (1.48 g, 12.98 mmol, 1 mL) at 0° C. The mixture was stirred at room temperature for 2 hours. After evaporation, the residue was purified with prep-HPLC (MeCN/0.1% HCOOH) to provide (5-(3-ethyl-1H-pyrrolo[2,3-b]pyridin-5-yl)-2-(methylamino)phenyl)dimethylphosphine oxide as yellow solid (18 mg, 94% yield). LC-MS (ESI) m/z: 328 $[M+H]^+$.

Example 72

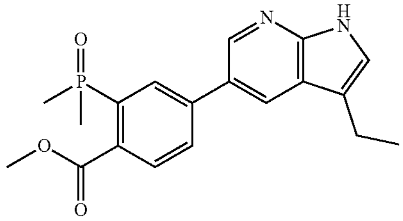 [SMILES: CCc1c[nH]c2ncc(-c3ccc(C(=O)OC)c(P(C)(C)=O)c3)cc12]

Methyl 2-(dimethylphosphoryl)-4-(3-ethyl-1H-pyrrolo[2,3-b]pyridin-5-yl)benzoate

The same procedures as Example 50, using Intermediate 20 in place of 2-bromo-4-iodo-1-methylbenzene in Step 1. LC-MS (ESI) m/z: 357 $[M+H]^+$.

Example 73

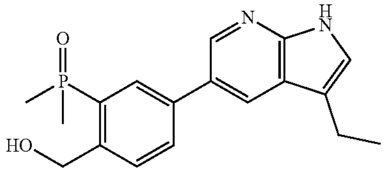 [SMILES: CCc1c[nH]c2ncc(-c3ccc(CO)c(P(C)(C)=O)c3)cc12]

(5-(3-Ethyl-1H-pyrrolo[2,3-b]pyridin-5-yl)-2-(hydroxymethyl)phenyl)dimethylphosphine oxide To a solution of methyl 2-dimethylphosphoryl-4-(3-ethyl-1H-pyrrolo[2,3-b]pyridin-5-yl)benzoate (139.61 mg, 391.78 umol) in dry THF (5 mL) was added lithium aluminum tetrahydride (26.58 mg, 783.56 umol) dropwise at 0° C. The mixture was stirred at room temperature for 1 hour, poured into ice water (10 mL) and extracted with DCM (10 mL×3). The organic layer was washed with brine (10 mL), dried over anhydrous sodium sulfate, filtered, and concentrated. The residue was purified with reverse phase chromatography (MeOH/0.1% trifluoroacetic acid) to provide (5-(3-ethyl-1H-pyrrolo[2,3-b]pyridin-5-yl)-2-(hydroxymethyl)phenyl)dimethylphosphine oxide as white solid (100 mg, 78% yield). LC-MS (ESI) m/z: 329 [M+I-1]'.

Example 74

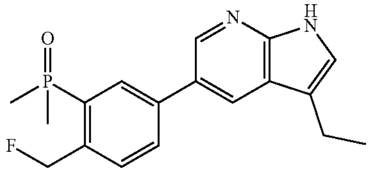 [SMILES: CCc1c[nH]c2ncc(-c3ccc(CF)c(P(C)(C)=O)c3)cc12]

(5-(3-Ethyl-1H-pyrrolo[2,3-b]pyridin-5-yl)-2-(fluoromethyl)phenyl)dimethylphosphine oxide To a solution of (5-(3-ethyl-1H-pyrrolo[2,3-b]pyridin-5-yl)-2-(hydroxymethyl)phenyl)dimethylphosphine oxide (200 mg, 609.12 umol) in DCM (5 mL) was added dropwise DAST (117.82 mg, 730.94 umol) at 0° C. The mixture was stirred at room temperature for 2 hours, and concentrated. The residue was purified with prep-HPLC (MeCN/0.05% trifluoroacetic acid) to provide (5-(3-ethyl-1H-pyrrolo[2,3-b]pyridin-5-yl)-2-(fluoromethyl)phenyl)dimethylphosphine oxide as white solid (2.5 mg, 1.5% yield). LC-MS (ESI) m/z: 331 $[M+H]^+$.

Example 75

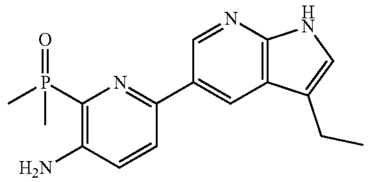 [SMILES: CCc1c[nH]c2ncc(-c3ccc(N)c(P(C)(C)=O)n3)cc12]

(3-Amino-6-(3-ethyl-1H-pyrrolo[2,3-b]pyridin-5-yl)pyridin-2-yl)dimethylphosphine oxide Step 1: A mixture of Intermediate 15 (330 mg, 1.10 mmol), dimethylphosphine oxide (103.40 mg, 1.32 mmol), palladium (II) acetate (24.79 mg, 110.40 umol), Xantphos (127.76 mg, 220.80 umol), and potassium phosphate (468.70 mg, 2.21 mmol) in DMF (15 mL) was stirred under nitrogen at 50° C. for 4 hours. After cooled down to room temperature, the mixture was filtered, and the filtrate was diluted with $H_2O$ (20 mL). The resulting mixture was extracted with EA (30 mL×3). The organic layer was washed with brine (30 mL×3), dried over anhydrous sodium sulfate, filtered and concentrated. The residue was purified with reverse phase column chromatography (MeOH in $H_2O$, from 0% to 100% v/v) to afford 6-bromo-2-dimethylphosphoryl-pyridin-3-amine as white solid (180 mg, 60% yield). LC-MS (ESI) m/z: 249 $[M+H]^+$.

Step 2: A mixture of 6-bromo-2-dimethylphosphoryl-pyridin-3-amine (100 mg, 401.53 umol), Intermediate 12 (131.13 mg, 481.84 umol), Pd(dppf)$Cl_2$DCM (29.38 mg, 40.15 umol), and potassium carbonate (110.99 mg, 803.07 umol) in dioxane (5 mL) and $H_2O$ (0.5 mL) was stirred under nitrogen at 90° C. overnight. After cooled down to room temperature, the mixture was filtered, and the filtrate was concentrated. The residue was diluted with EA (50 mL), washed with $H_2O$ (20 mL) and brine (20 mL), dried over anhydrous $Na_2SO_4$, filtered and concentrated. The residue was purified with prep-TLC (DCM/MeOH=10/1 v/v) to provide (3-amino-6-(3-ethyl-1H-pyrrolo[2,3-b]pyridin-5-yl)pyridin-2-yl)dimethylphosphine oxide as yellow solid (2 mg). LC-MS (ESI) m/z: 315 $[M+H]^+$.

Example 76

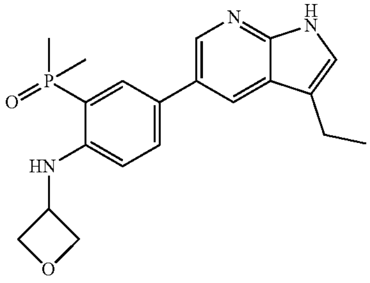 [SMILES: CCc1c[nH]c2ncc(-c3ccc(NC4COC4)c(P(C)(C)=O)c3)cc12]

(5-(3-Ethyl-1H-pyrrolo[2,3-b]pyridin-5-yl)-2-(oxetan-3-ylamino)phenyl)dimethylphosphine oxide The same procedures as Example 75, using Intermediate 30 in place of Intermediate 15 in Step 1. LC-MS (ESI) m/z: 370 $[M+H]^+$.

Example 77

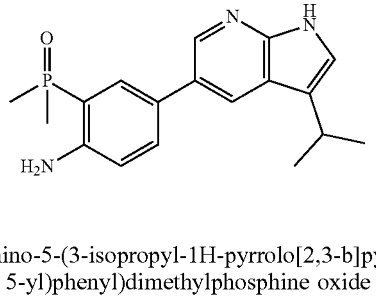

(2-Amino-5-(3-isopropyl-1H-pyrrolo[2,3-b]pyridin-5-yl)phenyl)dimethylphosphine oxide Step 1: To a solution of 1-(5-bromo-1H-pyrrolo[2,3-b]pyridin-3-yl)ethanone (590 mg, 2.47 mmol) in dry THF (25 mL) was added sodium hydride (60% suspend in oil, 71.99 mg, 3 mmol) in portions at 0° C. and the mixture was stirred at 0° C. for 1 hour. TsCl (714.90 mg, 3.75 mmol) was added to the above mixture in portions at 0° C. The mixture was stirred at room temperature for 2 hours, quenched with $H_2O$ (20 mL), and extracted with EA (30 mL×3). The organic layer was washed with brine (30 mL), dried over anhydrous sodium sulfate, filtered and concentrated. The residue was purified with flash column chromatography on silica gel (EA/PE=2/3 v/v) to provide 1-(5-bromo-1-tosyl-1H-pyrrolo[2,3-b]pyridin-3-yl)ethan-1-one as yellow solid (800 mg, 83% yield). LC-MS (ESI) m/z: 393 $[M+H]^+$.

Step 2: To a solution of 1-(5-bromo-1-tosyl-1H-pyrrolo[2,3-b]pyridin-3-yl)ethan-1-one (1.62 g, 4.12 mmol) in dry THF (20 mL) was added dropwise methylmagnesium bromide (3 M in ether, 6.87 mL, 20.6 mmol) at 0° C. The mixture was stirred at 0° C. for 2 hours, poured into ice-water (50 mL) and extracted with ethyl acetate (100 mL×3). The organic layer was washed with brine (50 mL), dried over anhydrous sodium sulfate, filtered and concentrated. The residue was purified with flash column chromatography on silica gel (EA/PE=1/4 v/v) to provide 2-(5-Bromo-1-tosyl-1H-pyrrolo[2,3-b]pyridin-3-yl)propan-2-ol as yellow solid (900 mg, 76% yield). LC-MS (ESI) m/z: 409 $[M+H]^+$.

Step 3: To a solution of 2-(5-Bromo-1-tosyl-1H-pyrrolo[2,3-b]pyridin-3-yl)propan-2-ol (900 mg, 2.20 mmol) in dry DCM (10 mL) were added $Et_3SiH$ (1.28 g, 10.99 mmol, 1.76 mL) and trifluoroacetic acid (1.25 g, 10.99 mmol, 847.02 uL) at 0° C. The mixture was stirred at room temperature overnight, poured into ice-water (20 mL), basified with saturated aqueous $NaHCO_3$ solution to pH 4-5, and extracted with DCM (30 mL×3). The organic layer was washed with brine (30 mL), dried over anhydrous sodium sulfate, filtered and concentrated. The residue was purified with flash column chromatography on silica gel (EA in PE, from 3% to 10% v/v) to provide 5-bromo-3-isopropyl-1-tosyl-1H-pyrrolo[2,3-b]pyridine as white solid (570 mg, 66% yield). LC-MS (ESI) m/z: 393 $[M+H]^+$.

Step 4: A mixture of 5-bromo-3-isopropyl-1-tosyl-1H-pyrrolo[2,3-b]pyridine (200 mg, 508.52 umol), Intermediate 13 (225.11 mg, 762.78 umol), Pd(dppf)$Cl_2$—$CH_2Cl_2$ (41.53 mg, 50.85 umol), and $K_2CO_3$ (210.85 mg, 1.53 mmol) in dioxane (3 mL) and $H_2O$ (0.43 mL) was stirred under $N_2$ at 100° C. overnight. After cooled down to room temperature, the mixture was concentrated and the residue was purified with flash column chromatography on silica gel (DCM/MeOH=20/1 v/v) to provide (2-amino-5-(3-isopropyl-1-tosyl-1H-pyrrolo[2,3-b]pyridin-5-yl)phenyl)dimethylphosphine oxide as brown oil (290 mg, 100% yield). LC-MS (ESI) m/z: 482 $[M+H]^+$.

Step 5: To a solution of (2-amino-5-(3-isopropyl-1-tosyl-1H-pyrrolo[2,3-b]pyridin-5-yl)phenyl)dimethylphosphine oxide (100 mg, 207.66 umol) in methanol (5 mL) was added aqueous NaOH solution (3 N, 3 mL, 9 mmol) at room temperature. The mixture was refluxed for 2 hours, and concentrated. The residue was diluted with $H_2O$ (10 mL), adjusted to pH~5 with diluted HCl solution (1 N), and extracted with DCM (20 mL×3). The organic layer was dried over anhydrous sodium sulfate, filtered, and concentrated. The residue was purified with prep-HPLC (MeCN/0.1% HCOOH) to provide (2-amino-5-(3-isopropyl-1H-pyrrolo[2,3-b]pyridin-5-yl)phenyl)dimethylphosphine oxide as white solid (10.8 mg, 16% yield). LC-MS (ESI) m/z: 328 $[M+H]^+$.

Example 78

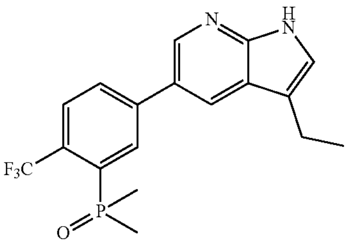 [SMILES: CCc1c[nH]c2ncc(-c3ccc(C(F)(F)F)c(P(C)(C)=O)c3)cc12]

(5-(3-Ethyl-1H-pyrrolo[2,3-b]pyridin-5-yl)-2-(trifluoromethyl)phenyl)dimethylphosphine oxide Step 1: The same procedure as Step 1 of Example 50, using 5-bromo-2-(trifluoromethyl)aniline in place of 2-bromo-4-iodo-1-methylbenzene. LC-MS (ESI) m/z: 306 $[M+H]^+$.

Step 2: To a solution of 5-(3-ethyl-1H-pyrrolo[2,3-b]pyridin-5-yl)-2-(trifluoromethyl)aniline (50 mg, 163.77 umol) in THF (5 mL) were added boron fluoride ethyl ether (92.98 mg, 655.10 umol, 82.28 uL) and tert-butylnitrite (59.11 mg, 573.21 umol, 68.18 uL) at −78° C. The mixture was stirred for 10 minutes at this temperature, warmed to room temperature and stirred for 30 minutes. The mixture was diluted with $Et_2O$ (10 mL), and filtered to remove the solid. The filtrate was concentrated (below 20° C.), and the resulting diazonium salt was added to a mixture of KI (40.78 mg, 245.66 umol) and iodine (14.66 mg, 114.64 umol) in acetone (5 mL) at 0° C. The resulting mixture was stirred at room temperature overnight, and concentrated. The residue was purified with flash column chromatographer on silica gel to provide 3-ethyl-5-(3-iodo-4-(trifluoromethyl)phenyl)-1H-pyrrolo[2,3-b]pyridine as yellow solid (30 mg, 44% yield). LC-MS (ESI) m/z: 417 $[M+H]^+$.

Step 3: The same procedure as Step 2 of Example 50, using 3-ethyl-5-(3-iodo-4-(trifluoromethyl)phenyl)-1H-pyrrolo[2,3-b]pyridine in place of 5-(3-bromo-4-methylphenyl)-3-ethyl-1H-pyrrolo[2,3-b]pyridine. LC-MS (ESI) m/z: 367 $[M+H]^+$.

The invention claimed is:

1. A compound represented by structural formula (I-2):

(I-2)

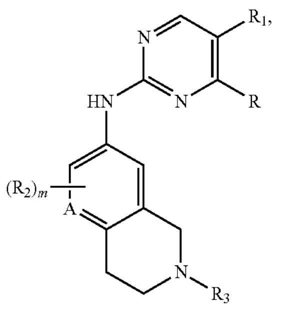

or a pharmaceutically acceptable salt or a stereoisomer thereof, wherein

A is $CR_2$ or N;

(i) R is

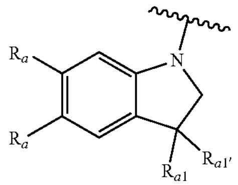

, wherein the  bond connects with the pyrimidine ring;

each instance of $R_a$ is independently H, F, or Cl;

$R_{a1}$ is independently H, $C_{1-4}$ alkyl, or $C_{1-4}$hydroxyalkyl:

$R_{a1}'$ is independently $-(CHR_{aa})_kOH$, $-(CHR_{aa})_kCN$, $-(CHR_{aa})_kC(O)OR_{11}$, $-(CHR_{aa})_kC(O)NR_{11}R_{12}$, $-(CHR_{aa})_kC(O)NR_{11}OR_{12}$, $-(CHR_{aa})_kC(O)NR_{11}S(=O)_2R_{12}$, $-(CHR_{aa})_kS(=O)_2R_{11}$, $-(CHR_{aa})_kS(=O)_2NR_{11}R_{12}$, $-(CHR_{aa})_kNR_{11}S(=O)_2R_{12}$, $-(CHR_{aa})_k$-5-6 membered heteroaryl, or $-(CHR_{aa})_kP(=O)R_{11}R_{12}$;

$R_{aa}$ is independently H or $C_{1-3}$ alkyl optionally substituted with halogen;

$R_1$ is H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, phenyl, 5-6 membered heteroaryl, $C_{3-6}$ cycloalkyl, or 3-7 membered heterocyclyl, wherein the alkyl, alkenyl, alkynyl, alkoxy, phenyl, heteroaryl, cycloalkyl, or heterocyclyl represented by $R_1$ or in the group represented by $R_1$ is optionally substituted with one to three substituents independently selected from the group consisting of halogen, OH, CN, $C_{1-4}$ alkyl, $C_{1-4}$ alkoxy, $C_{1-4}$ haloalkyl, $C_{1-4}$ haloalkoxy, and $NR_{11}R_{12}$; or (ii) R and $R_1$, together with the carbon atoms to which they are attached, form a ring represented below:

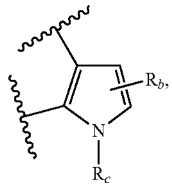

,

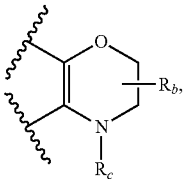

,

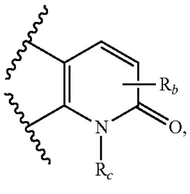

,

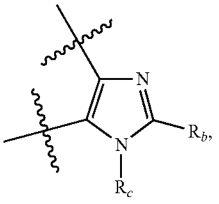

, or

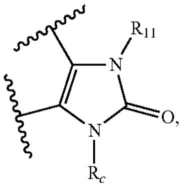

, wherein the  bonds connect with the pyrimidine ring;

each instance of $R_b$ is independently H, deuterium, halogen, OH, CN, $NH_2$, $NO_2$, COOH, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)NR_{11}OR_{12}$, $C(O)NR_{11}S({=}O)_2R_{12}$, $C(O)C_{1-6}$ alkyl, $C(O)OR_{11}$, $NR_{11}C(O)R_{12}$, $S({=}O)_2R_{11}$, $S({=}O)_2NR_{11}R_{12}$, $NR_{11}S({=}O)_2R_{12}$, $P({=}O)R_{11}R_{12}$, $C_{3-6}$ cycloalkyl, 3-7 membered heterocyclyl, or 5-6 membered heteroaryl, wherein the alkyl, alkenyl, alkynyl, alkoxy, cycloalkyl, heterocyclyl, or heteroaryl represented by $R_b$ or in the group represented by $R_b$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$haloalkoxy, $NR_{11}R_{12}$, $C(O)NR_{11}R_{12}$, $C(O)NR_{11}OR_{12}$, $C(O)NR_{11}S({=}O)_2R_{12}$, $C(O)OR_{11}$, $NR_{11}S({=}O)_2R_{12}$, $P({=}O)R_{11}R_{12}$, $S({=}O)_2R_{11}$, $S({=}O)_2NR_{11}R_{12}$, and 5-6 membered heteroaryl;

each instance of $R_c$ is independently phenyl, 5-6 membered monocyclic heterocyclyl having 1 to 3 heteroatoms selected from N and 0; 5-6 membered monocyclic heteroaryl having 1 to 3 heteroatoms selected from N and O; wherein the phenyl, heterocyclyl, or heteroaryl represented by $R_c$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$haloalkoxy, $NR_{11}R_{12}$, $C(O)NR_{11}R_{12}$, and $P(O)di\text{-}C_{1-6}$ alkyl;

each instance of $R_2$ is independently H, deuterium, halogen, OH, CN, $NH_2$, $NO_2$, $C_{1-6}$ alkyl, $C_{2-6}$ alkenyl, $C_{2-6}$ alkynyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, $P({=}O)R_{11}R_{12}$, $S({=}O)_2R_{11}$, or $S({=}O)_2NR_{11}R_{12}$, wherein the alkyl, alkenyl, alkynyl, or alkoxy represented by $R_2$ or in the group represented by $R_2$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12}$;

$R_3$ is H, $C_{1-6}$ alkyl, $C(O)C_{1-6}$ alkyl, $C_{3-6}$ cycloalkyl, or 3-7 membered heterocyclyl, wherein the alkyl, cycloalkyl, or heterocyclyl represented by $R_3$ or in the group represented by $R_3$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$haloalkoxy, $C_{3-6}$ cycloalkyl, 3-7 membered heterocyclyl, and $NR_{11}R_{12}$;

each instance of $R_{11}$ and $R_{12}$ is independently H or $C_{1-4}$ alkyl;

m is 0, 1, 2, or 3; and k is 0 or 1.

2. The compound of claim 1, or a pharmaceutically acceptable salt or a stereoisomer thereof, wherein $R_1$ is H, halogen, CN, $C_{1-6}$ alkyl, $C_{2-6}$ alkenyl, $C_{1-6}$ alkoxy, $NR_{11}R_{12}$, $C(O)NR_{11}R_{12}$, $C(O)C_{1-6}$ alkyl, $C(O)OC_{1-6}$ alkyl, $NR_{11}C(O)C_{1-6}$ alkyl, wherein the alkyl, alkenyl, or alkoxy represented by $R_1$ or in the group represented by $R_1$ is optionally substituted with one to three substituents independently selected from the group consisting of halogen, OH, CN, $C_{1-4}$ alkyl, $C_{1-4}$ alkoxy, $C_{1-4}$ haloalkyl, $C_{1-4}$ haloalkoxy, and $NR_{11}R_{12}$.

3. The compound of claim 2, or a pharmaceutically acceptable salt or a stereoisomer thereof, wherein $R_1$ is H, halogen, CN, $C_{1-4}$ alkyl, $C_{1-4}$ haloalkyl, $C_{2-4}$ alkenyl, $C_{1-4}$ alkoxy, or $C_{1-4}$ haloalkoxy.

4. The compound of claim 3, or a pharmaceutically acceptable salt or a stereoisomer thereof, wherein $R_1$ is H, F, Cl, CN, or $CF_3$.

5. The compound of claim 1, or a pharmaceutically acceptable salt or a stereoisomer thereof, wherein R is

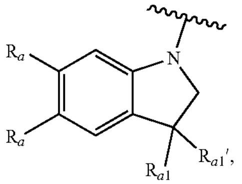

wherein the  bond connects with the pyrimidine ring, $R_{a1}$ is independently H, $C_{1-4}$ alkyl, or $C_{1-4}$hydroxyalkyl;

$R_{a1}'$ is independently $-(CHR_{aa})_kOH$, $-(CHR_{aa})_kCN$, $-(CHR_{aa})C(O)OR_{11}$, $-(CHR_{aa})_kC(O)NR_{11}R_{12}$, $-(CHR_{aa})_kC(O)NR_{11}OR_{12}$, $-(CHR_{aa})_kC(O)NR_{11}S({=}O)_2R_{12}$, $-(CHR_{aa})_kS({=}O)_2R_{11}$, $-(CHR_{aa})_kS({=}O)_2NR_{11}R_{12}$, $-(CHR_{aa})_kNR_{11}S({=}O)_2R_{12}$, $-(CHR_{aa})_k$-5-6 membered heteroaryl, or $-(CHR_{aa})_kP({=}O)R_{11}R_{12}$;

$R_{aa}$ is independently H or $C_{1-3}$ alkyl optionally substituted with halogen;

$R_a$ is independently H, F, or Cl;

$R_{11}$ and $R_{12}$ are independently H or $C_{1-4}$ alkyl;

k is 0 or 1.

6. The compound of claim 5, or a pharmaceutically acceptable salt or a stereoisomer thereof, wherein $R_{a1}$ is independently H, $CH_3$, or $CH_2OH$;

$R_{a1}'$ is independently $-(CHR_{aa})_kOH$, $-(CHR_{aa})_kCN$, $-(CHR_{aa})_kC(O)OR_{11}$, $-(CHR_{aa})_kC(O)NR_{11}R_{12}$, $-(CHR_{aa})_kC(O)NR_{11}OR_{12}$, $-(CHR_{aa})_kC(O)NR_{11}S({=}O)_2R_{12}$, $-(CHR_{aa})_kS({=}O)_2R_{11}$, $-(CHR_{aa})_kS({=}O)_2NR_{11}R_{12}$, $-(CHR_{aa})_kNR_{11}S({=}O)_2R_{12}$, $-(CHR_{aa})_k$-tetrazole, or $-(CHR_{aa})_kP({=}O)R_{11}R_{12}$;

$R_{aa}$ is independently H, $CH_3$, or $CF_3$;

$R_{11}$ and $R_{12}$ are independently H or $C_{1-2}$ alkyl;

each instance of $R_a$ is independently H or F; and k is 0 or 1.

7. The compound of claim 6, or a pharmaceutically acceptable salt or a stereoisomer thereof, wherein $R_1$ is Cl.

8. The compound of claim 1, or a pharmaceutically acceptable salt or a stereoisomer thereof, wherein (i) R and $R^1$, together with the carbon atoms to which they are attached, form a ring represented below:

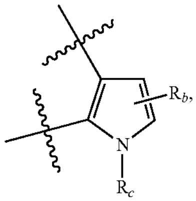

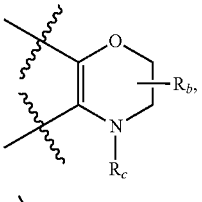

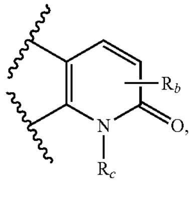

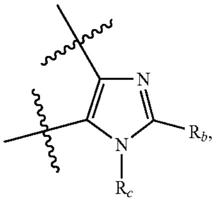

or

-continued

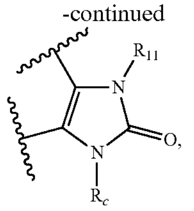

or (ii) R and $R^1$, together with the carbon atoms to which they are attached, form a ring represented below:

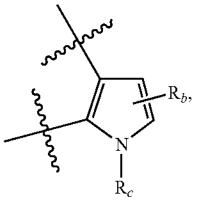

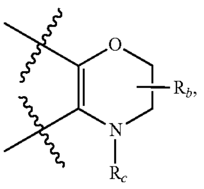

or

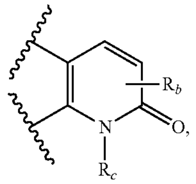

wherein the  bonds connect with the pyrimidine ring.

9. The compound of claim 8, or a pharmaceutically acceptable salt or a stereoisomer thereof, wherein (i) each instance of $R_b$ is independently H, halogen, OH, CN, $NH_2$, COOH, $C_{1-4}$ alkyl, $C_{1-4}$ haloalkyl, $C_{1-4}$ hydroxyalkyl, $C_{1-4}$ alkoxy, $C_{1-4}$haloalkoxy, $C_{1-4}$ hydroxyalkoxy, $NR_{11}R_{12}$, $C(O)NR_{11}R_{12}$, $C(O)C_{1-4}$ alkyl, $C(O)OC_{1-4}$ alkyl, $C(O)NR_{11}OR_{12}$, $S(=O)_2R_{11}$, $S(=O)_2NR_{11}R_{12}$, $NR_{11}(S=O)_2R_{12}$, $C(O)NR_{11}S(=O)_2R_{12}$, $P(=O)R_{11}R_{12}$, 5-6 membered heteroaryl, or $NR_{11}C(O)C_{1-4}$ alkyl; and each instance of $R_c$ is phenyl or pyridinyl, each of which is optionally substituted with one or two substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, and $P(=O)$di-$C_{1-6}$ alkyl;

(ii) each instance of $R_b$ is independently H, halogen, CN, COOH, $C_{1-2}$ alkyl, or $C_{1-2}$ haloalkyl;

each instance of $R_c$ is phenyl or pyridinyl, each of which is optionally substituted with one or two substituents independently selected from the group consisting of halogen, $C_{1-4}$ alkyl, $C_{1-4}$ haloalkyl, $C_{1-4}$ alkoxy, $C_{1-4}$ haloalkoxy, $NR_{11}R_{12}$, $C(O)NR_{11}R_{12}$, and $P(=O)$di-$C_{1-6}$ alkyl;

(iii) each instance of $R_b$ is independently H, CN, or COOH; and each instance of $R_c$ is phenyl or pyridinyl, each of which is optionally substituted with one or two substituents independently selected from the group consisting of $C_{1-4}$ alkyl, $C(O)N(CH_3)_2$, and $P(=O)(CH_3)_2$.

10. The compound of claim 7, or a pharmaceutically acceptable salt or a stereoisomer thereof, wherein

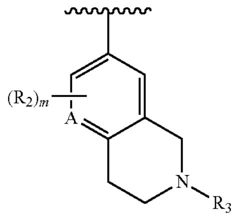

is

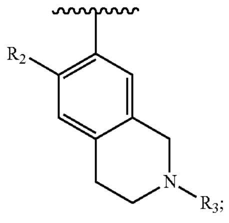

m is 0 or 1; and/or each instance of $R_2$ is H, halogen, $C_{1-4}$ alkyl, $C_{1-4}$ haloalkyl, $C_{1-4}$ alkoxy, $C_{1-4}$haloalkoxy; and $R_3$ is H, $C_{1-6}$ alkyl, $C_{1-6}$ hydroxyalkyl, or $COCH_2NR_{11}R_{12}$.

11. The compound of claim 10, or a pharmaceutically acceptable salt or a stereoisomer thereof, wherein each instance of $R_2$ is H, F, Cl, or $OCH_3$; and $R_3$ is H or $C_{1-4}$ alkyl.

12. A pharmaceutical composition comprising a therapeutically effective amount of the compound of claim 1 or a pharmaceutically acceptable salt or a stereoisomer thereof, and a pharmaceutically acceptable carrier.

13. A combination comprising a therapeutically effective amount of the compound of claim 1, or a pharmaceutically acceptable salt or a stereoisomer thereof, and one or more therapeutically active co-agents.

14. The compound of claim 1, or a pharmaceutically acceptable salt or a stereoisomer thereof, wherein each instance of $R_2$ is independently H, halogen, OH, CN, $NH_2$, $NO_2$, $C_{1-4}$ alkyl, $C_{1-4}$ alkoxy, $NR_{11}R_{12}$, $C(O)NR_{11}R_{12}$, $C(O)C_{1-4}$ alkyl, $C(O)OC_{1-4}$ alkyl, $NR_{11}C(O)C_{1-4}$ alkyl, $P(=O)R_{11}R_{12}$, $S(=O)_2R_{11}$, or $S(=O)_2NR_{11}R_{12}$, wherein the alkyl or alkoxy represented by $R_2$ or in the group represented by $R_2$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12}$.

15. The compound of claim 1, or a pharmaceutically acceptable salt or a stereoisomer thereof, wherein $R_3$ is H, $C_{1-6}$ alkyl, or $C(O)C_{1-6}$ alkyl, wherein the alkyl represented by $R_3$ or in the group represented by $R_3$ is optionally substituted with one to three substituents independently selected from the group consisting of halogen, OH, CN, $C_{1-4}$ alkyl, $C_{1-4}$ haloalkyl, $C_{1-4}$ alkoxy, $C_{1-4}$ haloalkoxy, and $NR_{11}R_{12}$.

16. The compound of claim 11, or a pharmaceutically acceptable salt or a stereoisomer thereof, wherein $R_{a1}$ is independently H, $CH_3$, or $CH_2OH$;

$R_{a1}'$ is $-CH_2COOH$; and each instance of $R_a$ is independently H or F.

17. A compound, or a pharmaceutically acceptable salt or a stereoisomer thereof, wherein the compound is
| Example No. | Structure |
|---|---|
| 36 | 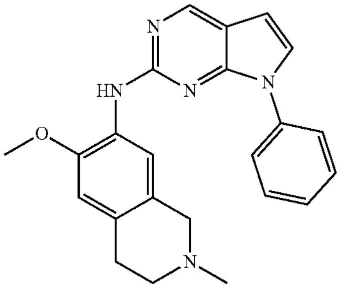 [SMILES: COc1cc2c(cc1Nc1ncc3ccn(-c4ccccc4)c3n1)CN(C)CC2] |
| 37 | 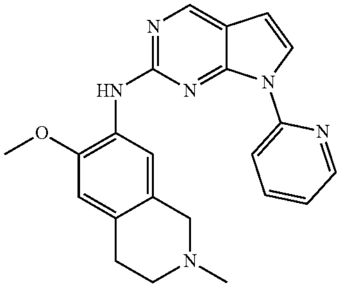 [SMILES: COc1cc2c(cc1Nc1ncc3ccn(-c4ccccn4)c3n1)CN(C)CC2] |
| 43 | 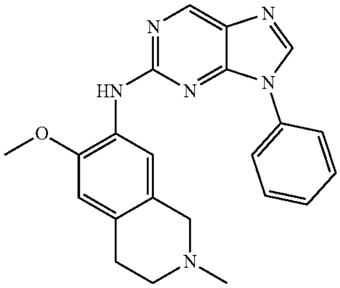 [SMILES: COc1cc2c(cc1Nc1ncc3ncn(-c4ccccc4)c3n1)CN(C)CC2] |
| 44 | 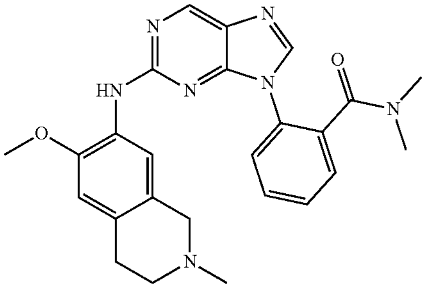 |
| 45 | 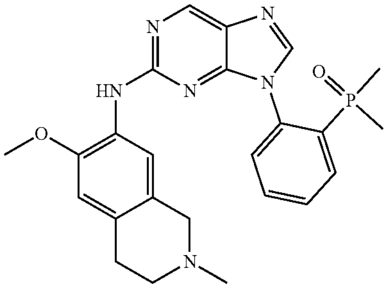 |
-continued
| Example No. | Structure |
|---|---|
| 38 | 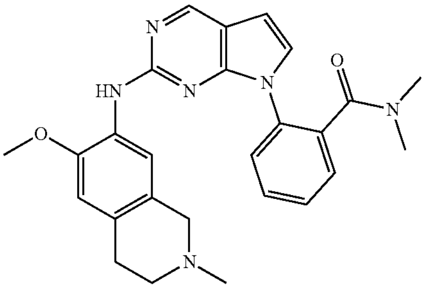 |
| 39 | 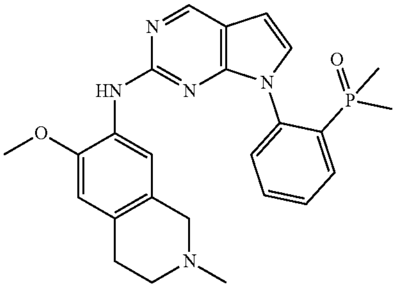 |
| 47 | 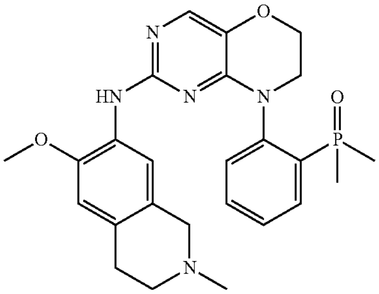 |
| 46 | 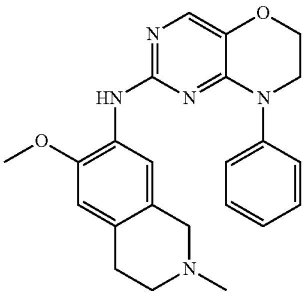 [SMILES: COc1cc2c(cc1Nc1ncc3c(n1)N(c1ccccc1)CCO3)CN(C)CC2] |
| 111 | 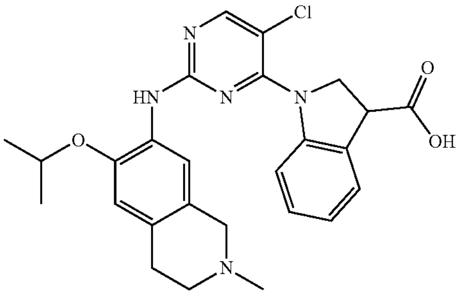 [SMILES: CC(C)Oc1cc2c(cc1Nc1ncc(Cl)c(N3CC(C(=O)O)c4ccccc43)n1)CN(C)CC2] |

-continued
| Example No. | Structure |
|---|---|
| 40 | 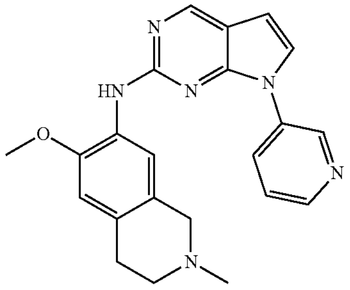 [SMILES: COc1cc2c(cc1Nc1ncc3ccn(-c4cccnc4)c3n1)CN(C)CC2] |
| 41 | 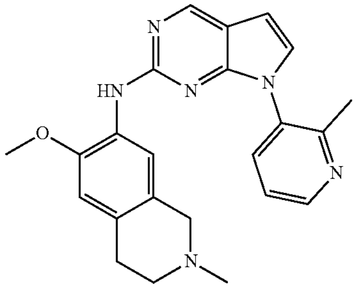 |
| 33 | 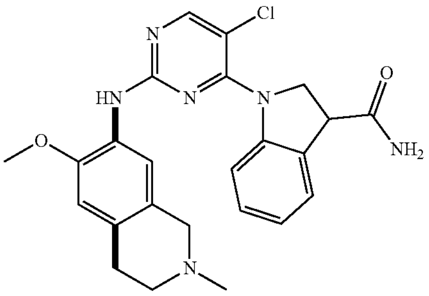 |
| 32 | 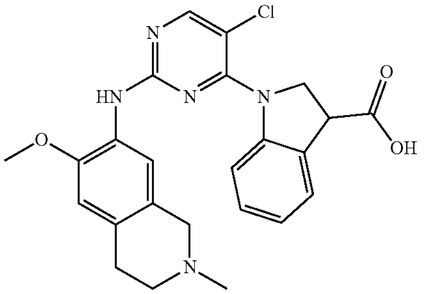 [SMILES: COc1cc2c(cc1Nc1ncc(Cl)c(N3CC(C(=O)O)c4ccccc43)n1)CN(C)CC2] |
| 95 | 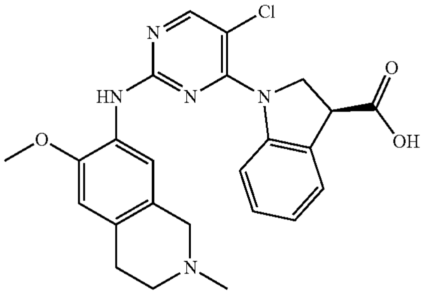 [SMILES: COc1cc2c(cc1Nc1ncc(Cl)c(N3C[C@@H](C(=O)O)c4ccccc43)n1)CN(C)CC2] |
-continued
| Example No. | Structure |
|---|---|
| 96 | 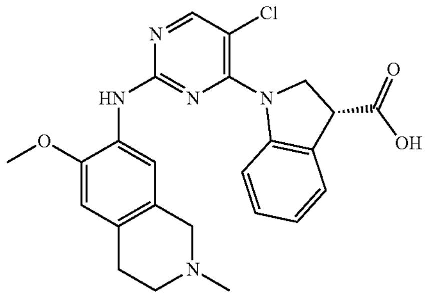 [SMILES: COc1cc2c(cc1Nc1ncc(Cl)c(N3C[C@H](C(=O)O)c4ccccc43)n1)CN(C)CC2] |
| 87 | 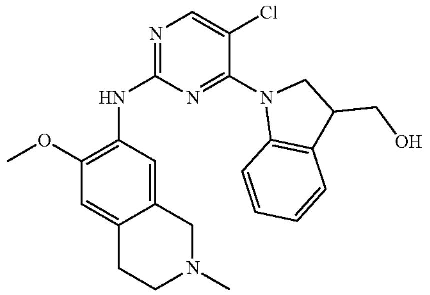 [SMILES: COc1cc2c(cc1Nc1ncc(Cl)c(N3CC(CO)c4ccccc43)n1)CN(C)CC2] |
| 115 | 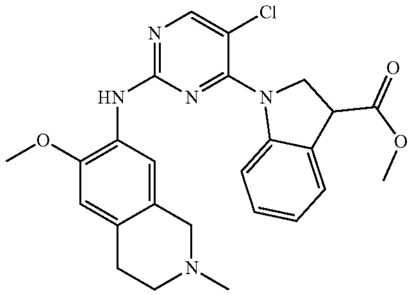 [SMILES: COC(=O)C1CN(c2nc(Nc3cc4c(cc3OC)CCN(C)C4)ncc2Cl)c2ccccc21] |
| 88 | 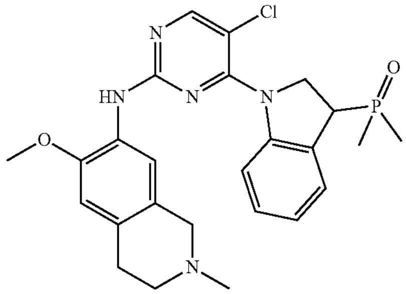 |
| 121 | 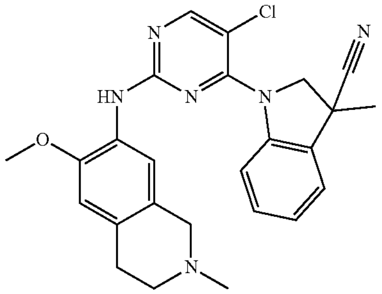 |

-continued
| Example No. | Structure |
|---|---|
| 81 | 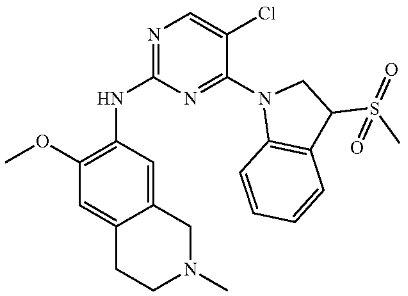 |
| 99 | 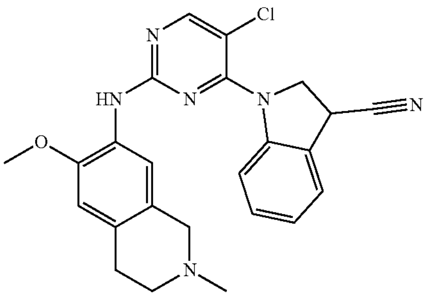 [SMILES: COc1cc2c(cc1Nc1ncc(Cl)c(N3CC(C#N)c4ccccc43)n1)CN(C)CC2] |
| 120 | 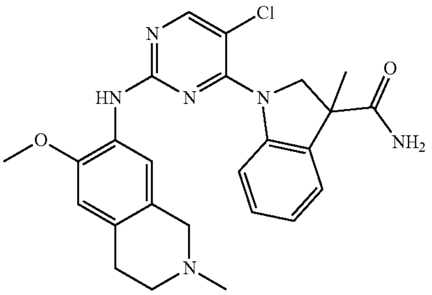 [SMILES: COc1cc2c(cc1Nc1ncc(Cl)c(N3CC(C)(C(N)=O)c4ccccc43)n1)CN(C)CC2] |
| 117 | 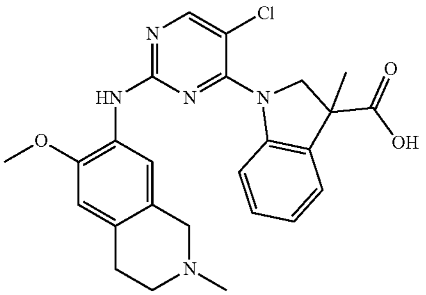 [SMILES: COc1cc2c(cc1Nc1ncc(Cl)c(N3CC(C)(C(=O)O)c4ccccc43)n1)CN(C)CC2] |
| 118 | 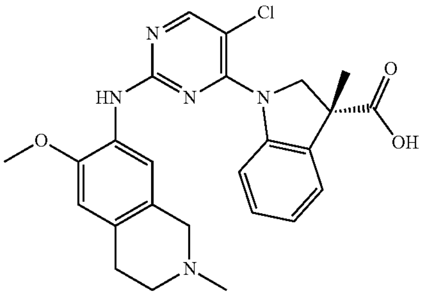 [SMILES: COc1cc2c(cc1Nc1ncc(Cl)c(N3C[C@](C)(C(=O)O)c4ccccc43)n1)CN(C)CC2] |
-continued
| Example No. | Structure |
|---|---|
| 119 | 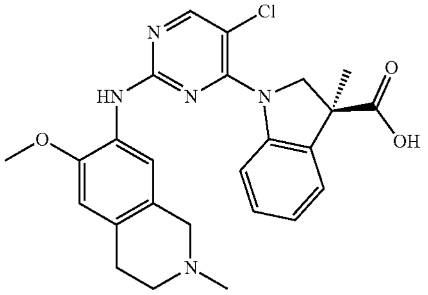 [SMILES: COc1cc2c(cc1Nc1ncc(Cl)c(N3C[C@@](C)(C(=O)O)c4ccccc43)n1)CN(C)CC2] |
| 116 | 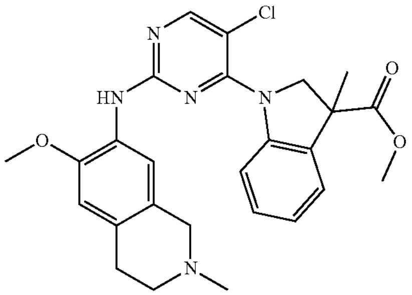 [SMILES: COC(=O)C1(C)CN(c2nc(Nc3cc4c(cc3OC)CCN(C)C4)ncc2Cl)c2ccccc21] |
| 97 | 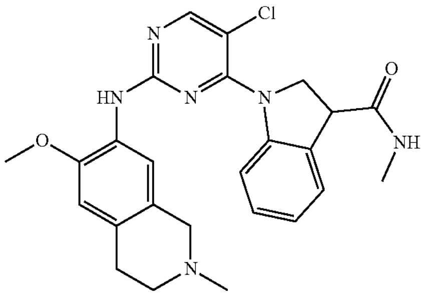 [SMILES: CNC(=O)C1CN(c2nc(Nc3cc4c(cc3OC)CCN(C)C4)ncc2Cl)c2ccccc21] |
| 122 | 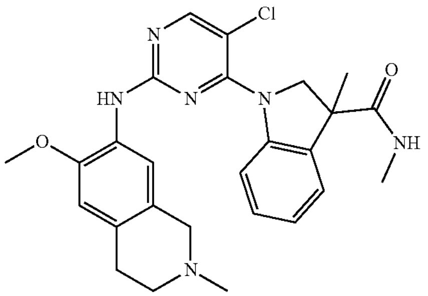 [SMILES: CNC(=O)C1(C)CN(c2nc(Nc3cc4c(cc3OC)CCN(C)C4)ncc2Cl)c2ccccc21] |
| 101 | 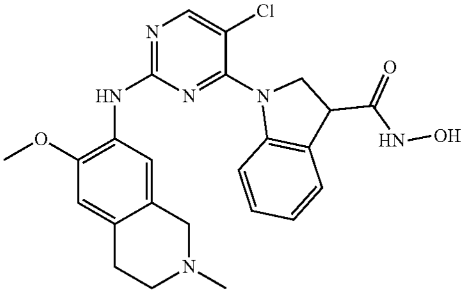 |

-continued
| Example No. | Structure |
|---|---|
| 102 | 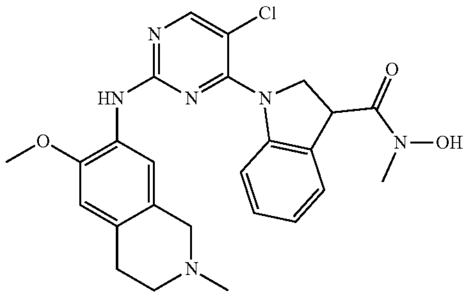 [SMILES: COc1cc2c(cc1Nc1ncc(Cl)c(N3CC(C(=O)N(C)O)c4ccccc43)n1)CN(C)CC2] |
| 100 | 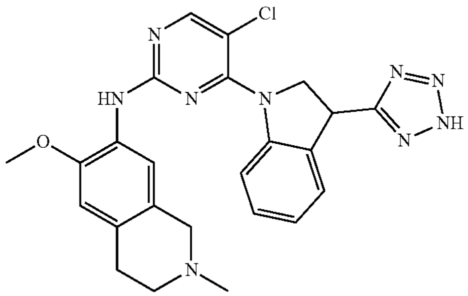 [SMILES: COc1cc2c(cc1Nc1ncc(Cl)c(N3CC(c4nn[nH]n4)c4ccccc43)n1)CN(C)CC2] |
| 127 | 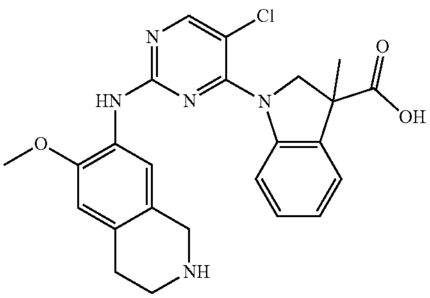 [SMILES: COc1cc2c(cc1Nc1ncc(Cl)c(N3CC(C)(C(=O)O)c4ccccc43)n1)CNCC2] |
| 123 | 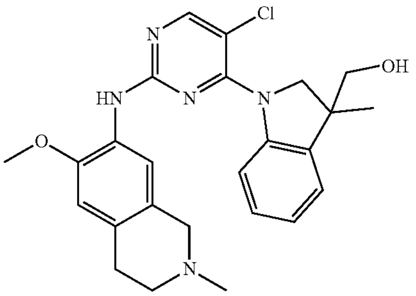 [SMILES: COc1cc2c(cc1Nc1ncc(Cl)c(N3CC(C)(CO)c4ccccc43)n1)CN(C)CC2] |
| 103 | 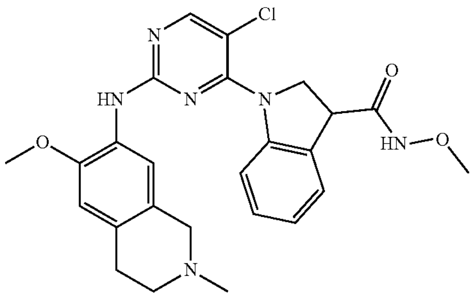 |
-continued
| Example No. | Structure |
|---|---|
| 128 | 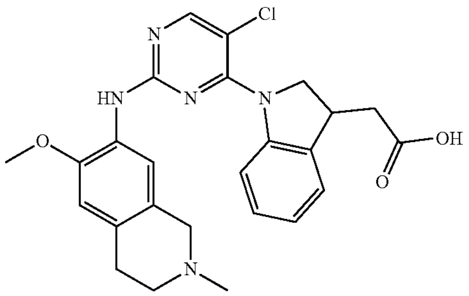 [SMILES: COc1cc2c(cc1Nc1ncc(Cl)c(N3CC(CC(=O)O)c4ccccc43)n1)CN(C)CC2] |
| 124 | 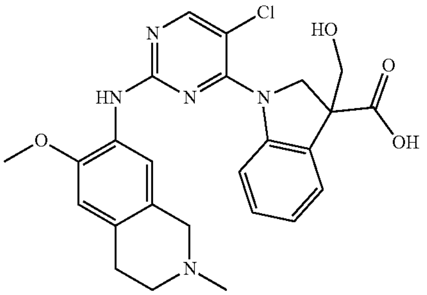 [SMILES: COc1cc2c(cc1Nc1ncc(Cl)c(N3CC(CO)(C(=O)O)c4ccccc43)n1)CN(C)CC2] |
| 98 | 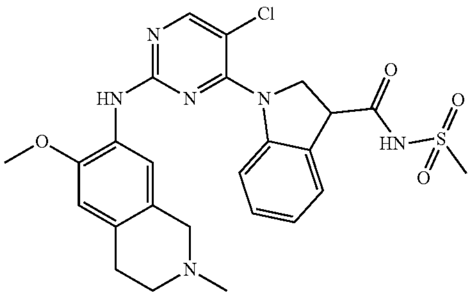 |
| 110 | 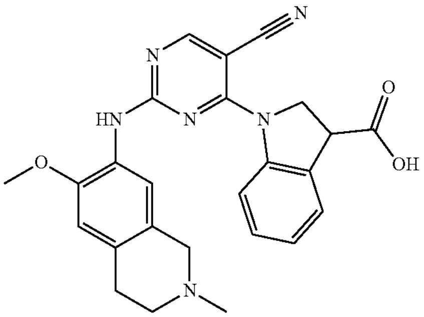 [SMILES: COc1cc2c(cc1Nc1ncc(C#N)c(N3CC(C(=O)O)c4ccccc43)n1)CN(C)CC2] |
| 163 | 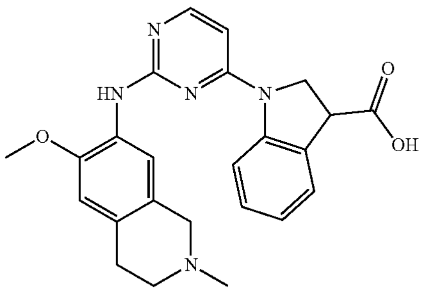 [SMILES: COc1cc2c(cc1Nc1nccc(N3CC(C(=O)O)c4ccccc43)n1)CN(C)CC2] |

-continued
| Example No. | Structure |
|---|---|
| 109 | 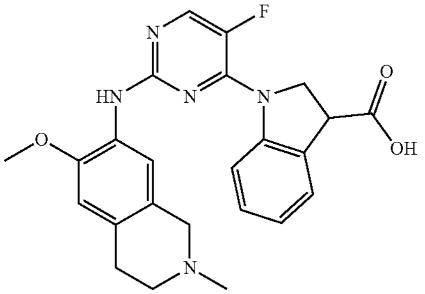 [SMILES: COc1cc2c(cc1Nc1ncc(F)c(N3CC(C(=O)O)c4ccccc43)n1)CN(C)CC2] |
| 112 | 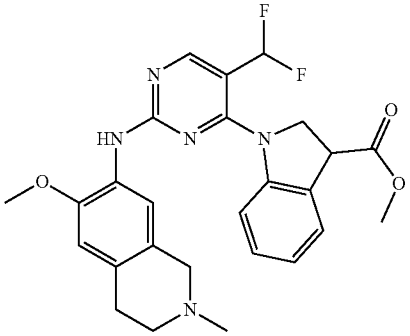 [SMILES: COC(=O)C1CN(c2nc(Nc3cc4c(cc3OC)CCN(C)C4)ncc2C(F)F)c2ccccc21] |
| 105 | 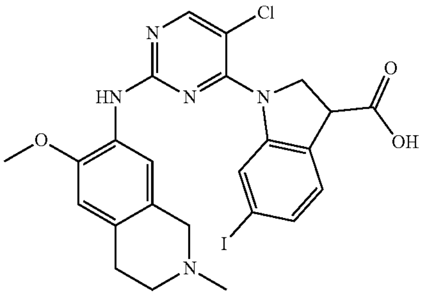 [SMILES: COc1cc2c(cc1Nc1ncc(Cl)c(N3CC(C(=O)O)c4ccc(I)cc43)n1)CN(C)CC2] |
| 104 | 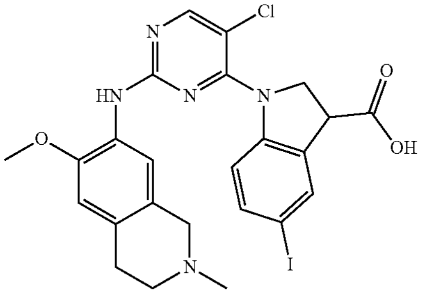 [SMILES: COc1cc2c(cc1Nc1ncc(Cl)c(N3CC(C(=O)O)c4cc(I)ccc43)n1)CN(C)CC2] |
| 126 | 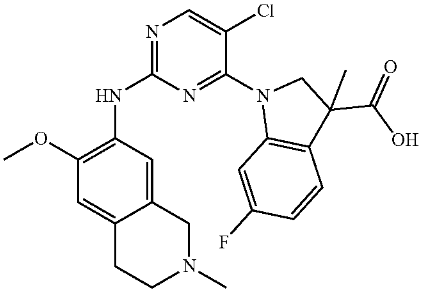 [SMILES: COc1cc2c(cc1Nc1ncc(Cl)c(N3CC(C)(C(=O)O)c4ccc(F)cc43)n1)CN(C)CC2] |
-continued
| Example No. | Structure |
|---|---|
| 125 | 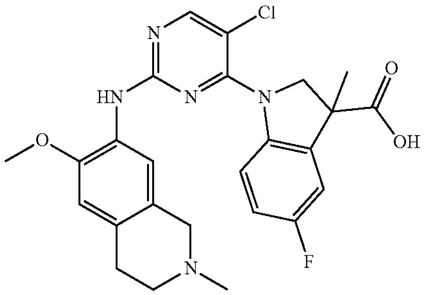 [SMILES: COc1cc2c(cc1Nc1ncc(Cl)c(N3CC(C)(C(=O)O)c4cc(F)ccc43)n1)CN(C)CC2] |
| 172 | 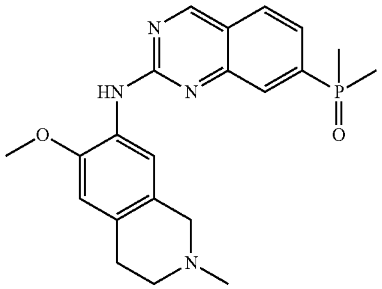 |
| 171 | 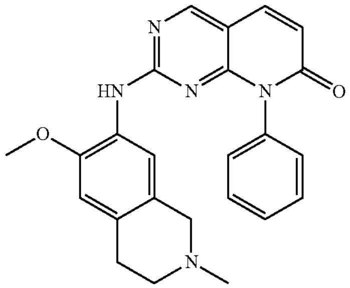 [SMILES: COc1cc2c(cc1Nc1ncc3ccc(=O)n(-c4ccccc4)c3n1)CN(C)CC2] |
| 166 | 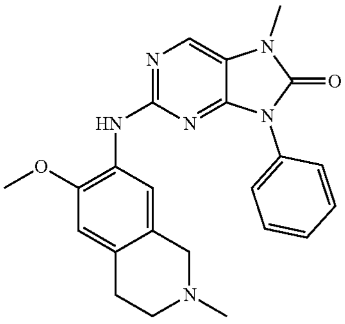 [SMILES: COc1cc2c(cc1Nc1ncc3c(n1)n(-c1ccccc1)c(=O)n3C)CN(C)CC2] |
| 145 | 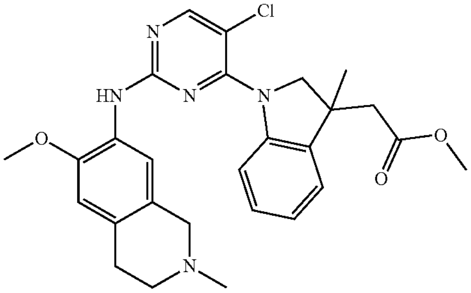 |

-continued
| Example No. | Structure |
| --- | --- |
| 149 | 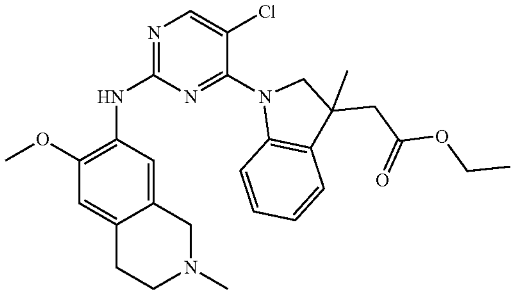 [SMILES: CCOC(=O)CC1(C)CN(c2nc(Nc3cc4c(cc3OC)CCN(C)C4)ncc2Cl)c2ccccc21] |
| 164 | 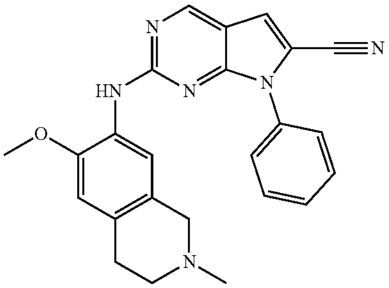 [SMILES: COc1cc2c(cc1Nc1ncc3cc(C#N)n(-c4ccccc4)c3n1)CN(C)CC2] |
| 150 | 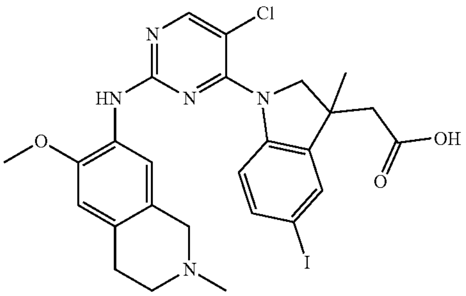 |
| 151 | 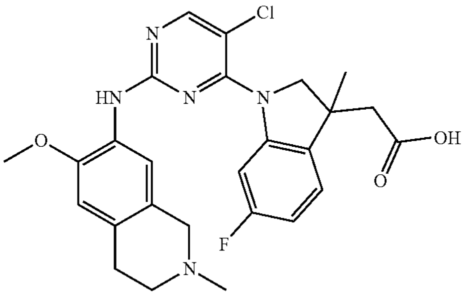 |
| 152 | 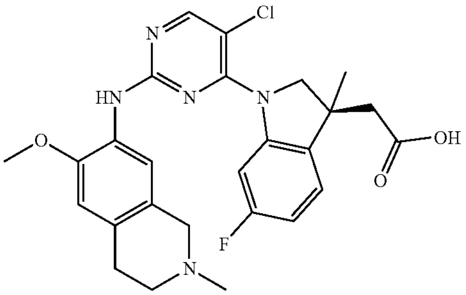 [SMILES: COc1cc2c(cc1Nc1ncc(Cl)c(N3C[C@@](C)(CC(=O)O)c4ccc(F)cc43)n1)CN(C)CC2] |
-continued
| Example No. | Structure |
| --- | --- |
| 153 | 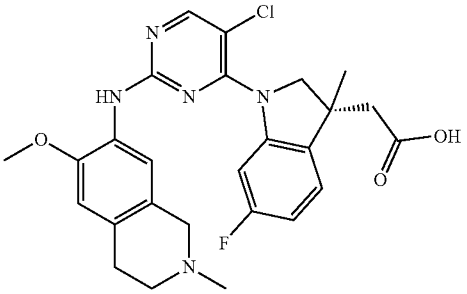 [SMILES: COc1cc2c(cc1Nc1ncc(Cl)c(N3C[C@](C)(CC(=O)O)c4ccc(F)cc43)n1)CN(C)CC2] |
| 154 | 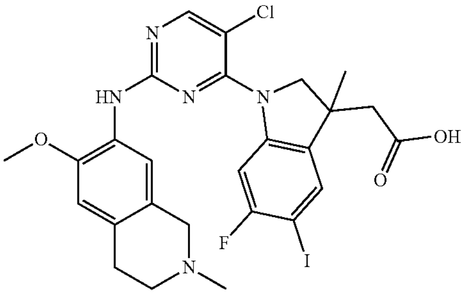 |
| 160 | 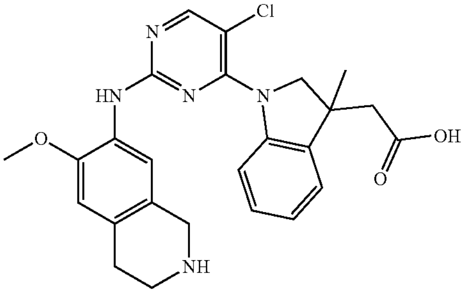 [SMILES: COc1cc2c(cc1Nc1ncc(Cl)c(N3CC(C)(CC(=O)O)c4ccccc43)n1)CNCC2] |
| 157 | 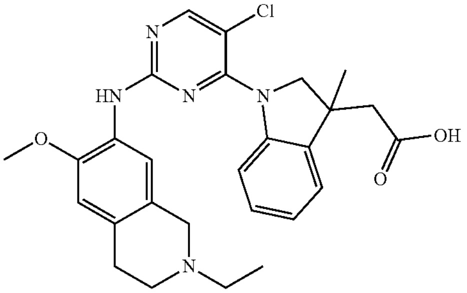 [SMILES: CCN1CCc2cc(OC)c(Nc3ncc(Cl)c(N4CC(C)(CC(=O)O)c5ccccc54)n3)cc2C1] |

-continued
| Example No. | Structure |
|---|---|
| 155 | 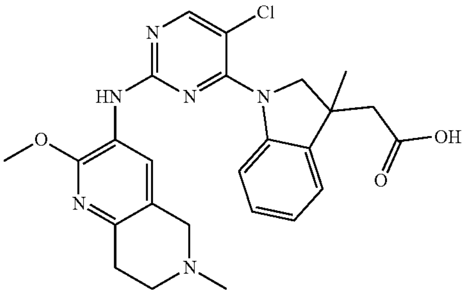 [SMILES: COc1nc2c(cc1Nc1ncc(Cl)c(N3CC(C)(CC(=O)O)c4ccccc43)n1)CN(C)CC2] |
| 158 | 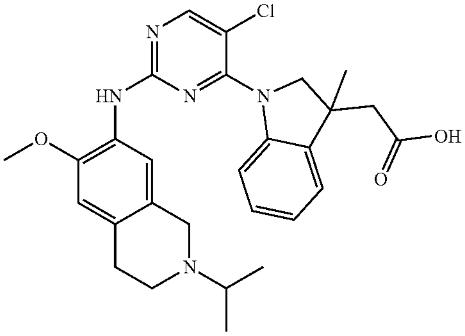 [SMILES: COc1cc2c(cc1Nc1ncc(Cl)c(N3CC(C)(CC(=O)O)c4ccccc43)n1)CN(C(C)C)CC2] |
| 156 | 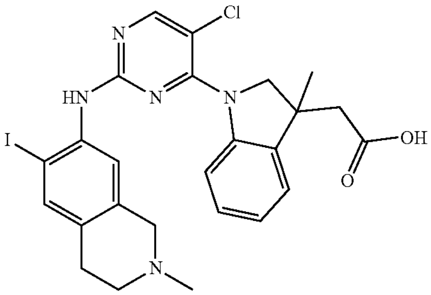 |
or
-continued
| Example No. | Structure |
|---|---|
| 165 | 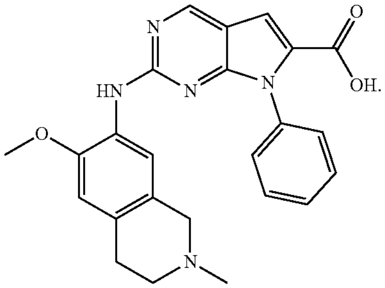 [SMILES: COc1cc2c(cc1Nc1ncc3cc(C(=O)O)n(-c4ccccc4)c3n1)CN(C)CC2] |
18. A compound, or a pharmaceutically acceptable salt, wherein the compound is
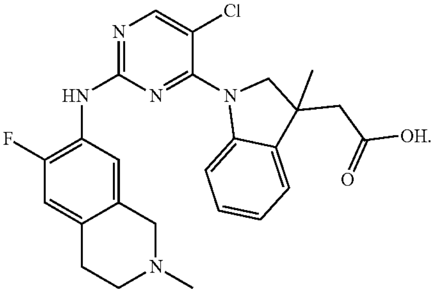 [SMILES: CN1CCc2cc(F)c(Nc3ncc(Cl)c(N4CC(C)(CC(=O)O)c5ccccc54)n3)cc2C1]
19. A stereoisomer of a compound, wherein the compound is
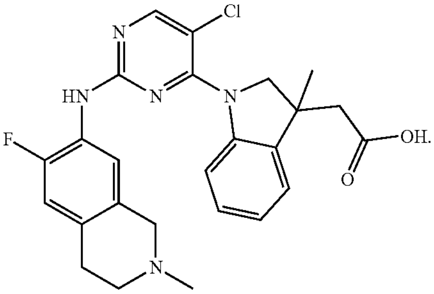 [SMILES: CN1CCc2cc(F)c(Nc3ncc(Cl)c(N4CC(C)(CC(=O)O)c5ccccc54)n3)cc2C1]
* * * * *